US008455497B2

(12) United States Patent
Hale et al.

(10) Patent No.: US 8,455,497 B2
(45) Date of Patent: Jun. 4, 2013

(54) INHIBITORS OF ASPARTYL PROTEASE

(75) Inventors: Michael R. Hale, Bedford, MA (US); Roger Tung, San Diego, CA (US); Stephen Price, Harlow (GB); Robin David Wilkes, West Hagbourne (GB); Wayne Carl Schairer, Westborough, MA (US); Ashley Nicholas Jarvis, Primrose Hill (GB); Andrew Spaltenstein, Raleigh, NC (US); Eric Steven Furfine, Croton on Hudson, NY (US); Vicente Samano, Chapel Hill, NC (US); Istvan Kaldor, Durham, NC (US); John Franklin Miller, Durham, NC (US); Michael Stephen Brieger, Greenwood, IN (US); Ronald George Sherrill, Cary, NC (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 237 days.

(21) Appl. No.: 12/370,175

(22) Filed: Feb. 12, 2009

(65) Prior Publication Data
US 2009/0274650 A1 Nov. 5, 2009

Related U.S. Application Data

(60) Continuation of application No. 10/691,333, filed on Oct. 21, 2003, now abandoned, which is a division of application No. 09/591,464, filed on Jun. 9, 2000, now Pat. No. 6,878,728.

(60) Provisional application No. 60/139,070, filed on Jun. 11, 1999, provisional application No. 60/190,211, filed on Mar. 17, 2000.

(51) Int. Cl.
*C07D 493/04* (2006.01)
*A61K 31/34* (2006.01)
*A61K 31/357* (2006.01)
*A61K 31/36* (2006.01)
*A61P 31/18* (2006.01)
*C07C 311/16* (2006.01)
*C07C 311/29* (2006.01)

(52) U.S. Cl.
USPC ...... 514/254.11; 514/272; 514/338; 514/339; 514/361; 514/364; 514/365; 514/378; 514/399; 514/406; 514/422; 514/452; 514/465; 514/359; 544/148; 544/297; 544/377; 546/271.7; 546/282.4; 546/283.7; 548/127; 548/131; 548/159; 548/204; 548/247; 548/249; 548/256; 548/311.7; 548/364.4; 548/526; 549/58; 549/60; 549/366; 549/435; 549/464

(58) Field of Classification Search
None
See application file for complete search history.

(56) References Cited

U.S. PATENT DOCUMENTS

| 3,743,722 | A | | 7/1973 | Mohrs et al. |
| 4,330,542 | A | | 5/1982 | Descamps et al. |
| 4,629,724 | A | | 12/1986 | Ryono et al. |
| 5,196,438 | A | | 3/1993 | Martin et al. |
| 5,354,866 | A | | 10/1994 | Kempf et al. |
| 5,585,397 | A | | 12/1996 | Tung et al. |
| 5,622,949 | A | | 4/1997 | Talley et al. |
| 5,723,490 | A | | 3/1998 | Tung et al. |
| 5,744,481 | A | | 4/1998 | Vazquez et al. |
| 5,808,056 | A | | 9/1998 | Amato et al. |
| 5,843,946 | A | | 12/1998 | Vazquez et al. |
| 6,127,372 | A | * | 10/2000 | Tung et al. ............... 514/253.11 |
| 6,319,946 | B1 | | 11/2001 | Hale et al. |
| 6,559,137 | B1 | * | 5/2003 | Tung et al. ...................... 514/99 |
| 6,613,743 | B2 | | 9/2003 | Hale et al. |
| 6,617,350 | B2 | | 9/2003 | Hale et al. |
| 6,878,728 | B1 | | 4/2005 | Hale et al. |
| 7,419,967 | B2 | * | 9/2008 | Hale et al. ........................ 514/49 |
| 2010/0124543 | A1 | * | 5/2010 | Tung et al. .................... 424/85.2 |

FOREIGN PATENT DOCUMENTS

| DE | 3542567 | 6/1986 |
| EP | 0022118 | 1/1981 |
| EP | 0181071 | 5/1986 |
| EP | 0264795 | 4/1988 |
| EP | 0346847 | 12/1989 |
| EP | 0364804 | 4/1990 |
| EP | 0434365 | 6/1991 |
| EP | 0468641 | 1/1992 |
| EP | 0486948 | 5/1992 |

(Continued)

OTHER PUBLICATIONS

Baker et al., "Design, Synthesis, and Conformational Analysis of a Novel Series of HIV Protease Inhibitors," *Bioorganic & Medicinal Chemistry Letter*, 8:3631-3636 (1998).
Banker et al., *Modern Pharmaceutics*, 627-629 (1996).
R. Bone et al., "X-ray Crystal Structure of the HIV Protease Complex with L-700,417, an Inhibitor with Pseudo $C_2$ Symmetry", *J. Am. Chem. Soc.*,113:9382-84 (1991).
J.C. Craig et al., "Antiviral Synergy Between Inhibitors of HIV Proteinase and Reverse Transcriptase", *Antiviral Chem. and Chemotherapy*, 4:161-66 (1990).

(Continued)

*Primary Examiner* — Fiona T Powers
(74) *Attorney, Agent, or Firm* — Ropes & Gray LLP; James F. Haley, Jr.; Karen Mangasarian

(57) ABSTRACT

The present invention relates to a novel class of sulfonamides which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention and methods for screening compounds for anti-HIV activity.

40 Claims, No Drawings

FOREIGN PATENT DOCUMENTS

| | | |
|---|---|---|
| EP | 0541168 | 5/1993 |
| EP | 0594540 | 4/1994 |
| EP | 0 885 887 | 5/2003 |
| GB | 2167759 | 6/1986 |
| GB | 2200115 | 7/1988 |
| JP | 59046252 | 3/1984 |
| JP | 59048449 | 3/1984 |
| JP | 61071830 | 4/1986 |
| WO | WO90/07329 | 7/1990 |
| WO | WO91/00725 | 1/1991 |
| WO | WO91/18866 | 12/1991 |
| WO | WO92/08688 | 5/1992 |
| WO | WO92/08698 | 5/1992 |
| WO | WO92/08699 | 5/1992 |
| WO | WO92/08700 | 5/1992 |
| WO | WO92/08701 | 5/1992 |
| WO | WO92/17176 | 10/1992 |
| WO | WO93/23368 | 11/1993 |
| WO | WO93/23379 | 11/1993 |
| WO | WO93/23388 | 11/1993 |
| WO | WO94/04491 | 3/1994 |
| WO | WO94/04492 | 3/1994 |
| WO | WO94/04493 | 3/1994 |
| WO | WO94/05639 | 3/1994 |
| WO | WO94/10134 | 5/1994 |
| WO | WO94/10136 | 5/1994 |
| WO | WO94/18192 | 8/1994 |
| WO | WO94/19322 | 9/1994 |
| WO | WO95/06030 | 3/1995 |
| WO | WO95/07269 | 3/1995 |
| WO | WO95/09843 | 4/1995 |
| WO | WO95/14016 | 5/1995 |
| WO | WO95/32185 | 11/1995 |
| WO | WO96/22287 | 7/1996 |
| WO | WO 96/27583 | 9/1996 |
| WO | WO96/28418 | 9/1996 |
| WO | WO96/28463 | 9/1996 |
| WO | WO96/28464 | 9/1996 |
| WO | WO96/28465 | 9/1996 |
| WO | WO 96/33184 | 10/1996 |
| WO | WO 96/33187 | 10/1996 |
| WO | WO97/18205 | 5/1997 |
| WO | WO 99/10373 | 3/1999 |
| WO | WO 99/65870 | * 12/1999 |

OTHER PUBLICATIONS

S. Crawford et al., "A Deletion Mutation in the 5' Part of the pol Gene of Moloney Murine Leukemia Virus Blocks Proteolytic Processing of the gag and pol Polyproteins", *J. Virol.*, 53:899-907 (1985).

M. Cushman et al., "Delvelopment of Methodology for the Synthesis of Stereochemically Pure Pheψ[CH₂N]Pro Linkages in HIV Protease Inhibitors", *J. Org. Chem.*, 56:4161-67 (1991).

D.S. Dhanoa et al., "The Synthesis of Potent Macrocyclic Renin Inhibitors", *Tetrahedron Lett.*, 33:1725-28 (1992).

G.B. Dreyer et al., "Hydroxyethylene Isostere Inhibitors of Human Immunodeficiency Virus-1 Protease: Structure-Activity Analysis Using Enzyme Kinetics, X-ray Crystallography, and Infected T-Cell Assays", *Biochemistry*, 31:6646-59 (1992).

G.A. Flynn et al., "An Acyl-Iminium Ion Cyclization Route to a Novel Conformationally Restricted Dipeptide Mimic: Applications to Angiotensin-Converting Enzyme Inhibition", *J. Am. Chem. Soc.*, 109:7914-15 (1989).

G. Fontenot et al., "PCR Amplification of HIV-1 Proteinase Sequences Directly from Lab Isolates Allows Determination of Five Conserved Domains", *Virology*, 190:1-10 (1992).

J. Freskos et al., "(Hydroxyethyl)sulfonamide HIV-1 Protease Inhibitors: Identification of the 2-Methylbenzoyl Moiety at P-2", *Bio. & Med. Chem. Lett.*, 6:445-450 (1996).

A. Ghosh et al., "Potent HIV Protease Inhibitors Incorporating High-Affinity $P_2$-Ligands and (R)-(Hydroxyethylamino)sulfonamide Isostere", *Bio. & Med. Chem. Lett.*, 8:687-690 (1998).

E.E. Gilbert, "Recent Developments in Preparative Sulfonation and Sulfation", *Synthesis*, 3-10 (1969).

A. Goldblum, "Modulation of the Affinity of Aspartic Proteases by the Mutated Residues in Active Site Models", *FEBS*, 261:241-44 (1990).

D. Grobelny et al., "Selective Phosphinate Transition-State Analogue Inhibitors of the Protease of Human Immunodeficiency Virus", *Biochem. Biophys. Res. Commun.*, 169:1111-16 (1990).

G.D. Hartman et al., "4-Substituted Thiophene- and Furan-2-sulfonamides as Topical Carbonic Anhydrase Inhibitors", *J. Med. Chem.*, 35:3822-31 (1992).

S. J. Hays et al., "Synthesis of cis-4-(Phosphonooxy)-2-piperidinecarboxylic Acid, an N-Methyl-D-aspartate Antagonist", *J. Org. Chem.*, 56:4984-4086 (1991).

J.R. Huff, "HIV Protease: A Novel Chemotherapeutic Target for AIDS", *Journal of Medicinal Chemistry*, 34:2305-14 (1991).

K.Y. Hui et al., "A Rational Approach in the Search for Potent Inhibitors Against HIV Proteinase", *FASEB*, 5:2606-10 (1991).

Y. Kiso et al., "'O→N Intramolecular Acyl Migration'-type Prodrugs of Tripeptide Inhibitors of HIV Protease", *Peptides: Chemistry, Structure and Biology*, 61:157-159 (1996).

N.E. Kohl et al., "Active HIV Protease Is Required for Viral Infectivity", *Proc. Natl. Acad. Sci. USA*, 85:4686-90 (1988).

X. Lin et al., "Enzymic Activities of Two-Chain Pepsinogen, Two-Chain Pepsin, and the Amino-Terminal Lobe of Pepsinogen", *J. Biol. Chem.*, 267:17257-63 (1992).

K.P. Manfredi et al., "Examination of HIV-1 Protease Secondary Structure Specificity Using Conformationally Constrained Inhibitors", *J. Med. Chem.*, 34:3395-99 (1991).

F.R. Marshall, "Computer-Aided Drug Design", *Ann. Ref. Pharmacol. Toxicol.*, 27:193-213 (1987).

J.A. Martin, "Recent Advances in the Design of HIV Proteinase Inhibitors", *Antiviral Research*, 17:265-78 (1992).

T.D. Meek et al., "Inhibition of HIV-1 Protease in Infected T-Lymphocytes by Synthetic Peptide Analogues", *Nature*, 343:90-92 (1990).

M. Miller et al., "Structure of Complex of Synthetic HIV-1 Protease with a Substrate-Based Inhibitor at 2.3 A Resolution", *Science*, 246:1149-52 (1989).

M. Miller et al., "Crystal Structure of a Retroviral Protease Proves Relationship to Aspartic Protease Family", *Nature*, 337:576-79 (1989).

K.H.M. Murthy et al., "Crystal Structures at 2.2-A Resolution of Hydroxyethylene-Based Inhibitors Bound to Human Immunodeficiency Virus Type 1 Protease Show That the Inhibitors Are Present in Two Distinct Orientations", *J. Biol. Chem.*, 267:22770-78 (1992).

J.B. Nichols et al., "A Molecular Mechanics Valence Force Field for Sulfonamides Derived by ab initio Methods", *J. Phys. Chem.*, 95:9803-11 (1991).

J. Palca, "Shooting at a New HIV Target", *Science*, 247:410 (1990).

L.H. Pearl et al., "A Structural Model for the Retroviral Proteases", *Nature*, 329:329-51 (1987).

J.W. Perich et al., "The Synthesis of Multiple O-Phosphoseryl-Containing Peptides via Phenyl Phosphate Protection", *J. Org. Chem.*, 53:4103-4105 (1988).

M.S. Plummer et al., "Design of Peptidomimetic Ligands for the pp60$^{src}$ SH2 Domain", *Bioorganic & Medicinal Chemistry*, 5:41-47 (1997).

M. Popvic et al., "Detection, Isolation, and Continuous Production of Cytopathic Retroviruses (HTLV-III) from Patients with AIDS and Pre-AIDS", *Science*, 224:497-500 (1984).

M.D. Power et al., "Nucleotide Sequence of SRV-1, a Type D Simian Acquired Immune Deficiency Syndrome Retrovirus", *Science*, 231:1567-73 (1986).

N.A. Roberts, "Rational Design of Peptide-Based HIV Proteinase Inhibitors", *Science*, 248:358-61 (1990).

S. Scharpe et al., "Proteases and Their Inhibitors: Today and Tomorrow", *Biochimie*, 73:121-26 (1991).

S.K. Sharma et al., "Could Angiotensin I Be Produced from a Renin Substrate by the HIV-1 Protease?" *Anal. Biochem.*, 198:363-67 (1991).

S. Yamaguchi et al., "Synthesis of HIV Protease Dipeptide Inhibitors and Prodrugs", *Peptide Chemistry 1996*, 297-300 (1997).

* cited by examiner

INHIBITORS OF ASPARTYL PROTEASE

CROSS-REFERENCE TO RELATED APPLICATIONS

This application is a continuation of U.S. application Ser. No. 10/691,333, filed Oct. 21, 2003, now abandoned, which is a divisional of U.S. application Ser. No. 09/591,464, filed Jun. 9, 2000, now U.S. Pat. No. 6,878,728, which claims priority benefit under 35 U.S.C. §119(e) of U.S. provisional application 60/190,211, filed Mar. 17, 2000 and U.S. provisional application 60/139,070, filed Jun. 11, 1999.

TECHNICAL FIELD OF THE INVENTION

The present invention relates to a novel class of sulfonamides which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention and methods for screening compounds for anti-HIV activity.

BACKGROUND OF THE INVENTION

The human immunodeficiency virus ("HIV") is the causative agent for acquired immunodeficiency syndrome ("AIDS")—a disease characterized by the destruction of the immune system, particularly of CD4$^+$ T-cells, with attendant susceptibility to opportunistic infections and its precursor AIDS-related complex ("ARC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", J. Virol., 53, p. 899 (1985)). These gene products include pol, which encodes the virion RNA-dependent DNA polymerase (reverse transcriptase), an endonuclease, HIV protease, and gag, which encodes the core-proteins of the virion (H. Toh et al., "Close Structural Resemblance Between Putative Polymerase of a *Drosophila* Transposable Genetic Element 17.6 and pol gene product of Moloney Murine Leukemia Virus", EMBO J., 4, p. 1267 (1985); L. H. Pearl et al., "A Structural Model for the Retroviral Proteases", Nature, pp. 329-351 (1987); M. D. Power et al., "Nucleotide Sequence of SRV-1, a Type D Simian Acquired Immune Deficiency Syndrome Retrovirus", Science, 231, p. 1567 (1986)).

A number of synthetic anti-viral agents have been designed to target various stages in the replication cycle of HIV. These agents include compounds which block viral binding to CD4$^+$ T-lymphocytes (for example, soluble CD4), and compounds which interfere with viral replication by inhibiting viral reverse transcriptase (for example, didanosine and zidovudine (AZT)) and inhibit integration of viral DNA into cellular DNA (M. S. Hirsh and R. T. D'Aquila, "Therapy for Human Immunodeficiency Virus Infection", N. Eng. J. Med., 328, p. 1686, (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, the focus of anti-viral drug design has been to create compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" Proc. Natl. Acad. Sci. USA, 85, p 4686 (1988)). The anti-viral potential of HIV protease inhibition has been demonstrated using peptidyl inhibitors.

More recently several small molecule protease inhibitors have become available for the treatment of HIV infections. Among these is the sulfonamide-containing molecule, Agenerase® (amprenavir). Agenerase® is described in U.S. Pat. No. 5,585,397. Other sulfonamide inhibitors of aspartyl protease are described in U.S. Pat. Nos. 5,691,372, 5,510,388, 5,521,219, 5,639,769, 5,714,605, 5,744,481, 5,786,483, 5,830,897 and 5,843,946

Because HIV-infected patients often develop resistance to particular protease inhibitors, the need still exists for additional compounds that can effectively inhibit the action of aspartyl proteases, particularly HIV protease, for use as agents for preventing and treating chronic and acute viral infections. Moreover, there is also a need for compounds that can effectively inhibit the action of HIV mutants which are resistant to conventional protease inhibitors.

SUMMARY OF THE INVENTION

The present invention provides a novel class of compounds, and pharmaceutically acceptable derivatives thereof, that are useful as inhibitors of aspartyl proteases, in particular, HIV aspartyl protease. These compounds can be used alone or in combination with other therapeutic or prophylactic agents, such as anti-virals, antibiotics, immunomodulators or vaccines, for the treatment or prophylaxis of viral infection.

According to a preferred embodiment, the compounds of this invention are capable of inhibiting HIV viral replication in human CD4$^+$ T-cells. These compounds are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system.

According to another preferred embodiment, the compounds of this invention are useful as therapeutic and prophylactic agents to treat or prevent infection by HIV mutants.

It is a principal object of this invention to provide a novel class of sulfonamides which are aspartyl protease inhibitors, and particularly, HIV aspartyl protease inhibitors. The novel sulfonamides of this invention are those of formula I:

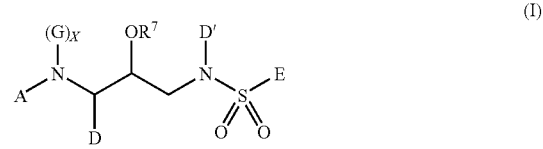

and pharmaceutically acceptable salts thereof; wherein:

A is selected from H; Ht; —$R^1$-Ht; —$R^1$—$C_1$-$C_6$ alkyl, which is optionally substituted with one or more groups independently selected from hydroxy, —CN, $C_1$-$C_4$ alkoxy, Ht, —O-Ht, —$NR^2$Ht, —$NR^2$—CO—$N(R^2)_2$, —$SO_2$—$N(R^2)_2$, —$SO_2$—$R^2$ or —CO—$N(R^2)_2$; —$R^1$—$C_2$-$C_6$ alkenyl, which is optionally substituted with one or more groups independently selected from hydroxy, $C_1$-$C_4$ alkoxy, Ht, —O-Ht, $NR^2$—CO—$N(R^2)_2$ or —CO—$N(R^2)_2$; or $R^7$;

each $R^1$ is independently selected from —C(O)—, —S(O)$_2$—, —C(O)—C(O)—, —O—C(O)—, —OS(O)$_2$, —$NR^2$—, —$NR^2$—S(O)$_2$—, —$NR^2$—C(O) or —$NR^2$—C(O)—C(O)—;

each Ht is independently selected from $C_3$-$C_7$ cycloalkyl; $C_5$-$C_7$ cycloalkenyl; $C_6$-$C_{14}$ aryl; or a 5-7 membered saturated or unsaturated heterocycle, containing one or more heteroatoms selected from N, $N(R^2)$, O, S and —S(O)$_n$; wherein said aryl or said heterocycle is optionally fused to Q; and wherein any member of said Ht is optionally substituted with one or more substituents independently selected from oxo, —$OR^2$, $SR^2$, —$R^2$, —$N(R^2)(R^2)$, —$R^2$—OH, —CN, —$CO_2R^2$, —C(O)—$N(R^2)_2$, —S(O)$_2$—$N(R^2)_2$, —$N(R^2)$—C(O)—$R^2$, —$N(R^2)$—C(O)O—$R^2$, —C(O)—$R^2$, —S(O)$_n$—$R^2$, —$OCF_3$, —S(O)$_n$-Q, methylenedioxy, —$N(R^2)$—S(O)$_2(R^2)$, halo, —$CF_3$, —$NO_2$, Q, —OQ, —$OR^7$, —$SR^7$, —$R^7$, —$N(R^2)(R^7)$ or —$N(R^7)_2$;

each $R^2$ is independently selected from H, or $C_1$-$C_4$ alkyl optionally substituted with a 3-7 membered saturated, partially saturated or unsaturated carbocyclic ring system; or a 5-7 membered saturated, partially saturated or unsaturated heterocyclic ring containing one or more heteroatoms selected from O, N, S, S(O)$_n$ or $N(R^{33})$; wherein any of said ring systems or $N(R^{33})$ is optionally substituted with 1 to 4 substituents independently selected from —X'—Y'—O-arylalkyl, —S-arylalkyl, —$N(Y')_2$, —N(H)-arylalkyl, —N($C_1$-$C_4$ alkyl)-arylalkyl, oxo, —O—($C_1$-$C_4$ alkyl), OH, $C_1$-$C_4$ alkyl, —$SO_2$H, —$SO_2$—($C_1$-$C_4$ alkyl)-$SO_2$—$NH_2$, —$SO_2$—NH($C_1$-$C_4$ alkyl), —$SO_2$—N($C_1$-$C_4$ alkyl)$_2$, —$NH_2$, —NH($C_1$-$C_4$ alkyl), —N($C_1$-$C_4$ alkyl)$_1$, —NH—C(O)H, —N($C_1$-$C_4$ alkyl)-C(O)H, —NH—C(O)—$C_1$-$C_4$ alkyl, —$C_1$-$C_4$ alkyl-OH, —OH, —CN, —C(O)OH, —C(O)O—$C_1$-$C_4$ alkyl, —C(O)—$NH_2$, —C(O)—NH($C_1$-$C_4$ alkyl), —C(O)—N($C_1$-$C_4$ alkyl)$_2$, halo or —$CF_3$;

X' is —O—, —S—, —NH—, —NHC(O)—, —NHC(O)O—, —$NHSO_2$—, or —N($C_1$-$C_4$)alkyl-;

Y' is $C_1$-$C_{15}$ alkyl, $C_2$-$C_{15}$ alkenyl or alkynyl, wherein one to five carbon atoms in Y are optionally substituted with $C_3$-$C_7$ cycloalkyl or $C_5$-$C_6$ cycloalkenyl, $C_6$-$C_{14}$ aryl or a 5-7 membered saturated or unsaturated heterocycle, containing one or more heteroatoms selected from N, NH, O, S and S(O)$_n$;

each $R^3$ is independently selected from H, Ht, $C_1$-$C_8$ alkyl, $C_2$-$C_6$ alkenyl, $C_2$-$C_8$ alkynyl, $C_3$-$C_6$ cycloalkyl or $C_5$-$C_6$ cycloalkenyl; wherein any member of said $R^3$, except H, is optionally substituted with one or more substituents selected from —$OR^2$—C(O)—$N(R^2)_2$, —S(O)$_n$—$N(R^2)_2$, —$N(R^2)_2$, —$N(R^2)$—C(O)O($R^2$), —$N(R^2)$—C(O)N($R^2)_2$, —$N(R^2)$—C)—$R^2$, Ht, —CN, —$SR^2$, —C(O)O$R^2$, $N(R^2)$—C(O)—$R^2$;

each $R^{33}$ is selected from H, $C_1$-$C_6$ alkyl, $C_2$-$C_6$ alkenyl, $C_2$-$C_6$ alkynyl, $C_3$-$C_6$ cycloalkyl or $C_5$-$C_6$ cycloalkenyl, $C_6$-$C_{14}$ aryl or a 5-7 membered saturated or unsaturated heterocycle, containing one or more heteroatoms selected from N, NH, O, S and S(O)$_n$;

each n is independently 1 or 2;

G, when present, is selected from H, $R^7$ or $C_1$-$C_4$ alkyl, or, when G is $C_1$-$C_4$ alkyl, G and $R^7$ are bound to one another either directly or through a $C_1$-$C_3$ linker to form a heterocyclic ring; or when G is not present (i.e., when x in $(G)_x$ is 0), then the nitrogen to which G is attached is bound directly to the $R^7$ group in —$OR^7$ with the concomitant displacement of one —ZM group from $R^7$;

D is selected from $C_1$-$C_6$ alkyl which is substituted with Q, which is optionally substituted with one or more groups selected from $C_3$-$C_6$ cycloalkyl, —$R^3$, —O-Q or Q; $C_2$-$C_{14}$ alkenyl which is substituted with Q, which is optionally substituted with one or more groups selected from —$OR^2$, —S-Ht, —$R^3$, —O-Q or Q; $C_{3-6}$ cycloalkyl, which is optionally substituted with or fused to Q; or $C_5$-$C_6$ cycloalkenyl, which is optionally substituted with or fused to Q;

each Q is independently selected from a 3-7 membered saturated, partially saturated or unsaturated carbocyclic ring system; or a 5-7 membered saturated, partially saturated or unsaturated heterocyclic ring containing one or more heteroatoms selected from O, N, S, S(O)$_n$, or $N(R^2)$; wherein Q contains one substituent selected from —$OR^2$, —$OR^8$, —O-arylalkyl, —$SR^8$, —S-arylalkyl, —$N(R^2)R^8$, —$N(R^2)$-arylalkyl and may be optionally substituted with one or more additional substituents independently selected from oxo, —$OR^8$, —O-arylalkyl —$SR^8$, —S-arylalkyl, ON($R^2$) $R^8$, —$N(R^2)$-arylalkyl, —$OR^2$, $R^2$, —$SO_2R^2$—$SO_2$—$N(R^2)_2$, —$N(R^2)_2$, —$N(R^2)$—C(O)—$R^2$, —OH, ($C_1$-$C_4$)—OH, —CN, —$CO_2R^2$, —C(O)—$N(R^2)_2$, halo or —$CF_3$;

each $R^8$ is independently selected from Ht, —$C_1$-$C_{15}$ branched or straight chain alkyl, alkenyl or alkynyl wherein one to five carbon atoms in said alkyl, alkenyl or alkynyl are independently replaced by W, or wherein one to five carbon atoms in said alkyl, alkenyl or alkynyl are substituted with Ht; and wherein $R^8$ is additionally and optionally substituted with one or more groups independently selected from —OH, —S($C_1$-$C_6$ alkyl), —CN, —$CF_3$, —$N(R^2)_2$, halo, —$C_1$-$C_4$ alkyl, —$C_1$-$C_4$-alkoxy; -Ht; —CO-Ht; —$NR^2$—CO—N$(R^2)_2$; —CO—N($R^2$), —$R^1$—$C_2$-$C_6$ alkenyl, which is optionally substituted with one or more groups independently selected from hydroxy, $C_1$-$C_4$ alkoxy, Ht, —O-Ht, —$NR^2$—CO—$N(R^2)_2$ or —CON$(R^2)_2$; or $R^7$;

wherein W is —O—, —$NR^2$—, —S—, —C(O)—, —C(S)—, —C($NR^2$)—, —S(O)$_2$—, —$NR^2$—S(O)$_2$—, —S(O)$_2$—$NR^2$—, —$NR^2$—C(O)O—, —O—C(O)$NR^2$—, $NR^2$—C(O)$NR^2$—, —$NR^2$—O(S)$NR^2$—, —CON$R^2$—$NR^2C$(O)—, —C(S)$NR^2$, —$NR^2C$(S)—, —$NR^2$—C(=N—CN)—$NR^2$—, —$NR^2C$(=N—CN)O— or —C(O)O—;

D' is selected from $C_1$-$C_{15}$ alkyl, $C_1$-$C_{15}$ alkoxy, $C_2$-$C_{15}$ alkenyl, $C_2$-$C_{15}$ alkenyloxy, $C_2$-$C_{15}$ alkyl, or $C_2$-$C_{15}$ alkynyloxy, wherein D' optionally comprises one or more substituents independently selected from Ht, oxo, halo, —$CF_3$, —$OCF_3$, —$NO_2$, azido, —SH, —$SR^3$—$N(R^3)$—$N(R^3)_2$, —O—$N(R^3)_2$, —($R^3$)N—O—($R^3$), —$N(R^3)_2$, —CN, —$CO_2R^3$, —C(O)—$N(R^3)_2$, —S(O)$_n$—$N(R^3)_2$, —$N(R^3)$—C(O)—$R^3$, —$N(R^3)$—C(O)—$N(R^3)_2$, —C(O)—$R^3$, —S(O)$_n$—$R^3$, —$N(R^3)$—S(O)$_n(R^3)$—($R^3$)—S(O)—$N(R^3)_2$—S—$NR^3$—C(O)$R^3$, —C(S)$N(R^3)_2$, —C(S)$R^3$—C(O)O$R^3$, —O—C(O)O$R^3$, —O—C(O)$N(R^3)_2$, —$NR^3$—C(S)$R^3$, =N—OH, =N—$OR^3$, =N—$N(R^3)_2$, —$NR^3$, =NN$R^3$C(O)$N(R^3)_2$, =NN$R^3$C(O)O$R^3$, =NN$R^3$S(O)$_n$—$N(R^3)_2$, —$NR^3$—C(S)O$R^3$, —$NR^3$—C(S)$N(R^3)_2$, —$N(R^3)$—C[=N($R^3$)]—$N(R^3)_2$, —$N(R^3)$—C[=N—$NO_2$]—$N(R^3)_2$, —$N(R^3)$—C[=N—$NO_2$]—$OR^3$, —OC(O)$R^3$, —OC(S)$R^3$, —OC(O)$N(R^3)_2$, —C(O)$N(R^3)$—$N(R^3)_2$, —$N(R^3)$—N($R^3$)

C(O)R³, —N(R³)—OC(O)R³, —N(R³)—OC(O)R³, —N(R³)—OC(O)R³, —OC(S)N(R³)₂, —OC(S)N(R³)(R³), or PO₃—R³;

E is selected from Ht; O-Ht; Ht-Ht; Ht fused with Ht; —O—R³; —N(R²)(R³); —N(R²)-Ht; C₁-C₆ alkyl, which is optionally substituted with one or more groups selected from R⁴ or Ht; C₂-C₆ alkenyl, which is optionally substituted with one or more groups selected from R⁴ or Ht; C₃-C₆ saturated carbocycle, which is optionally substituted with one or more groups selected from R⁴ or Ht; or C₅-C₆ unsaturated carbocycle, which is optionally substituted with one or more groups selected from R⁴ or Ht;

each R⁴ is independently selected from —R², —OR², —OR³, SR², —SOR², —SO₂R², —CO₂R², —OC(O)—R², —C(O)—N(R²)₂, —C(O)—NR²(OR²)—, —S(O)₂—N(R²)₂, halo, —NR²C(O)—R², —NR²—OR², —N(R²)₂ or —CN;

each R⁷ is independently selected from hydrogen,

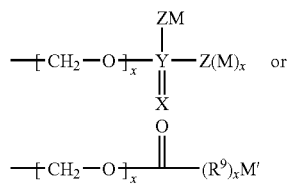

wherein each M is independently selected from H, Li, Na, K, Mg, Ca, Ba, —N(R²)₄, C₁-C₁₂-alkyl, C₂-C₁₂-alkenyl, or —R⁶; wherein 1 to 4 —CH₂ radicals of the allyl or alkenyl group, other than the —CH₂ that is bound to Z, is optionally replaced by a heteroatom group selected from O, S, S(O), S(O₂), or N(R²); and wherein any hydrogen in said alkyl, alkenyl or R⁶ is optionally replaced with a substituent selected from oxo, —C₁-C₄ alkyl, —N(R²)₂, —N(R²)₃, —OH, —O—(C₁-C₄ alkyl), —CN, —C(O)OR², —C(O)—N(R²)₂, S(O)₂—N(R²)₂, —N(R²)—C(O)—R₂, C(O)R², —S(O)ₙ—R², —OCF₃, —S(O)ₙ—R⁶, —N(R²)—S(O)₂(R²), halo, —CF₃, or —NO₂;

M' is H, C₁-C₁₂-alkyl, C₂-C₁₂-alkenyl, or —R⁶; wherein 1 to 4-CH₂ radicals of the alkyl or alkenyl group is optionally replaced by a heteroatom group selected from O, S, S(O), S(O₂) or N(R²); and wherein any hydrogen in said alkyl, alkenyl or R⁶ is optionally replaced with a substituent selected from oxo, —OR², —C₁₋₄ alkyl, —N(R²)₂, N(R²)₃, —OH, —O—(C₁-C₄ alkyl), —CN, —C(O)OR², —C(O)—N(R²)₂, —S(O)₂—N(R²)₂, —N(R²)—C(O)—R₂, —C(O)R², S(O)ₙ—R², —OCF₃, —S(O)ₙ—R⁶, —N(R²)—S(O)₂(R²), halo, —CF₃, or —NO₂;

x is 0 or 1;
Z is O, S, N(R²)₂, or, when M is not present, H.
Y is P or S;
X is O or S; and
R⁹ is (R²)₂, O or N(R²); and wherein when Y is S, Z is not S; and
R⁶ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, S(O)ₙ or N(R²); and wherein any of said ring systems optionally contains 1 to 4 substituents independently selected from —OH, —C₁-C₄ alkyl, —O—(C₁-C₄ alkyl) or —O—C(O)—(C₁-C₄ alkyl).

It is also an object of this invention to provide pharmaceutical compositions comprising the sulfonamides of formula (I) and methods for their use as inhibitors of HIV aspartyl protease.

DETAILED DESCRIPTION OF THE INVENTION

In order that the invention herein described may be more fully understood, the following detailed description is set forth. In the description, the following terms are employed herein:

Unless expressly stated to the contrary, the terms "—SO₂—" and "—S(O)₂—" as used herein refer to a sulfone or X sulfone derivative (i.e., both appended groups linked to the S), and not a sulfinate ester.

For the compounds of formula I, and intermediates thereof, the stereochemistry of OR⁷ is defined relative to D on the adjacent carbon atom, when the molecule is drawn in an extended zigzag representation (such as that drawn for compound of formula I). If both OR⁷ and D reside on the same side of the plane defined by the extended backbone of the compound, the stereochemistry of OR⁷ will be referred to as "syn". If OR⁷ and D reside on opposite sides of that plane, the stereochemistry of OR⁷ will be referred to as "anti".

The term "alkyl", alone or in combination with any other term, refers to a straight-chain or branch-chain saturated aliphatic hydrocarbon radical containing the specified number of carbon atoms, or where no number is specified, preferably from 1 to about 15 and more preferably from 1 to about 10 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl," alone or in combination with any other term, refers to a straight-chain or branched-chain mono- or poly-unsaturated aliphatic hydrocarbon radical containing the specified number of carbon atoms, or where no number is specified, preferably from 2 to about 18 carbon atoms and more preferably, from 2 to about 8 carbon atoms. Examples of alkenyl radicals include, but are not limited to, ethenyl, propenyl, isopropenyl, 1,4-butadienyl, pentenyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl," alone or in combination with any other term, refers to a carbocyclic aromatic radical (such as phenyl or naphthyl) containing the specified number of carbon atoms, preferably from 6-15 carbon atoms, and more preferably from 6-10 carbon atoms, optionally substituted with one or more substituents selected from C₁₋₆ alkoxy, (for example methoxy), nitro, cyano, —SCH₃, halogen, (for example chloro), amino, carboxylate and hydroxy. Examples of aryl radicals include, but are not limited to phenyl, naphthyl, indenyl, indanyl, azulenyl, fluorenyl, anthracenyl and the like.

The term "heterocyclyl" or "heterocycle" refers to a stable 3-7 membered monocyclic heterocyclic ring or 8-11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5-7 membered monocyclic heterocycles and 8-10 membered bicyclic heterocycles. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl-sulfone, oxazolyl, benzoxazolyl, oxopiperidinyl, oxopyrrolidinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuranyl.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing a virus infection, for example an HIV infection, in a patient. As used herein, the term "patient" refers to a mammal, including a human.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "thiocarbamates" refers to compounds containing the functional group N—$SO_2$—O.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization. The novel sulfonamides of this invention are those of formula

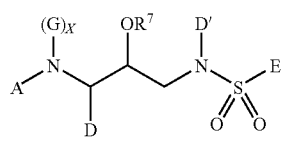

(I)

and pharmaceutically acceptable salts thereof; wherein:

A is selected from H; Ht; —$R^1$-Ht; —$R^1$—$C_1$-$C_6$ alkyl, which is optionally substituted with one or more groups independently selected from hydroxy, —CN, $C_1$-$C_4$ alkoxy, Ht, —O-Ht, —$NR^2$-Ht, —$NR^2$—CO—$N(R^2)_2$, —$SO_2$—$N(R^2)$, —$SO_3R^2$ or —CO—$N(R^2)_2$; —$R^1$—$C_2$-$C_6$ alkenyl, which is optionally substituted with one or more groups independently selected from hydroxy, $C_1$-$C_4$ alkoxy, Ht, —O-Ht, —$NR^2$—CO—$N(R^2)_2$ or —CO—$N(R^2)_2$; or $R^7$;

each $R^1$ is independently selected from —C(O)—, —$S(O)_2$—, —C(O)—C(O)—, —O—C(O)—, —O—$S(O)_2$, —$NR^2$—, —$NR^2$—$S(O)_2$—, —$NR^2$—C(O)— or —$NR^2$—C(O)—C(O)—;

each Ht is independently selected from $C_3$-$C_7$ cycloalkyl; $C_5$-$C_7$ cycloalkenyl; $C_6$-$C_{14}$ aryl; or a 5-7 membered saturated or unsaturated heterocycle, containing one or more heteroatoms selected from N, $N(R^2)$, O, S and $S(O)_n$; wherein said aryl or said heterocycle is optionally fused to Q; and wherein any member of said Ht is optionally substituted with one or more substituents independently selected from oxo, —$OR^2$, $SR^2$, —$R^2$, $N(R^2)(R^2)$—$R^2$—OH, —CN, —$CO_2R^2$, —C(O)—$N(R^2)_2$, —$S(O)_2$—$N(R^2)_2$, —$NR^2$)—C(O)—$R^2$, —$N(R^2)$ C(O)O—$R^2$, —C(O)—$R^2$, —S(O)—$R^2$, —$OCF_3$, —$S(O)_n$-Q, methylenedioxy, —$N(R^2)$—$S(O)_2(R^2)$, halo, $CF_3$, —$NO_2$, Q, —OQ, —$OR^7$, —$SR^7$, —$R^7$, —$N(R^2)(R^7)$ or —$N(R^7)_2$;

each $R^2$ is independently selected from H, or $C_1$-$C_4$ alkyl optionally substituted with a 3-7 membered saturated, partially saturated or unsaturated carbocyclic ring system; or a 5-7 membered saturated, partially saturated or unsaturated heterocyclic ring containing one or more heteroatoms selected from O, N, S, $S(O)_n$ or $N(R^{33})$; wherein any of said ring systems or $N(R^{33})$ is optionally substituted with 1 to 4 substituents independently selected from —X'—Y', —O-arylalkyl, —S-arylalkyl, —$N(Y')_2$, —N(H)-arylalkyl, —$N(C_1$-$C_4$ alkyl)-arylalkyl, oxo, —O—($C_1$-$C_4$ alkyl), OH, $C_1$-$C_4$ alkyl, —$SO_2$H, —$SO_2$—($C_1$-$C_4$ alkyl), —$SO_2$—$NH_2$, —$SO_2$—$NH(C_1$-$C_4$ alkyl), —$SO_2$—$N(C_1$-$C_4$ alkyl)$_2$, —$NH_2$, —$NH(C_1$-$C_4$ alkyl), —$N(C_1$-$C_4$ alkyl)$_2$, —NH—C(O) H, —$N(C_1$-$C_4$ alkyl)-C(O)H, —NH—C(O)—$C_1$-$C_4$ alkyl, —$C_1$-$C_4$ alkyl, —OH, —OH, —ON, —C(O)OH, —C(O)O—$C_1$-$C_4$ alkyl, —C(O)—$NH_2$, —(O)—$NH(C_1$-$C_4$ alkyl), —C(O)—$N(C_1$-$C_4$ alkyl)$_2$, halo or —$CF_3$;

X' is —O—, —S—, —NH—, —NHC(O)—, —NHC(O)O—, —$NHSO_2$—, or —$N(C_1$-$C_4$)alkyl-;

Y' is $C_1$-$C_{15}$ alkyl, $C_2$-$C_{15}$ alkenyl or alkynyl, wherein one to five carbon atoms in Y are optionally substituted with $C_3$-$C_7$ cycloalkyl or $C_5$-$C_6$ cycloalkenyl, $C_6$-$C_{14}$ aryl or a 5-7 membered saturated or unsaturated heterocycle, containing one or more heteroatoms selected from N, NH, O, S and $S(O)_n$;

each $R^3$ is independently selected from H, Ht, $C_1$-$C_9$ alkyl, $C_2$-$C_6$ alkenyl, $C_2$-$C_6$ alkynyl $C_3$-$C_8$ cycloalkyl or $C_5$-$C_6$ cycloalkenyl; wherein any member of said $R^3$, except H, is optionally substituted with one or more substituents selected from —$OR^2$, —C(O)—$N(R^2)_2$, —$S(O)_n$—$N(R^2)_2$, —$N(R^2)_2$—$N(R^2$—C(O)O($R^2$), —$N(R^2)$ C(O)$N(R^2)_2$, —$N(R^2)$—C(O)—$R^2$, Ht, —CN, —$SR^2$, $C(O)OR^2$, $N(R^2)$—$C(O)R^2$;

each $R^{33}$ is selected from H, $C_1$-$C_6$ alkyl, $C_2$-$C_6$ alkenyl, $C_3$-$C_6$ alkynyl, $C_3$-$C_6$ cycloalkyl or $C_5$-$C_6$ cycloalkenyl, $C_6$-$C_{14}$ aryl or a 5-7 membered saturated or unsaturated heterocycle, containing one or more heteroatoms selected from N, NH, O, S and $S(O)_n$;

each n is independently 1 or 2;

G, when present, is selected from H, $R^7$ or $C_1$-$C_4$ alkyl, or, when G is $C_1$-$C_4$ alkyl, G and $R^7$ are bound to one another either directly or through a $C_1$-$C_3$ linker to form a heterocyclic ring; or when G is not present (i.e., when x in (G)$_x$ is 0), then the nitrogen to which G is attached is bound directly to the R$^7$ group in —OR$^7$ with the concomitant displacement of one —ZM group from R$^7$;

D is selected from C$_1$-C$_6$ alkyl which is substituted with Q, which is optionally substituted with one or more groups selected from C$_3$-C$_6$ cycloalkyl, —R$^3$—O-Q or Q; C$_2$-C$_4$ alkenyl which is substituted with Q, which is optionally substituted with one or more groups selected from —OR$^2$, —S-Ht, —R$^3$, —O-Q or Q; C$_3$-C$_6$, cycloalkyl, which is optionally substituted with or fused to Q; or C$_5$-C$_6$ cycloalkenyl, which is optionally substituted with or fused to Q;

each Q is independently selected from a 3-7 membered saturated, partially saturated or unsaturated carbocyclic ring system; or a 5-7 membered saturated, partially saturated or unsaturated heterocyclic ring containing one or more heteroatoms selected from O, N, S, S(O)$_n$ or N(R$^2$); wherein Q contains one substituent selected from —OR$^2$, OR$^8$, —O-arylalkyl, —SR$^8$, —S-arylalkyl, —N(R$^2$)R$^8$, —N(R$^2$)-arylalkyl and may be optionally substituted with one or more additional substituents independently selected from oxo, —OR$^8$, —O-arylalkyl —SR$^8$, —S-arylalkyl, —N(R$^2$)R$^8$, —N(R$^2$)-arylalkyl, —OR$^2$, —R$^2$, —SO$_2$R$^2$, —SO$_2$—N(R$^2$)$_2$, —N(R$^2$)$_2$, —N(R$^2$)—C(O)R$^2$, —OH, (C$_1$-C$_4$)—OH, —CN, —CO$_2$R$^2$, —C(O)—N(R$^2$)$_2$, halo or —CF$_3$;

each R$^8$ is independently selected from Ht, —C$_1$-C$_{15}$ branched or straight chain alkyl, alkenyl or alkynyl wherein one to five carbon atoms in said alkyl, alkenyl or alkynyl are independently replaced by W, or wherein one to five carbon atoms in said alkyl, alkenyl or alkynyl are substituted with Ht; and wherein R$^8$ is additionally and optionally substituted with one or more groups independently selected from —OH, —S(C$_1$-C$_6$ alkyl), —CN, —CF$_3$, —N(R$^2$)$_2$, halo, —C$_1$-C$_4$-alkyl, —C$_1$-C$_4$-alkoxy; -Ht; —O-Ht; —NR$^2$—CO—N(R$^2$)$_2$; —CO—N(R$^2$)$_2$; —R$^1$—C$_2$-C$_6$ alkenyl, which is optionally substituted with one or more groups independently selected from hydroxy, C$_1$-C$_4$ alkoxy, Ht, —O-Ht, —NR$^2$—CO—N(R$^2$)$_2$ or —CO—N(R$^2$)$_2$; or R$^7$;

wherein W is —O', —NR$^2$—, —S—, —C(O)—, —C(S)—, —C(=NR$^2$)—, —S(O)$_2$—, —NR$^2$—S(O)$_2$—, —S(O)$_2$—NR$^2$—, —NR$^2$—C(O)—O—, —O—C(O)N$^2$—, —NR$^2$—C(O)NR$^2$—, —NR$^2$—C(S)NR$^2$—, —CONR$^2$, —NR$^2$C(O)—, —C(S)NR$^2$, —NR$^2$C(S)—, —NR$^2$—C(=N—CN)—NR$^2$—, —NR$^2$C(=N—CN)O— or —C(O)O—;

D' is selected from C$_1$-C$_{15}$ alkyl, C$_1$-C$_{15}$ alkoxy, C$_2$-C$_3$S alkenyl, C$_2$-C$_{15}$ alkenyloxy, C$_2$-C$_{15}$ alkynyl, or C$_2$-C$_{15}$ alkynyloxy, wherein D' optionally comprises one or more substituents independently selected from Ht, oxo, halo, —CF$_3$, —OCF$_3$, —NO$_2$, azido, —SH, —SR$^3$, —N(R$^3$)—N(R$^3$)$_2$, —O—N(R$^3$)$_2$, —(R$^3$)N—O—(R$^3$), —N(R$^3$)$_2$, —CN, —CO$_2$R$^3$, —C(O)—N(R$^3$)$_2$, —S(O)$_n$—N(R$^3$)$_2$, —N(R$^3$)—C(O)—R$^3$, —N(R$^3$)—C(O)—N(R$^3$)$_2$, —C(O)—R$^3$, —S(O)$_n$—R$^3$, —N(R$^3$)—S(O)$_n$(R$^3$), —N(R$^3$)—S(O)$_n$—N(R$^3$)$_2$, —S—NR$^3$—C(O)R$^3$, —C(S)N(R$^3$)$_2$, —C(S)R$^3$, —NR$^3$—C(O)OR$^3$, —O—C(O)OR$^3$, —O—C(O)N(R$^3$)$_2$, —NR$^3$—C(S)R$^3$, =N—OH, =N—OR$^3$, =N—N(R$^3$)$_2$, =NR$^3$, =NNR$^3$C(O)N(R$^3$)$_2$, =NNR$^3$C(O)OR$^3$, =NNR$^3$S(O)$_n$—NR$^3$)$_2$—NR$^3$—C(S)OR$^3$, —NR$^3$—C(S)N(R$^3$)$_2$, —NR$^3$—C[=N(R$^3$)]—N(R$^3$)$_2$—N(R$^3$)—C[=N—NO$_2$]—N(R$^3$)$_2$, —N(R$^3$)—C[=N—NO$_2$]—OR$^3$, —OC(O)R$^3$, —OC(S)R$^3$, —OC(O)N(R$^3$)$_2$, —C(O)N(R$^3$)—N(R$^3$)$_2$, —N(R$^3$)—N(R$^3$)C(O)R$^3$, —N(R$^3$)—OC(O)$^3$, —N(R$^3$)—OC(O)R$^3$, —N(R$^3$)—OC(O)R$^3$, —OC(S)N(R$^3$)$_2$, —OC(S)N(R$^3$)(R$^3$), or —PO$_3$—R$^3$;

E is selected from Ht; O-Ht; Ht-Ht; Ht fused with Ht; —O—R$^3$; —N(R$^2$)(R$^3$); —N(R$^3$)-Ht; C$_1$-C$_6$ alkyl, which is optionally substituted with one or more groups selected from R$^4$ or Ht; C$_2$-C$_6$ alkenyl, which is optionally substituted with one or more groups selected from R$^4$ or Ht; C$_3$-C$_6$ saturated carbocycle, which is optionally substituted with one or more groups selected from R$^4$ or Ht; or C$_5$-C$_6$ unsaturated carbocycle, which is optionally substituted with one or more groups selected from R$^4$ or Ht;

each R$^4$ is independently selected from —R$^2$—OR$^2$, —OR$^3$, —SR$^2$, —SOR$^2$, —SO$_2$R$^2$—CO$_2$R$^2$, —OC(O)—R$^2$, —C(O)—N(R$^2$)$_2$, —C(O)—NR$^2$(OR$^2$), —S(O)$_2$—N(R$^2$)$_2$, halo, —NR$^2$C(O)—R$^2$, —NR$^2$—OR$^2$, —N(R$^2$)$_2$ or —CN;

each R$^7$ is independently selected from hydrogen,

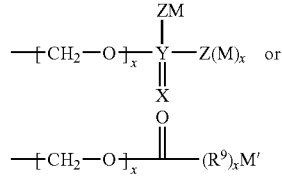

wherein each M is independently selected from H, Li, Na, K, Mg, Ca, Ba, —N(R$^2$)$_4$, C$_1$-C$_{12}$-alkyl, C$_2$-C$_{12}$-alkenyl, or —R$^6$; wherein 1 to 4-CH$_2$ radicals of the alkyl or alkenyl group, other than the —CH$_2$ that is bound to Z, is optionally replaced by a heteroatom group selected from O, S, S(O), S(O$_2$), or N(R$^2$); and wherein any hydrogen in said alkyl, alkenyl or R$^6$ is optionally replaced with a substituent selected from oxo, —C$_1$-C$_4$ alkyl, —N(R$^2$)$_2$, —N(R$^2$)$_3$, —OH, —O—(C$_1$-C$_4$ alkyl), —CN, —C(O)OR$^2$, C(O)—N(R$^2$)$_2$, S(O)$_2$—N(R$^2$)$_2$, —N(R$^2$)—C(O)—R$_2$, —C(O)R$^2$, —S(O)$_n$—R$^2$, —OCF$_3$, —S(O)$_n$—R$^6$, —N(R$^2$)—S(O)$_2$(R$^2$), halo, —CF$_3$, or —NO$_2$;

M' is H, C$_1$-C$_{12}$-alkyl, C$_2$-C$_{12}$-alkenyl, or —R$^6$; wherein 1 to 4 —CH$_2$ radicals of the alkyl or alkenyl group is optionally replaced by a heteroatom group selected from O, S, S(O), S(O$_2$), or N(R$^2$); and wherein any hydrogen in said alkyl, alkenyl or R$^6$ is optionally replaced with a substituent selected from oxo, —OR$^2$, C$_1$-C$_4$ alkyl, —N(R$^2$)$_2$, N(R$^2$)$_3$, —OH, —O—(C$_1$-C$_4$ alkyl), —CN, —C(O)OR$^2$, —C(O)—N(R$^2$)$_2$, —S(O)$_2$—N(R$^2$)$_2$, —N(R$^2$)—C(O)—R$_2$, —C(O)R$^2$), —S(S)$_n$—R$^2$, —OCF$_3$, —S(O)$_n$—R$^6$, —N(R$^2$)—S(O)$_2$(R$^2$), halo, —CF$_3$, or —NO$_2$;

x is 0 or 1;

Z is O, S, N(R$^2$)$_2$, or, when M is not present, H.

Y is P or S;

X is O or S; and

R$^9$ is C(R$^2$)$_2$, O or N(R$^2$); and wherein when Y is S, Z is not S; and

R$^6$ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, S(O)$_n$ or N(R$^2$); and wherein any of said ring systems optionally contains 1 to 4 substituents independently selected from —OH, —C$_1$-C$_4$ alkyl, —O—(C$_1$-C$_4$ alkyl) or —O—C(O)—(C$_1$-C$_4$ alkyl).

Preferably, at least one R$^7$ is selected from:

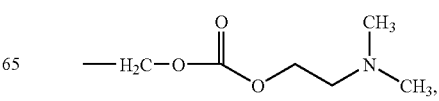

-continued

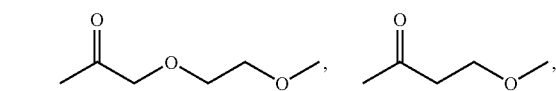

-L-lysine, —PO$_3$Na$_2$,

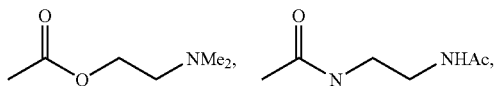

-(L)-tyrosine,

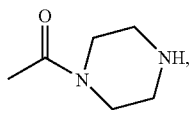

—PO$_3$Mg, —PO$_3$(NH$_4$)$_2$, —CH$_2$—OPO$_3$Na$_2$,

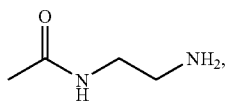

-(L)-serine, —SO$_3$Na$_2$,

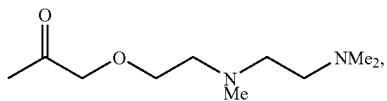

—SO$_3$Mg, —SO$_3$(NH$_4$)$_2$, —CH$_2$—OSO$_3$Na$_2$, —CH$_2$—OSO$_3$(NH$_4$)$_2$,

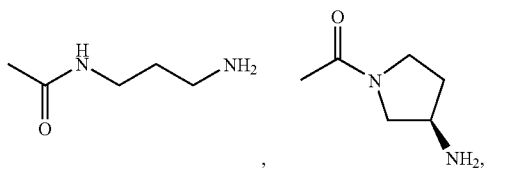

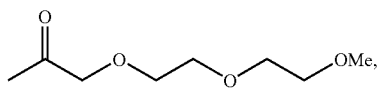

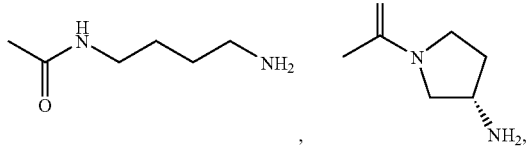

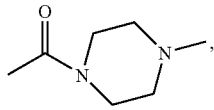

acetyl,

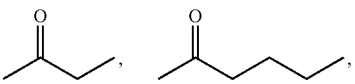

-(L)-valine, -(L)-glutamic acid, -(L)-aspartic acid, -(L)-γ-t-butyl-aspartic acid,

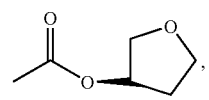

-(L)-(L)-3-pyridylalanine, -(L)-histidine, —CHO,

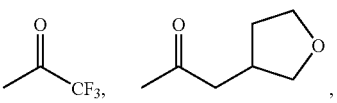

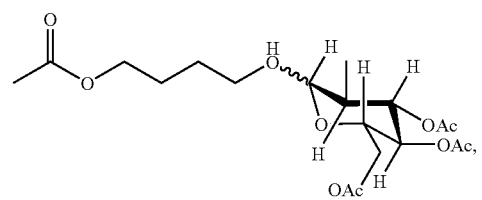

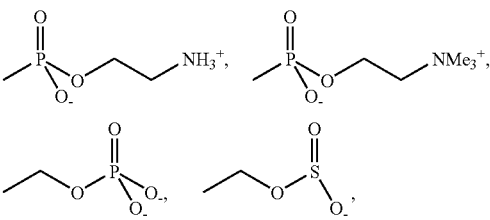

PO$_3$K$_2$, PO$_3$Ca, PO$_3$-spermine, PO$_3$— (spermidine) 2 or PO$_3$— (meglamine)$_2$.

It will be understood by those of skill in the art that component M or M' in the formulae set forth herein will have either a covalent, a covalent/zwitterionic, or an ionic association with either Z or R$^9$ depending upon the actual choice for M or M'. When M or M' is hydrogen, alkyl, alkenyl, or R$^6$, M or M' is covalently bound to R$^9$ or Z. If M is a mono- or bivalent metal or other charged species (i.e., NH$_4$$^+$), there is an ionic interaction between M and Z and the resulting compound is a salt.

When x is 0 in (M)$_x$, Z may be a charged species. When that occurs, the other M may be oppositely charged to produce a 0 net charge on the molecule. Alternatively, the counter ion may located elsewhere in the molecule.

According to yet another preferred embodiment, A is R'—C(O), wherein R' is selected from any of the R' groups indicated in Tables 1, 2 and 3, below. More preferably, R' is selected from —R$^1$—C$_1$-C$_8$ alkyl,

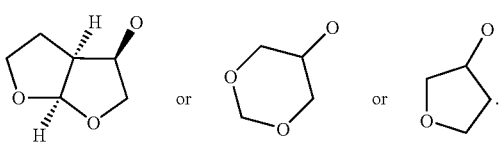 [SMILES: O[C@H]1CO[C@H]2OCC[C@H]21 ; "or" ; OC1COCOC1 ; "or" ; OC1CCOC1 ; "."]

In another preferred embodiment, D' is —CH₂—R'', wherein R'' is selected from any of the R'' groups indicated in Tables 1, 2 and 3, below. More preferably, R'' is selected from:

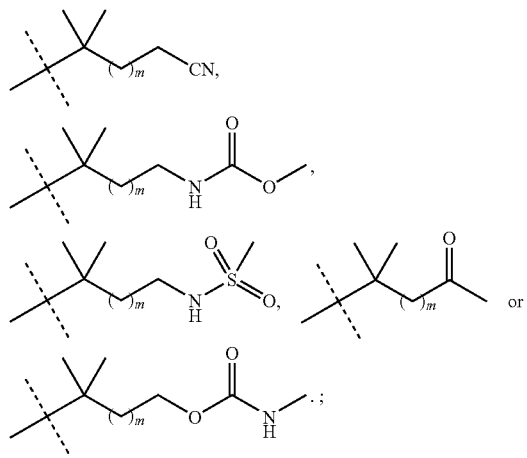

wherein m is 0 to 3.

According to another preferred embodiment, E is selected from any of the E groups indicated in Tables 1, 2 and 3, below. More preferably, E is selected from:

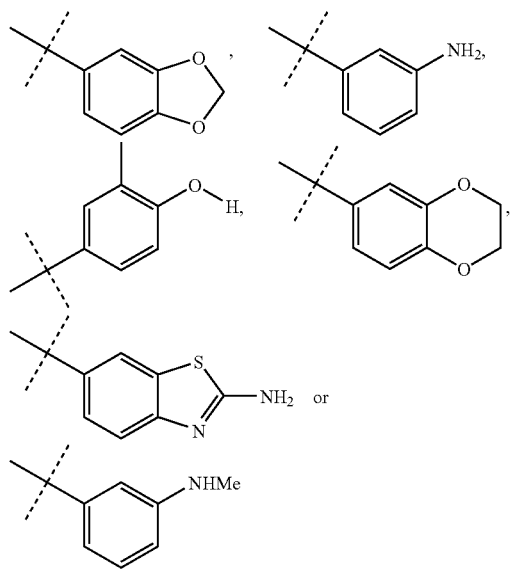

Preferably, W is —O—, —NR²—, —NR²—S(O)₂—, —NR²—C(O)O—, —O—C(O)NR²—, —NR²—C(O) NR²—, —NR²—C(S)NR²—, —NR²C(O)—, —C(O)NR², —NR²—C(═N—CN)—NR²—, —NR²C(═N—CN)O— or —C(O)O—.

More preferably, W is —NR²—, —NR²C(O)— or —C(O) NR². Most preferably, W is —NH—, —NHC(O) or —C(O) NH—.

According to a preferred embodiment, R⁸ is —C₁-C₄— branched or straight chain alkyl, wherein one to two carbon atoms in said alkyl are independently replaced by W, wherein R⁸ is additionally and optionally substituted with one or more groups independently selected from —OH; —C₁-C₄-alkoxy; Ht; —O-Ht; —NR²—CO—N(R²)₂; —CO—N(R²)₂; —R¹—C₂-C₆ alkenyl, which is optionally substituted with one or more groups independently selected from hydroxy, C₁-C₄ alkoxy, Ht, —O-Ht, —NR²CO—N(R²)₂; —CO—N(R²)₂; or R⁷.

According to another preferred embodiment, R⁸ is Ht, wherein Ht is C₆₋₁₄ aryl or a 5-7 membered saturated or unsaturated heterocycle, containing one or more heteroatoms selected from N, N(R²), O, S and S(O)ₙ, wherein Ht is optionally substituted as defined above.

According to another preferred embodiment, R⁸ is a —C₁-C₄-branched or straight alkyl chain, wherein one to two carbon atoms are substituted with Ht, wherein Ht is C₆₋₁₄ aryl or a 5-7 membered saturated or unsaturated heterocycle, containing one or more heteroatoms selected from N, N(R²), O, S and S(O)ₙ, wherein Ht is optionally substituted as defined above.

According to a more preferred embodiment, R⁸ is a —C₁-C₄-branched or straight alkyl chain, wherein one carbon atom in said alkyl chain is substituted with Ht, wherein Ht is phenyl or Ht is a 5-6 membered saturated or unsaturated heterocycle, containing one or more heteroatoms selected from N, N(R²), O and S, wherein Ht is optionally substituted as defined above. Preferably, said Ht in R⁸ is selected from 2-thienyl, 3-thienyl, 2-furyl, 3-furyl, 2-pyridyl, 3-pyridyl, 4-pyridyl, thiazolyl, morpholinyl, pyrimidinyl, thiazolidinyl, imidazolyl, 1,2,3-triazolyl, pyrrolidinyl, pyrazolyl, piperazyl, 1,2,4-oxadiazolyl, 4-4'-thiadiazolyl, 1,2,3-thiadiazolyl, isoxazolyl, and isothiazolyl, wherein said Ht is optionally substituted, as defined above. More preferably, R⁸ is selected from any of the R⁸ groups depicted in Tables 1, 2 and 3.

Most preferably, R⁸ is selected from:

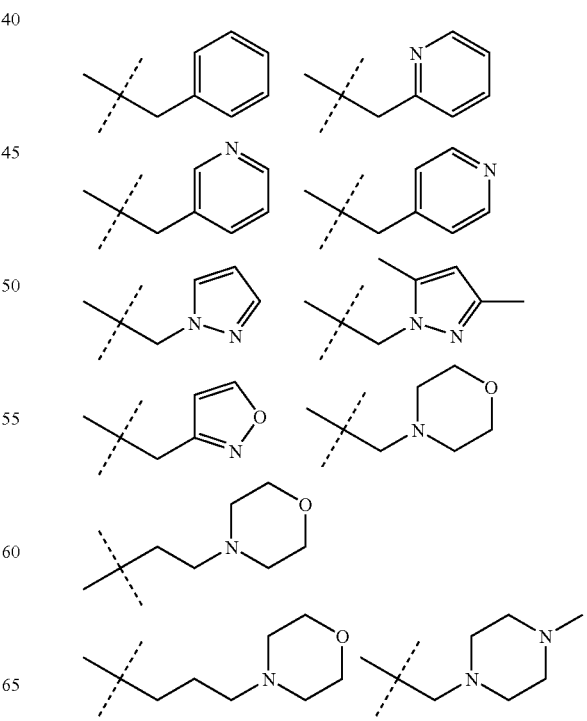

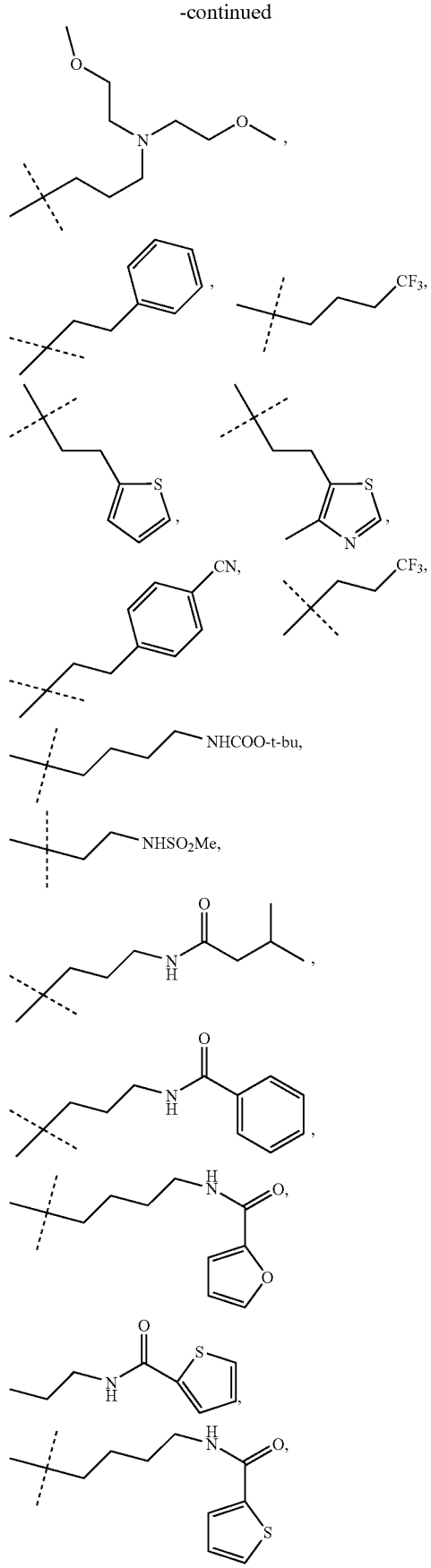
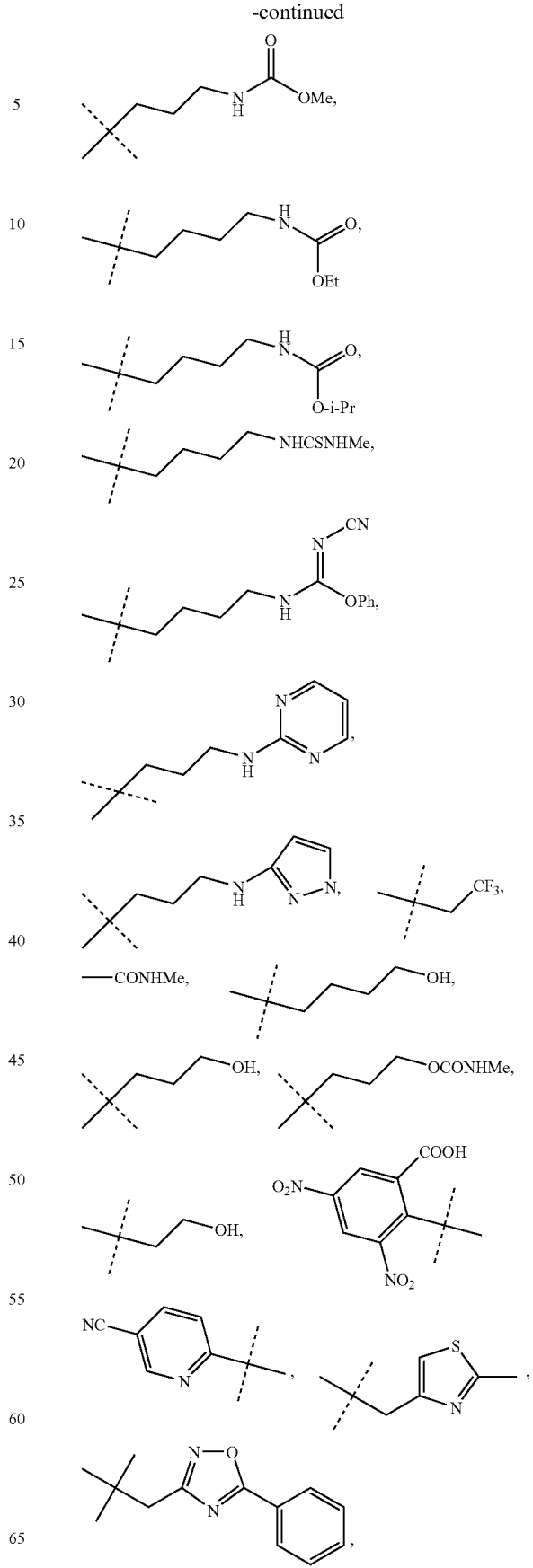

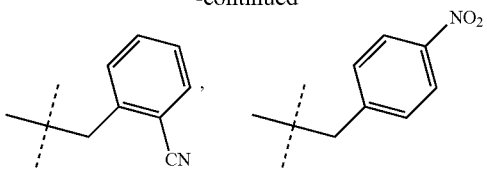

More preferred compounds of formula I are those represented by formula II:

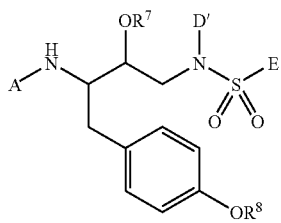

(II)

wherein A, $R^7$, D', E and $R^8$ are as defined above.

Preferred compounds of formula II set forth above are those, wherein $R^7$ in —$OR^7$ is —$PO(OM)_2$ or $C(O)CH_2OCH_2CH_2OCH_2CH_2OCH_3$; wherein M is H, Li, Na, Ca, Mg, K or $C_1$-$C_4$ alkyl.

Also preferred are compounds of formula II, wherein $R^8$ is selected from —$C_1$-$C_{15}$ branched or straight chain alkyl, alkenyl or alkynyl wherein one to five carbon atoms in said alkyl, alkenyl or alkynyl are independently replaced by W, or wherein one to five carbon atoms in, said alkyl, alkenyl or alkynyl are substituted with Ht; and wherein $R^8$ is additionally and optionally substituted with one or more groups independently selected from —OH, —$SCH_3$, —CN, —$CF_3$, amino, halo, —$C_1$-$C_4$-alkyl, —$C_1$-$C_4$-alkoxy; -Ht; —O-Ht; —$NR^2CO$—$N(R^2)_2$; —CO—$N(R^2)_2$; —$R^1$—$C_2$-$C_6$ alkenyl, which is optionally substituted with one or more groups independently selected from hydroxy, $C_1$-$C_4$ alkoxy, Ht, —O-Ht, —$NR^2$—CO—$N(R^2)_2$ or —CO—$N(R^2)_2$; or $R^7$.

More preferably, $R^8$ in compounds of formula II is selected from any of the $R^3$ groups depicted in Tables 1, 2 and 3. According to another more preferred embodiment, $R^8$ in compounds of formula II is selected from the group consisting of:

Most preferably, $R^8$ is selected from:

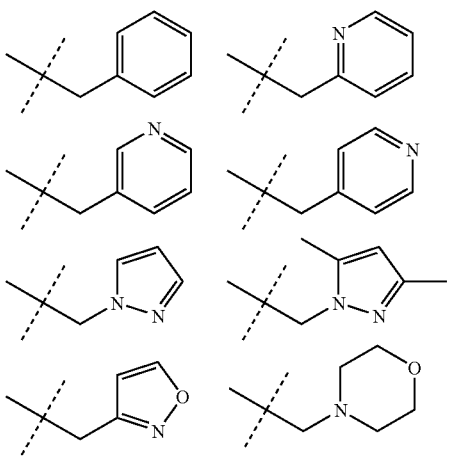

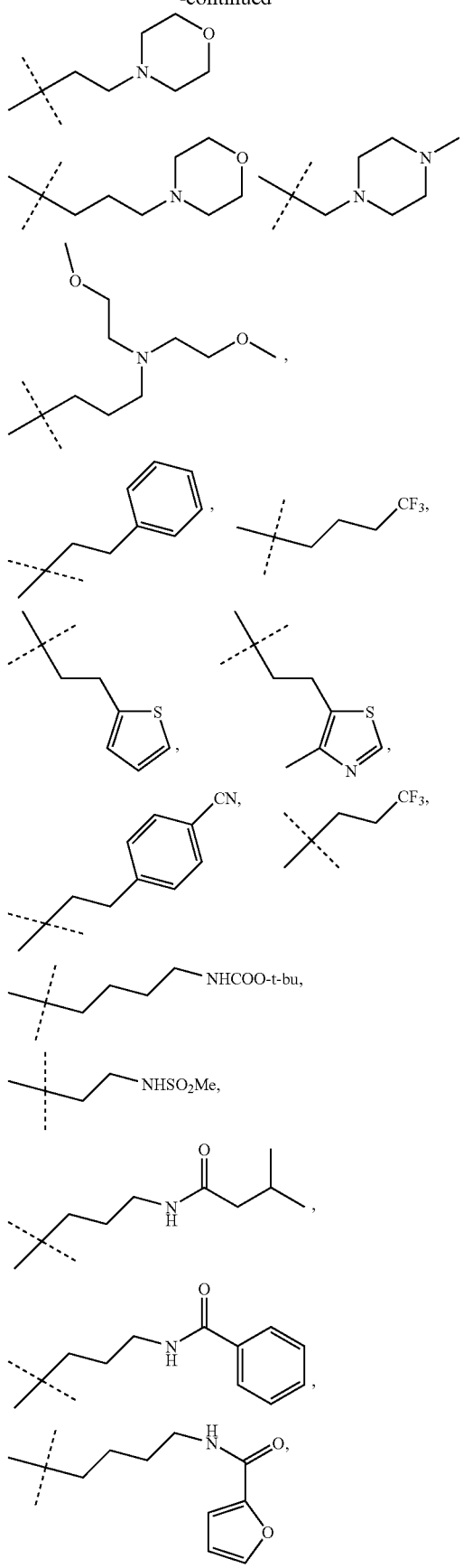

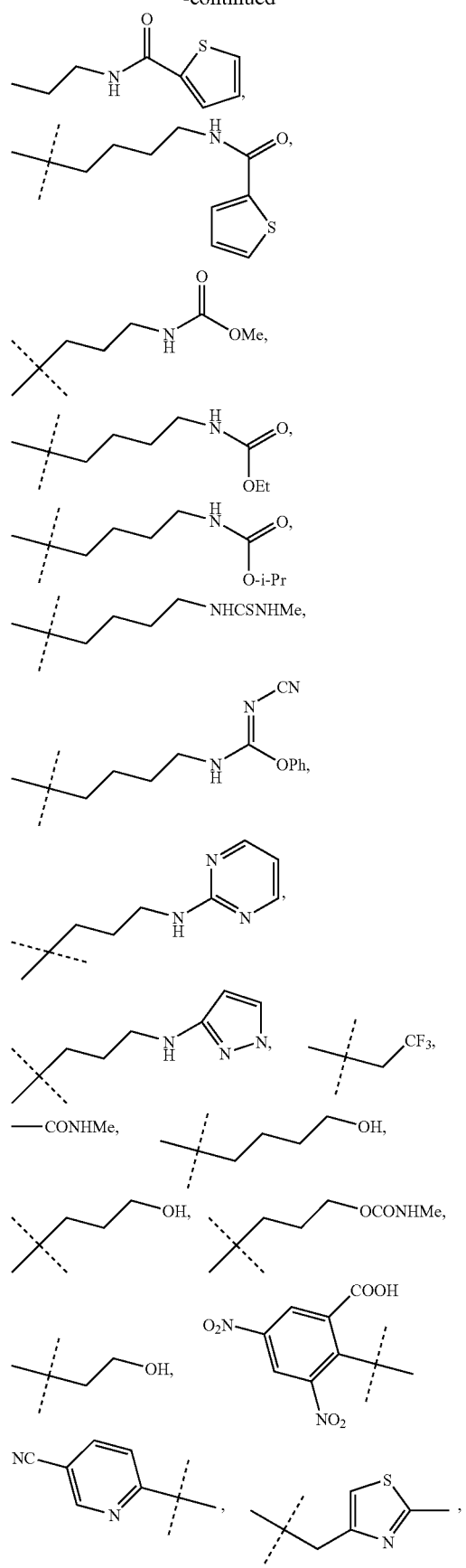
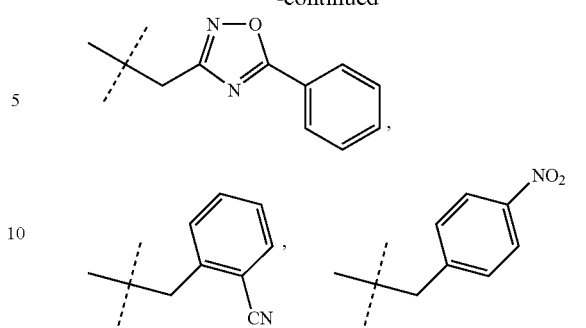
According to another more preferred embodiment, $R^8$ is selected from:
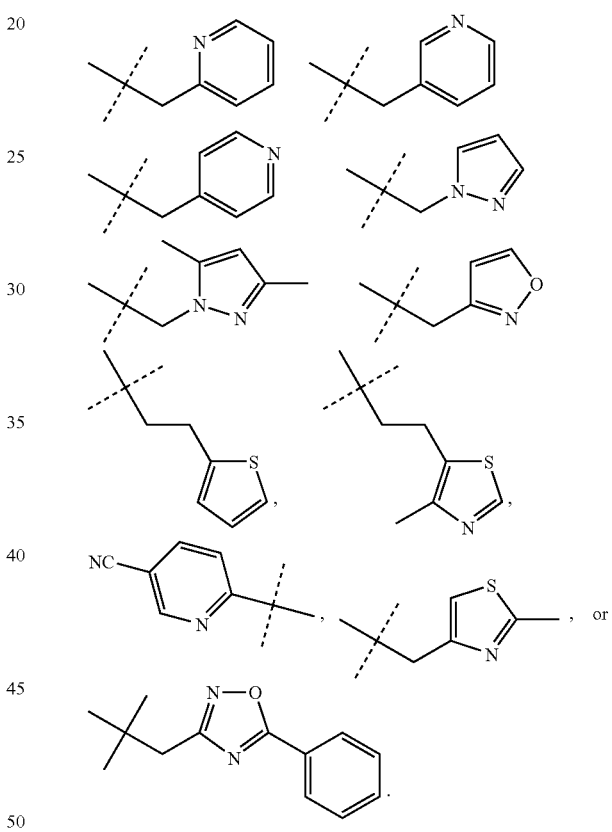
According to another more preferred embodiment, $R^8$ is selected from:
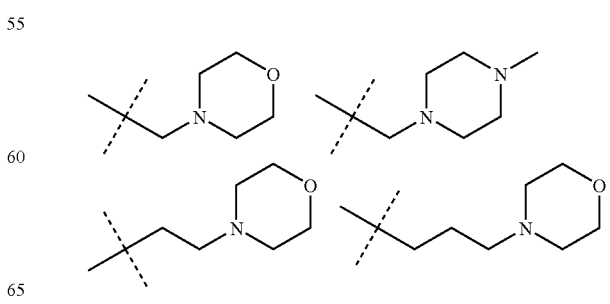

According to another more preferred embodiment, R⁸ is selected from:
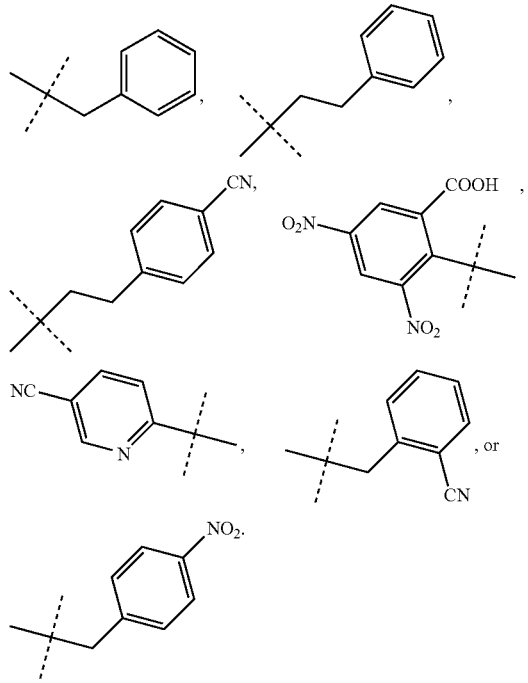
According to another more preferred embodiment, R⁸ is selected from:
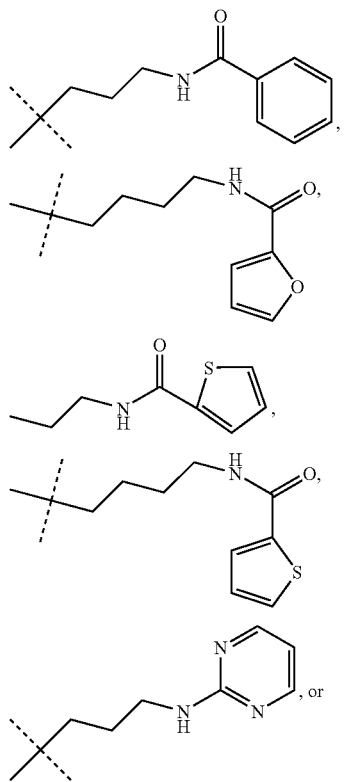
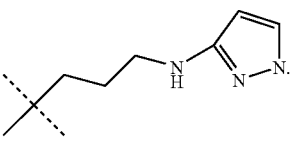
According to another more preferred embodiment, R⁸ is selected from:
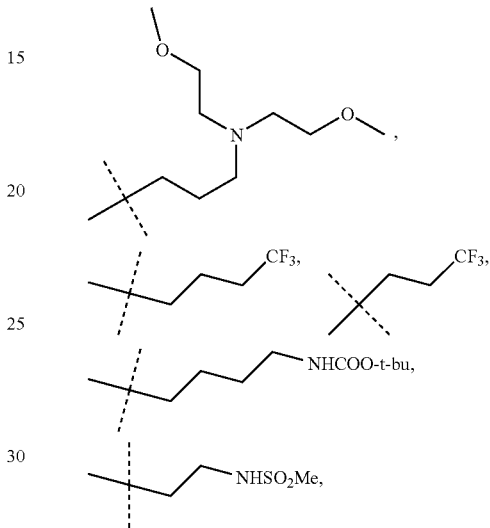
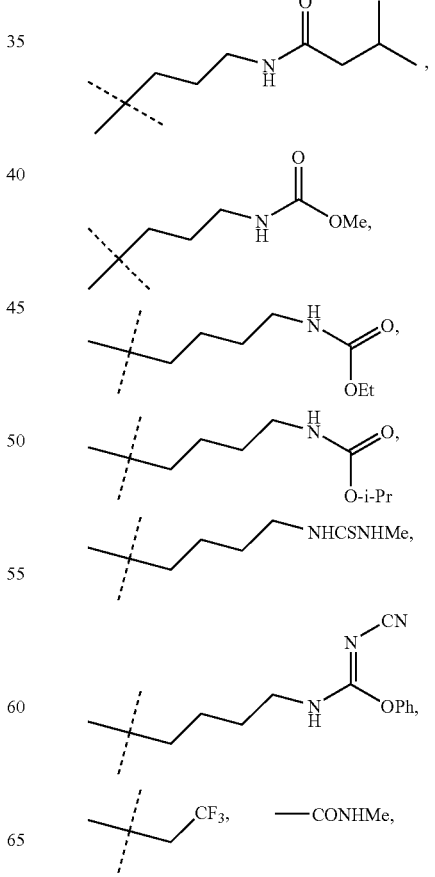

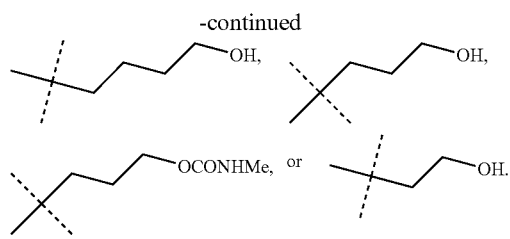

The compounds according to the invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Specific preferred compounds of the present invention are set forth below in Tables 1, 2 and 3. The arrows in Tables 1 and 2, and the dotted lines in Table 3 indicate where the indicated moiety attaches to the rest of the molecule.

TABLE 1

TABLE 1-continued
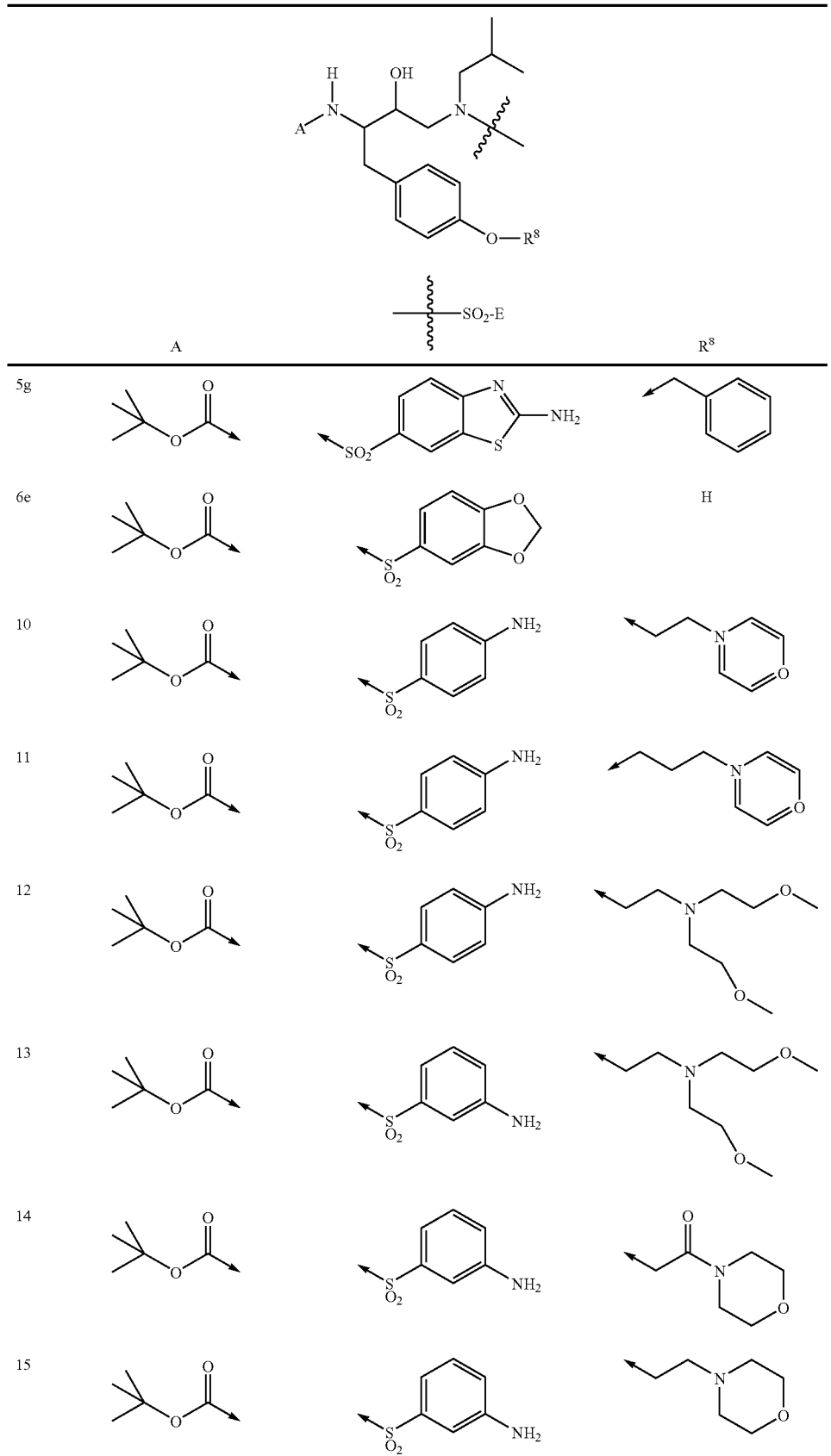

TABLE 1-continued
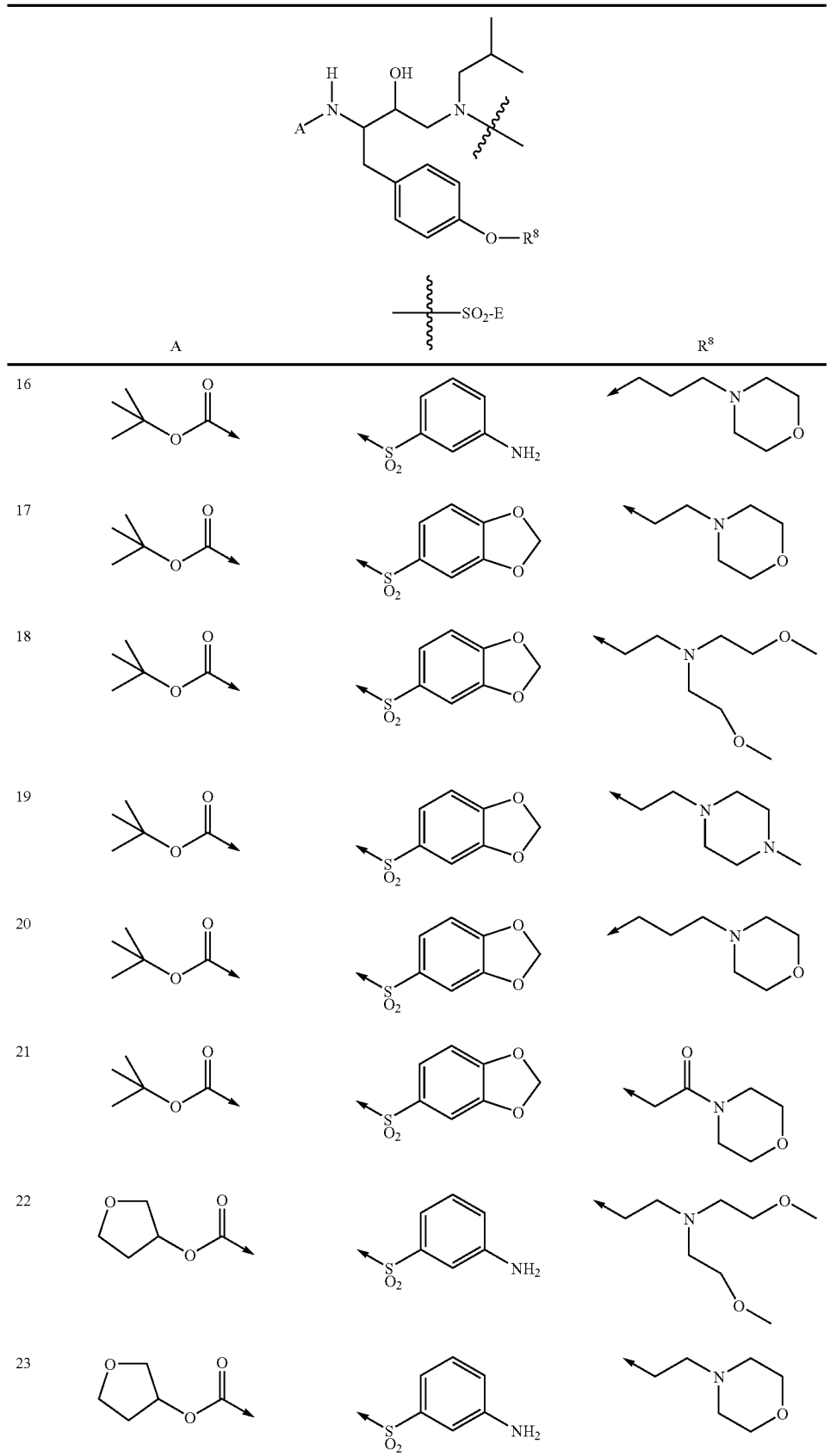

TABLE 1-continued
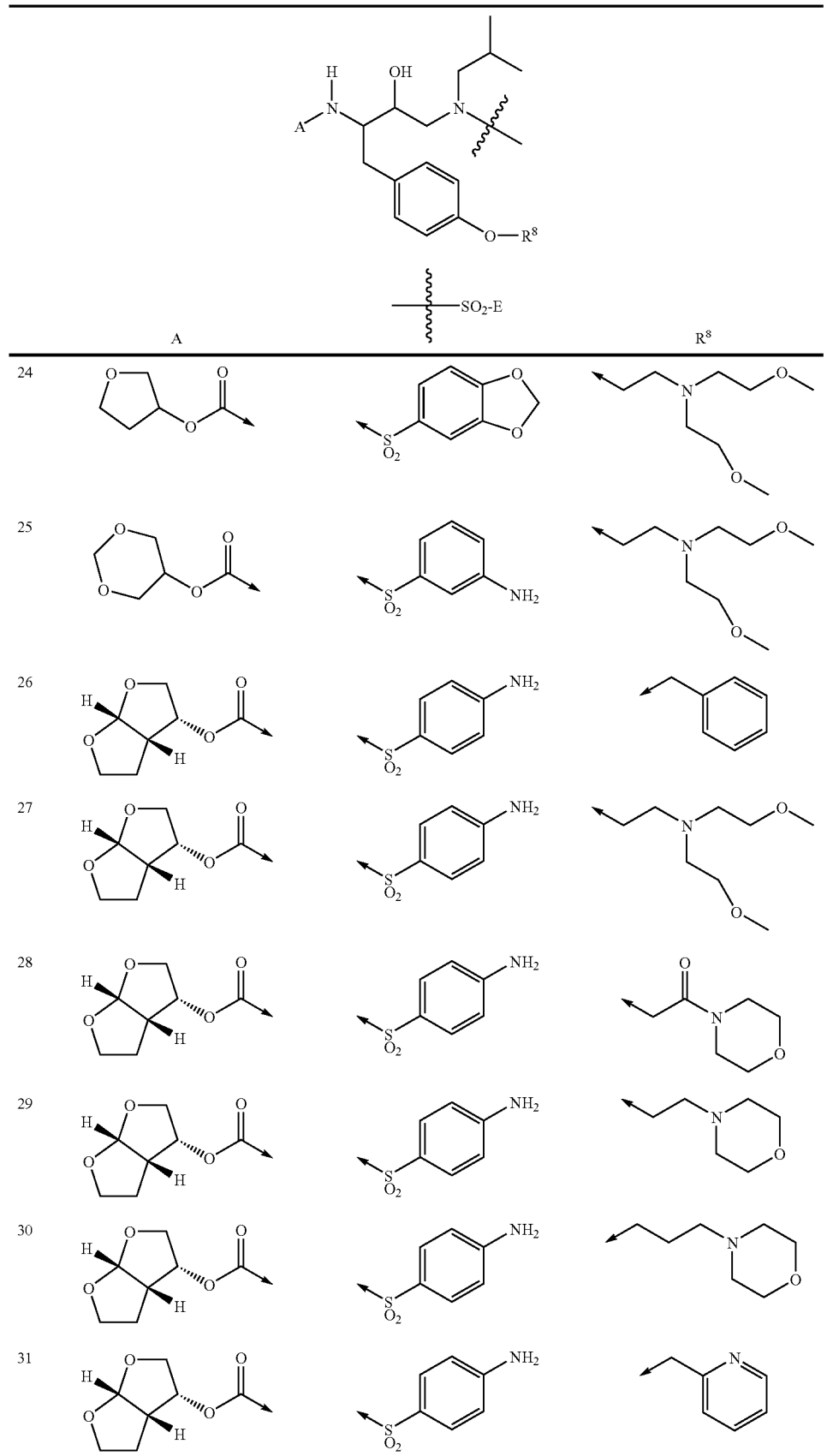

TABLE 1-continued
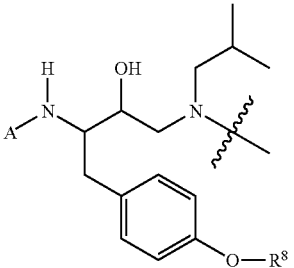
| | A | | R⁸ |
|---|---|---|---|
| 32 | 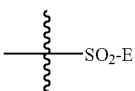 | 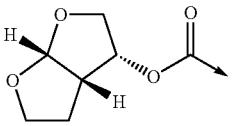 | H |
| 33 | 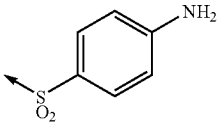 | 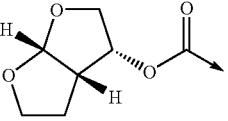 | 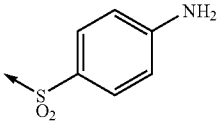 |
| 34 | 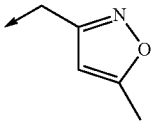 | 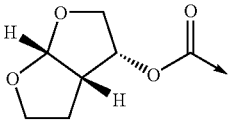 | 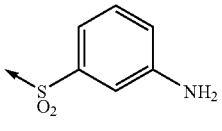 |
| 35 | 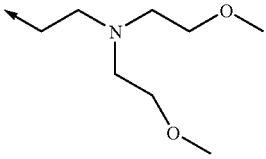 | 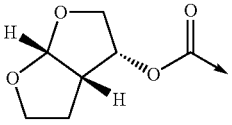 | 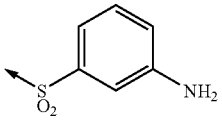 |
| 36 | 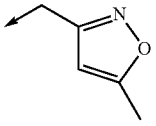 | 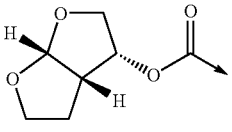 | 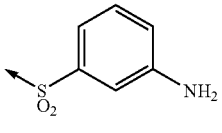 |
| 37 | 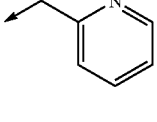 | 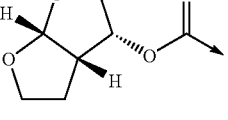 | 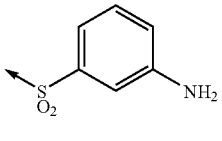 |
| 38 | 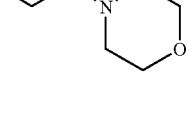 | 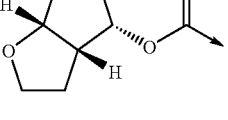 | 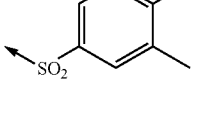 |
| 39 | 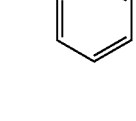 | 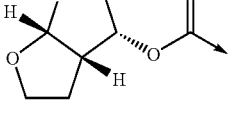 | H |

TABLE 1-continued
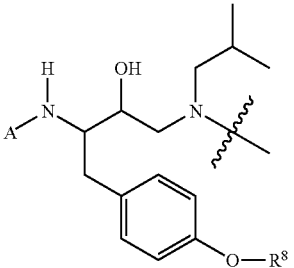
| | A | SO₂-E | R⁸ |
|---|---|---|---|
| 40 | 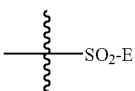 | 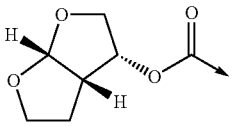 | 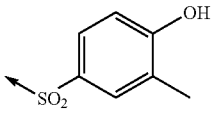 |
| 41 | 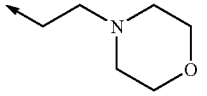 | 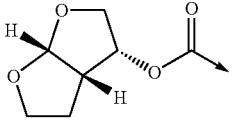 | 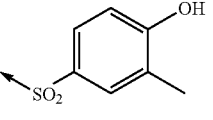 |
| 42 | 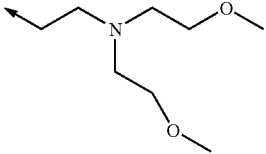 | 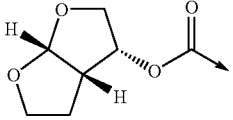 | 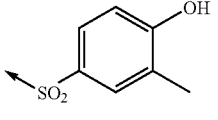 |
| 43 | 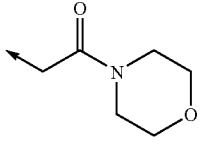 | 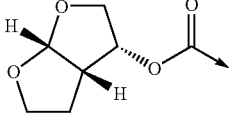 | 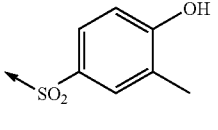 |
| 44 | 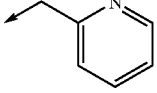 | 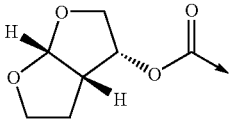 | 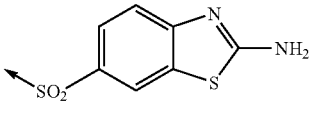 |
| 46 | 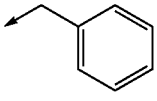 | 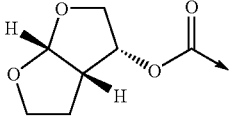 | 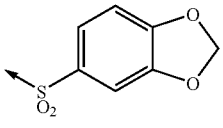 |
| 47 | 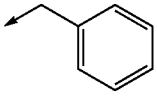 | 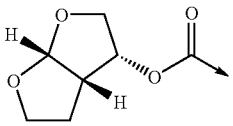 | H |
| 48 | 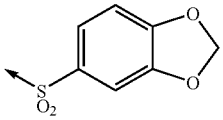 | 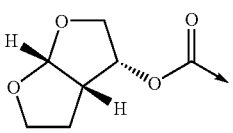 | 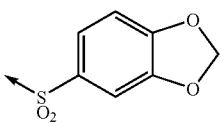 |

TABLE 1-continued
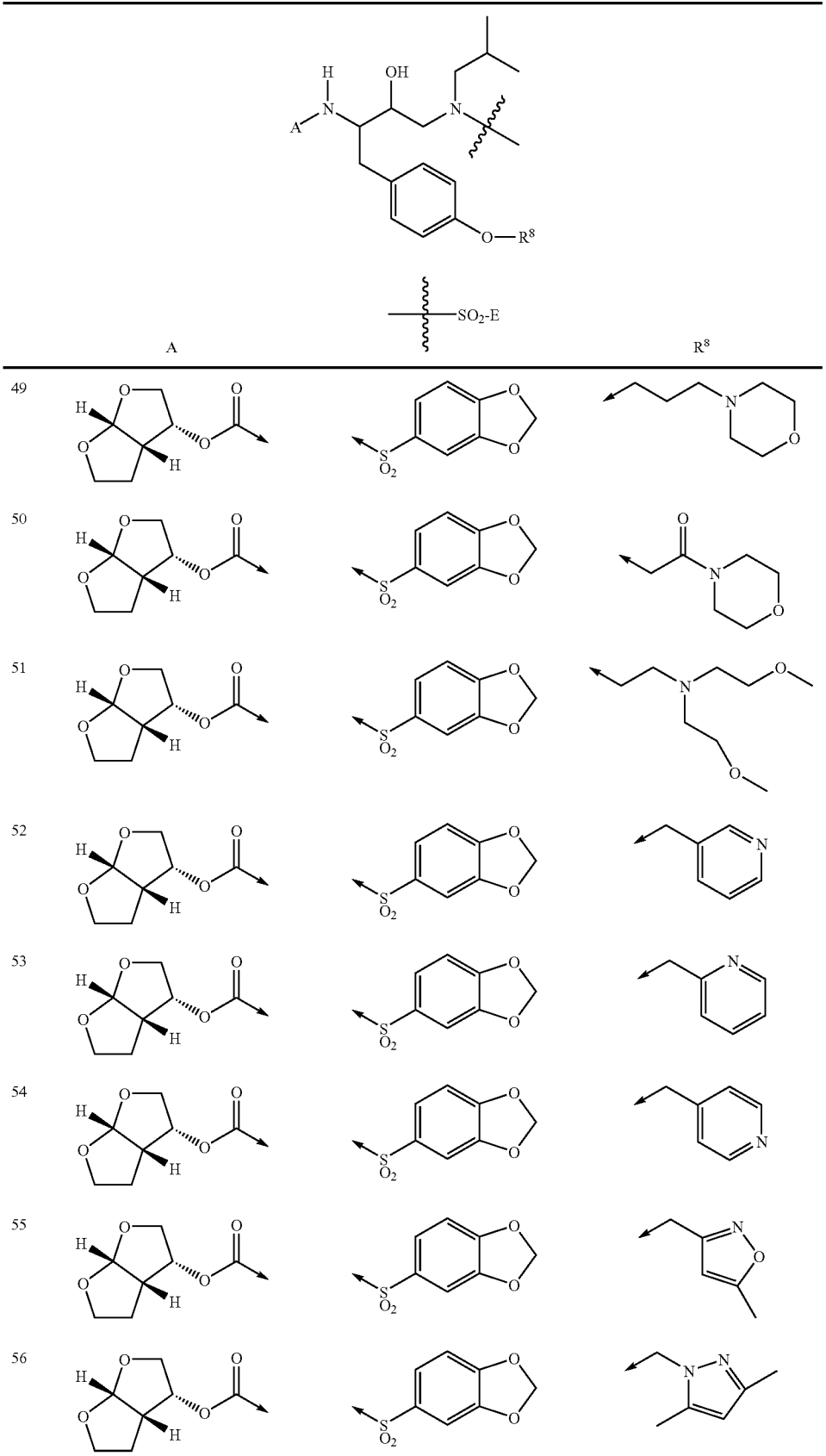

TABLE 1-continued
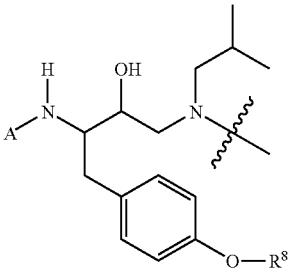
| | A | -SO$_2$-E | R$^8$ |
|---|---|---|---|
| 57 | 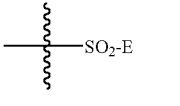 |  | 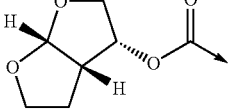 |
| 58 | 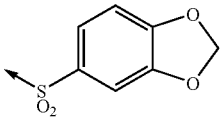 | 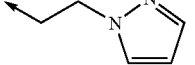 | 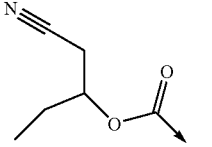 |
| 59 | 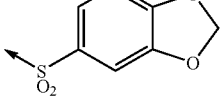 | 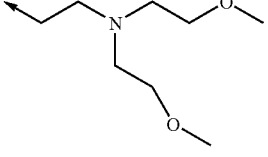 | 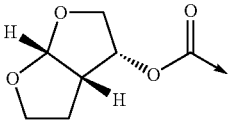 |
| 60 | 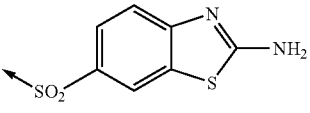 | 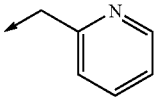 | 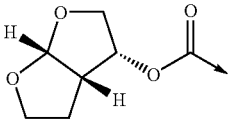 |
| 61 | 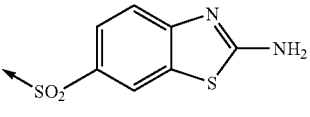 | 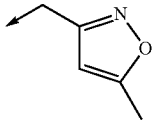 | 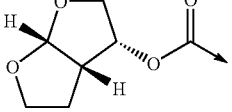 |
| 62 | 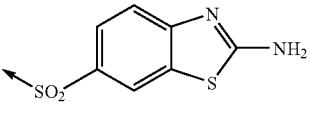 | 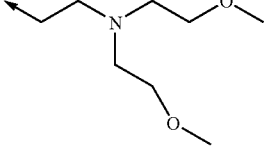 | 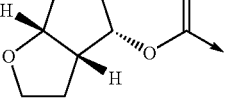 |
| 63 | 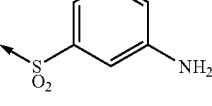 | 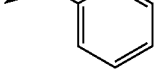 | 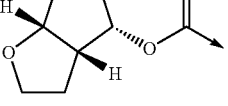 |

TABLE 2
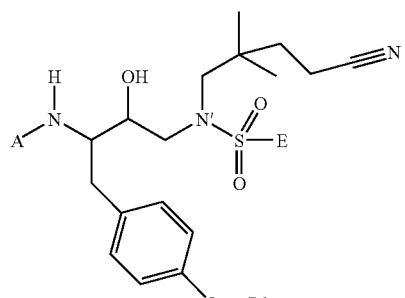
| | A | S(O)₂E | R⁸ |
|---|---|---|---|
| 67 | 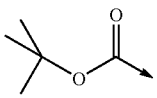 | 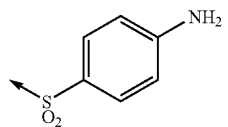 | 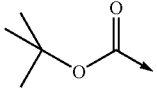 |
| 68 | 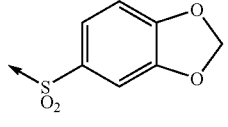 | 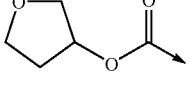 | 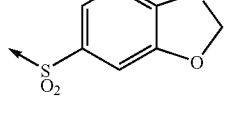 |
| 69 | 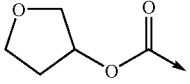 | 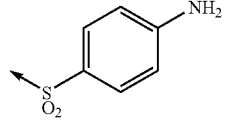 | 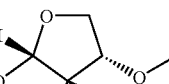 |
| 70 | 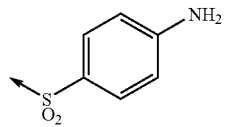 | 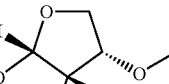 | 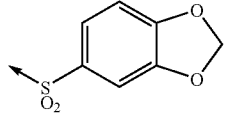 |
| 71 | 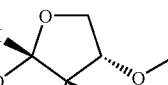 | 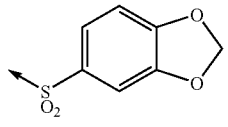 |  |
| 72 |  |  |  |
| 73 |  |  |  |

TABLE 2-continued

| | A | S(O)₂E | R⁸ |
|---|---|---|---|
| 74 | hexahydrofuro[2,3-b]furan-3-yl ester | 4-aminophenylsulfonyl | -CH₂CH₂-N(CH₂CH₂OCH₃)₂ |
| 75 | hexahydrofuro[2,3-b]furan-3-yl ester | 3-aminophenylsulfonyl | benzyl |

TABLE 3

| | A | R⁸ | D' | E |
|---|---|---|---|---|
| 201 | hexahydrofuro[2,3-b]furan-3-yl ester (isobutyryl) | —H | isobutyl | benzo[1,3]dioxol-5-yl |
| 202 | hexahydrofuro[2,3-b]furan-3-yl ester (isobutyryl) | 2-phenylethyl (gem-dimethyl) | isobutyl | benzo[1,3]dioxol-5-yl |
| 203 | hexahydrofuro[2,3-b]furan-3-yl ester (isobutyryl) | 3-phenylpropyl (gem-dimethyl) | isobutyl | benzo[1,3]dioxol-5-yl |

TABLE 3-continued
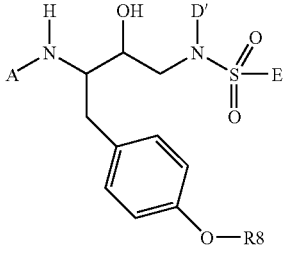
| | A | R⁸ | D' | E |
|---|---|---|---|---|
| 204 | 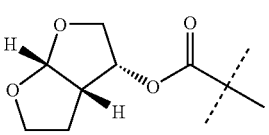 |  | 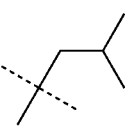 | 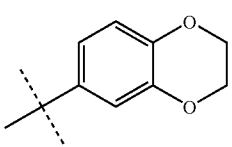 |
| 205 | 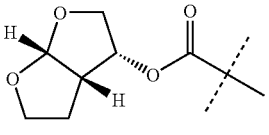 | 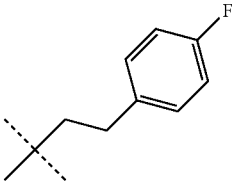 |  | 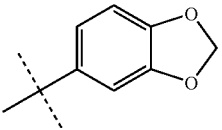 |
| 206 | 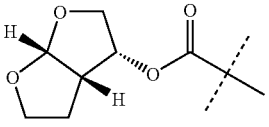 | 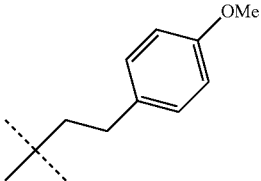 | 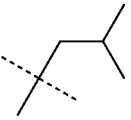 | 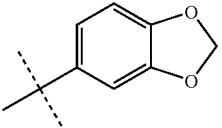 |
| 207 | 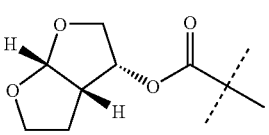 | 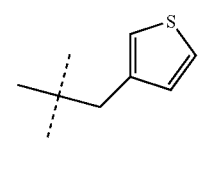 | 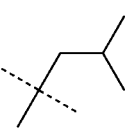 | 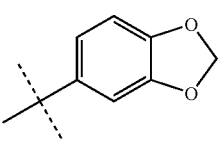 |
| 208 | 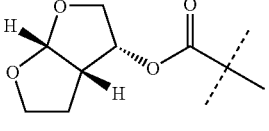 | 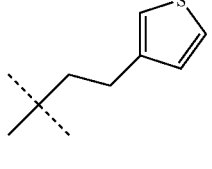 | 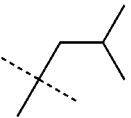 | 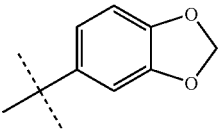 |
| 209 | 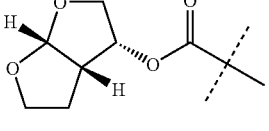 | 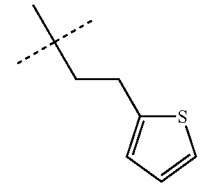 | 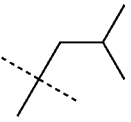 | 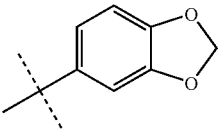 |
| 210 | 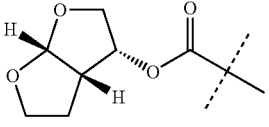 | 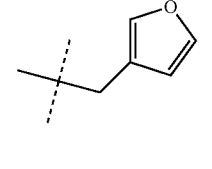 | 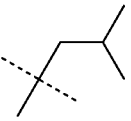 | 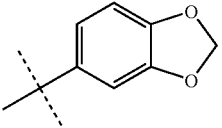 |

TABLE 3-continued

| | A | R8 | D' | E |
|---|---|---|---|---|
| 211 | hexahydrofuro[3,2-b]furan-3-yl ester | 2-(pyridin-4-yl)ethyl (gem-dimethyl) | isobutyl | benzo[1,3]dioxol-5-yl |
| 212 | hexahydrofuro[3,2-b]furan-3-yl ester | 2-(pyridin-2-yl)ethyl (gem-dimethyl) | isobutyl | benzo[1,3]dioxol-5-yl |
| 213 | hexahydrofuro[3,2-b]furan-3-yl ester | 2-(4-methylthiazol-5-yl)ethyl (gem-dimethyl) | isobutyl | benzo[1,3]dioxol-5-yl |
| 214 | hexahydrofuro[3,2-b]furan-3-yl ester | 2-(pyridin-3-yl)ethyl (gem-dimethyl) | isobutyl | benzo[1,3]dioxol-5-yl |
| 215 | hexahydrofuro[3,2-b]furan-3-yl ester | 2-(4-cyanophenyl)ethyl (gem-dimethyl) | isobutyl | benzo[1,3]dioxol-5-yl |
| 216 | hexahydrofuro[3,2-b]furan-3-yl ester | 4,4,4-trifluorobutyl (gem-dimethyl) | isobutyl | benzo[1,3]dioxol-5-yl |
| 217 | hexahydrofuro[3,2-b]furan-3-yl ester | 4,4,4-trifluorobutyl (gem-dimethyl) | isobutyl | benzo[1,3]dioxol-5-yl |

TABLE 3-continued

| | A | R⁸ | D' | E |
|---|---|---|---|---|
| 218 | hexahydrofuro[2,3-b]furan-3-yl ester | -CH₂C(CH₃)₂-C₆H₄-NH₂ | isobutyl | benzo[1,3]dioxol-5-yl |
| 219 | hexahydrofuro[2,3-b]furan-3-yl ester | -CH₂C(CH₃)₂CH₂-NHCOOt-bu | isobutyl | benzo[1,3]dioxol-5-yl |
| 220 | hexahydrofuro[2,3-b]furan-3-yl ester | -CH₂C(CH₃)₂CH₂-NH₂ | isobutyl | benzo[1,3]dioxol-5-yl |
| 221 | hexahydrofuro[2,3-b]furan-3-yl ester | -CH₂C(CH₃)₂CH₂CH₂-NHCOOt-bu | isobutyl | benzo[1,3]dioxol-5-yl |
| 222 | hexahydrofuro[2,3-b]furan-3-yl ester | -CH₂C(CH₃)₂CH₂CH₂-NH₂ | isobutyl | benzo[1,3]dioxol-5-yl |
| 223 | hexahydrofuro[2,3-b]furan-3-yl ester | -CH₂C(CH₃)₂CH₂CH₂CH₂-NHCOO-t-bu | isobutyl | benzo[1,3]dioxol-5-yl |
| 224 | hexahydrofuro[2,3-b]furan-3-yl ester | -CH₂C(CH₃)₂CH₂CH₂CH₂-NH₂ | isobutyl | benzo[1,3]dioxol-5-yl |
| 225 | hexahydrofuro[2,3-b]furan-3-yl ester | -CH₂C(CH₃)₂CH₂CH₂-NHAc | isobutyl | benzo[1,3]dioxol-5-yl |

TABLE 3-continued
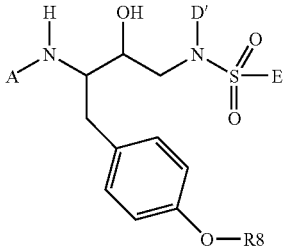
| | A | R⁸ | D' | E |
|---|---|---|---|---|
| 226 | 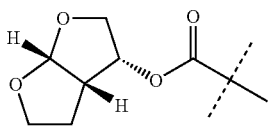 | 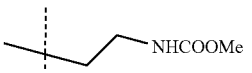—NHCOOMe | 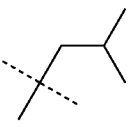 | 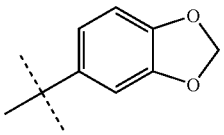 |
| 227 | 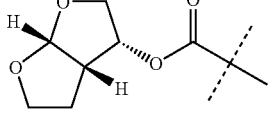 | 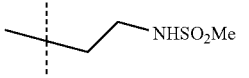—NHSO₂Me | 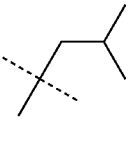 | 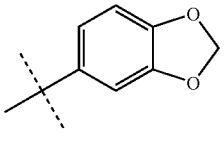 |
| 228 | 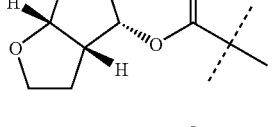 | 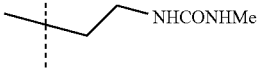—NHCONHMe | 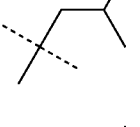 | 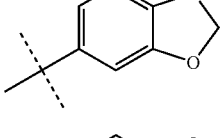 |
| 229 | 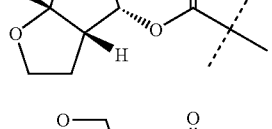 | NHAc |  | 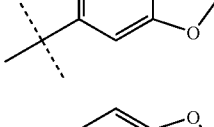 |
| 230 | 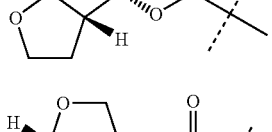 | NHAc |  | 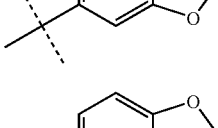 |
| 231 | 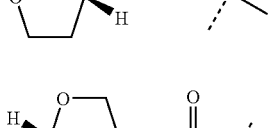 | 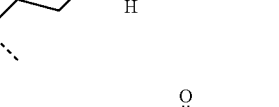 |  | 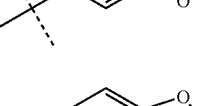 |
| 232 | 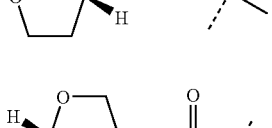 | 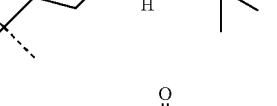 |  | 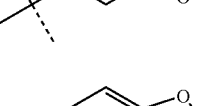 |
| 233 | 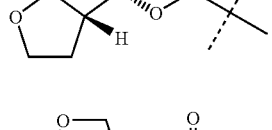 | 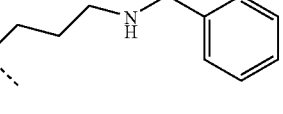 |  | 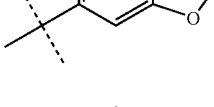 |
| 234 | 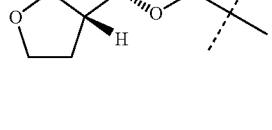 | 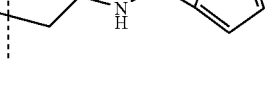 |  | 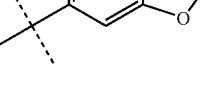 |

TABLE 3-continued
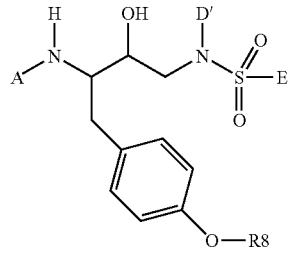
| | A | R⁸ | D' | E |
|---|---|---|---|---|
| 235 | 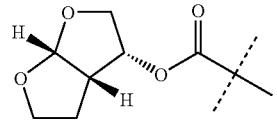 | 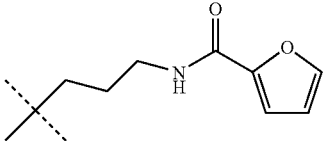 | 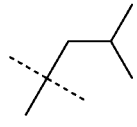 | 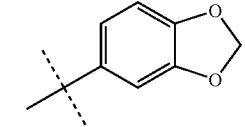 |
| 236 | 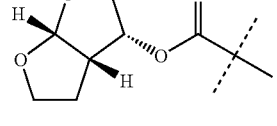 | 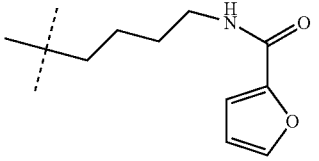 | 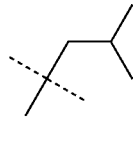 | 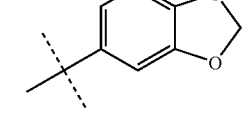 |
| 237 | 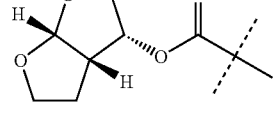 | 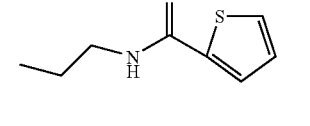 | 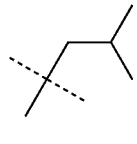 | 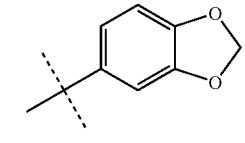 |
| 238 | 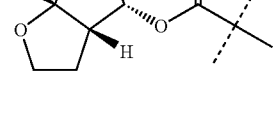 | 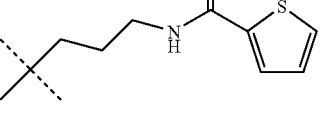 | 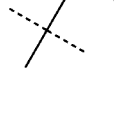 | 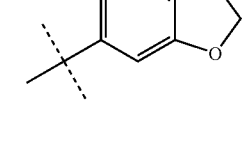 |
| 239 | 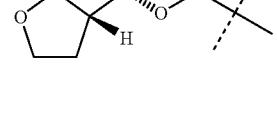 |  | 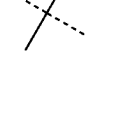 | 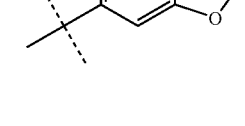 |
| 240 | 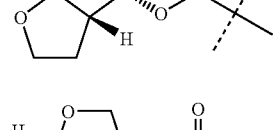 | 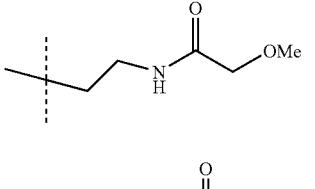 | 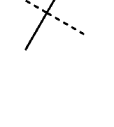 | 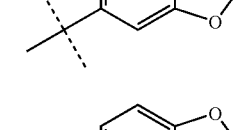 |
| 241 | 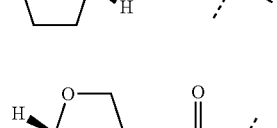 | 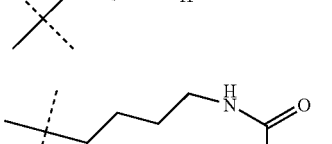 |  | 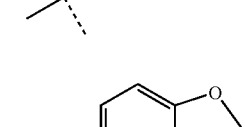 |
| 242 | 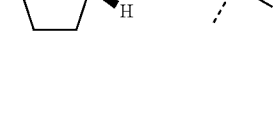 |  | 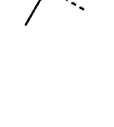 |  |

TABLE 3-continued

| | A | R⁸ | D' | E |
|---|---|---|---|---|
| 243 | hexahydrofuro[2,3-b]furan-3-yl pivalate | -CH₂C(CH₃)₂CH₂NHC(O)OMe | isobutyl | benzo[1,3]dioxol-5-yl |
| 244 | hexahydrofuro[2,3-b]furan-3-yl pivalate | -CH₂C(CH₃)₂CH₂CH₂NHC(O)OMe | isobutyl | benzo[1,3]dioxol-5-yl |
| 245 | hexahydrofuro[2,3-b]furan-3-yl pivalate | -CH₂C(CH₃)₂CH₂NHC(O)OEt | isobutyl | benzo[1,3]dioxol-5-yl |
| 246 | hexahydrofuro[2,3-b]furan-3-yl pivalate | -CH₂C(CH₃)₂CH₂CH₂NHC(O)OEt | isobutyl | benzo[1,3]dioxol-5-yl |
| 247 | hexahydrofuro[2,3-b]furan-3-yl pivalate | -CH₂C(CH₃)₂CH₂CH₂CH₂NHC(O)OEt | isobutyl | benzo[1,3]dioxol-5-yl |
| 248 | hexahydrofuro[2,3-b]furan-3-yl pivalate | -CH₂C(CH₃)₂CH₂NHC(O)O-i-Pr | isobutyl | benzo[1,3]dioxol-5-yl |
| 249 | hexahydrofuro[2,3-b]furan-3-yl pivalate | -CH₂C(CH₃)₂CH₂CH₂NHC(O)O-i-Pr | isobutyl | benzo[1,3]dioxol-5-yl |
| 250 | hexahydrofuro[2,3-b]furan-3-yl pivalate | -CH₂C(CH₃)₂CH₂CH₂CH₂NHC(O)O-i-Pr | isobutyl | benzo[1,3]dioxol-5-yl |

TABLE 3-continued

| | A | R8 | D' | E |
|---|---|---|---|---|
| 251 | hexahydrofuro[3,2-b]furanyl ester | CH2CH2NHSO2Me (branched) | isobutyl | benzo[1,3]dioxole |
| 252 | hexahydrofuro[3,2-b]furanyl ester | (CH2)3NHSO2Me | isobutyl | benzo[1,3]dioxole |
| 253 | hexahydrofuro[3,2-b]furanyl ester | CH2CH2NHCONMe2 (branched) | isobutyl | benzo[1,3]dioxole |
| 254 | hexahydrofuro[3,2-b]furanyl ester | (CH2)3NHCONMe2 | isobutyl | benzo[1,3]dioxole |
| 255 | hexahydrofuro[3,2-b]furanyl ester | (CH2)4NHCONMe2 | isobutyl | benzo[1,3]dioxole |
| 256 | hexahydrofuro[3,2-b]furanyl ester | (CH2)3NHCONHMe | isobutyl | benzo[1,3]dioxole |
| 257 | hexahydrofuro[3,2-b]furanyl ester | (CH2)4NHCONHMe | isobutyl | benzo[1,3]dioxole |
| 258 | hexahydrofuro[3,2-b]furanyl ester | CH2CH2NHCSNHMe (branched) | isobutyl | benzo[1,3]dioxole |
| 259 | hexahydrofuro[3,2-b]furanyl ester | (CH2)3NHCSNHMe | isobutyl | benzo[1,3]dioxole |

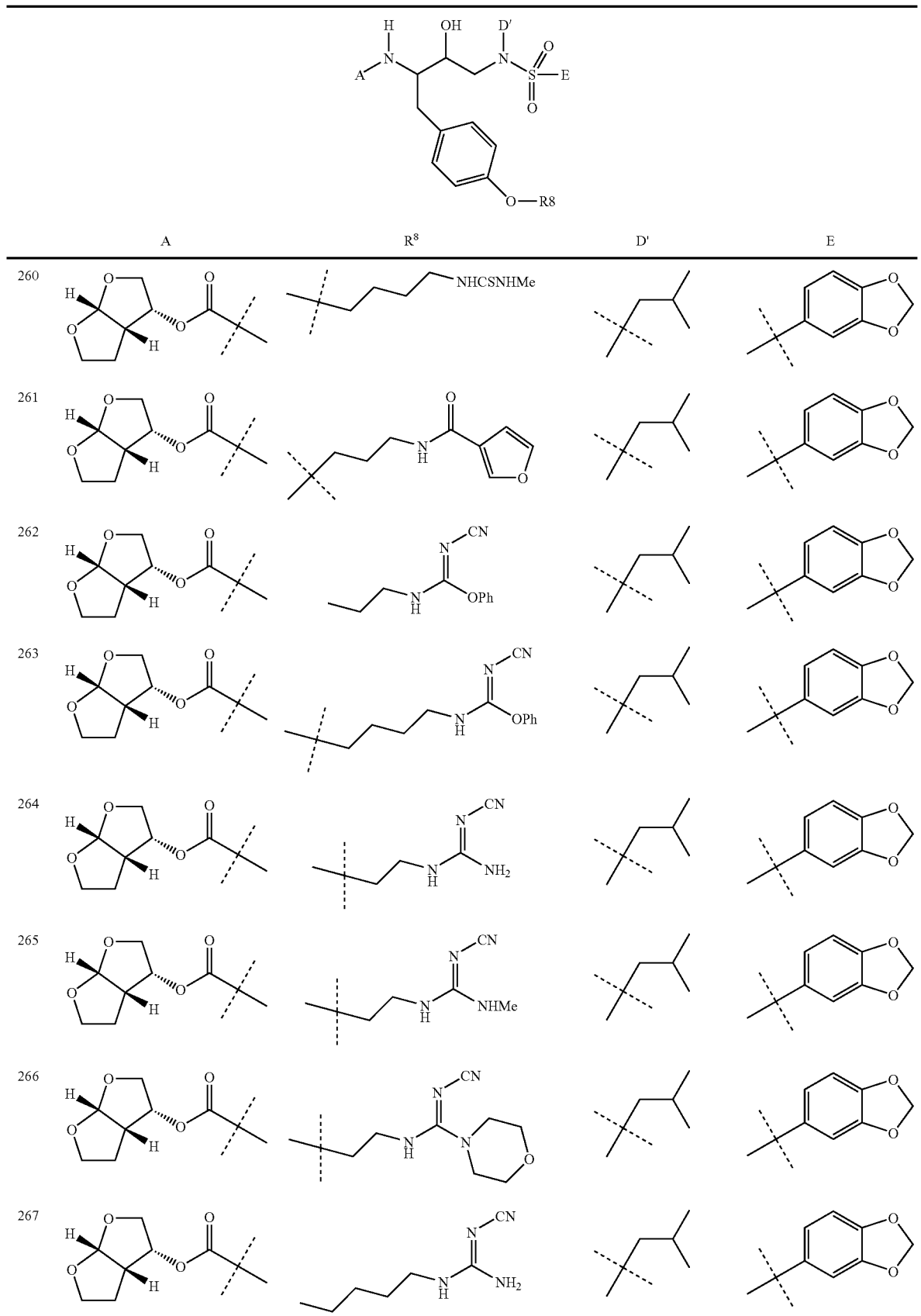

US 8,455,497 B2

TABLE 3-continued

| | A | R⁸ | D' | E |
|---|---|---|---|---|
| 268 | | | | |
| 269 | | | | |
| 270 | | | | |
| 271 | | | | |
| 272 | | | | |
| 273 | | | | |
| 274 | | | | |
| 275 | | | | |
| 276 | | | | |

TABLE 3-continued
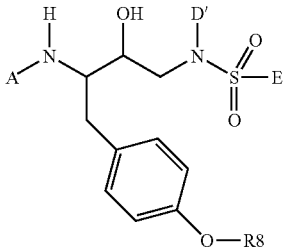
| | A | R⁸ | D' | E |
|---|---|---|---|---|
| 277 | 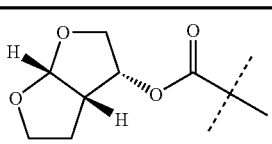 | 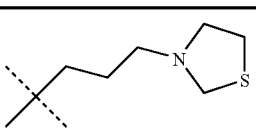 |  | 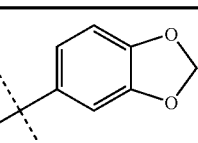 |
| 278 | 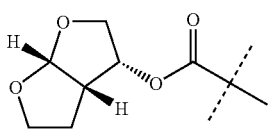 | 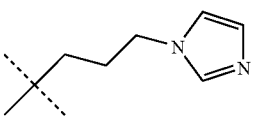 | 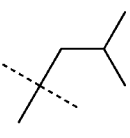 | 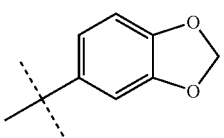 |
| 279 | 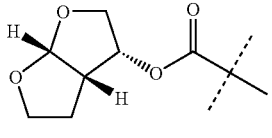 | 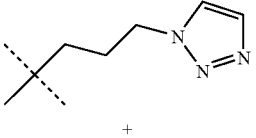  +  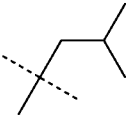 | 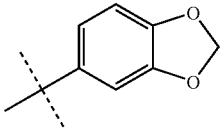 | 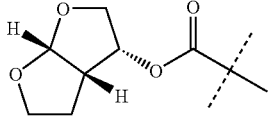 |
| 280 | 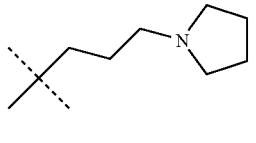 | 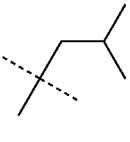 | 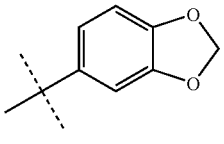 | 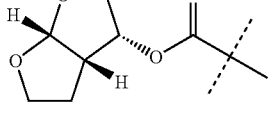 |
| 281 | 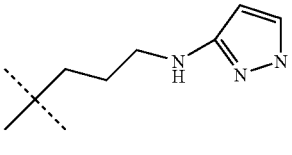 | 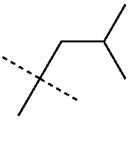 | 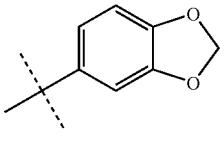 | 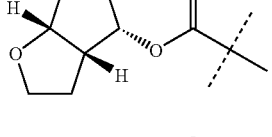 |
| 282 | 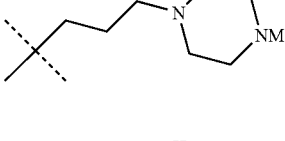 | 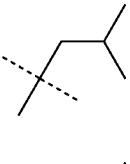 | 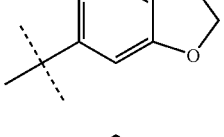 | 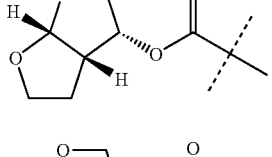 |
| 283 |  | 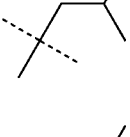 | 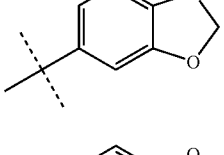 | 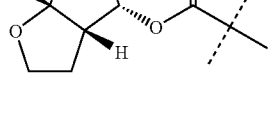 |
| 284 | 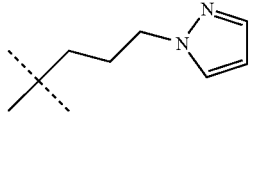 | 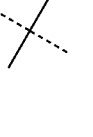 | | 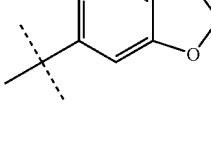 |

TABLE 3-continued

| | A | R⁸ | D' | E |
|---|---|---|---|---|
| 285 | hexahydrofuro[3,2-b]furan-3-yl pivalate | -(CH₂)₅-CONH₂ | isobutyl | benzo[1,3]dioxol-5-yl |
| 286 | hexahydrofuro[3,2-b]furan-3-yl pivalate | -(CH₂)₅-CONHMe | isobutyl | benzo[1,3]dioxol-5-yl |
| 287 | hexahydrofuro[3,2-b]furan-3-yl pivalate | -(CH₂)₅-CONMe₂ | isobutyl | benzo[1,3]dioxol-5-yl |
| 288 | hexahydrofuro[3,2-b]furan-3-yl pivalate | -(CH₂)₅-CONHBu | isobutyl | benzo[1,3]dioxol-5-yl |
| 289 | hexahydrofuro[3,2-b]furan-3-yl pivalate | -CH₂-(3-cyanophenyl) | isobutyl | 3-aminophenyl |
| 290 | hexahydrofuro[3,2-b]furan-3-yl pivalate | -CH₂-phenyl | isobutyl | 3-aminophenyl |
| 291 | hexahydrofuro[3,2-b]furan-3-yl pivalate | H | isobutyl | 3-aminophenyl |
| 292 | hexahydrofuro[3,2-b]furan-3-yl pivalate | -(CH₂)₄-NH₂ | isobutyl | 3-aminophenyl |
| 293 | hexahydrofuro[3,2-b]furan-3-yl pivalate | -CH₂-(pyridin-2-yl) | isobutyl | 3-aminophenyl |

TABLE 3-continued
| | A | R⁸ | D' | E |
|---|---|---|---|---|
| 294 | 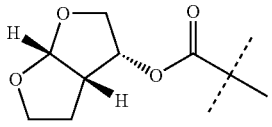 | 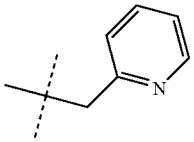 | 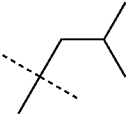 | 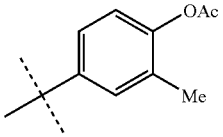 |
| 295 | 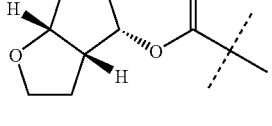 | 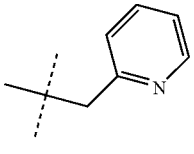 | 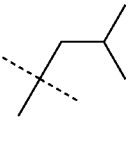 | 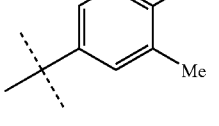 |
| 296 | 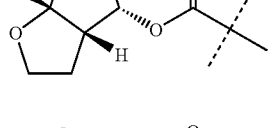 | 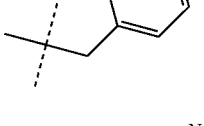 |  | 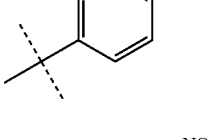 |
| 297 | 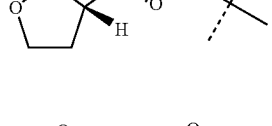 | 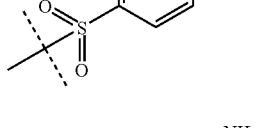 |  | 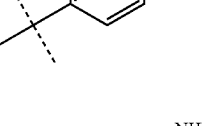 |
| 298 | 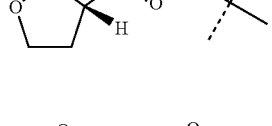 | 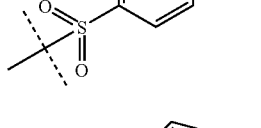 |  | 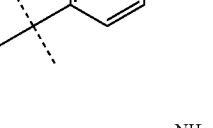 |
| 299 | 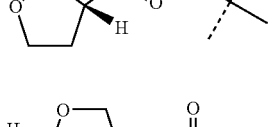 | 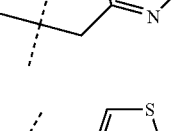 |  | 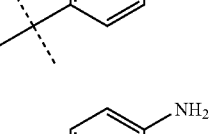 |
| 300 | 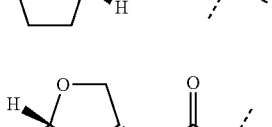 | 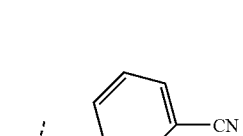 | 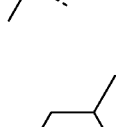 | 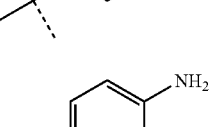 |
| 301 |  |  |  |  |

TABLE 3-continued

| | A | R⁸ | D' | E |
|---|---|---|---|---|
| 302 | bicyclic furan-furan ester | 3-cyanobenzyl | isobutyl | 4-(N-hydroxyamino)phenyl |
| 303 | bicyclic furan-furan ester | –CH₂C(CH₃)₂CH₂CH₂COOMe | isobutyl | benzo[1,3]dioxole-5-yl |
| 304 | bicyclic furan-furan ester | –CH₂C(CH₃)₂CF₃ | isobutyl | benzo[1,3]dioxole-5-yl |
| 305 | bicyclic furan-furan ester | benzyl | –C(CH₃)₂CH₂CH₂CN | benzo[1,3]dioxole-5-yl |
| 306 | 1,3-dioxan-5-yl ester | benzyl | –C(CH₃)₂CH₂CH₂CN | benzo[1,3]dioxole-5-yl |
| 307 | tetrahydrofuran-3-yl ester | benzyl | –C(CH₃)₂CH₂CH₂CN | benzo[1,3]dioxole-5-yl |
| 308 | bicyclic furan-pyran ester | benzyl | isobutyl | 2,3-dihydro-benzo[1,4]dioxin-6-yl |
| 309 | bicyclic furan-furan ester | —CONHMe | isobutyl | benzo[1,3]dioxole-5-yl |

TABLE 3-continued
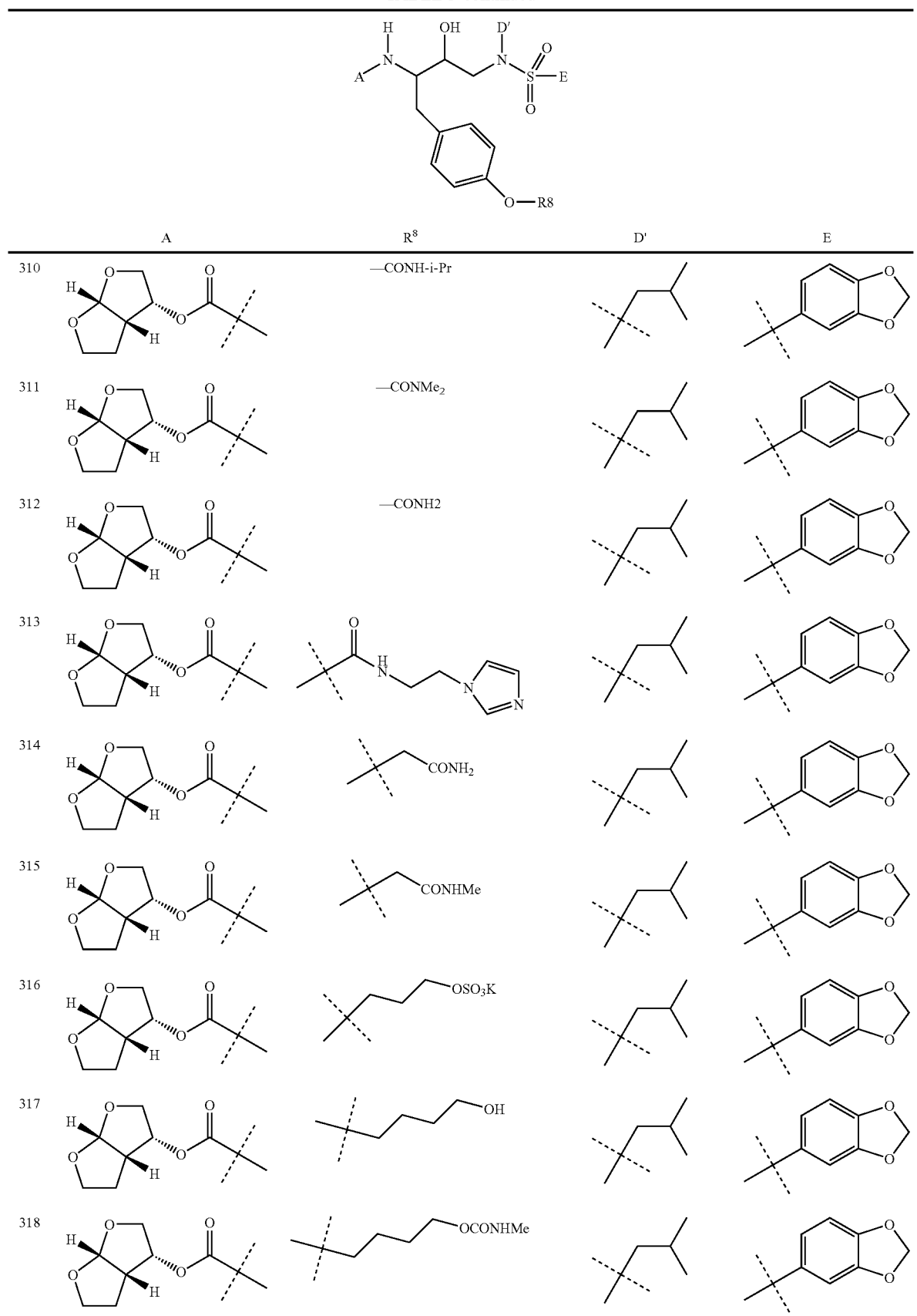

TABLE 3-continued
| | A | R8 | D' | E |
|---|---|---|---|---|
| 319 | 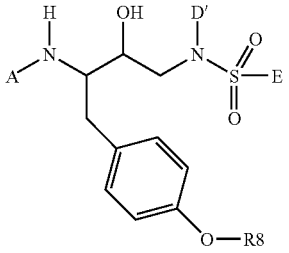 | 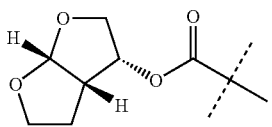 OH | 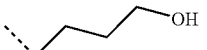 | 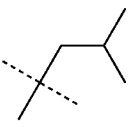 |
| 320 | 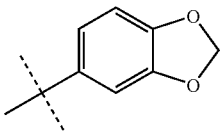 | 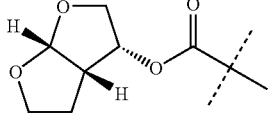 OCONHMe | 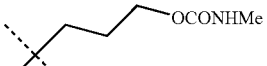 | 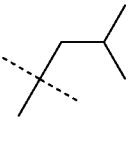 |
| 321 | 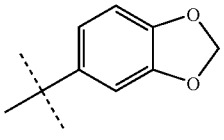 | 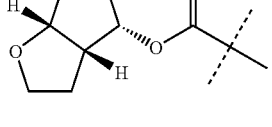 OCONH2 | 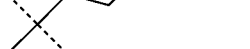 | 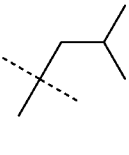 |
| 322 | 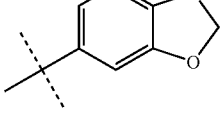 | 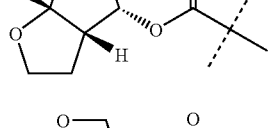 OH | 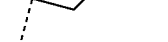 |  |
| 323 | 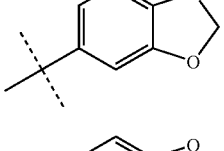 | 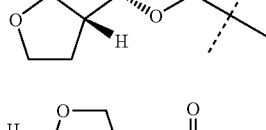 OCONHMe |  |  |
| 324 | 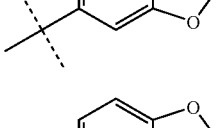 | 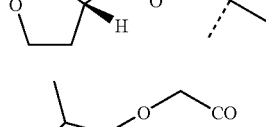 |  |  |
| 325 | 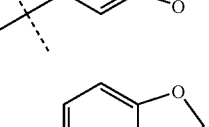 | 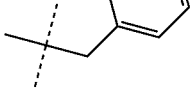 |  | 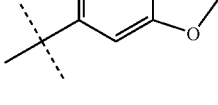 |
| 326 | 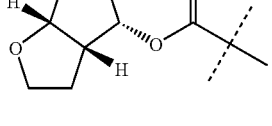 | 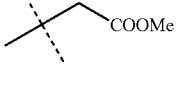 COOMe | 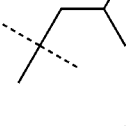 | 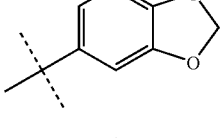 |
| 327 | 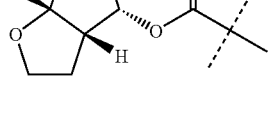 | 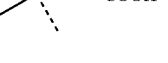 COOH |  | 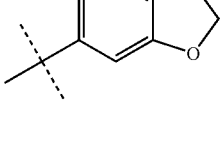 |

TABLE 3-continued
| | A | R⁸ | D' | E |
|---|---|---|---|---|
| 328 | 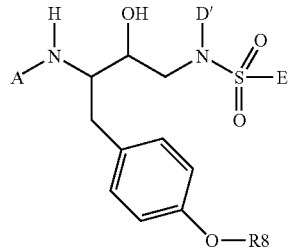 | 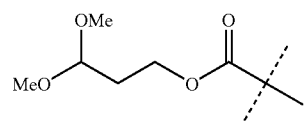 | 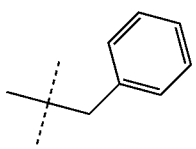 | 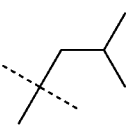 |
| 329 | 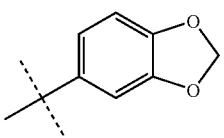 | 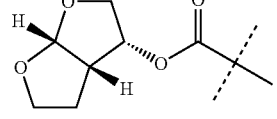 | 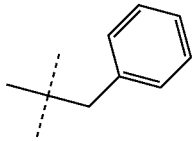 | 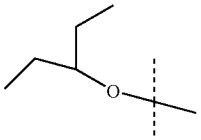 |
| 330 | 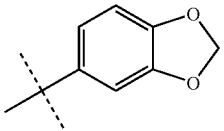 | 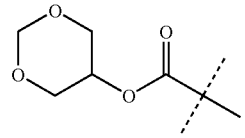 | 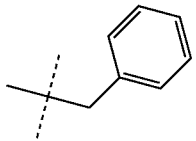 | 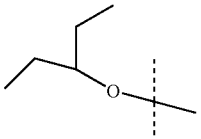 |
| 331 | 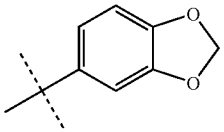 | 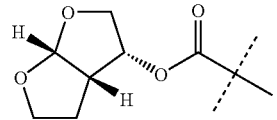 | 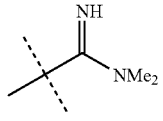 | 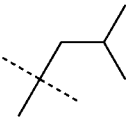 |
| 332 | 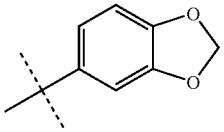 | 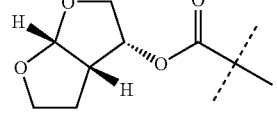 | 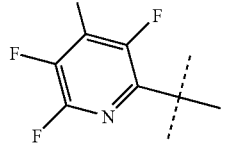 | 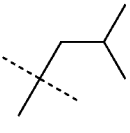 |
| 333 | 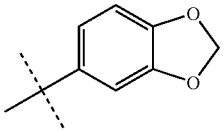 | 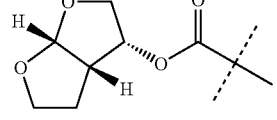 | 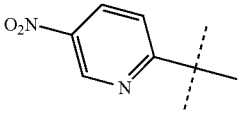 | 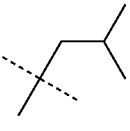 |
| 334 | 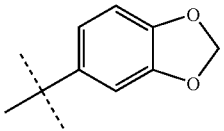 | 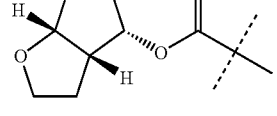 | 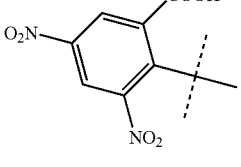 | 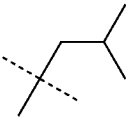 |
| 335 | 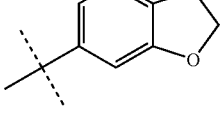 | 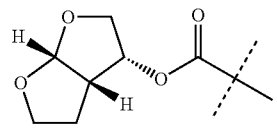 | 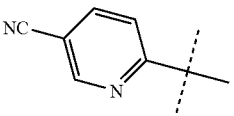 | 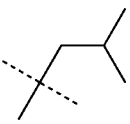 |

TABLE 3-continued
| | A | R⁸ | D' | E |
|---|---|---|---|---|
| 336 | 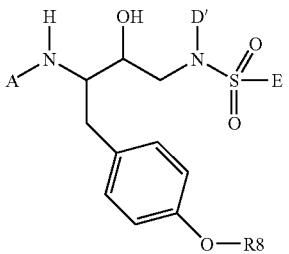 | 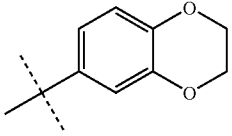 | 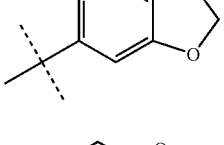 | 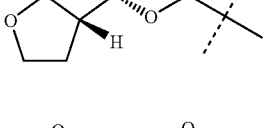 |
| 337 | 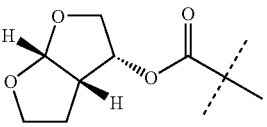 | 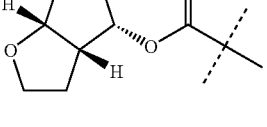 | 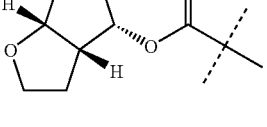 | 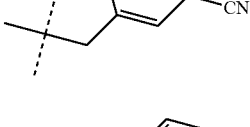 |
| 338 | 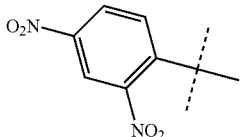 | 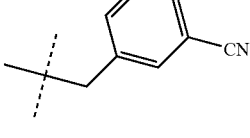 | 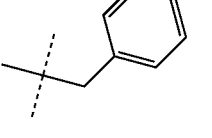 |  |
| 339 | 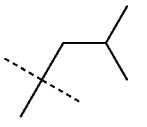 | 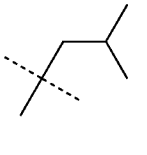 | 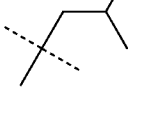 | 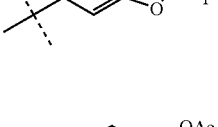 |
| 340 | 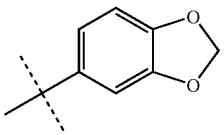 | 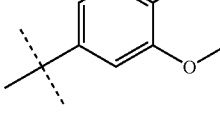 | 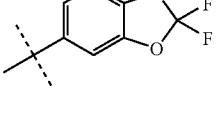 | 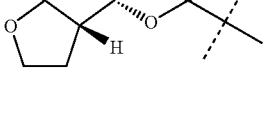 |
| 341 | 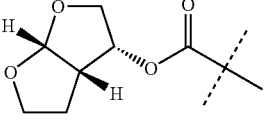 | H | 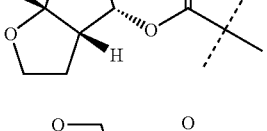 | 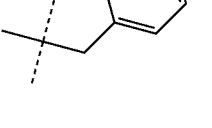 |
| 342 | 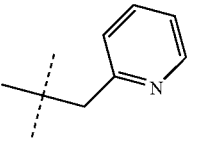 | 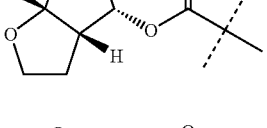 | 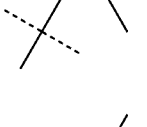 | 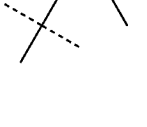 |
| 343 | 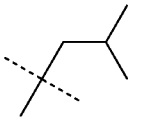 |  | 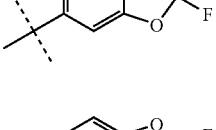 | 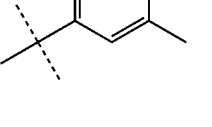 |

TABLE 3-continued

| | A | R⁸ | D' | E |
|---|---|---|---|---|
| 344 | hexahydrofuro[3,2-b]furan-3-yl pivaloyl | benzyl | neopentyl | 4-tert-butyl-2-methylphenol |
| 345 | hexahydrofuro[3,2-b]furan-3-yl pivaloyl | H | neopentyl | 4-tert-butyl-2-methylphenyl OAc |
| 346 | hexahydrofuro[3,2-b]furan-3-yl pivaloyl | 3-cyanobenzyl | neopentyl | 4-tert-butyl-2-methylphenol |
| 347 | hexahydrofuro[3,2-b]furan-3-yl pivaloyl | (2-methylthiazol-4-yl)methyl | neopentyl | 4-tert-butyl-2-methylphenyl OAc |
| 348 | hexahydrofuro[3,2-b]furan-3-yl pivaloyl | (2-methylthiazol-4-yl)methyl | neopentyl | 4-tert-butyl-2-methylphenol |
| 349 | hexahydrofuro[3,2-b]furan-3-yl pivaloyl | benzo[d][1,3]dioxol-5-ylsulfonyl | neopentyl | benzo[d][1,3]dioxol-5-yl |
| 350 | 2-(2,6-dimethylphenoxy)acetyl | benzo[d][1,3]dioxol-5-ylsulfonyl | neopentyl | benzo[d][1,3]dioxol-5-yl |
| 351 | hexahydrofuro[3,2-b]furan-3-yl pivaloyl | H | neopentyl | benzo[d][1,3]dioxol-5-yl |

TABLE 3-continued
| | A | R8 | D' | E |
|---|---|---|---|---|
| 352 | 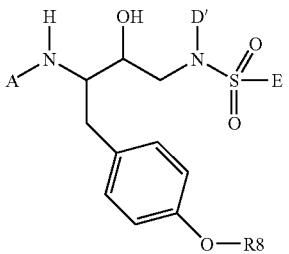 | 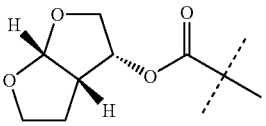 | 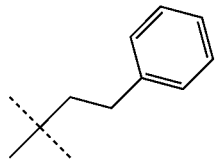 | 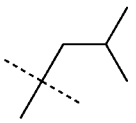 |
| 353 | 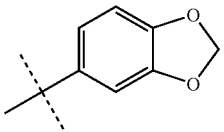 | 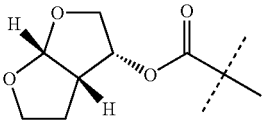 | 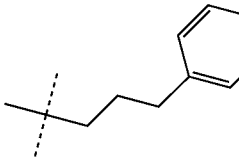 | 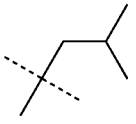 |
| 354 | 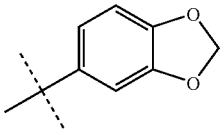 | 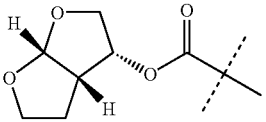 | 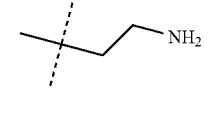 | 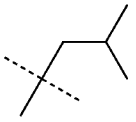 |
| 355 | 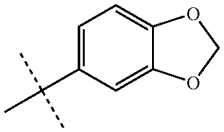 | 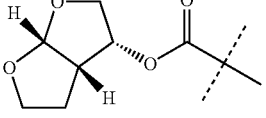 | 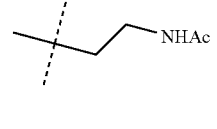 | 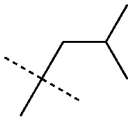 |
| 356 | 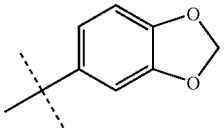 | 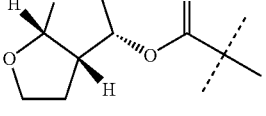 | 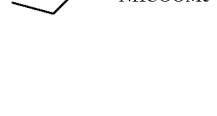 | 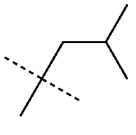 |
| 357 | 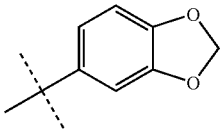 | 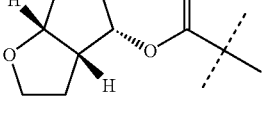 | 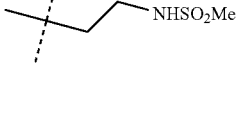 | 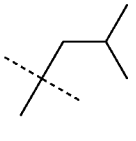 |
| 358 | 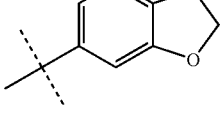 | 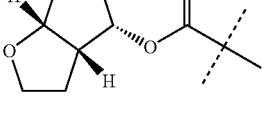 | 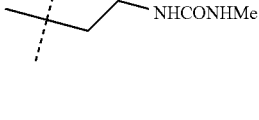 | 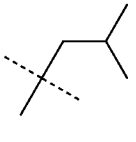 |
| 359 | 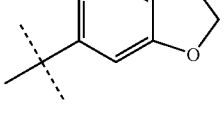 | 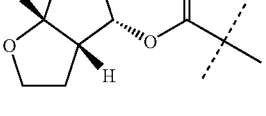 |  | 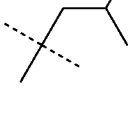 |

TABLE 3-continued

TABLE 3-continued

| | A | R⁸ | D' | E |
|---|---|---|---|---|
| 369 | hexahydrofuro[3,2-b]furan-3-yl pivalate | 4-(SMe)phenylmethyl | 3,3-dimethylbutyl | benzo[d][1,3]dioxol-5-yl |
| 370 | hexahydrofuro[3,2-b]furan-3-yl pivalate | 5-tert-butyl-1,2,4-oxadiazol-3-yl-methyl | 3,3-dimethylbutyl | benzo[d][1,3]dioxol-5-yl |
| 371 | hexahydrofuro[3,2-b]furan-3-yl pivalate | 4-F-phenylmethyl | 3,3-dimethylbutyl | benzo[d][1,3]dioxol-5-yl |
| 372 | hexahydrofuro[3,2-b]furan-3-yl pivalate | 4-CF₃-phenylethyl | 3,3-dimethylbutyl | benzo[d][1,3]dioxol-5-yl |
| 373 | hexahydrofuro[3,2-b]furan-3-yl pivalate | 3-CF₃-phenylmethyl | 3,3-dimethylbutyl | benzo[d][1,3]dioxol-5-yl |
| 374 | hexahydrofuro[3,2-b]furan-3-yl pivalate | 4-(1,2,3-thiadiazol-4-yl)phenylmethyl | 3,3-dimethylbutyl | benzo[d][1,3]dioxol-5-yl |
| 375 | hexahydrofuro[3,2-b]furan-3-yl pivalate | 5-phenyl-1,2,4-oxadiazol-3-yl-methyl | 3,3-dimethylbutyl | benzo[d][1,3]dioxol-5-yl |
| 376 | hexahydrofuro[3,2-b]furan-3-yl pivalate | naphthalen-2-ylmethyl | 3,3-dimethylbutyl | benzo[d][1,3]dioxol-5-yl |

TABLE 3-continued
| | A | R⁸ | D' | E |
|---|---|---|---|---|
| 377 | 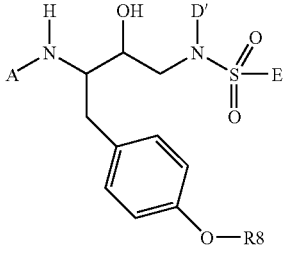 | 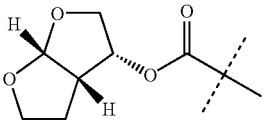 | 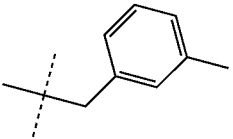 | 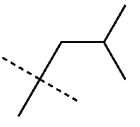 |
| 378 | 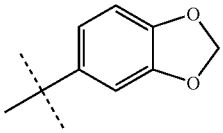 | 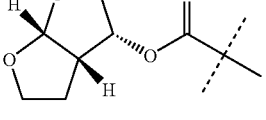 | 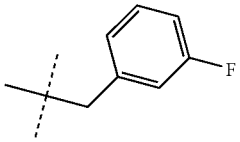 | 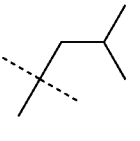 |
| 379 | 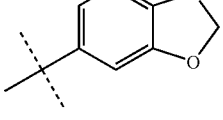 | 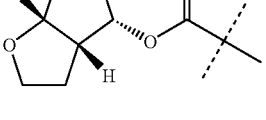 | 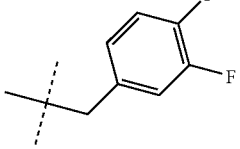 | 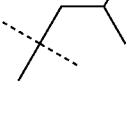 |
| 380 | 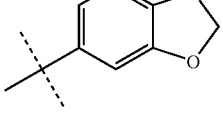 | 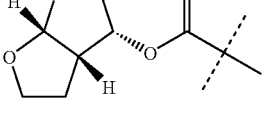 | 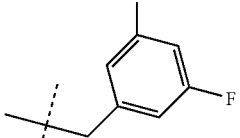 | 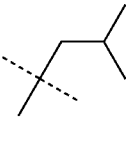 |
| 381 | 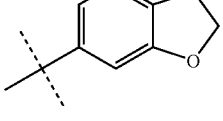 | 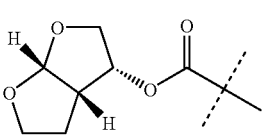 | 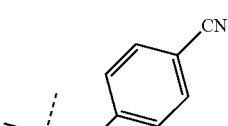 | 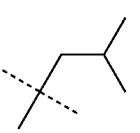 |
| 382 | 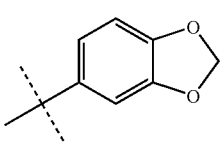 | 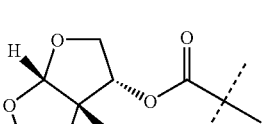 | 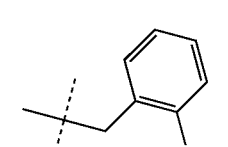 | 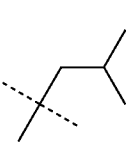 |
| 383 | 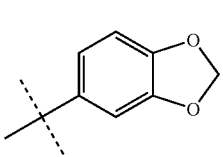 | 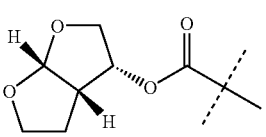 | 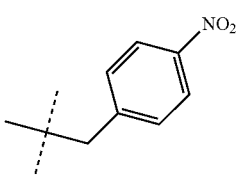 | 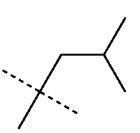 |

TABLE 3-continued
| | A | R⁸ | D' | E |
|---|---|---|---|---|
| 384 | 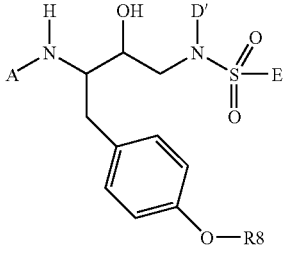 | 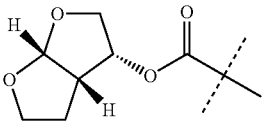 | 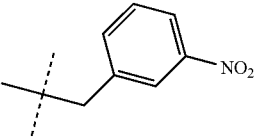 | 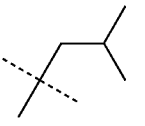 |
| 385 | 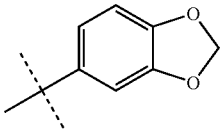 | 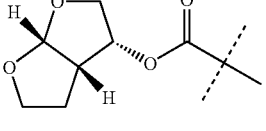 | 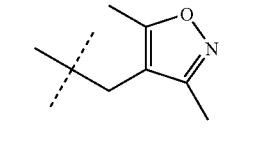 | 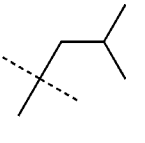 |
| 386 | 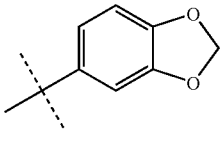 | 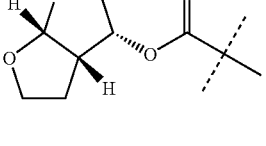 | 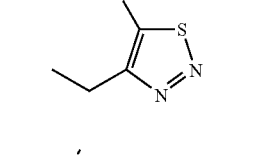 | 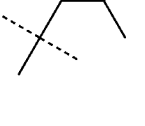 |
| 387 | 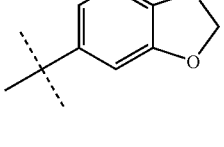 | 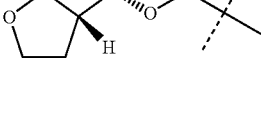 | 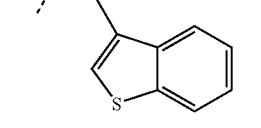 |  |
| 388 | 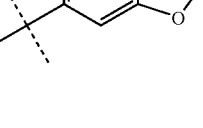 | 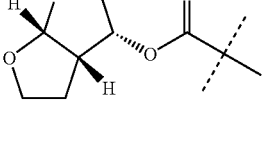 | 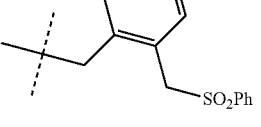 | 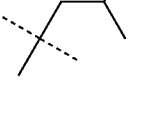 |
| 389 | 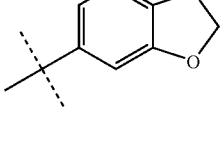 | 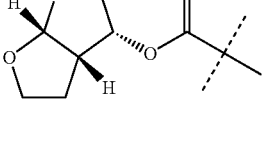 | 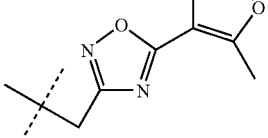 | 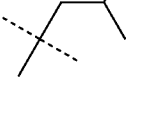 |
| 390 | 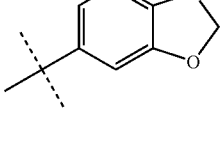 | 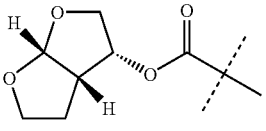 | 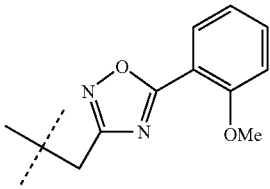 | 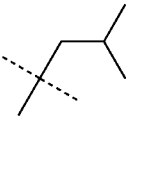 |

TABLE 3-continued
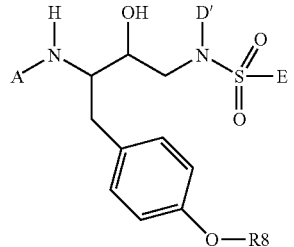
| | A | R⁸ | D' | E |
|---|---|---|---|---|
| 391 | 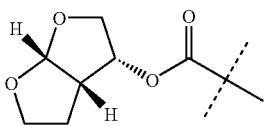 | 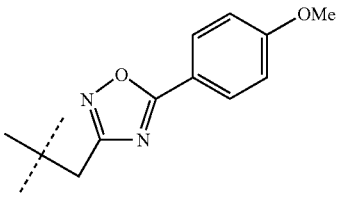 | 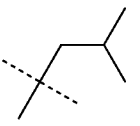 | 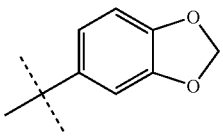 |
| 392 | 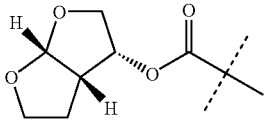 | 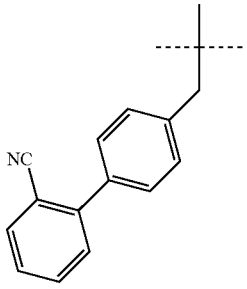 | 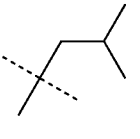 | 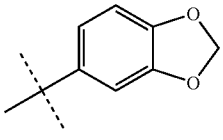 |
| 393 | 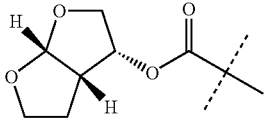 | 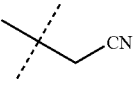 | 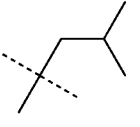 | 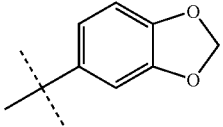 |
| 394 | 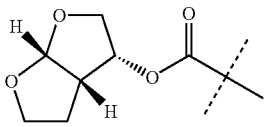 | 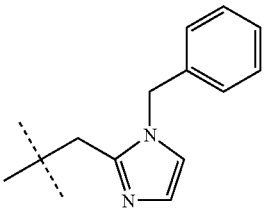 | 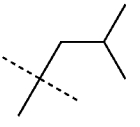 | 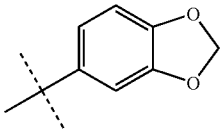 |
| 395 | 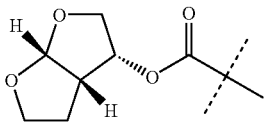 | 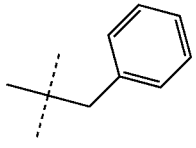 | 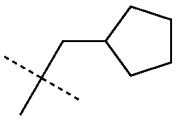 | 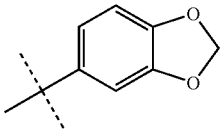 |
| 396 | 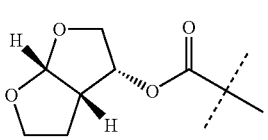 | 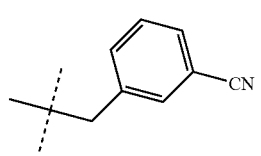 | 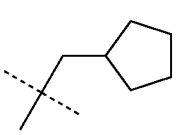 | 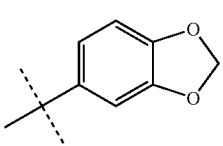 |

TABLE 3-continued

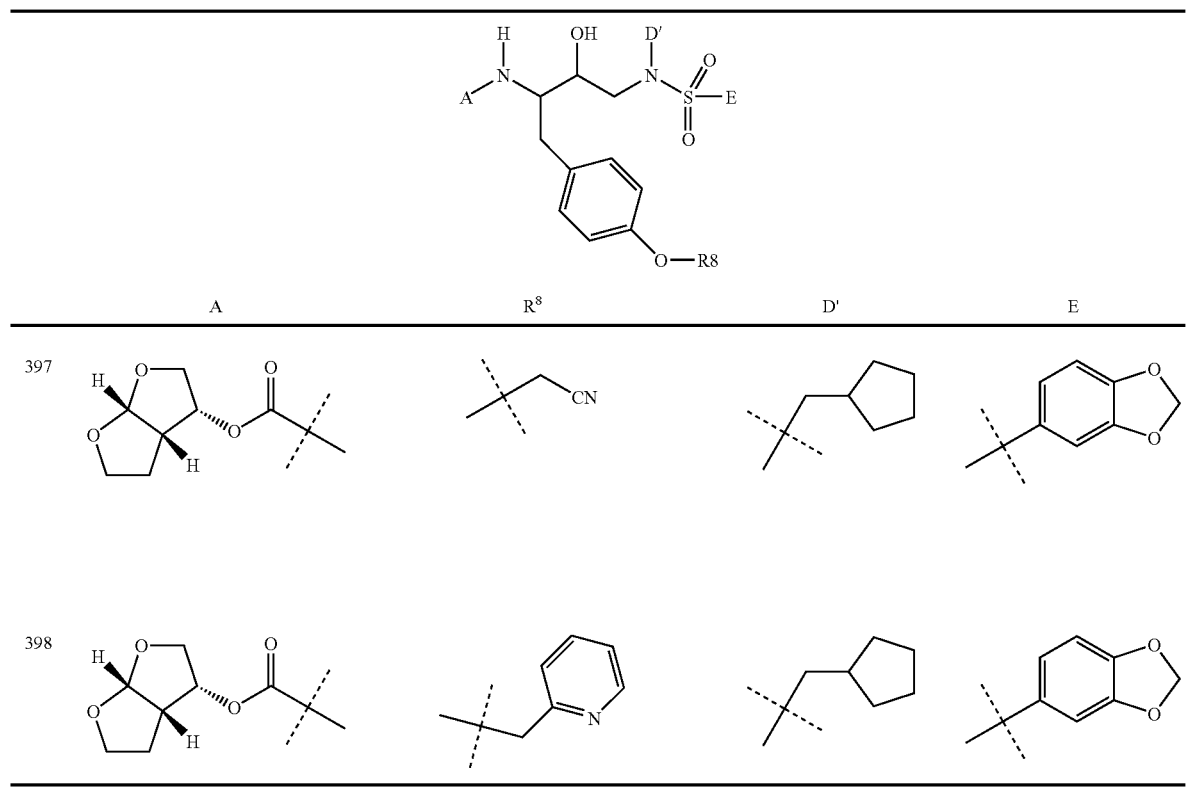

| A | R⁸ | D' | E |
|---|----|----|---|
| 397 | | | |
| 398 | | | |

Preferred compound of the present invention are compound numbers: 18, 19, 20, 22, 24, 25, 26, 27, 31, 33, 35, 36, 38, 41, 43, 48, 49, 51, 52, 53, 54, 55, 56, 57, 58, 59, 60, 68, 69, 71, 72, 73, 74, 202-204, 209, 213, 215, 217, 223, 227, 231, 233, 236, 237, 239, 243, 247, 250, 260, 263, 271, 281, 289, 293, 295, 304, 309, 317, 319, 320, 322, 334, 335, 348, 364, 367, 368, 375, 382, 383 and 396.

More preferred are compound numbers: 26, 27, 31, 33, 35, 36, 38, 41, 43, 48, 49, 51, 52, 53, 54, 55, 56, 57, 58, 59, 60, 69, 71, 72, 73, 74, 209, 215, 227, 233, 237, 281, 289, 295, 304, 309, 322, 335, 364, 368, 382 and 383.

Most preferred are compound numbers: 54, 209, 237, 281, 295, 309, 367 and 368.

The compounds of the present invention can be readily prepared by techniques known in the art. Scheme I illustrates a general synthetic route to the compounds of this invention.

SCHEME I

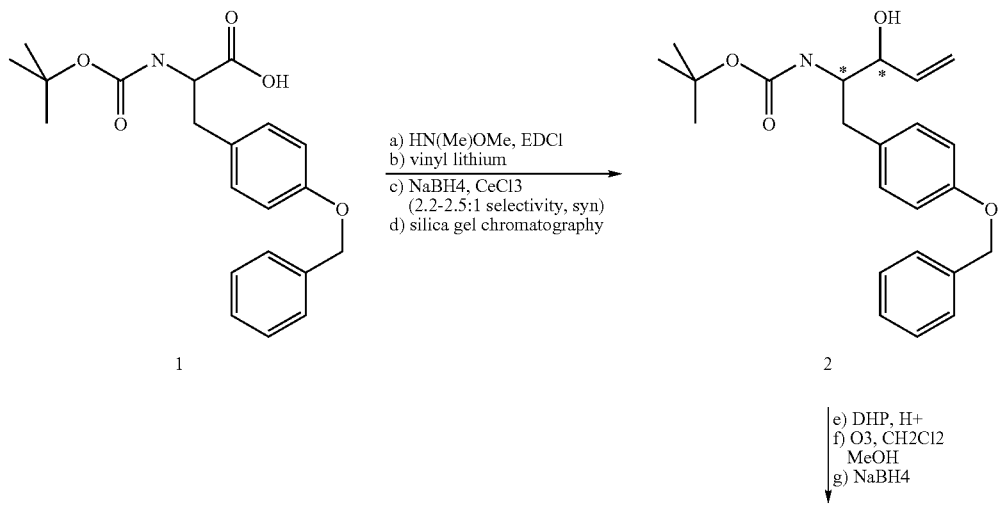

a) HN(Me)OMe, EDCl
b) vinyl lithium
c) NaBH4, CeCl3
   (2.2-2.5:1 selectivity, syn)
d) silica gel chromatography e) DHP, H+
f) O3, CH2Cl2
   MeOH
g) NaBH4

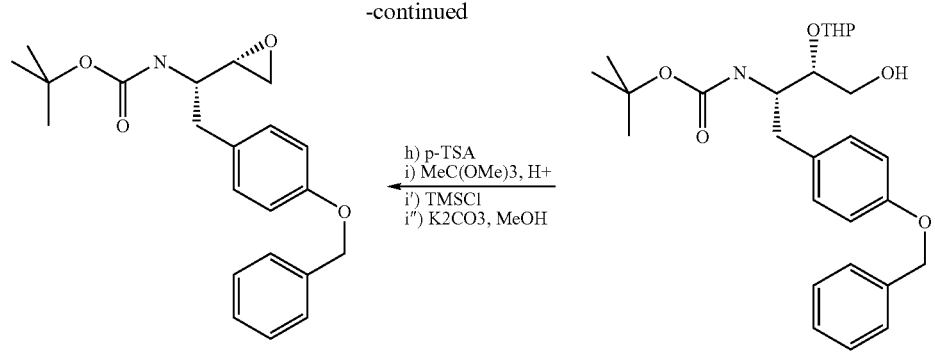

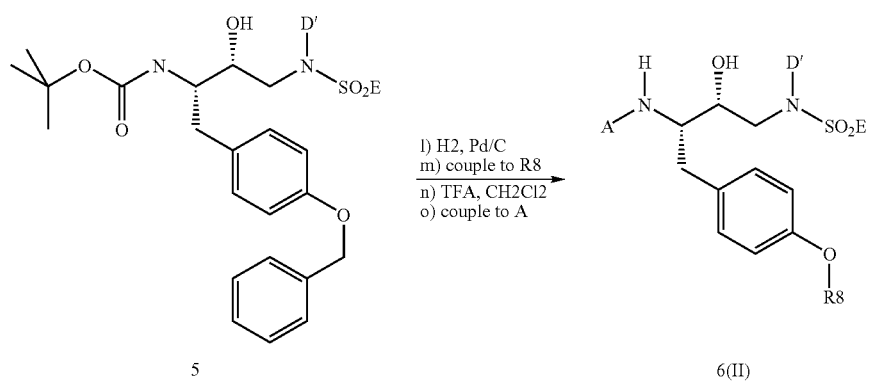

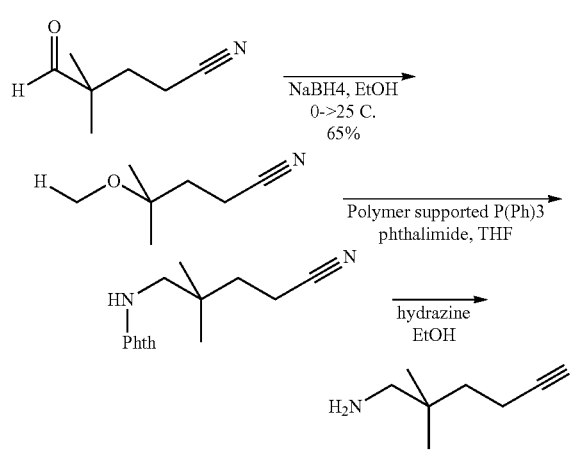

In Step 1 of Scheme I, the bis protected amino acid is homologated through initial conversion to the Wienreb Amide (a) followed by alkylation with vinyl lithium (b) and stereoselective reduction (c). The diastereomers can be separated by silica gel chromatography (d). In step 2, the secondary alcohol is protected as a THP ether (e), as was found necessary for the oxidation step. The olefin was then oxidized to the aldehyde by ozone and the resulting ozonide reduced to the alcohol by sodium borohydride (steps f and g). After removal of the THP group (h) under acidic conditions the diol was converted to the epoxide (i, i' and i'') in one pot according to the method of Sharpless [K. B. Sharpless Tetrahedron 1992, 48 (35), pp. 10515-10530. The epoxide, 4, was then opened by $H_2N-D'$ and further acylated in the presence of i-$Pr_2Net$ by E-$SO_2Cl$ to generate compounds of the formula schematically represented as 5. Alternate D' groups may be introduced at this point too. The synthesis of the D' as shown in compounds illustrated in Table II is shown in Scheme II.

These compounds could then be further manipulated by removal of the Bn group and introduction of a variety of $R^8$ groups by reacting with the corresponding alkyl halides. Further elaboration was possible by removal of the t-Butyl carbonate (1) and reintroduction of another group or carbamate designated as A, to provide compounds represented as 6 (formula II). We found that coupling as in reaction "m" was efficient under the following general conditions: alkyl halide ($R^8$—Cl, 2.5 EQ. $CsCO_3$, dioxane, 80° C., 2-4 hours. Similar alkylating conditions are reported in J. Med. Chem. 1992, 1688 along with representative routes for the synthesis of some $R^8$—Cl intermediates. The coupling as illustrated for bringing in A, step "o", was generally efficient under the following conditions: activated p-$NO_2$-phenyl carbonate (p-$NO_2$—O-A)) i-$Pr_2NEt$, $CH_2Cl_2$, RT, 12 hours. Use of the activated succinate provides an alternative coupling reagent (Succinate-A).

Alternatively, compounds of the present invention can also be prepared according to Scheme III below.

SCHEME III

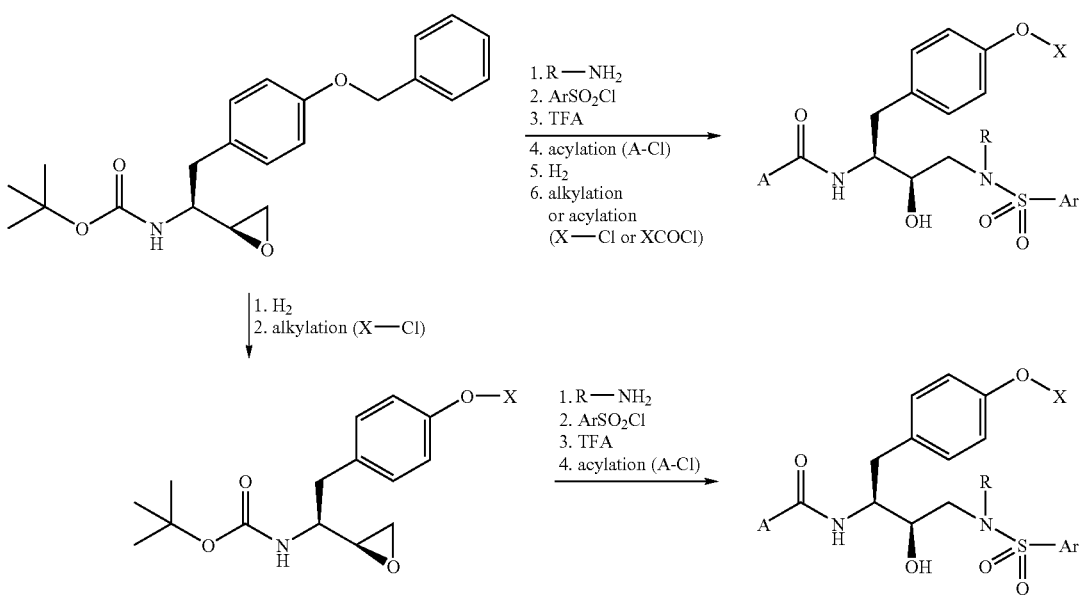

Thus, the synthetic approach illustrated in Scheme I and Scheme III can be readily extended to produce other compounds of the present invention. The above synthetic schemes are not intended to comprise a comprehensive list of all means by which compounds described and claimed in this application may be synthesized. Further methods will be evident to those of ordinary skill in the art.

As discussed above, the novel compounds of the present invention are excellent ligands for aspartyl proteases, particularly HIV-1 and HIV-2 proteases. Accordingly, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. Compounds according to this invention advantageously inhibit the ability of the HIV-1 virus to infect immortalized human T cells over a period of days, as determined by an assay of extracellular p24 antigen—a specific marker of viral replication. Other anti-viral assays have confirmed the potency of these compounds.

The compounds of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period time against HIV infection. As such, the novel protease inhibitors of this invention can be administered as agents for treating or preventing HIV infection in a mammal.

The compounds of formula I, especially those having a molecular weight of less than about 700 g/mole, may be readily absorbed by the bloodstream of mammals upon oral administration. Compounds of formula I having a molecular weight of less than about 600 g/mole are most likely to demonstrate oral availability. This surprisingly impressive oral availability makes such compounds excellent agents for orally-administered treatment and prevention regimens against HIV infection.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), alcitabine (ddC), d4T, zidovudine (AZT), polysulfated polysaccharides, sT4 (soluble CD4), ganiclovir, dideoxycytidine, trisodium phosphonoformate, eflornithine, ribavirin, acyclovir, alpha interferon and trimenotrexate. Additionally, non-nucleoside inhibitors of reverse transcriptase, such as TIBO or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert a synergistic effect in inhibiting HIV replication because each component agent of the combination acts on a different site of HIV replication. The use of such combinations also advantageously reduces the dosage of a given conventional anti-retroviral agent which would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce potential of resistance to single agent therapies, while minimizing any associated toxicity. These combinations may also increase the efficacy of the conventional agent without increasing the associated toxicity. In particular, we have discovered that these compounds act synergistically in preventing the replication of HIV in human T cells. Preferred combination therapies include the administration of a compound of this invention with AZT, ddI, ddC or d4T.

Alternatively, the compounds of this invention may also be co-administered with other HIV protease inhibitors such as Ro 31-8959 (Roche), L-735,524 (Merck), XM 323 (Du-Pont Merck) and A-80,987 (Abbott) to increase the effect of therapy or prophylaxis against various viral mutants or members of other HIV quasi species.

We prefer administering the compounds of this invention as single agents or in combination with retroviral reverse transcriptase inhibitors, such as derivatives of AZT, or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone and rEPO); and antibiotics (e.g., pentamidine isethiorate) to prevent or combat infection and disease associated with HIV infections, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include, as well as other AIDS-like diseases caused by retroviruses, such as simian immunodeficiency viruses, but are not limited to, HTLV-I and HTLV-II. In addition, the compounds of this invention may also be used to inhibit other aspartyl proteases, and in particular, other human aspartyl proteases, including renin and aspartyl proteases that process endothelin precursors. Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid; potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application, For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 50 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of target peptide or may be derivatized to bind to a stable resin as a tethered substrate for affinity chromatography applications. These and other uses which characterize commercial aspartyl protease inhibitors will be evident to those of ordinary skill in the art.

As used herein, the compounds according to the invention are defined to include pharmaceutically acceptable derivatives or prodrugs thereof. A "pharmaceutically acceptable derivative" or "pharmaceutically acceptable prodrug" means any pharmaceutically acceptable salt, ester, salt of an ester, or other derivative of a compound of this invention which, upon administration to a recipient, is capable of providing (directly or indirectly) a compound of this invention or an active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

The compounds according to the invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectianate, persulfate, phenylproprionate, picrate, pivalate, propionate, succinate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium) ammonium and $^+NW4$ (wherein W is $C_{1-4}$ alkyl). Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as Nat, $NH_4^+$, and $NW_4^+$ (wherein W is a $C_{1-4}$ alkyl group).

Pharmaceutically acceptable salts include salts of organic carboxylic acids such as ascorbic, acetic, citric, lactic, tartaric, malic, maleic, isethionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

For therapeutic use, salts of the compounds according to the invention will be pharmaceutically acceptable. However, salts of acids and bases which are non-pharmaceutically acceptable may also find use, for example, in the preparation or purification of a pharmaceutically acceptable compound.

Preferred salts include salts formed from hydrochloric, sulfuric, acetic, succinic, citric and ascorbic acids.

Preferred esters of the compounds according to the invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate-esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

Any reference to any of the above compounds also includes a reference to a pharmaceutically acceptable salts thereof.

The compounds according to the invention are especially useful for the treatment of AIDS and related clinical conditions such as AIDS related complex (ARC), progressive generalized lymphadenopathy (PGL), Kaposi's sarcoma, thrombocytopenic purpura, AIDS-related neurological conditions such as AIDS dementia complex, multiple sclerosis or tropical paraperesis, and also anti-HIV antibody-positive and HIV-positive conditions, including such conditions in asymptomatic patients.

In a further aspect of the invention there are provided the compounds according to the invention for use in medical therapy particularly for the treatment or prophylaxis of viral infections such as HIV infections.

According to another aspect, the present invention provides a method for the treatment or prevention of the symptoms or effects of a viral infection in an infected animal, for example, a mammal including a human, which comprises treating said animal with a therapeutically effective amount of a compound according to the invention. According to a particular embodiment of this aspect of the invention, the viral infection is an HIV infection. A further aspect of the invention includes a method for the treatment or prevention of the symptoms or effects of an HBV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in an animal, for example, a mammal including a human which clinical condition includes those which have been discussed in the introduction hereinbefore, which comprises treating said animal with a therapeutically effective amount of a compound according to the invention. The present invention also includes a method for the treatment or prophylaxis of any of the aforementioned infections or conditions.

Reference herein to treatment extends to prophylaxis as well as the treatment of established infections or symptoms.

The above compounds according to the invention and their pharmaceutically acceptable derivatives may be employed in combination with other therapeutic agents for the treatment of the above infections or conditions. Combination therapies according to the present invention comprise the administration of at least one compound of the formula (I) or a pharmaceutically acceptable derivative thereof and at least one other pharmaceutically active ingredient. The active ingredient(s) and pharmaceutically active agents may be administered simultaneously in either the same or different pharmaceutical formulations or sequentially in any order. The amounts of the active ingredient(s) and pharmaceutically active agent(s) and the relative timings of administration will be selected in order to achieve the desired combined therapeutic effect. Preferably the combination therapy involves the administration of one compound according to the invention and one of the agents mentioned herein below.

Examples of such further therapeutic agents include agents that are effective for the treatment of viral infections or associated conditions such as (1 alpha, 2 beta, 3 alpha)-9-[2,3-bis (hydroxymethyl) cyclobutyl]guanine [(−) BHCG, SQ-34514), oxetanocin-G (3,4-bis-(hydroxymethyl)-2-oxetanosyl]guanine), acyclic nucleosides (e.g. acyclovir, valaciclovir, famciclovir, ganciclovir, penciclovir), acyclic nucleoside phosphonates (e.g. (S)-1-(3-hydroxy-2-phosphonylmethoxypropyl)cytosine (HPMPC) and PMEA analogs thereof, ribonucleotide reductase inhibitors such as 2-acetylpyridine 5-[(2-chloroanilino)thiocarbonyl) thiocarbonohydrazone, 3'azido-3'-deoxythymidine, other 2',3'-dideoxynucleosides such as 2',3'-dideoxycytidine, 2',3'-dideoxyadenosine, 2',3'-dideoxyinosine, 2',3'-didehydrothymidine, protease inhibitors such as indinavir, ritonavir, nelfinavir, [3S-[3R*(1R*,2S*)]]-[3[[(4-aminophenyl)sulfonyl](2-methylpropyl)amino]-2-hydroxy-1-(phenylmethyl) propyl]-tetrahydro-3-furanyl ester (141H94), oxathiolane nucleoside analogues such as (−)-cis-1-(2-hydroxymethyl)-1,3-oxathiolane 5-yl)-cytosine (lamivudine) or cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9H-purin-9-yl]-2-cyclopentene-1-methanol, ribavirin, 9-[4-hydroxy-2-(hydroxymethyl) but-1-yl]-guanine (H2G), tat inhibitors such as 7-chloro-5-(2-pyrryl)-3H-1,4-benzodiazepin-2-(H)one (Ro5-3335), 7-chloro-1,3-dihydro-5-(1H-pyrrol-2-yl)-3H-1,4-benzodiazepin-2-amine (Ro24-7429), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, or non-nucleoside reverse transcriptase inhibitors (NNRTIs) such as nevirapine (BI-RG-587), loviride (α-APA) and delavuridine (BHAP), and phosphonoformic acid, and 1,4-dihydro-2H-3, 1-benzoxazin-2-ones NNRTIs such as (−)-6-chloro-4-cyclopropylethynyl-4-trifluoromethyl-1,4-dihydro-2H-3,1-benzoxazin-2-one (L-743,726 or DMP-266), and qinoxaline NNRTIs such as isopropyl (2S)-7-fluoro-3,4-dihydro-2-ethyl-3-oxo-1(2H)-quinoxalinecarboxylate (HBY1293).

More preferably the combination therapy involves the administration of one of the above mentioned agents and a compound within one of the preferred or particularly preferred sub-groups within formula (I) as described above. Most preferably the combination therapy involves the joint use of one of the above named agents together with one of the compounds of formula (I) specifically named herein.

The present invention further includes the use of a compound according to the invention in the manufacture of a medicament for simultaneous or sequential administration with at least one other therapeutic agent, such as those defined herein before.

In order that this invention may be more fully understood, the following examples are set forth. These examples are for the purpose of illustration only and are not to be construed as limiting the scope of the invention in any way. Compounds for which experimentals are not shown may be made through similar methodologies.

Example 1

Synthesis of BOC Benzyl Tyrosine Based Weinreb Amide (Scheme 1, Step a)

N-t-BOC—O-Benzyl-L-Tyrosine (1, Sigma) (25 g, 67.3 mmol) was combined with anhydrous DMF (200 ml) and cooled to 0° C. under a $N_2$ atmosphere. HOBT (15.5 g, 114.4 mmol, 1.7 eq.) and EDC (15.5 g, 80.8 mmol, 1.2 eq.) were added as solids and stirred to dissolve. Diisopropylethylamine (17.6 ml, 101 mmol, 1.5 eq.) and 4-dimethylaminopyridine (0.001 g) were added and the reaction was stirred for 50 minutes at 0° C. N,O-Dimethylhydroxylamine hydrochloride (8.5 g, 87.5 mmol, 1.3 eq.) was added as a solid and the reaction was stirred for 10 minutes at 0° C. then allowed to warm to room temperature and stirred overnight. After 18 hours at room temperature, the reaction was cooled to 0° C., and quenched with 200 mL of a 5% sodium bicarbonate solution. The reaction was extracted twice with EtOAc. The combined organics were washed with five times with water, and then brine, dried over $MgSO_4$, filtered and the solvent was removed in vacuo. The yield was 28 g of amide which was used as is. HPLC (5-100% $CH_3CN$/water) showed 1 peak at 10.77 min and the NMR ($CDCl_2$) was consistent with the expected structure.

Example 2

BOC Benzyl Tyrosine Derived Vinyl Ketone (Scheme 1, Step b)

N-t-BOC—O-Benzyl-L-Tyrosine Weinreb amide (18.8 g, 45.3 mmoles) was combined with anhydrous THF (200 ml) and cooled to −78° C. A vinyl lithium solution (2.3 M, 50 ml, 2.5 eq.) was added via addition funnel dropwise over 20 minutes at −78° C. Ten mL of anhydrous THF was added to rinse the funnel. The reaction was stirred at −78° C. under a $N_2$ atmosphere. HPLC at 1.5 hours showed the reaction was ~50% complete. Another 1.0 eq (20 ml) of vinyl lithium was added over 10 minutes at −78° C. and washed in with 15 mL of THF. The reaction stirred overnight at −78° C. After 18 hours, HPLC showed 15% Weinreb amide left. Another 0.2 eq (4 ml) of vinyl lithium was added at −78° C. After 26 hours at −78° C., the reaction was quenched with a slow addition of 300 mL of 1N HCl. The reaction was partitioned between EtOAc and water. The aqueous phase was extracted with EtOAc. The combined organics were washed consecutively with saturated bicarbonate solution and brine, dried over $MgSO_4$, filtered and the solvent was removed in vacuo. The yield was 19.9 g crude material.

The material was purified by flash chromatography (gradient: $CH_2Cl_2$ to 10% EtOAc/$CH_2Cl_2$) to give 13.5 g (78%) of pure material.
HPLC (5-100% $CH_3CN$/water) showed 1 peak at 13.37 min and the LC/MS showed 1 peak with an M+H=382.4 for the desired compound.

Example 3

BOC Benzyl Tyrosine Derived Allyl Alcohol (Scheme 1, Step c. Compound 2)

N-t-BOC—O-benzyl-L-tyrosine vinyl ketone (13.5 g, 35.4 mmol) was combined with methanol (120 ml) and Methylene Chloride (30 mL) and cooled to 0° C. Cerium chloride heptahydrate (14.5 g, 39 mmol, 1.1 eq.) was then added as a solid. The reaction was stirred at 0° C. for 5 minutes and then cooled to −78° C. A solution of sodium borohydride (2.0 g, 53.1 mmol, 1.5 eq) in 40 mL of MeOH was cooled to −78° C. and cannulated into the reaction dropwise over 40 minutes. The reaction became a thick white suspension and 50 mL of MeOH was added to aid stirring. The reaction was stirred at −78° C. for 1.5 hours and was then quenched at −78° C. with 150 mL of a saturated ammonium chloride solution. The reaction was extracted three times with EtOAc, and the combined organics were washed with saturated bicarbonate solution, followed by brine, dried over $Na_2SO_4$, filtered and the solvent was removed in vacuo to give 13.6 g crude material.

Proton NMR ($CDCl_3$): shows a 7:3 ratio of diastereomers. The material was purified via chromatography (4:5:1, Hexanes:$CH_2Cl_2$:EtOAc) to give 5.4 g of desired material (83:17 ratio of diastereomers) as well as 7.3 g of allyl alcohol as a mix of diastereomers to be repurified. Proton NMR ($CDCl_3$): was consistent with structure for the desired material.

Example 4

BOC Benzyl Tyrosine Allyl Alcohol (THP Protected) Scheme 1, Step e

BOC benzyl tyrosine allyl alcohol (1.59 g, 4.1 mmole) was dissolved in 10 mL of anhydrous $CH_2Cl_2$. Dihydropyran (500 µL, 5.4 mmol, 1.3 eq.) and pyridinium paratoluenesulfonate (210 mg, 0.8 mmol, 0.2 eq.) was added and the reaction was stirred at room temperature under a $N_2$ atmosphere. After 19 hours, the solvent was removed in vacuo and the residue was partitioned between EtOAc and a 10%; citric acid solution. The organics were separated, washed with brine, and then saturated bicarbonate solution, dried over $Na_2SO_4$, filtered and the solvent was removed in vacuo to give 1.98 g crude material as a white solid.

The material was purified via chromatography (25% EtOAc/Hexanes, (with 0.5 ml $NEt_3$/L) to give 1.85 g (96%) of desired material. NMR ($CDCl_3$): was consistent with structure as a mix of diastereomers (1:1) at THP alcohol.

Example 5

BOC Benzyl Tyrosine Diol (THP Protected) (Scheme 1, Steps f and g, Compound 3)

THP protected BOC benzyl tyrosine allyl alcohol (1.5 g, 3.2 mmol) was dissolved in methanol (5 ml) and methylene chloride (20 mL) and cooled to −78° C. Ozone was bubbled into the stirred solution for 1.5 hours at −78° C. The solution was then flushed with nitrogen to remove the ozone. Sodium borohydride (920 my, 25.6 mmol, 8 eq.) was then added in small portions over 5 minutes at −78° C. Methanol (35 mL) was added and the reaction was stirred at 78° C. for 5 minutes; then was slowly warmed to 0° C. Vigorous bubbling began at −20° C. After 1.5 hours at 0° C. the reaction was quenched with saturated bicarbonate solution and extracted with $CH_2Cl_2$. The combined organics were washed with brine, dried over $Na_2SO_4$, filtered and the solvent was removed in vacuo to give 1.49 g crude material.

The material was purified via chromatography (EtOAc/Hexanes, 20%-30%-40%, containing 0.5 ml $NEt_3$/L) to give 1.15 g (76%) of desired material. HPLC (5-100% $CH_3CN$/water) showed 1 peak at 13.81 min and the proton NMR (CDCl$_3$): was consistent with structure as a mix of diastereomers (~1:1) at the THP alcohol.

Example 6

Epoxide (4)

THP-protected diol (3) (0.40 g, 0.85 mmol) was combined with a catalytic amount of p-toluenesulfonic acid (0.004 g) in methanol (20 mL) under a N$_2$ atmosphere. After stirring at room temperature for ca. 15 minutes, the initial white suspension dissolved completely. Stirring at room temperature was continued for ca. 1 hour, after which time complete disappearance of starting material (3) was confirmed by TLC. The solvent was removed in vacuo to give diol as a white solid, combined with residual p-toluenesulfonic acid. The crude diol was dissolved in anhydrous dichloromethane (15 mL), and trimethylorthoacetate (0.130 mL, 1.02 mmol) was added dropwise with stirring. Upon addition of trimethylorthoacetate, the cloudy solution became colourless. After stirring at room temperature for ca. 1 hour, TLC again indicated complete disappearance of starting material. The solvent was removed in vacuo to give the desired cyclic orthoacetate as a viscous white oil, which was re-dissolved in anhydrous DCM (15 mL). Trimethysilyl chloride (0.129 mL, 1.02 mmol) was added dropwise with stirring. After 1.5 hours at room temperature generally no further starting material remained. The solvent was removed in vacuo to give the desired chloroacetates as a yellow oil, which was dissolved in methanol (20 mL). Cesium carbonate (0.48 g, 1.48 mmol) was added in one portion, and the solution was stirred at room temperature for 2 hours, after which time, TLC confirmed the absence of any starting material. The solvent was removed in vacuo to give a pale yellow oil, which was partitioned between saturated aqueous ammonium chloride solution (30 mL) and DCM (30 mL). The organic layer was taken, and the aqueous layer re-extracted with DCM (2×30 mL). The combined organic extracts were dried over MgSO$_4$, and the solvent removed in vacuo to give crude epoxide (4) as a yellow oil. This material was either used in the crude form, or could be purified by flash column chromatography (3:7 ethyl acetate/hexane to 4:1 ethyl acetate/methanol) to give epoxide (4) as a white solid: R$_f$=0.60 (3:7 ethyl acetate/hexane); $^1$H NMR (CDCl$_3$): 7.49-7.29 (5H, m), 7.14 (2H, d, J=8.3 Hz), 6.93 (2H, d, J=8.3 Hz), 5.05 (2H, s), 4.44 (1H, br. s), 3.64 (1H, br. s), 2.97-2.86 (2H, m), 2.85-2.72 (3H, m), 1.39 (9H, s); coupled LCMS showed the product as a single major peak with m/z 370 [(M+H]$^+$ or m/z 312 [M+H-$^t$Bu]$^+$ at R$_T$ 2.84 min; HPLC (205 nm) over an extended 20 minute run time showed the crude material to be a 9:1 mixture of diastereoisomeric epoxides at R$_T$s of 14.2 min. (major diastereoisomer) & 14.3 min. (minor diastereoisomer).

Example 7

Isobutylamino Alcohol (Scheme 1, Step j)

Crude epoxide (4) (0.37 g, 0.85 mmol) was combined with isobutylamine (large excess, 4 mL) in ethanol (4 mL) under a N$_2$ atmosphere. The reaction mixture was heated to reflux with stirring for 2.5 hours. The solvent was removed in vacuo to give a pale yellow oily residue. Trituration with hexane gave the isobutylamino alcohol (0.285 g, 75%) as a white solid: R$_f$=0.05 (3:7 ethyl acetate/hexane); $^1$H NMR (CDCl$_3$): 7.47-7.29 (5H, m), 7.15 (2H, d, J=8.5 Hz), 6.91 (2H, d, J=8.5 Hz), 5.04 (2H, s), 4.69 (1H, br. d, J=8.8 Hz), 3.76 (1H, br. s), 3.49-3.40 (1H, m), 2.91 (1H, dd, J=14.1, 4.7 Hz), 2.87-2.77 (1H, m), 2.67 (2H; d, J=4.7 Hz), 2.40 (2H, d, J=6.7 Hz), 1.71 (1H, septet, J=6.7 Hz), 1.36 (9H, s), 0.91 (3H, d, J=6.7 Hz), 0.90 (3H, d, J=6.7 Hz), OH and NH signals not observed; distinct minor diastereoisomer signals observed: 4.55 (1H, d, J=8.7 Hz), 2.49 (2H, d, J=6.6 Hz); NMR integration showed the triturated product to be a 9:1 mixture of diastereoisomeric isobutylamino alcohols; coupled LCMS showed the product as a single major peak with m/z 443 [M+H]$^+$ at R$_T$ 2.41 min.

Example 8

Boc Methylenedioxybenzenesulfonamide Benzyl Ether (Scheme 1, Compound 5e)

Isobutylamino alcohol (0.170 g, 0.38 mmol) was combined with methylenedioxybenzenesulfonyl chloride (0.085 g, 0.38 mmol) in anhydrous DCM (5 mL) under a N$_2$ atmosphere. The solution was cooled to 0° C. using an ice bath, and diisopropylethylamine (0.20 mL, 1.20 mmol) was added dropwise, and the reaction was allowed to warm to room temperature with stirring for 4 hours. The solvent was removed in vacuo, and the resultant pale yellow oil was purified by flash column chromatography (3:7 ethyl acetate/hexane) to give Boc methylenedioxybenzenesulfonamide benzyl ether (0.185 g, 75%) as a white foam: R$_f$=0.30 (3:7 ethyl acetate/hexane); $^1$H NMR (CDCl$_3$): 7.47-7.29 (6H, m), 7.21-7.11 (3H, m), 6.92 (2H, d, J=8.4 Hz), 6.88 (1H, d, J=8.2 Hz), 6.07 (2H, s), 5.04 (2H, s), 4.67-4.58 (1H, m), 3.97-3.85 (1H, m), 3.82-3.56 (2H, m), 3.10-3.02 (2H, m), 2.98-2.72 (4H, m), 1.84 (1H, septet, J=6.5 Hz), 1.36 (9H, s), 0.91 (3H, d, J=6.5 Hz), 0.87 (3H, d, J=6.5 Hz); coupled LCMS showed the product as a single major peak with m/z 627 [M+H]$^+$ at R$_T$ 3.16 min.

Example 9

Boc m-nitrobenzenesulfonamide

Benzyl Ether (Scheme 1, Compound 5c)

The isobutylamino alcohol (0.059 g, 0.13 mmol), as made in Scheme I by the addition of i-BuNH$_2$ to compound 4, was combined with m-nitrobenzenesulfonyl chloride (0.044 g, 0.20 mmol) in anhydrous DCM (2 mL) under a N$_2$ atmosphere. Diisopropylethylamine (0.070 mL, 0.40 mmol) was added dropwise, and the reaction was stirred at room temperature for 48 hours. The solvent was removed in vacuo, and the resultant yellow oil was purified by flash column chromatography (3:7 ethyl acetate/hexane) to give Boc m-nitrobenzenesulfonamide benzyl (5) (0.050 g, 61%) as a colourless oil: R$_f$ 0.31 (3:7 ethyl acetate/hexane); $^1$H NMR (CDCl$_3$): 8.63 (1H, d, J=1.8 Hz) 8.41 (1H, d, J=8.1 Hz), 8.10 (1H, d, J=6.8 Hz), 7.72 (1H, t, J=7.9 Hz), 7.50-7.28 (5H, m), 7.15 (2H, d, J=8.6 Hz), 6.92 (2H, d, J=8.6 Hz), 5.00 (2H, s), 4.65-4.55 (1H, m), 3.99-3.84 (1H, m), 3.83-3.74 (1H, m), 3.74-3.64 (1H, m), 3.21 (2H, d, J=5.4 Hz), 3.01 (2H, d, J=7.2 Hz), 2.93-2.80 (2H, m), 1.88 (1H, septet, J=6.4 Hz), 1.36 (9H, s), 0.91-0.75 (6H, m).

Example 10

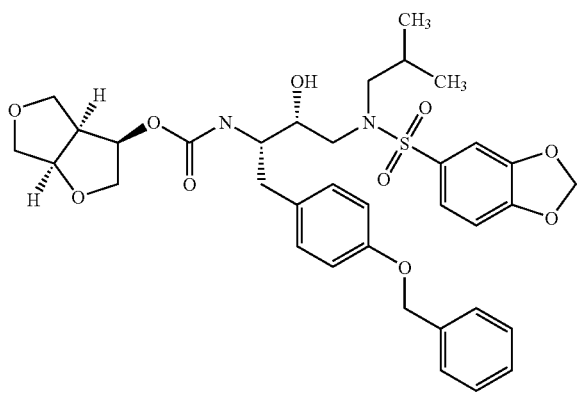 [SMILES: CC(C)CN(C[C@@H](O)[C@H](Cc1ccc(OCc2ccccc2)cc1)NC(=O)O[C@H]1CO[C@H]2COC[C@H]21)S(=O)(=O)c1ccc2c(c1)OCO2]

Bis-THF Methylenedioxybenzenesulfonamide
Benzyl Ether (46)

Boc methylenedioxybenzenesulfonamide benzyl ether (0.040 g, 0.064 mmol) was dissolved in DCM (2 mL). Trifluoroacetic acid (1 mL) was added dropwise, and the reaction was stirred at room temperature for 1 hour. The solvent was removed in vacuo, and the resultant orange oil was dissolved in DCM (1.5 mL) and the solution cooled to 0° C. using an ice bath. Diisopropylethylamine (0.33 mL, 1.92 mmol) was added dropwise with stirring, followed by (3R,3aS,6aR) hexahydrofuro[2,3-b]furan-2-yl 4-nitrophenyl carbonate (0.021 g, 0.071 mmol) in one portion as a solid. After 5 minutes, the ice bath was removed and the reaction mixture was allowed to warm to room temperature with stirring overnight. The solvent was removed in vacuo, and the resultant yellow oil was purified by flash column chromatography (1:1 ethyl acetate/hexane) to give bis-THF methylenedioxybenzenesulfonamide benzyl ether (46) (0.035 g, 80%) as a white foam: $R_f$=0.31 (1:1 ethyl acetate/hexane); $^1$H NMR (CDCl$_3$): 7.45-7.29 (6H, m), 7.17 (1H, d, J=1.8 Hz), 7.13 (2H, d, J=8.3 Hz), 6.90 (2H, d, J=8.3 Hz), 6.94-6.86 (1H, m), 6.07 (2H, s), 5.66 (1H, d, J=5.2 Hz), 5.10-4.98 (1H, m), 5.02 (2H, s), 4.94 (1H, d, J=8.5 Hz), 3.96 (1H, dd, J=9.6, 6.4 Hz), 3.89-3.78 (3H, m), 3.76-3.65 (2H, m), 3.18-3.09 (1H, m), 3.04-2.85 (4H, m), 2.82-2.70 (2H, m), 1.90-1.77 (1H, m), 1.73-1.48 (2H, m), 0.93 (3H, d, J=6.5 Hz), 0.89 (3H, d, J=6.5 Hz), H signal not observed; coupled LCMS showed the product as a single major peak with m/z 683 [M+H]$^+$; HPLC (205 nm) showed the material as a single major peak at $R_T$ of 2.73 min. (purity=96%).

Example 11

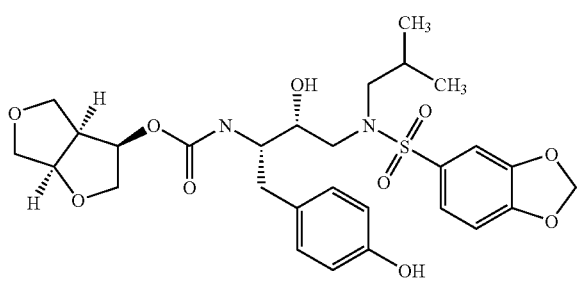 [SMILES: CC(C)CN(C[C@@H](O)[C@H](Cc1ccc(O)cc1)NC(=O)O[C@H]1CO[C@H]2COC[C@H]21)S(=O)(=O)c1ccc2c(c1)OCO2]

Bis-THF methylenedioxybenzenesulfonamide Free Phenol (47)

A solution of bis-THF methylenedioxybenzenesulfonamide benzyl ether (46) (0.022 g, 0.032 mmol) and 10% palladium on carbon (wet; Degussa variant) (0.008 g) in degassed ethyl acetate (10 mL) was stirred under a balloon of hydrogen. The reaction was monitored by TLC, and after 20 hours the starting material (47) had not been consumed. A fresh portion of 10% palladium on carbon (wet; Degussa variant) (0.008 g) was added to the reaction mixture, and the reaction stirred under a balloon of hydrogen for a further 4.5 hours. The reaction mixture was filtered through a pad of celite, and the filtrate was dried in vacuo to give a pale yellow oil. Flash column:chromatography (1:1 ethyl acetate/hexane) gave bis-THF methylenedioxybenzenesulfonamide free phenol (47) (0.008 g, 42%) as a colourless oil: $R_f$=0.44 (1:1 ethyl acetate/hexane); $^1$H NMR (CDCl$_3$); 7.33 (1H, dd, J=8.2, 1.7 Hz) 7.17 (1H, s), 7.07 (2H, d, J=8.1 Hz), 6.90 (1H, d, J=8.2 Hz), 6.74 (2H, d, J=8.1 Hz), 6.09 (2H, s), 5.66 (1H, d, J=5.2 Hz), 5.10-5.00 (2H, m), 4.05-3.68 (7H, m), 3.18-3.07 (1H, m), 3.06-2.90 (4H, m), 2.87-2.68 (2H, m), 1.89-1.48 (3H, m), 0.93 (3H, d, J=6.6 Hz), 0.89 (3H, d, J=6.6 Hz); OH signal not observed; coupled LCMS showed the product as a single major peak with m/z 593 [M+H]$^+$; HPLC (205 nm) showed the material as a single major peak at $R_T$ of 1.94 min. (purity=98%).

Example 12

Boc Methylenedioxybenzenesulfonamide Free Phenol (Scheme 1, Compound 6e)

A solution of Boc methylenedioxybenzenesulfonamide benzyl ether (0.063 g, 0.101 mmol) and 10% palladium on carbon (wet; Degussa variant) (0.024 g) in degassed ethyl acetate (10 mL) was stirred under a balloon of hydrogen. The reaction was monitored by TLC, and after 2 hours the starting material had not been consumed. A fresh portion of 10% palladium on carbon (wet; Degussa variant) (0.024 g) was added to the reaction mixture, and the reaction stirred under a balloon of hydrogen for a further 5 hours. The reaction mixture was filtered through a pad of celite, and the filtrate was dried in vacuo to give a colourless oil. Flash column chromatography (1:1 ethyl acetate/hexane) gave Boc methylenedioxybenzenesulfonamide free phenol (6) (0.036 g, 60%) as a white foam: $R_f$=0.74 (1:1 ethyl acetate/hexane); 3H NMR (CDCl$_3$); 7.32 (1H, d, J=8.3 Hz), 7.17 (1H, s), 7.12-7.02 (2H, m), 6.88 (1H, d, J=8.3 Hz), 6.78-6.69 (2H, m), 6.08 (2H, s), 4.75 (1H, d, J=8.1 Hz), 3.88-3.62 (3H, m), 3.49 (1H, s), 3.09-3.01 (2H, m), 2.97-2.85 (2H, m), 2.84-2.72 (2H, m), 1.84 (1H, septet, J=6.6 Hz), 1.37 (9H, s), 0.90 (3H, d, J=6.6 Hz), 0.86 (3H, d, J=6.6 Hz); coupled LCMS showed the product as a single major peak with m/z 537 [M+H]$^+$ at $R_T$ 2.50 min.

Example 13

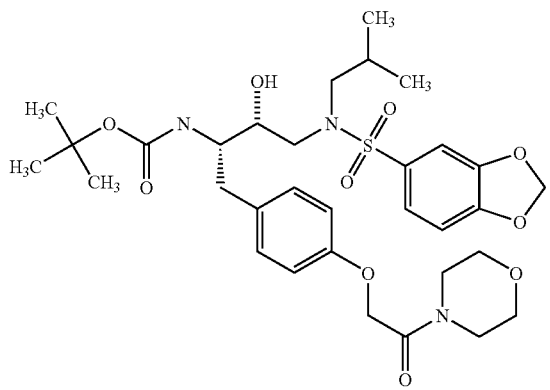 [SMILES: CC(C)CN(C[C@@H](O)[C@H](Cc1ccc(OCC(=O)N2CCOCC2)cc1)NC(=O)OC(C)(C)C)S(=O)(=O)c1ccc2c(c1)OCO2]

Boc methylenedioxybenzenesulfonamide
Acetylmorpholine Tethered Product (21)

A solution of Boc methylenedioxybenzenesulfonamide free phenol (0.036 g, 0.067 mmol) in 1,4-dioxane (1 mL) was combined with cesium carbonate (0.055 g, 0.168 mmol) and 4-(2-chloroacetyl)morpholine (0.016 g, 0.100 mmol). The solution was heated to 85° C. with stirring for 2 hours, and was cooled and dried in vacuo to give a pale yellow oil. Flash column chromatography (ethyl acetate) gave Boc methylenedioxybenzenesulfonamide acetylmorpholine tethered product (21) (0.032 g, 71%) as a white foam: $R_f$=0.51 (ethyl acetate); $^1$H NMR (CDCl$_3$); 7.34 (1H, dd, J=8.0, 1.7 Hz), 7.22-7.14 (3H, m), 6.93-6.84 (3H, m), 6.09, (2H, s), 4.70-4.59 (1H, m), 4.67 (2H, s), 3.97-3.90 (1H, m), 3.82-3.58 (10H, m), 3.12-3.04 (2H, m), 2.99-2.78 (4H, m), 1.84 (1H, septet, J=6.6 Hz), 1.36 (9H, s), 0.91 (3H, d, J=6.6 Hz), 0.88 (3H, d, J=6.6 Hz); coupled LCMS showed the product as a single major peak with m/z 664 [M+H]$^+$; HPLC (205 nm) showed the material as a single major peak at $R_T$ of 2.38 min. (purity=99%).

Example 14

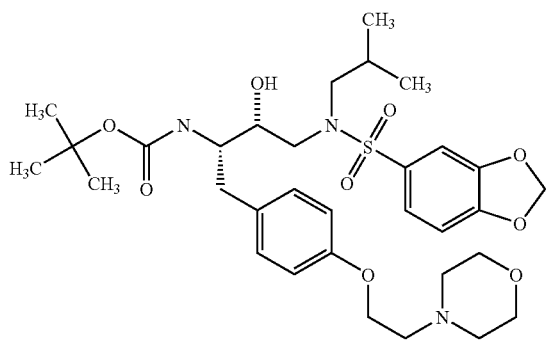 [SMILES: CC(C)CN(C[C@@H](O)[C@H](Cc1ccc(OCCN2CCOCC2)cc1)NC(=O)OC(C)(C)C)S(=O)(=O)c1ccc2c(c1)OCO2]

Boc Methylenedioxybenzenesulfonamide
Ethylmorpholine Tethered Product (17)

A solution of Boc methylenedioxybenzenesulfonamide free phenol (0.034 g, 0.063 mmol) in 1,4-dioxane (1 mL) was combined with cesium carbonate (0.052 g, 0.158 mmol) and N-(2-chloroethyl)morpholine (0.014 g, 0.095 mmol). The solution was heated to 85° C. with stirring for 5 hours, and was cooled and dried in vacuo to give a pale yellow oil. Flash column chromatography (4:1 ethyl acetate/hexane) gave Boc methylenedioxybenzenesulfonamide ethylmorpholine tethered product (17) (0.012 g, 29%) as a pale yellow oil: $R_f$=0.32 (4:1 ethyl acetate/hexane); $^1$H NMR (CDCl$_3$); 7.32 (1H, dd, J=8.2, 1.5 Hz), 7.18 (1H, d, J=1.5 Hz), 7.15 (2H, d, J=8.3 Hz), 6.88 (1H, d, J=8.2 Hz), 6.84 (2H, d, J=8.3 Hz), 6.09 (2H, s), 4.63 (1H, d, J=8.2 Hz), 3.93 (1H, br. s), 3.83-3.64 (7H, m), 3.06 (2H, d, J=4.9 Hz), 2.98-2.76 (6H, m), 2.68-2.55 (4H, m), 2.54-2.48 (1H, m), 1.84 (1H, septet, J=6.7 Hz), 1.35 (9H, s), 0.90 (3H, d, J=6.7 Hz), 0.87 (3H, d, J=6.7 Hz); coupled LCMS showed the product as a single major peak with m/z 650 [M+H]$^+$; HPLC (205 nm) showed the material as a single major peak at $R_T$ of 2.06 min. (purity=92%).

Example 15

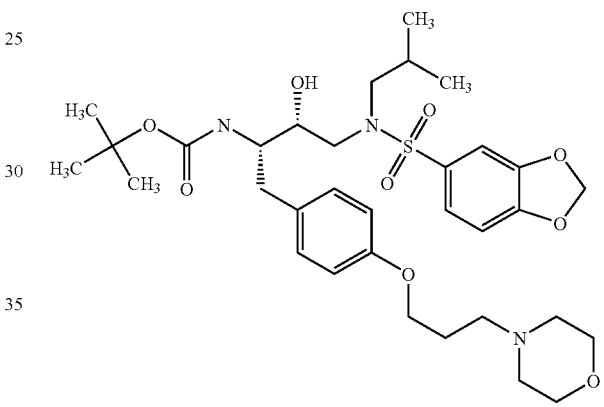

Boc Methylenedioxybenzenesulfonamide
Propylmorpholine Tethered Product (20)

A solution of Boc methylenedioxybenzenesulfonamide free phenol (0.038 g, 0.071 mmol) in 1,4-dioxane (1 mL) was combined with cesium carbonate (0.058 g, 0.177 mmol) and N-(3-chloropropyl)morpholine (0.017 g, 0.107 mmol). The solution was heated to 85° C. with stirring for 8 hours, and was cooled and dried in vacuo to give a pale yellow oil. Flash column chromatography (4:1 ethyl acetate/hexane) gave Boc methylenedioxybenzenesulfonamide propylmorpholine tethered product (20) (0.006 g, 13%) as a pale yellow oil: $R_f$=0.15 (4:1 ethyl acetate/hexane); $^1$H NMR (CDCl$_3$); 7.32 (1H, dd, J=8.1, 1.8 Hz), 7.19 (1H, d, J=1.8 Hz), 7.14 (2H, d, J=8.4 Hz), 6.88 (1H, d, J=8.1 Hz), 6.83 (2H, d, J=8.4 Hz), 6.08 (2H, s), 4.62 (1H, br. s), 4.00 (2H, t, J=6.3 Hz), 3.84-3.65 (8H, m), 3.61 (2H, t, J=6.6 Hz), 3.10-3.03 (2H, m), 3.00-2.77 (3H, m), 2.64-2.35 (4H, m), 2.05-1.91 (2H, m), 1.85 (1H, septet, J=6.6 Hz), 1.37 (9H, s), 0.90 (3H, d, J=6.6 Hz), 0.87 (3H, d, J=6.6 Hz); coupled LCMS showed the product as a single major peak with m/z 664 [M+H]$^+$; HPLC (205 nm) showed the material as a single major peak at $R_T$ of 2.23 min. (purity=80%).

Example 16

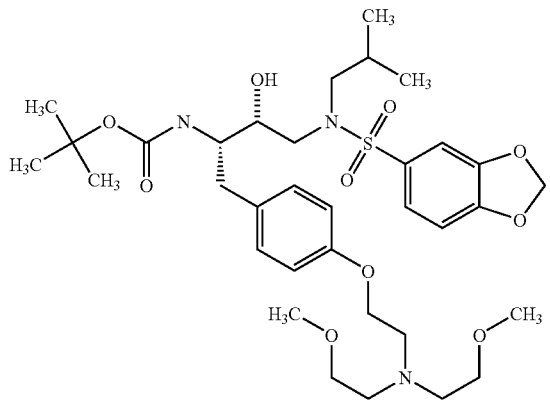 [SMILES: COCCN(CCOC)CCOc1ccc(C[C@H](NC(=O)OC(C)(C)C)[C@H](O)CN(CC(C)C)S(=O)(=O)c2ccc3c(c2)OCO3)cc1]

Boc Methylenedioxybenzenesulfonamide
Bis-Methoxyethylamine Tethered Product (18)

A solution of Boc methylenedioxybenzenesulfonamide free phenol (0.034 g, 0.063 mmol) in 1,4-dioxane (1 mL) was combined with cesium carbonate (0.052 g, 0.158 mmol) and freshly prepared 2-[N,N-bis-(2-methoxyethyl)amino]ethyl chloride (ca. 0.031 g, ca. 0.016 mmol). The solution was heated to 85° C. with stirring for 3.5 hours, and was cooled and dried in vacuo to give a pale yellow oil. Flash column chromatography (ethyl acetate) gave Boc methylenedioxybenzenesulfonamide bis-methoxyethylamine tethered product (18) (0.024 g, 54%) as a white foam: $R_f$=0.35 (ethyl acetate); $^1$H NMR (CDCl$_3$): 7.32 (1H, dd, J=8.2, 1.6 Hz), 7.18 (1H, d, J=1.6 Hz), 7.14 (2H, d, J=8.5 Hz), 6.88 (1H, d, J=8.2 Hz), 6.83 (2H, d, J=8.5 Hz), 6.08 (2H, s), 4.63 (1H, d, J=7.7 Hz), 4.03 (2H, t, J=6.1 Hz), 3.92 (1H, br. s), 3.81-3.73 (1H, m), 3.73-3.63 (1H, m), 3.50 (4H, t, J=5.8 Hz), 3.34 (6H, s), 3.10-3.03 (2H, m), 3.01 (2H, t, J=6.1 Hz), 2.98-2.75 (4H, m), 2.84 (4H, t, J=5.8 Hz), 1.83 (1H, septet, J=6.6 Hz), 1.35 (9H, s), 0.90 (3H, d, J=6.6 Hz), 0.87 (3H, d, J=6.6 Hz); coupled LCMS showed the product as a single major peak with m/z 696 [M+H]$^+$; HPLC (205 nm) showed the material as a single major peak at $R_T$ of 2.20 min. (purity=100%).

Example 17

Boc Methylenedioxybenzenesulfonamide 3-picolyl Tethered Product (Intermediate on Route to Compound 53)

A solution of Boc methylenedioxybenzenesulfonamide free phenol (0.010 g, 0.020 mmol) in 1,4-dioxane (1 mL) was combined with cesium carbonate (0.015 g, 0.047 mmol), 3-(chloromethyl)pyridine (ca. 0.004 g, ca. 0.030 mmol; prepared by dissolving 10 mg of 3-(chloromethyl)pyridine hydrochloride in sodium hydroxide (1.5 mL) and diethyl ether (1.5 mL), the organic extract was dried over MgSO$_4$ and the solvent removed in vacuo) and potassium iodide (~1 mg, 0.006 mmol). The solution was heated to 60° C. with stirring for 8 hours, and was cooled and dried in vacuo to give a pale yellow oil. Flash column chromatography (3:7 ethyl acetate/hexane) gave Boc methylenedioxybenzenesulfonamide 3-picolyl tethered product (0.004 g, 34%) as a colourless oil: $R_f$=0.05 (1:1 ethyl acetate/hexane); coupled LCMS showed the product as a single major peak with m/z 628 [M+H]$^+$ at $R_T$ of 2.27 min.

Example 18

Boc Methylenedioxybenzenesulfonamide 2-picolyl Tethered Product (Intermediate en Route to 52)

A solution of Boc methylenedioxybenzenesulfonamide free phenol (0.010 g, 0.020 mmol) in 1,4-dioxane (1 mL) was combined with cesium carbonate (0.015 g, 0.047 mmol), 2-(chloromethyl)pyridine (ca. 0.004 g, ca. 0.030 mmol; prepared by dissolving 10 mg of 2-(chloromethyl)pyridine hydrochloride in sodium hydroxide (1.5 mL) and diethyl ether (1.5 mL), the organic extract was dried over MgSO$_4$ and the solvent removed in vacuo) and potassium iodide (~1 mg, 0.006 mmol). The solution was heated to 60° C. with stirring for 8 hours, and was cooled and dried in vacuo to give a pale yellow oil. Flash column chromatography (3:7 ethyl acetate/hexane) gave Boc methylenedioxybenzenesulfonamide 2-picolyl tethered product (0.004 g, 34%) as a colourless oil: $R_f$=0.3 (1:1 ethyl acetate/hexane); coupled LCMS showed the product with m/z 628 [M+H]$^+$ at $R_T$ of 2.35 min.

Example 19

Boc Methylenedioxybenzenesulfonamide 4-picolyl Tethered Product (Intermediate en Route to Compound 54)

A solution of Boc methylenedioxybenzenesulfonamide free phenol (0.01 g, 0.020 mmol) in 1,4-dioxane (1 mL) was combined with cesium carbonate (0.015 g, 0.047 mmol), 4-(chloromethyl)pyridine (ca. 0.004 g, ca. 0.030 mmol; prepared by dissolving 10 mg of 4-(chloromethyl)pyridine hydrochloride in sodium hydroxide (1.5 mL) and diethyl ether (1.5 mL), the organic extract was dried over MgSO$_4$ and the solvent removed in vacuo) and potassium iodide (~1 mg, 0.006 mmol). The solution was heated to 60° C. with stirring for 16 hours, and was cooled and dried in vacuo to give a pale yellow oil, Flash column chromatography (3:7 ethyl acetate/hexane) gave Boc methylenedioxybenzenesulfonamide 4-picolyl tethered product (0.004 g, 34%) as a colourless oil: $R_f$=0.10 (2:3 ethyl acetate/hexane); coupled LCMS showed the product with m/z 628 [M+H]$^+$ at $R_T$ of 2.24 min.

Example 20

Boc Methylenedioxybenzenesulfonamide 3-methyl-5-methylisoxazole Tethered Product (Intermediate en Route to Compound 55)

A solution of Boc methylenedioxybenzenesulfonamide free phenol (0.010 g, 0.020 mmol) in 1,4-dioxane (1 mL) was combined with cesium carbonate (0.015 g, 0.047 mmol), 3-chloromethyl-5-methyl isoxazole (0.004 g, 0.028 mmol) and potassium iodide (~1 mg, 0.006 mmol). The solution was heated to 60° C. with stirring for 16 hours, and was cooled and dried in vacuo to give a pale yellow oil. Flash column chromatography (3:7 ethyl acetate/hexane) gave Boc methylenedioxybenzenesulfonamide 3-methyl-5-methylisoxazole tethered product (0.005 g, 42%) as a colourless oil: $R_f$0.25 (3:7 ethyl acetate/hexane); $^1$H NMR (CDCl$_3$): 7.34 (1H, dd, J=8.4, 1.8 Hz), 7.21-7.13 (3H, m), 6.90 (3H, m), 6.11 (1H, s), 6.09 (2H, s), 5.09 (2H, s), 4.65 (1H, d, J=8.2 Hz), 3.92 (1H, br. s), 3.82-3.75 (1H, m), 3.73-3.63 (1H, m), 3.09-3.03 (2H, m), 2.98-2.80 (4H, m), 2.43 (3H, s), 1.84 (1H, septet, J=6.6 Hz), 1.36 (9H, s), 0.91 (3H, d, J=6.6 Hz), 0.88 (3H, d, J=6.6 Hz).

Example 21A

Boc Methylenedioxybenzenesulfonamide 1-methyl-3,5-dimethylpyrazole Tethered Product (Intermediate en Route to Compound 56)

A solution of Hoc methylenedioxybenzenesulfonamide free phenol (0.010 g, 0.020 mmol) in DMF (1 mL) was combined with anhydrous cesium carbonate (0.015 g, 0.047 mmol). Freshly prepared 1-chloromethyl-3,5-dimethylpyrazole hydrochloride (0.006 g, 0.033 mmol) in DMF (0.5 ml) was added dropwise. The solution was heated to 60° C. with stirring for 15 minutes, and was cooled and dried in vacuo to give a green oil. Flash column chromatography (1:1 ethyl acetate/hexane) gave Doc methylenedioxybenzenesulfonamide 1-methyl-3,5-dimethylpyrazole tethered product (0.002 g, 17%) as a colourless oil: $R_f$=0.25 (1:1 ethyl acetate/hexane); coupled LCMS showed the product as a single major peak with m/z 645 $[M+H]^+$ at $R_T$ of 1.68 min.

Example 21B

Boc Methylenedioxybenzenesulfonamide Ethylpyrazole Tethered Product (Intermediate en Route to Compound 57)

A solution of Boc methylenedioxybenzenesulfonamide free phenol (0.010 g, 0.020 mmol) in acetone (1 mL) was combined with cesium carbonate (0.015 g, 0.047 mmol), 1-(2-chloroethyl)pyrazole (0.004 g, 0.031 mmol) and sodium iodide (~1 mg, 0.007 mmol). The solution was heated to 55° C. with stirring for 60 hours, and was cooled and dried in vacuo to give a yellow oil. Flash column:chromatography (1:3 ethyl acetate/hexane) gave Boc methylenedioxybenzenesulfonamide ethylpyrazole tethered product 0.0015 g, 13%) as a colourless oil: $R_f$=0.20 (1:1 ethyl acetate/hexane); coupled LCMS showed the product as a single major peak with m/z 631 $[M+H]^+$ at $R_T$ of 1.65 min.

Example 22

Bis-THF m-nitrobenzenesulfonamide Benzyl Ether (Intermediate en Route to Compounds: 25, 34-37)

Boc m-nitrobenzenesulfonamide benzyl (5 c; 0.050 g, 0.08 mmol) was dissolved in DCM (3.4 mL). Trifluoroacetic acid (1.6 mL) was added dropwise, and the reaction was stirred at room temperature for 1 hour. The solvent was removed in vacuo, and the resultant orange oil was dissolved in DCM (1.5 mL) and the solution cooled to 0° C. using an ice bath. Diisopropylethylamine (0.42 mL, 2.39 mmol) was added dropwise with stirring, followed by (3R, 3aS,6aR) hexahydrofuro[2,3-b]furan-2-yl 4-nitrophenyl carbonate (0.026 g, 0.088 mmol) in one portion as a solid. After 5 minutes, the ice bath was removed and the reaction mixture was allowed to warm to room temperature with stirring overnight. The solvent was removed in vacuo, and the resultant yellow oil was purified by flash column chromatography (1:1 ethyl acetate/hexane) to give bis-THF m-nitrobenzenesulfonamide benzyl ether (6; 0.036 g, 66%) as a white foam:

$R_f$=0.39 (1:1 ethyl acetate/hexane); $^1$H NMR (CDCl$_3$): 8.62 (1H, d, J=2.3 Hz), 8.42 (1H, dt, J=8.1, 0.9 Hz), 8.10 (1H, d, J=7.7 Hz), 7.73 (1H, t, J=8.1 Hz), 7.45-7.29 (5H, m), 7.12 (2H, d, J=8.6 Hz), 6.89 (2H, d, J=8.6 Hz), 5.65 (1H, d, J=5.4 Hz), 5.10-4.98 (1H, m), 5.02 (2H, s), 4.93 (1H, d, J=8.1 Hz), 3.96 (1H, dd, J=9.0, 6.3 Hz), 3.91-3.76 (3H, m), 3.76-3.61 (2H, m), 3.24 (1H, dd, J=15.4, 8.1 Hz), 3.16 (1H, dd, 15.2, 3.0 Hz), 3.06-2.96 (3H, m), 2.96-2.88 (1H, m), 2.74 (1H, dd, J=14.2, 9.3 Hz), 1.88 (1H, septet, J=6.7 Hz), 1.73-1.59 (1H, m), 1.59-1.48 (1H, m), 0.90 (6H, t, J=6.3 Hz), OH signal not observed.

Example 23

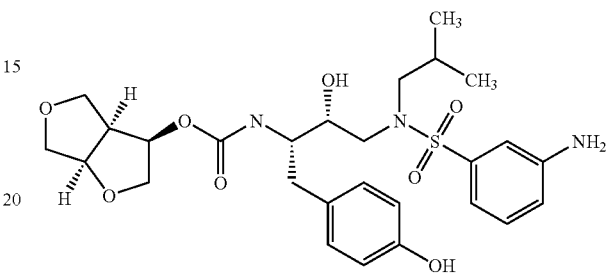

Bis-THP m-aminophenylsulfonamide Benzyl Ether and Bis-THP m-aminophenylsulfonamide Free Phenol (Intermediates en Route to Compounds 34-37)

A solution of bis-THF m-nitrobenzenesulfonamide benzyl ether (5 c; 0.036 g, 0.053 mmol) and 10% palladium on carbon (wet Degussa) (0.012 g) in degassed ethyl acetate (15 rat) was stirred under a balloon of hydrogen. The reaction was monitored by TLC, and after 2 hours the starting material had been consumed. An aliquot (5 mL) of the reaction mixture was removed, and filtered through a pad of celite. The filtrate was dried in vacuo to give bis-THF m-aminophenylsulfonamide benzyl ether (compound 22) as an off-white oily solid (0.010 g, 29%).

A fresh portion of 10% palladium on carbon (wet Degussa) (0.012 g) was added to the remainder of the reaction mixture, and the reaction stirred under a balloon of hydrogen for a further 2 hours. TLC indicated that an amount of intermediate product remained, so a further portion of 10% palladium on carbon (wet Degussa) (0.012 g) was added to the reaction mixture, and the reaction stirred under a balloon of hydrogen overnight. The reaction mixture was filtered through a pad of celite, and the filtrate was dried in vacuo to give bis-THF m-aminophenylsulfonamide free phenol (6: R8=H, D'=i-Bu, E=m-NH2Ph, A=bis-THF-CO—) as an off-white oily solid (0.016 g, 54%).

For bis-THF m-aminophenylsulfonamide benzyl ether: $R_f$=0.47 (3:1 ethyl acetate/hexane); $^1$H NMR (CDCl$_3$); 7.45-7.28 (7H, m), 7.28-7.19 (1H, m), 7.17-7.08 (3H, m), 6.89 (2H, d; J=8.1 Hz), 5.65 (1H, dd, J=9.3, 5.2 Hz), 5.10-4.95 (4H, m), 4.00-3.60 (6H, m), 3.30-2.80 (6H, m), 2.74 (1H, dd, J=10.4, 9.0 Hz), 1.92-1.80 (1H, m), 1.75-1.43 (2H, m), 0.95-0.88 (6H, m); OH and NH$_2$ signals not observed; coupled LCMS showed the product as a single major peak with m/z 654 $[M+H]^+$; HPLC (205 nm) showed the material to be split into 2 peaks at $R_T$s of 2.33 min. & 2.38 min. (combined purity=89%).

For bis-THF m-aminophenylsulfonamide free phenol: D=i-Bu, E=m-NH2Ph, A=bis-THF-CO—, R8=H): $R_f$=0.21 (3:1 ethyl acetate/hexane); $^1$H NMR (CDCl$_3$); 7.28 (1H, dd, J=15.3, 7.2 Hz), 7.13-7.10 (1H, m), 7.08 (2H, d, J=8.1 Hz), 7.03-6.99 (1H, m) 6.86 (1H, dd, J=7.9, 1.6 Hz), 6.75 (2H, d, J=8.6 Hz), 5.66 (1H, d, J=4.9 Hz), 5.05 (2H, d, J=7.7 Hz), 4.01-3.59 (7H, m), 3.17-3.04 (1H, m), 3.04-2.89 (4H, m), 2.86-2.74 (2H, m), 1.91-1.50 (3H, m), 0.93 (3H, d, J=6.5 Hz), 0.81 (3H, d, J=6.5 Hz); OH and NH$_2$ signals hot observed; coupled LCMS showed the product as a single major peak with m/z 565 [M+H]$^+$; HPLC (205 nm) showed the material as a single major peak at R$_T$ of 1.53 min. (purity=92%).

Example 25

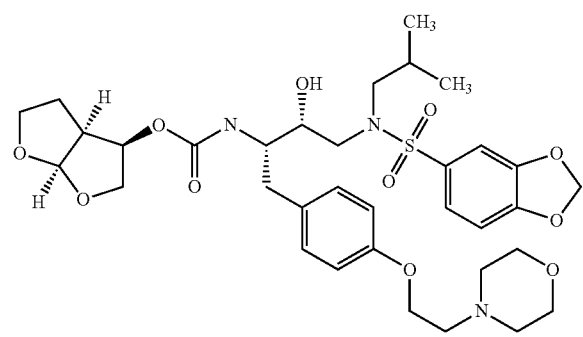 [SMILES: CC(C)CN(C[C@@H](O)[C@H](Cc1ccc(OCCN2CCOCC2)cc1)NC(=O)O[C@H]1CO[C@H]2OCC[C@H]21)S(=O)(=O)c1ccc2c(c1)OCO2]

Bis-THF Methylenedioxybenzenesulfonamide
Ethylmorpholine Tethered Product (Compound 48)

Boc methylenedioxybenzenesulfonamide ethylmorpholine tethered product (Compound 17; 0.011 g, 0.017 mmol) was dissolved in DCM (1 mL). Trifluoroacetic acid (0.5 mL) was added dropwise, and the reaction was stirred at room temperature for 1 hour. The solvent was removed in vacuo, and the resultant orange oil was dissolved in DCM (0.3 mL) and the solution cooled to 0° C. using an ice bath. Diisopropylethylamine (0.088 mL, 0.51 mmol) was added dropwise with stirring, followed by (3R,3aS,6aR) hexahydrofuro[2,3-b]furan-2-yl 4-nitrophenyl carbonate (0.006 g, 0.020 mmol) in one portion as a solid. After 5 minutes, the ice bath was removed and the reaction mixture was allowed to warm to room temperature with stirring overnight. The solvent was removed in vacuo, and the resultant yellow oil was purified by flash column chromatography (from 4:1 ethyl acetate/hexane to 9:1 DCM/methanol) to give bis-THF methylenedioxybenzenesulfonamide ethylmorpholine tethered product (Compound 48) (0.0095 g, 79%) as a pale yellow oil: R$_f$=0.50 (9:1 DCM/methanol); $^1$H NMR (CDCl$_3$): 7.40-7.28 (1H, m), 7.23-7.04 (3H, m), 6.97-6.87 (1H, m), 6.87-6.77 (2H, m), 6.12 (2H, s), 5.68 (1H, d, J=4.8 Hz), 5.11-5.00 (1H, m), 5.00-4.87 (1H, m), 4.03-3.92 (2H, m), 3.92-3.53 (10H, m), 3.21-3.07 (2H, m), 3.07-2.92 (3H, m), 2.92-2.74 (4H, m), 2.74-2.54 (4H, m), 1.96-1.37 (3H, m), 1.02-0.78 (6H, m), OH signal not observed; coupled LCMS showed the product as a single major peak with m/z 706 [M+H]$^+$; HPLC (205 nm) showed the material as a single major peak at R$_T$ of 1.83 min. (purity=95%).

Example 26

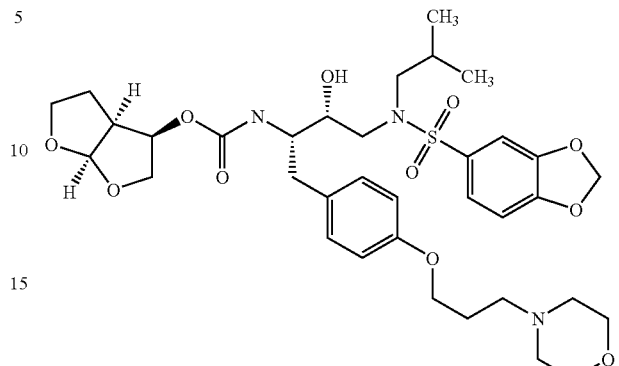

Bis-THF Methylenedioxybenzenesulfonamide
Propylmorpholine Tethered Product (Compound 49)

Boc methylenedioxybenzenesulfonamide propylmorpholine tethered product (20) (0.006 g, 0.009 mmol) was dissolved in DCM (1 mL). Trifluoroacetic acid (0.5 mW) was added dropwise, and the reaction was stirred at room temperature for 1 hour. The solvent was removed in vacuo, and the resultant orange oil was dissolved in 0.20 DCM (0.3 mL) and the solution cooled to 0° C. using an ice bath. Diisopropylethylamine (0.047 mL, 0.27 mmol) was added dropwise with stirring, followed by (3R,3aS,6aR) hexahydrofuro[2,3-b]furan-2-yl 4-nitrophenyl carbonate (0.003 g, 0.011 mmol) in one portion as a solid. After 5 minutes, the ice bath was removed and the reaction mixture was allowed to warm to room temperature with stirring overnight. The solvent was removed in vacuo, and the resultant yellow oil was purified by flash column chromatography (from 4:1 ethyl acetate/hexane to 9:1 DCM/methanol) to give bis-THF methylenedioxybenzenesulfonamide propylmorpholine tethered product (Compound 49) (0.0045 g, 69%) as a yellow oil: R$_f$ 0.50 (9:1 DCM/methanol); 3H NMR (CDCl$_3$) 7.36-7.30 (1H, m), 7.19 (1H, s), 7.13 (2H, d, J=8.4 Hz), 6.91 (1H, d, J=8.3 Hz), 6.82 (2H, d, J=8.3 Hz), 6.11 (2H, s), 5.67 (1H, d, J=5.1 Hz), 5.19-5.08 (1H, dd, J=13.6, 6.1 Hz), 4.92 (1H, d, J=9.0 Hz), 4.07-3.92 (4H, m), 3.92-3.65 (8H, m), 3.19-3.08 (1H, m), 3.05-2.85 (4H, m), 2.85-2.71 (2H, m), 2.71-2.43 (6H, m), 2.13-1.94 (2H, m), 1.94-1.77 (1H, m), 1.77-1.49 (2H, m), 0.95 (3H, d, J=6.5 Hz), 0.90 (3H, d, J=6.7 Hz), OH signal not observed; coupled LCMS showed the product as a single major peak with m/z 720 [M+H]$^+$; HPLC (205 nm) showed the material as a single major peak at R$_T$ of 1-90 min. (purity=93%).

Example 27

Boc Benzothiazole Sulfonamide Benzyl Ether
(Compound 5g, Scheme 1)

The isobutylamino alcohol (0.50 g, 1.13 mmol) was combined with 2-aminobenzothiazole-6-sulfonyl chloride (0.373 g, 1.50 mmol) in anhydrous DCM (10 mL) under a N$_2$-atmosphere. Diisopropylethylamine (0.59 mL, 3.39 mmol) was added dropwise, and the reaction was stirred at room temperature for 42 hours. The solvent was removed in vacuo, and the resultant yellow oil was purified by flash column chromatography (4:1 ethyl acetate/hexane) to give Boc benzothiazole sulfonamide benzyl ether (5: D=i-Bu, E=2-aminobenzothiazole) (0.30 g, 42%) as a white solid: $R_f$=0.60 (4:1 ethyl acetate/hexane); $^1$H NMR (CDCl$_3$): 8.05 (1H, d, J=1.8 Hz), 7.72 (1H, dd, J=8.6, 1.8 Hz), 7.60 (1H, d, J=8.6 Hz), 7.49-7.32 (5H, m), 7.19 (2H, d, J=8.6 Hz), 6.94 (2H, d, J=8.6 Hz), 5.67 (2H, br.s, NH$_2$), 5.07 (2H, s), 4.70 (1H, br.d, J=7.7 Hz), 4.00 (1H, br.s, OH), 3.89-3.80 (1H, m), 3.80-3.66 (1H, m), 3.23-3.06 (2H, m), 3.06-2.77 (4H, m), 1.89 (1H, septet, J=7.2 Hz), 1.38 (9H, s), 0.94 (3H, d, J=6.3 Hz), 0.90 (3H, d, J=6.3 Hz).

Example 28

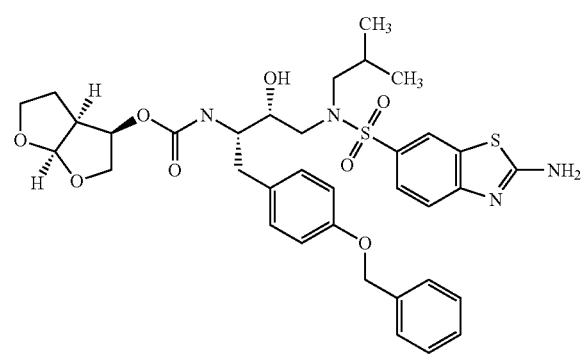 [SMILES: CC(C)CN(C[C@@H](O)[C@H](Cc1ccc(OCc2ccccc2)cc1)NC(=O)O[C@H]1CO[C@H]2OCC[C@H]21)S(=O)(=O)c1ccc2nc(N)sc2c1]

Bis-THF Benzothiazolesulfonamide Benzyl Ether (Compound 44)

Boc benzothiazole sulfonamide benzyl ether (Compound 5, Scheme 1: D'=i-Bu, E=2-aminobenzothiazole) (0.30 g, 0.46 mmol) was dissolved in DCM (10 mL). Trifluoroacetic acid (5 mL) was added dropwise, and the reaction was stirred at room temperature for 1 hour. The solvent was removed in vacuo, and the resultant orange oil was dissolved in DCM (15 mL). Triethylamine (1.28 mL, 9.20 mmol) was added dropwise with stirring, followed by (3R, 3aS,6aR) hexahydrofuro[2,3-b]furan-2-yl 4-nitrophenyl carbonate (0.149 g, 0.50 mmol) in one portion as a solid. The reaction mixture was allowed to stir at room temperature overnight. The solvent was removed in vacuo, and the resultant yellow oil was purified by flash column chromatography (ethyl acetate) to give bis-THF benzothiazole sulfonamide benzyl ether (Compound 44) (0.158 g, 48%) as a white solid: $R_f$=0.50 (ethyl acetate); $^1$H NMR (CDCl$_3$): 8.03 (1H, s), 7.71 (1H, d, J=8.6 Hz), 7.58 (1H, d, J=8.6 Hz), 7.48-7.32 (5H, m), 7.15 (2H, d, J=8.1 Hz), 6.91 (2H, d, J=8.6 Hz), 5.93 (2H, br.s, NH$_2$) 5.67 (1H, d, J=5.4 Hz), 5.16 (1H, d, J=8.6 Hz), 5.04 (2H, s), 4.05-3.60 (7H, m), 3.27-3.15 (1H, m), 3.12-2.97 (4H, m), 2.97-2.83 (2H, m), 2.78 (1H, dd, J=14.3, 8.8 Hz), 1.95-1.48 (3H, m), 0.96 (3H, d, J=6.8 Hz), 0.92 (3H, d, J=6.8 Hz); coupled LCMS showed the product as a single major peak with m/z 712 [M+H]$^+$; HPLC (205 nm) showed the material as a single major peak at $R_T$ of 2.26 min. (purity=100%).

Example 29

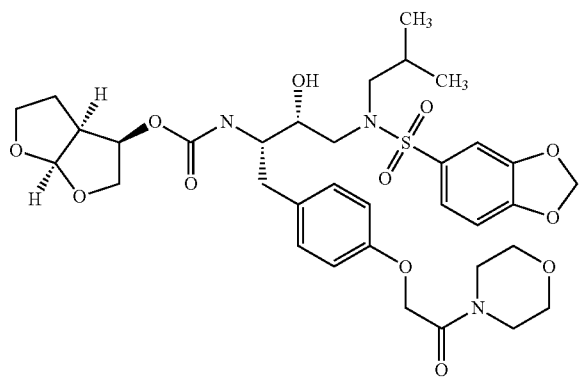 [SMILES: CC(C)CN(C[C@@H](O)[C@H](Cc1ccc(OCC(=O)N2CCOCC2)cc1)NC(=O)O[C@H]1CO[C@H]2OCC[C@H]21)S(=O)(=O)c1ccc2c(c1)OCO2]

Bis-THF Methylenedioxybenzenesulfonamide Acetylmorpholine Tethered Product (50)

Boc methylenedioxybenzenesulfonamide acetylmorpholine tethered product (21) (0.027 g, 0.041 mmol) was dissolved in DCM (2 mL). Trifluoroacetic acid (1 mL) was added dropwise, and the reaction was stirred at room temperature for 1 hour. The solvent was removed in vacuo, and the resultant orange oil was dissolved in DCM (1.5 mL) and the solution cooled to 0° C. using an ice bath. Diisopropylethylamine (0.21 mL, 1.22 mmol) was added dropwise with stirring, followed by (3R,3aS,6aR) hexahydrofuro[2,3-b]furan-2-yl 4-nitrophenyl carbonate (0.013 g, 0.045 mmol) in one portion as a solid. After 5 minutes, the ice bath was removed and the reaction mixture was allowed to warm to room temperature with stirring overnight. The solvent was removed in vacuo, and the resultant yellow oil was purified by flash column chromatography (ethyl acetate to methanol) to give bis-THF methylenedioxybenzenesulfonamide acetylmorpholine tethered product (50) (0.011 g, 38%) as a yellow foam: $R_f$=0.10 (ethyl acetate); $^1$H NMR (CDCl$_3$): 7.33 (1H, d, J=8.1 Hz), 7.20-7.08 (3H, m), 6.94-6.83 (3H, m), 6.09 (2H, s), 5.72-5.61 (1H, m), 5.10-4.97 (2H, m), 4.67 (2H, s), 4.02-3.92 (1H, m), 3.91-3.77 (3H, m), 3.76-3.56 (10H, m), 3.19-3.07 (1H, m), 3.06-2.88 (4H, m), 2.87-2.71 (2H, m), 1.89-1.75 (1H, m), 1.74-1.62 (1H, m), 1.61-1.48 (1H, m), 0.93 (3H, d, J=6.6 Hz), 0.89 (3H, d, J=6.6 Hz), OH signal not observed; coupled LCMS showed the product as a single major peak with m/z 720 [M+H]$^+$; HPLC (205 nm) showed the material as a single major peak at $R_T$ of 2.02 min. (purity=88%).

Example 32

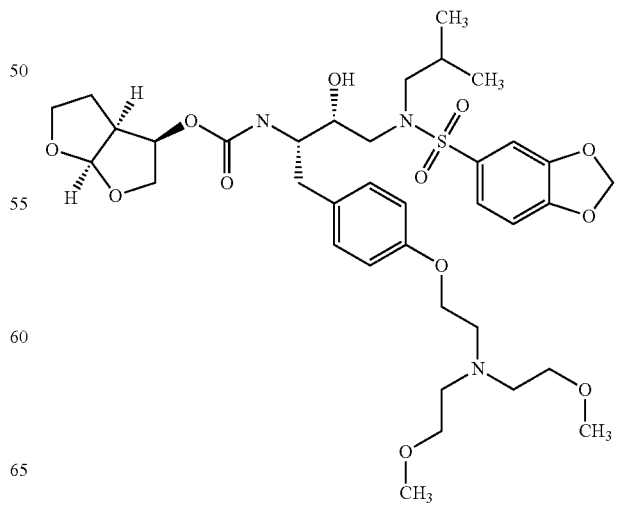

Bis-THF Methylenedioxybenzenesulfonamide
Bis-Methoxyethylamine Tethered Product (51)

Boc methylenedioxybenzenesulfonamide bis-methoxyethylamine tethered product (18) (0.023 g, 0.033 mmol) was dissolved in DCM (1 mL). Trifluoroacetic acid (0.5 mL) was added dropwise, and the reaction was stirred at room temperature for 1 hour. The solvent was removed in vacuo, and the resultant orange oil was dissolved in DCM (1 mL) and the solution cooled to 0° C. using an ice bath. Diisopropylethylamine (0.173 mL, 0.99 mmol) was added dropwise with stirring, followed by (3R,3aS,6aR) hexahydrofuro[2,3-b]furan-2-yl 4-nitrophenyl carbonate (0.012 g, 0.040 mmol) in one portion as a solid. After 5 minutes, the ice bath was removed and the reaction mixture was allowed to warm to room temperature with stirring overnight. The solvent was removed in vacuo, and the resultant yellow oil was purified by flash column:chromatography (4:1 ethyl acetate/hexane to ethyl acetate to 9:1 DCM/methanol) to give bis-THE methylenedioxybenzenesulfonamide bis-methoxyethylamine tethered product (51) (0.022 g, 89%) as a yellow foam: $R_f$=0.50 (9:1 DCM/methanol); $^1$H NMR (CDCl$_3$): 7.33 (1H, dd, J=8.2, 1.8 Hz), 7.17 (1H, d, J=1.8 Hz), 7.13 (2H, d, J=8.6 Hz) 6.89 (1H, d, J=8.2 Hz), 6.80 (2H, d, J=8.6 Hz), 6.09 (2H, s), 5.65 (1H, 8, J=5.2 Hz), 5.08-4.98 (2H, m), 4.35-4.24 (2H, m), 4.00-3.90 (1H, m), 3.90-3.63 (6H, m), 3.61-3.49 (2H, m), 3.42-3.31 (2H, m), 3.35 (6H, s), 3.16-3.07 (2H, m), 3.05-2.88 (4H, m), 2.88-2.74 (2H, m), 1.83 (1H; septet, J=6.6 Hz), 1.74-1.54 (1H, m), 1.48-1.35 (5H, m); 0.92 (3H, d, J=6.6 Hz), 0.88 (3H, d, J=6.6 Hz), OH signal not observed; coupled LCMS showed the product as a single major peak with m/z 752 [M+H]$^+$; HPLC (205 nm) showed the material as a single major peak at $R_T$ of 1.92 min. (purity=91%).

Example 33

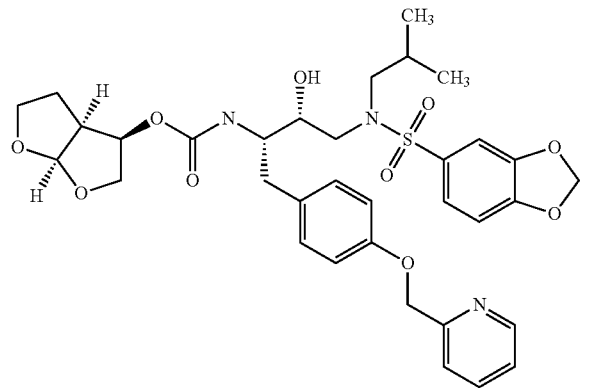 [SMILES: CC(C)CN(C[C@@H](O)[C@H](Cc1ccc(OCc2ccccn2)cc1)NC(=O)O[C@H]1CO[C@H]2OCC[C@H]21)S(=O)(=O)c1ccc2c(c1)OCO2]

Bis-THF Methylenedioxybenzenesulfonamide
2-picolyl Tethered Product (53)

Boc methylenedioxybenzenesulfonamide 2-picolyl tethered product (0.004 g, 0.006 mmol) was dissolved in DCM (0.6 mL). Trifluoroacetic acid (0.3 mL) was added dropwise, and the reaction was stirred at room temperature for 45 minutes. The solvent was removed in vacuo, and the resultant orange oil was dissolved in DCM (1.5 mL). Diisopropylethylamine (0.060 mL, 0.33 mmol) was added dropwise with stirring at room temperature, followed by (3R,3aS,6aR) hexahydrofuro[2,3-b]furan-2-yl 4-nitrophenyl carbonate (0.005 g, 0.017 mmol) in one portion as a solid. The yellow reaction mixture was stirred at room temperature overnight. The solvent was removed in vacuo, and the resultant yellow oil was purified by flash column chromatography (from 2:3 ethyl acetate/hexane to 5:1 ethyl acetate/methanol) to give bis-THF methylenedioxybenzenesulfonamide 2-picolyl tethered product (53) (0.0013 g, 30%) as a pale yellow oil: $R_f$=0.35 (5:1 ethyl acetate/methanol); $^1$H NMR (CDCl$_3$): 8.62-8.57 (1H, m), 7.75-7.70 (1H, m), 7.55-7.48 (1H, m), 7.34 (1H, dd, J=8.1, 1.8 Hz), 7.28-7.20 (1H, obscured m), 7.17-7.10 (3H, m), 6.93-6.87 (3H, m), 6.08 (2H, s), 5.65 (1H, d, J=5.0 Hz), 5.17 (2H, br. s), 5.07-5.01 (1H, m), 4.95-4.89 (1H, m), 4.01-3.93 (1H, m), 3.89-3.80 (3H, m), 3.76-3.67 (1H, m), 3.62-3.58 (1H, m), 3.18-3.09 (1H, m), 3.04-2.87 (4H, m), 2.83-2.73 (2H, m), 1.88-1.79 (1H, m), 1.70-1.47 (2H, obscured m), 0.93 (3H, d, J=6.3 Hz), 0.89 (3H, d, J=6.3 Hz), OH signal not observed; coupled LCMS showed the product as a single major peak with m/z 684 [M+H]$^+$; integrated LCMS (205 nm) showed the material as a single major peak at $R_T$ of 2.15 min. (purity=93%).

Example 34

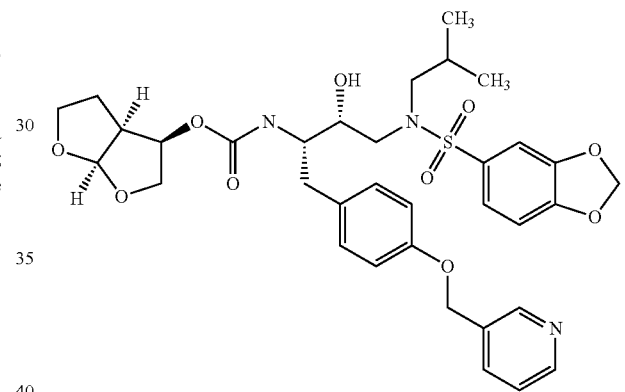

Bis-THF Methylenedioxybenzenesulfonamide
3-picolyl Tethered Product (52)

Boc methylenedioxybenzenesulfonamide 3-picolyl tethered product (0.004 g, 0.006 mmol) was dissolved in DCM (0.6 mL). Trifluoroacetic acid (0.3 mL) was added dropwise, and the reaction was stirred at room temperature for 45 minutes. The solvent was removed in vacuo, and the resultant orange oil was dissolved in DCM (1 mL).

Diisopropylethylamine (0.030 mL, 0.19 mmol) was added dropwise with stirring at room temperature, followed by (3R, 3aS,6aR) hexahydrofuro[2,3-b]furan-2-yl 4-nitrophenyl carbonate (0.003 g, 0.009 mmol) in one portion as a solid. The yellow reaction mixture was stirred at room temperature overnight. The solvent was removed in vacuo, and the resultant yellow oil was purified by flash column chromatography (2:3 ethyl acetate/hexane) to give bis-THF methylenedioxybenzenesulfonamide 3-picolyl tethered product (52) as a pale yellow oil (0.0012 g; an inseparable mixture with alkylated oxazolidinone): $R_f$=0.20 (ethyl acetate); $^1$H NMR (CDCl$_3$): 8.68 (1H, br. s), 8.63-8.56 (1H, m), 7.81-7.74 (1H, m), 7.39-7.30 (1H, obscured m), 7.34 (1H, dd, J=8.2, 1.8 Hz), 7.22-7.12 (3H, m), 6.94-6.85 (1H, obscured m), 6.90 (2H, d, J=8.6 Hz), 6.09 (2H, s), 5.67 (1H, d, J=5.5 Hz), 5.05 (2H, br. s), 4.95 (1H, d, J=8.6 Hz), 4.03-3.92 (1H, m), 3.91-3.79 (3H, m), 3.76-3.67 (2H, m), 3.67-3.63 (1H, m), 3.24-3.07 (2H, m), 3.05-2.85 (4H, m), 2.84-2.76 (1H, m), 1.91-1.78 (1H, m), 1.77-1.46 (2H, obscured m), 0.91-0.85 (6H, m), OH signal not observed; coupled LCMS showed the products (alkylated bis-THF derivative/alkylated oxazolidinone) as a single major peak with m/z 684 [M+H]$^+$; integrated LCMS (204.5 nm) showed the materials (alkylated bis-THF derivative/alkylated oxazolidinone) as a single major peak at R$_T$ of 2.03 min. (combined purity=80%; desired material and alkylated oxazolidinone).

Example 32

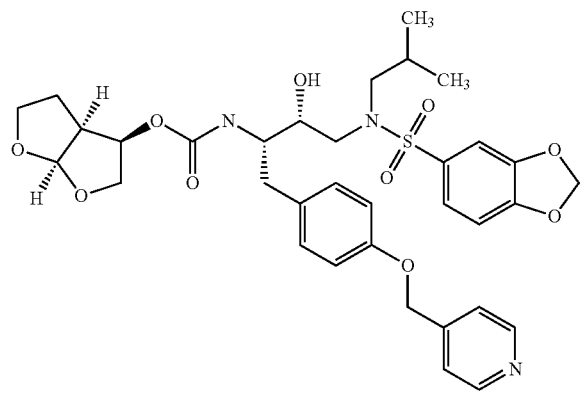 [SMILES: CC(C)CN(C[C@@H](O)[C@H](Cc1ccc(OCc2ccncc2)cc1)NC(=O)O[C@H]1CO[C@H]2OCC[C@H]21)S(=O)(=O)c1ccc2c(c1)OCO2]

Bis-THF Methylenedioxybenzenesulfonamide 4-picolyl Tethered Product (54)

Boc methylenedioxybenzenesulfonamide 4-picolyl tethered product (0.004 g, 0.006 mmol) was dissolved in DCM (0.3 mL). Trifluoroacetic acid (0.1 mL) was added dropwise, and the reaction was stirred at room temperature for 45 minutes. The solvent was removed in vacuo, and the resultant orange oil was dissolved in DCM (1 mL). Diisopropylethylamine (0.030 mL, 0.19 mmol) was added dropwise with stirring at room temperature, followed by (3R,3aS,6aR) hexahydrofuro[2,3-b]furan-2-yl 4-nitrophenyl carbonate (0.003 g, 0.009 mmol) in one portion as a solid. The yellow reaction mixture was stirred for 7 hours at room temperature. The solvent was removed in vacuo, and the resultant yellow oil was purified by flash column chromatography (2:3 ethyl acetate/hexane to 5:1 ethyl acetate/methanol) to give bis-THF methylenedioxybenzenesulfonamide 4-picolyl tethered product (54) as a pale yellow oil (0.0015 g; an inseparable mixture with alkylated oxazolidinone): R$_f$=0.40 (5:1 ethyl acetate/methanol); coupled LCMS showed the products (alkylated bis-THF derivative/alkylated oxazolidinone) with m/z 684 [M+H]$^+$; HPLC (205 nm) showed the materials (alkylated bis-THF derivative/alkylated oxazolidinone) as a peak at R$_T$ Of 1.97 min. (combined purity=60%; desired material and alkylated oxazolidinone).

Example 36

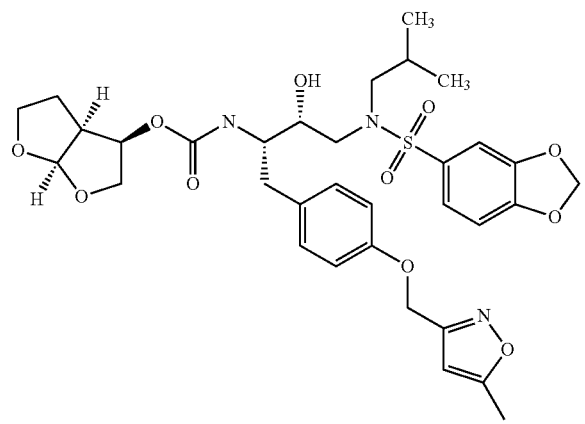 [SMILES: Cc1cc(COc2ccc(C[C@H](NC(=O)O[C@H]3CO[C@H]4OCC[C@H]43)[C@H](O)CN(CC(C)C)S(=O)(=O)c3ccc4c(c3)OCO4)cc2)no1]

Bis-THF Methylenedioxybenzenesulfonamide 3-methyl-5-methylisoxazole Tethered Product (55)

Boa methylenedioxybenzenesulfonamide 3-methyl-5-methylisoxazole tethered product (0.005 g, 0.008 mmol) was dissolved in DCM (0.3 mL). Trifluoroacetic acid (0.1 mL) was added dropwise, and the reaction was stirred at room temperature for 45 minutes. The solvent was removed in vacuo, and the resultant orange oil was dissolved in DCM (1.5 mL). Diisopropylethylamine (0.040 mL, 0.24 mmol) was added dropwise with stirring at room temperature, followed by (3R,3aS,6aR) hexahydrofuro[2,3-b]furan-2-yl 4-nitrophenyl carbonate (0.004 g, 0.012 mmol) in one portion as a solid. The yellow reaction mixture was stirred for 9 hours at room temperature. The solvent was removed in vacuo, and the resultant yellow oil was purified by flash column chromatography (from ethyl acetate to 5:1 ethyl acetate/methanol) to give bis-THF methylenedioxybenzenesulfonamide 3-methyl-5-methylisoxazole tethered product (55) (0.005 g, 97%) as a pale yellow oil: R$_f$=0.50 (5:1 ethyl acetate/methanol); $^1$H NMR (CDCl$_3$): 7.33 (1H, dd, J=8.2, 1.4 Hz), 7.17-7.10 (3H, m), 6.91-6.86 (3H, m), 6.09 (3H, br. s), 5.65 (1H, d, J=5.0 Hz), 5.06 (2H, s), 4.94 (1H, d, J=8.7 Hz), 4.00-3.92 (2H, m), 3.88-3.79 (3H, m), 3.74-3.66 (2H, m), 3.64-3.58 (1H, m), 3.17-3.07 (1H, m), 3.03-2.87 (4H, m), 2.82-2.71 (2H, m), 2.42 (3H, s), 1.86-1.76 (1H, m), 1.70-1.49 (2H, m), 0.93 (3H, d, J=6.6 Hz), 0.88 (3H, d, J=6.6 Hz); coupled LCMS showed the product as a single major peak with m/z 688 [M+H]; HPLC (205 nm) showed the material as a single major peak at R$_T$ of 2.38 min. (purity=82%).

Example 37

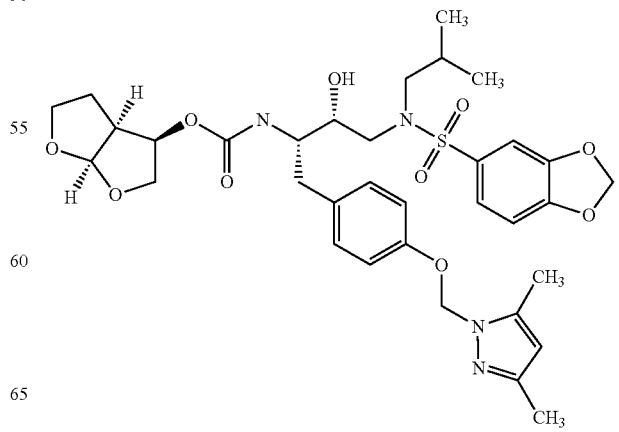

Bis-THF Methylenedioxybenzenesulfonamide 1-methyl-3,5-dimethylpyrazole Tethered Product (56)

Boc methylenedioxybenzenesulfonamide 1-methyl-3,5-dimethylpyrazole tethered product (0.003 g, 0.005 mmol) was dissolved in DCM (0.15 mL). Trifluoroacetic acid (0.05 mL) was added dropwise, and the reaction was stirred at room temperature for 45 minutes. The solvent was removed in vacuo, and the resultant orange oil was dissolved in DCM (1 mL). Diisopropylethylamine (0.030 mL, 0.18 mmol) was added dropwise with stirring at room temperature, followed by (3R,3aS,6aR) hexahydrofuro[2,3-b]furan-2-yl 4-nitrophenyl carbonate (0.002 g, 0.007 mmol) in one portion as a solid. The yellow reaction mixture was stirred for 9 hours at room temperature. The solvent was removed in vacuo, and the resultant yellow oil was purified by flash column chromatography (1:1 ethyl acetate/hexane) to give bis-THF methylenedioxybenzenesulfonamide 1-methyl-3,5-dimethylpyrazole tethered product (56) (0.001 g, 31%) as a colourless oil: $R_f$=0.50 (ethyl acetate); coupled LCMS showed the product as a single major peak with m/z 701 [M+H]$^+$; integrated LCMS (204.5 nm) showed the material as a single major peak at $R_T$ of 1.52 min. (purity=91%).

Example 38

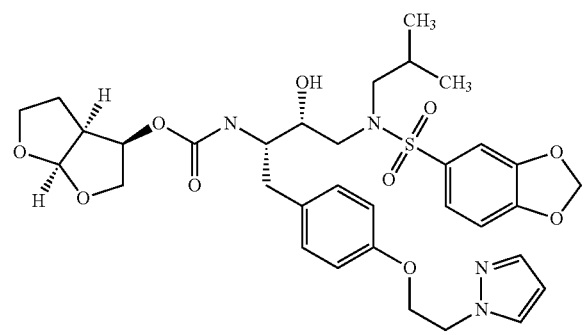 [SMILES: CC(C)CN(C[C@@H](O)[C@H](Cc1ccc(OCCn2cccn2)cc1)NC(=O)O[C@H]1CO[C@H]2OCC[C@H]21)S(=O)(=O)c1ccc2c(c1)OCO2]

Bis-THF Methylenedioxybenzenesulfonamide Ethylpyrazole Tethered Product (57)

Boc methylenedioxybenzenesulfonamide ethylpyrazole tethered product (0.003 g, 0.005 mmol) was dissolved in DCM (0.15 mL). Trifluoroacetic acid (0.05 mL) was added dropwise, and the reaction was stirred at room temperature for 45 minutes. The solvent was removed in vacuo, and the resultant orange oil was dissolved in DCM (1 mL). Diisopropylethylamine (0.030 mL, 0.18 mmol) was added dropwise with stirring at room temperature, followed by (3R,3aS,6aR) hexahydrofuro[2,3-b]furan-2-yl 4-nitrophenyl carbonate (0.002 g, 0.007 mmol) in one portion as a solid. The yellow reaction mixture was stirred for 9 hours at room temperature. The solvent was removed in vacuo, and the resultant yellow oil was purified by flash column chromatography (1:1 ethyl acetate/hexane) to give bis-THF methylenedioxybenzenesulfonamide ethylpyrazole tethered product (57) (0.001 g, 31%) as a colourless oil: $R_f$=0.30 (ethyl acetate); coupled LCMS showed the product as a single major peak with m/z 687 [M+H]$^+$; integrated LCMS (204.5 nm) showed the material as a single major peak at $R_T$ of 1.49 min. (purity=94%).

Example 39

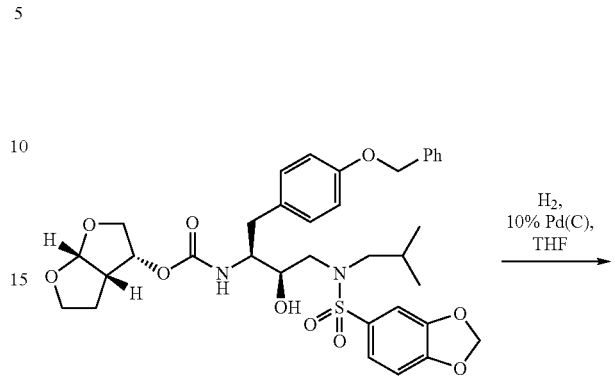

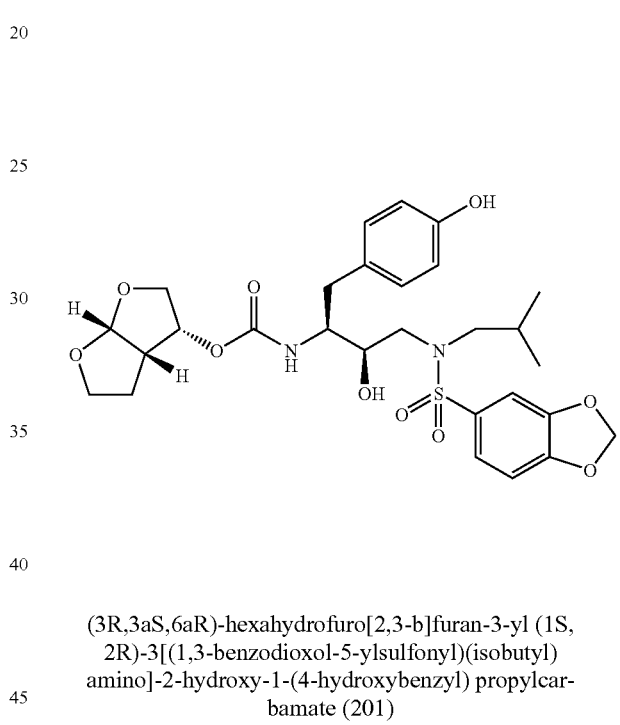

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-(4-hydroxybenzyl) propylcarbamate (201)

A solution of 8.00 g (11.7 mmol) of (3R,3aS,6aR)-hexahydrofuro[2,3-b]furan-3-yl (1S,2R)-3-[(1,3-benzodioxol-5-ylsulfonyl)(isobutyl)amino]-1-[4-(benzyloxy)benzyl]-2-hydroxypropylcarbamate in 200 mL of THF was subjected to hydrogenation at 50 psi in the presence of 8.0 g of 10% palladium on carbon (Degussa type). After 18 hours the reaction vessel was purged with nitrogen, catalyst removed by filtration through celite, and the filtrate concentrated at reduced pressure to a volume of 30 mL. The solution was rapidly stirred with addition of 30 mL of EtOAc followed by 250 mL of hexane. A white suspension resulted which was stirred at RT for 1 hour. The solid was collected by vacuum filtration and dried in vacuo to afford 6.83 g (98%) of the desired compound as a white powder. $^1$H NMR (DMSO-d$_6$): 9.00 (s, 1H), 7.25 (d, 1H), 7.17 (s, 1H), 7.12 (d, 1H), 7.01 (d, 1H), 6.92 (d, 2H), 6.52 (d, 2H), 6.12 (s, 2H), 5.46 (d, 1H), 4.93 (d, 1H), 4.80 (q, 1H), 3.80 (dd, 1H), 3.70 (t, 1H), 3.52 (m, 3H), 3.40 (m, 1H), 3.25 (m, 1H), 3.01-2.62 (m, 5H), 2.28 (t, 1H), 1.89 (m, 1H), 1.38 (m, 1H), 1.22 (m, 1H), 0.80 (d, 3H), 0.72 (d, 3H). MS(ESI): 593(M+H).

Example 40

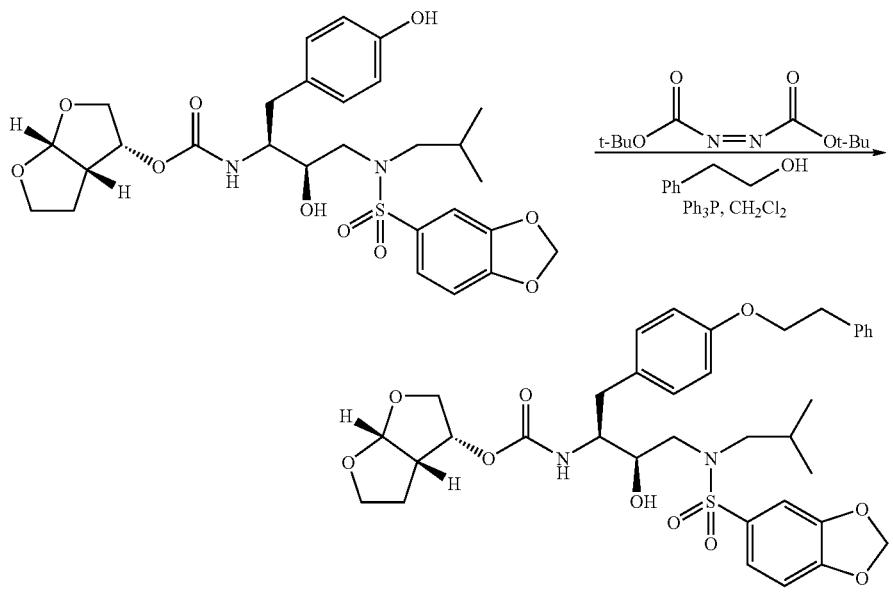

(3R,3aS,6aR)hexahydrofuro[2,3-b]furan-3-yl (1S, 2R)-3-[(1,3-benzodioxol-5-ylsulfonyl)(isobutyl) amino]-2-hydroxy-1-[4-(phenethyloxy)benzyl]propylcarbamate (202)

To a solution of 66 mg (0.25 mmol) of triphenylphosphine and 30 µL (0.25 mmol) of phenethyl alcohol in 3 mL of anhydrous $CH_2Cl_2$ was added 58 mg (0.25 mmol) of di-tert-butyl azodicarboxylate. The resulting solution was stirred at RT for 5 minutes and was then treated with a solution of 50 mg (0.084 mmol) of (3R,3aS,6aR)hexahydrofuro[2,3-b]furan-3-yl (1S,2R)-3-[(1,3-benzodioxol-5-ylsulfonyl)(isobutyl) amino]-2-hydroxy-1-(4-hydroxybenzyl)propylcarbamate in 2 mL of $CH_2Cl_2$. After stirring at RT for 1.5 hours the solution was concentrated to dryness and the residue purified by flash chromatography ($SiO_2$, 4:6 hexane/EtOAc) to give the desired product as a white foam in 72% yield, $^1$H NMR ($CDCl_3$): 7.34-7.17 (m, 6H), 7.15 (s, 1H), 7.07 (d, 2H), 6.86 (d, 1H), 6.78 (d, 2H), 6.03 (s, 2H), 5.61 (d, 1H) 4.98 (m, 1H), 4.86 (d, 1H), 4.09 (t, 2H), 3.92 (m, 1H), 3.84-3.56 (m, 6H), 3.17-3.01 (m, 3H), 3.00-2.81 (m, 4H), 2.80-2.64 (m, 2H), 1.78 (m, 1H), 1.56 (m, 1H), 1.47 (m, 1H), 0.91 (d, 3H), 0.85 (d, 3H). MS(ESI): 697(M+H).

Example 41

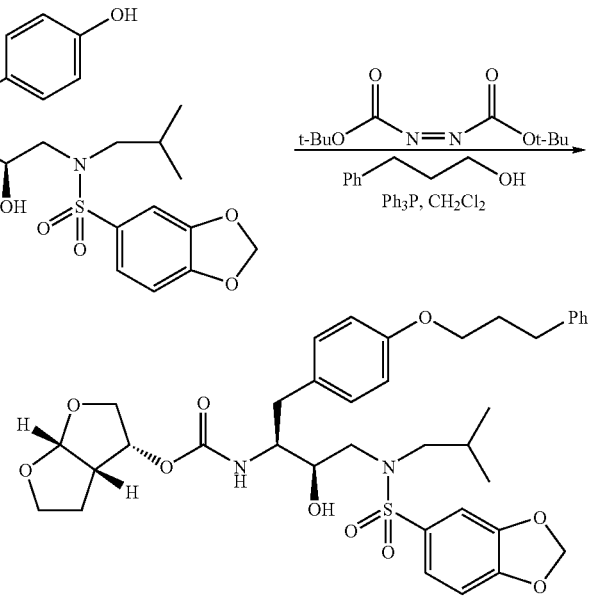

(3R,3aS,6aR)hexahydrofuro[2,3-b]furan-3-yl (1S,2R)-3-[(1,3-benzodioxol-5-ylsulfonyl)(isobutyl)amino]-2-hydroxy-1-[4-([3-phenylpropyl]oxy)benzyl]propylcarbamate (203)

The title compound was prepared according to example 202 with the exception that 3-phenyl-1-propanol was used instead of phenethyl alcohol. ¹H NMR (CDCl₃): 7.33-7.11 (m, 7H), 7.07 (d, 2H), 6.86 (d, 1H), 6.76 (d, 2H), 6.04 (s, 2H), 5.61 (d, 1H), 4.99 (q, 1H), 4.86 (d, 1H), 3.97-3.72 (m, 7H), 3.65 (m, 2H), 3.09 (dd, 1H), 3.01-2.81 (m, 4H), 2.80-2.64 (m, 4H), 2.06 (m, 2H), 1.85-1.40 (m, 3H), 0.91 (d, 3H), 0.84 (d, 3H). MS ESI): 711(M+H).

Example 42

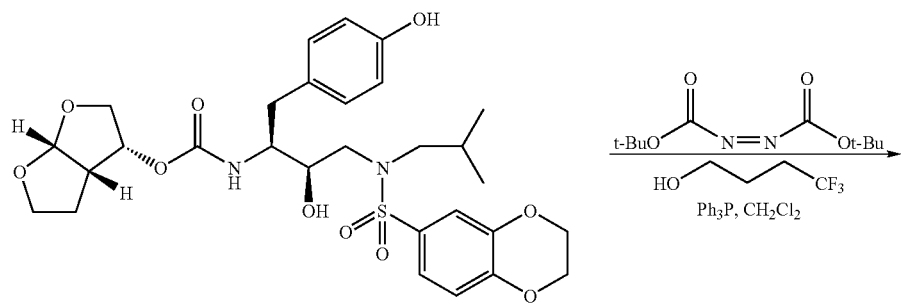

(3R,3aS,6aR)-hexahydrofuro[2,3-b]furan-3-yl (1S,2R)-3-[(2,3-dihydro-1,4-benzodioxin-6-ylsulfonyl)(isobutyl)amino]-2-hydroxy-1-[4-(4,4,4-trifluorobutoxy)benzyl]propylcarbamate (204)

The title compound was prepared according to example 202 with the exception that 4,4,4-trifluorobutanol was used instead of phenethyl alcohol. ¹H NMR (CDCl₃): 7.28-7.16 (m, 2H), 7.08 (d, 2H), 6.91 (d, 1H), 6.75 (d, 2H), 5.61 (d, 1H), 5.04-4.85 (m, 2H), 4.25 (m, 4H), 3.91 (m, 3H), 3.88-3.51 (m, 9H), 3.07 (m, 1H), 3.10-2.82 (m, 4H), 2.81-2.65 (m, 2H), 2.26 (m, 2H), 2.00 (m, 2H), 1.84-1.43 (m, 3H), 0.90 (d, 3H), 0.82 (d, 0.3H). MS(ESI): 717(M+H).

Example 43

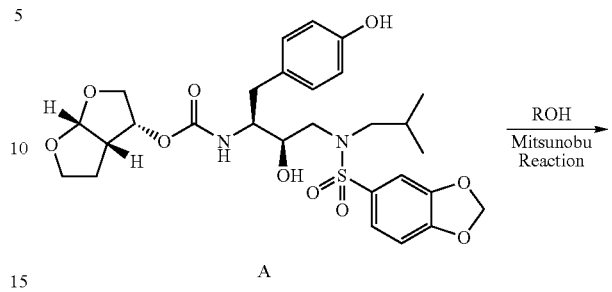

A

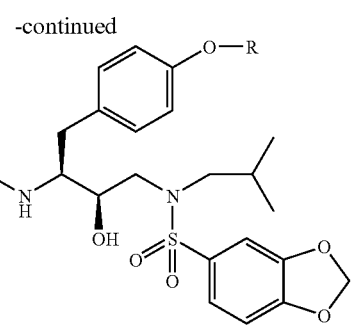

-continued

General Procedure for Mitsunobu Alkylations of Phenol Scaffold a with Various Alcohols (205-218)

A solution of 2-5 equivalents each of triphenylphosphine and the appropriate alcohol in anhydrous dichloromethane (typically at a concentration of 0-05 M) was treated with di-t-butyl azodicarboxylate (2-5 equivalents). Polymer supported triphenylphosphine (Aldrich Chemical) was employed for examples 15-18 to facilitate removal of the triphenylphosphine oxide by-product. After stirring at RT for 5 minutes the solution was treated with 1 equivalent of solid (3R,3aS,6aR)hexahydrofuro[2,3b]furan-3-yl (1S,2R)-3-[(1,3-benzodioxol-5-ylsulfonyl)(isobutyl)amino]-2-hydroxy-1-(4-hydroxybenzyl)propylcarbamate and stirring at RT was continued. When the reaction was determined to be complete by thin layer chromatography (2-18 hours) the solution was concentrated in vacuo and the residue purified by flash chromatography (silica gel, hexane/EtOAc or dichloromethane/2M $NH_3$ in MeOH) to afford the desired product.

Mass Spectral Data for Compounds 205-218:

| Example | R | MS (ESI) |
|---|---|---|
| 205 | 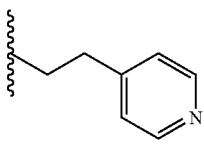 | 715 (M + H) |
| 206 | 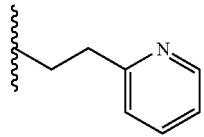 | 727 (M + H) |
| 207 | 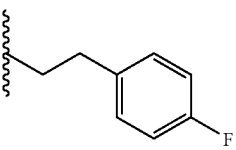 [SMILES: *CCc1ccc(F)cc1] | 689 (M + H) |
| 208 | 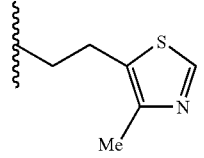 | 703 (M + H) |
| 209 | 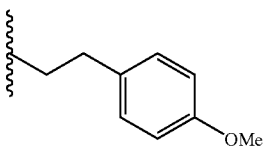 [SMILES: *CCc1ccc(OC)cc1] | 703 (M + H) |
| 210 | 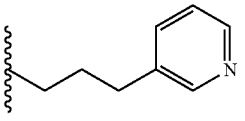 [SMILES: *CCCc1cccnc1] | 673 (M + H) |
| 211 | 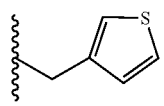 | 698 (M + H) |
| 212 | 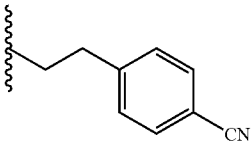 [SMILES: *CCc1ccc(C#N)cc1] | 698 (M + H) |
| 213 | 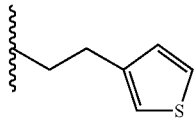 | 718 (M + H) |
| 214 | 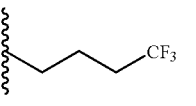 [SMILES: *CCCC(F)(F)F] | 712 (M + H) |
| 215 | 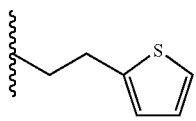 | 722 (M + H) |
| 216 | 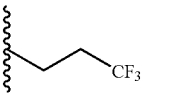 [SMILES: *CCC(F)(F)F] | 703 (M + H) |
| 217 | 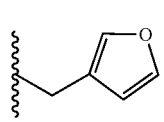 | 689 (M + H) |
| 218 | 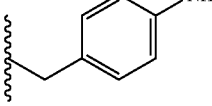 | 698 (M + H) |

Proton NMR Data for Selected Compounds from the Above Table:

Example (Compound 209) $^1$H NMR (CDCl$_3$): 7.28 (d, 1H), 7.17-7.04 (m, 4H), 6.95-6.76 (m, 5H), 6.03 (so 2H), 5.61 (d, 1H); 5.00 (q, 1H), 4.85 (d, 1H), 4.10 (t, 2H), 3.92 (dd, 1H), 3.79 (m, 3H), 3.71-3.48 (m, 3H), 3.24 (to 2H), 3.10 (m, 1H), 3.01-2.82 (m, 4H), 2.72 (m, 2H), 1.78 (m, 1H), 1.65-1.42 (m, 2H), 0.90 (d, 3H), 0.84 (d, 3H).

Example (Compound 211) $^1$H NMR (CDCl$_3$): 8.53 (br s, 2H) 7.28 (m, 3H), 7.13 (d, 1H), 7.09 (d, 2H), 6.84 (d, 1H), 6.76 (d, 2H), 6.03 (s, 2H), 5.61 (d, 1H), 5.01-4.85 (m, 2H), 4.15 (t, 2H), 3.92 (dd, 1H), 3.85-3.55 (m, 6H), 3.08 (m, 3H), 3.01-2.81 (m, 4H), 2.72 (m, 2H), 1.79 (m, 1H), 1.64-1.41 (m, 2H), 0.89 (d, 3H), 0.82 (d, 3H).

Example (Compound 213) $^1$H NMR (CDCl$_3$): 8.60 (s, 1H), 7.29 (d, 1H), 7.12 (s, 1H), 7.09 (s, 2H), 6.83 (d, 1H), 6.78 (d, 2H), 6.03 (s, 2H), 5.61 (d, 1H), 4.99 (q, 1H), 4.89 (d, 1H), 4.05 (t, 2H), 3.92 (dd, 1H), 3.78 (m, 3H), 3.63 (m, 3H), 3.20 (t, 2H), 3.08 (m, 1H), 3.01-2.81 (m, 4H), 0.2-0.72 (m, 2H), 2.41 (s, 3H), 1.78 (m, 1H), 1.58 (m, 1H), 1.46 (m, 1), 0.89 (s, 3H), 0.82 (s, 3H).

Example (Compound 214) $^1$H NMR (CDCl$_3$): 8.42 (br s, 2H), 7.56 (d, 1H), 7.34-7.19 (m, 2H), 7.13 (s, 1H), 7.07 (d, 2H), 6.85 (d, 1H), 6.73 (d, 2H), 6.03 (s, 2H), 5.60 (d, 1H), 5.10-4.89 (m, 2H), 3.98-3.58 (m, 9H), 3.14-2.65 (m, 9H), 2.08 (m, 2H), 1.80 (m, 1H), 1.61 (m, 1H), 1.50 (m, 1H), 0.89 (d, 3H), 0.81 (d, 3H).

Example (Compound 215) $^1$H NMR (CDCl$_3$): 7.56 (d, 2H) t 7.35 (d, 2H), 7.27 (d, 1H), 7.14 (s, 1H), 7.07 (d, 2H), 6.83 (d, 1H), 6.73 (d, 2H), 6.02 (s, 2H), 5.61 (d, 1H), 4.98 (q, 1H), 4.89 (d, 1H), 4.12 (t, 2H), 3.97-3.58 (m, 7H), 3.08 (m, 3H), 3.01-2.81 (m, 4H), 2.81-2.63 (m, 2H), 1.79 (m, 1H), 1.62-1.38 (m, 2H), 0.89 (d, 3H), 0.83 (d, 3H).

Example (Compound 216) $^1$H NMR (CDCl$_3$): 7.38 (d, 1H), 7.21 (s, 1H), 7.17 (d, 2H), 6.94 (d, 1H), 6.84 (d, 2H), 6.12 (s, 1H), 5.69 (d, 1H), 5.13-4.92 (m, 2H), 4.01 (m, 3H), 3.88 (m, 3H), 3.74 (m, 3H), 3.16 (m, 1H), 3.10-2.89 (m, 4H), 2.81 (m, 2H), 2.43-2.20 (m, 2H), 2.08 (m, 2H), 1.94-1.50 (m, 3H), 0.98 (d, 3H), 0.92 (d, 3H).

Example (Compound 217) $^1$H NMR (CDCl$_3$): 7.29 (d, 1H), 7.12 (m, 3H), 6.84 (d, 1H), 6.79 (d, 2H), 6.04 (s, 2H), 5.62 (d; 1H), 5.00 (q, 1H), 4.89 (d, 1H), 4.12 (t, 2H), 3.92 (dd, 1H), 3.80 (m, 2H), 3.66 (m, 2H), 3.12 (dd, 1H), 3.01-2.83 (m, 4H), 2.75 (m, 2H), 2.56 (m, 2H), 1.83-1.44 (m, 5H), 0.91 (d, 3H), 0.83 (d, 3H).

Example 44

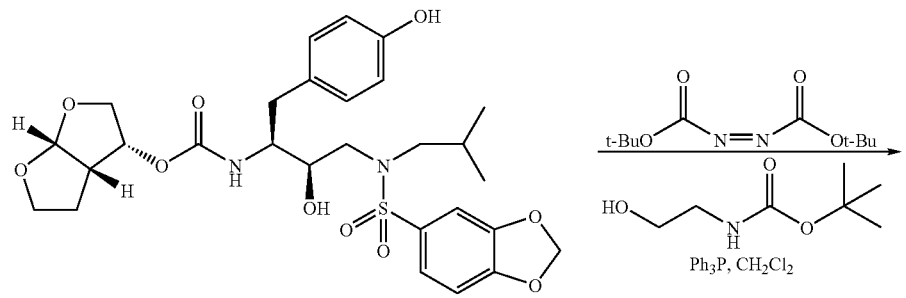

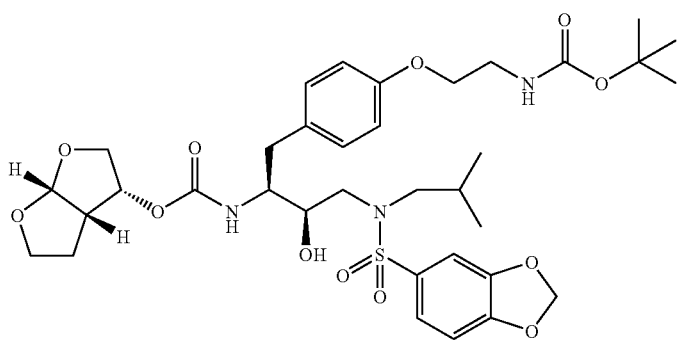

(3R,3aS,6aR)-hexahydrofuro[2,3-b]furan-3-yl (1S, 2R)-3-[(1,3-benzodioxol-5-ylsulfonyl)(isobutyl) amino]-1-(4-{2-[(tert-butoxycarbonyl)amino] ethoxy}benzyl)-2-hydroxypropylcarbamate (219)

The title compound was prepared according to example 202 with the exception that tert-butyl 2-hydroxyethylcarbamate was used instead of phenethyl alcohol. $^1$H NMR (CDCl$_3$): 7.30 (dd, 1H), 7.10 (m, 3H), 6.86 (d, 1H), 6.77 (d, 2H), 6.04 (s, 2H), 5.61 (d, 1H), 5.03-4.82 (m, 3H), 3.92 (m, 3H), 3.80 (m, 3H), 3.68 (m, 2H), 3.57 (s, in H), 3.48 (m, 2H) r 3.08 (dd, 1H), 2.92 (m, 4H), 2.75 (m, 2H), 1.78 (m, 1H), 1.64 (m, 1H), 1.41 (m, 10H), 0.90 (d, 31), 0.83 (d, 3H). MS(ESI): 736(M+H).

Example 45

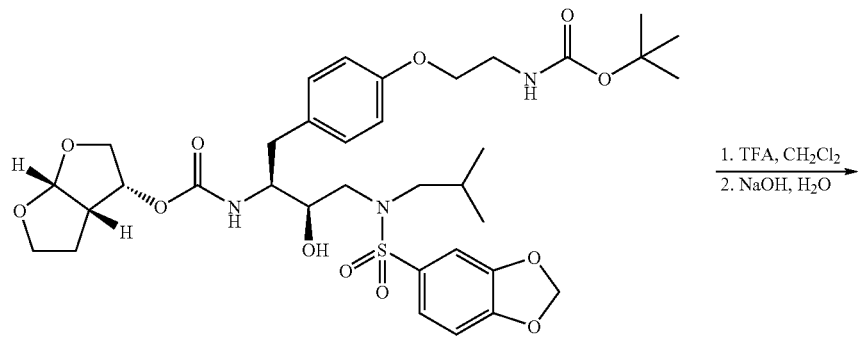

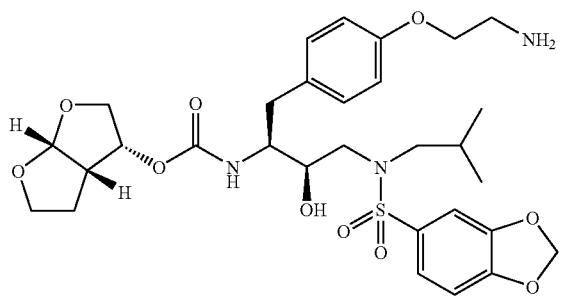

(3R,3aS,6aR)-hexahydrofuro[2,3-b]furan-3-yl (1S, 2R)-1-[4-(2-aminoethoxy)benzyl]-3-[(1,3-benzodioxol-5-ylsulfonyl)(isobutyl)amino]-2-hydroxypropylcarbamate (220)

A solution of 0.65 g (0.89 mmol) of (3R,3aS,6aR)-1-hexahydrofuro[2,3-b]furan-3-yl (1S,2R)-3-[(1,3-benzodioxol-5-ylsulfonyl)(isobutyl)amino]-1-(4-{2-[(tert-1-butoxycarbonyl)amino]ethoxy}benzyl)-2-hydroxypropylcarbamate in 10 mL of anhydrous $CH_2Cl_2$ was treated with 15 mL of TFA and the resulting solution was stirred at RT. After 2 hours the solution was evaporated at reduced pressure and the residue redissolved in $CH_2Cl_2$. The solution was washed with 0.5 M aqueous NaOH (1×), water (2×), dried over $MgSO_4$, and concentrated in vacuo. The crude product was purified by flash chromatography ($SiO_2$, 95:5 $CH_2Cl_2$/2M $NH_3$ in MeOH) to afford 0.40 g (70%) of the desired compound as a white foam. $^1$H NMR ($CDCl_3$): 7.39 (dd, 1H), 7.12 (s, 1H), 7.08 (d, 2H), 6.84 (d, 1H), 6.77 (d, 2H), 6.03 (s, 2H), 5.61 (d, 1H), 4.95 (m, 2H), 4.00-3.60 (m, 8H), 3.16-2.62 (m, 10H), 2.20-1.40 (m, 5H), 0.90 (d, 3H), 0.82 (d, 3H). MS(ESI): 636(M+H).

Example 46

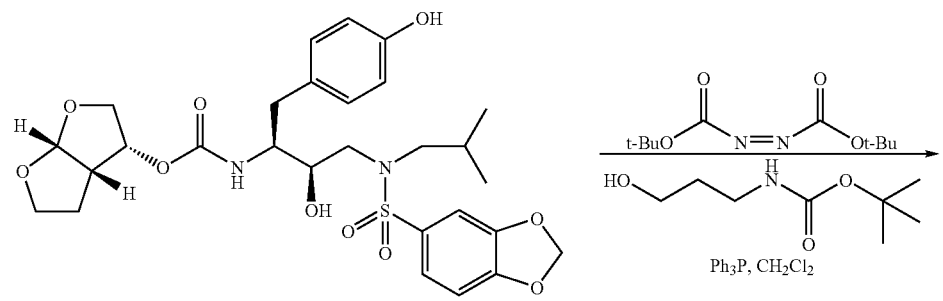

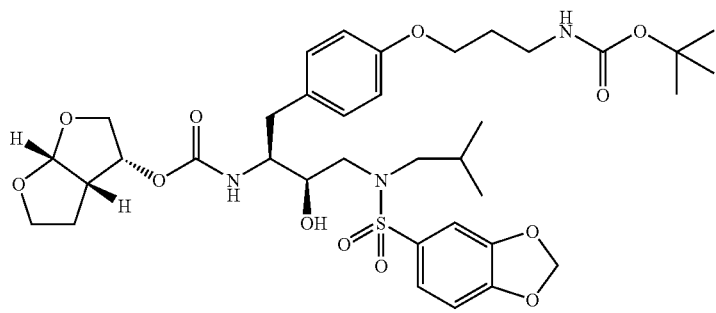

(3R,3aS,6aR)-hexahydrofuro[2,3-b]furan-3-yl (1S, 2R)-3-[(1,3-benzodioxol-5-ylsulfonyl)(isobutyl)amino]-1-(4-{3-[(tert-butoxycarbonyl)amino]propoxy}benzyl)-2-hydroxypropylcarbamate (221)

The title compound was prepared according to example 202 with the exception that tert-butyl 3-hydroxypropylcarbamate was used instead of phenethyl alcohol. $^1$H NMR (CDCl$_3$): 7.30 (d, 1H), 7.13 (s, 1H), 7.08 (d, 2H), 6.84 (d, 1H), 6.76 (d, 2H), 6.06 (s, 2H), 5.61 (d, 1H), 5.00 (q, 1H), 4.88 (d, 1H), 4.70 (br s, 1H) 3.93 (m, 3H), 3.80 (m, 4H), 3.67 (m, 2H), 3.26 (m, 2H), 3.09 (dd, 1H), 2.92 (m, 4H), 2.72 (m, 2H), 1.91 (m, 2H), 1.79 (m, 1H), 1.62 (m, 1H), 1.51 (m, 1H), 1.40 (s, 9H), 0.90 (d, 3H), 0.83 (d, 3H).). MS(ESI): 750(M+H).

(3R,3aS,6aR)-hexahydrofuro[2,3-b]furan-3-yl (1S, 2R)-1-[4-(3-aminopropoxy)benzyl]-3-[(1,3-benzodioxol-5-ylsulfonyl)(isobutyl)amino]-2-hydroxypropylcarbamate (222)

The title compound was prepared according to example 202.

$^1$H NMR (CDCl$_3$): 7.29 (d, 1H), 7.15 (s, 1H), 7.09 (d, 2H), 6.85 (d, 1H), 6.78 (d, 2H), 6.04 (s, 2H), 5.61 (d, 1H), 5.00 (m, 2H), 4.03-3.87 (m, 4H), 3.80 (m, 3H), 3.66 (m, 2H), 3.14-2.40 (m, 11H), 1.94 (m, 2H), 1.80 (m, 1H), 1.62 (m, 1H), 1.49 (m, 1H), 0.90 (d, 3H), 0.82 (d, 3H). MS(ESI): 650(M+H).

Example 47

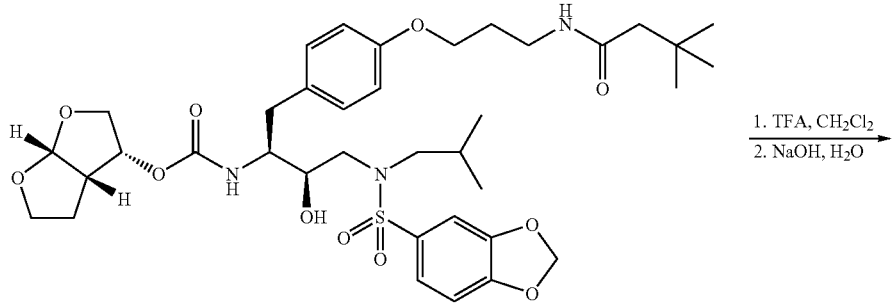

1. TFA, CH$_2$Cl$_2$
2. NaOH, H$_2$O

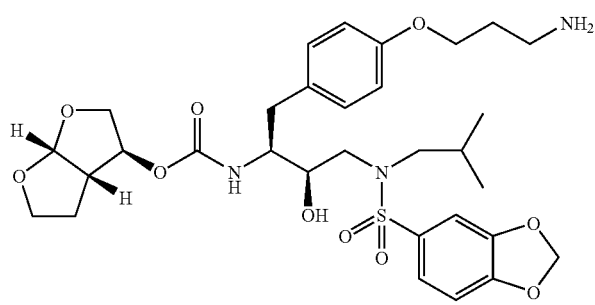

Example 48

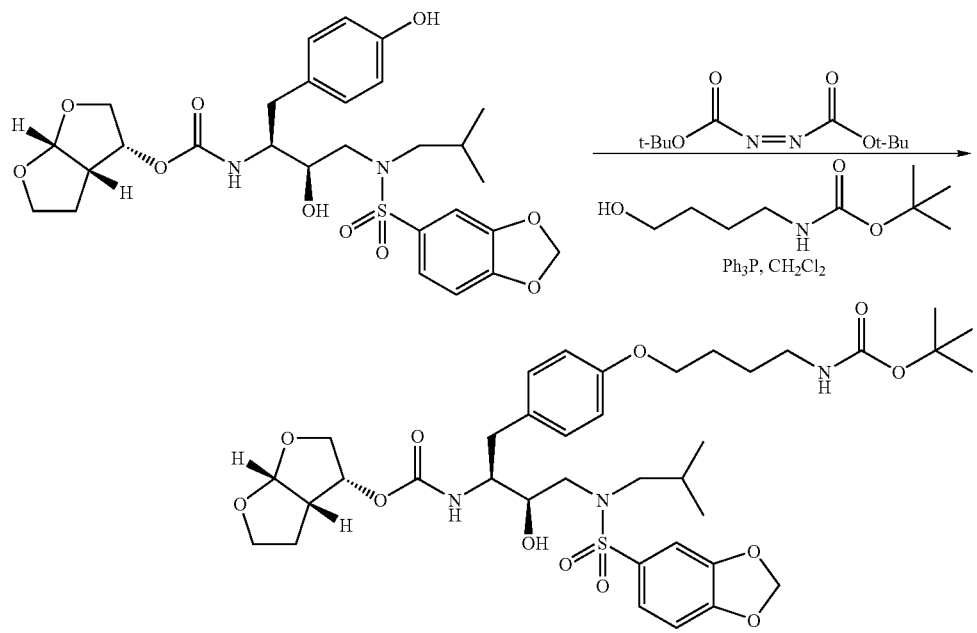

(3R,3aS,6aR)-hexahydrofuro[2,3-b]furan-3-yl (1S, 2R)-3-(1,3-benzodioxol-5-ylsulfonyl)(isobutyl) amino-1-(4-{4-[(tert-butoxycarbonyl)amino] butoxy}benzyl)-2-hydroxypropylcarbamate (223)

The title compound was prepared according to example 202 with the exception that tert-butyl 3 hydroxybutylcarbamate (prepared by reaction of 4-amino-1-butanol with di-tert-butyl-dicarbonate in $CH_2Cl_2$) was used instead of phenethyl alcohol. $^1H$ NMR ($CDCl_3$): 7.37 (d, 1H), 7.21 (s, 1H), 7.14 (d, 2H), 6.93 (d, 1H), 6.84 (d, 2H), 6.13 (s, 2H), 5.69 (d, 1H), 5.08 (q, 1H), 4.95 (d, 1H), 4.63 (br s, 1H), 4.08-3.63 (m, 9H), 3.30-2.72 (m, 9H), 1.96-1.40 (m, 0.1H), 0.97 (d, 3H), 0.90 (d, 3H). MS(ESI): 764(M+H).

Example 49

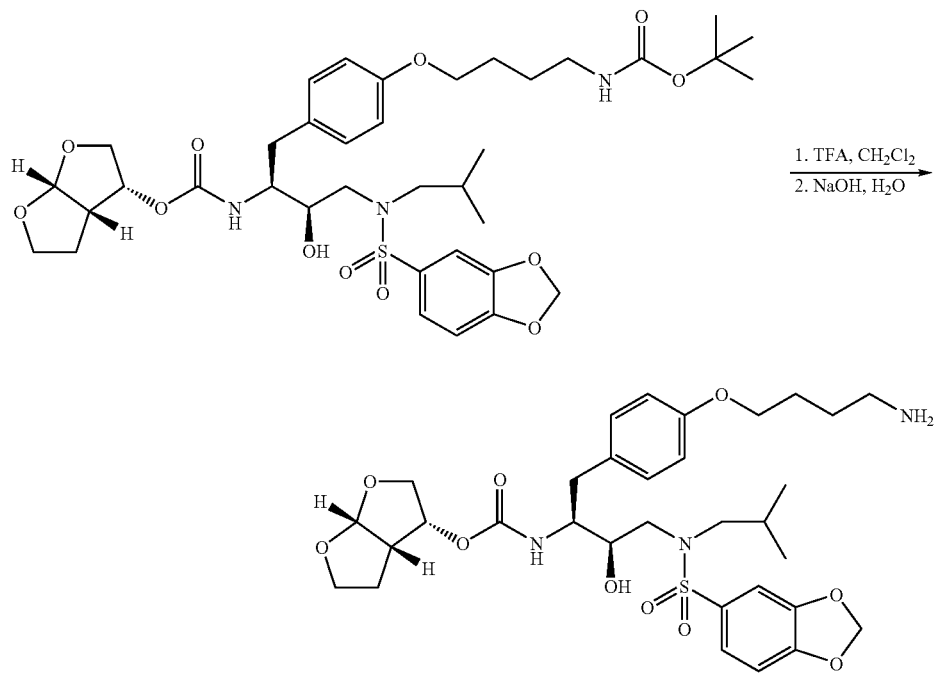

(3R,3aS,6aR)-hexahydrofuro[2,3-b]furan-3-yl (1S,
2R)-1-[4-(4-aminobutoxy)benzyl]-3-[(1,3-benzo-
dioxol-5-ylsulfonyl) (isobutyl)amino]-2-hydroxypro-
pylcarbamate (224)

The title compound was prepared according to example 202.

$^1$H NMR (CDCl$_3$): 7.30 (d, 1H), 7.13 (s, 1H), 7.06 (d, 2H), 6.85 (d, 1H), 6.75 (d, 2H), 6.04 (s, 2H), 5.60 (d, 1H), 5.00 (m, 2H), 3.97-3.71 (m, 7H), 3.66 (m, 2H), 3.22-2.60 (m, 11H), 1.87-1.53 (m, 6H), 1.43 (m, 1H), 0.88 (d, 3H), 0.82 (d, 3H). MS(ESI): 664(M+H).

Example 50

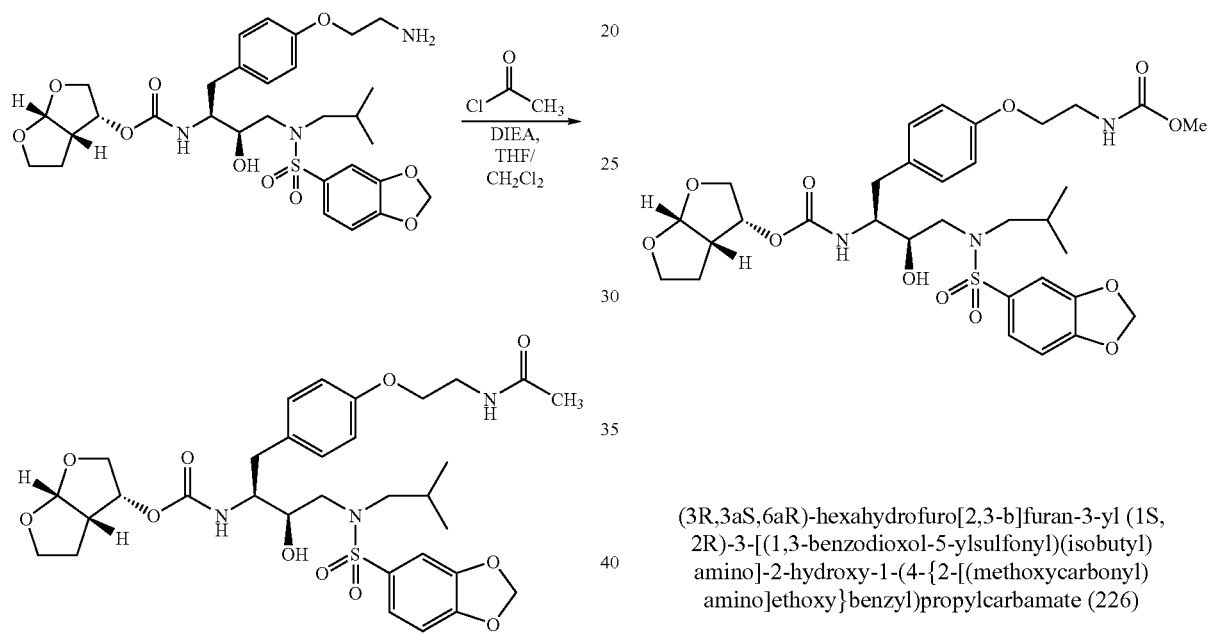

(3R,3aS,6aR)-hexahydrofuro[2,3-b]furan-3-yl (1S,
2R)-1-{4-[2-(acetylamino) ethoxy]benzyl}-3-[(1,3-
benzodioxol-5-ylsulfonyl)(isobutyl)amino]-2-hy-
droxypropylcarbamate (225)

A solution of 21 mg (0.033 mmol) of (3R,3aS,6aR)-hexahydrofuro[2,3-b]furan-3-yl (1S,2R)-1-[4-(2-aminoethoxy)benzyl]-3-[(1,3-benzodioxol-5-ylsulfonyl)(isobutyl) amino]-2-hydroxypropylcarbamate in 2 mL of 1:1 THF/CH$_2$Cl$_2$ was treated with 9 μL (0.050 mmol) of N,N-diisopropylethylamine followed by 2.6 mL (0.036 mmol) of acetyl chloride. The resulting solution was stirred at RT. After 1.5 hours the solution was concentrated in vacuo and the residue subjected to flash chromatography (SiO$_2$, 95:5 CH$_2$Cl$_2$/MeOH) to afford the desired compound in 86% yield as a white foam. $^1$H NMR (CDCl$_3$): 7.29 (dd, 1H), 7.16-7.04 (m, 3H), 7.05 (d, 1H), 6.76 (d, 2H), 6.05 (s, 2H), 5.91 (br s, 1H), 5.01 (d, 1H), 5.05-4.89 (m, 2H), 3.94 (m, 3H), 3.80 (m, 3H), 3.72-3.51 (m, 5H), 3.08 (dd, 1H), 3.01-2.83 (m, 4H), 2.74 (m, 2H), 1.97 (s, 3H), 1.86-1.45 (m, 3H), 0.90 (d, 3H), 0.84 (d, 3H). MS(ESI): 678(M+H).

Example 51

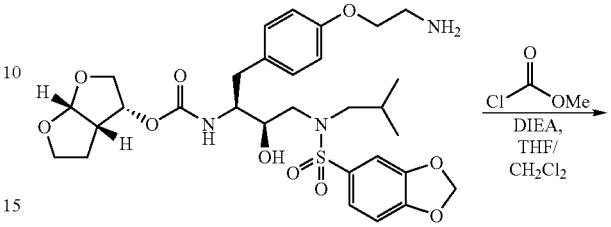

(3R,3aS,6aR)-hexahydrofuro[2,3-b]furan-3-yl (1S,
2R)-3-[(1,3-benzodioxol-5-ylsulfonyl)(isobutyl)
amino]-2-hydroxy-1-(4-{2-[(methoxycarbonyl)
amino]ethoxy}benzyl)propylcarbamate (226)

The title compound was prepared according to example 225 with the exception that methyl chloroformate was used instead of acetyl chloride. $^1$H NMR (CDCl$_3$): 7.29 (dd, 1H), 7.16-7.02 (m, 3H), 6.84 (d, 1H), 6.76 (d, 2H), 6.04 (s, 2H), 5.61 (d, 1H), 5.18-4.84 (m, 3H), 4.02-3.43 (m, 14H), 3.09 (m, 1H), 2.91 (m, 4H), 2.72 (m, 2H), 1.85-1.43 (m, 3H), 0.89 (d, 3H), 0.92 (d, 3H). MS(ESI): 694(M+H).

Example 52

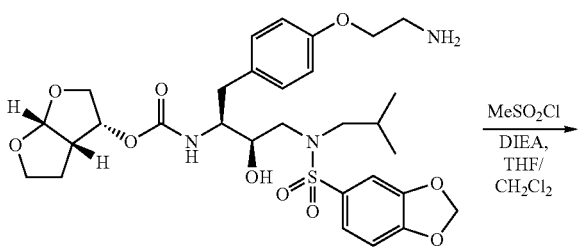

-continued

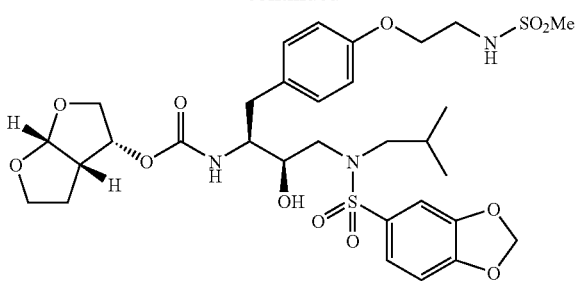

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-(4-{2-[(methylsulfonyl)amino] ethoxy}benzyl)propylcarbamate (227)

The title compound was prepared according to example 225 with the exception that methanesulfonyl chloride was used instead of acetyl chloride. $^1$H NMR (CDCl$_3$): 7.29 (dd, 1H), 7.11 (m, 3H), 6.86 (d, 1H), 6.77 (d, 2H), 6.04 (s, 2H), 5.61 (d, 1H), 4.98 (m, 2H), 4.84 (m, 1H), 4.09-3.44 (m, 11H), 3.12-2.82 (m, 8H), 2.74 (m, 2H), 1.88-1.43 (m, 3H), 0.89 (d, 3H), 0.81 (d, 3H). MS(ESI): 714(M+H).

Example 53

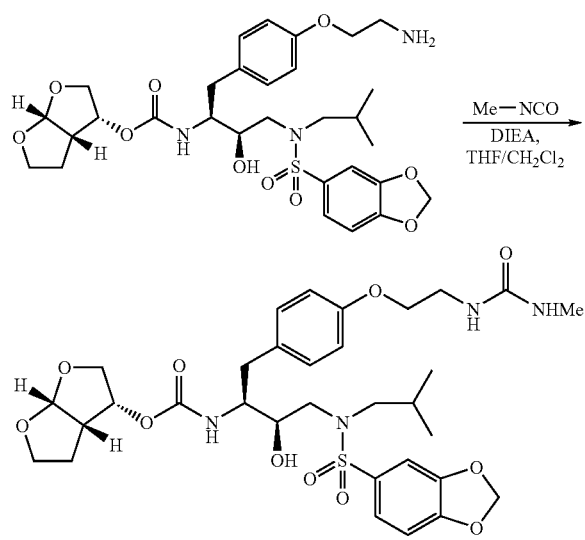

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-[4-(2-{[(methylamino)carbonyl]amino}ethoxy)benzyl]propylcarbamate (228)

The title compound was prepared according to example 225 with the exception that methyl isocyanate was used instead of acetyl chloride. $^1$H NMR (CDCl$_3$): 7.29 (dd, 1H), 7.13 (s, 1H), 7.08 (d, 2H), 6.84 (d, 1H), 6.76 (d, 2H), 6.05 (s, 2H), 5.61 (d, 1H), 5.10-4.90 (m, 2H), 4.04-3.48 (m, 11H), 3.15-2.67 (m, 10H), 1.80 (m, 1H), 1.62 (m, 1H), 1.47 (m, 1H), 0.85 (m, 6H). MS(ESI): 693(M+H).

Example 54

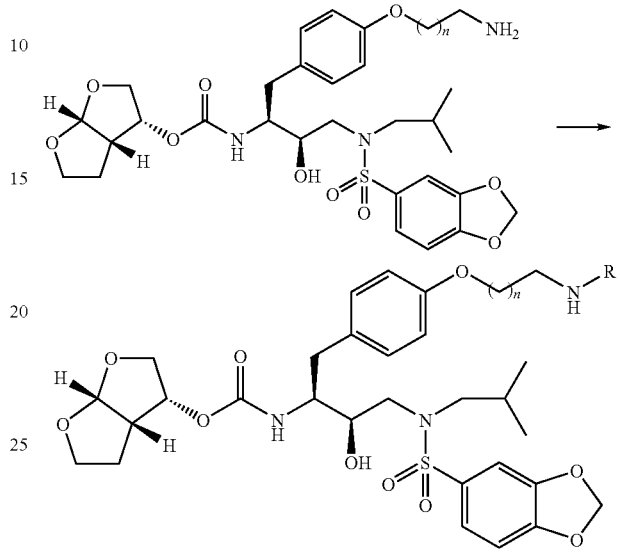

General procedure for reactions of primary amine scaffolds with various electrophiles (229-260): A solution of the primary amine (0.02 M) in anhydrous CH$_2$Cl$_2$ at 0° C. was treated with 1.5 equivalents of N,N-diisopropylethylamine (omitted for reactions with isocyanates and isothiocyanates, examples 56-60) followed by 1.05 equivalent of the appropriate electrophile (acid chloride, chloroformate, sulfonyl chloride, carbamyl chloride, isocyanate, isothiocyanate). The resulting solution was allowed to warm to RT with stirring. When analysis by TLC indicated the reaction to be complete (2-18 hours) the solution was concentrated in vacuo and the residue subjected to flash chromatography (SiO$_2$, CH$_2$Cl$_2$/MeOH or hexane/EtOAc) to afford the desired product.

Mass Spectral Data for Compounds 29-60:

| Example | n | R | MS (ESI) |
|---|---|---|---|
| 229 | 2 | | 692 (M + H) |
| 230 | 3 | | 706 (M + H) |
| 231 | 2 | ₂) | 734 (M + H) |

-continued

| Example | n | R | MS (ESI) |
|---|---|---|---|
| 232 | 2 | C(=O)C(CH3)3 | 734 (M + H) |
| 233 | 2 | C(=O)Ph | 754 (M + H) |
| 234 | 1 | C(=O)-2-furyl | 730 (M + H) |
| 235 | 2 | C(=O)-2-furyl | 744 (M + H) |
| 236 | 3 | C(=O)-2-furyl | 758 (M + H) |
| 237 | 1 | C(=O)-2-thienyl | 746 (M + H) |
| 238 | 2 | C(=O)-2-thienyl | 760 (M + H) |
| 239 | 3 | C(=O)-2-thienyl | 774 (M + H) |
| 240 | 1 | C(=O)CH2OMe | 708 (M + H) |
| 241 | 2 | C(=O)CH2OMe | 722 (M + H) |
| 242 | 3 | C(=O)CH2OMe | 736 (M + H) |

-continued

| Example | n | R | MS (ESI) |
|---|---|---|---|
| 243 | 2 | C(=O)OMe | 708 (M + H) |
| 244 | 3 | C(=O)OMe | 722 (M + H) |
| 245 | 1 | C(=O)OEt | 708 (M + H) |
| 246 | 2 | C(=O)OEt | 722 (M + H) |
| 247 | 3 | C(=O)OEt | 736 (M + H) |
| 248 | 1 | C(=O)OiPr | 722 (M + H) |
| 249 | 2 | C(=O)OiPr | 736 (M + H) |
| 250 | 3 | C(=O)OiPr | 750 (M + H) |
| 251 | 2 | SO2Me | 728 (M + H) |
| 252 | 3 | SO2Me | 742 (M + H) |
| 253 | 1 | C(=O)NMe2 | 707 (M + H) |
| 254 | 2 | C(=O)NMe2 | 721 (M + H) |

-continued

| Example | n | R | MS (ESI) |
|---------|---|---|----------|
| 255 | 3 | 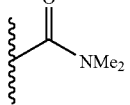 C(=O)NMe₂ | 735 (M + H) |
| 256 | 2 | 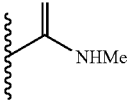 C(=O)NHMe | 707 (M + H) |
| 257 | 3 | 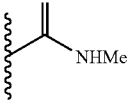 C(=O)NHMe | 721 (M + H) |
| 258 | 1 | 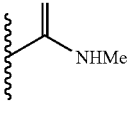 C(=S)NHMe | 709 (M + H) |
| 259 | 2 | 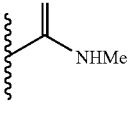 C(=S)NHMe | 723 (M + H) |
| 260 | 3 | 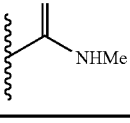 C(=S)NHMe | 737 (M + H) |

Proton NMR Data for Selected Compounds from the Above Table:

Example (Compound 231) NMR (CDCl₃): 7.29 (d, 1H), 7.13 (s, 1H), 7.08 (d, 2H), 6.86 (d, 1H), 6.75 (d, 2H), 6.04 (s, 2H), 5.80 (br s, 1H), 5.60 (d, 1H), 4.98 (m, 2H), 3.92 (m, 3H), 3.79 (m, 3H), 3.65 (m, 2H), 3.40 (q, 2H), 3.15-2.65 (m, 8H), 2.13-1.90 (m, 5H), 1.80 (m, 1H), 1.62 (ma 1H), 1.49 (m, 1H), 0.95-0.78 (m, 12H).

Example (Compound 233) NMR (CDCl₃): 7.72 (d, 2H), 7.43 (d, 1H), 7.38 (m, 2H), 7.29 (d, 1H), 7.10 (m, 3H), 6.84 (d, 1H), 6.77 (d, 2H), 6.65 (br s, 1H), 6.03 (s, 2H), 5.59 (d, 1H), 4.98 (m, 2H), 4.02 (t, 2H), 3.91 (dd, 1H), 3.79 (m 3H), 3.63 (m, 5H), 3.14-2.66 (m, 7H), 2.07 (m, 2H), 1.79 m, 1H), 1.61 (m, 1H), 1.49 (m, 1H), 0.89 (d, 3H), 0.92 (d, 3H).

Example (Compound 23S) NMR (CDCl₃): 7.41 (s, 1H), 7.28 (d, 1H), 7.18-7.04 (m, 4H), 6.87 (d, 1H), 6.79 (m, 3H), 6.45 (m, 1H), 6.04 (s, 2H), δ 60 (d, 1H), 4.96 (m, 2H), 4.02 (t, 2H), 3.91 (dd, 1H), 3.80 (m, 3H), 3.73-3.52 (m, 5H) 3.08 (m, 1H), 3.01-2.82 (m, 4H), 2.74 (m, 2H), 2.05 (m, 2H), 1.80 (m, 1H), 1.63 (m, 1H), 1.50 (m, 1H), 0.90 (d, 3H) 0.82 (d, 3H).

Example (Compound 236) NMR (CDCl₃): 7.38 (s, 1H), 7.29 (d, 1H), 7.13 (s, 1H), 7.07 (m, 3H), 6.84 (d, 1H) r 6.77 (d, 2H), 6.46 (m, 2H), 6.03 (s, 2H), 5.60 (d, 1H), 4.96 (m, 2H), 3.92 (m, 3H), 3.80 (m, 3H) t 3.66 (m, 3H), 3.47 (q, 2H), 3.08 (dd, 1H), 2.92 (m, 4H), 2.73 (m, 2H), 1.80 (m, 5H), 1.62 (m, 1H), 1.48 (m, 1H), 0.90 (d, 3H), 0.82 (d, 3H).

Example (Compound 237) NMR (CDCl₃): 7.50 (m, 1H), 7.43 (d, 1H), 7.29 (d, 1H), 7.12 (m, 3H), 7.02 (m, 1H), 6.85 (d, 1H), 6.80 (d, 2H) G 6.43 (br s, 1H), 6.04 (m, 2H)S 5.60 (d, 1H), 4.96 (m, 2H), 4.05 (t, 2H), 3.91 (dd, 1H), 3.80 (m, 6H), 3.66 (m, 2H), 3.08 (dd, 1H), 3.00-2.81 (m, 4H), 2.73 (m, 2H), 1.80 (m, 1H), 1.62 (m; 1H), 50 (m, 1H), 0.89 (d, 3H), 0.82 (d, 3H).

Example (Compound 238) NMR (CDCl₃): 7.47 (d, 1H), 7.42 (d, 1H), 7.30 (d, 1H), 7.11 (m, 3H), 7.03 (t, 1H), 6.85 (t, 1H), 6.79 (d, 2H), 6.51 (br s, 1H), 6.04 (s, 2H), 5.61 (d, 1H), 4.98 (m, 2H), 4.02 (t, 2H), 3.91 (dd, 1H), 3.80 (m, 3H), 3.70-3.52 (m, 4H), 3.08 (m, 1H), 3.00-2.83 (m, 5H); 2.81-2.67 (m, 2H), 2.07 (m, 2H), 1.80 (m, 1H), 1.62 (m, 1H), 1.50 (m, 1H), 0.89 (d, 3H), 0.81 (d, 3H).

Example (Compound 241) NMR (CDCl₃): 7.29 (d, 1H), 7.12 (s, 1H), 7.08 (d, 2H), 6.89 (br s, 1H), 6.85 (d, 1H), 6.77 (d, 2H), 6.04 (s, 2H), 5.61 (d, 1H), 4.99 (q, 1H), 4.91 (d, 1H), 4.01-3.89 (m, 3H), 3.88-3.72 (m, 6H), 3.67 (m, 2H), 3.46 (q, 2H), 3.39 (s, 3H), 3.09 (dd, 1H), 3.01-2.82 (m, 4H), 2.81-2.67 (m, 2H), 1.98 (m, 2H), 1.80 (m, 1H), 1.63 (m, 1H), 1.50 (m, 1H), 0.89 (d, 3H), 0.82 (d, 3H).

Example (Compound 243) NMR (CDCl₃): 7.38 (d, 1H), 7.20 (s, 1H), 7.16 (d, 2H), 6.92 (d, 1H), 6.85 (d, 2H), 6.12 (s, 2H), 5.69 (d, 1H), 5.14-4.89 (m, 3H), 4.01 (m, 3H), 3.89 (m, 3H), 3.73 (m, 6H), 3.42 (m, 2H), 3.18 (dd, 1H), 3.11-2.90 (m, 4H), 2.82 (m, 2H), 2.01 (m, 2H), 1.93-1.52 (m, 3H), 0.98 (d, 3H), 0.92 (d, 3H).

Example (Compound 244) NMR (CDCl₃): 7.38 (d, 1H), 7.22 (s, 1H), 7.14 (d, 2H), 6.93 (d, 1H), 6.85 (d, 2H), 6.13 (s, 2H), 5.69 (d, 1H), 5.12-4.90 (m, 2H), 4.82 (br s, 1H), 4.07-3.61 (m, 12H), 3.36-3.10 (m, 3H), 3.09-2.90 (m, 4H), 2.90-2.70 (m, 2H), 1.95-1.62 (m, 6H), 1.56 (m, 1H), 0.98° (d, 3H), 0.91 (d, 3H).

Example (Compound 247) NMR (CDCl₃): 7.29 (d, 1H), 7.13 (s, 1H), 7.07 (d, 2H), 6.84 (d, 1H), 6.76 (d, 2H), 6.06 (s, 2H), 5.61 (d, 1H), 5.02-4.84 (m, 2H), 4.71 (br s, 1H), 4.08 (q, 2H), 3.97-3.73 (m, 7H), 3.65 (m, 2H), 3.20 (m, 2H), 3.08 (dd, 1H), 3.00-2.82 (m, 4H), 2.73 (m, 2H), 1.78 (m, 3H), 1.64 (m, 3H), 1.49 (m, 1H), 1.20 (t, 3H), 0.8 (d, 3H), 0.82 (d, 3H).

Example (Compound 249) NMR (CDCl₃): 7.29 (d, 1H), 7.12 (s, 1H), 7.09 (d, 24), 6.84 (d, 1H), 6.77 (d, 2H), 6.06 (s, 2H), 5.61 (d, 1H), 5.04-4.70 (m, 4H), 3.94 (m, 3H), 3.80 (m, 3H), 3.67 (m, 2H), 3.32 (m, 2H), 3.07 (dd, 1H), 2.91 (m, 5H), 2.75 (m, 2H), 1.94 (m, 2H), 1.80 (m, 1H), 1.63 (m, 1H), 1.51 m, 1H), 1.20 (d, 6H), 0.90 (d, 3H), 0.82 (d, 3H).

Example (Compound 250) NMR (CDCl₃): 7.29 (d, 1H), 7.12 (s, 1H), 7.02 (d, 2H), 6.84 (d, 1H), 6.76 (d, 2H), 6.03 (s, 0.2H), 5.61 (d, 1H), 5.00 (q, 1H), 4.88 (m, 2H), 4.65 (br s, 1H), 3.90 (m, 3H), 3.80 (m, 3H), 3.66 (m, 2H), 3.20 (m, 2H), 3.10 (dd, 1H), 2.91 (m, 5H), 2.73 (m, 2H), 1.78 (m, 3H), 1.62 (m, 1H), 1.48 (m, 1H), 1.20 (d, 6H), 0.89 (d, 3H), 0.81 (d, 3H).

Example (Compound 252) NMR (CDCl₃): 7.29 (d, 1H), 7.13 (s, 1H), 7.08 (d, 2H), 6.83 (d, 1H), 6.76 (d, 2H), 6.04 (s, 2H), 5.60 (d, 1H), 4.96 (m, 2H), 4.53 (br s, 1H), 3.92 (m, 3H), 3.79 (m, 3H), 3.67 (m, 2H), 3.16 (m, 2H), 3.07 (dd, 1H), 3.04-2.82 (m, 8H), 2.81-2.65 (m, 2H), 1.87-1.54 (m, 6H), 1.49 (m, 1H), 0.89 (d, 3H), 0.82 (d, 3H).

Example (Compound 254) NMR (CDCl₃): 7.29 (d, 1H), 7.12 (s, 1H), 7.08 (d, 2H), 6.85 (d, 1H), 6.74 (d, 2H), 6.04 (s, 2H), 5.60 (d, 1H), 5.00 (m, 2H), 4.82 (br s, 1H), 4.01-3.88 (m, 3H), 3.80 (m, 3H), 3.66 (m, 2H), 3.37 (t, 2H), 3.15-2.82 (m, 12H), 2.81-2.65 (m, 2H), 1.96 (m, 2H), 1.80 (m, 1H), 1.62 (m, 1H), 1.50 (m, 1H), 0.90 (d, 3H), 0.82 (d, 3H).

Example (Compound 260) NMR (CDCl₃): 7.29 (d, 1H), 7.13 (s, 1H), 7.07 (d, 2H), 6.86 (d, 1H), 6.75 (d, 2H), 6.04 (s, 2H), 5.60 (d, 1H), 4.98 (m, 2H), 3.90 (m, 3H), 3.80 (m, 3H), 3.65 (m, 2H), 3.48 (br s, 2H), 3.08 (m, 1H), 3.02-2.81 (m, 10H), 2.80-2.62 (m, 2H), 1.80 (m, 5H), 1.61 (m, 1H), 1.48 (m, 1H), 0.88 (d, 3H), 0.81 (d, 3H).

Example 55

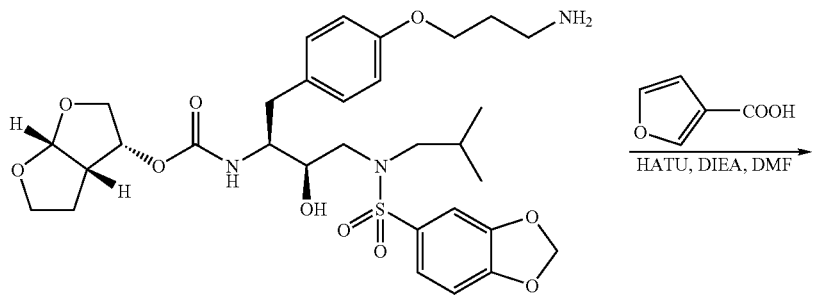

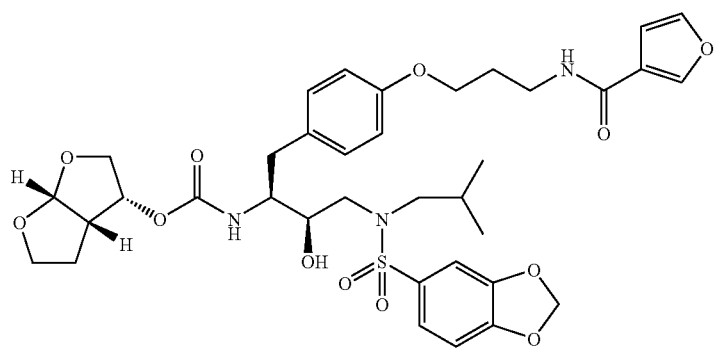

(3R,3aS,6aR)-hexahydrofuro[2,3-b]furan-3-yl (1S,2R)-3-[(1,3-benzodioxol-5-ylsulfonyl)(isobutyl)amino]-1-{4-[3-(3-furoylamino)propoxy]benzyl}-2-hydroxypropylcarbamate (261)

A solution of 44 mg (0.068 mmol) of (3R,3aS,6aR)-hexahydrofuro[2,3-b]furan-3-yl (1S,2R)-1-[4-(3-aminopropoxy)benzyl]-3-[(1,3-benzodioxol-5-ylsulfonyl)(isobutyl)amino]-2-hydroxypropylcarbamate, 15 mg (0.14 mmol) of 3-furoic acid, and 36 µL (0.20 mmol) of N,N-diisopropylethylamine in 2 mL of anhydrous DMF was treated with 52 mg (0.14 mmol) of O-(7-azabenzotriazol-1-yl)-1,1,3,3-tetramethyluronium hexafluorophosphate (HATU) and the resulting solution was stirred at RT. After 18 hours the solution was concentrated in vacuo and the residue subjected to flash chromatography (SiO$_2$, 97:3 CH$_2$Cl$_2$/MeOH) to afford 38 mg (75%) of the desired compound as a white foam. $^1$H NMR (CDCl$_3$): 7.88 (s, 1H), 7.38 (s, 1H), 7.29 (d, 1H) t 7.10 (m, 3H), 6.84 (d, 1H), 6.76 (d, 2H), 6.56 (s, 1H), 6.34 (br s, 1H), 6.05 (s, 2H), 5.60 (d, 1H), 5.00 (m, 2H), 4.01 (t, 2H), 3.90 (dd, 1H), 3.80 (m, 3H), 3.64 (m, 2H), 3.55 (q, 2H), 3.17-2.63 (m, 8H), 2.03 (m, 2H), 1.80 (m, 1H), 1.61 (m, 1H), 1.49 (m, 1H), 0.89 (d, 3H), 0.83 (d, 3H). MS(ESI): 744(M+H).

Example 56

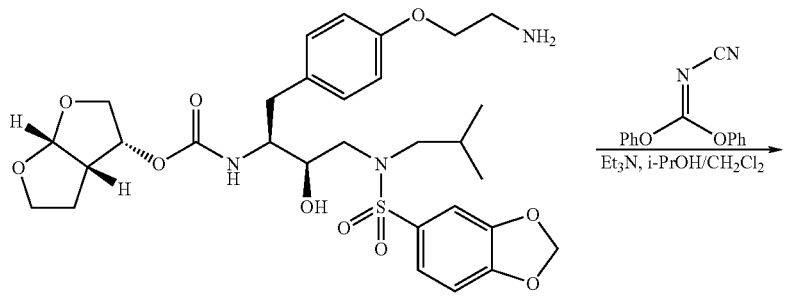

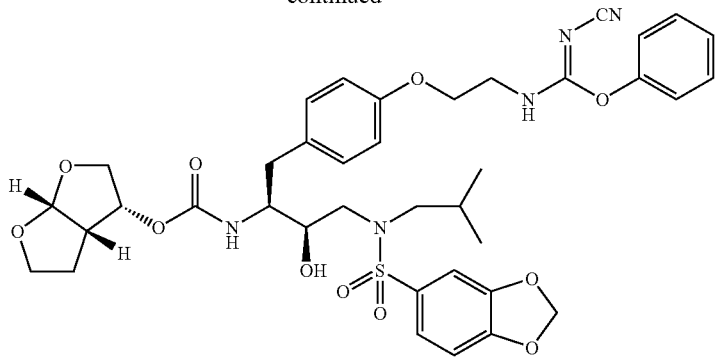

(3R,3aS,6aR)-hexahydrofuro[2,3-b]furan-3-yl (1S, 2R)-3-[(1,3-benzodioxol-5-ylsulfonyl)(isobutyl) amino]-1-[4-(2-{[(E and/or Z)-(cyanoimino)(phenoxy)methyl]amino}ethoxy)benzyl]-2-hydroxypropylcarbamate (262)

A solution of 0.20 g (0.32 mmol) of (3R,3aS,6aR)-hexahydrofuro[2,3-b]furan-3-yl (1S,2R)-1-[4-(2-aminoethoxy)benzyl]-3-[(1,3-benzodioxol-5-ylsulfonyl)(isobutyl)amino]-2-hydroxypropylcarbamate, 83 mg (0.35 mmol) of diphenyl cyanocarbonimidate, and 66 μL of (0.47 mmol) triethylamine in 12 mL of 1:1 i-PrOH/CH₂Cl₂ was stirred at RT. After 2.5 hours the solution was concentrated to dryness at reduced pressure and the residue subjected to flash chromatography (SiO₂, 95:5 CH₂Cl₂/MeOH) to afford 0.24 g (96%) of the desired compound as a white foam. ¹H NMR (CDCl₃): 7.47-7.21 (m, 4H), 7.20-7.02 (m, 5H), 6.88-6.63 (m, 3H), 6.42 (br s, 1H), 6.05 (s, 2H), 5.61 (d, 1H), 4.99 (m, 2H), 4.20-3.50 (m, 11H), 3.09 (m, 1H), 3.01-2.82 (m, 4H), 2.76 (m, 2H), 1.78 (m, 1H), 1.72-1.43 (m, 2H), 0.90 (d, 3H), 0.81 (d, 3H). MS(ESI): 780(M+H).

Example 57

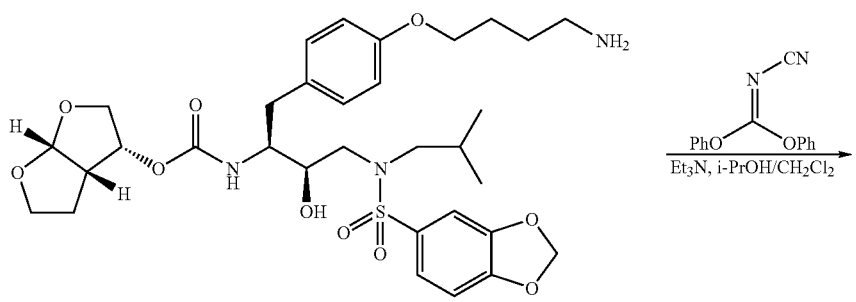

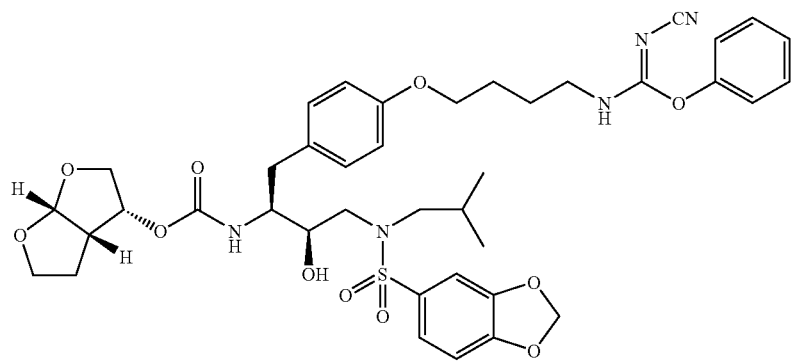

(3R,3aS,6aR)-hexahydrofuro[2,3-b]furan-3-yl (1S, 2R)-3-[(1,3-benzodioxol-5-ylsulfonyl)(isobutyl) amino]-1-[4-(4{[(E and/or Z)-(cyanoimino)(phenoxy)methyl]amino}butoxy)benzyl]-2-hydroxypropylcarbamate (263)

According to example 262, (3R,3aS,6aR)-hexahydrofuro[2,3-b]furan-3-yl (1S,2R)-1-[4-(4-aminobutoxy)benzyl]-3-[(2,3-benzodioxol-5-ylsulfonyl)(isobutyl)amino]-2-hydroxypropylcarbamate was converted to the desired compound which was obtained in 98% yield as a white foam. $^1$H NMR (CDCl$_3$): 7.52-7.26 (m, 4H), 7.25-7.07 (m, 5H), 6.97-6.67 (m, 4H), 6.12 (s, 2H), 5.69 (d, 1H), 5.06 (m, 2H), 4.10-3.40 (m, 11H), 3.22-2.73 (m, 7H), 2.00-1.55 (m, 7H), 0.96 (d, 3H), 0.91 (d, 3H). MS(ESI): 808(M+H).

Example 58

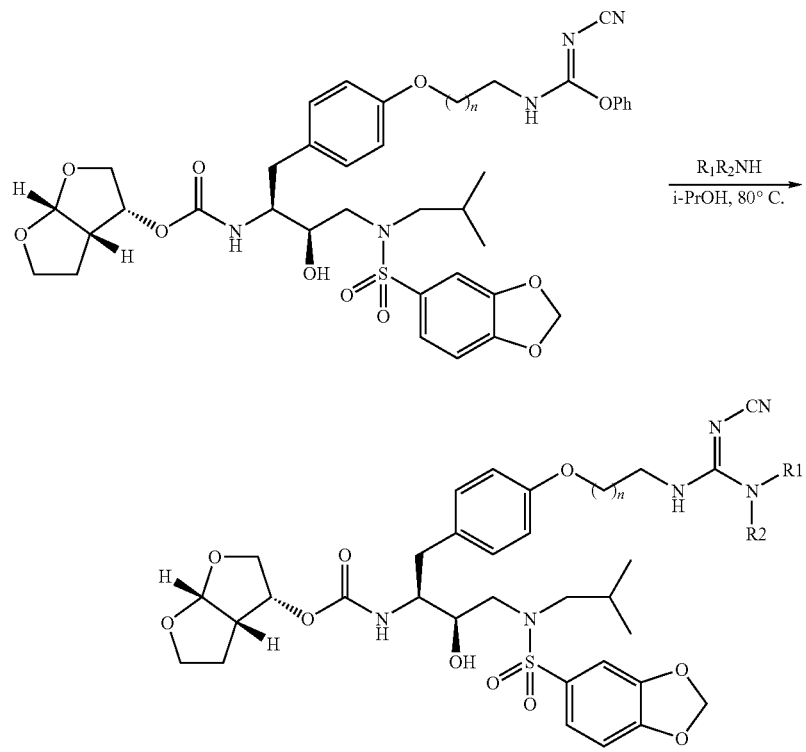

-continued

| Example | n | R$_1$ | R$_2$ | MS (ESI) |
|---|---|---|---|---|
| 266 | 1 | —CH$_2$CH$_2$OCH$_2$CH$_2$— | | 773 (M + H) |

General Procedure for the Synthesis of Cyanoguanidines from Imidocarbamate Scaffolds (264-269)

A mixture of 0.05 mmol of imidocarbamate intermediate in 3 mL of isopropanol in a sealed tube was treated with 10-20 equivalents of amine (2M NH$_3$ in MeOH, 8M MeNH$_2$ in EtOH, 2M Me$_2$NH in THF, neat morpholine). Upon heating, the solid starting material dissolved to give a clear solution. After stirring at 80° C. for 3 hours the solution was cooled to RT and concentrated to dryness at reduced pressure. The residue was subjected to flash chromatography (SiO$_2$, CH$_2$Cl$_2$/MeOH or Cl$_2$Cl$_2$/2M NH$_3$ in MeOH) to afford the desired compound as white foam.

Mass Spectral Data for Compounds 264-269

| Example | n | R$_1$ | R$_2$ | MS (ESI) |
|---|---|---|---|---|
| 264 | 1 | H | H | 703 (M + H) |
| 265 | 1 | Me | H | 717 (M + H) |

-continued

| Example | n | R$_1$ | R$_2$ | MS (ESI) |
|---|---|---|---|---|
| 267 | 3 | H | H | 731 (M + H) |
| 268 | 3 | Me | H | 745 (M + H) |
| 269 | 3 | Me | Me | 759 (M + H) |

Proton NMR Data for Selected Compounds from the Above Table:

Example (Compound 265) $^1$H NMR (CDCl$_3$): 7.30 (d, 1H), 7.11 (m, 3H), 6.86 (d, 1H), 6.76 (d, 2H), 6.04 (s, 2H), 5.87 (br s, 1H), 5.65-5.42 (m, 2H), 5.09 (d, 1H), 5.00 (q, 1H), 4-01 (m, 2H), 3.92 (dd, 1H), 3.79 (m, 3H), 3.71-3.52 (m, 5H), 3.11-2.66 (10H), 1.80 (m, 1H), 1.61 (m, 1H), 1.50 (m, 1H), 0.86 (m, 6H).

Example (Compound 269) $^1$H NMR (CDCl$_3$): 7.29 (d, 1H), 7.12 (1H), 7.08 (d, 2H), 6.84 (d, 1H), 6.74 (d, 2H), 6.03 (s, 2H), 5.60 (d, 1H), 5.06-4.87 (m, 3H), 3.91 (m, 3H), 3.79 (m, 3H), 3.64 (m, 3H), 3.49 (q, 2H), 3.15-2.65 (m, 13H), 1.89-1.54 (m, 6H), 1.48 (m, 1H), 0.86 (m, 6H).

Example 59

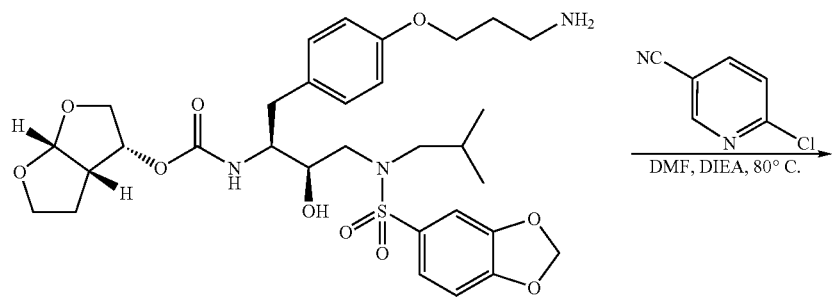

(3R,3aS,6aR)-hexahydrofuro[2,3-b]furan-3-yl (1S, 2R)-3-[(1,3-benzodioxol-5-ylsulfonyl)(isobutyl) amino]-1-(4-{3[(5-cyano-2-pyridinyl)amino] propoxy}benzyl)-2-hydroxypropylcarbamate (270)

A solution of 35 mg (0.054 mmol) of (3R,3aS,6aR)-hexahydrofuro[2,3-b]furan-3-yl (1S,2R)-1-[4-(3-aminopropoxy)benzyl]3-[(1,3-benzodioxol-5-ylsulfonyl)(isobutyl) amino]-2-hydroxypropylcarbamate, 22 mg (0.16 mmol) of 2-chloro-5-cyanopyridine, and 38 μL (0.22 mmol) of N,N-diisopropylethylamine in 0.5 mL of anhydrous DMF was heated to 80° C. with stirring. After 6 hours the solution was cooled to RT and concentrated to dryness in vacuo. The residue was purified by flash chromatography (SiO$_2$, 95:5 CH$_2$Cl$_2$/MeOH) to afford 33 mg (80%) of the desired compound as a white foam. $^1$H NMR (CDCl$_3$): 8.30 (s, 1H), 7.50 (d, 1H), 7.29 (d, 1H), 7.13 (s, 1H), 7.09 (d, 2H), 6.84 (d, 1H), 6.78 (d, 2H), 6.37 (d, 1H), 6.04 (s, 2H), 5.62 (d, 1H), 5.44 (br s, 1H), 4.96 (m, 2H), 4.00 (t, 2H), 3.91 (m, 1H), 3.80 (m, 3H), 3.71-3.49 (m, 5H), 3.18-2.65 (m, 7H), 2.08 (m, 2H), 1.80 (m, 1H), 1.61 (m, 1H), 1.50 (m, 1H), 0.90 (d, 3H), 0.81 (d, 3H). MS(ESI): 752(M+H).

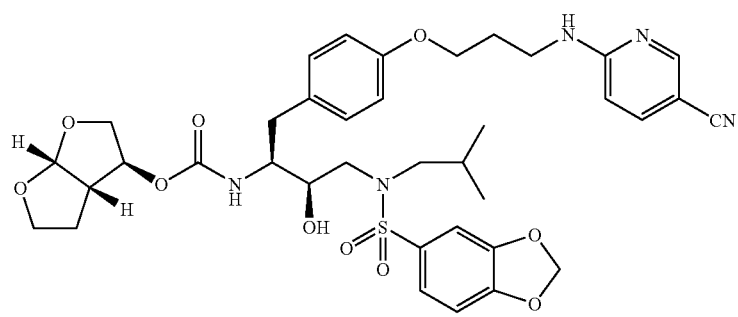

Example 60

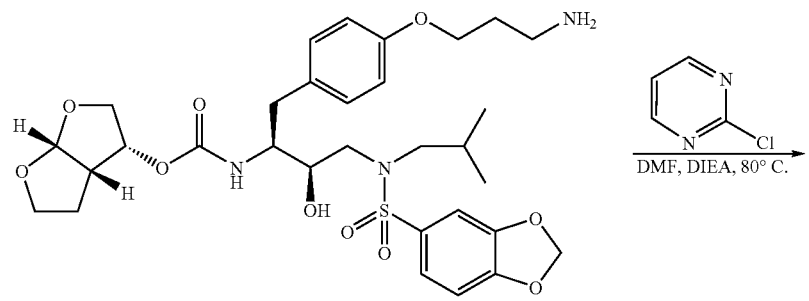

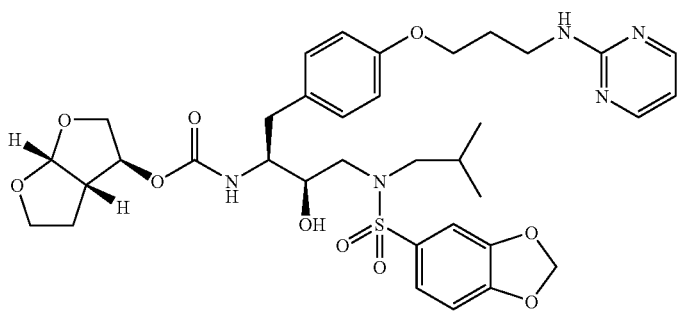

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[3-(2-pyrimidinylamino) propoxy]benzyl}propylcarbamate (271)

The title compound was prepared according to example 270 with the exception that 2-chloropyrimidine was used instead of 2-chloro-5-cyanopyridine in NMR (CDCl$_3$): 8.23 (m, 2H), 7.29 (d, 1H), 7.12 (s, 1H), 7.06 (d, 2H), 6.86 (d, 1H), 6.80 (d, 2H), 6.50 (t, 1H), 6.06 (s, 2H), 5.60 (d, 1H), 5.50 (br s, 1H), 5.00 (m, 1H), 4.88 (d, 1H), 4.00 (t, 2H), 3.92 (m, 1H), 3.80 (m, 3H), 3.71-3.52 (m, 5H), 3.09 (m, 1H), 3.00-2.81 (m, 4H), 2.73 (m, 2H), 2.13-1.71 (m, 3H), 1.64 (m, 1H), 1.52 (m, 1H), 0.90 (d, 3H), 0.83 (4, 3H). MS(ESI): 728(M+H).

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-[4-(3-{[5-(trifluoromethyl)-2-pyridinyl]amino}propoxy)benzyl]propylcarbamate (272)

The title compound was prepared according to example 270 with the exception that 2-bromo-5-(trifluoromethyl)pyridine was used instead of 2-chloro-5-cyanopyridine. $^1$H NMR (CDCl$_3$): 8.34 (s, 1H), 7.60 (d, 1H), 7.37 (d, 1H), (s, 1H), 7.16 (d, 2H), 6.93 (d, 1H), 6.86 (d, 2H), (d, 1H), 6.12 (s, 2H), 5.69 (d, 2H), 5.32 (br s, 1H), 5.07 (m, 2H), 4.15-3.66 (m, 9H), 3.60 (m, 2H), 3.22 (m, 7H), 2.13 (m, 2H), 1.87 (m, 1H), 1.77-1.48 (m, 2H), 0.98 (d, 3H), 0.91 (d, 3H). MS(ESI): 795(M+H).

Example 61

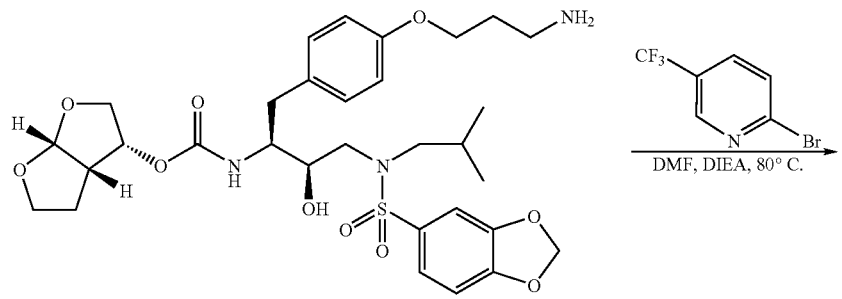

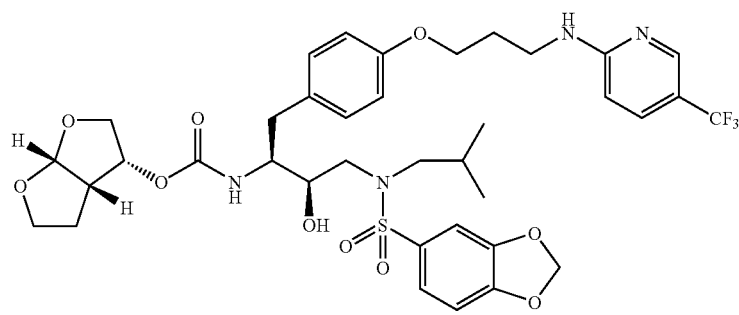

Example 62

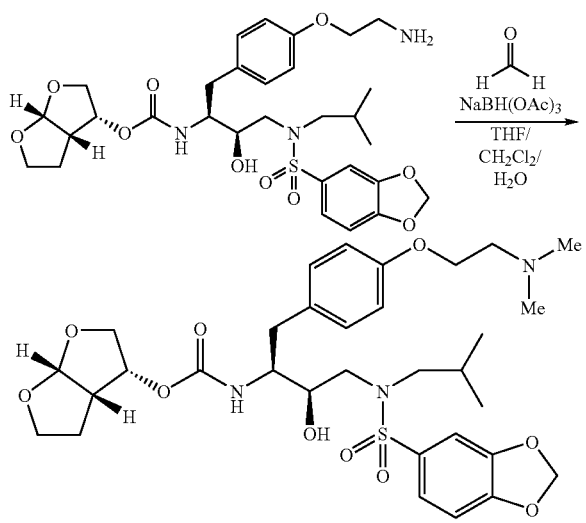

(3R,3aS,6aR)-hexahydrofuro[2,3-b]furan-3-yl (1S,2R)-3-[(1,3-benzodioxol-5-ylsulfonyl)(isobutyl)amino]-1-{4-[2-(dimethylamino)ethoxy]benzyl}-2-hydroxypropylcarbamate (273)

A solution of 21 mg (0.033 mmol) of (3R,3aS,6aR)-hexahydrofuro[2,3-b]furan-3-yl (1S,2R)-1-[4-(2-aminoethoxy)benzyl]-3-[(1,3-benzodioxol-5-ylsulfonyl)(isobutyl)amino]-2-hydroxypropylcarbamate in 3 mL of 8:2 THF/$CH_2Cl_2$ was treated with 13 μL (0.17 mmol) of 37% aqueous formaldehyde followed by 35 mg (0.17 mmol) of NaBH(OAc)$_3$ and the resulting cloudy solution was stirred at RT. After 3 hours the solution was filtered to remove solids and the filtrate concentrated in vacuo. The residue was purified by flash chromatography (SiO$_2$, 95:5 $CH_2Cl_2$/2M NH$_3$ in MeOH) to give the desired compound as a white foam in 68% yield. $^1$H NMR (CDCl$_3$): 7.29 (dd, 1H), 7.13 (s, 1H), 7.07 (d, 2H), 6.85 (d, 1H), 6.80 (d, 2H), 6.03 (s, 2H), 5.61 (d, 1H), 4.98 (q, 1H), 4.89 (d, 1H), 4.01 (t, 2H), 3.92 (m, 1H), 3.80 (m, 3H), 3.66 (m, 2H), 3.09 (dd, 1H), 2.92 (m, 5H), 2.74 (m, 4H), 2.32 (s, 6H), 1.80 (m, 1H), 1.63 (m, 1H), 1.42 (m, 1H), 0.90 (d, 3H), 0.84 (d, 3H). MS(ESI): 664(M+H).

Example 63

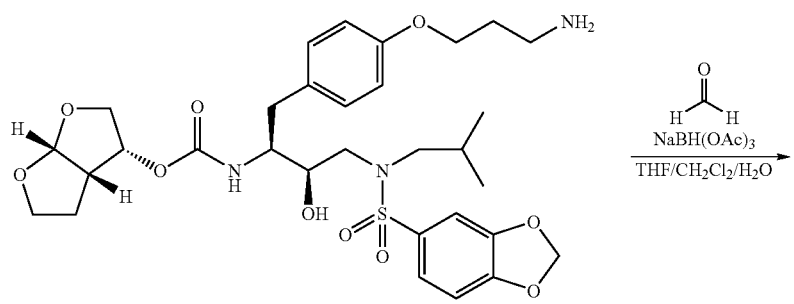

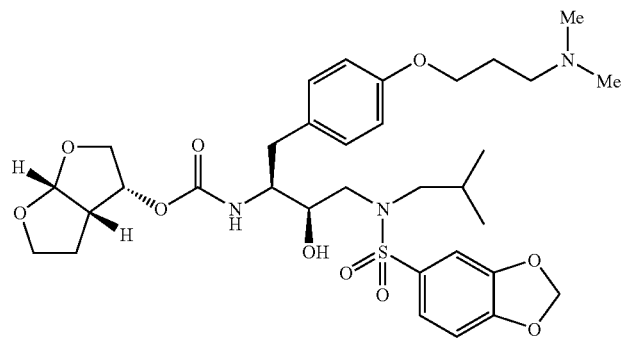

(3R,3aS,6aR)-hexahydrofuro[2,3-b]furan-3-yl (1S,2R)-3-[(1,3-benzodioxol-5-ylsulfonyl)(isobutyl) amino]-1-{4-[3-(dimethylamino)propoxy]benzyl}-2-hydroxypropylcarbamate (274)

According to example 273, (3R,3aS,6aR)-hexahydrofuro[2,3-b]furan-3-yl (1S,2R)-1-[4-(3-aminopropoxy)benzyl]-3-[(1,3-benzodioxol-5-ylsulfonyl)(isobutyl)amino]-2-hydroxypropylcarbamate was subjected to reductive alkylation with formaldehyde to give the desired compound as a white foam in 76% yield. $^1$H NMR (CDCl$_3$): 7.37 (d, 1H), 7.22 (s, 1H), 7.15 (d, 2H), 6.92 (d, 1H), 6.84 (d, 2H), 6.13 (s, 2H), 5.70 (d, 1H), 5.07 (q, 1H), 4.95 (d, 1H), 4.08-3.63 (m, 9H), 3.18 (dd, 1H), 3.00 (m, 4H), 2.82 (m, 2H), 2.50 (t, 2H), 2.31 (s, 6H), 2.10-1.50 (m, 5H), 0.97 (d, 3H), 0.91 (d, 3H). MS(ESI): 678(M+H).

Example 64

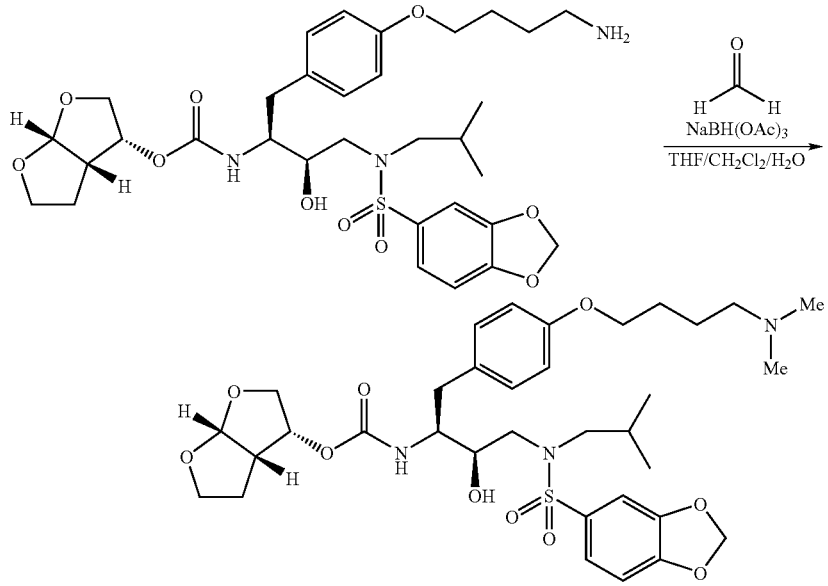

(3R,3aS,6aR)-hexahydrofuro[2,3-b]furan-3-yl (1S,2R)-3-[(1,3-benzodioxol-5-ylsulfonyl)(isobutyl) amino]-1-{4-[4-(dimethylamino)butoxy]benzyl}-2-hydroxypropylcarbamate (275)

According to example 273, (3R,3aS,6aR)-hexahydrofuro[2,3-b]furan-3-yl (1S,2R)-1-[4-(4-aminobutoxy)benzyl]-3-[(1,3-benzodioxol-5-ylsulfonyl)(isobutyl)amino]-2-hydroxypropylcarbamate was subjected to reductive alkylation with formaldehyde to give the desired compound as a white foam in 74% yield. $^1$H NMR (CDCl$_3$): 7.37 (d, 1H), 7.22 (s 0.1H), 7.15 (d, 2H), 6.93 (d, 1H), 6.86 (d, 2H), 6.12 (s, 2H), 5.69 (d, 1H), 5.07 (q, 1H), 4.94 (d, 1H), 4.06-3.60 (m, 9H), 3.17 (dd, 1H), 3.00 (m, 4H), 2.81 (m, 2H), 2.40 (t, 2H), 2.32 (s, 6H), 1.95-1.50 (m, 7H), 0.98 (d, 3H), 0.91 (d, 3H). MS(ESI): 692(M+H).

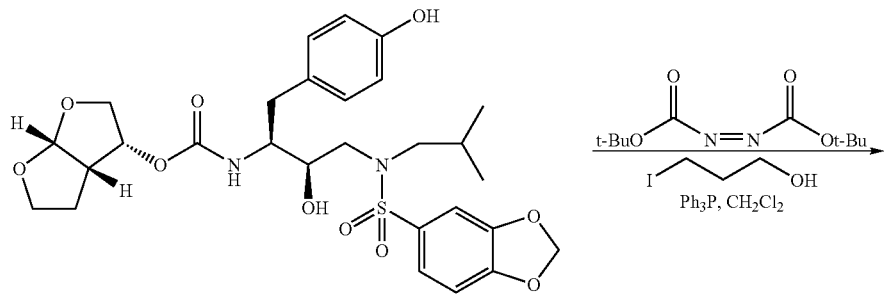

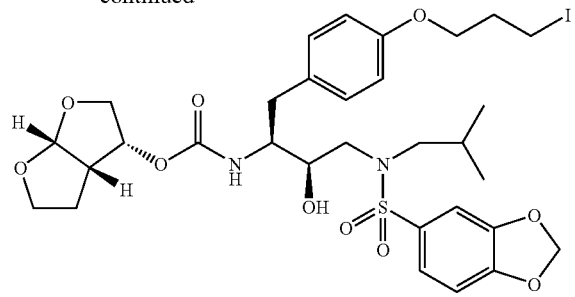

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-[4-(3-iodopropoxy)benzyl]propylcarbamate (276)

The title compound was prepared according to example 202 with the exception that 3-iodo-1-propanol was used instead of phenethyl alcohol. $^1$H NMR (CDCl$_3$): 7.29 (d, 1H), 7.13 (s, 1H), 7.09 (d, 2H), 6.86 (d, 1H), 6.78 (d, 2H), 6.04 (s, 2H), 5.61 (d, 1H), 4.99 (q, 1H), 4.85 (d, 1H), 3.94 (m, 3H), 3.80 (m, 3H), 3.67 (m, 2H), 3.55 (m, 1H), 3.32 (t, 2H), 3.09 (dd, 1H), 3.92 (m, 4H), 2.73 (m, 2H), 2.21 (m, 2H), 1.80 (m, 1H), 1.63 (m, 1H), 1.49 (m, 1H), 0.90 (d, 3H), 0.83 (d, 3H). MS(ESI): 761(M+H).

Example 66

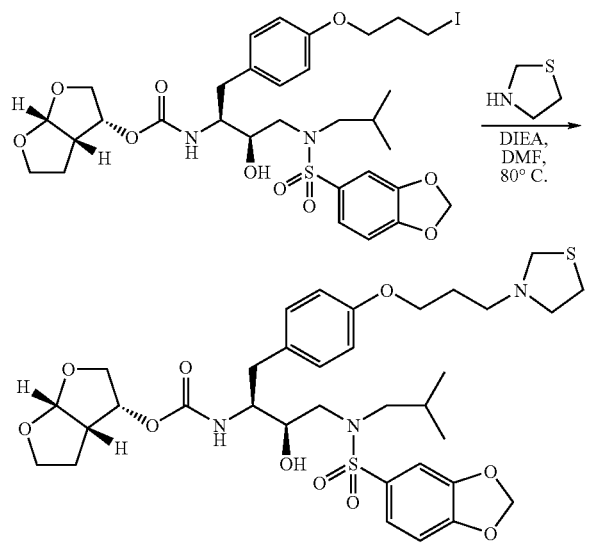

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[3-(1,3-thiazolidin-3-yl) propoxy]benzyl}propylcarbamate (277)

A solution of 35 mg (0.046 mmol) of (3R,3aS,6aR)-hexahydrofuro[2,3-b]furan-3-yl (1S,2R)-3-[(1,3-benzodioxol-5-ylsulfonyl)(isobutyl)amino]-2-hydroxy-1-[4-(3-iodopropoxy)benzyl]propylcarbamate, 11 µL (0.14 mmol) of thiazolidine, and 32 µL (0.18 mmol) of N,N-diisopropylethylamine in 0.5 mL of anhydrous DMF was heated to 80° C. with stirring. After 1.5 hours TLC indicated the reaction to be complete. The solution was cooled to RT and concentrated in vacuo. The residue was subjected to flash chromatography (SiO$_2$, 95:5 CH$_2$Cl$_2$/MeOH) to afford 22 mg (67%) of the desired compound as a white foam. $^1$H NMR (CDCl$_3$): 7.29 (d, 1H), 7.13 (s, 1H), 7.08 (d, 2H), 7.85 (d, 1H), 6.77 (d, 2H), 6.04 (s, 2H), 5.60 (d, 1H), 5.00 (q, 1H), 4.88 (d, 1H), 4.01 (s, 2H), 4.00-3.88 (m, 3H), 3.80 (m, 3H), 3.67 (m, 2H), 3.55 (br s, 1H), 3.19-3.01 (m, 4H), 3.00-2.65 (m, 7H), 2.52 (t, 2H), 1.93 (m, 2H), 1.79 (m, 1H), 1.70-1.42 (m, 2H), 0.89 (d, 3H), 0.83 (d, 3H). MS(ESI): 722(M+H).

Example 67

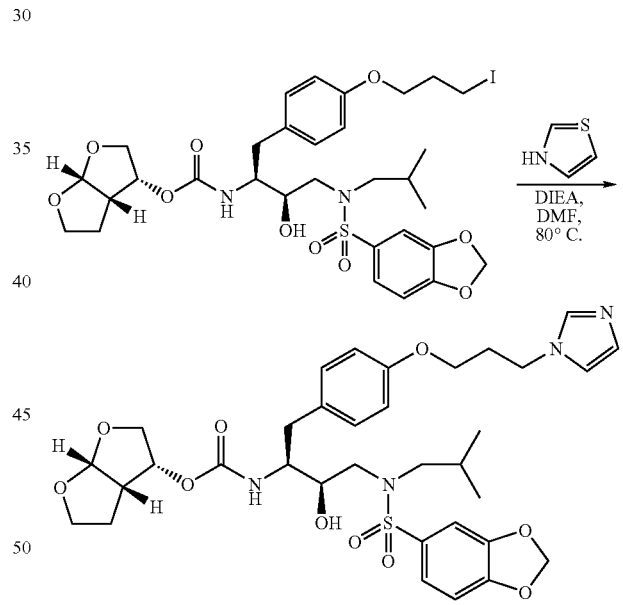

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[3-(1H-imidazol-1-yl)propoxy]benzyl}propylcarbamate (278)

The title compound was prepared according to example 66 with the exception that imidazole was substituted for thiazolidine. $^1$H NMR (CDCl$_3$): 7.54 (s, 1H), 7.38 (d, 1H), 7.21 (s, 1H), 7.17 (d, 2H), 7.11 (s, 1H), 6.92 (m, 2H), 6.82 (d, 2H), 6.13 (s, 2H), 5.70 (d, 2H), 5.09 (m, 2H), 4.22 (t, 2H), 4.07-3.68 (m, 8H), 3.22-2.73 (m, 5H), 2.25 (m, 2H), 1.88 (m, 1H), 1.77-1.55 (m, 2H), 0.93 (m, 6H). MS(ESI): 701(M+H).

Example 68

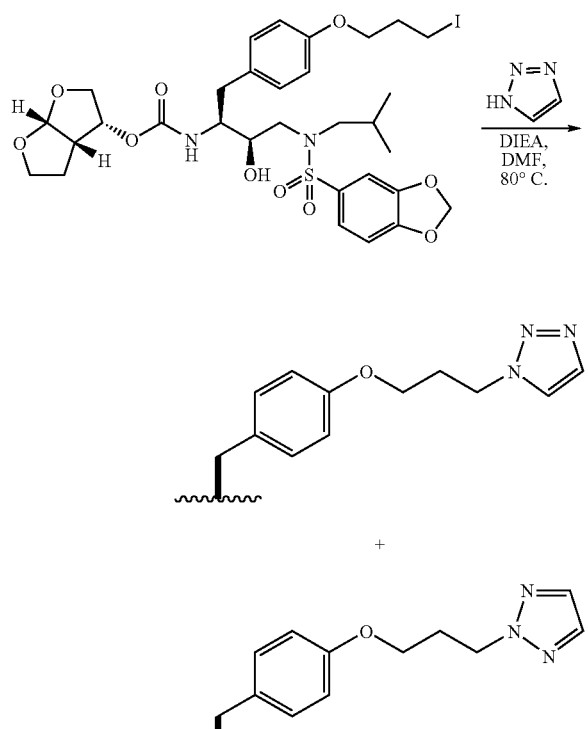

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[3-(1H-1,2,3-triazol-1-yl) propoxy]benzyl}propylcarbamate and (3R,3aS,6aR)-hexahydrofuro[2,3-b]furan-3-yl (1S,2R)-3-[(1,3-benzodioxol-5-ylsulfonyl)(isobutyl)amino]-2-hydroxy-1-{4-[3-(2H-1,2,3-triazol-2-yl)propoxy] benzyl}propylcarbamate (279)

According to example 66, (3R,3aS,6aR)-hexahydrofuro[2,3-b]furan-3-yl (1S,2R)-3-[(1,3-benzodioxol-5-ylsulfonyl) (isobutyl)amino]-2-hydroxy-1-[4-(3-iodopropoxy)benzyl] propylcarbamate was reacted with 1,2,3-triazole to afford an approximately 1:1 mixture of triazole isomers (as determined by $^1$H-NMR and HPLC). MS(ESI): 702(M+H).

Example 69

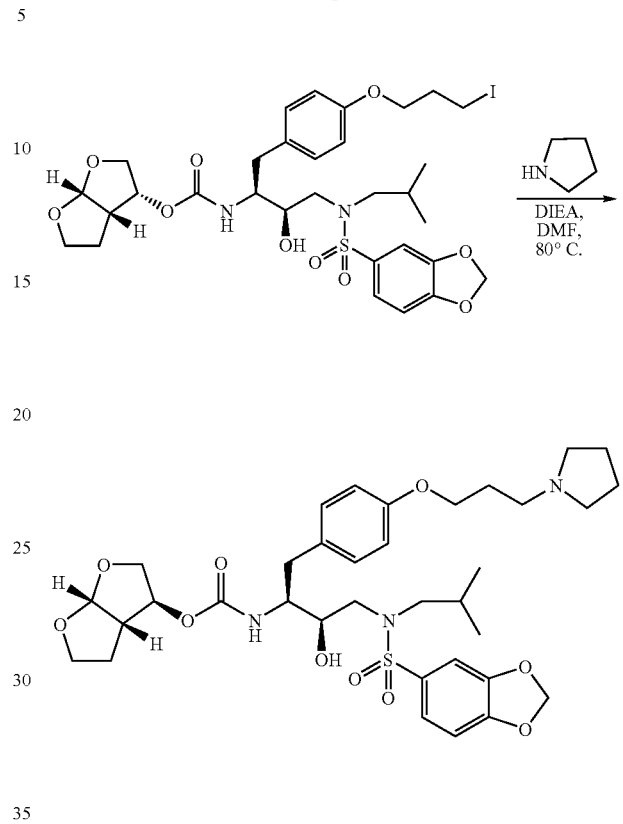

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[3-(1-pyrrolidinyl)propoxy]-3-benzyl}propylcarbamate (280)

The title compound was prepared according to example 66 with the exception that pyrrolidine was substituted for thiazolidine. $^1$H NMR (CDCl$_3$): 7.36 (d, 1H), 7.21 (s, 1H), 7.13 (d, 2H), 6.92 (d, 1H), 6.83 (d, 2H), 6.12 (s, 2H), 5.68 (d, 1H), 5.02 (m, 2H), 4.00 (m, 3H), 3.93-3.62 (m, 6H), 3.15 (dd, 1H), 3.00 (m, 4H), 2.88-2.61 (m, 8H), 2.10 (m, 2H), 1.88 (m, 5H), 1.78-1.50 (m, 2H), 0.96 (d, 3H), 0.91 (d, 3H). MS(ESI): 704(M+H).

Example 70

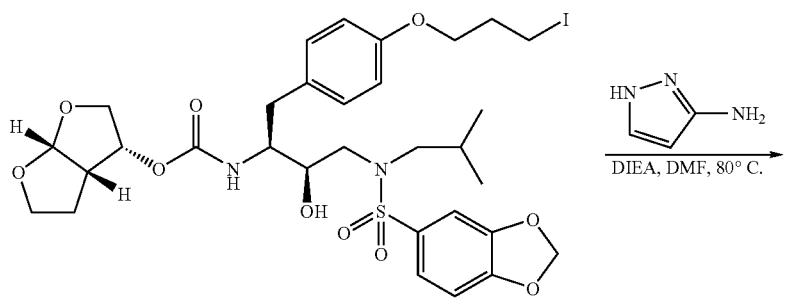

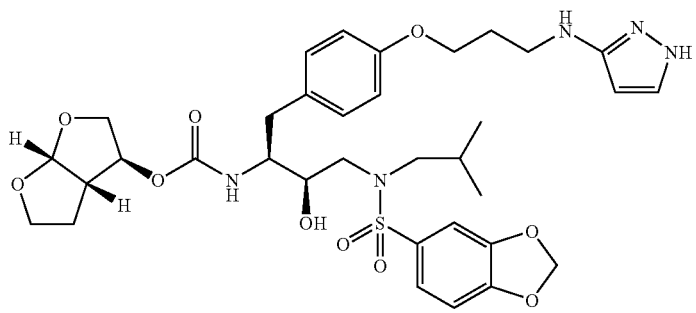

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[3-(1H-pyrazol-3-ylamino) propoxy]benzyl}propylcarbamate (281)

The title compound was prepared according to example 66 with the exception that 3-aminopyrazole was substituted for thiazolidine. $^1$H NMR (CDCl$_3$): 7.28 (m, 2H), 7.14 (s, 1H), 7.05 (d, 2H), 6.84 (d, 1H), 6.75 (d, 2H), 6.03 (s, 2H), 5.58 (m, 2H), 5.15 (d, 1H), 4.99 (q, 1H), 4.80-4.20 (br s, 2H), 4.00 (t, 2H), 3.90 (dd, 1H), 3.78 (m, 3H), 3.67 (m, 2H), 3.31 (t, 2H), 3.08 (m, 1H), 3.01-2.63 (m, 7H), 2.01 (m, 2H), 1.80 (m, 1H), 1.61 (m, 1H), 1.47 (m, 1H), 0.88 (d, 3H), 0.81 (d, 3H). MS(ESI): 716(M+H).

Example 71

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[3-(4-methyl-1-piperazinyl) propoxy]benzyl}propylcarbamate (282)

The title compound was prepared according to example 66 with the exception that 1-methylpiperazine was substituted for thiazolidine. $^1$H NMR (CDCl$_3$): 7.37 (d, 1H), 7.20 (s, 1H), 7.14 (d, 2H), 6.92 (d, 1H), 6.84 (d, 2H), 6.12 (s, 2H), 5.68 (d, 1H), 5.14-4.92 (m, 2H), 4.00 (m, 3H), 3.86 (m, 3H), 3.72 (m, 3H), 3.16 (dd, 1H), 3.08-2.90 (m, 4H), 2.89-2.39 (m, 12H), 2.33 (s, 3H), 2.00 (m, 2H), 1.87 (m, 1H), 1.68 (m, 1H), 1.52 (m, 1H), 0.98 (d, 3H), 0.91 (d, 3H). MS(ESI): 733(M+H).

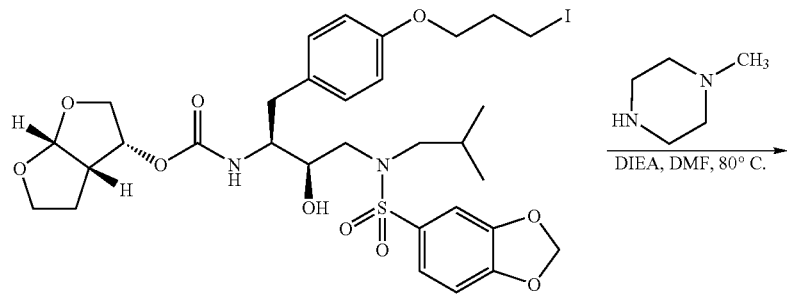

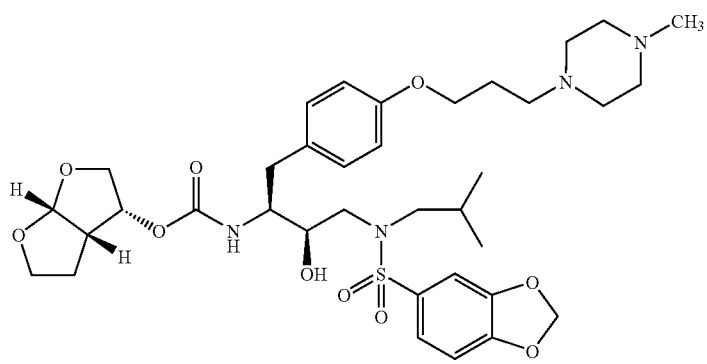

Example 72

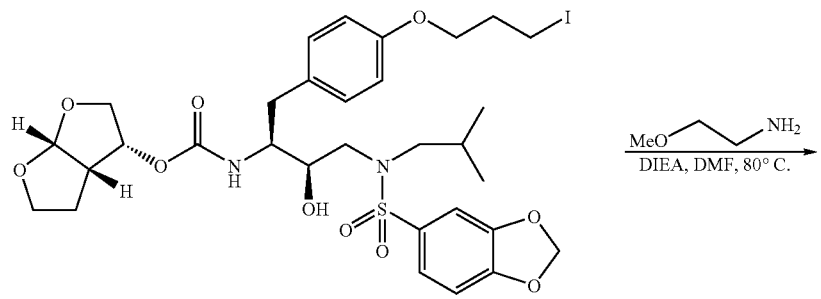

(3R,3aS,6aR)-hexahydrofuro[2,3-b]furan-3-yl (1S,2R)-3-[(1,3-benzodioxol-5-ylsulfonyl)(isobutyl)amino]-2-hydroxy-1-(4-{3-[(2-methoxyethyl)amino]propoxy}benzyl) propylcarbamate (283)

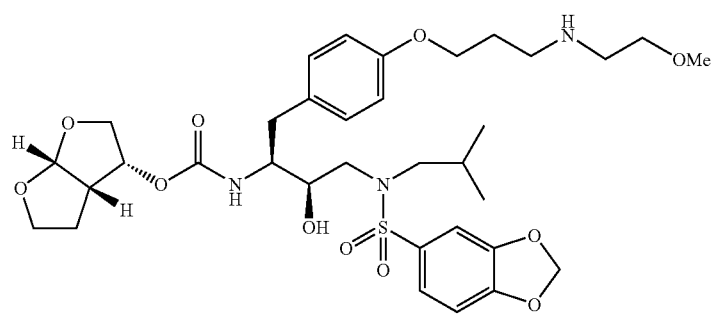

The title compound was prepared according to example 66 with the exception that 2-methoxyethylamine was substituted for thiazolidine. $^1$H NMR (CDCl$_3$): 7.38 (d, 0.1H), 7.20 (s, 1H), 7.14 (d, 2H), 6.91 (d, 1H), 6.86 (d, 2H), 6.12 (s, 2H), 5.69 (d, 1H), 5.13-4.90 (m, 2H), 4.01 (m, 3H), 3.87 (m, 3H), 3.74 (m, 3H), 3.52 (t, 2H), 3.40 (s, 3H), 3.18 (dd, 1H), 3.00 (m, 4H), 2.81 (m, 7H), 2.08-1.50 (m, 5H), 0.98 (d, 3H), 0.91 (d, 35). MS(ESI): 708(M+H).

Example 73

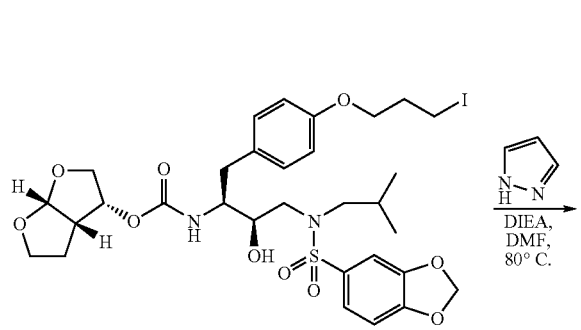

(3R,3aS,6aR)-hexahydrofuro[2,3-b]furan-3-yl (1S,2R)-3-[(1,3-benzodioxol-5-ylsulfonyl)(isobutyl)amino]-2-hydroxy-1-{4-[3-(1H-pyrazol-1-yl)propoxy]benzyl}propylcarbamate (284)

The title compound was prepared according to example 66 with the exception that pyrazole was substituted for thiazolidine. $^1$H NMR (CDCl$_3$): 7.50 (s, 1H), 7.32 (s, 1H), 7.29 (d, 1H), 7.13 (s, 1H), 7.08 (d, 2H), 6.85 (d, 1H), 6.76 (d, 2H), 6.20 (s, 1H), 6.06 (s, 2H), 5.61 (d, 1H), 5.00 (q, 1H), 4.88 (d, 1H), 4.33 (t, 2H), 3.92 (dd, 1H) 3.80 (m, 5H), 3.68 (m, 2H), 3.58 (br s, 1H), 3.09 (dd, 1H), 2.90 (m, 4H), 2.73 (m, 2H), 2.28 (m, 2H), 1.85-1.43 (m, 3H), 0.89 (d, 3H), 0.82 (d, 3H). MS(ESI): 701(M+H).

Example 74

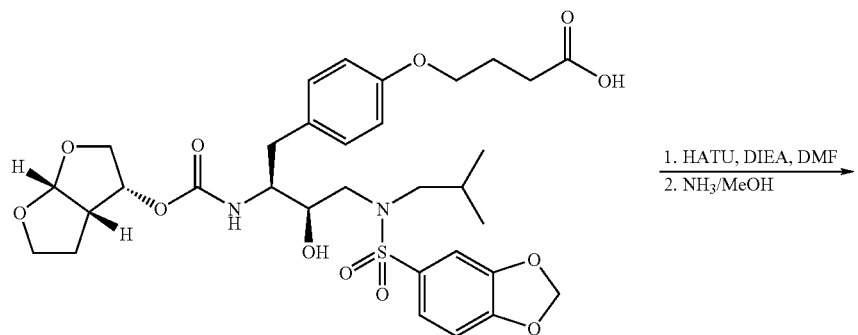

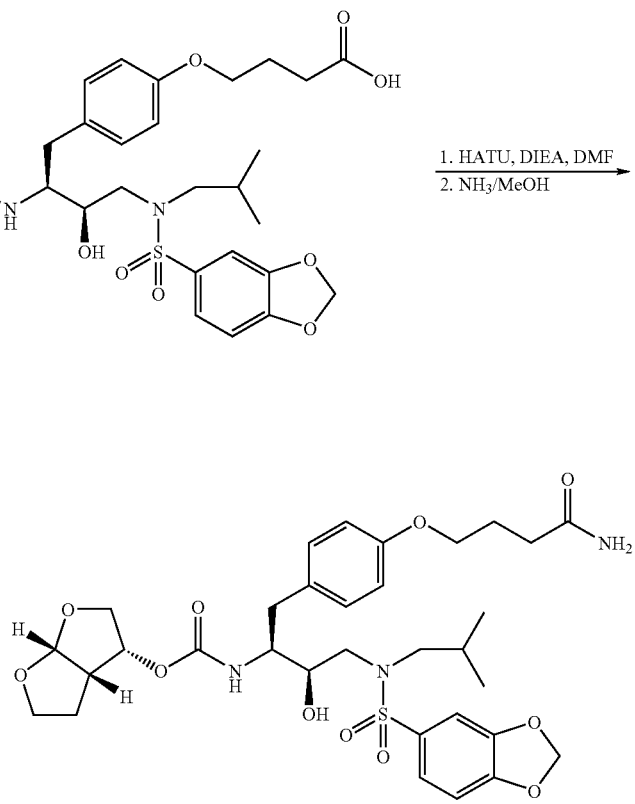

(3R,3aS,6aR)-hexahydrofuro[2,3-b]furan-3-yl (1S,2R)-1-[4-(4-amino-4-oxobutoxy)benzyl]-3-[(1,3-benzodioxol-5-ylsulfonyl)(isobutyl)amino]-2-hydroxypropylcarbamate (285)

A solution of 25 mg (0.037 mmol) of 4-(4-{(2S,3R)-2-({[(3R,3aS,6aR)-hexahydrofuro[2,3-b]furan-3-yloxy]carbonyl}amino)-4-[(1,3-benzodioxol-5-ylsulfonyl)(isobutyl)amino]-3-hydroxybutyl}phenoxy)butanoic acid and 19 μL (0.11 mmol) of N,N-diisopropylethylamine in 1 mL of anhydrous DMF was treated with 28 mg (0.074 mmol) of O-(7-azabenzotriazol-* 1-yl) 1,1,3,3-tetramethyluronium hexafluorophosphate (HATU). The resulting solution was stirred at RT for 15 minutes and was then treated with 0.5 mL of 2M NH$_3$ in MeOH. After 20 minutes TLC indicated the reaction to be complete. The solution was concentrated to dryness at reduced pressure and the residue subjected to flash chromatography (SiO$_2$, 95:5 CH$_2$Cl$_2$/2M NH$_3$ in MeOH) to afford 11 mg (44%) of the desired compound as a white powder. $^1$H NMR (CDCl$_3$): 7.30 (d, 1H), 7.14 (s, 1H), 7.07 (d, 2H), 6.85 (d 2H), 6.75 (d, 2H), 6.05 (s, 2H), 5.60 (d, 1H), 5.56-5.34 (m, 2H), 4.97 (m, 2H), 3.94 (m, 3H), 3.78 (m, 3H), 3.66 (m, 2H), 3.09 (m, 1H), 3.00-2.64 (m, 7H), 2.40 (t, 2H), 2.08 (m, 2H), 1.80 (m, 1H), 1.61 (m, 1H), 1.48 (m, 1H), 0.90 (d, 3H), 0.82 (d, 3H). MS(ESI): 678(M+H).

Example 75

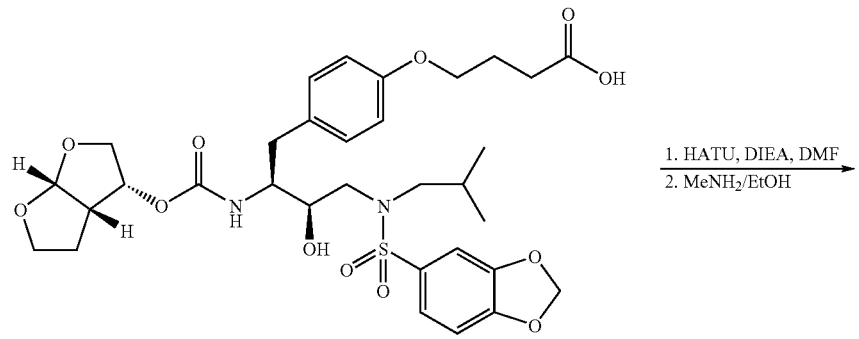

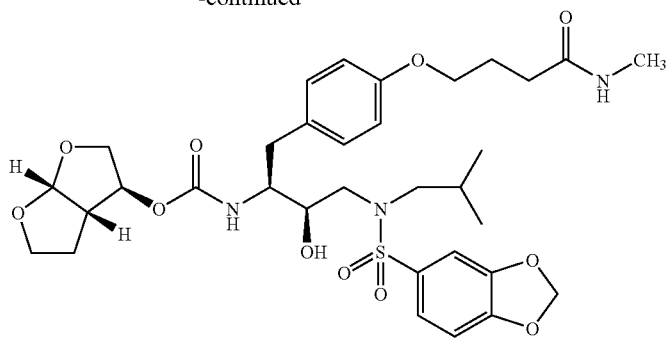

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[4-(methylamino)-4-oxobutoxy]benzyl}propylcarbamate (286)

A solution of 35 mg (0.052 mmol) of 4-(4-{(2S,3R)-2-({[(3R,3aS,6aR)-hexahydrofuro[2,3-b]furan-3-yloxy]carbonyl}amino)-4-[(1,3-benzodioxol-5-ylsulfonyl)(isobutyl)amino]-3-hydroxybutyl}phenoxy)butanoic acid and 27 µL (0.16 mmol) of N,N-diisopropylethylamine in 1 mL of anhydrous DMF was treated with 49 mg (0.13 mmol) of O-(7-azabenzotriazol-1-yl)-1,1,3,3-tetramethyluronium hexafluorophosphate (HATU). The resulting solution was stirred at RT for 15 minutes and was then treated with 0.5 mL of 8M MeNH$_2$ in EtOH. After 18 hours TLC indicated the reaction to be complete. The solution was concentrated to dryness at reduced pressure and the residue subjected to flash chromatography (SiO$_2$, 95:5 CH$_2$Cl$_2$/MeOH) to afford 22 mg (61%) of the desired compound as a white powder. $^1$H NMR (CDCl$_3$): 7.37 (d, 1H), 7.22 (s, 1H), 7.13 (d, 2H), 6.92 (d, 1H), 6.82 (d, 2H), 6.13 (s 2H), 5.67 (m, 2H), 5.05 (m, 2H), 4.00 (m, 3H), 3.88 (m, 3H), 3.72 (m, 2H), 3.24-2.71 (m, 11H), 2.40 (t, 2H), 2.16 (m, 2H), 1.88 (m, 1H), 1.67 (m, 1H), 1.53 (m, 1H), 0.94 (m, 6H). MS(ESI): 692(M+H).

Example 76

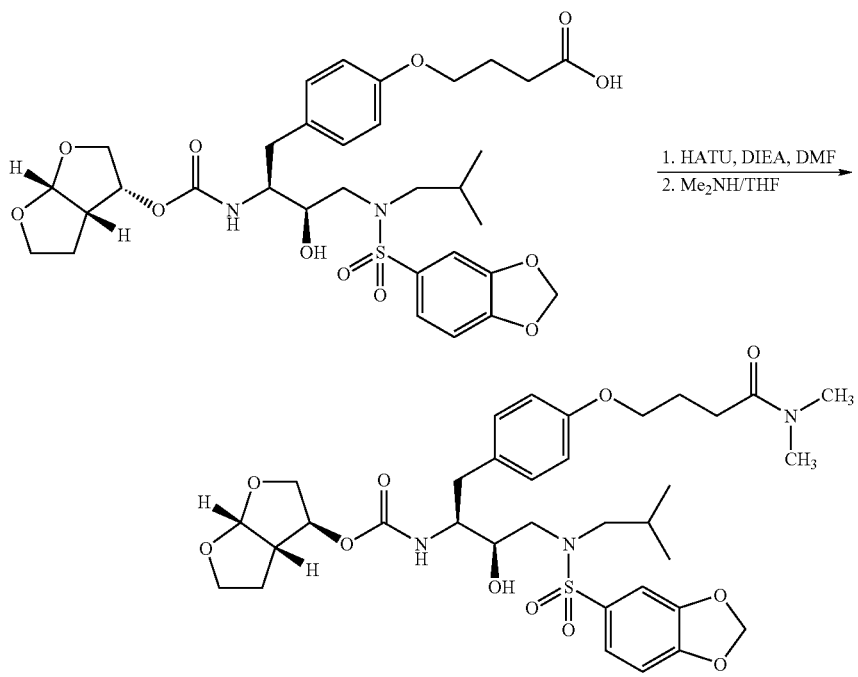

(3R,3aS,6aR)-hexahydrofuro[2,3-b]furan-3-yl (1S, 2R)-3-[(1,3-benzodioxol-5-ylsulfonyl)(isobutyl) amino]-1-{4-[4-(dimethylamino)-4-oxobutoxy]benzyl}-2-hydroxypropylcarbamate (287)

The title compound was prepared according to example 286 with the exception that 1 mL of 2M Me$_2$NH/THF was substituted for MeNH$_2$/EtOH. $^1$H NMR (CDCl$_3$): 7.36 (d, 1H), 7.21 (s, 1H), 7.13 (d, 2H), 0.92 (d, 1H), 6.85 (d, 2H), 6.12 (s, 2H), 5.69 (d, 1H), 5.02 (m, 2H), 4.01 (m, 3H), 3.87 (m, 3H), 3.73 (m, 2H), 3.16 (dd, 1H), 3.10-2.88 (m, 11H), 2.81 (m, 2H), 2.54 (t, 2H), 2.16 (m, 2H), 1.86 (m, 1H), 1.79-1.50 (m, 2H), 0.98 (d, 3H), 0.90 (d, 3H). MS(ESI): 706(M+H).

Example 77

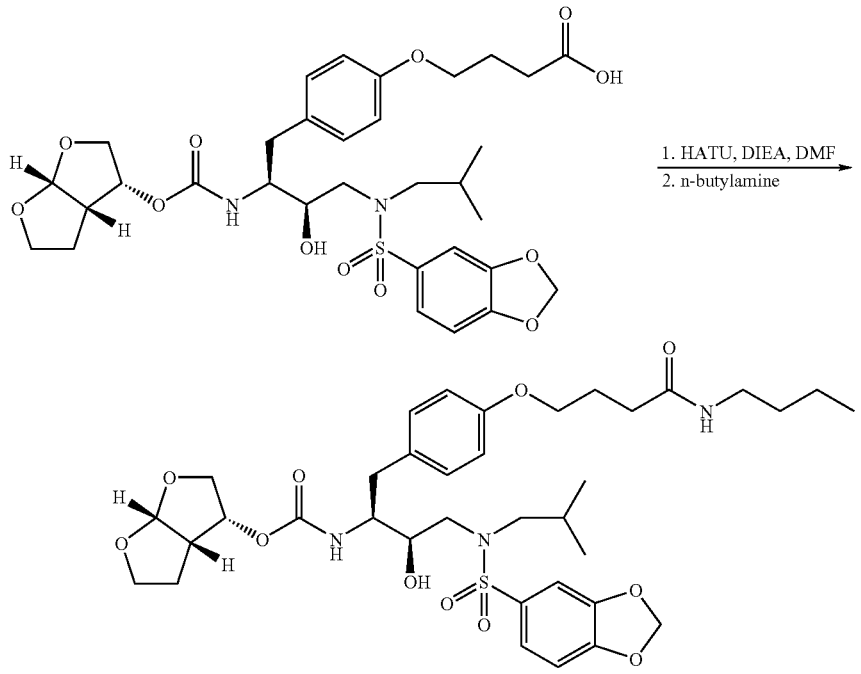

(3R,3aS,6aR)-hexahydrofuro[2,3-b]furan-3-yl (1S, 2R)-3-[(1,3-benzodioxol-5-ylsulfonyl)(isobutyl) amino]-1-{4-[4-(butylamino)-4-oxobutoxy]benzyl}-2-hydroxypropylcarbamate (288)

The title compound was prepared according to example 286 with the exception that 60 μL of n-butylamine was substituted for MeNH$_{22}$/EtOH. $^1$H NMR (CDCl$_3$): 7.38 (d, 1H) 7.21 (s, 1H), 7.14 (d, 2H), 6.93 (d, 1H), 6.84 (d, 2H), 6.12 (s, 2H), 5.69 (d, 1H), 5.60 (br s, 1H), 5.03 (m, 2H), 4.00 (m, 3H), 3.87 (m, 3H), 3.73 (m, 2H), 3.39-2.72 (m, 10H), 2.39 (t, 2H), 2.13 (m, 2H), 1.88 (m, 1H), 1.69 (m, 1H), 1.60-1.27 (m, 5H), 0.93 (m, 9H). MS(ESI): 734(M+H).

Example 78

Step 1 t-Butyl-(1S,2R)-1-(4-benzyloxy-benzyl)-3-i-butylamino-2-hydroxypropyl-carbamate

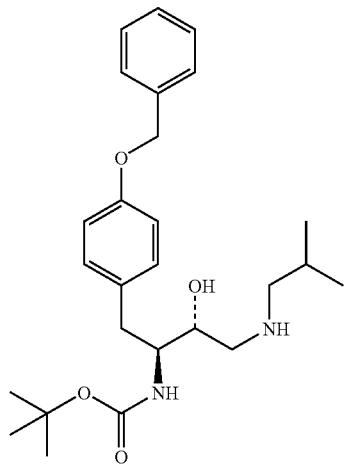 [SMILES: CC(C)CNC[C@@H](O)[C@H](Cc1ccc(OCc2ccccc2)cc1)NC(=O)OC(C)(C)C]

i-Butylamine (7.0 g, 94.7 mmol) was added to a solution of t-butyl-(1S,2R)-1-(4-benzyloxy-benzyl)-2,3-epoxydo-propyl-carbamate (5.0 g, 13.5 mmol) (prepared according to the reference by Chen, P. at all., *Tetrahedron Letters* 1997, 38, 3175-3178), in i-propanol (70 mL). The mixture was stirred at 85° C. for 2 hours, then cooled to 5° C. Water (400 mL) was added dropwise. The resulting suspension was stirred for 30 minutes at 5° C., then filtered. The solid was washed with water (3×100 mL), and dried in vacuo to yield title product (5.5 g, 92%).

$^1$H NMR (CDCl$_3$): δ 0.88 (6H, d), 1.34 (9H, s), 1.68 (1H, m), 2.38 (2H, d), 2.64 (2H, d), 2.80 (1H, m), 2.86 (1H, dd), 3.40 (1H, m), 3.70 (2H, broad s), 4.63 (1H, d), 5.01 (2H, s), 6.88 (2H, d), 7.12 (2H, d), 7.40 (5H, m).

Step 2 t-Butyl-N((1S,2R)-1-(4-benzyloxy-benzyl)-3-i-butyl-[(3-nitrobenzene)sulfonyl]-amino-2-hydroxypropyl-carbamate

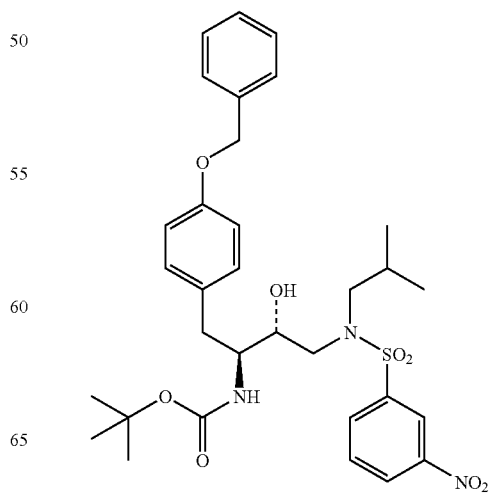

A CH$_2$Cl$_2$ (50 mL) solution of the product from Step 1 (1.7 g, 3.8 mmol), 3-nitrobenzenesulfonylchloride (1.1 g, 4.8 mmol), and diisopropylethylamine (1.0 g, 7.8 mmol) was stirred at 20° C. for 4 hours. Water (70 mL) was then added to the reaction mixture and the phases were separated. The aqueous phase was extracted with CH$_2$Cl$_2$ (3×100 ml). The combined organic phases were dried over MgSO$_4$ and concentrated. The residue was dissolved in ether (300 mL), and silicagel (50 g) was added to the solution. The mixture was then filtered. The filtrate was concentrated under reduced pressure. The residue was added hexane (300 mL), stirred for three hours at 20° C., and then the white solid was filtered and dried to afford title compound (1.9 g, 80%).

$^1$H NMR (CDCl$_3$): δ 0.88 (6H, d), 1.35 (9H, s), 1.86 (1H, m), 2.85 (2H, m), 2.99 (2H, d), 3.19 (2H, d), 3.77 (2H, m), 4.57 (1H, d), 5.03 (2H, s), 6.90 (1H, d), 7.12 (1H, d), 7.40 (5H, m), 7.69 (1H t), 8.08 (1H, d), 8.39 (1H, d), 8.62 (1H, s).

Step 3

(3R,3aS,6aR)-Hexahydrofuro[2,3-b]furan-3-yl-N ((1S,2R)-1-(4-benzyloxy-benzyl)-3-i-butyl-[(3-nitrobenzene)sulfonyl]-amino-2-hydroxypropyl-carbamate

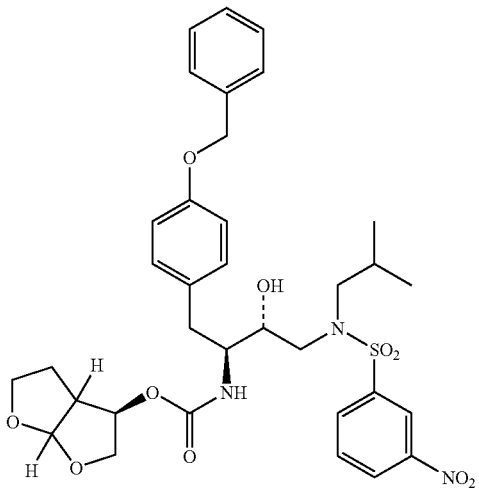 [SMILES: CC(C)CN(C[C@@H](O)[C@H](Cc1ccc(OCc2ccccc2)cc1)NC(=O)O[C@H]1COC2OCCC21)S(=O)(=O)c1cccc([N+](=O)[O-])c1]

Trifluoroacetic acid (15 mL) was added dropwise to a solution of the product from Step 2 (1.5 g, 5 mmol) in CH$_2$Cl$_2$ (40 mL). The mixture was stirred for 1 hour at 20° C., then concentrated under reduced pressure. The residue was dissolved in CH$_2$Cl$_2$ (200 mL) and 10% aqueous Na$_2$CO$_3$ solution (100 mL) was added. The mixture was stirred at 20° C. for 15 minutes. Phases were separated, and the aqueous phase was extracted with additional CH$_2$Cl$_2$ (0.2×50 ml). The combined organic phases were then dried over Na$_2$CO$_3$ and concentrated under reduced pressure. The residue was dissolved in acetonitrile (40 mL). Diisopropylethylamine (2.0 g, 15.3 mmol) and (3R,3aS,6aR)-hexahydrofuro[2,3-b]furan-3-yl-4-nitrophenyl carbonate (2.0 g, 6.7 mmol) were added, and the solution was stirred for 12 hours at 20° C. Then 25% aqueous ammonium hydroxide solution (6 mL) was added, and the mixture was stirred for an additional 0.5 hour. The solvents were removed under reduced pressure. The residue was dissolved in EtOAc (100 mL), and the solution was extracted with 5% aqueous Na$_2$CO$_3$ solution (10×75 ml) and washed with brine (1×75 mL). The organic phase was dried over Na$_2$CO$_3$, and concentrated in vacuo. Hexane (30 mL) was added to the residue and the mixture was stirred at 20° C. for 1 hour. Then the white solid was filtered and air dried to yield title compound (1.5 g, 60%).

$^1$H NMR (CDCl$_3$): δ 0.86 (3H, d), 0.88 (3H, d), 1.54 (1H, m), 1.65 (1H, m), 1.85 (1H, m), 2.75 (1H, m), 2.97 (4H, m), 3.14 (2H, m), 3.37 (1H, m), 3.68 (2H, m), 3.82 (2H, m), 3.94 (2H, m), 4.85 (1H, d), 5.00 (3H, s), 5.60 (1H, d), 6.88 (2H, d), 7.09 (2H, d), 7.35 (5H, m), 7.72 (1H, t), 8.07 (1H, d), 8.38 (1H, d), 8.61 (1H, s); MS 684 (M$^+$).

Step 4

N-(3R,3aS,6aR)-Hexahydrofuro[2,3-b]furan-3-yl-oxycarbonyl-(4S,5R)-4-(4-benzyloxy-benzyl)-5-i-butyl-[(3-nitrobenzene)sulfonyl]-aminomethyl-2,2-dimethyl-1-oxazolidine

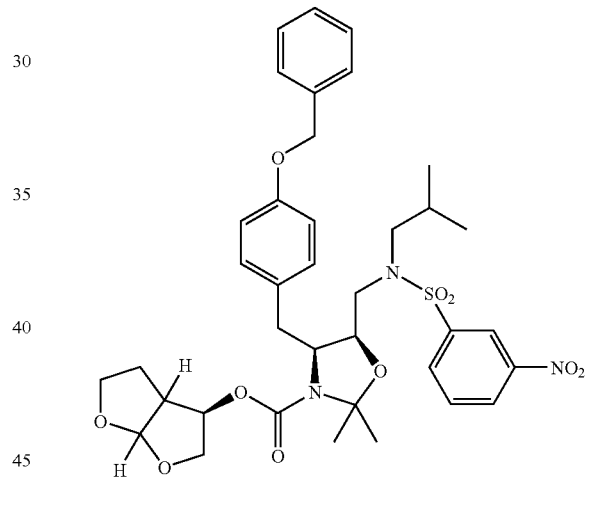

A CH$_2$Cl$_2$ (8 mL) solution of the product of Step 3 (0.5 g, 0.7 mmol) was added 2,2-dimethoxy-propane (0.8 mL, 6.5 mmol) and p-toluenesulfonic acid (40 mg, 0.2 mmol). The mixture was refluxed for 4 hours, cooled to 20° C., and washed with 5% aqueous Na$_2$CO$_3$ solution (10 mL). The organic phase was dried over MgSO$_4$, filtered; and concentrated under reduced pressure. The residue was chromatographed on SiO$_2$ using hexane-EtOAc (1:1) as eluent, to provide title compound (0.5 g, 95%).

$^1$H NMR (CDCl$_3$): δ 0.83 (3H, d), 0.91 (3H, d), 1.33, 1.40 (3H, s)*, 1.50, 1.57 (3H, s)*, 1.85 (2H, m), 1.97 (1H, m), 2.70 (3H, m), 3.10 (3H, m), 3.22 (1H, d), 3.36 (1H, d), 3.43 (1H, m), 3.80 (2H, m), 3.94 (1H, m), 4.21 (2H, m), 5.03 (2H, s), 5.65, 5.68 (1H, d)*, 6.87 (2H, d), 7.02 (1H, d), 7.38 (5H, m), 7.62 (1H, t), 7.85 (1H, d), 8.35 (1H, t), 8.54 (1H, s); MS: 724 (M$^+$).

*possible indication for rotamers.

Step 5

N-(3R,3aS,6aR)-Hexahydrofuro[2,3-b]furan-3-yl-oxycarbonyl-(4S,5R)-4-(4-hydroxybenzyl)-5-i-butyl-[(3-aminobenzene)sulfonyl]-aminomethyl-2,2-dimethyl-oxazolidine

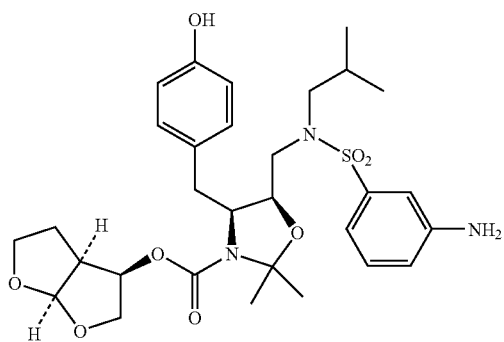 [SMILES: CC(C)CN(C[C@H]1OC(C)(C)N(C(=O)O[C@H]2CO[C@H]3OCC[C@H]32)[C@H]1Cc1ccc(O)cc1)S(=O)(=O)c1cccc(N)c1]

Pd/C (10% Pd, Degussa type) (0.5 g) was added to a THF (10 mL) solution of the product of Step 4 (0.5 g, 0.7 mmol). The mixture was hydrogenated under atmospheric pressure $H_2$ for 12 hours. The catalyst was removed by filtration through Celite, and the solvent was evaporated in vacuo. The residue was triturated in hexane. The white solid was then filtered and washed with hexane (2×20 ml) to afford title compound (210 mg, 50%).

$^1$H NMR (DMSO-$d_6$): δ0.80 (6H, m), 1.22, 1.35 (3H, s), 1.45, 1.53 (3H, s)*, 1.75 (2H, m), 1.95 (1H, m), 2.50-3.30 (10H, m), 3.60 (2H, d), 3.80 (1H, m), 4.06 (1H, m), 4.74 (1H, dd), 5.52 (2H, d), 6.65 (3H, m), 6.90 (3H, m), 7.12 (1H, t), 9.22 (1H, s); MS: 604 (M$^+$).

*possible indication for rotamers.

Step 6

(3R,3aS,6aR)-Hexahydrofuro[2,3-b]furan-3-yl-N ((1S,2R)-1-[4-(3-cyanobenzyloxy)-benzyl]-3-i-butyl-[(3-aminobenzene)sulfonyl]-amino-2-hydroxypropyl-carbamate (289)

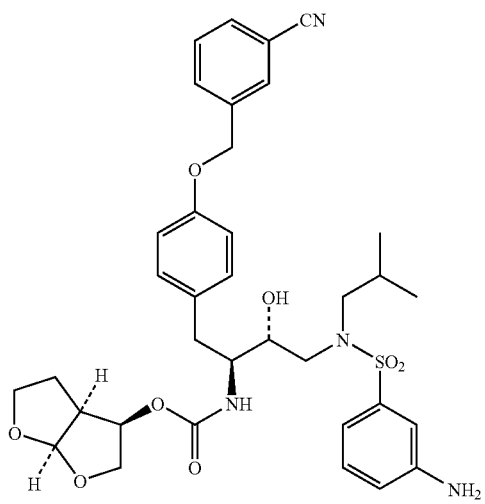 [SMILES: CC(C)CN(C[C@@H](O)[C@H](Cc1ccc(OCc2cccc(C#N)c2)cc1)NC(=O)O[C@H]1CO[C@H]2OCC[C@H]21)S(=O)(=O)c1cccc(N)c1]

$Cs_2CO_3$ (134.4 mg, 0.4 mmol) and 3-(bromomethyl)benzonitrile (65 mg, 0.3 mmol) were added to the product of Step 5 (200 mg, 0.3 mmol) in DMF (2 mL). The mixture was stirred at 20° C. for 4 hours, diluted with $Et_2O$ (50 mL), and filtered. The filtrate was washed with water (1×35 mL), dried over $MgSO_4$, and concentrated under reduced pressure. The residue, dissolved in 1,4-dioxane (6 mL), was added 4 M HCl in dioxane (7.5 ml) and water (0.2 g). The solution was stirred at 20° C. for 2 hours and then diluted with water (50 mL). A solution of 5% aqueous $Na_2CO_3$ was added until pH 12-14, and the mixture was extracted with $CH_2Cl_2$ (3×20 mL). The combined organic phases were dried over $MgSO_4$ and concentrated under reduced pressure. The residue was chromatographed on $SiO_2$ using EtOAc-hexane (4:1) as eluent to afford title compound (85 mg, 45%).

$^1$H NMR (DMSO-$d_6$): δ 0.78 (3H, d), 0.83 (3H, d), 1.25 (2H, m), 1.34 (1H, m), 1.90 (1H, m), 2.36 (1H, t), 2.71 (3H, m), 2.93 (2H, m), 3.54 (4H, m), 3.66 (1H, t), 3.80 (1H, dd), 4.80 (1H, dd), 4.95 (1H, d), 5.08 (2H, s), 5.47 (1H, d), 5.53 (2H, s), 6.73 (1H, d), 6-80 (1H, d), 6-84 (2H, d), 6.92 (1H, s), 7.10 (2H, d), 7.15 (2H, t), 7.57 (1H, t), 7.75 (2H, t), 7.85 (1H, s); MS: 679 (M$^+$).

Example 79

(3R,3aS,6aR)-Hexahydrofuro[2,3-b]furan-3-yl-N ((1S,2R)-1-(4-benzyloxy-benzyl)-3-i-butyl-[(3-aminobenzene)sulfonyl]-amino-2-hydroxypropyl-carbamate (290)

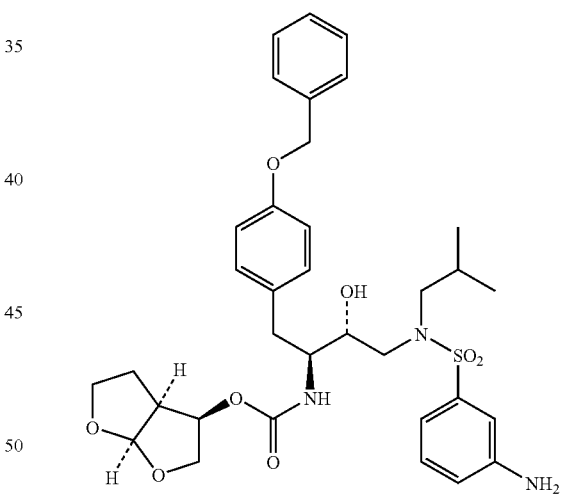

(3R,3aS,6aR)-Hexahydrofuro[2,3-b]furan-3-yl-N((1S,2R)-1-(4-benzyloxy-benzyl)-3-i-butyl-[(3-nitrobenzene)sulfonyl]-amino-2-hydroxypropyl-carbamate (100 mg, 0.15 mmol) in THF (3 mL) was added Pt/C (3% Pt) (30 mg). The mixture was hydrogenated under atmospheric pressure $H_2$ for 12 hours. The catalyst was removed by filtration through Celite, and the solvent was evaporated in vacuo to yield title compound (60 mg, 65%).

$^1$H NMR (CDCl$_3$): δ 0.82 (3H, d), 0.89 (3H, d), 1.22 (1H, m), 1.60 (1H, m), 1.81 (2H, m), 2.77 (2H, m), 2.97 (4H, m), 3.15 (1H, m), 3.64 (3H, m), 3.82 (3H, m), 3.95 (1H, m) r 4.96 (1H, d), 5.02 (3H, d), 5.63 (1H, d), 6.80 (1H, d), 6.88 (2H, d), 6.96 (3H, m), 7.08 (3H, m), 7.12 (1H, m), 7.35 (4H, m); MS: 654 (M$^+$).

Example 80

(3R,3aS,6aR)-Hexahydrofuro[2,3-b]furan-3-yl-N((1S,2R)-1-(4-hydroxybenzyl)-3-i-butyl-[(3-aminobenzene)sulfonyl]-amino-2-hydroxypropyl-carbamate (291)

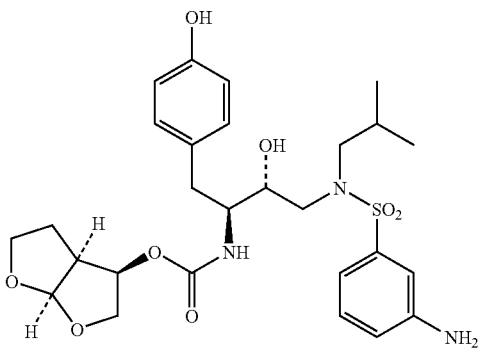 [SMILES: CC(C)CN(C[C@@H](O)[C@H](Cc1ccc(O)cc1)NC(=O)O[C@H]1CO[C@H]2OCC[C@H]21)S(=O)(=O)c1cccc(N)c1]

(3R,3aS,6aR)-Hexahydrofuro[2,3-b]furan-3-yl-N((1S,2R)-1-(4-benzyloxy-benzyl)-3-i-butyl-[(3-nitrobenzene)sulfonyl]-amino-2-hydroxypropyl-carbamate (300 mg, 0.44 mmol) in THF (8 mL) was added Pd/C (10% Pd, Degussa Type) (300 mg). The mixture was hydrogenated under atmospheric pressure $H_2$ for 12 hours. The catalyst was removed by filtration through Celite, and the solvent was evaporated in vacuo to yield title compound (95 mg, 50%).

$^1$H NMR (DMSO-$d_6$): δ 0.75 (3H, d), 0.82 (3H, d), 1.25 (2H, m), 1.40 (1H, m), 1.93 (1H, m), 2.32 (1H, t), 2.72 (3H, m), 2.85 (1H, d), 2.95 (1H, m), 3.55 (4H, m), 3.71 (1H, t), 3.81 (1H, dd), 4.82 (1H, dd), 4.92 (1H, m), 5.48 (1H, d), 5.53 (2H, s), 6.56 (2H, d), 6.73 (1H, d), 6.79 (1H, d), 6.94 (3H, m), 7.14 (2H, m), 9.00 (1H, s).

Example 81

(3R,3aS,6aR)-Hexahydrofuro[2,3-b]furan-3-yl-N((1S,2R)-1-(4-(butylamine)benzyl)-3-i-butyl-[(3-aminobenzene) sulfonyl]-amino-2-hydroxypropyl-carbamate (292)

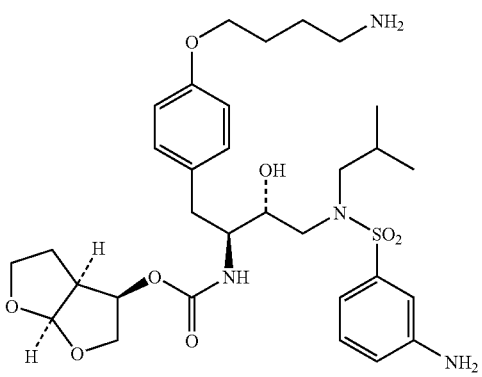 [SMILES: CC(C)CN(C[C@@H](O)[C@H](Cc1ccc(OCCCCN)cc1)NC(=O)O[C@H]1CO[C@H]2OCC[C@H]21)S(=O)(=O)c1cccc(N)c1]

t-Butyl-N-(4-hydroxybutyl) carbamate (75.7 mg, 0.40 mmol) and triphenylphosphine (105 mg, 0.40 mmol) were mixed in $CH_2Cl_2$ (5 mL) and stirred at 0° C. for 30 minutes. Di-t-butyl azodicarboxylate (92.1 mg, 0.40 mmol) was then added, followed by (3R,3aS,6aR)-Hexahydrofuro[2,3-b]furan-3-yl-N((1S,2R)-1-(4-hydroxybenzyl)-3-i-butyl-[(3-aminobenzene) sulfonyl]amino-2-hydroxypropyl-carbamate (90 mg, 0.16 mmol). The mixture was stirred at 20° C. for 12 hours. The solvent was then evaporated, and the residue was chromatographed on $SiO_2$ using EtOAc-hexane (4:1) as eluent. The isolated intermediate was dissolved in $CH_2Cl_2$ (16 mL). TFA (4 mL) was added. The mixture was stirred for 2 hours at room temperature, and concentrated to afford title compound (65 mg, 50%) as a TFA salt.

$^1$H NMR (DMSO-$d_6$): δ 0.75 (3H, d), 0.82 (3H, d), 1.20 (2H, m), 1.38 (1H, m), 1.60 (6H, m), 1.90 (1H, m), 2.38 (1H, t), 2.75 (3H, m), 2.92 (1H, m), 3.37 (2H, m), 3.72 (1H, t), 3.82 (1H, dd), 3.90 (1H, m), 4.37 (1H, t), 4.80 (1H, dd), 5.48 (1H, d), 6.77 (3H, m), 6.85 (1H, d), 6.97 (1H, s), 7.09 (2H, d), 7.16 (2H, dd), 7.65 (2H, broad s); MS: 635 ($M^+$).

Example 82

Step 1 t-Butyl-(1S,2R)-1-(4-hydroxybenzyl)-2,3-epoxydopropyl-carbamate

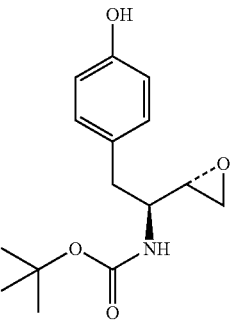

Pd(OH)$_2$/C (20% Pd, Degussa Type) (70 mg) was added to a solution of t-butyl-(1S,2R)-1-(4-benzyloxy-benzyl)-2,3-epoxydo-propyl-carbamate (700 mg, 1.9 mmol) (prepared according to the reference by Chen, P. at all., *Tetrahedron Letters* 1997, 38, 3175-3178) in EtOH (12 mL) and EtOAc (3 mL). The mixture was hydrogenated under atmospheric pressure $H_2$ for 2 hours, filtrated through Celite, and concentrated to yield title compound (530 mg, 100%).

$^1$H NMR (DMSO-$d_6$): δ 1.25 (9H, s), 2.55 (4H, m), 2.82 (1H, m), 3.36 (1H, m), 6.60 (2H, d), 6.75 (1H, d), 6.95 (2H, d), 9.09 (1H, s).

Step 2 t-Butyl-(1S,2R)-1-(4-(2-pyridylmethyloxy)benzyl)-2,3-epoxydo-propyl-carbamate

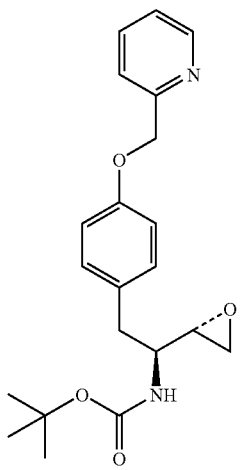

Cs$_2$CO$_3$ (1.60 g, 5.05 mmol) in DMF (10 mL) was added 2-picolylchloride hydrochloride (400 mg, 2.44 mmol). After stirring for 0.5 minutes at room temperature, t-Butyl-(1S,2R)-1-(4-hydroxybenzyl)-2,3-epoxydo-propyl-carbamate (450 mg, 1.61 mmol) was added. The mixture was stirred for an additional 2 hours at 20° C., diluted with Et$_2$O (50 mL), and filtered. The filtrate was washed with water, dried over MgSO$_4$, and concentrated. The residue was chromatographed on silicagel using EtOAc-hexane (3:2) as eluent to afford title compound (505 mg, 85%).

$^1$H NMR (DMSO-d$_5$) δ 1.22 (9H, s), 2.45 (1H, s), 2.62 (1H, m), 2.74 (1H, dd), 2.84 (1H, m), 3.42 (1H, n), 5.08 (2H, s), 6.79 (1H, d), 6.87 (2H, d), 7.07 (2H, d), 7.28 (1H, dd), 7.44 (1H, d), 7.78 (1H, t), 8.52 (1H, d); MS: 371 (M$^+$).

Step 3 t-Butyl-(1S,2R)-1-(4-(2-pyridylmethyloxy)benzyl)-3-i-butylamino-2-hydroxypropyl-carbamate

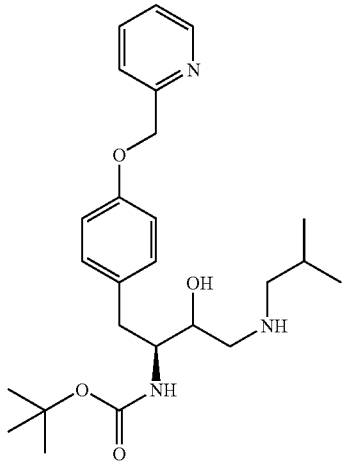 [SMILES: CC(C)CNCC(O)[C@H](Cc1ccc(OCc2ccccn2)cc1)NC(=O)OC(C)(C)C]

i-Butylamine (610 mg, 8.33 mmol) was added to a solution of t-Butyl-(1S,2R)-1-(4-(2-pyridylmethyloxy)benzyl)-2,3-epoxydo-propyl-carbamate (440 mg, 1.20 mmol) in i-propanol (10 mL). The mixture was then stirred at 85° C. for 2 hours, cooled to 5° C., diluted with water (75 mL), and extracted with CHCl$_3$ (4×70 ml). The combined organic phases were dried over MgSO$_4$, filtered, and concentrated to afford title product (320 mg, 60%).

$^1$H NMR (CDCl$_3$): δ 0.87 (6H, d), 1.33 (9H, s), 1.67 (1H, m), 2.37 (2H, d), 2.65 (2H, d), 2.77 (1H, m), 2.85 (1H, dd), 3.41 (1H, m), 3.72 (2H, m), 4.63 (1H, d), 5.15 (2H, s), 6.89 (2H, d), 7.12 (2H, d), 7.19 (1H, dd), 7.49 (1H, d), 7.67 (1H, t), 8.57 (1H, d).

Step 4 t-Butyl-N((1S,2R)-1-(4-(2-pyridylmethyloxy)benzyl)-3-i-butyl-[(3-nitrobenzene)sulfonyl]-amino-2-hydroxropyl-carbamate

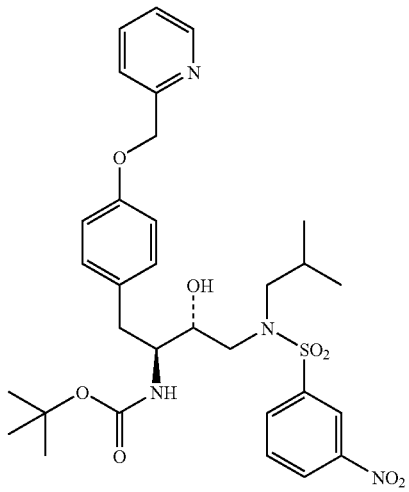

A CH$_2$Cl$_2$ (10 mL) solution of t-Butyl-(1S,2R)-1-(4-(2-pyridylmethyloxy)benzyl)-3-i-butylamino-2-hydroxypropyl-carbamate (320 mg, 0.72 mmol), 3-nitrobenzenesulfonyl chloride (200 mg, 0.90 mmol), and diisopropylethylamine (186 mg, 1.44 mmol) was stirred at 20° C. for 12 hours. Water (20 mL) was then added to the reaction mixture and the phases were separated. The aqueous phase was extracted with CH$_2$Cl$_2$ (3×25 mL). The combined organic phases were dried over MgSO$_4$ and concentrated. The residue was then filtered through SiO$_2$ using CH$_2$Cl$_2$-acetone. (3:2) as eluent. The filtrate was concentrated under reduced pressure to yield title product (330 mg, 7.5).

$^1$H NMR (DMSO-d$_6$): δ 0.78 (6H, d), 1.20 (9H, s), 1.93 (1H, m), 2.37 (1H, dd), 2.85 (1H, dd), 3.10 (2H, m), 3.42 (1H, d), 4.88 (1H, d), 5.08 (2H, s), 6.61 (1H, d), 6.85 (2H, d), 7.04 (2H, d), 7.29 (1H, m), 7.44 (1H, d), 7.82 (2H, m), 8.19 (1H, d), 8.43 (2H, s), 8.53 (1H, d).

Step 5

(3R,3aS,6aR)-Hexahydrofuro[2,3-b]furan-3-yl-N((1S,2R)-1-(4-(2-pyridylmethyloxy)benzyl)-3-i-butyl-[(3-nitrobenzene)sulfonyl]-amino-2-hydroxypropyl-carbamate

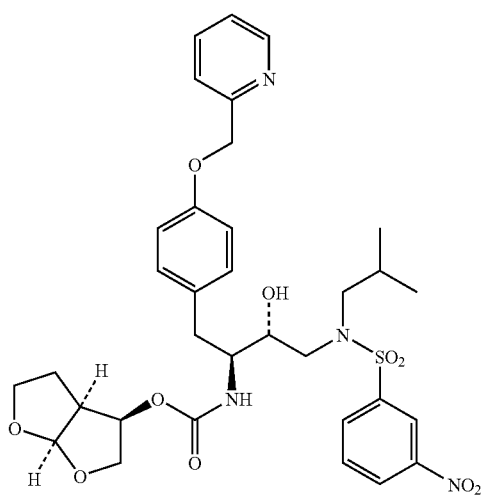 [SMILES: CC(C)CN(C[C@@H](O)[C@H](Cc1ccc(OCc2ccccn2)cc1)NC(=O)O[C@H]1CO[C@H]2OCC[C@H]21)S(=O)(=O)c1cccc([N+](=O)[O-])c1]

Trifluoroacetic acid (4 mL) was added dropwise to a solution of t-Butyl-N (1S,2R)-(4-(2-pyridylmethyloxy)benzyl)-3-i-butyl-[(3-nitrobenzene)sulfonyl]-amino-2-hydroxypropyl-carbamate (330 mg, 0.52 mmol) in $CH_2Cl_2$ (8 rat). The mixture was stirred at 20° C. for 1.5 hour, then concentrated under reduced pressure. The residue was dissolved in $CH_2Cl_2$ (150 mL) and 10% aqueous $Na_2CO_3$ solution (50 mL) was added. The mixture was stirred at 20° C. for 15 minutes. Phases were separated, and the aqueous phase was extracted with additional $CH_2Cl_2$ (2×50 ml). The combined organic phases were then dried over $Na_2CO_3$ and concentrated under reduced pressure. The residue was dissolved in acetonitrile (7 mL). Diisopropylethylamine (269 mg, 2.08 mmol) and (3R,3aS,6aR)-hexahydrofuro[2,3-b]furan-3-yl-4-nitrophenyl carbonate (272 mg, 0.92 mmol) were added, and the solution was stirred at 20° C. for 12 hours. Then, 25% aqueous ammonium hydroxide-solution (2 mL) was added, and the mixture was stirred for an additional 0.5 hour. The solvents were removed under reduced pressure. The residue was dissolved in EtOAc (50 mL), and the solution was extracted with 5% aqueous $Na_2CO_3$ solution (10×25 ml) and washed with brine (1×75 mL). The organic phase was dried over $Na_2CO_3$, and concentrated in vacuo. The residue was chromatographed on $SiO_2$ using EtOAc as eluent to afford title compound (175 mg, 50%).

$^1H$ NMR (DMSO-$d_6$): δ 0.78 (3H, d), 0.82 (3H, d), 1.21 (1H, m), 1.33 (1H, m), 1.92 (1H, m), 2.35 (1H, dd), 2.73 (1H, m), 2.85 (2H, m), 3.05 (1H, m), 3-12 (1H, m), 3.45 (1H, m), 3.52 (1H, m), 3.64 (1H, t), 3.78 (1H, dd), 4.81 (1H, q), 4.97 (1H, d), 5.06 (2H, s), 5.46 (1H, d), 6.85 (2H, d), 7.05 (2H, d), 7.17 (1H, d), 7.29 (1H, dd), 7.44 (1H, d), 7.78 (1H, t), 7.84 (1H, t), 8.19 (1H, d), 8.42 (2H, m), 8.53 (1H, d): MS: 685 ($M^+$).

Step 6

(3R,3aS,6aR-Hexahydrofuro[2,3-b]furan-3-yl-N((1S,2R)-1-(4-(2-pyridylmethyloxy)benzyl)-3-i-butyl-[(3-aminobenzene)sulfonyl]-amino-2-hydroxypropyl-carbamate (293)

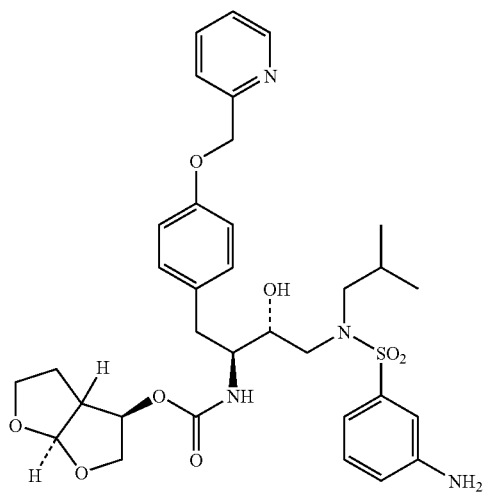 [SMILES: CC(C)CN(C[C@@H](O)[C@H](Cc1ccc(OCc2ccccn2)cc1)NC(=O)O[C@H]1CO[C@H]2OCCC21)S(=O)(=O)c1cccc(N)c1]

(3R,3aS,6aR)-Hexahydrofuro[2,3-b]furan-3-yl-N((1S,2R)-1-(4-(2-pyridylmethyloxy)benzyl)-3-i-butyl-[(3-nitrobenzene)sulfonyl]-amino-2-hydroxypropyl-carbamate (170 mg, 0.25 mmol) in THP (7 mL) was added Pt/C (3% Pt) (100 mg). The mixture was hydrogenated under atmospheric pressure $H_2$ for 12 hours. The catalyst was removed by filtration through Celite, and the solvent was evaporated in vacuo. The residue was chromatographed on $SiO_2$ using EtAOc as eluent to yield title compound (75 mg, 46%).

$^1H$ NMR (DMSO-$d_6$): δ 0.78 (3H, d), 0.82 (3H, d), 1.21 (1H, m), 1.30 (1H, m), 1.93 (1H, m), 2.36 (1H, t), 2.72 (3H, m), 2.97 (2H, m), 3.55 (4H, m), 3.65 (1H, t), 3.79 (3H, dd), 4.80 (1H, m), 4.95 (1H, d), 5.06 (2H, s), 5.45 (1H, dd), 5.53 (2H, broad s), 6.72 (1H, d), 6.79 (1H, d), 6.83 (2H, d), 6.91 (1H, s), 7.08 (2H, d), 7.13 (1H, t), 7.17 (1H, d), 7.28 (1H, d), 7.45 (1H, d), 7.77 (1H, t), 8.53 (1H, d); MS: 655 ($M^+$).

Example 83

Step 1 t-Butyl-N((1S,2R)-1-(4-(2-pyridylmethyloxy)benzyl)-3-i-butyl-[(3-methyl-4-acetoxy)benzenesulfonyl]-amino-2-hydroxypropyl-carbamate

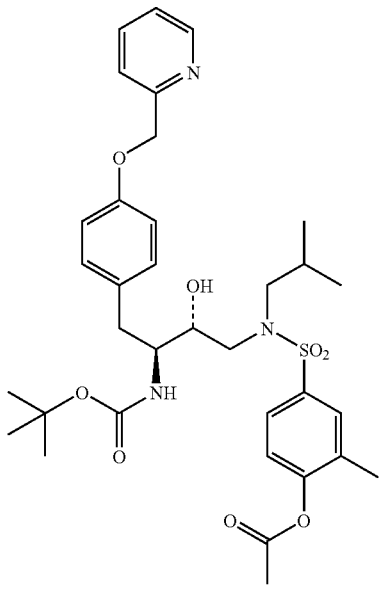 [SMILES: CC(=O)Oc1ccc(S(=O)(=O)N(CC(C)C)C[C@@H](O)[C@H](Cc2ccc(OCc3ccccn3)cc2)NC(=O)OC(C)(C)C)cc1C]

A CH$_2$Cl$_2$ (15 mL) solution of t-Butyl-(1S,2R)-1-(4-(2-pyridylmethyloxy)benzyl)-3-i-butylamino-2-hydroxypropyl-carbamate (630 mg, 1.42 mmol) was added (3-methyl-4-acetoxy)benzenesulfonyl chloride (442 mg, 1.78 mmol), and diisopropylethylamine (367 mg, 2.84 mmol). The mixture was stirred at room temperature for 1 hour, and concentrated. The residue was added water (50 mL), and stirred at 20° C. for 30 minutes to afford title compound (675 mg, 75%).
MS: 656 (M$^+$).

Step 2

(3R,3aS,6aR)-Hexahydrofuro[2,3-b]furan-3-yl-N((1S,2R)-1-(4-(2-pyridylmethyloxy)benzyl)-3-i-butyl-[(3-methyl-4-acetoxy)benzenesulfonyl]-amino-2-hydroxypropyl-carbamate (294)

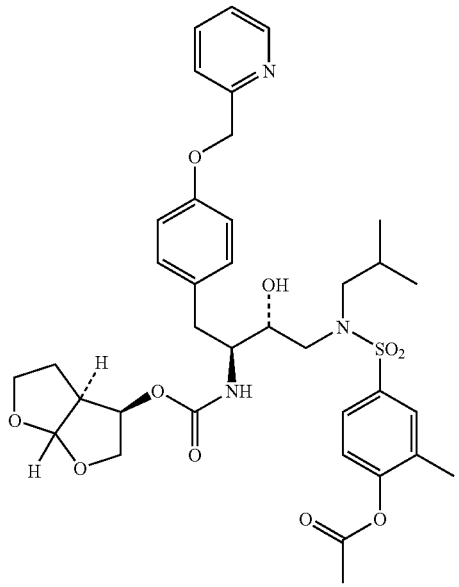 [SMILES: CC(=O)Oc1ccc(S(=O)(=O)N(CC(C)C)C[C@@H](O)[C@H](Cc2ccc(OCc3ccccn3)cc2)NC(=O)O[C@H]2COC3OCC[C@H]32)cc1C]

A CH$_2$Cl$_2$ (15 mL) and TFA (7.5 mL) solution of t-Butyl-N((1S,2R)-1-(4-(2-pyridylmethyloxy)benzyl)-3-i-butyl-[(3-methyl-4-acetoxy)benzenesulfonyl]-amino-2-hydroxypropyl-carbamate (650 mg, 1 mmol) was stirred at 20° C. for 1 hour, and concentrated. The residue was dissolved in EtOAc (50 ml), and washed with 2% aqueous NaHCO$_3$ solution (3×25 mL). The organic phase was dried over MgSO$_4$, and filtered. Diisopropylethylamine (517 mg, 4 mmol) and (3R, 3aS,6aR)-hexahydrofuro [2,3-b]furan-3-yl-4-nitrophenyl carbonate (517 mg, 1.75 mmol) were then added, and the solvent was evaporated. The residue was dissolved in CH$_3$CN (20 mL), and more diisopropylethylamine (517 mg, 4 mmol) was added. The resulting solution was stirred at room temperature for 3 hours, and concentrated. The residue was dissolved in EtOAc (150 mL), then washed with water (1×100 mL), 5% aqueous Na$_2$CO$_3$ (10×100 mL), and brine (1×100 mL) The organic phase was dried over MgSO$_4$, filtered, and concentrated. The residue was then chromatographed on SiO$_2$ using EtOAc as eluent to yield title compound (385 mg, 55%).

$^1$H NMR (DMSO-d$_6$): δ 0.78 (3H, d), 0.82 (3H, d), 1.20 (1H, m), 1.35 (1H, m), 2.17 (3H, s), 2.30 (3H, s), 2.37 (1H, t), 2.76 (3H, m), 2.91 (1H, d), 3.04 (1H, dd), 3.56 (4H, m), 3.66 (1H, t), 3.79 (1-1, dd), 4.80 (1H, dd), 5.01 (1H, d), 5.07 (2H, s), 5.46 (1H, d), 6.85 (2H, d), 7.09 (2H, d), 7.19 (1H, d), 7.26 (1H, d), 7.30 (2H, t), 7.46 (1H, d), 7.61 (1H, d), 7.70 (1H, s), 7.78 (1H, t), 8.53 (1H, d); MS: 712 (M$^+$).

Example 84

(3R,3aS,6aR)-Hexahydrofuro[2,3-b]furan-3-yl-N((1S,2R)-1-(4-(2-pyridylmethyloxy)benzyl)-3-i-butyl-[(3-methyl-4-hydroxy)benzenesulfonyl]-amino-2-hydroxypropyl-carbamate (295)

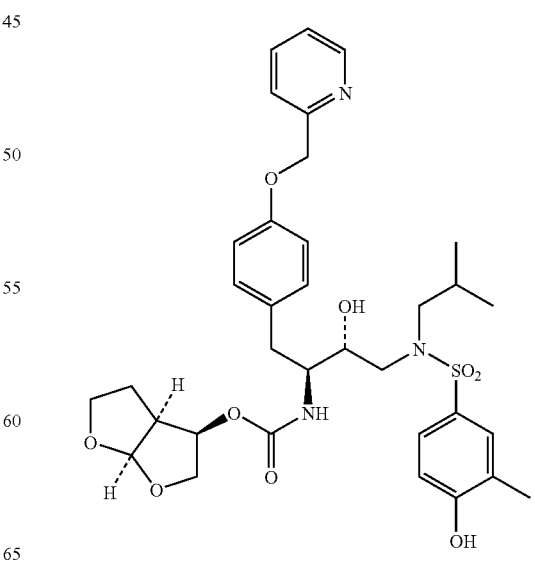

(3R,3aS,6aR)-Hexahydrofuro[2,3-b]furan-3'-yl-N((1S,2R)-1-(4-(2-pyridylmethyloxy)benzyl)-3-i-butyl-[(3-methyl-4-acetoxy)benzenesulfonyl]-amino-2-hydroxypropyl-carbamate (180 mg, 0.25 mmol) was dissolved in MeOH (3 mL), and K$_2$CO$_3$ (30 mg) was added. The mixture was stirred at room temperature for 30 minutes, diluted with EtOAc (50 mL), and washed with water (3×50 mL). The organic phase was dried over MgSO$_4$, concentrated, and dried in vacuo to yield title compound (115 mg, 70%). —H. NMR (DMSO-d$_6$): δ 0.78 (3H, d), 0.82 (3H, d), 1.18 (1H, m), 1.27 (1H, m), 1.90 (1H, m), 2.37 (1H, t), 2.65 (3H, m), 2.91 (2H, m), 3.52 (4H, m), 3.65 (1H, t), 3.80 (1H, dd), 4.79 (1H, dd), 5.06 (2H, s), 5.46 (1H, d), 6.84 (3H, m), 7.07 (2H, d), 7.18 (1H, d), 7.30 (1H, dd), 7.38 (1H, d), 7.45 (2H, d), 7.78 (1H, d), 8.52 (1H, d), 10.31 (1H, s); MS: 670 (M$^+$).

Example 85

(3S,3aS,6aR)-hexahydrofuro[2,3-b]furan-3-yl (1S,2R)-3-[[(4-aminophenyl)sulfonyl](isobutyl)amino]-1-[4-(benzyloxy)benzyl]-2-hydroxypropylcarbamate (296)

To a stirred solution of (3S,3aS,6aR)-hexahydrofuro[2,3-b]furan-3-yl (1S,2R)-1-[4-(benzyloxy)benzyl]-2-hydroxy-3-{isobutyl[(4-nitrophenyl)sulfonyl]amino}propylcarbamate (0.20 g, 0.29 mmol) in 3 mL of ethanol was added 64 mg of platinum (on activated-carbon, 3%. Pt). The mixture was stirred under an atmosphere pressure of hydrogen for 12 hours. The catalyst was filtered, and the solvent was removed under reduced pressure. The residue was purified on silica gel using ethyl acetate-hexanes (4:1) as eluent to provide 0.10 g (52%) of the title compound.

$^1$H-NMR (DMSO-d$_6$): δ 0.74 (3H, d), 0.81 (3H, d), 1.19 (1H, m), 1.29 (1H, m), 1.89 (1H, m), 2.34 (1H, t), 2.54-2.62 (2H, m), 2.71 (1H, m), 2.90 (2H, m), 3.22 (1H, d), 3.46 (1H, m), 3.52-3.59 (3H, m), 3.66 (1H, t), 3.83 (1H, dd), 4.80 (1H, q), 4.92 (1H, d, b), 4.99 (2H, s), 5.47 (1H, d), 5.94 (2H, s), 6.54 (2H, d), 6.81 (2H, d), 7.07 (2H, d), 7.19 (1H, d), 7.28 (1H, d), 7.35 (5H, m). MS: 655 (M$^+$).

Example 86

Step 1

(3S,3aS,6aR)-hexahydrofuro[2,3-b]furan-3-yl (4S,5R)-4-[4-(benzyloxy)benzyl]-5-({isobutyl[(4-nitrophenyl)sulfonyl]amino}methyl)-2,2-dimethyl-1,3-oxazolidine-3-carboxylate

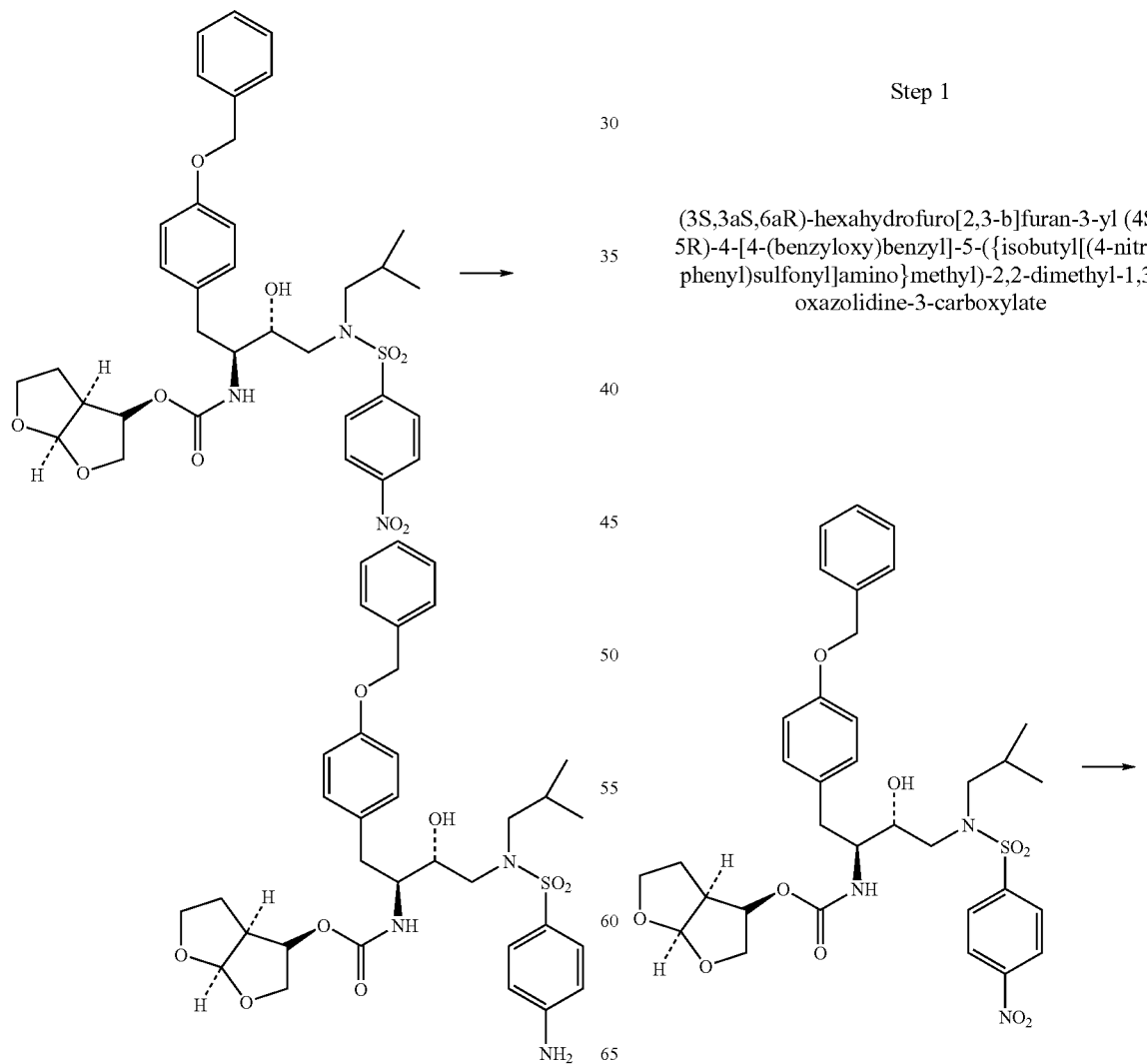

-continued

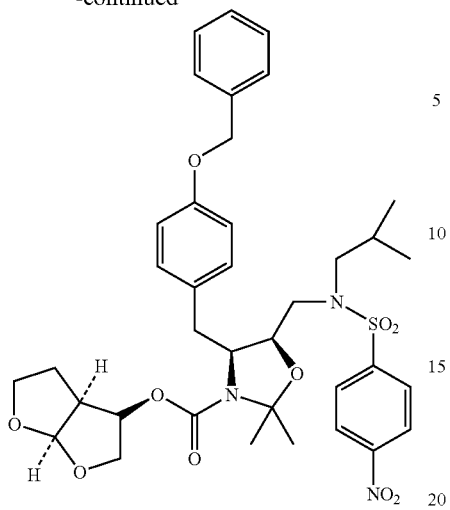

To a solution of (3S,3aS,6aR)-hexahydrofuro[2,3-b]furan-3-yl (1S,2R)-1-[4-(benzyloxy)benzyl]-2-hydroxy-3-{isobutyl[(4-nitrophenyl)sulfonyl]amino}propylcarbamate (1.00 g, 1.5 mmol) in 20 mL of dichloromethane was added 2,2-dimethoxypropane (1.5 g, 14.6 mmol) and p-toluenesulfonic acid (0.09 g, 0.5 mmol). The solution was refluxed for 12 hours, and the solvent was removed under reduced pressure. The residue was purified on silica gel using ethyl acetate-hexanes (3.5:6.5) as eluent to provide 0.70 g (70%) of the title compound.

$^{1}$H-NMR (CDCl$_3$): δ 0.85 (3H, d), 0.90 (3H, d), 1.35, 1.44 (3H, s)*, 1.55, 1.61 (3H, s)*, 1.84-2.00 (3H m, b), 2.61-2.91 (4H, m), 2.91-3.08 (3H, m), 3.17, 3.33 (1H, d)*, 3.56 (1H, t), 3.80-3.86 (2H, m), 3.91-3.98 (1H, m), 4.23-4.27 (2H, m), 5.02-5.16 (2H, s), 5.67 (1H, d), 6.91 (2H, d), 7.03 (1H, d), 7.14 (1H, d), 7.31 (1H, d), 7.38 (2H, m), 7.45 (2H, d), 7.67 (2H, d), 8.25 (2H, d).
*possible indication for rotamers.

Step 2

(3S,3aS,6aR)-hexahydrofuro[2,3-b]furan-3-yl (4S,5R)-5-{[[(4-aminophenyl)sulfonyl](isobutyl) amino]methyl}-4-(4-hydroxybenzyl)-2,2-dimethyl-1,3-oxazolidine-3-carboxylate

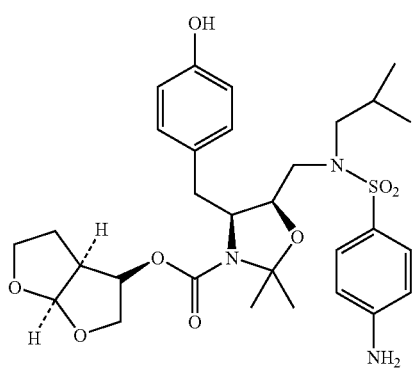

To a stirred solution of (3S,3aS,6aR)-hexahydrofuro[2,3-b]furan-3-yl (4S,5R)-4-[4-(benzyloxy)benzyl]-5-({isobutyl[(4-nitrophenyl)sulfonyl]amino}methyl)-2,2-dimethyl-1,3-oxazolidine-3-carboxylate. (0.18 g, 0.25 mmol) in 6 mL of a 2M solution of ammonia in methanol was added 0.18 g of palladium (on charcoal, 10% Pd, Degussa type). The mixture was stirred under an atmospheric pressure of hydrogen for 12 hours. The catalyst was filtered, and the solvent was removed under reduced pressure. The residue was purified on silica gel using ethyl acetate-hexanes (7:3) as eluent to provide 81 mg (54%) of the title compound.

$^{1}$H-NMR (DMSO-d$_6$): δ 0.76 (3H, d), 0.80 (3H, d), 1.19, 1.33 (3H, s)*, 1.44, 1.50 (3H, s)*, 1.74 (2H, m), 1.89 (1H, m), 2.49-2.75 (6H, m), 2.89-2.99 (2H, m), 3.19 (1H, m), 3.61 (2H, m), 3.80 (1H, m), 4.07 (1H, m), 4.74 (1H, q), 5.50, 5.54 (1H, d)*, 5.94 (2H, s, b), 6.54 (2H, d), 6.64 (2H, d), 6.93, 6.99 (2H, d)*, 7.13, 7.20 (2H, d)*, 9.20, 9.22 (1H, s)*. MS: 605 (M$^+$).
*possible indication for rotamers.

Step 3

(3S,3aS,6aR)-hexahydrofuro[2,3-b]furan-3-yl (4S,5R)-5-{[[(4-aminophenyl)sulfonyl](isobutyl)amino]methyl}-4-{4-[(3-cyanobenzyl) oxy]-benzyl}-2,2-dimethyl-1,3-oxazolidine-3-carboxylate

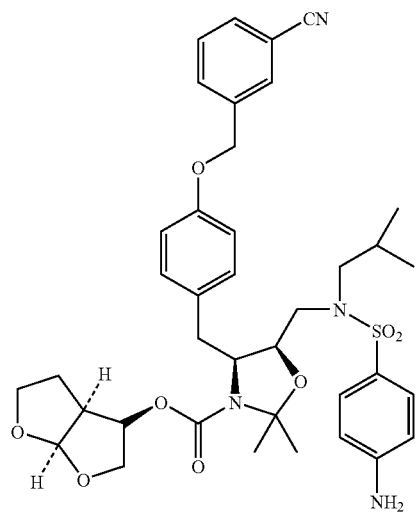

To a stirred mixture of (3S,3aS,6aR)-hexahydrofuro[2,3-b]furan-3-yl (4S,5R)-5-{[[(4-aminophenyl)sulfonyl](isobutyl)amino]methyl}-4-(4-hydroxybenzyl) 2,2-dimethyl-1,3-oxazolidine-3-carboxylate (40 mg, 0.07 mmol) and cesium carbonate (22 mg, 0.07 mmol) in 1.5 mL of N,N-dimethylformamide was added 3-bromomethylbenzonitrile (13 mg, 0.07 mmol). The mixture was stirred at room temperature for 12 hours followed by dilution with 25 mL of ether. The ether was extracted with water (5×15 mL). The organic phase was dried with magnesium sulfate, filtered, and concentrated under reduced pressure. The residue was purified on silica gel using ethyl acetate-hexanes (8.5:1.5) as eluent to provide 41 mg (85%) of the title compound.

$^{1}$H-NMR (DMSO-d$_6$): δ 0.80-0.86 (6H, dd), 1.37 (3H, s), 1.48, 1.55 (3H, s)*, 1.75 (2H, m), 1.94 (1H, m), 2.58-2.78 (6H, m), 2.92-3.09 (2H, m), 3.15-3.21 (1H, m), 3.61 (2H, m), 3.81 (1H, m), 4.14 (1H, m), 4.74 (1H, q), 5.17 (2H, s), 5.53, 5.57 (1H, d)*, 5.99 (2H, s, b), 6.58 (2H, d), 6.95 (2H, d), 7.11, 7.14 (2H, d)*, 7.22, 7.28 (2H, d)*, 7.60 (1H, t), 7.80 (2H, m, b), 7.91 (1H, s).
*possible indication for rotamers.

Step 4

(3S,3aS,6aR)-hexahydrofuro[2,3-b]furan-3-yl (1S,2R)-3-[[(4-aminophenyl)sulfonyl](isobutyl)amino]-1-{4-[(3-cyanobenzyl) oxy]benzyl}-2-hydroxypropylcarbamate (301)

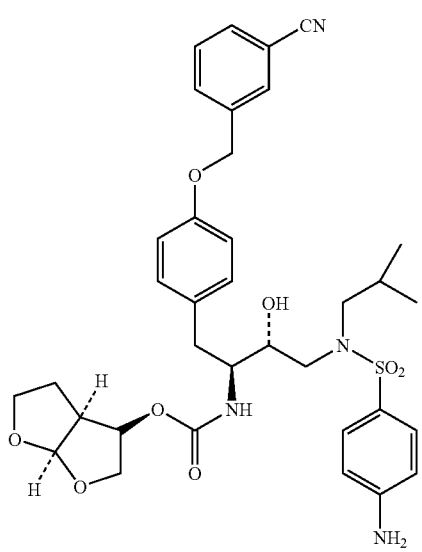

To a stirred solution of (3S,3aS,6aR)-hexahydrofuro[2,3-b]furan-3-yl (4S,5R) 5-{[[(4-aminophenyl)sulfonyl](isobutyl)amino]methyl}-4-{4-[(3-cyanobenzyl) oxy]benzyl}-2,2-dimethyl-1,3-oxazolidine-3-carboxylate in 3 mL of dioxane was added 4M hydrochloric acid in dioxane (1.5 mL) and water (0.05 µL). The solution was stirred for 1 hour followed by neutralization with 10% aqueous $Na_2CO_3$. The solution was extracted with dichloromethane (3×15 mL). The organic phase was dried with magnesium sulfate, filtered, and concentrated under reduced pressure. The residue was purified on silica gel using ethyl acetate-hexanes (8:2) as eluent to provide 17 mg (61%) of the title compound.

$^1$H-NMR (DMSO-$d_6$): δ 0.74 (3H, d), 0.81 (3H, d), 1.18 (1H, m), 1.28 (1H, m), 1.89 (1H, m), 2.35 (1H, t), 2.54-2.60 (2H, m), 2.71 (1H, m), 2.86-2.93 (2H, m), 3.22-3.29 (1H, dd), 3.42-3.48 (1H, m), 3.53-3.59 (3H, m), 3.65 (1H, t), 3.82 (1H, q), 4.80 (1H, q), 4.93 (1H, d, b), 5.07 (2H, s), 5.47 (1H, d), 5.94 (2H, s, b), 6.54 (2H, d), 6.83 (2H, d), 7.08 (2H, d), 7.19 (1H, d), 7.33 (2H, d), 7.56 (1H, t), 7.74 (2H, t), 7.85 (1H, s). MS: 680 (M$^+$).

Example 81

Step 1 tert-butyl (1S,2R)-1-[4-(benzyloxy)benzyl]-2-hydroxy-3-(isobutylamino)propylcarbamate

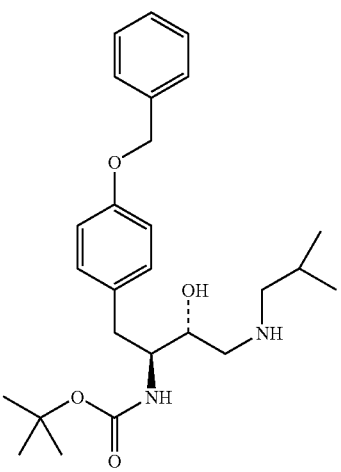 [SMILES: CC(C)CNC[C@@H](O)[C@H](Cc1ccc(OCc2ccccc2)cc1)NC(=O)OC(C)(C)C]

To a solution of t-Butyl-(1S,2R)-1-(4-benzyloxy-benzyl)-2,3-epoxydo-propyl-carbamate (3.2 g, 8.7 mmol) in 50 mL of i-propanol was added i-butylamine (4.6 g, 62.4 mmol). The mixture was stirred at 85° C. for 2 hours, and then it was cooled to 5° C. followed by dropwise addition into 250 mL of water. The resulting suspension was stirred for 30 minutes at 5° C. and then filtered. The solid was washed with water (3×150 mL) and dried under reduced pressure to yield 2.4 g (61%) of the title compound.

$^1$H-NMR (CDCl$_3$): δ 0.91 (6H, d), 1.34 (9H, s), 1.77 (1H, m), 2.37-2.48 (2H, m), 2.66-2.75 (2H, m), 2.82-2.93 (2H, m), 3.42 (1H, m), 3.77 (1H, m), 4.64 (1H, d), 5.01 (2H, s), 6.89 (2H, d), 7.12 (2H, d), 7.27-7.31 (1H, m), 7.34-7.41 (4H, m).

Step 2 tert-butyl (1S,2R)-2-hydroxy-1-(4-hydroxybenzyl)-3-(isobutylamino) propylcarbamate

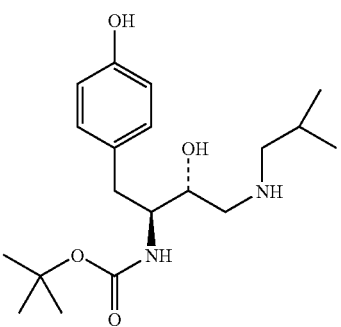 [SMILES: CC(C)CNC[C@@H](O)[C@H](Cc1ccc(O)cc1)NC(=O)OC(C)(C)C]

To a stirred solution of tert-butyl (1S,2R)-1-[4-(benzyloxy) benzyl]-2-hydroxy-3-(isobutylamino) propylcarbamate (0.5 g, 1.1 mmol) in anhydrous tetrahydrofuran (12 mL) was added 0.5 g of palladium (on charcoal, 10% Pd, Degussa type). The mixture was stirred under an atmospheric pressure of hydrogen for 12 hours. The catalyst was filtered and the solvent was removed under reduced pressure resulting in 0.4 g (98%) of the title compound.

$^1$H-NMR (CDCl$_3$): δ 0.92 (6H, dd), 1.35 (9H, s), 1.83 (1H, m), 2.44-2.55 (2H, m), 2.73-2.85 (4H, m), 3.49 (1H, m), 3.70-3.79 (1H, m, b), 4.66 (1H, d), 6.72 (2H, d), 7.05 (2H, d).

Step 3

4-((2S,3R)-2-[(tert-butoxycrbonyl)amino]-3-hydroxy-4-{isobutyl[(4-nitrophenyl)sulfonyl]-amino}butyl)phenyl 4-nitrobenzenesulfonate

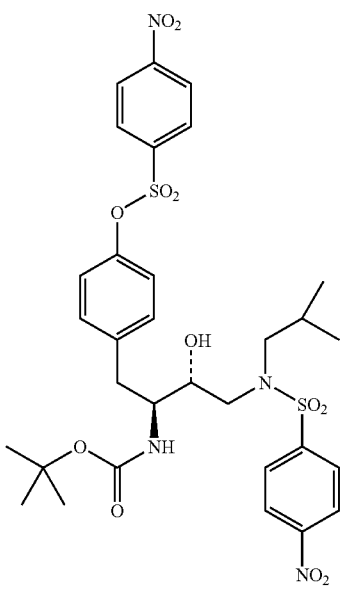 [SMILES: CC(C)CN(C[C@@H](O)[C@H](Cc1ccc(OS(=O)(=O)c2ccc([N+](=O)[O-])cc2)cc1)NC(=O)OC(C)(C)C)S(=O)(=O)c1ccc([N+](=O)[O-])cc1]

To a solution of tert-butyl (1S,2R)-2-hydroxy-1-(4-hydroxybenzyl)-3-(isobutylamino) propylcarbamate (50 mg, 0.14 mmol) in 3 mL of anhydrous dichloromethane were added 4-nitrobenzenesulfonyl chloride (38 mg, 0.17 mmol) and N-ethyldiisopropylamine (74 mg, 0.57 mmol). After 2 hours, the solvent was removed under reduced pressure. The residue was purified on silica gel using ethyl acetate-hexanes (2:3) as eluent to provide 66 mg (87%) of the title compound.

$^1$H-NMR (DMSO-d$_6$): δ 0.77, 0.79 (6H, dd), 1.17 (9H, s), 1.91 (1H, m), 2.36-2.43 (1H, m), 2.84-2.95 (2H, m), 2.97-3.01 (2H, m), 3.07-7.12 (2H, m), 3.39-3.47 (1H, m), 4.95 (1H, d), 6.67 (1H, d), 6.91 (2H, d), 7.13 (2H, d), 8.00 (2H, d), 8.07 (2H, d), 8.32 (2H, d), 8.38 (2H, d).

Step 4

4-((2S,3R)-2-({[(3S,3aS,6aR)-hexahydrofuro[2,3-b]furan-3-yloxy]carbonyl}amino)-3-hydroxy-4-{isobutyl[(4-nitrophenyl)sulfonyl]amino}butyl)phenyl 4-nitrobenzenesulfonate (297)

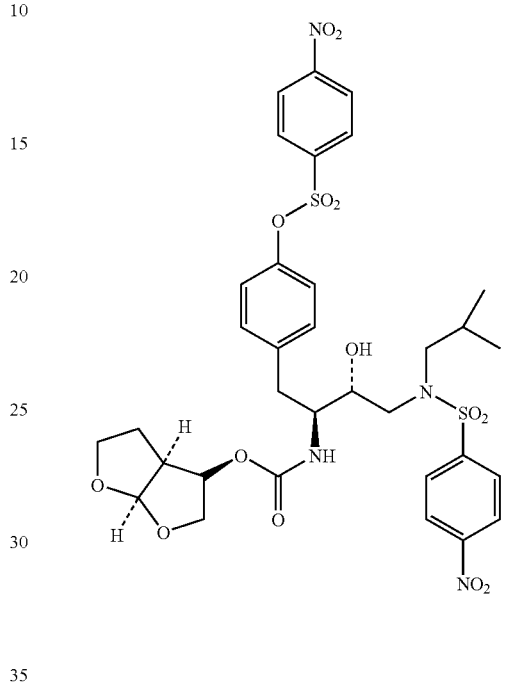

To a solution of 4-((2S,3R)-2-[(tert-butoxycarbonyl)amino]-3-hydroxy-4-{isobutyl[(4-nitrophenyl)sulfonyl]-amino}butyl)phenyl 4-nitrobenzenesulfonate (0.21 mg, 0.29 mmol) in 10 mL of dichloromethane was added dropwise trifluoroacetic acid (2 mL). The mixture was stirred for 1 hour at room temperature. The solvents were removed under reduced pressure; the residue was redissolved in 50 mL of dichloromethane and 20 mL of 5% aqueous sodium carbonate was added. The aqueous phase was separated and extracted with dichloromethane (2×20 mL). The combined organic phases were dried over sodium carbonate, filtered, and concentrated under reduced pressure. The residue was redissolved in 10 mL of acetonitrile. N-Ethyldiisopropylamine (80 uL, 0.05 mmol) and (3R,3aS,6aR)-hexahydrofuro[2,3-b]furan-3-yl-4-nitrophenylcarbonate (0.11 g, 0.37 mmol) were added, and the solution was stirred for 12 hours. The solvents were removed under reduced pressure. The residue was redissolved in ethyl acetate (30 mL), and the organic phase was extracted with water (20 mL) followed by 5% aqueous sodium carbonate solution (5×20 mL). The organic phase was dried with sodium carbonate, filtered, and concentrated under reduced pressure. The residue was purified on silica gel using ethyl acetate-hexanes as eluent to provide 0.12 g (55%) of the title compound.

$^1$H-NMR (CD$_3$OD): δ 0.84 (3H, d), 0.90 (3H, d), 1.46 (1H, m), 1.58 (1H, m), 1.99 (1H, m), 2.47 (1H, t), 2.87-2.97 (2H, m), 3.04-3.10 (2H, m), 3.18 (1H, m), 3.44-3.47 (1H, dd), 3.62-3.68 (4H, m), 3.79 (1H, m), 3.89 (1H, q), 4.91 (1H, q), 5.57 (1H, d), 6.91 (2H, d), 7.20 (2H, d), 8.02-8.05 (4H, d+d), 8.36-8.42 (4H, d+d). MS: 778 (M$^-$).

Example 82

(3S,3aS,6aR)-hexahydrofuro[2,3-b]furan-3-yl (1S,2R)-3-[(4-aminobenzyl)(isobutyl)amino]-1-{4-[(4-aminobenzyl)oxy]benzyl}-2-hydroxypropylcarbamate (298)

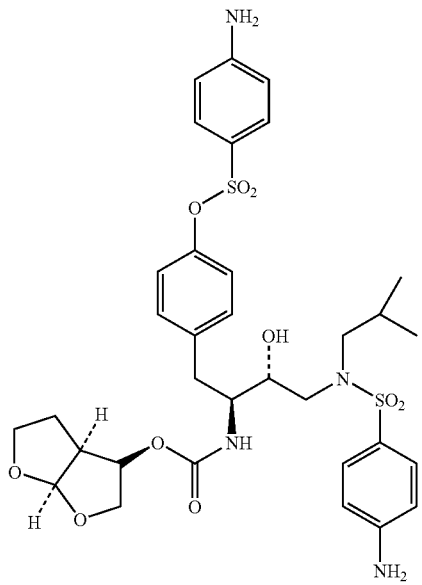

To a stirred solution of 4-((2S,3R)-2-({[(3S,3aS,6aR)-hexahydrofuro [2,3-b]furan-3-yloxy]carbonyl}amino)-3-hydroxy-4-{fisobutyl[(4-nitrophenyl)sulfonyl]amino}butyl) phenyl 4-nitrobenzenesulfonate (0.12 g, 0.15 mmol) in 2 mL of anhydrous tetrahydrofuran was added 36 mg of platinum (on activated carbon, 3% Pt). The mixture was stirred under an atmospheric pressure of hydrogen for 3 hours. The catalyst was filtered, and the solvent was removed under reduced pressure. The residue was purified on silica gel using ethyl acetate-hexanes (9:1) as eluent to provide 39 mg (35%) of the title compound.

$^1$H-NMR (CD$_3$OD): δ 0.84 (3H, d), 0.90 (3H, d), 1.38-1.43 (1H, m), 1.53-1.59 μH m), 1.96 (1H, m), 2.47 (1H, t), 2.70-2.88 (4H, m), 2.98 (1H, m), 3.13, 3.21 (1H, dd), 3.31, 3.35 (1H, dd), 3.64-3.71 (4H, m), 3.73-3.82 (3H, m), 3.85-3.92 (1H, m), 4.91 (1H, q), 5.57 (1H, d), 6.62, 6.66 (4H, d+d), 6.82 (2H, d), 7.16 (2H, d), 7.38 (2H, d), 7.45 (2H, d). MS: 720 (M$^+$).

Example 83

Step 1 tert-butyl (1S)-2-(4-hydroxyphenyl)-1-[(2S)-oxiranyl]ethylcarbamate

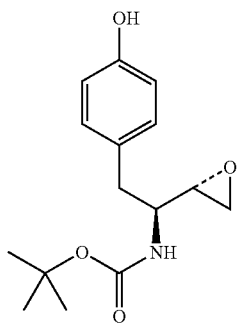

To a stirred solution of t-Butyl-(1S,2R)-1-(4-benzyloxybenzyl) 2,3-epoxydo-propylcarbamate in a mixture of ethanol-ethyl acetate (4:1) was added palladium hydroxide (on carbon, 20% palladium). The mixture was stirred under an atmospheric pressure of hydrogen for 2 hours. The catalyst was filtered and washed one time each with ethanol, methanol, and ethyl acetate. The solvent was removed under reduced pressure providing 0.5 g (quantitative) of the title compound.

$^1$H-NMR (DMSO-d$_6$): δ 1.30 (9H, s), 2.59-2.75 (4H, m), 2.85 (1H, m), 3.35-3.46 (1H, m), 6.63 (2H, d), 6.78 (1H, d), 6.98 (2H, d), 9.03, 9.12 (1H, s)*.

*possible indication for rotamers.

Step 2

General Procedure for the Alkylation of Product from Procedure 11

To a stirred mixture of tert-butyl (1S)-2-(4-hydroxyphenyl)-1-[(2S)-oxiranyl]ethylcarbamate (0.25 g, 0.90 mmol) and cesium carbonate (0.173 g, 2.2 mmol) in 5 mL of N,N-dimethylformamide was added the desired alkyl halide [1] (0.90 mmol). The mixture was stirred at room temperature for 12 hours followed by dilution with 125 mL of ether. The ether was extracted with water (5×75 mL). The organic phase was dried with magnesium sulfate, filtered, and concentrated under reduced pressure. The residue was purified on silica gel using ethyl acetate-hexanes [2] as eluent to provide the following compounds [Y:(3)]:

1. tert-butyl (1S)-1-[(2S)-oxiranyl]-2-[4-(2-pyridinylmethoxy)phenyl]ethylcarbamate

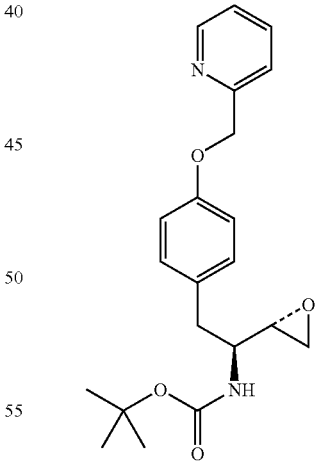

[1]: 2-Picolyl chloride hydrochloride; [2]: no purification; [3]: 91%.

$^1$H-NMR (DMSO-d$_6$): δ 1.23 (9H, s) t 2.56-2.63 (3H, m), 2.71-2.76 (1H, m), 2.85 (1H, m), 3.40 (1H, m), 5.08 (2H, s), 6.79 (1H, d), 6.87 (2H, d), 7.07 (2H, d), 7.29 (1H, m), 7.44 (1H, d), 7.77 (1H, t), 8.52 (1H, d).

Example 84

Step 1

2. tert-butyl (1S)-2-{4-[(2-methyl-1,3-thiazol-4-yl)methoxy]phenyl}-1-[(2S)-oxiranyl]-ethylcarbamate

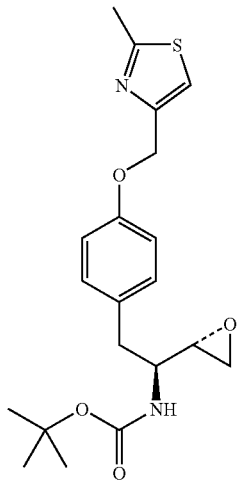

[1]: 4-Chloromethyl-2-methylthiazole hydrochloride*; [2]: (6:4); [3]: 35%.

$^1$H-NMR (DMSO-$d_6$): δ 1.24 (9H, s), 2.57-2.63 (6H, m+s), 2.72, 2.76 (1H, dd), 2.84 (1H, m), 3.41 (1H, m), 5.00 (2H, s), 6.79 (1H, d), 6.87 (2H, d), 7.07 (2H, d), 7.46 (1H, s).
*added excess sodium iodide to the reaction.

Example 85

Step 1

3. tert-butyl (1S)-2-{4-[(3-cyanobenzyl)oxy]phenyl}-1-[(2S)-oxiranyl]ethylcarbamate

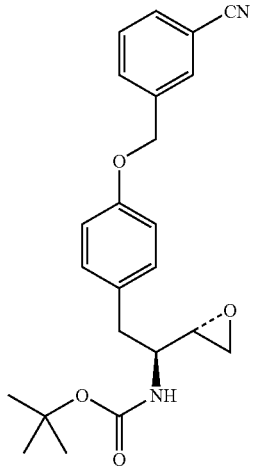

[1]: 3-(Bromomethyl)benzonitrile; [2]: (1:1); [3]: 75%.

$^1$H-NMR (DMSO-$d_6$): δ 1.23 (9H, s), 2.55-2.63 (3H, m), 2.72, 2.75 (1H, dd), 2.84 (1H, m), 3.41 (1H, m), 5.09 (2H, s), 6.79 (1H, d), 6.88 (2H, d), 7.08 (2H, d), 7.56 (1H, t), 7.74 (2H, t), 17.84 (1H, s).

Example 83

Step 3

General Procedure for the Ring-Opening

To a solution of the product from the previous step (0.4 g, 1.2 mmol) in i-propanol was added i-butylamine (0.4 g, 5.8 mmol). The mixture was stirred at 85° C. for 2 hours, and then it was cooled to 5° C. followed by dropwise addition into 50 mL of water. The resulting suspension was stirred for 30 minutes at 5° C. and then filtered. The solid was washed with water (3×25 mL) and dried under reduced pressure to provide the following compounds [Y:(1)]:

1. tert-butyl (1S,2R)-2-hydroxy-3-(isobutylamino)-1-[4-(2-pyridinylmethoxy)benzyl]-propylcarbamate

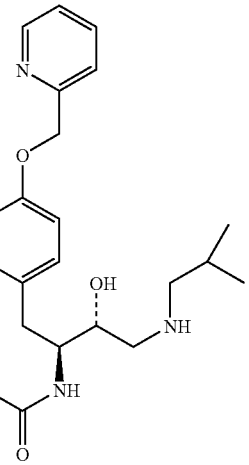

[1]: 82%.

$^1$H-NMR (DMSO-$d_6$): δ 0.82 (6H, dd), 1.21 (9H, s), 1.59 (1H, m), 2.25 (2H, d), 2.39-2.42 (2H, m), 2.51 (1H, m), 2.85 (1H, dd), 3.34-3.43 (3H, m), 4.71 (1H, s, b), 5.08 (2H, s), 6.65 (1H, d), 6.85 (2H, d), 7.04 (2H, d), 7.29 (1H, m), 7.43 (1H, d), 7.77 (1H, t), 8.52 (1H, d).

Example 84

Step 2 tert-butyl (1S,2R)-2-hydroxy-3-(isobutylamino)-1-{4-[(2-methyl-1,3-thiazol-4-yl)methoxy]benzyl}propylcarbamate

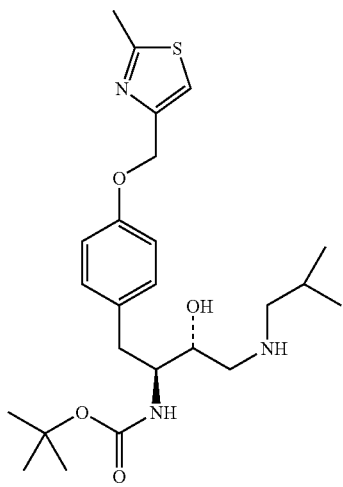 [SMILES: Cc1nc(COc2ccc(C[C@H](NC(=O)OC(C)(C)C)[C@H](O)CNCC(C)C)cc2)cs1]

[1]: 66%.

$^1$H-NMR (DMSO-d$_6$): δ 0.81 (6H, d), 1.22 (9H, s), 1.60 (1H, m), 2.27 (2H, m), 2.40-2.55 (2H, m, b), 2.60 (3H, s), 2.86 (1H, d, b), 3.35-3.42 (3H, m), 4.73 (1H, s, b), 4.99 (2H, s), 6.65 (1H, d), 6.85 (2H, d), 7.03 (2H, d), 7.45 (1H, s).

Example 85

Step 2 tert-butyl (1S,2R)-1-{4-[(3-cyanobenzyl)oxy]benzyl}-2-hydroxy-3-(isobutylamino)-propylcarbamate

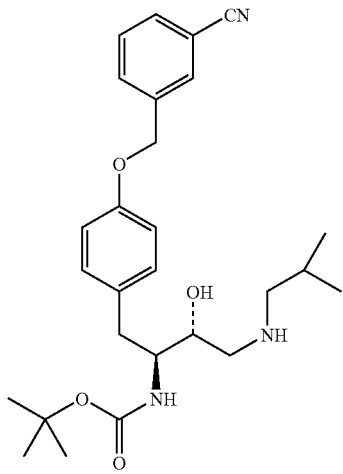 [SMILES: CC(C)CNC[C@@H](O)[C@H](Cc1ccc(OCc2cccc(C#N)c2)cc1)NC(=O)OC(C)(C)C]

[1]: 88%.

$^1$H-NMR (DMSO-d$_6$): δ 0.80 (6H, d), 1.21 (9H, s), 1.59 (1H, m), 2.25 (2H, d), 2.43 (2H, m), 2.51 (1H, m), 2.86 (1H, dd), 3.34 (1H, m), 3.41 (1H, m), 4.70 (1H, s, b) 5.07 (2H, s), 6.64 (1H, d), 6.85 (2H, d), 7.04 (2H, d), 7.55 (1H, t), 7.74 (2H, t), 7.84 (1H, s).

Example 83

Step 4

General Procedure for the Sulfonylation

To a stirred solution of the product from the previous step (0.42 g, 0.96 mmol) in 20 mL of anhydrous dichloromethane were added 4-nitrobenzenesulfonyl chloride (0.25 g, 1.1 mmol) and N-ethyldiisopropylamine (0.15 g, 1.7 mmol) The mixture was allowed to react for the given number of hours [1] and at which time the solvent was removed under reduced pressure. The residue was redissolved in dichlormethane and extracted with water (3×50 mL). The organic phase was dried with magnesium sulfate, filtered, and removed under reduced pressure. The residue was purified on silica gel using ethyl acetate-hexanes [2] as eluent to provide the following compounds [Y:(3)]:

1. tert-butyl (1S,2R)-2-hydroxy-3-{isobutyl[(4-nitrophenyl)sulfonyl]amino}-1-[4-(2-pyridinylmethoxy)benzyl]propylcarbamate

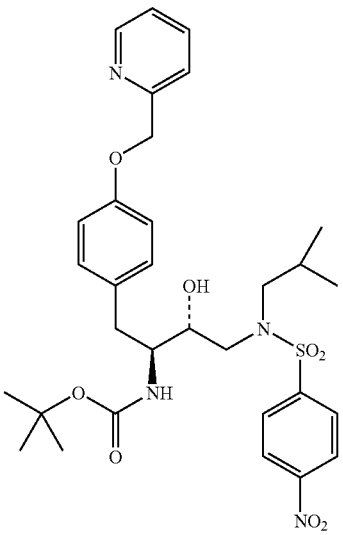 [SMILES: CC(C)CN(C[C@@H](O)[C@H](Cc1ccc(OCc2ccccn2)cc1)NC(=O)OC(C)(C)C)S(=O)(=O)c1ccc([N+](=O)[O-])cc1]

[1]: 6 hours; [2]: (7:3); [3]: 87%.

$^1$H-NMR (DMSO-d$_6$): δ 0.77, 0.80 (6H, dd), 1.20 (9H, s), 1.92 (1H, m), 2.36 (2H, d), 2.80-2.91 (2H, m), 2.98-3.13 (2H, m), 3.42-3.46 (2H, m), 4.89 (1H, d), 5.07 (2H, s), 6.61 (1H, d), 6.84 (2H, d), 7.03 (2H, d), 7.29 (1H, m), 7.43 (1H, d), 7.76 (1H, m), 8.00 (2H, d), 8.32 (2H, d), 8.52 (1H, d).

Example 84

Step 3 tert-butyl (1S,2R)-2-hydroxy-3-{isobutyl[(4-nitrophenyl)-sulfonyl]amino}-1-{4-[(2-methyl-1,3-thiazol-4-yl)methoxy]enzyl}propylcarbamate

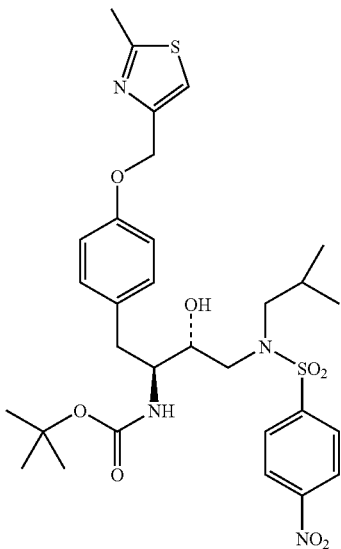 [SMILES: Cc1nc(COc2ccc(C[C@H](NC(=O)OC(C)(C)C)[C@H](O)CN(CC(C)C)S(=O)(=O)c3ccc([N+](=O)[O-])cc3)cc2)cs1]

[1]: 12 hours; [2]: (1:1); [3]: 83%.
¹H-NMR (DMSO-d₆): δ 0.79 (6H, dd), 1.21 (9H, s), 1.93 (1H, m), 2.34-2.40 (2H, m), 2.60 (3H, s), 2.80-2.91 (2H, m), 2.99-3.13 (2H, m), 3.33 (1H, m), 3.44 (1H, m), 4.89 (1H, d), 4.99 (2H, s), 6.63 (1H, d), 6.85 (2H, d), 7.04 (2H, d), 7.45 (1H, s), 8.01 (2H, d), 8.33 (2H, d).

Example 85

Step 3 tert-butyl (1S,2R)-1-{4-[(3-cyanobenzyl)oxy]benzyl}-2-hydroxy-3-{isobutyl[(4-nitrophenyl)sulfonyl]amino}propylcarbamate

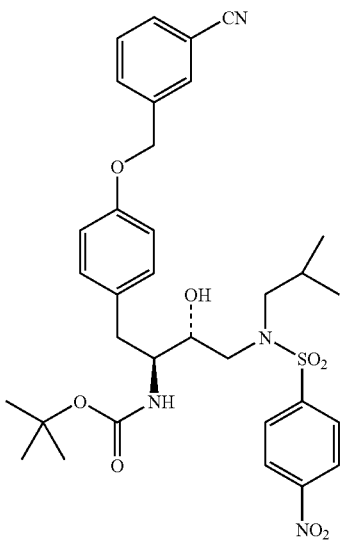 [SMILES: CC(C)CN(C[C@@H](O)[C@H](Cc1ccc(OCc2cccc(C#N)c2)cc1)NC(=O)OC(C)(C)C)S(=O)(=O)c1ccc([N+](=O)[O-])cc1]

[1]: 12 hours; [2]: (1:1); [3]: 95%.
¹H-NMR (DMSO-d₆): δ 0.78 (6H, d+d), 1.19 (9H, s), 1.92 (1H, m), 2.36 (2H, m), 2.80-2.91 (2H, m), 2.98-3.13 (2H, m), 3.32 (1H, m), 3.42 (1H, m), 4.89 (1H, d), 5.07 (2H, s), 6.61 (1H, d), 6.84 (2H, d), 7.04 (2H, d), 7.55 (1H, t), 7.74 (2H, t), 7.83 (1H, s), 8.00 (2H, d), 8.31 (2H, d).

Example 83

Step 5

General Procedure for the Addition of BisTHF Units

To a solution of the product from the previous step (0.36 g, 0.57 mmol) in 20 mL of anhydrous dichloromethane was added dropwise trifluoroacetic acid (5 mL). The mixture was stirred for 1 hour at room temperature. The solvents were removed under reduced pressure; the residue was redissolved in 50 mL of dichloromethane and 30 mL of 10% aqueous sodium carbonate was added. The aqueous phase was separated and extracted with dichloromethane (2×25 mL). The combined organic phases were dried with sodium carbonate, filtered, and concentrated under reduced pressure. The residue was redissolved in 10 mL of acetonitrile. N-Ethyldiisopropylamine (0.15 g, 1.1 mmol) and (3R,3aS,6aR)-hexahydrofuro[2,3-b]furan-3-yl-4-nitrophenylcarbonate (0.20 g, 0.68 mmol) were added, and the solution was stirred for 12 hours. The solvents were removed under reduced pressure. The residue was redissolved in ethyl acetate (50 mL), and the organic phase was extracted with water (30 mL) followed by 5% aqueous sodium carbonate solution (5×50 mL). The organic phase was dried with sodium carbonate, filtered, and concentrated under reduced pressure. The residue was purified on silica gel using ethyl acetate-hexanes [1] as eluent to provide the following compounds [Y:(2)]:

1. (3S,3aS,6aR)-hexahydrofuro[2,3-b]furan-3-yl (1S,2R)-2-hydroxy-3-{isobutyl[(4-nitrophenyl)sulfonyl]amino}-1-[4-(2-pyridinylmethoxy)benzyl]propylcarbamate

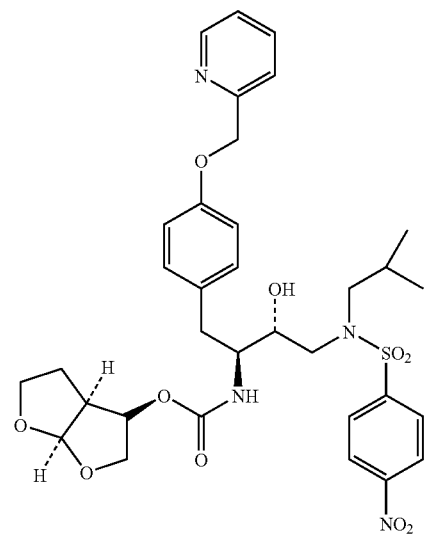

[1] (9:1→100%) [2]: Y: 77%.

¹H NMR (DMSO-d₆): δ 0.77 (3H, d), 0.81 (3H, d), 1.20 (1H, m), 1.32 (1H, m), 1.92 (1H, m), 2.32 (1H, t), 2.72 (1H, m), 2.84-2.89 (2H, dd, b), 2.95-3.00 (1H, m), 3.08-3.14 (1H, m), 3.33 (1H, d), 3.45 (2H, m, b), 3.50-3.57 (24H, m), 3.65 (1H, t), 3.80 (1H, q), 4.80 (1H, q), 4.98 (1H, d), 5.06 (2H, s), 5.46 (1H, d), 6.83 (2H, d), 7.05 (2H, d), 7.18 (1H, d), 7.29 (1H, m), 7.44 (1H, d), 7.78 (1H, m), 8.01 (2H, d), 8.34 (2H, d)₈.₅₂ (1H, d).

Example 84

Step 4

(3S,3aS,6aR)-hexahydrofuro[2,3-b]furan-3-yl (1S, 2R)-2-hydroxy-3-{isobutyl[(4-nitrophenyl)sulfonyl]amino}-1-{4-[(2-methyl-1,3-thiazol-4-yl)methoxy]benzyl}propylcarbamate

[1]: (8:2); [2]: 59%.

¹H-NMR (DMSO-d₆): δ 0.77 (3H, d), 0.81 (3H, d), 1.20 (1H, m), 1.29-1.36 (1H, m), 1.92 (1H, m), 2.29-2.35 (1H, m), 2.60 (3H, s), 2.71-2.76 (1H, m), 2.85-2.89 (2H, dd), 2.95-3.01 (1H, m), 3.08-3.14 (1H, m), 3.33 (1H, d), 3.45 (2H, m, b), 3.50-3.58 (2H, m), 3.67 (1H, t), 3.80 (1H, q), 4.80 (1H, q), 4.98 (3H, s, b), 5.47 (1H, d), 6.83 (2H, d), 7.05 (2H, d), 7.18 (1H, d), 7.47 (1H, s), 8.01 (2H, d), 8.34 (2H, d).

Example 85

Step 4

(3S,3aS,6aR)-hexahydrofuro[2,3-b]furan-3-yl (1S, 2R)-1-{4-[(3-cyanobenzyl)oxy]benzyl}-2-hydroxy-3-{isobutyl[(4-nitrophenyl)sulfonyl]amino}propylcarbamate

[1] (2:8); [2]: 74%.

¹H-NMR (DMSO-d₆): δ 0.76 (3H, d), 0.80 (3H, d), 1.16-1.20 (1H, m), 1.27-1.37 (1H, m), 1.92 (1H, m), 2.32 (1H, t), 2.72 (1H, m), 2.86 (2H, dd), 2.94-3.00 (1H, m), 3.08-3.14 (1H, m), 3.33 (1H, d), 3.45 (2H, m, b), 3.50-3.58 (2H, m)₁, 3.65 (1H, t), 3.80 (1H, q), 4.80 (1H, q), 4.98 (1H, d), 5.06 (2H, s), 5.46 (1H, d), 6.83 (2H, d), 7.06 (2H, d), 7.18 (1H, d), 7.56 (1H, t), 7.74 (2H, t), 7.84 (1H, s), 8.00 (2H, d), 8.33 (2H, d).

Example 83

Step 6

General Procedure for the Reduction of the Nitro Group

To a stirred solution of the product obtained from the previous step (0.23 g, 0.34 mmol) in 4 mL of anhydrous tetrahydrofuran was added 70 mg of platinum (on activated carbon, 3% Pt). The mixture was stirred under an atmospheric pressure of hydrogen for the indicated number of hours [1]. The catalyst was filtered, and the solvent was removed under reduced pressure. The residue was purified on silica gel using ethyl acetate-hexanes [2] as eluent to provide the following compounds (Y: [3]):

(3S,3aS,6aR)-hexahydrofuro[2,3-b]furan-3-yl (1S, 2R)-3-[[(4-aminophenyl)sulfonyl]-(iobutyl)amino]-2-hydroxy-1-[4-(2-pyridinylmethoxy)benzyl]propyl-carbamate (299)

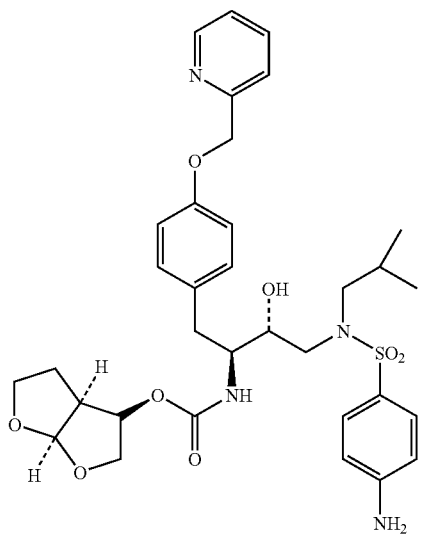

[1]: 12 hours; [2]: (9:1); [3]: 90%*.
$^1$H-NMR (DMSO-$d_6$): δ 0.74 (3H, d), 0.81 (3H, d), 1.20-1.16 (1H, m), 1.29 (1H, m), 1.89 (1H, m), 2.34 (1H, t), 2.54-2.66 (2H, m), 2.71 (1H, m), 2.86-2.96 (2H, m), 3.22, 3.25 (1H, dd), 3.40-3.59 (4H, m, b), 3.65 (1H, t), 3.82 (1H, m), 4.80 (1H, q), 4.92, 4.95 (1H, dd), 5.06, 5.08 (2H, s), 5.46 (1H, d), 5.94 (1H, s), 6.54 (1H, d), 6.82 (3H, m), 7.08 (2H, d), 7.20 (1H, m), 7.31 (2H, m), 7.44 (1H, d), 7.49 (1H, d), 7.78 (1H, t), 8.52 (2H, d), 8.64 (s)*, 8.94 (s)*. MS: 657 (M$^+$), 673 (M$^+$)*.
*Note: This was obtained as a 3:1 mixture with respect to the hydroxylamine derivative (by $^1$H NMR).

Example 84

Step 5

(3S,3aS,6aR)-hexahydrofuro[2,3-b]furan-3-yl (1S, 2R)-3-[[(4-aminophenyl)sulfonyl]-(isobutyl)amino]-2-hydroxy-1-{4-[(2-methyl-1,3-thiazol-4-yl)methoxy]benzyl}propylcarbamate (300)

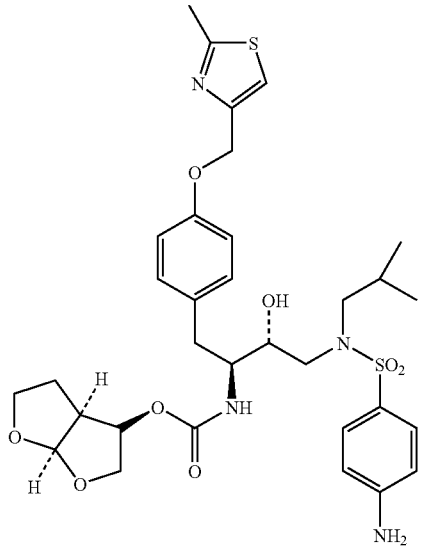

[1]: 77 hours; [2] (9:1); [3]: 53%.
$^1$H-NMR (DMSO-$d_6$): δ 0.75 (3H, d), 0.81 (3H, d), 1.19 (1H, m), 1.32 (1H, m), 1.89 (1H, m), 2.35 (1H, t), 2.54-2.69 (5H, dd+s), 2.72 (1H, m), 2.87-2.93 (2H, m), 3.22 (1H, d), 3.47 (1H, m), 3.53-3.60 (3H, m), 3.68 (1H, t), 3.82 (1H, dd) 4.80 (1H, q), 4.93 (1H, m), 4.98 (2H, s, b), 5.47 (1H, d), 5.94 (2H, s, b), 6.55 (2H, d), 6.83 (2H, d), 7.07 (2H, d), 7.19 (1H, d), 7.33 (2H, d), 7.47 (1H, s). MS: 676 (M$^+$).

Example 85

Step 5

(3S,3aS,6aR)-hexahydrofuro[2,3-b]furan-3-yl (1S, 2R)-3-[[(4-aminophenyl)sulfonyl]-(isobutyl)amino]-1-{4-[(3-cyanobenzyl) oxy]benzyl}-2-hydroxypropylcarbamate (301)

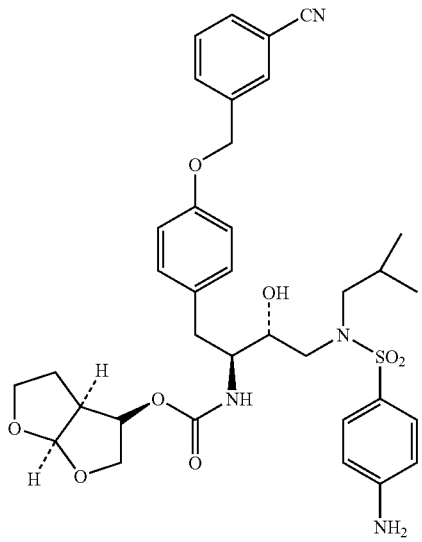

analytical data see Example 301 (Route 1) above

Example 86

(3S,3aS,6aR)-hexahydrofuro[2,3-b]furan-3-yl (1S, 2R)-2-hydroxy-3-[[4-(hydroxyamino)benzyl](isobutyl)amino]-1-{4-[(2-methyl-1,3-thiazol-4-yl)methoxy]-benzyl}propylcarbamate (302)

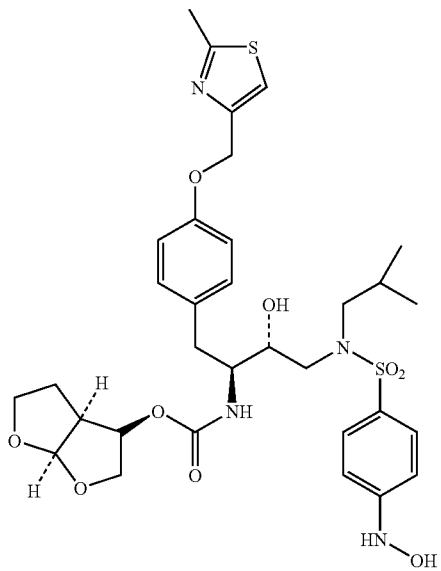

[1]: 3 hours; [2]: no purification; [3]: quantitative.
¹H-NMR (DMSO-d₆): δ 0.74 (3H, d), 0.81 (3H, d), 1.15-1.20 (1H, m), 1.34 (1H, m), 1.90 (1H, m), 2.35 (1H, t), 2.60-2.75 (7H, m+s), 2.87-2.96 (1H, m), 3.29 (1H, d, b), 3.42-3.56 (4H, m), 3.68 (1H, t), 3.82 (1H, dd), 4.80 (1H, q), 4.98, 4.95 (3H, s+d), 5.47 (1H, d), 6.82, 6.84 (4H, d+d), 7.07 (2H, d), 7.20 (1H, d), 7.48, 7.51 (3H, sd), 8.64 (1H, s), 8.94 (1H, s). MS: 676 (M⁺).

Example 87

Step 1 t-butyl (4S,5R)-5-{[(1,3-benzodioxol-5-ylsulfonyl)(isobutyl)amino]methyl}-4-[4-(benzyloxy)benzyl]-2,2-dimethyl-1,3-oxazolidine-3-carboxylate

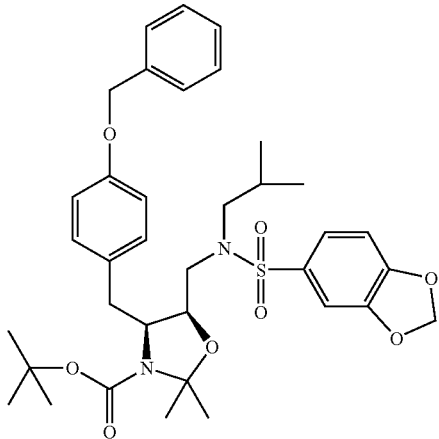 [SMILES: CC(C)CN(C[C@H]1OC(C)(C)N(C(=O)OC(C)(C)C)[C@H]1Cc1ccc(OCc2ccccc2)cc1)S(=O)(=O)c1ccc2c(c1)OCO2]

The reaction was carried out as described for analogous transformations above, starting with previously described tert-butyl (1S,2R)-3-[(1,3-benzodioxol-5-ylsulfonyl)(isobutyl)amino]-1-[4-(benzyloxy)benzyl]-2-hydroxypropylcarbamate The residue was purified on silica gel hexane-ethyl:acetate (3:1) as eluant to a ford 2.689 (88%) of the title compound.

¹H-NMR: (CDCl₃): δ0.86 (3H, d), 0.98 (3H, d), 1.40, 1-45 (3H, s)*, 1.50, 1.55 (3H, s)*, 1.64 (3H, s), 1.66 (3H, s), 1.68 (3H, s), 1.99 (1H, m), 2.65-3.09 (5H, m), 3.24-3.32 (1H, m), 4.17-4.28 (2H, m), 5.09 (2H, s), 6.05 (2H, s), 6.82 (1H, d), 6.96 (2H, d), 7.05-7.18 (4H, m), 7.29-7.50 (5H, m). MS: 667 (M⁺). C₃₆H₄₆N₂O₈S.

*: Possible indication for rotamers.

Step 2 t-butyl (4S,5R)-5-{[1,3-benzodioxol-5-ylsulfonyl)(isobutyl)amino]methyl}-4-(4-hydroxybenzyl)-2,2-dimethyl-1,3-oxazolidine-3-carboxylate

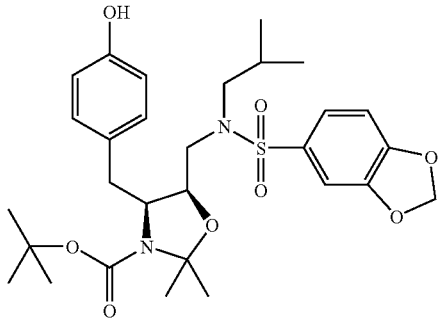 [SMILES: CC(C)CN(C[C@H]1OC(C)(C)N(C(=O)OC(C)(C)C)[C@H]1Cc1ccc(O)cc1)S(=O)(=O)c1ccc2c(c1)OCO2]

The reaction was carried out as described previously staring from t-butyl (4S,5R)-5-{[(1,3-benzodioxol-5-ylsulfonyl)(isobutyl)amino]methyl}-4-[4-(benzyloxy)benzyl]-2,2-dimethyl-1,3-oxazolidine-3-carboxylate to afford 2.31 g (100%) of the title compound.

¹H-NMR: (CDCl₃): δ 0.86 (3H, d), 0.98 (3H, d), 1.40, 1.45 (3H, s)*, 1.50, 1.55 (3H, s)*, 1.66 (3H, s), 1.68 (3H, s), 1.70 (3H, s), 1.99 (1H, m), 2.63-3.09 (5H, m), 3.23-3.31 (1H, m), 3.80 (1H, m), 4.14-4.27 (2H, m), 6.11 (2H, s), 6.77-6.87 (3H, m), 7.02-7.19 (4H, m). MS: 576 (M⁺). C₂₉H₄₀N₂O₈S.

*: Possible indication for rotamers.

Step 3 t-butyl 4S,5R)-5-{[1,3-benzodioxol-5-ylsulfonyl)(isobutyl)amino]methyl}-4-{4-(4-methoxy-4-oxobutoxy)benzyl}-2,2-dimethyl-1,3-oxazolidine-3-carboxylate

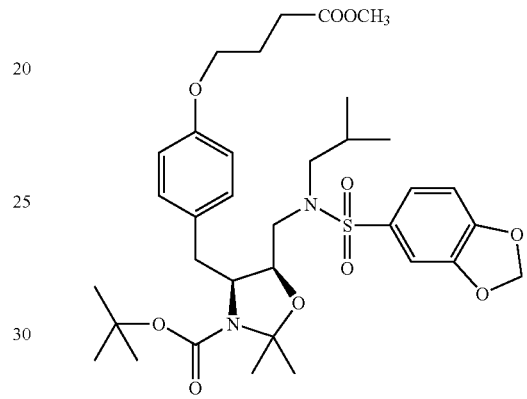

The reaction was carried out as described previously for analogous transformations, starting from 1.83 g (3.17 mmol) of t-butyl (4S,5R)-5-{[1,3-benzodioxol-5-ylsulfonyl)(isobutyl)amino]methyl}-4-(4-hydroxybenzyl)-2,2-dimethyl-1,3-oxazolidine-3-carboxylate except methyl-4-iodobutyrate was used as alkylating reagent.

[2]: room temperature; [3]: 5 hours.

The residue was purified on silica gel using hexane-ethyl acetate (2:1/1:1) as eluant to afford 2.1 g (98%) of the title compound.

¹H-NMR: (CDCl₃): δ0.86 (3H), 0.98 (3H, d), 1.36, 1.38 (3H, s)*, 1.44, 1.49 (3H, s)*, 1.56 (3H, s), 1.59 (3H, s), 1.64 (3H, s), 1.99 (1H, m), 2.14-2.19 (1H, m), 2.47-3.08 (7H, m), 3.23-3.30 (2H, m), 3.72 (3H, s), 4.03-4.27 (4H, m), 6.10 (2H, s), 6.80-6.87 (3H, m), 7.06-7.19 (4H, m). MS: 677 (M⁺). C₃₄H₄₈N₂O₁₀S.

*: Possible indication for rotamers.

Step 4

Methyl 4-(4{(2S,3R)-2-amino-4-[(1,3-benzodioxol-5-ylsulfonyl) (isobutyl)amino]-3-hydroxybutyl}phenoxy) butanoate

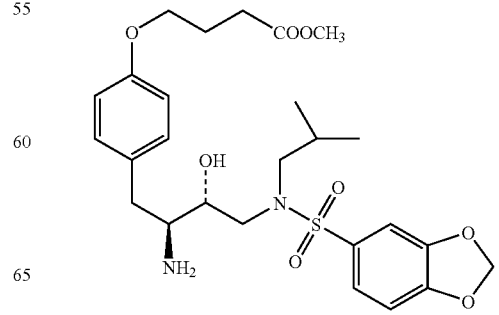

The reaction was carried out as described previously for similar transformations starting t-butyl (4S,5R)-5-{[1,3-benzodioxol-5-ylsulfonyl)(isobutyl)amino]methyl}-4-{4-(4-methoxy-4-oxobutoxy)benzyl}-2,2-dimethyl-1,3-oxazolidine-3-carboxylate, to afford 1.6 g (96%) of the title compound.

Used in the next step without further purification.

$^1$H-NMR: (Methanol-$d_4$): δ0.86 (3H, d), 0.98 (3H, d), 1.99 (1H, m), 2.02-2.92 (3H, m), 2.45-2.60 (2H, m), 2.67-3.17 (6H, m), 3.28-3.47 (2H, m), 3.57-3.62 (1H, m), 3.70 (3H, s), 3.75-3.82 (1H, m), 3.92-4.18 (2H, m), 6.14 (H, s), 6.81-7.03 (4H, m), 7.13-7.22 (2H, m), 7.39 (1H, d). MS: 537 (M$^+$). $C_{26}H_{36}N_2O_8S$.

Step 5

Methyl 4-(4-{(2S,3R)-2-({[3R,3aS,6aR)-hexahydrofuro[2,3-b]furan-3-yloxy]carbonyl}amino)-4-[(1,3-benzodioxol-5-ylsulfonyl)(isobutyl)amino]-3-hydroxybutyl}phenoxy) butanoate (303)

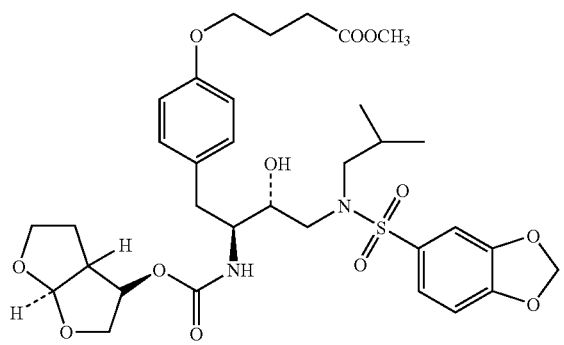

The reaction was carried out as described previously for analogous transformations, starting Methyl 4-(4-{(2S,3R)-2-amino-4-[(1,3-benzodioxol-5-ylsulfonyl)(isobutyl)amino]-3-hydroxybutyl}phenoxy)butanoate The residue was purified by silica gel using hexane-ethyl:acetate (2:1/1:1/1:2) as eluant to afford 0.91 g (44%) of the title compound.

$^1$H-NMR: (CDCl$_3$): δ0.94 (3H, d), 1.00 (3H, d), 1.25-1.35 (1H, m), 1.56-1.69 (2H, m), 1.89 (1H, m), 2.08-2.18 (3H, m), 2.53-2.58 (2H, m), 2.75-2.82 (2H, m), 2.84-3.13 (4H, m), 3.18-3.21 (2H, m), 3.61 (1H, s), 3.72 (3H, s), 3.78-3.97 (2H, m), 4.01-4.17 (3H, m), 4.90 (1H, d), 5.06 (1H, q), 5.70 (1H, d), 6.13 (2H, m), 6.83 (2H, d), 6.93 (1H, d), 7.13-7.19 (3H, m), 7.37 (1H, d). MS: 693 (M$^+$). $C_{33}H_{44}N_2O_{12}S$.

Example 88

Step 1 t-butyl(4S,5R)-5-{[(1,3-benzodioxol-5-ylsulfonyl)(isobutyl)amino]methyl}-2,2-dimethyl-4-[4-(2,2,2-trifluoroethoxy)benzyl]-1,3-oxazolidine-3-carboxylate

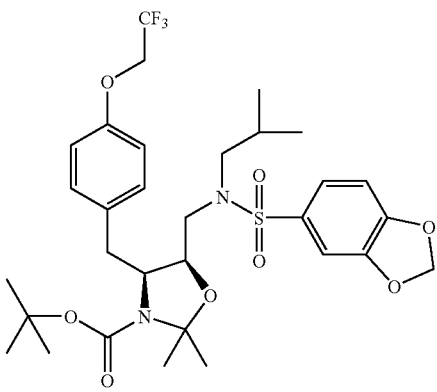 [SMILES: CC(C)CN(C[C@H]1OC(C)(C)N(C(=O)OC(C)(C)C)[C@H]1Cc1ccc(OCC(F)(F)F)cc1)S(=O)(=O)c1ccc2c(c1)OCO2]

To a solution of t-butyl (4S,5R)-5-{[1,3-benzodioxol-5-ylsulfonyl)(isobutyl)amino]methyl}-4-(4-hydroxybenzyl)-2,2-dimethyl-1,3-oxazolidine-3-carboxylate (0.25 g, 0.433 mmol) in 6 ml of dichloromethane-THF (2:1) was added tetrabutylammonium hydrogensulfate (8.9 mg, 0.026 mmol), 40% aqueous sodium hydroxide (0.1-36 ml) and 2,2,2-trifluoroethyltrifluoromethanesulfonate (100 mg, 0.433 mmol). The mixture was heated to reflux for 2.5 hours. Diluted with 10 ml of dichloromethane and 10 ml of water and the organic phase was separated, dried with sodium sulfate, filtered and concentrated under reduced pressure.

The residue was purified on silica gel using hexane-ethyl acetate (2:1) as eluant to afford 90 mg (32%) of the title compound.

$^1$H-NMR: (CDCl$_3$): δ 0.87 (3H, d), 0.96 (3H, d), 1.45, 1.48 (3H, s)*, 1.51, 1.57 (3H, s)*, 1.60 (3H, s), 1.62 (3H, s), 1.65 (3H, s), 1.99 (1H, m), 2.68-3.19 (5H, m), 3.25-3.30 (1H, m), 4.26-4.40 ((4H, m), 6-09 (2H, s), 6.81-7.01 (4H, m), 7.17-7.29 (3H, m). MS: 659 (M$^+$). $C_{31}H_{41}F_3N_2O_8S$.

*: Possible indication for rotamers.

Step 2

N-{(2R,3S)-3-amino-2-hydroxy-4-[4-(2,2,2-trifluoroethoxy)phenyl]butyl}-N-isobutyl-1,3-benzodioxole-5-sulfonamide

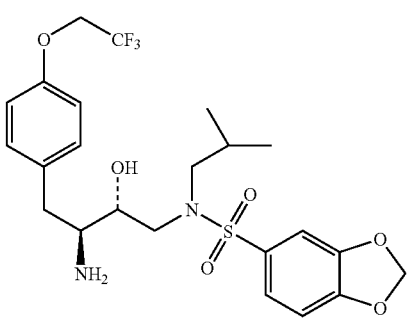 [SMILES: CC(C)CN(C[C@@H](O)[C@@H](N)Cc1ccc(OCC(F)(F)F)cc1)S(=O)(=O)c1ccc2c(c1)OCO2]

The reaction was carried out as previously for similar transformations from t-butyl (4S,5R)-5-{[(1,3-benzodioxol-5-yl-sulfonyl)(isobutyl)amino]methyl}-2,2-dimethyl-4-[4-(2,2,2-trifluoroethoxy)benzyl]-1,3-oxazolidine-3-carboxylate to afford 70 mg (99%) of the title compound.

Used in the next step without further purification.

$^1$H-NMR: (DMSO-d$_6$): δ 0.78 (3H, d), 0.84 (3H, d), 1.99 (1H, m), 2.60-3.58 (11H, m), 4.72-4.84 (2H, m), 6.16 (2H, s), 6.93-7.18 (4H, m), 7.21-7.34 (3H, m). MS: 519 (M$^+$) C$_{23}$H$_{29}$F$_3$N$_2$O$_6$S.

Step 3

(3R,3aS,6aR)-hexahydrofuro[2,3-b]furan-3-yl (1S,2R)-3-[(1,3-benzodioxol-5-ylsulfonyl)(isobutyl)amino]-2-hydroxy-1-[4-(2,2,2-trifluoroethoxy)benzyl]propylcarbamate (304)

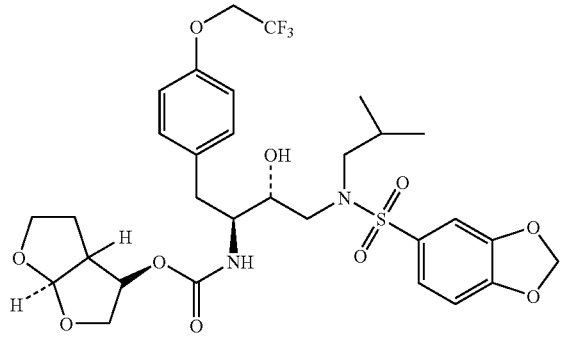

The reaction was carried out as described previously for similar transformations from N-{(2R,3S)-3-amino-2-hydroxy-4-[4-(2,2,2-trifluoroethoxy)phenyl]butyl}-N-isobutyl-1,3-benzodioxole-5-sulfonamide The residue was purified by silica gel using hexane-ethyl acetate (1:1) as eluant to afford 43 mg (47%) of the title compound.

$^1$H-NMR: (CDCl$_3$): δ 0.86 (3H, d), 0.95 (3H, d), 1.31-1.39 (1H, m), 1.59-1.88 (4H, m), 2.79-2.86 (2H, m), 2.97-3.08 (2H, m), 3.12-3.20 (2H, m), 3.64-4.06 (6H, m), 4.32-4.40 (2H, m), 4.75 (1H, d), 5.05 (1H, q), 5.70 (1H, d), 6.13 (2H, s), 6.89-6.99 (3H, m), 7.15-7.29 (3H, m), 7.36 (1H, d) MS: 675 (M$^+$). C$_{30}$H$_{37}$F$_3$N$_2$O$_{10}$S.

Example 89

Step 1

N-{(2R,3S)-3-Amino-4-[4-(benzyloxy)phenyl]-2-hydroxybutyl}-N-(5-cyano-2,2-dimethylpentyl)-1,3-benzodioxole-5-sulfonamide

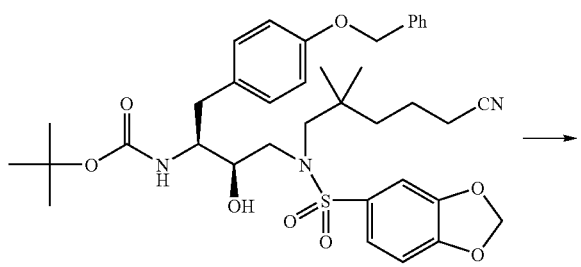

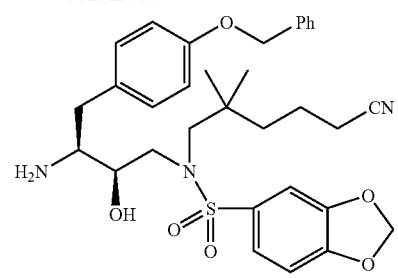

Treatment of tert-butyl (1S,2R)-3-[(1,3-benzodioxol-5-ylsulfonyl) (5-cyano-2,2-dimethylpentyl)amino]-1-[4-(benzyloxy)benzyl]-2-hydroxypropylcarbamate with trifluoroacetic acid/dichloromethane as previously described provided the title compound as a solid foam. $^1$H NMR (DMSO-d$_6$): δ0.95 (6H, s), 1.15 (1H, br d), 1.2-1.6 (5H, m), 2.2° (1H, t), 2.42 (2H, br s), 2.6 (2H, br d), 2.9 (1H, d), 3.05 (1H, dd), 3.3 (1H, br s), 3.45 (2H, br d), 4.62 (1H, s), 5.0 (2H, s), 6.15 (2H, s), 6.89 (2H, d), 7.0 (1H, d), 7.06 (2H, d), 7.22-7.42 (7H, m); MS: 594 (MH$^+$).

Step 2

(3R,3aS,6aR)-Hexahydrofuro[2,3-b]furan-3-yl (1S,2R)-3-[(1,3-benzodioxol-5-ylsulfonyl)(5-cyano-2,2-dimethylpentyl)amino]-1-[4-(benzyloxy)benzyl]-2-hydroxypropylcarbamate (305)

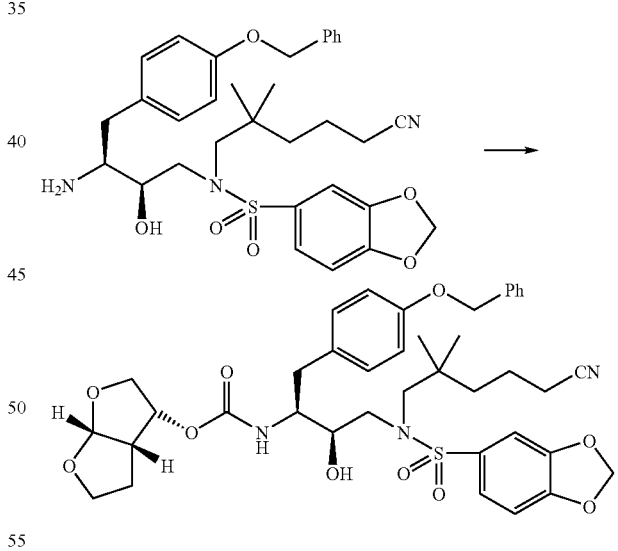

N-{(2R,3S)-3-Amino-4-[4-(benzyloxy)phenyl]-2-hydroxybutyl}-N-(5-cyano-2,2-dimethylpentyl)-1,3-benzodioxole-5-sulfonamide was treated with [(3R,3aS,6aR) hexahydrofuro[2,3-b]furan-3-yl][4-nitrophenyl]carbonate, diisopropylethylamine and acetonitrile as previously described to provide the title compound as a solid foam. $^1$H NMR (DMSO-d$_6$): δ 0.87 (3H, s), 0.92 (3H, s), 1.10-1.13 (1H, m), 1.32-1.38 (3H, m), 1.5-1.6 (2H, m), 2.33 (1H, t), 2.4 (2H, t), 2.65-2.75 (2H, m), 2.7-2.9 (2H, m), 3.3-3.4 (3H, m), 3.5-3.6 (2H, m), 3.65 (1H, t), 3.7 (1H, dd), 3.8 (1H, dd), 4.8 (1H, dd), 5.0 (2H, s), 5.03 (1H, d), 5.45 (1H, d), 6.15 (2H, s), 6.82 (2H, d), 7.03 (1H, d), 7.04 (2H, d), 7.16 (1H, d), 7.22 (1H, s), 7.26-7.40 (6H, m); MS: 750 (MH+);

Example 90

1,3-Dioxan-5-yl (1S,2R)-3-[(1,3-benzodioxol-5-ylsulfonyl)(5-cyano-2,2-dimethylpentyl)amino]-1-[4-(benzyloxy)benzyl]-2-hydroxypropylcarbamate (306)

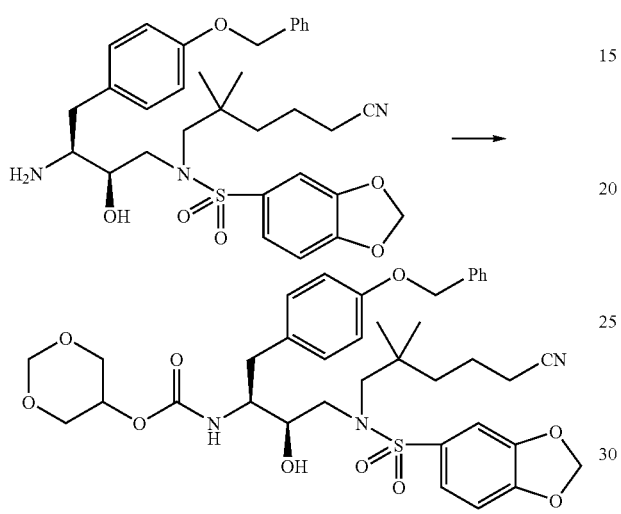

N-{(2R,3S)-3-Amino-4-[4-(benzyloxy)phenyl]-2-hydroxybutyl}-N-(5-cyano-2,2-dimethylpentyl)-1,3-benzodioxole-5-sulfonamide was treated with 1,3-dioxan-5-yl 4-nitrophenyl carbamate/diisopropylamine/acetonitrile as previously described to afford the title compound as a solid foam. $^1$H NMR (DMSO-$d_6$): δ 0.88 (3H, s), 0.89 (3H, s), 1.3-1.4 (2H, m), 1.5-1.6 (2H, m), 2.4-2.5 (3H, m), 2.70-2.82 (2H, m), 2.95 (1H, dd), 3.3-3.4 (3H, m), 3.5 (1H, d), 3.65-3.75 (2H, m), 3.79 (1H, d), 3.89 (1H, d), 4.25 (1H, s), 4.65 (1H, d), 4.8 (1H, d), 4.97 (1H, d), 5.0 (2H, s), 6.15 (2H, s), 6.84 (2H, d), 7.0 (1H, d), 7.15 (2H, d), 7.2 (1H, d), 7.25 (1H, s), 7.26-7.40 (6H, m); MS: 724 (MH+)

Example 91

(3S)-Tetrahydro-3-furanyl (1S,2R)-3-[(1,3-benzodioxol-5-ylsulfonyl)(5-cyano-2,2-dimethylpentyl)amino]-1-[4-(benzyloxy)benzyl]-2-hydroxypropylcarbamate (307)

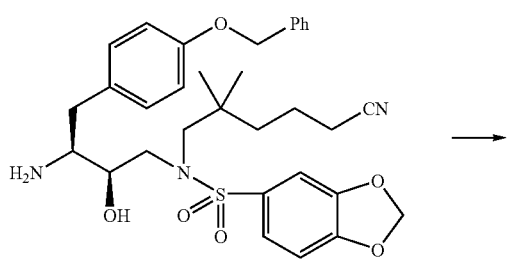

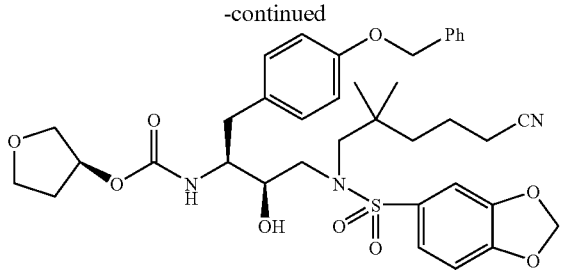

N-{(2R,3S)-3-Amino-4-[4-(benzyloxy)phenyl]-2-hydroxybutyl}-N-(5-cyano-2,2-dimethylpentyl)-1,3-benzodioxole-5-sulfonamide was treated with 1-({[(3S)-tetrahydro-3-furanyloxy]carbonyl}oxy)-2,5-pyrrolidinedione/diisopropylamine/acetonitrile as previously described to provide the title product as a solid foam. $^1$H NMR (DMSO-$d_6$): δ 0.88 (3H, s), 0.90 (3H, s), 1.3 (2H, dd), 1.5-1.6 (2H, m), 1.7-1.8 (1H, m), 2.0-2.2 (1H, m), 2.37 (1H, t), 2.4 (2H, t), 2.75-2.85 (3H, m), 2.9 (1H, dd), 3.30-3.45 (3H, m), 3.55 (1H, dd), 3.65 (1H, dd), 3.7 (2H, dd), 4.9 (1H, s), 4.98 (1H, d), 5.0 (2H, s), 6.15 (2H, s), 6.8 (2H, d), 7.0 (2H, d), 7.06 (2H, d), 7.24 (1H, s), 7.25-7.42 (6H, m); MS: 708 (MH+);

Example 92

Step 1

N-{(2R,3S)-3-Amino-4-[4-(benzyloxy)phenyl]-2-hydroxybutyl}-N-isobutyl-1,3-benzodioxole-5-sulfonamide (308)

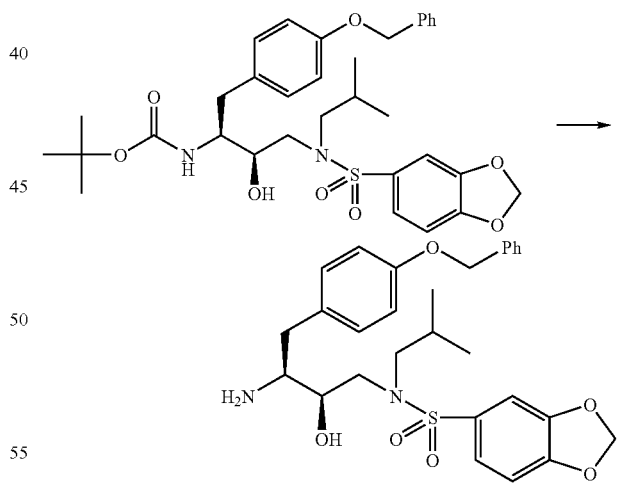

Treatment of tert-butyl (1S,2R)-3-[(1,3-benzodioxol-5-yl)(isobutyl)amino]-1-[4-(benzyloxy)benzyl]-2-hydroxypropylcarbamate with trifluoroacetic acid as previously described afforded the title compound as a solid foam. $^1$H NMR (DMSO-$d_6$): δ 0.90 (3H, d), 0.94 (3H, d), 1.8-2.0 (2H, m), 2.3 (1H, dd), 2.70-2.85 (3H, m) 2.9-3.0 (2H, m), 3.2-3.3 (2H, m), 3.4-3.5 (2H, m), 4.7 (1H, d), 5.03 (2H, s), 6.18 (2H, s), 6.9 (2H, d), 7.02 (1H, d), 7.1 (2H, d), 7.24 (1H, s), 7.25-7.43 (5H, m); MS: 527 (MH+)

Step 2

Hexahydro-4H-furo[2,3-b]pyran-3-yl (1S,2R)-3-[(1,3-benzodioxol-5-ylsulfonyl)(isobutyl)amino]-1-[4-(benzyloxy)benzyl]-2-hydroxypropylcarbamate

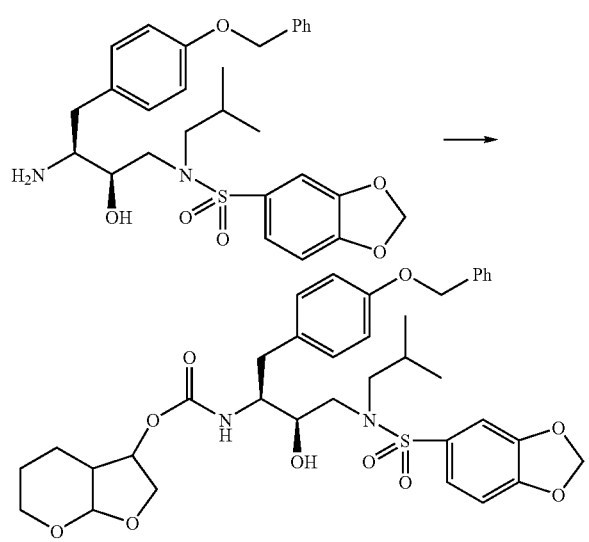

N-{(2R,3S)-3-Amino-4-[4-(benzyloxy)phenyl]-2-hydroxybutyl}-N-isobutyl-1,3-benzodioxole-5-sulfonamide was treated with hexahydro-4H-furo[2,3-b]pyran-3-yl 4-nitrophenyl carbonate/diisopropylethylamine/acetonitrile as previously described to afford after silica gel chromatography (dichloromethane/methanol, 49:1) the title diastereomers as a solid foams. Diastereomer A: ¹H NMR (DMSO-d₆): δ 0.76 (3H, d), 0.80 (3H, d), 1.2 (1H, br s) 1.6 (2H, br s), 1.9 (1H, br s), 2.1 (1H, br s), 2.4 (1H, br s), 2.75 (1H, dd), 2.8-3.0 (3H, m), 3.2-3.3 (3H, m), 3.4-3.6 (3H, m), 3.7 (1H, d), 4.0 (1H, m), 4.8-4.9 (2H, m), 5.0 (3H, br s), 6.15 (2H, s), 6.8 (2H, d), 7.0-7.2 (4H, m), 7.21-7.42 (7H, m); MS: 719 (M+23) Diastereomer B: ¹H NMR (DMSO-d₆): δ 0.76 (3H, d), 0.82 (3H, d), 1.0 (1H, br s), 1.3 (1H, br s), 1.5 (1H, br s), 1.95 (2H, br s), 2.4 (1H, t), 2.7 (2H, td), 2.9 (1H, d), 2.97 (1H, dd), 3.2-3.3 (3H, m), 3.5 (1H, br s), 3.55 (1H, br s), 3.64 (2H, br s), 4.0 (1H, dd), 4.9 (1H, s), 4.95-5.05 (4H, m), 6.15 (2H, s), 6.8 (2H, d), 7.0-7.2 (4H, m), 7.22, (1H, s), 7.25-7.40 (6H, m); MS: 719 (M+23)

Example 93

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-(4-{[(methylamino)carbonyl]oxy}benzyl)propylcarbamate (309)

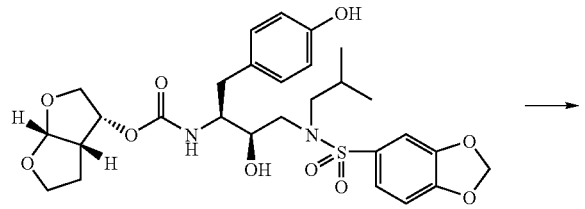

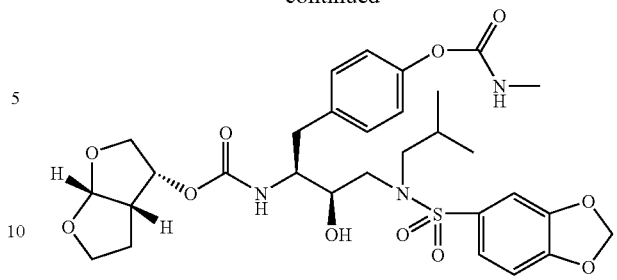

A mixture of (3R,3aS,6aR)-hexahydrofuro[2,3-b]furan-3-yl (1S,2R)-3-[(1,3-benzodioxol-5-ylsulfonyl)(isobutyl)amino]-2-hydroxy-1-(4-hydroxybenzyl)propylcarbamate (80 mg), methyl isocyanate (0.5 mL), dichloromethane (3 mL) and diisopropylamine (0.05 mL) was stirred at ambient temperature for 1 h. Solvent was evaporated and the residue was purified by chromatography (silica gel, hexanes/ethyl acetate, 3:1) to provide the title compound as a solid foam (57 mg). ¹H NMR (DMSO-d₆) δ 0.78 (3H, d), 0.82 (3H, d), 1.17 (1H, dd), 1.30-1.45 (1H, m), 1.9-2.0 (1H, m), 2.42 (1H, t), 2.6 (3H, d), 2.62-2.80 (3H, m), 2.99 (2H, dd), 3.15-3.20 (1H, m), 3.50-3.63 (4H, m), 3.7 (13H, t), 3.8 (1H, dd), 4.8 (1H, dd), 5.04 (1H, d), 5.5 (1H, d), 6.18 (2H, s), 6.95 (2H, d), 7.05 (1H, d), 7.15 (2H, d), 7.2 (1H, s), 7.25 (1H, d), 7.5 (1H, quartet), 8.08 (1H, d); MS: 650 (MH⁺).

Example 94

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-(4-{[(isopropylamino)carbonyl]oxy}benzyl)propylcarbamate (310)

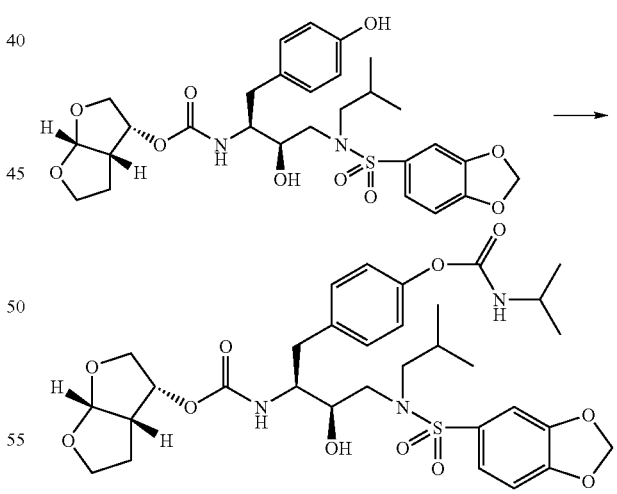

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-(4-hydroxybenzyl)propylcarbamate was treated with isopropyl isocyanate/triethylamine/dichloromethane as described in Example 93 to provide the title compound as a solid foam. ¹H NMR (DMSO-d₆): δ 0.76 (3H, d), 0.82 (3H, d), 0.98 (3H, d), 1.1 (1H, d), 1.35-1.42 (1H, m), 1.90-1.95 (1H, m), 2.4 (1H, t), 2.65-2.80 (3H, m), 2.9-3.0 (2H, m), 3.3-3.4 (1H, m), 3.50-3.63 (6H, m), 3.7 (1H, t), 3.8 (1H, dd), 4.8 (1H, dt), 5.05 (1H, br d), 5.45 (1H, d), 6.18 (2H, s), 6.92 (2H, d), 7.0 (1H, d), 7.18 (2H, d), 7.22 (1H, s), 7.3 (2H, d), 7.58 (1H, d); MS: 678 (MH+); C₃₂H₄₃N₃O₁₁S.

Example 95

Step 1

4-{(2S,3R)-2-({[(3R,3aS,6aR)-Hexahydrofuro[2,3-b]furan-3-yloxy]carbonyl}amino)-4-[(1,3-benzodioxol-5-ylsulfonyl)(isobutyl)amino]-3-hydroxybutyl}phenyl 4-nitrophenyl carbonate

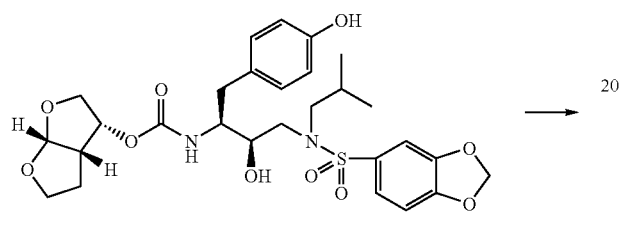

To a solution of (3R,3aS,6aR)-hexahydrofuro[2,3-b]furan-3-yl (1S,2R)-3-[(1,3-benzodioxol-5-ylsulfonyl)(isobutyl)amino]-2-hydroxy-1 (4-hydroxybenzyl)propylcarbamate (0.5 g, 0.84 mmol) in dichloromethane (4 mL) at 0° C. was added pyridine (0.16 mL, 0.158 g, 2.0 mmol) and 4-nitrophenyl chloroformate (0.22 g, 1.09 mmol) and the mixture was stirred at ambient temperature for 1 h. Dichloromethane was added and the mixture was washed with 15% citric acid/water (2×), saturated sodium bicarbonate/water, dried (sodium sulfate), evaporated, and purified by chromatography (silica gel, dichloromethane/methanol, 49:1) to provide the title compound as a solid foam (0.5 g, 79% yield). ¹H NMR (DMSO-d₆): δ 0.78 (3H, d), 0.82 (3H, d), 1.16 (1H, dd), 1.3-1.4 (1H, m), 1.9-2.0 (1H, m), 2.42 (1H, t), 2.65-2.80 (3H, m), 3.0 (2H, dd), 3.3-3.4 (1H, m), 3.5-3.6 (4H, m), 3.7 (1H, t), 3.8 (1H, dd), 4.8 (1H, d), 5.1 (1H, d), 5.5 (1H, d), 6.18 (2H, s), 7.05 (1H, d), 7.2-7.4 (7H, m), 7.7 (2H, d), 8.35 (2H, d)

Step 2

(3R,3aS,6aR)-Hexahydrofuro[2,3-b]furan-3-yl (1S,2R)-3[(1,3-benzodioxol-5-ylsulfonyl)(isobutyl) amino]-1-(4-{[(dimethylamino)carbonyl]oxy}benzyl)-2-hydroxypropylcarbamate (311)

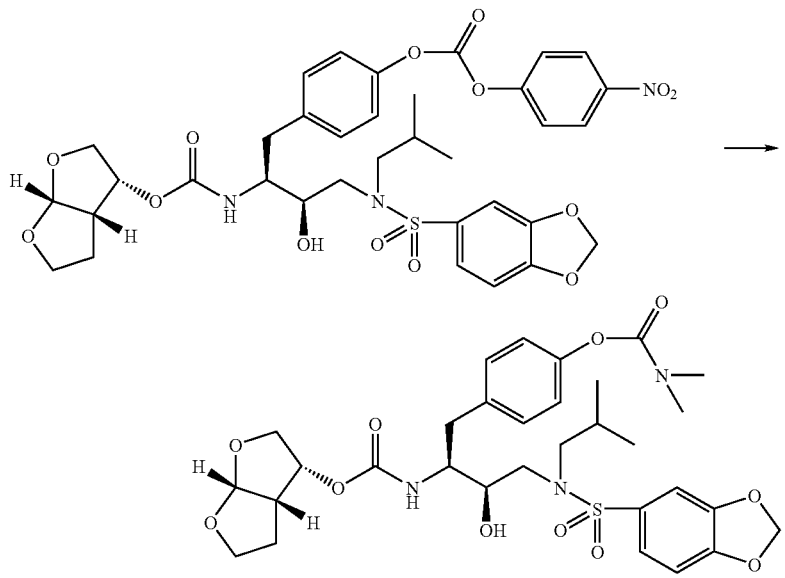

To a solution of 4-{(2S,3R)-2-({[(3R,3aS,6aR)-Hexahydrofuro[2,3-b]furan-3-yloxy]carbonyl}amino)-4-[(1,3-benzodioxol-5-ylsulfonyl)(isobutyl)amino]-3-hydroxybutyl}phenyl 4-nitrophenyl carbonate (60 mg) in tetrahydrofuran (0.5 mL) was added 2M dimethylamine/tetrahydrofuran (0.5 mL) and the mixture is was stirred at ambient temperature for 30 min. Ethyl acetate was added and the mixture was washed with saturated sodium bicarbonate/water (4×), dried (sodium sulfate), evaporated, and purified by chromatography (silica gel, hexanes/ethyl acetate, 3:7) to provide the title compound as a solid foam. ¹H NMR (DMSO-d₆): δ 0.76 (3H, d), 0.82 (3H, d), 1.1-1.2 (1H, m), 1.2 (1H, br quintuplet), 1.9-2.0 (if, m), 2.2 (1H, t), 2.6-2.8 (3H, m), 2.81 (3H, s), 2.9 (3H, s), 3.0 (1H, br s), 3.2-3.3 (2H, m), 3.4-3.6 (4H, m), 3.7 (1H, t), 3.8 (1H, dd), 4.8 (1H, dt), 5.0 (1H, br s), 5.5 (1H, d), 6.1 (2H, s), 6.9 (2H, d), 7.0 (1H, d), 7.15 (2H, d), 7.19 (1H, s), 7.22 (2H, br d); MS: 664 (MH+); C₃₁H₄₁N₃O₁₁S.

-continued

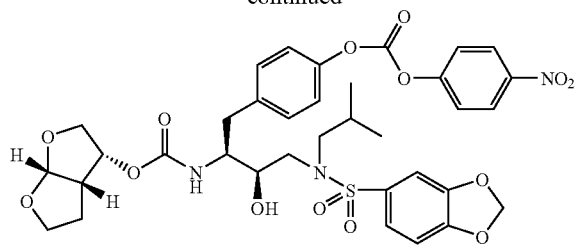

Example 96A (3R,3aS,6aR)-Hexahydrofuro[2,3-b]furan-3-yl (1S,2R)-1-{4-[(aminocarbonyl)oxy]benzyl}-3-[(1,3-benzodioxol-5-ylsulfonyl)(isobutyl)amino]-2-hydroxypropylcarbamate (312)

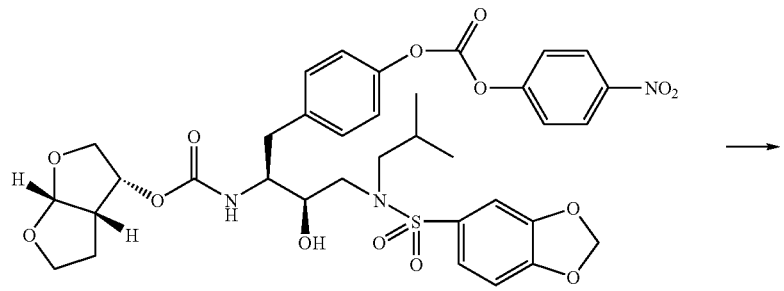

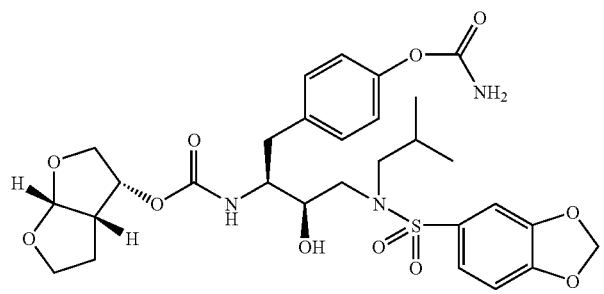

4-{(2S,3R)-2-({[(3R,3aS,6aR)-Hexahydrofuro[2,3-b]furan-3-yloxy]carbonyl}amino)-4-[(1,3-benzodioxol-5-ylsulfonyl)(isobutyl)amino]-3-hydroxybutyl}phenyl 4-nitrophenyl carbonate was treated with concentrated ammonium hydroxide as described in Example 311 to afford the title compound as a white solid. $^1$H NMR (DMSO-$d_6$): 0.78 (3H, d), 0.86 (3H, d), 1.2 (1H, dd), 1.4 (1H, br quintuplet), 1.85-1.95 (1H, m), 2.2 (1H, t), 2.65-2.80 (3H, m), 2.9-3.0 (2H, m), 3.25-3.30 (1H, m), 3.5-3.6 (4H, m), 3.7 (1H, t), 3.8 (1H, dd), 4.8 (1H, dt), 5.0 (1H, d), 5.4 (1H, d), 6.18 (2H, d), 6.8 (2H, br d), 6.9 (2H, d), 7.0 (1H, d), 7.15 (2H, d), 7.2 (1H, s), 7.25-7.30 (2H, m); MS: 636 (MH$^+$).

Example 96B (3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-{4-[({[2-(1H-imidazol-1-yl)ethyl]amino}carbonyl) oxy]benzyl}propylcarbamate (313)

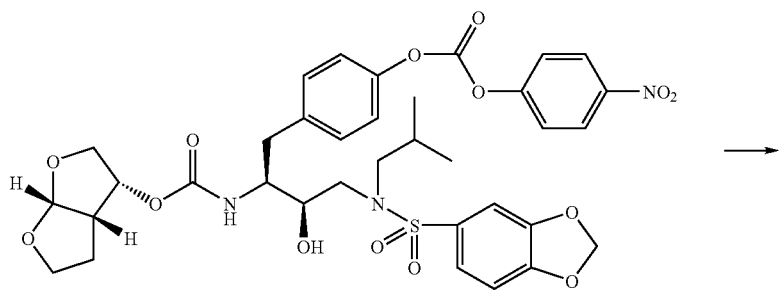

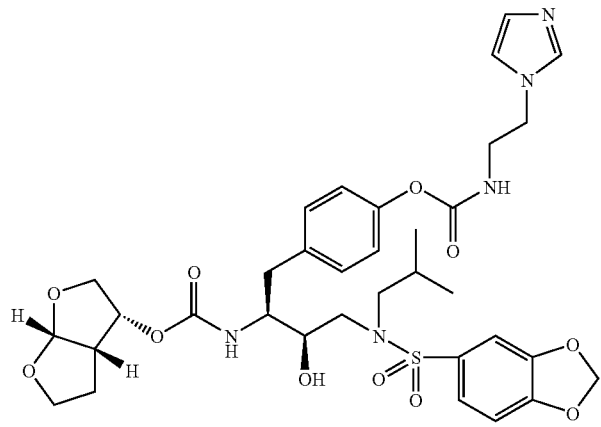

To a solution of 4-{(2S,3R)-2-({[(3R,3aS,6aR)-Hexahydrofuro [2,3-b]furan-3-yloxy]carbonyl}amino)-4-[(1,3-benzodioxol-5-ylsulfonyl)(isobutyl)amino]-3-hydroxybutyl}phenyl 4-nitrophenyl carbonate (50 mg, 0.07 mmol) in 1,4-dioxane (1 mL) was added 2-(1H-imidazol-1-yl)ethanamine (50 mg, 0.45 mmol, *Synthetic Communications* 1991, 21, 535-544) and the mixture was stirred at ambient temperature for 30 min. The mixture was diluted with ethyl acetate and washed with saturated sodium bicarbonate/water (4×), dried (sodium sulfate), evaporated and purified by chromatography (silica gel, dichloromethane/2M ethanolic ammonia, 93:7) to provide the title compound as a white solid (25 mg). $^1$H NMR (DMSO-d$_6$): δ 0.78 (3H, d), 0.82 (3H, d), 1.2 (1H, dd), 1.4 (1H, quintuplet), 1.9-2.0 (1H, m), 2.4 (1H, t), 2.55-2.80 (3H, m), 2.9-3.0 (2H, m), 3.3-3.4 (3H, m), 3.5-3.6 (4H, m), 3.7 (1H, t), 3.8 (1H, dd), 4.03-4.07 (2H, m), 4.8 (1H, dt), 0.505 (1H, d), 5.5 (1H, d), 6.18 (2H, s), 6.87 (1H, s), 6.9 (2H, d), 7.05 (1H, d), 7.15 (1H, s), 7.2 (2H, d), 7.23 (1H, s), 7.25-7.30 (2H, m), 7.6 (1H, s), 7.8 (1H, t); MS: 730 (MH$^+$)

Example 97

(3R,3aS,6aR)-Hexahydrofuro[2,3-b]furan-3-yl (1S, 2R)-1-[4-(2-amino-2-oxoethoxy)benzyl]-3-[(1,3-benzodioxol-5-ylsulfonyl)(isobutyl)amino]-2-hydroxypropylcarbamate (314)

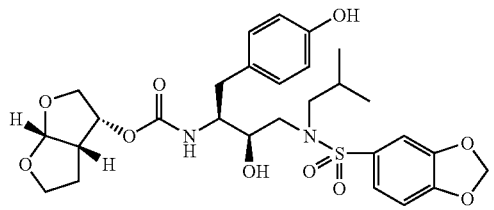

To a solution of (3R,3aS,6aR)-hexahydrofuro[2,3-b]furan-3-yl (1S,2R)-3-[(1,3-benzodioxol-5-ylsulfonyl) (isobutyl) amino]-2-hydroxy-1-(4-hydroxybenzyl)propylcarbamate (47 mg, 0.08 mmol) in anhydrous dimethylformamide (2 mL) was added cesium carbonate (78 mg, 0.24 mmol) and 2-bromoacetamide (22 mg, 0.16 mmol). After 1 h at ambient temperature, the mixture was diluted with ethyl acetate, washed with water (3×), brine, dried (sodium sulfate), and evaporated. The residue was purified by chromatography (silica gel, dichloromethane/methanol, 97:3) to afford the title product as a white solid (45 mg) $^1$H NMR (DMSO-d$_6$): δ 0.78 (3H, d), 0.82 (3H, d), 1.2 (1H, dd), 1.4 (1H, quintuplet), 1.9-2.0 (1H, m), 2.35 (1H, t), 2.6-2.8 (3H, m), 2.9 (1H, d), 2.95 (1H, dd), 3.25-3.30 (1H, m), 3.45 (1H, br s), 3.5-3.6 (3H, m), 3.7 (1H, t), 3.8 (1H, dd), 4.3 (2H, s), 4.8 (1H, dt), 5.0 (1H, d), 5.5 (1H, d), 6.18 (2H, s), 6.8 (2H, d), 7.0-7.15 (3H, m), 7.22 (1H, s), 7.24 (1H, d), 7.26 (1H, d), 7.32 (1H, s), 7.42 (1H, s); MS: 650 (MH$^+$)

Example 98

(3R,3aS,6aR)-Hexahydrofuro[2,3-b]furan-3-yl (1S, 2R)-3-[(1,3-benzodioxol-5-ylsulfonyl)(isobutyl) amino]-2-hydroxy-1-{4-[2-(methylamino)-2-oxoethoxy]benzyl}propylcarbamate (315)

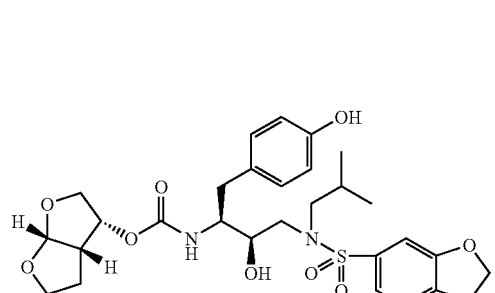

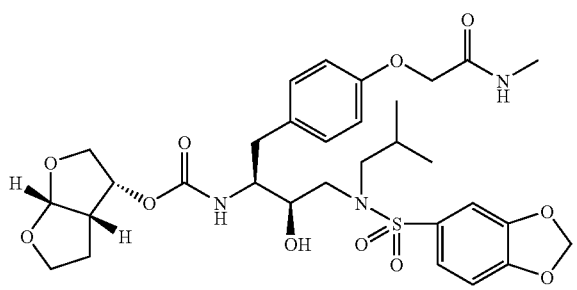

To a solution of (3R,3aS,6aR)-hexahydrofuro[2,3-b]furan-3-yl (1S,2R)-3-[(1,3-benzodioxol-5-ylsulfonyl)(isobutyl) amino]-2-hydroxy-1-(4-hydroxybenzyl)propylcarbamate (60 mg, 0.1 mmol) in anhydrous tetrahydrofuran (1.5 mL) was added 60% sodium hydride/mineral oil dispersion (4 mg, 0.1 mmol). The mixture was stirred for 10 min at ambient temperature under nitrogen atmosphere and a solution of N-methyl-2-bromoacetamide (17 mg, 0.11 mmol) in anhydrous tetrahydrofuran (0.5 mL) was added. After 2 h, an additional portion of 60% sodium hydride/mineral oil dispersion (4 mg, 0.1 mmol) was added. After 15 min, acetic acid (0.1 mL) was added and the mixture was diluted with ethyl acetate, washed with saturated sodium bicarbonate/water, dried (sodium sulfate), evaporated, and purified by chromatography (silica gel, ethyl acetate) to provide the title compound as a white solid (10 mg). $^1$H NMR (DMSO-$d_6$): δ 0.78 (3H, d), 0.82 (3H, d) 1.15-1.22 9 (1H, m), 1.2 (1H, quintuplet), 1.9-2.0 (1H, m), 2.35 (1H, t), 2.6 (3H, d), 2.65-2.80 (3H, m), 2.9 (1H, d), 2.95 (1H, dd), 3.2-3.3 (1H, m), 3.4-3.5 (1H, m) 3.5-3.6 (3H, m), 3.7 (1H, t), 3.8 (1H, dd), 4.4 (2H, s), 4.8 (1H, dt), 5.0 (1H, d), 5.5 (1H, d), 6.2 (2H, s), 6.8 (2H, d), 7.0-7.2 (3H, m), 7.22 (1H, s), 7.25 (1H, d), 7.3 (1H, d), 8.0 (1H; br s); MS: 664 (MH$^+$);

Example 99

(3R,3aS,6aR)-Hexahydrofuro[2,3-b]furan-3-yl (1S, 2R)-3-[(1,3-benzodioxol-5-ylsulfonyl)(isobutyl) amino]-2-hydroxy-1-{4-[3-(sulfoxy)propoxy] benzyl}propylcarbamate Potassium Salt (316)

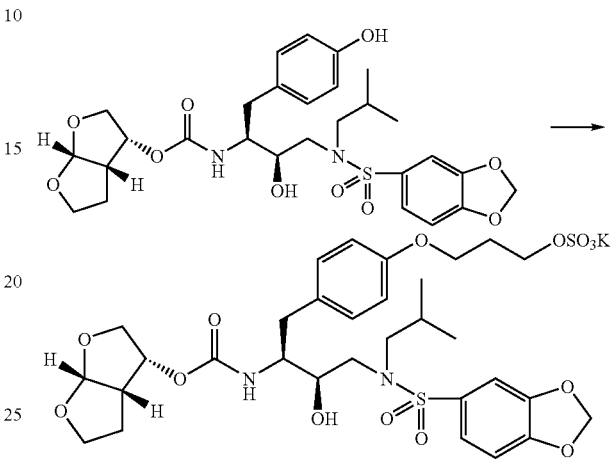

A mixture of (3R,3aS,6aR)-hexahydrofuro[2,3-b]furan-3-yl (1S,2R)-3-[(1,3-benzodioxol-5-ylsulfonyl)(isobutyl) amino]-2-hydroxy-1-(4-hydroxybenzyl)propylcarbamate (35 mg, 0.06 mmol), potassium carbonate (8.1 mg, 0.06 mmol), 1,3,2-dioxathiane 2,2-dioxide (8.9 mg, 0.065 mmol, *J. Am. Chem. Soc.* 1988, 110, 7538-7539) and acetonitrile was heated at 82° C. under nitrogen atmosphere for 36 h and filtered while hot. The filtrate was allowed to cool to ambient temperature for 18 h and the resulting solid was filtered and washed with diethyl ether to provide the title compound as a white solid (25 mg). $^1$H NMR (DMSO-$d_6$): δ 0.78 (3H, d), 0.82 (3H, d), 1.25 (1H, dd), 1.4 (1H, quintuplet), 1.9-2.0 (3H, m), 2.2 (1H, t), 2.7-2.8 (3H, m), 2.9 (1H, d), 3.0 (1H, dd), 3.25-3.00 (1H, m), 3.4-3.5 (1H, m), 3.50-3.65 (3H, m), 3.7 (1H, t), 3.75-3.82 (3H, m), 3.9 (1H, t), 4.08 (1H, dd), 4.8 (1H, dt), 4.97 (1H, d), 5.5 (1H, d), 6.18 (2H, s), 6.78 (2H, d), 7.0-7.1 (3H, m), 7.19 (1H, d), 7.20 (1H, s), 7.30 (1H, d); MS: 730 (MH$^+$)

Step 1

(3R,3aS,6aR)-Hexahydrofuro[2,3-b]-furan-3-yl (1S, 2R)-3-[(1,3-benzodioxol-5-ylsulfonyl)(isobutyl) amino]-1-[4-(4-{[tert-butyl(dimethyl) silyl] oxy}butoxy)benzyl]-2-hydroxypropylcarbamate

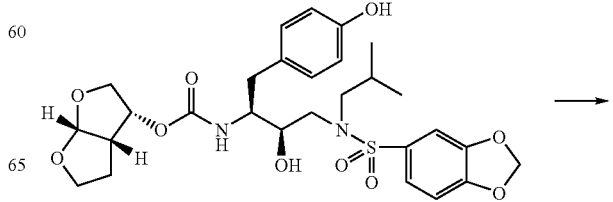

-continued

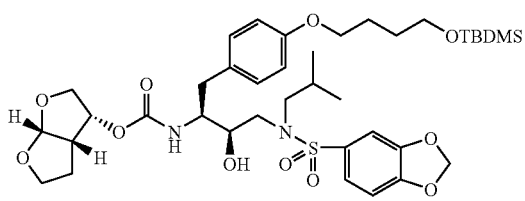

To a solution of (3R,3aS,6aR)-hexahydrofuro[2,3-b]furan-3-yl (1S,2R)-3-[(1,3-benzodioxol-5-ylsulfonyl)(isobutyl)amino]-2-hydroxy-1-(4-hydroxybenzyl)propylcarbamate (0.6 g, 1.01 mmol), triphenyl phosphine (0.4 g, 1.52 mmol), and 4-{[tert-butyl(dimethyl)silyl]oxy}-1-butanol (0.31 g, 1.52 mmol, *J. Org. Chem.* 1986, 51, 3388-3390) in anhydrous dichloromethane (9 mL) at 0° C. under nitrogen atmosphere was slowly added a solution of diisopropyl azodicarboxylate (0.29 mL, 0.3 g, 1.52 mmol) in anhydrous dichloromethane (2 mL) and the mixture was stirred at ambient temperature for 2 h. Solvent was evaporated and the residue was purified by chromatography (silica gel, hexanes/ethyl acetate, 1:1) to provide the title compound as a solid foam (0.39 g). In NMR (DMSO-$d_6$): δ 0.0 (6H, s), 0.78 (3H, d), 08.0 (3H, d), 0.82 (9H, s), 1.22 (1H, dd), 1.4 (1H, quintuplet), 1.55 (2H, quintuplet), 1.7 (2H, quintuplet), 1.8-1.9 (1H, m), 2-35 (1H, t), 2.65-2.80 (3H, m), 2.9 (1H, d), 3.0 (1H, dd), 3.2-3.3 (2H, m), 3.4-3.5 (1H, m), 3.52-3.62 (4H, m), 3.7 (1H, t), 3.8 (1H, dd), 3.9 (2H, t), 4.8 (1H, dt), 5.0 (1H, br s), 5.5 (1H, d), 6.18 (2H, s), 6.77 (2H, d), 7.0-7.1 (3H, m), 7.19 (1H, d), 7.21 (1H, s), 7.3 (1H, d); MS: 801 (M+23); $C_{38}H_{58}N_2O_{11}SSi$.

Step 2

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-[4-(4-hydroxybutoxy)benzyl]propylcarbamate (317)

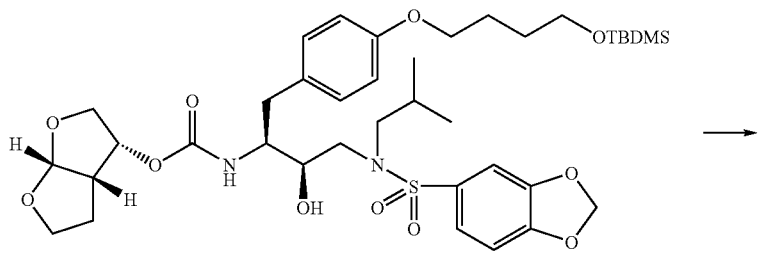

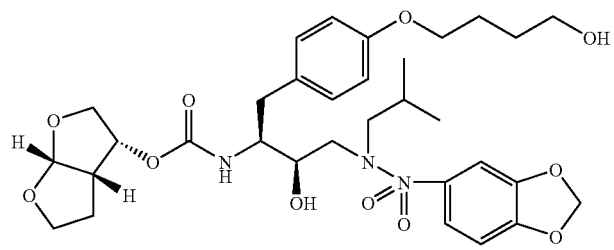

To a solution of (3R,3aS,6aR)-Hexahydrofuro[2,3-b]furan-3-yl (1S,2R)-3-[(1,3-benzodioxol-5-ylsulfonyl)(isobutyl)-amino]-1-[4-(4-{[tert-butyl(dimethyl)silyl]oxy}butoxy)benzyl]-2-hydroxypropylcarbamate (0.38 g, 0.48 mmol) in tetrahydrofuran (5 mL) at 0° C. was added a 1:1 mixture of 1M tetra-n-butyl ammonium fluoride/tetrahydrofuran and acetic acid (1.2 mL) and the mixture was stirred at ambient temperature for 18 h. The mixture was diluted with ethyl acetate and washed with water (4×), dried (sodium sulfate) and evaporated. The resulting solid was triturated with diethyl ether and filtered to afford the title compound as a white solid (0.24 g) $^1$H NMR (DMSO-$d_6$): δ 0.78 (3H, d), 0.82 (3H, d), 1.2 (1H, dd), 1.38 (1H, quintuplet), 1.5 (2H, quintuplet), 1.65 (2H, quintuplet), 1.9-2.0 (1H, m), 2.18 (1H, t), 2.7-2.8 (3H, m), 2.9 (1H, d), 2.97 (1H, dd), 3.20-3.25 (1H, m), 3.38 (2H, t), 3.4-3.5 (1H, m), 3.52-3.62 (3H, m), 3.7 (1H, t), 3.8 (1H, dd), 3.93 (2H, t), 4.2 (1H, br s), 4.8 (1H, dt), 5.0 (1H, d), 5.5 (1H, d), 6.18 (2H, s), 6.78 (2H, d), 7.0-7.1 (3H, m), 7.2 (1H, d), 7.26 (1H, s), 7.3 (1H, d); MS: 665 (MH$^+$)

Example 101

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-[4-(4-{[(methylamino)carbonyl]oxy}butoxy)benzyl]propylcarbamate (318)

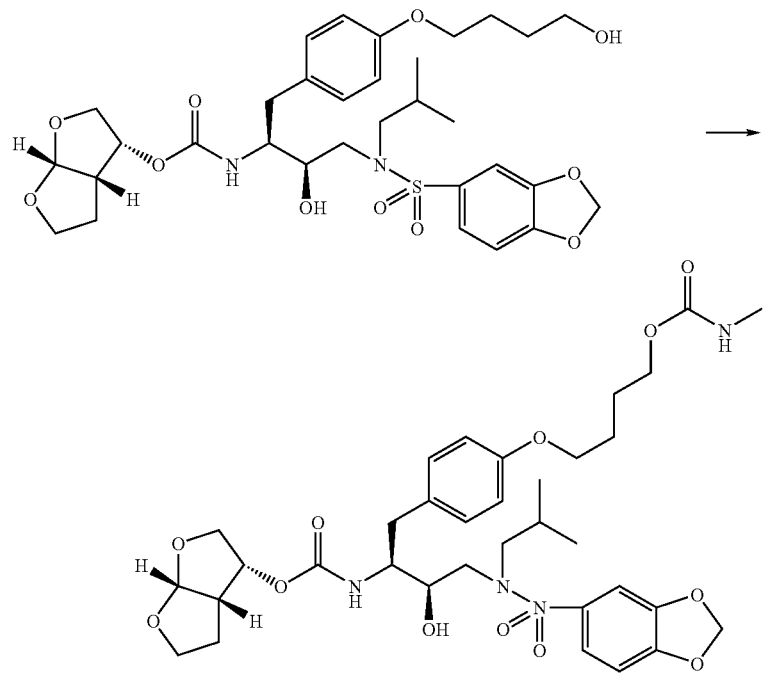

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-[4-(4-hydroxybutoxy)benzyl]propylcarbamate was treated with methyl isocyanate/dichloromethane as described earlier to afford the title compound as a solid foam. $^1$H NMR (DMSO-$d_6$): δ 0.78 (3H, d), 0.82 (3H, d), 1.2 (1H, dd), 1.4 (1H, quintuplet), 1.6-1.8 (4H, m), 1.9-2.0 (1H, m), 2.38 (1H, t), 2.5 (3H, d), 2.7-2.8 (3H, m), 2.9 (1H, d), 2.98 (1H, dd), 3.3-3.4 (1H, m), 34-3.5 (1H, m), 3.5-3.6 (3H, m), 3.7 (1H, t), 3.8 (1H, dd), 3.9 (2H, t), 3.95 (2H, t), 4.8 (1H, dt), 5.0 (1H, br s), 5.5 (1H, d), 6.18 (2H, s), 6.78 (2H, d), 6.9 (1H, br s), 7.0-7.1 (3H, m), 7.2 (1H, d), 7.25 (1H, s), 7.3 (1H, d); MS: 744 (M+23); $C_{34}H_{47}N_3O_{12}S$.

Example 102

Step 1

(3R,3aS,6aR)-Hexahydrofuro[2,3-b]furan-3-yl (1S,2R)-3-[(1,3-benzodioxol-5-ylsulfonyl)(isobutyl)amino]-1-[4-(3-{[tert-butyl(dimethyl)silyl]oxy}propoxy)benzyl]-2-hydroxypropylcarbamate

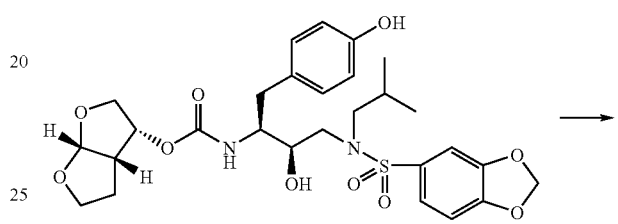

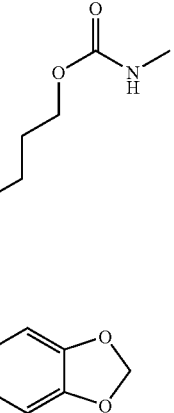

-continued

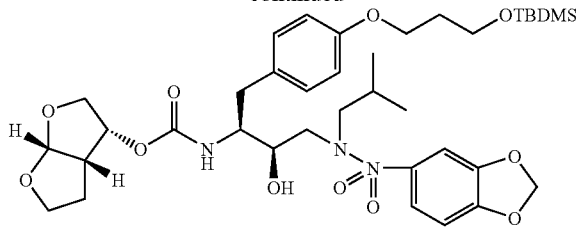

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-(4-hydroxybenzyl)propylcarbamate was treated with 3-{[tert-butyl(dimethyl)silyl]oxy}-1-propanol (*J. Org. Chem.* 1986, 51, 3388-3390)/triphenyl phosphine/diisopropyl azodicarboxylate as described in step a (Example 213) to provide the title compound as solid foam. $^1$H NMR (DMSO-d$_6$): δ 0.0 (6H, s), 0.78 (3H, d), 0.8 (9H, s), 0.82 (3H, d), 1.2 (1H, dd), 1.4 (1H, quintuplet), 1.8 (2H, quintuplet), 1.9-2.0 (1H, m), 2.38 (1H, dd), 2.6-2.8 (3H, m), 2.9 (1H, d), 2.98 (1H, dd), 3.2-3.3 (2H, m), 3.35-3.45 (1H, m), 3.5-3.6 (3H, m), 3.7 (2H, t), 3.8 (1H, dd), 3.9 (2H, t), 4.8 (1H, dt), 5.0 (1H, d), 5.5 (1H, d)Y 6.18 (2H, s), 6.75 (2H, d), 7.0-7.1 (3H, m), 7.18 (1H, d)Y 7.2 (1H, s), 7.28 (1H, d); MS: 765 (MH$^+$)

Step 2

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-[4-(3-hydroxypropoxy)benzyl]propylcarbamate (319)

(3R,3aS,6aR)-Hexahydro-furo[2,3-b]furan-3-yl (1S,2R)-3-[(1,3-benzodioxol-5-ylsulfonyl)(isobutyl)amino]-1-[4-(3-{[tert-butyl(dimethyl)silyl]oxy}propoxy)benzyl]-2-hydroxypropylcarbamate was treated with 1M tetra-n-butyl ammonium fluoride/tetrahydrofuran/acetic acid as described in step b (Example 213) to afford the title compound as a white solid. $^1$H NMR (DMSO-d$_6$): δ 0.78 (3H, d), 0.82 (3H, d), 1.2 (1H, dd), 1.38 (1H, quintuplet), 1.8 (2H, quintuplet), 1.9-2.0 (1H, m), 2.38 (1H, t), 2.6-2.8 (3H, m), 2.9 (1H, d), 2.96 (1H, dd), 3.3 (1H, br s) 3.4-3.6 (6H, m), 3.7 (1H, t), 3.8 (1H, dd), 3.9 (2H, t), 4.5 (1H, t), 4.8 (1H, dt), 5.0 (1H, d), 5.5 (1H, d), 6.18 (2H, s), 6.78 (2H, d), 7.0-7.1 (3H, m), 7.2 (1H, d), 7.25 (1H, s), 7.3 (1H, d); MS: 651 (MH$^+$)

Example 103

Step 1

3-(4-{(2S,3R)-2-({[(3R,3aS,6aR)-Hexahydrofuro[2,3-b]furan-3-yloxy]carbonyl}amino)-4-[(1,3-benzodioxol-5-ylsulfonyl)(isobutyl)amino]-3-hydroxybutyl}phenoxy)propyl 4-nitrophenyl carbonate

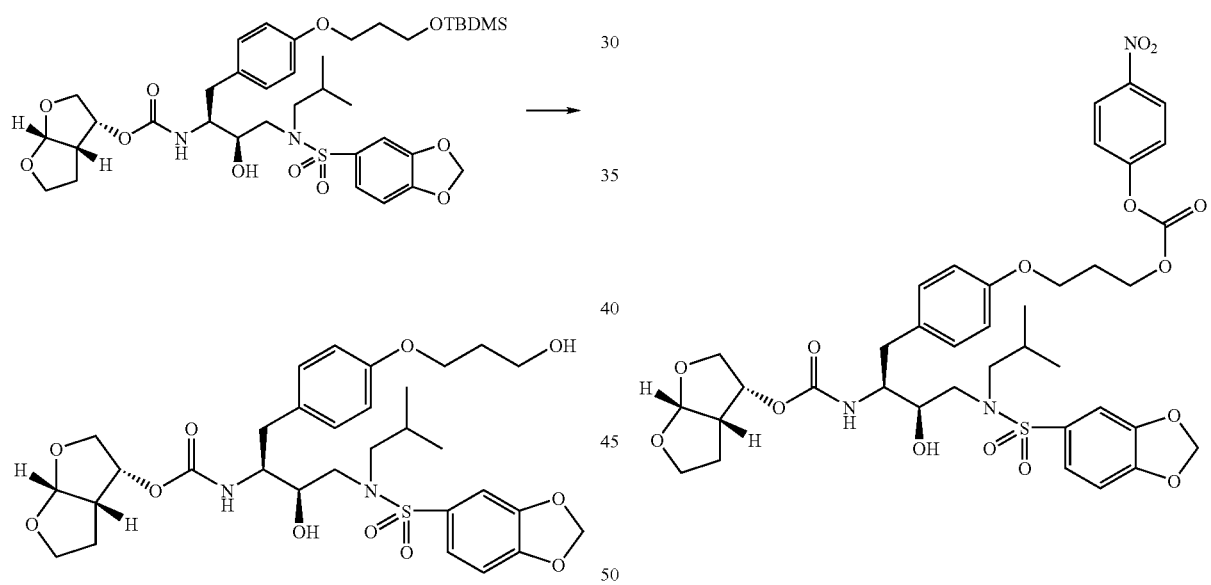

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-[4-(3-hydroxypropoxy)benzyl]propylcarbamate was treated with 4-nitrophenyl chloroformate as described previously to provide the title compound as a solid foam.

$^1$H NMR (DMSO-d$_6$): δ 0.86 (3H, d), 0.92 (3H, d), 1.2 (1H, dd), 1.38 (1H, quintuplet), 1.9-2.0 (1H, m), 2.05-2.15 (2H, m), 2.2 (1H, t), 2.6-2.8 (3H, m), 2.9 (1H, d), 2.96 (1H, dd), 3.2-3.3 (2H, m), 3.4-3.5 (1H, m), 3.5-3.6 (2H, m), 3.7 (1H, t), 3.8 (1H, dd), 4.0 (2H, t), 4.37 (2H, t), 4.8 (1H, dt), 5.0 (1H, d), 5.45 (1H, d), 6.18 (2H, s) 6.78 (2H, d), 7.0-7.1 (3H, m), 7.20-7.25 (2H, m), 7.3 (1H, dd), 7.56 (2H, d), 8.25 (2H, d); MS: 816 (MH$^+$)

Step 2

(3R,3aS,6aR)-Hexahydrofuro[2,3-b]furan-3-yl (1S,2R)-3[(1,3-benzodioxol-5-ylsulfonyl)(isobutyl)amino]-2-hydroxy-1-[4-(3-{[(methylamino) carbonyl]oxy}propoxy) benzyl]propylcarbamate (320)

Example 104

(3R,3aS,6aR)-Hexahydrofuro[2,3-b]furan-3-yl (1S,2R)-1-(4-{3-[(aminocarbonyl)oxy]propoxy}benzyl)-3-[(1,3-benzodioxol-5-ylsulfonyl)(isobutyl)amino]-2-hydroxypropylcarbamate (321)

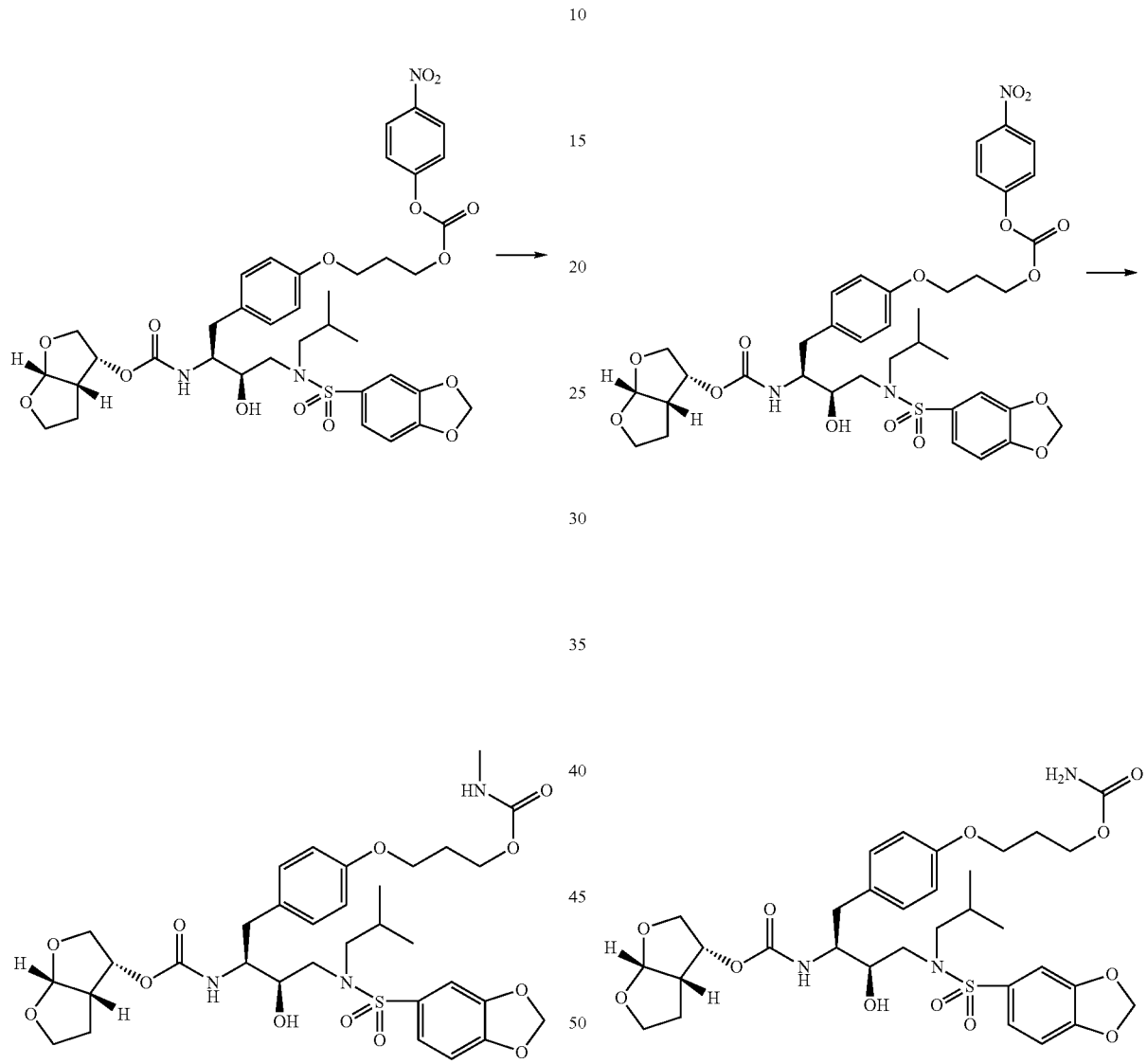

3-(4-{(2S,3R)-2-([{(3R,3aS,6aR)-Hexahydrofuro[2,3-b]furan-3-yloxy]carbonyl}amino)-4-[(1,3-benzodioxol-5-ylsulfonyl)(isobutyl)amino]-3-hydroxybutyl}phenoxy) propyl 4-nitrophenyl carbonate was treated with 2M methylamine/tetrahydrofuran as described above to provide the title compound as a white solid. $^1$H NMR (DMSO-$d_6$): a 0.78 (3H, d), 0.84 (3H, d), 1.1-1.2 (1H, m), 1.2 (1H, br quintuplet), 1.9-2.0 (3H, m), 2.17 (1H, t), 2.45 (3H, d), 2.6-2.8 (3H, m), 2.83-3.00 (2H, m), 3.4-3.6 (5H, m), 3.7 (1H, br s), 3.8 (1H, br s), 3.9 (2H, br s), 4.0 (2H, br s), 4.8-4.9 (1H, m), 5.0 (1H, d), 5.5 (1H, d), 6.17 (2H, s), 6.7-6.8 (2H, m), 6.9 (1H, br s), 7.0-7.1 (3H, m), 7.2-7.4 (3H, m); MS: 708 (MH$^+$);

3-(4-{(2S,3R)-2-({[(3R,3aS,6aR)-Hexahydrofuro[2,3-b]furan-3-yloxy]carbonyl}amino)-4-[(1,3-benzodioxol-5-ylsulfonyl)(isobutyl)amino]-3-hydroxybutyl}phenoxy) propyl 4-nitrophenyl carbonate was treated with concentrated ammonium hydroxide as described above to afford the title compound as a white solid. $^1$H NMR (DMSO-$d_6$): δ 0.78 (3H, d), 0.82 (3H, d), 1.2-1.3 (1H, m), 1.4 (1H, quintuplet), 1.9-2.0 (3H, m), 2.2 (1H, t), 2.6-2.8 (3H, m), 2.9 (1H, d), 2.97 (1H, dd), 3.2-3.3 (1H, m), 3.4-3.6 (4H, m), 3.7 (1H, t), 3.8 (1H, dd), 3.9 (2H, t), 4.0 (2H, t), 4.8 (1H, dt), 5.0 (1H, d), 5.5 (1H, d), 6.17 (2H, s), 6.4 (2H, br S), 6.78 (2H, d), 7.0-7.1 (3H, m), 7.2-7.3 (3H, m); MS: 694 (MH$^+$)

Example 105

Step 1

(3R,3aS,6aR)-Hexahydrofuro[2,3-b]furan-3-yl-(1S,2R)-3-[(1,3-benzodioxol-5-ylsulfonyl)(isobutyl)amino]-1-[4-(2-{[tert-butyl(dimethyl)silyl]oxy}ethoxy)benzyl]-2-hydroxypropylcarbamate

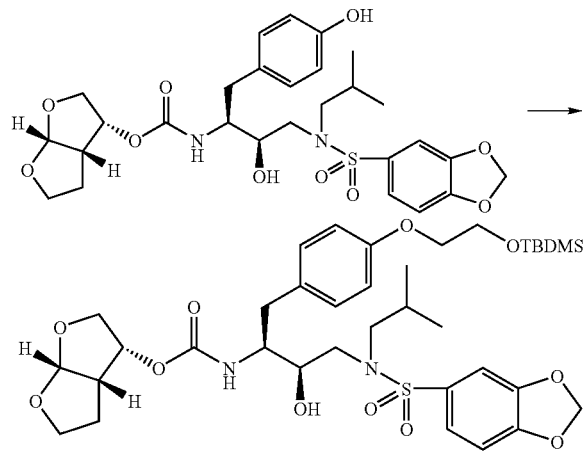

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-(4-hydroxybenzyl)propylcarbamate was treated with 2-{[tert-butyl(dimethyl)silyl]oxy}-1-ethanol (*J. Org. Chem.* 1986, 51, 3388-3390)/triphenyl phosphine/diisopropyl azodicarboxylate as described above to provide the title compound as solid foam. $^1$H NMR (DMSO-$d_6$): 0.0 (6H, s), 0.78 (3H, d), 0.82 (3H, d), 0.84 (9H, s), 1.2 (1H, dd), 1.37 (1H, quintuplet), 1.9-2.0 (1H, m), 2.37 (1H, dd), 2.6-2.8 (2H, m), 2.9 (1H, d), 2.98 (1H, dd), 3.2-3.3 (1H, m), 3.4-3.5 (1H, m), 3.5-3.6 (4H, m), 3.7 (1H, t), 3.8 (1H, dd), 3.88 (2H, dd), 3.93 (2H, dd), 4.8 (1H, dt), 5.0 (1H, d), 5.45 (1H, d), 6.18 (2H, s), 6.78 (2H, d), 7.0-7.1 (3H, m), 7.18 (1H, d), 7.2 (1H, s), 7.28 (1H, d); MS: 751 (MH$^+$)

Step 0.2

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-[4-(2-hydroxyethoxy)benzyl]propylcarbamate (322)

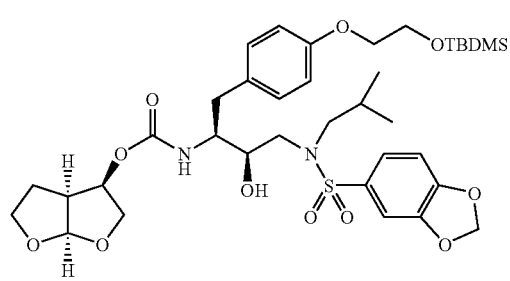

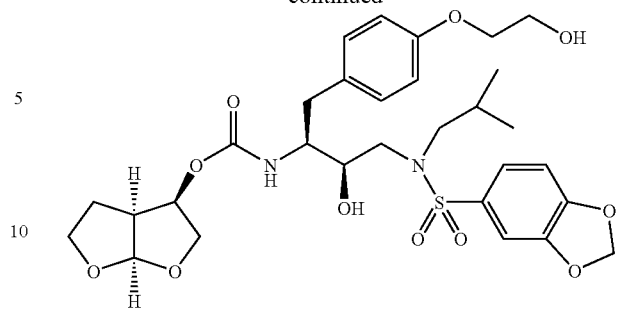

To a stirred solution of (3R,3aS,6aR)-Hexahydrofuro[2,3-b]furan-3-yl-(1S,2R)-3-[(1,3-benzodioxol-5-ylsulfonyl)(isobutyl)amino]-1-[4-(2-{[tert-1-butyl(dimethyl) silyl]oxy}ethoxy)benzyl]-2-hydroxypropylcarbamate (160 mg, 0.21 mmol) in tetrahydrofuran (3 mL) at 5° C. was added a mixture of tetrabutylammonium fluoride (0.3 mL, 1M in tetrahydrofuran) and glacial acetic acid (0.3 ml) over 2 minutes. The reaction was allowed to warm to ambient temperature and stirred for 18 hours. The mixture was diluted with ethyl acetate (50 mL), washed with water (25 mL) followed by saturated sodium bicarbonate (20 mL) and then brine (20 mL), dried (magnesium sulfate) and concentrated in vacuo to afford the title compound (135 mg, guant.) as a white solid. $^1$H NMR (DMSO-$d_6$): δ 0.78 (6H, dd), 1.17-1.42 (2H, ma), 1.92 (1H, m), 2.33 (1H, t), 2.64-2.78 (3H, m), 2.89-3.02 (2H, m), 3.24-3.29 (1H, m), 3.52-3.73 (7H, m), 3.78-3.82 (1H, m), 3.86 (2H, t), 4.78-4.82 (2H, m), 4.99 (1H, d), 5.46 (1H, d), 6.12 (2H, s), 6.73 (2H, d), 7.02-7.28 (6H, m); MS: 637 (MH$^+$)

Example 106

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-[4-(2-{[(methylamino) carbonyl]oxy}ethoxy) benzyl]propylcarbamate (323)

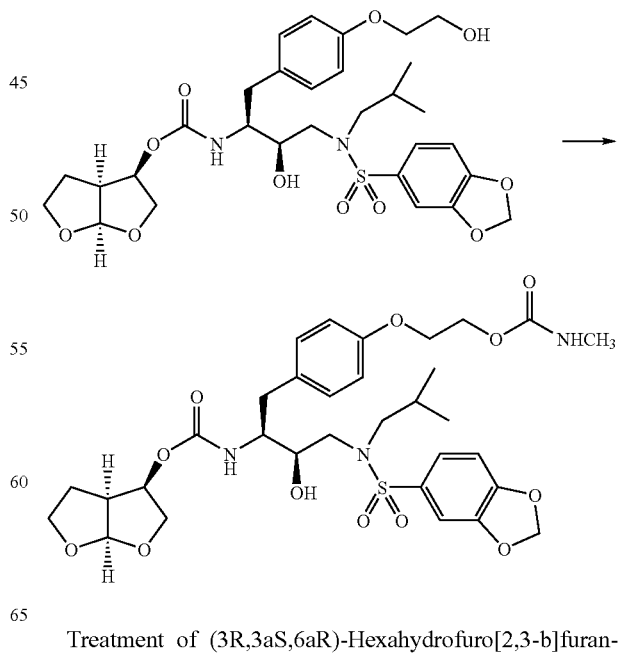

Treatment of (3R,3aS,6aR)-Hexahydrofuro[2,3-b]furan-3-yl (1S,2R)-3-[(1,3-benzodioxol-5-ylsulfonyl) (isobutyl)

amino]-2-hydroxy-1-[4-(2-hydroxyethoxy)benzyl]propylcarbamate with methyl isocyanate in dichloromethane as described earlier afforded the title compound as a white foam in 52% yield.

$^1$H NMR (DMSO-d$_6$): δ 0.78 (6H, dd), 1.17-1.42 (2H, m), 1.92 (1H, m), 2.33 (1H, t), 2.60 (3H, d), 2.64-2.78 (3H, m), 2.88-2.98 (2H, m), 3.24-3.29 (1H, m), 3.40-3.60 (4H, m), 3.70 (1H, t), 3.78-3.82 (1H, m), 3.97-4.04 (2H, m), 4.19 (2H, t), 4.80 (1H, q), 4.99 (1H, d), 5.46 (1H, d), 6.12 (2H, d), 6.74 (2H, d), 7.02-7.28 (6H, m), 8.07 (1H, m); MS: 694 (MH$^+$)

Example 107

Step 1

2-(4-{(2S,3R)-2-({[(3R,3aS,6aR)-Hexahydrofuro[2,3-b]furan-3-yloxy]carbonyl}amino)-4-[(1,3-benzodioxol-5-ylsulfonyl)(isobutyl)amino]-3-hydroxybutyl}phenoxy)ethyl 4-methylbenzenesulfonate

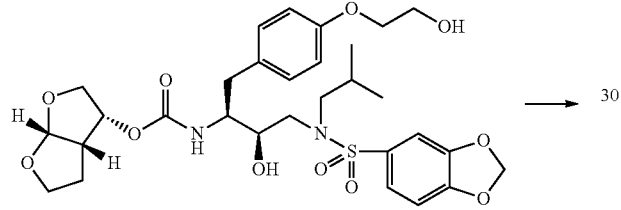

To a solution of (3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-[4-(2-hydroxyethoxy)benzyl]propylcarbamate (0.11 g, 0.18 mmol), triethyl amine (0.055 mL, 40 mg, 0.39 mmol), and 4-dimethylaminopyridine (2 mg), in dichloromethane at 0° C. was added p-toluenesulfonyl chloride (38 mg, 0.2 mmol) and the mixture was stirred at ambient temperature for 4 h. Solvent was evaporated and the residue was purified by chromatography (silica gel, dichloromethane/methanol, 98:2) to provide the title compound as a solid foam (0.105 g) $^1$H NMR (DMSO-d$_6$): δ 0.78 (3H, d), 0.82 (3H, d), 1.2 (1H, dd), 1.37 (1H, quintuplet), 1.9-2.0 (1H, m), 2.3 (1H, dd), 2.38 (3H, s), 2.6-2.8 (2H, m), 2.9 (1H, d), 2.97 (1H, dd), 3.2-3.3 (1H, m), 3.4-3.5 (1H, m), 3.5-3.6 (4H, m), 3.7 (1H, t), 3.8 (1H, dd), 4.0 (2H, d), 4.3 (2H, t), 4.8 (1H, dt), 5.0 (1H, d), 5.5 (1H, d), 6.18 (2H, s), 6.7 (2H, d), 7.0-7.1 (3H, m), 7.2 (1H, d), 7.22 (1H, s), 7.29 (1H, d), 7.4 (2H, d), 7.8 (2H, d); MS: 791 (MH$^+$)

Step 2

(3R,3aS,6aR)-Hexahydrofuro[2,3-b]furan-3-yl (1S,2R)-3-[(1,3-benzodioxol-5-ylsulfonyl)(isobutyl)amino]-2-hydroxy-1-{4-[2-(1,3-thiazolidin-3-yl)ethoxy]benzyl}propylcarbamate (324)

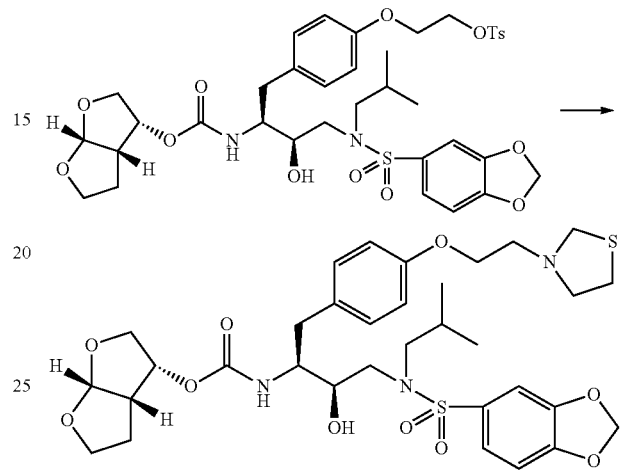

A mixture of 2-(4-{(2S,3R)-2-({[(3R,3aS,6aR)-Hexahydrofuro[2,3-b]furan-3-yloxy]carbonyl}amino)-4-[(1,3-benzodioxol-5-ylsulfonyl)(isobutyl)amino]-3-hydroxybutyl}phenoxy)ethyl 4-methylbenzenesulfonate (50 mg, 0.06 mmol), thiazolidine (0.02 mL, 0.02 g, 0.25 mmol) and dimethylsulfoxide (1 mL) was heated to 70° C. under nitrogen atmosphere for 2 h. The mixture was diluted with water and extracted with ethyl ether (2×). The organic phase was dried (sodium sulfate), evaporated, and the residue was purified by chromatography (silica gel, dichloromethane/methanol, 98:2) to provide the title compound (25 mg) as a solid foam. $^1$H NMR (DMSO-d$_6$): δ 0.78 (3H, d), 0.82 (3H, d), 1.2 (1H, dd), 1.4 (1H, quintuplet), 1.9-2.0 (1H, m), 2.3 (1H, dd), 2.6-2.8 (7H, m), 2.8-3.0 (5H, m), 3.4-3.6 (4H, m), 3.7 (1H, t), 3.8 (1H, dd), 4-0 (2H, br s), 4.05 (2H, br s), 4.8 (1H, dt), 5.0 (1H, d), 5.5 (1H, d), 6.18 (2H, s), 6.8 (2H, d), 7.0-7.1 (3H, d), 7.18 (1H, d), 7.2 (1H, s), 7.3 (1H, d); MS: 708 (MH$^+$)

Example 108

Step 1

Ethyl 2',6'-dimethylphenoxyacetate

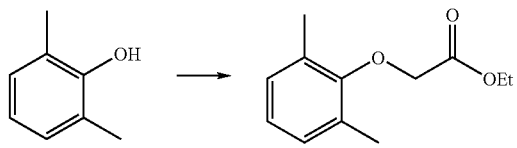

A mixture of 2,6-dimethylphenol (5.18 g, 42.4 mmol), potassium carbonate (7.33 g, 53.0 mmol) and ethyl bromoacetate (5.17 mL, 46.6 mmol) in acetone (40 mL) was stirred at ambient temperature for 24 hours. The reaction was filtered and the filtered solid was rinsed with acetone. The filtrate was concentrated in vacuo, taken up in ethyl acetate (100 mL), washed with 0.1N sodium hydroxide (3×60 mL), dried (magnesium sulfate) and concentrated in vacuo to afford the crude title compound (8.79 g, quant.) as a pale yellow liquid. $^1$H NMR (DMSO-d$_6$): 1.17 (3H, t), 2.18 (6H, s), 4.14 (2H, q), 4.40 (2H, s), 6.86-6.98 (3H, m)

Step 2

2',6'-Dimethylphenoxyacetic Acid

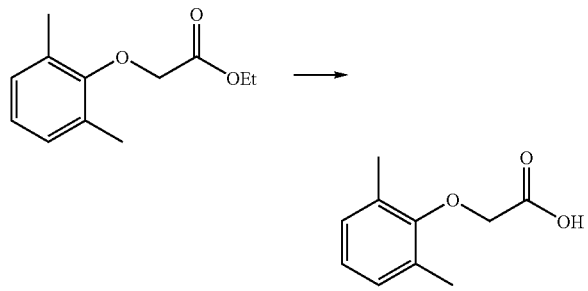

To an ice cold solution of ethyl 2',6'-dimethylphenoxyacetate (8.79 g, 42.4 mmol) in tetrahydrofuran/water (120 mL, 3:1) was added lithium hydroxide monohydrate (3.55 g, 84.8 mmol). After stirring for 3 hours at 5° C., the tetrahydrofuran was removed in vacuo and the residual aqueous was diluted with water (70 mL) and extracted with ether (60 ml). The aqueous was then cooled in an ice bath and acidified to ~pH 2 with 1N hydrochloric acid. The resulting precipitate was extracted into ethyl acetate (150 mL), washed with water (50 mL), dried (magnesium sulfate) and concentrated in vacuo to afford the title compound (6.76 g, 88%) as a white solid. $^1$H NMR (CDCl$_3$): δ 2.28 (6H, s), 4.46 (2H, s), 6.93-7.01 (3H, m), 10.25 (1H, broad)

Step 3

N-{(1S,2R)-3-[(1,3-Benzodioxol-5-ylsulfonyl)(isobutyl)amino]-1-[4-(benzyloxy)benzyl]-2-hydroxypropyl}-2-(2,6-dimethylphenoxy)acetamide (325)

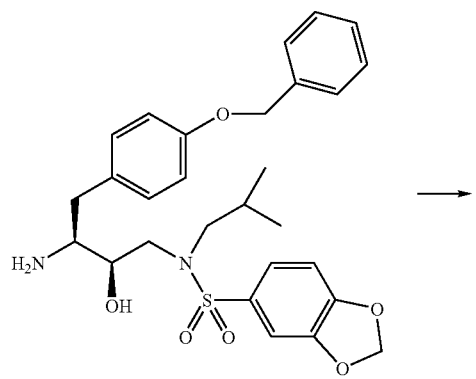

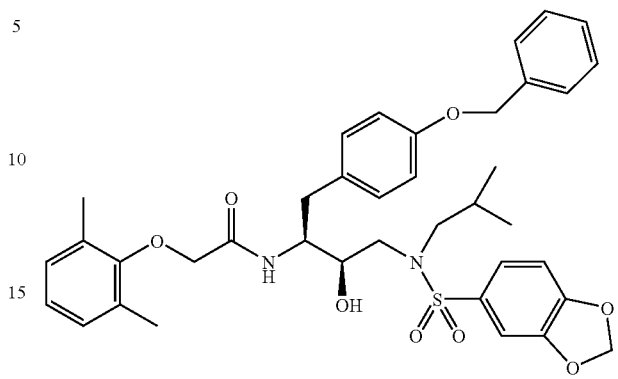

To a stirred solution of N-{(2R,3S)-3-amino-4-[4-(benzyloxy)phenyl]-2-hydroxybutyl}-N-isobutyl-1,3-benzodioxole-5-sulfonamide (360 mg, 0.68 mmol), 2',6'-dimethylphenoxyacetic acid (160 mg, 0.89 mmol) and N,N-diisopropylethylamine (0.47 mL, 2.7 mmol) in acetonitrile (7 mL) was added O-benzotriazol-1-yl-N,N,N',N'-tetramethyluronium hexafluorophosphate (390 mg, 1.0 mmol). After stirring at ambient temperature for 1.5 h, the reaction was concentrated in vacuo, taken up in ethyl acetate (60 mL), washed with 0.1N sodium hydroxide (3×50 mL) followed by brine (40 mL), dried (magnesium sulfate) and concentrated. The residue was purified by silica gel chromatography (60:40; hexane:ethyl acetate) to afford the title compound (450 mg, 95%) as a white foam. $^1$H NMR (DMSO-d$_6$): δ 0.78 (6H, dd), 1.94 (1H, m), 2.09 (6H, s), 2.63 (1H, dd), 2.72 (1H, dd), 2.83 (1H, dd), 2.93-3.02 (2H, m), 3.28-3.35 (1H, m), 3.64-3.72 (1H, m), 3.88 (1H, d), 3.89-3.96 (1H, m), 4.06 (1H, d), 5.01 (2H, s), 5.07 (1H, d), 6.11 (2H, s), 6.82-7.12 (8H, m), 7.25-7.40 (7H, m), 7.86 (1H, d); MS: 689 (MH$^+$); $C_{38}H_{44}N_2O_8S$.

Example 109

Ethyl (4-{(2S,3R)-2-({[(3R,3aS,6aR)-hexahydrofuro[2,3-b]furan-3-yloxy]carbonyl}amino)-4-[(1,3-benzodioxol-5-ylsulfonyl)(isobutyl)amino]-3-hydroxybutyl}phenoxy) acetate (326)

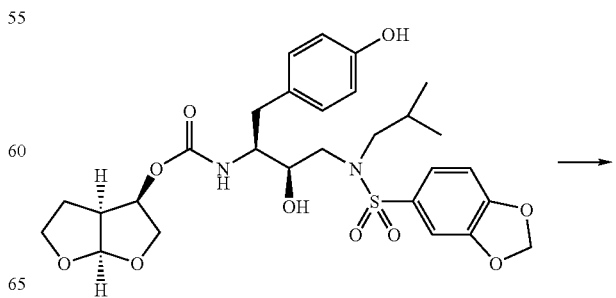

-continued

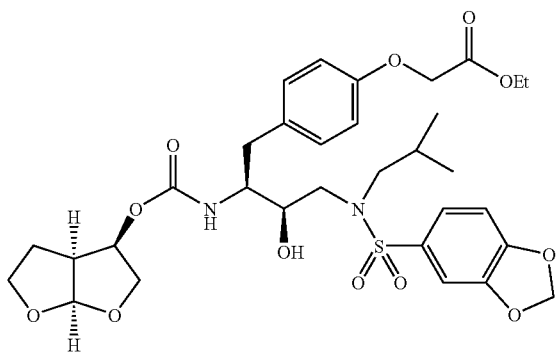

To a stirred mixture of (3R,3aS,6aR)-hexahydrofuro[2,3-b]furan-3-yl (1S,2R)-3-[(1,3-benzodioxol-5-ylsulfonyl)(isobutyl)amino]-2-hydroxy-1-(4-hydroxybenzyl)propylcarbamate (200 mg, 0.34 mmol) and cesium carbonate (330 mg, 1.0 mmol) in N,N-dimethylformamide (5 mL) was added ethyl bromoacetate (75 μL, 0.67 mmol). After stirring at ambient temperature for 2 h, the reaction was diluted with ethyl acetate (50 mL), washed with water (3×40 mL), dried (magnesium sulfate) and concentrated in vacuo. The residue was purified by silica gel chromatography (60:40; ethyl acetate:hexane) to afford the title compound (162 mg, 71%) as a white foam. $^1$H NMR (DMSO-$d_6$): δ 0.78 (6H, dd), 1.16 (3H, t), 1.17-1.43 (2H, m), 1.92 (1H, m), 2.35 (1H, t), 2.64-2.78 (5H, m), 2.88-3.01 (2H, m), 3.24-3.29 (1H, m), 3.40-3.60 (4H, m), 3.70 (1H, t), 3.78-3.82 (1H, m), 4.10 (2H, q), 4.65 (2H, s), 4.81 (1H, q), 5.00 (1H, d), 5.46 (1H, d), 6.12 (2H, s), 6.73 (2H, d), 7.02-7.07 (3H, m), 7.20-7.28 (3H, m); MS: 679 (MH$^+$)

Example 110

(4-{(2S,3R)-2-({[(3R,3aS,6aR)-Hexahydrofuro[2,3-b]furan-3-yloxy]carbonyl}amino)-4-[(1,3-benzodioxol-5-ylsulfonyl)(isobutyl)amino]-3-hydroxybutyl}phenoxy)acetic acid (327)

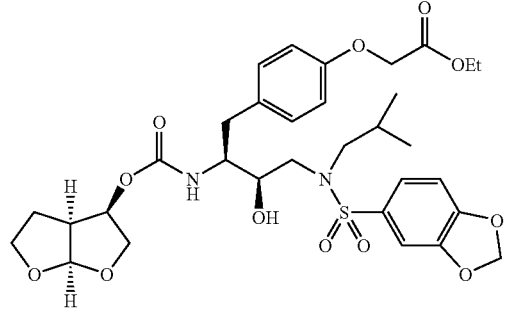

-continued

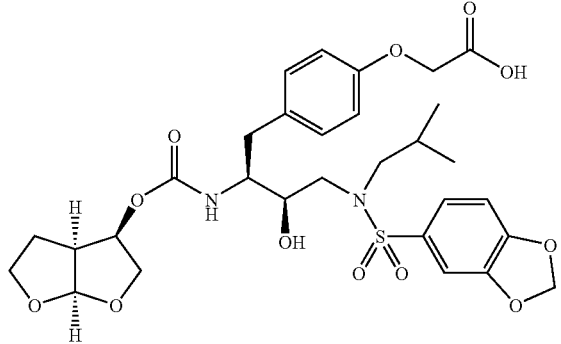

To an ice cold solution of Ethyl (4-{(2S,3R)-2-({[(3R,3aS,6aR)-hexahydrofuro[2,3-b]furan-3-yloxy]carbonyl}amino)-4-[(1,3-benzodioxol-5-ylsulfonyl)(isobutyl)amino]-3-hydroxybutyl}phenoxy) acetate (107 mg, 0.16 mmol) in tetrahydrofuran/water (4 mL, 3:1) was added lithium hydroxide monohydrate (21 mg, 0.48 mmol). The reaction was allowed to warm to ambient temperature and stir for 1 h. The tetrahydrofuran was evaporated and the residue id diluted with water (30 mL). The aqueous was then extracted with ether (30 mL), cooled in an ice bath and acidified to pH ~2 with 1.0 N hydrochloric acid. The resulting precipitate was extracted into ethyl acetate (30 mL), washed with water (20 mL), dried (magnesium sulfate) and concentrated in vacuo to a white solid. Triturated with 10% ether in hexane and filtered to afford the title compound (77 mg) as a 2:1 mixture with the compound derived from the loss of the bis-tetrahydrofuran alcohol and subsequent ring closure at the 2-hydroxy position. The mixture was confirmed by NMR, HPLC and mass spectra. Data for major product: $^1$H NMR (DMSO-$d_6$): δ 0.78 (6H, dd), 1.17-1.45 (2H, m), 1.92 (1H, m), 2.35 (1H, t), 2.64-2.78 (3H, m), 2.88-3.02 (2H, m), 3.24-3.30 (1H, m), 3.40-3.60 (4H, m), 3.70 (1H, t), 3.78-3.82 (1H, m), 4.54 (2H, s), 4.82 (1H, q), 5.00 (1H, d), 5.46 (1H, d), 6.12 (2H, s), 6.71 (2H, d), 7.00-7.30 (6H, m), 12.85 (1H, broad); MS: 651 (MH$^+$); $C_{30}H_{38}N_2O_{12}S$ (by-product MS: 521 (MH$^+$); $C_{24}H_{28}N_2O_9S$).

Example 328

Step 1

3,3-Diethoxypropan-1-yl-4'-nitrophenyl carbonate

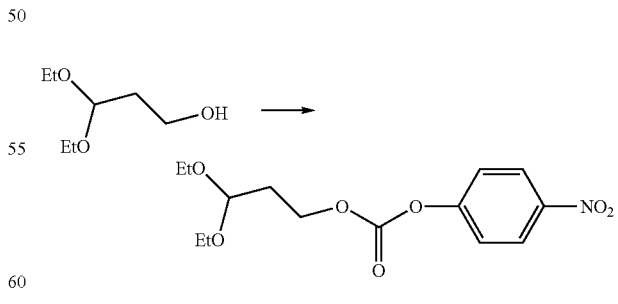

To an ice cold solution of 3,3-diethoxy-1-propanol (1.5 g, 10.1 mmol) and pyridine (1.0 mL, 12.2 mmol) in dichloromethane (30 mL) was added 4-nitrophenylchloroformate (2.24 g, 11.1 mmol). The reaction was allowed to warm to ambient temperature. After stirring for 18 h, the reaction was concentrated in vacuo, taken up in ethyl acetate (60 mL), washed with 5% aqueous citric acid (2×40 mL) followed by saturated sodium carbonate (3×40 mL), dried (magnesium sulfate) and concentrated. The residue was purified by silica gel chromatography (20% ethyl acetate in hexane) to afford the title compound (1.05 g, 33%) as an oil. $^1$H NMR (CDCl$_3$): δ 1.19 (6H, t), 2.05 (2H, q), 3.50 (2H, dq) 3.66 (2H, dq), 4.36 (2H, t), 4.66 (1H, t), 7-35 (2H, d), 8.25 (2H, d);

Step 2

3,3-Diethoxypropyl (1S,2R)-3-[(1,3-benzodioxol-5-ylsulfonyl)(isobutyl)amino]-1-[4-(benzyloxy)benzyl]-2-hydroxypropylcarbamate (328)

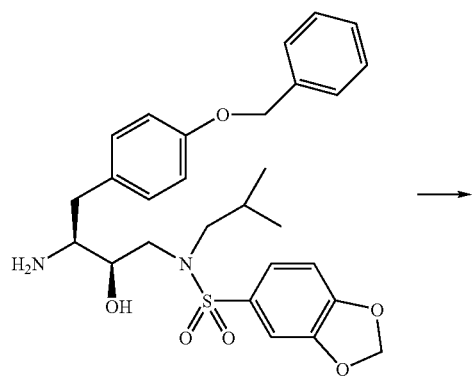

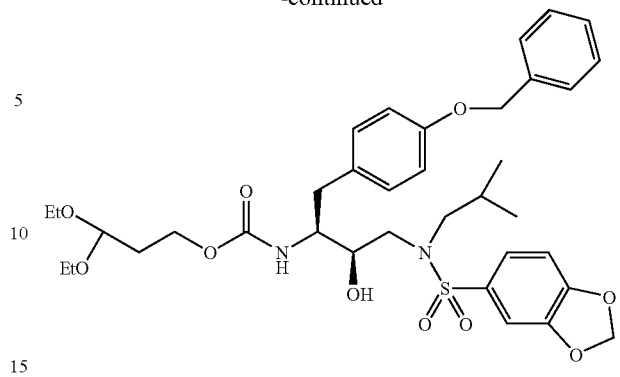

Treatment of N-{(2R,3S)-3-amino-4-[4-(benzyloxy)phenyl]-2-hydroxybutyl}-N-isobutyl-1,3-benzodioxole-5-sulfonamide with 3,3-diethoxypropan-1-yl-4'-nitrophenyl carbonate as described above provided the title compound as a white foam in 51% yield. $^1$H NMR (DMSO-d$_6$): δ 0.78 (6H, dd), 1.33 (6H, dt), 1.65 (2H, q), 1.92 (1H, m), 2.46 (1H, t), 2.69-3.02 (4H, m), 3.27-3.58 (7H, m), 3.80 (2H, t), 4.43 (1H, t), 4.94 (1H, d)-4.99 (2H, s), 6.12 (2H, s), 6.83 (2H, d), 6.97 (1H, d), 7.03 (1H, d), 7.07 (2H, d), 7.23-7.39 (7H, m); MS: 701 (MH$^+$)

Example 112

Step 1 tert-Butyl (1S,2R)-3-[(1,3-benzbdioxol-5-ylsulfonyl)(1-ethylpropoxy)amino]-1-[4-(benzyloxy)benzyl]-2-hydroxypropylcarbamate

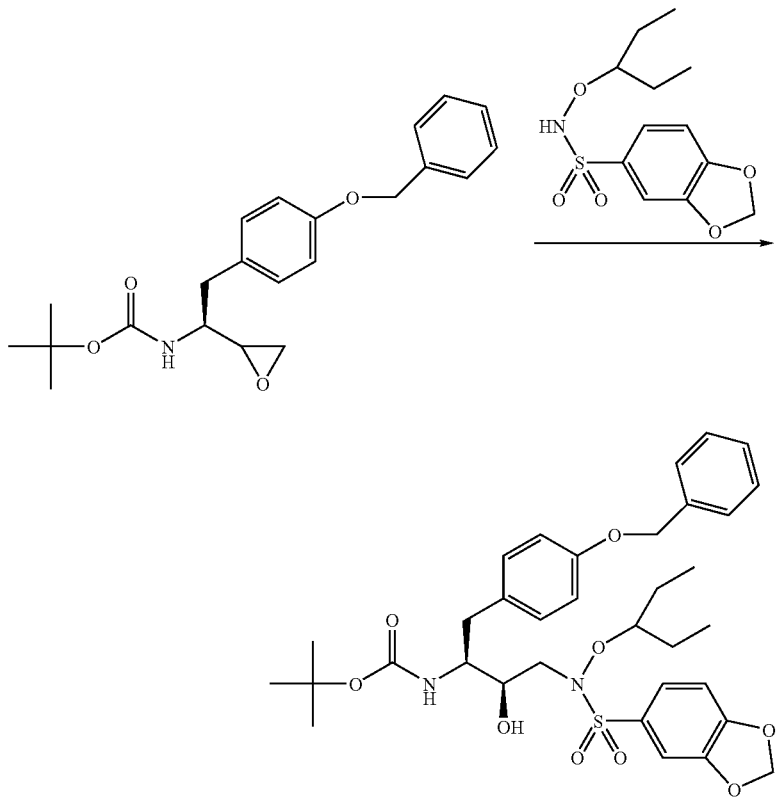

To a solution of tert-butyl (1S)-2-[4-(benzyloxy)phenyl]-1-[(2S)-oxiranyl]ethylcarbamate (2.66 g, 7.2 mmol) and the N-(1-ethylpropoxy)-1,3-benzodioxole-5-sulfonamide (2.30 g, 9.0 mmol) in tetrahydrofuran (12 mL) was added phosphazene base P4 tert-butyl solution (1.44 mL, 1.44 mmol, 1M in hexane). After stirring at ambient temperature for 18 h, the reaction was concentrated in vacuo, taken up in ethyl acetate (100 mL), washed with 0.5 N hydrochloric acid (2×40 mL) followed by water (40 mL), saturated sodium bicarbonate (40 mL) and brine (40 mL), dried (magnesium sulfate) and concentrated. The residue was purified by silica gel chromatography (20% ethyl acetate in hexane) to afford the title compound (4.25 g, 90%) as a white foam. $^1$H NMR (DMSO-$d_6$): δ 0.79 (6H, dt), 1.11-1.74 (4H, m), 1.17 (9H, s), 2.37 (1H, t), 2.60-3.02 (3H, m), 3.38-3.49 (1H, m), 3.50-3.61 (1H, m), 4.03 (1H, m), 5.00 (2H, s), 5.04 (1H, d), 6.15 (2H, s), 6.60 (1H, d), 7.03 (2H, d), 7.10 (1H, d), 7.17-7.38 (9H, m)

Step 2

N-{(2R,3S)-3-Amino-4-[4-(benzyloxy)phenyl]-2-hydroxybutyl}-N-(1-ethylpropoxy)-1,3-benzodioxole-5-sulfonamide

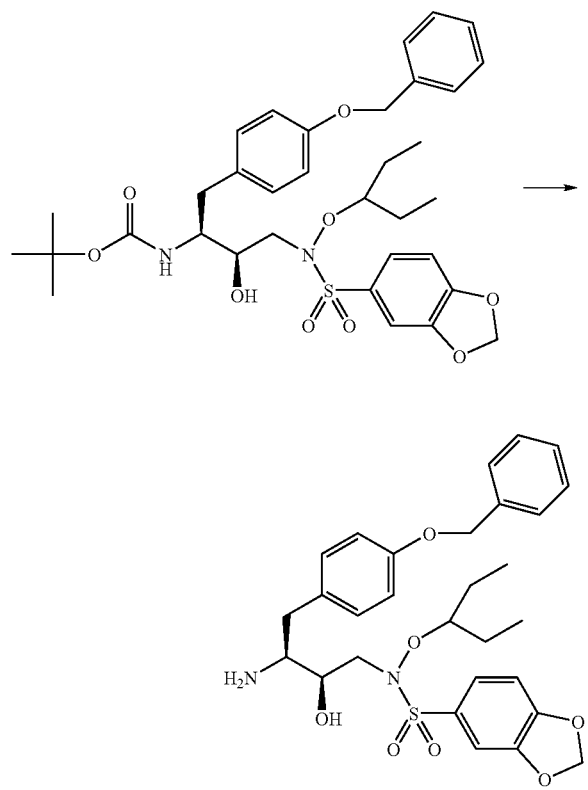

To an ice cold solution of tert-Butyl (1S,2R)-3-[(1,3-benzodioxol-5-ylsulfonyl) (1-ethylpropoxy)amino]-1-[4-(benzyloxy)benzyl]-2-hydroxypropylcarbamate (1.5 g, 2.3 mmol) in dichloromethane (15 mL) was added trifluoroacetic acid (10 mL). After stirring at 5° C. for 3 h, the reaction was concentrated in vacuo, taken up in ethyl acetate (80 mL), washed with saturated sodium bicarbonate (2×50 ml), dried (magnesium sulfate) and concentrated in vacuo to afford the title compound (1.27 g, quant.) as an off-white foam. $^1$H NMR (DMSO-$d_6$): δ 0.77 (6H, dt), 1.07-1.72 (4H, m), 1.82 (2H, br), 2.28 (1H, t), 2.58-3.05 (4H, m), 3.43-3.53 (1H, m), 3.95-4.03 (1H, m), 4.86 (1H, br s), 5.01 (2H, s), 6.16 (2H, s), 6.86 (2H, d), 7.03 (2H, d), 7.12-7.40 (8H, m);

Step 3

(3R,3aS,6aR)-Hexahydrofuro[2,3-b]furan-3-yl (1S,2R)-3-[(1,3-benzodioxol-5-ylsulfonyl)(1-ethylpropoxy)amino]-1-[4-(benzyloxy)benzyl]-2-hydroxypropylcarbamate (329)

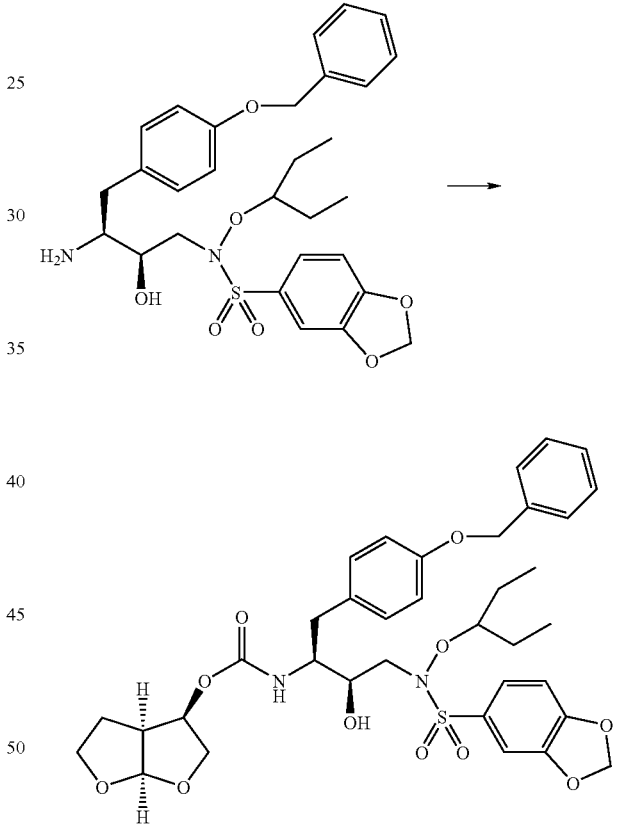

Treatment of N-{(2R,3S)-3-Amino-4-[4-(benzyloxy)phenyl]-2-hydroxybutyl}-N-(1-ethylpropoxy)-1,3-benzodioxole-5-sulfonamide with [(3R,3aS,6aR)hexahydrofuro[2,3-b]furan-3-yl][4-nitrophenyl]carbonate as described above provided the title compound as a white foam in 66% yield.

$^1$H NMR (DMSO-$d_6$): δ 0.82 (6H, t), 1.11-1.74 (6H, m), 2.32 (1H, t), 2.69-2.94 (4H, m), 3.45-3.66 (5H, m), 3.75-3.79 (1H, m), 3.99-4.03 (1H, m), 4.78 (1H, q), 5.00 (2H, s), 5.16 (1H, d), 5.46 (1H, d), 6.16 (2H, s), 6.82 (2H, d), 0.7.03 (2H, d), 7.11-7.38 (9H, m); MS: 713 (MH$^+$); $C_{36}H_{44}N_2O_{11}S$.

Example 113

1,3-Dioxan-5-yl (1S,2R)-3-[(1,3-benzodioxol-5-ylsulfonyl) (1-ethylpropoxy)amino]-1-[4-(benzyloxy)benzyl]-2-hydroxypropylcarbamate (330)

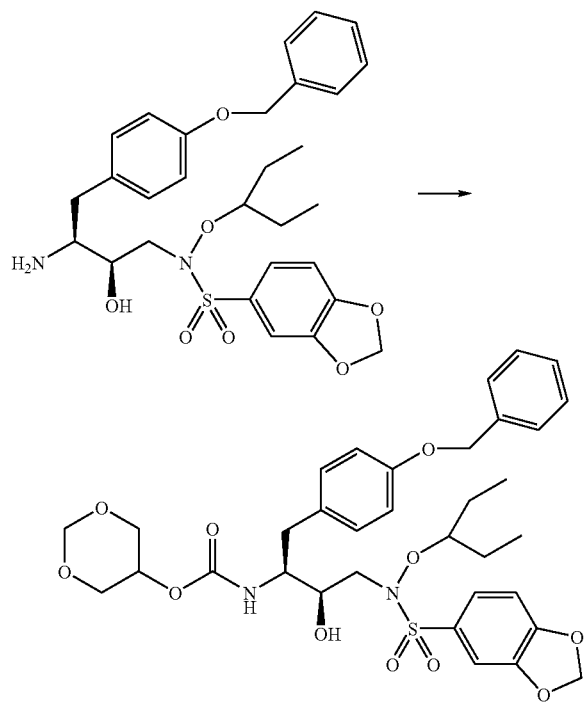

Treatment of N-{(2R,3S)-3-Amino-4-[4-(benzyloxy)phenyl]-2-hydroxybutyl}-N-(1-ethylpropoxy)-1,3-benzodioxole-5-sulfonamide with 1,3-dioxan-5-yl-4'-nitrophenyl carbonate as described earlier provided the title compound as a white foam in 65% yield. $^1$H NMR (DMSO-d$_6$): δ 0.79 (6H, dt), 1.11-1.74 (4H, m), 2.39 (1H, t), 2.60-3.00 (3H, m), 3.45-3.63 (4H, m), 3.76-3.85 (2H, m), 4.02-4.04 (1H, m), 4.25 (1H, br s), 4.66 (1H, d), 4.74 (1H, d), 4.99 (2H, s), 5.09 (1H, d), 6.16 (2H, s), 6.82 (2H, d), 7.04 (2H, d), 7.12 (1H, d), 7.26-7.39 (7H, m); MS: 687 (MH$^+$)

Example 114

(3R,3aS,6aR)-Hexahydrofuro[2,3-b]furan-3-yl (1S,2R)-3-[(1,3-benzodioxol-5-ylsulfonyl)(isobutyl)amino]-1-{4-[(dimethylamino) (imino)methoxy]benzyl}-2-hydroxypropylcarbamate (331)

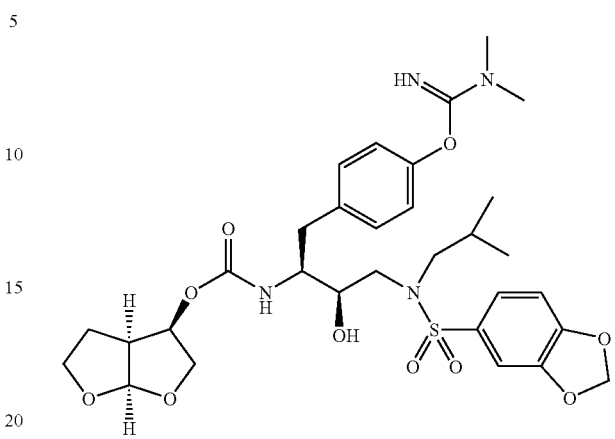

To an ice cold solution of (3R,3aS,6aR)-1-hexahydrofuro[2,3-b]furan-3-yl (1S,2R)-3-[(1,3-benzodioxol-5-ylsulfonyl)(isobutyl)amino]-2-hydroxy-1-(4-hydroxybenzyl)propylcarbamate (100 mg, 0.17 mmol) and cyanogen bromide (36 mg, 0.34 mmol) in acetone (2 mL) was added a solution of triethylamine (30 mL, 0.21 mmol) in acetone (1 mL) over 1 h. After stirring at 5° C. for an additional 2 h, the reaction was concentrated in vacuo, taken up in ethyl acetate (40 mL), washed with water (2×25 mL) followed by brine (25 my) dried (magnesium sulfate) and concentrated to afford the crude cyanate (100 mg) as an oil. The cyanate was dissolved in fresh acetone (3 m) and cooled to 5° C. Dimethylamine (3 drops, 2 M in tetrahydrofuran) was added and the reaction was stirred for 30 minutes. The acetone was evaporated and the residue was purified by silica gel chromatography (90:10:2; chloroform:methanol:ammonium hydroxide) to afford the title compound (45 mg, 40%) as a white solid.

$^1$H NMR (DMSO-d$_6$): δ 0.78 (6H, dd), 1.18-1.45 (2H, m), 1.92 (1H, m), 2.44 (1H, t), 2.65-2.78 (3H, m), 2.86-3.02 (3H, m), 2.88 (6H, s), 3.24-3.29 (1H, m), 3.47-3.61 (4H, m), 3.69 (1H, t), 3.77-3.82 (1H, m), 4.82 (1H, q), 5.05 (1H, d), 5.47 (1H, d), 6.12 (2H, s), 6.95 (2H, d), 7.03 (1H, d), 7.17-7.31 (5H, m); MS: 663 (MH$^+$)

Example 115

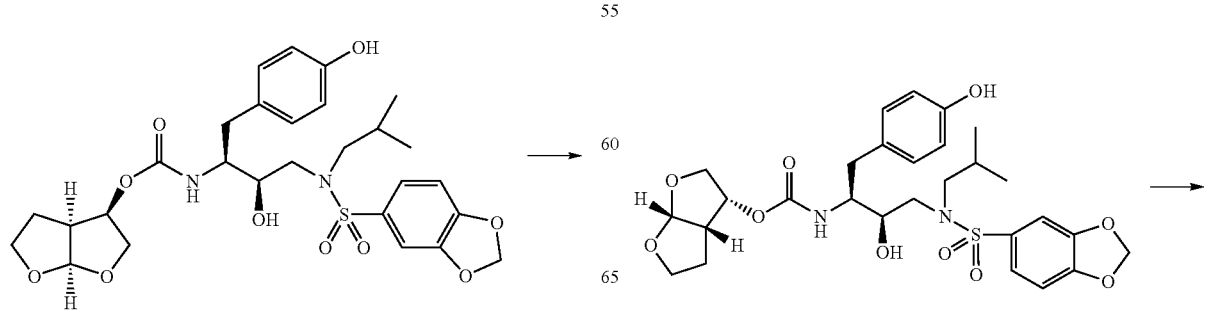

247
-continued

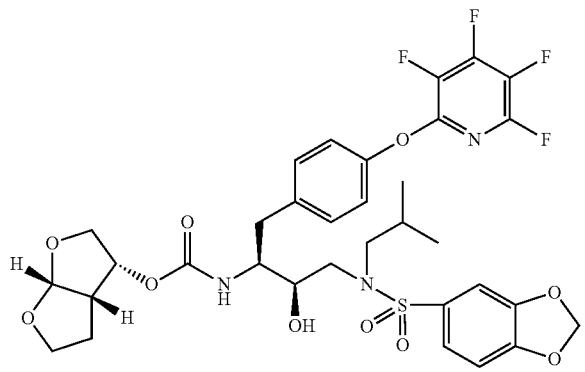

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[(3,4,5,6-tetrafluoro-2-pyridinyl)oxy]benzyl}propylcarbamate (332)

A mixture of 59 mg (0.1 mmol) of (3R,3aS,6aR)-hexahydrofuro[2,3-b]furan-3-yl (1S,2R)-3-[(1,3-benzodioxol-5-ylsulfonyl)(isobutyl)amino]-2-hydroxy-1-(4-hydroxybenzyl)propylcarbamate, 51 mg (0.3 mMol) of pertafluoropyridine and 65 mg (0.2 mMol) of cesium carbonate in 0.5 mL of dimethyl formamide was stirred at rt for 3 h. The mixture was diluted with ethyl acetate and extracted with water. Evaporation of the solvent and chromatography on silica gel (1:1 ethyl acetate/hexane) gave the title compound (32 mg) as a white foam. $^1$HNMR: 0.85 96H, dd), 1.55 (1H, m), 1.65 (1H, m), 1.8 (1H, m), 2.78 (2H, m), 2.9-3.2 (5H, m), 3.7 (3H, m), 3.8 (3H, m), 3.95 (1H, m), 4.95 (2H, m), 5.62 (1H, d), 6.04 (2H, s), 6.85 (1H, d), 6.95 (2H, d), 7.17 (1H, s), 7.2 (2H, d), 7.34 (1H, d). MS: 742(M+H)

Example 116

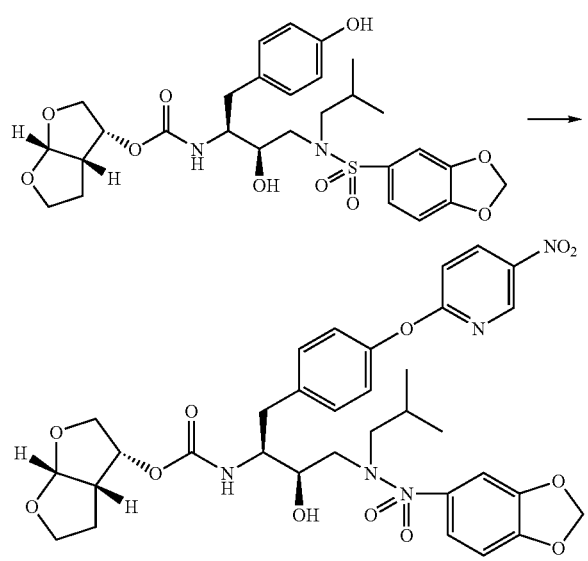

(3R,3aS,6aR)-hexahydrofuro[2,3-b]furan-3-yl (1S, 2R)-3-[(1,3-benzodioxol-5-ylsulfonyl)(isobutyl) amino]-2-hydroxy-1-{4-[(5-nitro-2-pyridinyl)oxy] benzyl}propylcarbamate (333)

A mixture of 59 mg (0.1 mmol) of (3R,3aS,6aR)-hexahydrofuro[2,3-b]furan-3-yl (1S,2R)-3-[(1,3-benzodioxol-5-ylsulfonyl)(isobutyl)amino]-2-hydroxy-1 (4-hydroxybenzyl)propylcarbamate, 42 mg (0.3 mmol) of 2-chloro-5-nitropyridine and 65 mg (0.2 mmol) of cesium carbonate in 0.5 mL of dimethyl formamide was stirred at rt for 12 h. The mixture was diluted with ethyl acetate and extracted with water. Evaporation of the solvent and chromatography on silica gel (1:1 ethyl acetate/hexane) gave the title compound (38 mg) as a white foam.

$^1$H-NMR: 0.83 (6H, dd), 1.7 (2H, m), 1.8 (2H, m), 2.8-3.2 (7H, m), 3.7 (3H, m), 3.8-4 (4H, m), 5.0 (2H, m), 5.62 (1H, d), 6.03 (2H, s), 6.85 (1H, d), 6.97 (1H, d), 7.02 (2H, d), 7.18 (1 h, s), 7.35 (2H, d), 7.4 (1H, d), 8.42 (1H, d), 8.90 (1H, d). MS: 715

Example 117

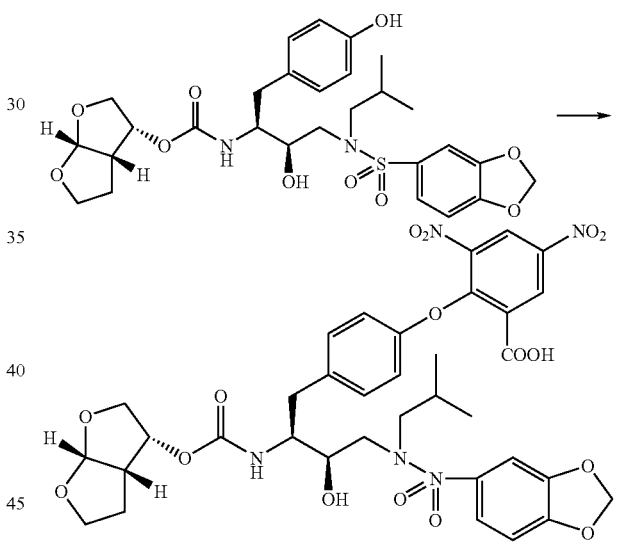

2-(4-{(2S,3R)-2-({[(3R,3aS,6aR)-hexahydrofuro[2, 3-b]furan-3-yloxy]carbonyl}amino)-4-[(1,3-benzodioxol-5-ylsulfonyl)(isobutyl)amino]-3-hydroxybutyl}phenoxy)-3,5-dinitrobenzoic Acid (334)

A mixture of 59 mg (0.1 mMol) of (3R,3aS,6aR)-hexahydrofuro[2,3-b]furan-3-yl (1S,2R)-3-[(1,3-benzodioxol-5-ylsulfonyl)(isobutyl)amino]-2-hydroxy-1-(4-hydroxybenzyl)propylcarbamate, 50 of 2-fluoro-3,5-dinitronitrobenzoic acid and 65 mg (0.2 mMol) of cesium carbonate in 0.5 mL of dimethyl formamide was stirred at rt for 2 h. The mixture was diluted with ethyl acetate and extracted with 1N HCl. Evaporation of the solvent and chromatography on silica gel (5% methanolic ammonia in dichloromethane) gave the title compound (25 mg) as a yellow foam. $^1$H NMR: 0.82 (6H, dd), 1.42 (1H, m), 1.63 (1H, m), 1.90 (2H, m), 2.46 (1H, dd), 2.8 (1H, dd), 2.82-3.02 (5H, m), 3.2 (1H, m), 3.6-3.95 (6H, m), 4.94 (1H, q), 5.58 (1H, d), 6.02 (2H, s), 6.61 (1H, d), 6.75 (2H, d), 6.82 (1H, d), 7.05 (2H, d), 7.3 (1H, d), 7.45 (1H, s), 8.6 (2H, ss).

Example 118

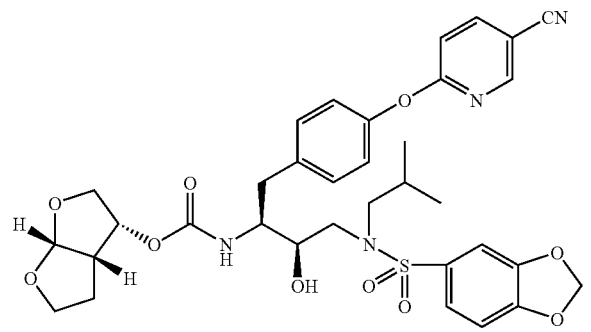 [SMILES: CC(C)CN(C[C@@H](O)[C@H](Cc1ccc(Oc2ccc(C#N)cn2)cc1)NC(=O)O[C@H]1CO[C@H]2OCC[C@H]21)S(=O)(=O)c1ccc2c(c1)OCO2]

(3R,3aS,6aR)-hexahydrofuro[2,3-b]furan-3-yl (1S,2R)-3-[(1,3-benzodioxol-5-ylsulfonyl)(isobutyl)amino]-1-{4-[(S-cyano-2-pyridinyl) oxy]benzyl}-2-hydroxypropylcarbamate (335)

A mixture of 59 mg (0.1 mMol) of (3R,3aS,6aR)-hexahydrofuro[2,3-b]furan-3-yl (1S,2R)-3-[(1,3-benzodioxol-5-ylsulfonyl) (isobutyl)amino]-2-hydroxy-1-(4-hydroxybenzyl) propylcarbamate, 120 mg of 2-chloro-5-cyanopyridine and 65 mg (0.2 mMol) of cesium carbonate in 0.5 mL of dimethyl formamide was stirred at rt for 5 h. The mixture was diluted with ethyl acetate and extracted with water. Evaporation of the solvent and chromatography on silica gel (1:1 ethyl acetate-hexanes) gave the title compound (16 mg). ¹H NMR: 0.88 (6H, dd), 1.55-1.8 (3H, m), 2.8-3.2 (7 h, m), 3.65 (2H, m), 3.8 (2H, m), 3.95 (1H, m), 5.0 (2H, m), 5.6 (1H, d), 6.05 (2H, s), 6.82 (1H, d), 6.95 (1H, d), 7.0 (2H, d), 7.1-7.4 (4H, m), 7.9 (1H, d), 8.4 (1H, bs). MS: 695(M+H)

Example 119

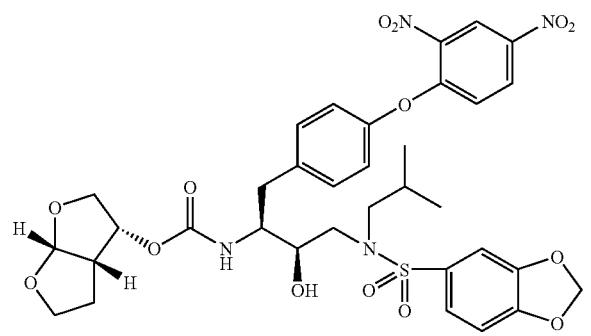 [SMILES: CC(C)CN(C[C@@H](O)[C@H](Cc1ccc(Oc2ccc([N+](=O)[O-])cc2[N+](=O)[O-])cc1)NC(=O)O[C@H]1CO[C@H]2OCC[C@H]21)S(=O)(=O)c1ccc2c(c1)OCO2]

(3R,3aS,6aR)-hexahydrofuro[2,3-b]furan-3-yl (1S,2R)-3-[(1,3-benzodioxol-5-ylsulfonyl)(isobutyl)amino]-1-[4-(2,4-dinitrophenoxy)benzyl]-2-hydroxypropylcarbamate (336)

A mixture of 100 mg (0.17 mMol) of (3R,3aS,6aR)-hexahydrofuro[2,3-b]furan-3-yl (1S,2R)-3-[(1,3-benzo-dioxol-5-ylsulfonyl)(isobutyl)amino]-2-hydroxy-1-(4-hydroxybenzyl)propylcarbamate, 24 mg of 2-chloro-5-cyanopyridine and 27 mg of triethylamine in 0.5 mL of dimethyl formamide was stirred at rt for 5 h. The mixture was diluted with ethyl acetate and extracted with 1N HCl and water. Evaporation of the solvent and chromatography on silica gel (1:1 ethyl acetate-hexanes) gave the title compound (140 mg) as a yellow solid. ¹H NMR: 0.9 (6H, dd), 1.6-1.8 (3H, m), 2.8-3.2 (9H, m), 3.7 (3H, m), 3.84 (4H, m), 5.0 (2H, m), 5.6 (1H, d), 6.05 (2H, s), 6.85 (1H, d), 6.99 (1H, d), 7.05 (2H, d), 7.25 (1H, s), 7.3 (3H, m), 8.3 (1H, dd), 9.0 (1H, d). MS: 759(M+H)

Example 120

Step 1

(3R,3aS,6aR)-hexahydrofuro[2,3-b]furan-3-yl (4S,5R)-5-{[(2,3-dihydro-1,4-benzodioxin-6-ylsulfonyl)(isobutyl)amino]methyl}-4-(4-hydroxybenzyl)-2,2-dimethyl-1,3-oxazolidine-3-carboxylate

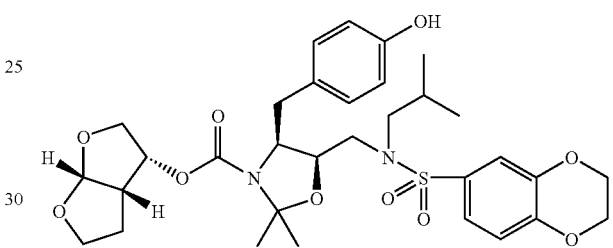

250 mg of (3R,3aS,6aR)-hexahydrofuro[2,3-b]furan-3-yl (1S,2R)-3-[(2,3-dihydro-1,4-benzodioxin-6-ylsulfonyl)(isobutyl)amino]-2-hydroxy-1-(4-benzyloxybenzyl)propylcarbamate, 2 mL of 2,2-dimethoxypropane, 0.5 g of p-toluenesulfonic acid in 50 mL of dichloromethane were refluxed for 3 h and then extracted with sodium bicarbonate solution. Chromatography on silica gel (1:1 ethylacetate/hexanes) gave 220 mg of the desired compound as an oil which was dissolved in methanol and hydrogenated (at 50 psi) over 5% palladium on carbon. Filtration and evaporation of the volatiles gave the desired title compound as an oil

Step 2

(3R,3aS,6aR)-hexahydrofuro[2,3-b]furan-3-yl (4S,5R)-5-{[(2,3-dihydro-1,4-benzodioxin-6-ylsulfonyl)(isobutyl)amino]methyl}-2,2-dimethyl-4-[4-(2-pyridinylmethoxy)benzyl]-1,3-oxazolidine-3-carboxylate

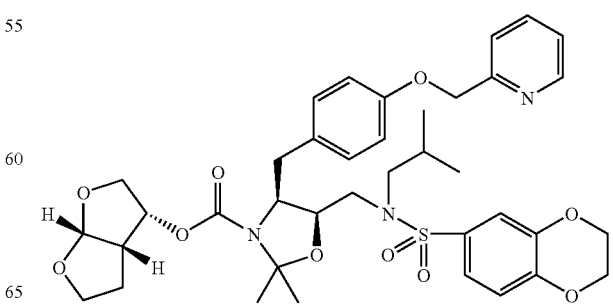

0.1 g of (3R,3aS,6aR)-hexahydrofuro[2,3-b]furan-3-yl (4S,5R)-5-{[(2,3-dihydro-1,4-benzodioxin-6-ylsulfonyl)(isobutyl)amino]methyl}-4-(4-hydroxybenzyl)-2,2-dimethyl-1,3-oxazolidine-3-carboxylate, 0.03 g of o-picolylchloride-hydrochloride and 0.15 g of cesium carbonate were suspended in 0.5 mL of dimethyl formamide and heated to 60 degrees for 3 h. The mixture was diluted with ethyl acetate and washed with water. Chromatography on silica gel (9:1 ethyl acetate/hexanes) gave 72 mg of the desired material Step 3

(3R,3aS,6aR)-hexahydrofuro[2,3-b]furan-3-yl (1S,2S)-3-[(2,3-dihydro-1,4-benzodioxin-6-ylsulfonyl)(isobutyl)amino]-2-hydroxy-1-[4-(2-pyridinylmethoxy)benzyl]propylcarbamate (337)

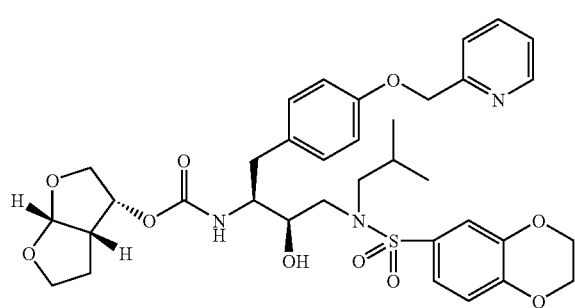 [SMILES: CC(C)CN(C[C@@H](O)[C@H](Cc1ccc(OCc2ccccn2)cc1)NC(=O)O[C@H]1CO[C@H]2OCC[C@H]21)S(=O)(=O)c1ccc2c(c1)OCCO2]

70 mg of (3R,3aS,6aR)-hexahydrofuro[2,3-b]furan-3-yl (4S,5R)-5-{[(2,3-dihydro-1,4-benzodioxin-6-ylsulfonyl)(isobutyl)amino]methy}-2,2-dimethyl-4-[4-(2-pyridinylmethoxy)benzyl]-1,3-oxazolidine-3-carboxylate were dissolved in 15 mL of isopropanol and 5 ml of concentrated hydrochloric acid. After 2 h, the reaction was treated with excess 3N sodium hydroxide and extracted with ethyl acetate. Evaporation of the solvent gave 67 mg of the desired product. $^1$H NMR: 08.3 (6H, dd), 1.4-1.8 (4H, m), 2.6-3.2 (7H, m), 3.6 (2H, m), 3.75 (2H, m), 3.9 (2H, m), 4.25 (4H, bs), 4.95 (1H, d), 5.0 (1H, m), 5.6 (1H, d), 6.9 (2H, d), 6.95 (2H, d), 7.1 (2H, d), 7.2 (2H, d), 7.45 (1H, d), 7.7 (1H, t), 8.58 (1H, d).

Example 121

(3R,3aS,6aR)-hexahydrofuro[2,3-b]furan-3-yl (1S,2R)-1-{4-[(3-cyanobenzyl)oxy]benzyl}-3-[(2,3-dihydro-1,4-benzodioxin-6-ylsulfonyl)(isobutyl)amino]-2-hydroxypropylcarbamate (338)

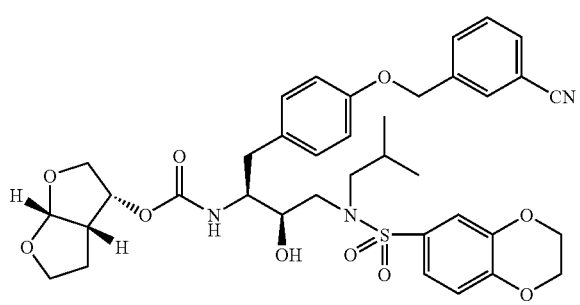 [SMILES: CC(C)CN(C[C@@H](O)[C@H](Cc1ccc(OCc2cccc(C#N)c2)cc1)NC(=O)O[C@H]1CO[C@H]2OCC[C@H]21)S(=O)(=O)c1ccc2c(c1)OCCO2]

49 mg of (3R,3aS,6aR)-hexahydrofuro[2,3-b]furan-3-yl (1S,2R)-3-[(2,3-dihydro-1,4-benzodioxin-6-ylsulfonyl)(isobutyl)amino]-2-hydroxy-1-(4-hydroxy benzyl)propylcarbamate, 20 mg of m-cyanobenzylchloride, 20 mg of cesium carbonate and 0.5 ml of dimethyl formamide were stirred at rt for 5 h. The mixture was diluted with ethyl acetate and extracted with water. Chromatography on silica gel (1:1 ethylacetate/hexane) gave the title compound as a white solid (20 mg). $^1$H NMR: 0.87 (6H, dd), 1.58 (2H, m), 1.8 (1H, m), 2.75 (2H, m), 2.9 (4H, m), 3.1 (1H, m), 3.62 (3H, m), 3.8 (3H, m), 3.95 (1H, m), 4.25 (4H, m), 4.95 (2H, m), 5.0 (2H, s), 5.62 (1H, d), 6.82 (2H, d), 6.92 (1H, d), 7.1 (2H, d), 7.2 (2H, m), 7.45 (1H, t), 7.6 (2H, m), 7.75 (1H, s). MS:722(M+H)

Example 122

4-(4-{(2S,3R)-2-({[(3R,3aS,6aR)-hexahydrofuro[2,3-b]furan-3-yloxy]carbonyl}amino)-4-[(1,3-benzodioxol-5-ylsulfonyl)(isobutyl)amino]-3-hydroxybutyl}phenoxy) butanoic acid (339)

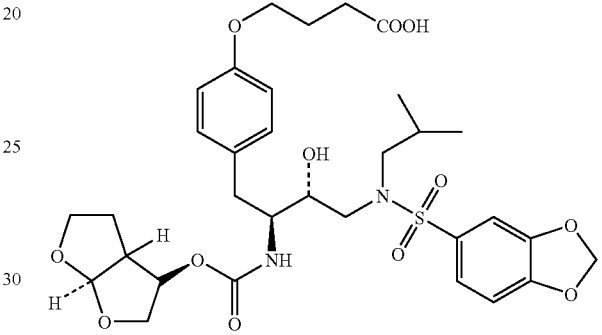

To a 0° C. solution of Methyl 4-(4-{(2S,3R)-2-({[3R,3aS,6aR)-hexahydrofuro[2,3-b]furan-3-yloxy]carbonyl}amino)-4-[(1,3-benzodioxol-5-ylsulfonyl)(isobutyl)amino]-3-hydroxybutyl}phenoxy)butanoate (0.9 g, 0.144 mmol) in 8 ml of THF-H$_2$O (3:1) was added lithium hydroxide monohydrate (30 mg, 0.715 mmol). The ice bath was removed and the reaction mixture was stirred at room temperature for 2 hours. Carefully acidified to pH 2 with 1N HCl and diluted with 50 ml of dichloromethane. The organic layer was washed with water and then dried with sodium sulfate, filtered and concentrated under reduced pressure. Residue was triturated with diethyl ether and filtered to afford 85 mg (87%) of the title compound.
$^1$H-NMR: (DMSO-d$_6$): 0.79 (3H, d), 0.83 (3H, d), 1.20-1.31 (2H, m), 1.35-1.45 (2H, m), 1.80-1.98 (3H, m), 2.30-2.41 (2H, m), 2.65-2.82 (3H, m), 2.85-3.06 (3H, m), 3.34-3.61 (4H, m), 3.70-3.76 (1H, m), 3.82-3.98 (3H, m), 4.84 (1H, q), 5.01 (1H, d), 5.51 (1H, d), 6.17 (2H, s), 6.77 (2H, d), 6.88 (1H, d), 7.01-7.18 (3H, m), 7.23 (1H, d), 12.06 (1H, br s). MS: 679 (M$^+$). C$_{32}$H$_{42}$N$_2$O$_{12}$S.

Example 123

Step 1

2,2-difluoro-1,3-benzodioxole-5-sulfonyl chloride

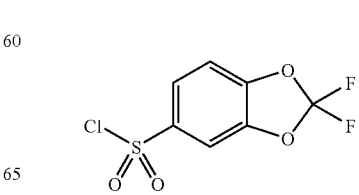

A solution of 2.37 g (10 mmol) 5-bromo-2,2-difluoro-1,3-benzodioxole in 25 ml anhydrous ether, cooled to −30° C., and 4 ml (10 mmol) n butyllithium (2.5 M in hexanes) was added at −30° C., over 10 minutes. The mixture was stirred at −30° C. for 1 hour, then sulfur dioxide gas was passed through the mixture at −20° C. for 5 minutes. The mixture then was allowed to warm up to −20° C., and the precipitate was filtered and washed with 20 ml hexane. The solid was suspended in 20 ml hexanes, 1.35 g (10 mmol) sulfuryl chloride was added, the mixture was stirred at 20° C. for 48 hours. The mixture then was filtered and the filtrate was concentrated under reduced pressure to obtain 1.6 g (62%) title compound. The product was used in the next step without further purification.

$^1$H-NMR (CDCl$_3$): δ 7.27 (1H, d), 7.74 (1H, s), 7.88 (1H, d).

Step 2 tert-butyl (1S,2R)-1-[4-(benzyloxy)benzyl]-3-[[(2,2-difluoro-1,3-benzodioxol-5-yl) sulfonyl](isobutyl)amino]-2-hydroxypropylcarbamate

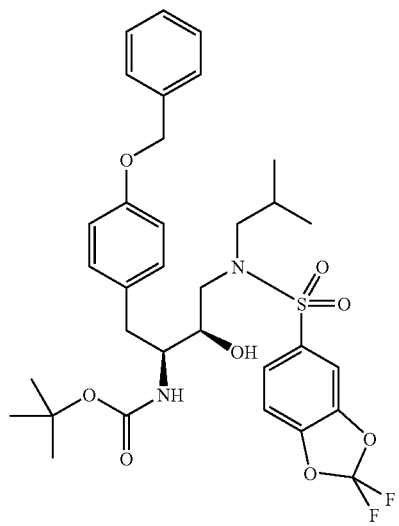 [SMILES: CC(C)CN(C[C@@H](O)[C@H](Cc1ccc(OCc2ccccc2)cc1)NC(=O)OC(C)(C)C)S(=O)(=O)c1ccc2c(c1)OC(F)(F)O2]

The sulfonamide formation was carried out as described for t-Butyl-N((S,2R)-1-(4-benzyloxy-benzyl)-3-i-butyl-[(3,4-methylenedioxyphenyl)sulfonyl]-amino-2-hydroxypropyl-carmamate. (Y=73%)

$^1$H-NMR (CDCl$_3$): δ 0.86 (3H, d), 0.88 (3H, d), 1.34 (9H, s), 1.84 (1H, m), 2.85 (4H, m), 3.09 (2H, d), 3.68 (1H, s(br)), 3.78 (2H, m), 4.57 (1H, d(br)), 5.02 (2H, s), 6.90 (2H, d), 7.13 (2H, d), 7.15-60 (8H, m).

Step 3

(3R,3aS,6aR)-hexahydrofuro[2,3-b]furan-3-yl (1S,2R)-1-[4-(benzyloxy)benzyl]-3-[[(2,2-difluoro-1,3-benzodioxol-5-yl)sulfonyl](isobutyl)amino]-2-hydroxypropylcarbamate (340)

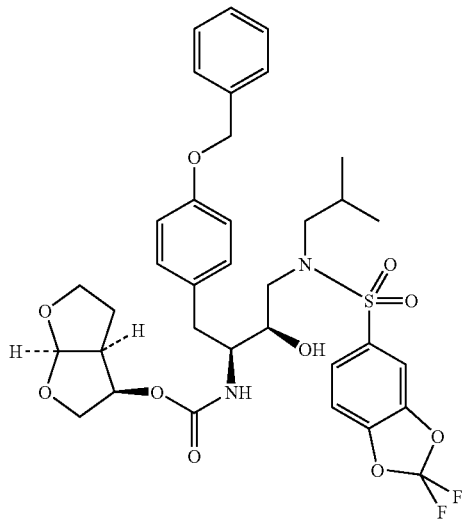 [SMILES: CC(C)CN(C[C@@H](O)[C@H](Cc1ccc(OCc2ccccc2)cc1)NC(=O)O[C@H]1CO[C@H]2OCC[C@H]21)S(=O)(=O)c1ccc2c(c1)OC(F)(F)O2]

The carbamate formation was carried out as described for (3R,3aS,6aR)-Hexahydrofuro[2,3-b]furan-3-yl-N((1S,2R)-1-(4-benzyloxy-benzyl)-3-i-butyl-[(3,4-methylenedioxyphenyl)sulfonyl-amino-2-hydroxypropyl-carmamate. (Y=48%)

$^1$H-NMR (DMSO-d$_6$): δ 0.77 (3H, d), 0.82 (3H, d), 1.20 (1H, m) 1.35 (1H, m), 1.90 (1H, m), 2.35 (1H, t), 2.70-3.00 (5H, m), 3.04 (0.1H, dd), 3.40-3.60 (4H, t), 3.66 (1H, t), 3.8.0 (1H, dd), 4.81 (1H, dd), 4.98 (1H, d), 4.99 (2H, s), 5.47 (1H, d), 6.82 (2H, d), 7.06 (2H, d), 7.18 (1H, d), 7.20-7.45 (5H, m), 7.56 (1H, d), 7.65 (1H, d), 7.81 (1H, s). MS: 719 (M+1)$^+$.

Example 124

(3R,3aS,6aR)-hexahydrofuro[2,3-b]furan-3-yl (1S,2R)-3-[[(2,2-difluoro-1,3-benzodioxol-5-yl)sulfonyl](isobutyl)amino]-2-hydroxy-1-(4-hydroxybenzyl)propylcarbamate (341)

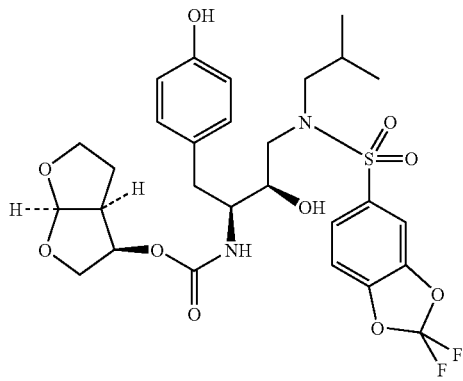 [SMILES: CC(C)CN(C[C@@H](O)[C@H](Cc1ccc(O)cc1)NC(=O)O[C@H]1CO[C@H]2OCC[C@H]21)S(=O)(=O)c1ccc2c(c1)OC(F)(F)O2]

The debenzylation was carried out as described for N-(3R,3aS,6aR)-Hexahydrofuro[2,3-b]furan-3-yl-oxycarbonyl-,(4S,5R)-4-(4-hydroxybenzyl)-5-i-butyl-[(3,4-methylenedioxyphenyl)sulfonyl]-aminomethyl-2,2-dimethyl-oxazolidine. (Y=100%)

¹H-NMR (DMSO-d₆): δ 0.77 (3H, d), 0.82 (3H, d), 1.25 (1H, m) 1.40 (1H, m), 1.92 (1H, m), 2.30 (1H, t), 2.70-3.00 (5H, m), 3.02 (1H, dd), 3.40-3.60 (4H, m), 3.70 (1H, t), 3.80 (1H, dd), 4.82 (1H, dd), 4.95 (1H, d), 5.47 (1H, d), 6.56 (2H, d), 6.92 (2H, d), 7.13 (1H, d), 7.56 (1H, d), 7.64 (1H, d), 7.81 (1H, s), 9.00 (1H, s).

Example 125

(3R,3aS,6aR)-hexahydrofuro[2,3-b]furan-3-yl (1S,2R)-1-{4-[(3-cyanobenzyl)oxy]benzyl}-3-[[(2,2-difluoro-1,3-benzodioxol-5-yl)sulfonyl](isobutyl)amino]-2-hydroxypropylcarbamate (342)

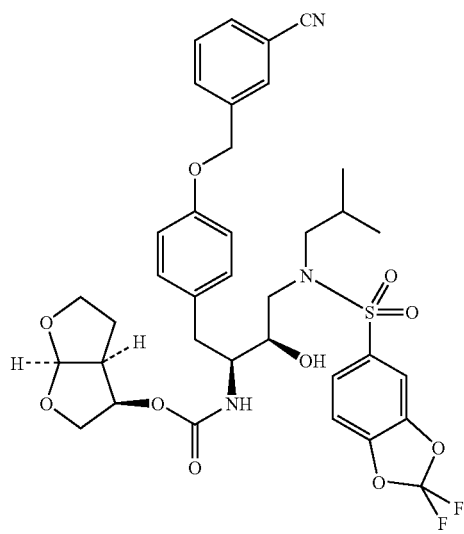 [SMILES: CC(C)CN(C[C@@H](O)[C@H](Cc1ccc(OCc2cccc(C#N)c2)cc1)NC(=O)O[C@H]1CO[C@H]2OCC[C@H]21)S(=O)(=O)c1ccc2c(c1)OC(F)(F)O2]

The alkylation step was carried out as described for N-(3R,3aS,6aR)-Hexahydrofuro[2,3-b]furan-3-yl-oxycarbonyl-,(4S,5R)-4-[4-(3-cyanobenzyloxy)-benzyl]-5-i-butyl-[(3,4-methylenedioxyphenyl)sulfonyl]-aminomethyl-2,2-dimethyl-oxazolidine. (Y=84%)

¹H-NMR (DMSO-d₆): δ 0.77 (3H, d), 0.81 (3H, d), 1.21 (1H, m), 1.32 (1H, m), 1.92 (1H, m), 2.35 (1H, t), 2.65-3.00 (5H, m), 3.05 (1H, t), 3.40-3.60 (4H, m), 3.65 (1H, t(br)), 3.80 (1H, t(br)), 4.81 (1H, d(br)), 4.99 (1H, m), 5.08 (2H, s), 5.47 (1H, d), 6.84 (2H, d), 7.07 (2H, d), 7.19 (1H, d), 7.50-7.90 (0.7H, m). MS: 744 (M+1)⁺.

Example 126

Step 1

4-(chlorosulfonyl)-2-methylphenyl Acetate

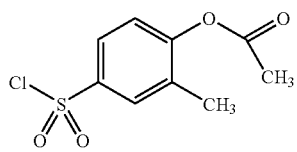

21 g (205 mmol) acetic anhydride was added to a stirred mixture of 18.8 g (100 mmol) 3-methyl, 4-hydroxy sulfonic acid in 100 ml dichloromethane. The mixture was stirred for 12 hours, then the solvent was removed under reduced pressure. The residue was dissolved in 100 ml ether, and 75 g (364 mmol) phosphorus pentachloride was added to the stirred solution in small portions. After the addition, the mixture was stirred for 15 minutes at 20° C., then poured into 500 g crushed ice. An additional 200 ml ether was added, and the organic phase was separated, extracted with cold water, then dried over anhydrous magnesium sulfate. The solvent was removed under reduced pressure, 150 ml ether and 150 ml hexane was added, and the solid was filtered. The filtrate was concentrated under reduced pressure again, then hexane (neat) was added, and the mixture was cooled to 0° C. The solid was filtered, washed with cold hexane, and dried under reduced pressure, to yield 6.8 g (Y=275k) title compound.

¹H-NMR (CDCl₃): δ2.29 (3H, s), 2.36 (3H, s), 7.27 (1H, d), 7.88 (1H, d), 7.91 (1H, s).

Step 2

4-{[{(2R,3S)-4-[4-(benzyloxy)phenyl]-3-[(tert-butoxycarbonyl)amino]-2-hydroxybutyl}(isobutyl)amino]sulfonyl}-2-methylphenyl acetate

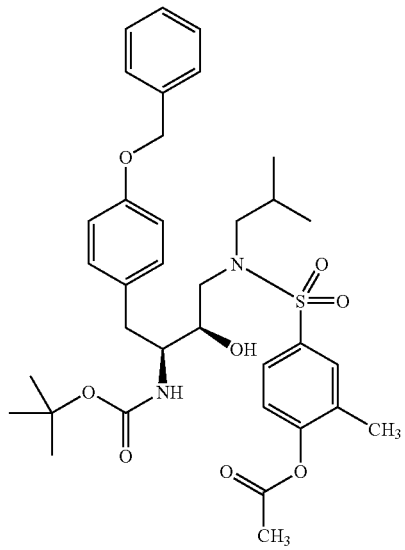 [SMILES: CC(=O)Oc1ccc(S(=O)(=O)N(CC(C)C)C[C@@H](O)[C@H](Cc2ccc(OCc3ccccc3)cc2)NC(=O)OC(C)(C)C)cc1C]

The sulfonamide formation was carried out as described for t-Butyl-N((1S,2R)-1-(4-benzyloxy-benzyl)-3-i-butyl-

[(3,4-methylenedioxyphenyl)sulfonyl]-amino-2-hydroxypropyl-carmamate. (Y=74%)

¹H NMR (CDCl₃): δ 0.85 (3H, d), 0.89 (3H, d), 1.33 (9H, s), 1.84 (1H, m), 2.23 (3H, s), 2.32 (3H, s), 2.80-3.15 (6H, m), 3.86 (1H, s(br)), 3.77 (1H, s(br)), 3.90 (1H, s), 4.59 (1H, d), 5.02 (2H, s), 6.89 (2H, d), 7.10-7.25 (8H, m), 7.59 (1H, d), 7.64 (1H, s).

Step 3

4-{[{(2R,3S)-3-({[(3R,3aS,6aR)-hexahydrofuro[2,3-b]furan-3-yloxy]carbonyl}amino)-4-[4-(benzyloxy)phenyl]-2-hydroxybutyl}(isobutyl)amino]sulfonyl}-2-methylphenyl acetate (343)

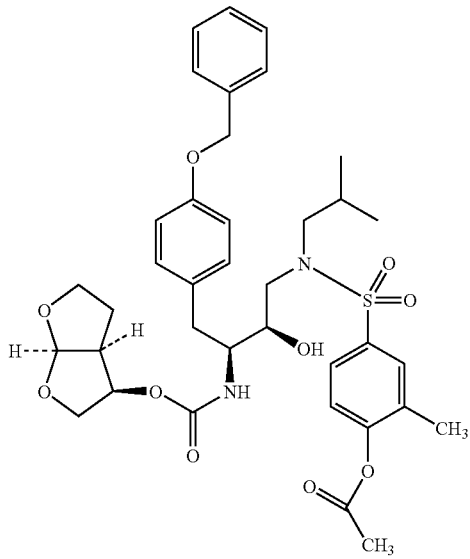 [SMILES: CC(=O)Oc1ccc(S(=O)(=O)N(CC(C)C)C[C@@H](O)[C@H](Cc2ccc(OCc3ccccc3)cc2)NC(=O)O[C@H]2CO[C@H]3OCC[C@H]32)cc1C]

The carbamate formation was carried out as described for (3R,3aS,6aR)-Hexahydrofuro[2,3-b]furan-3-yl-N((1S,2R)-1-(4-benzyloxy-benzyl)-3-i-butyl-[(3,4-methylenedioxyphenyl)sulfonyl]-amino-2-hydroxypropyl-carbamate. (Y=29%)

¹H-NMR (DMSO-d₆): δ 0.76 (3H, d), 0.81 (3H, d), 1.21 (2H, m), 1.32 (1H, m), 1.93 (1H, m), 2.16 (3H, s), 2.29 (3H, s), 2.36 (1H, t), 2.70-2.90 (3H, m), 2.93 (1H, d), 3.03 (1H, dd), 3.35 (1H, m), 3.45-3.60 (4H, m), 3.66 (1H, dd), 3.80 (1H, dd), 4.80 (1H, dd), 4.99 (3H, s), 5.46 (1H, d), 6.82 (2H, d), 7.07 (2H, d), 7.18 (1H, d), 7.22-7.42 (5H, m), 7.61 (1H, d), 7.70 (1H, s).

Example 127

(3R,3aS,6aR)-hexahydrofuro[2,3-b]furan-3-yl (1S,2R)-1-[4-(benzyloxy)benzyl]-2-hydroxy-3-[[(4-hydroxy-3-methyl phenyl)sulfonyl](isobutyl) amino] propylcarbamate (344)

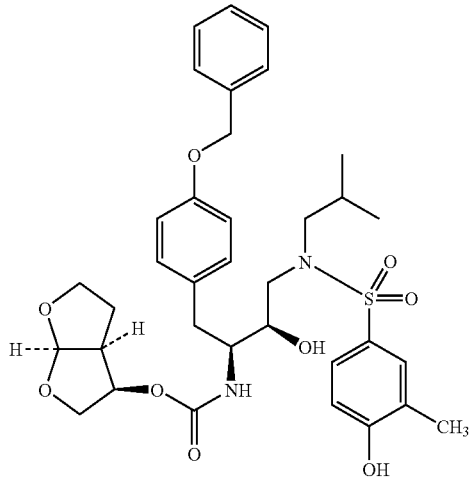 [SMILES: Cc1cc(S(=O)(=O)N(CC(C)C)C[C@@H](O)[C@H](Cc2ccc(OCc3ccccc3)cc2)NC(=O)O[C@H]2CO[C@H]3OCC[C@H]32)ccc1O]

100 mg (0.14 mmol) product from the previous procedure dissolved in 10 ml methanol. 12 mg potassium carbonate was added to the solution, and the mixture was stirred is for 30 minutes at 20° C. The solvent was removed under reduced pressure, and the residue was dissolved in dioxane. The pH was adjusted to pH=4 with hydrochloric acid (4M in dioxane), the mixture was filtered, and the filtrate was concentrated under reduced pressure. The product crystallized from hexane-ethyl acetate (1:1) at −20° C. the yield 75 mg title compound. (Y=79%).

¹H-NMR (DMSO-d₆): δ 0.75 (3H, d), 0.81 (3H, d), 1.20 (1H, m) 1.30 (1H, m), 1.90 (1H, m), 2.12 (3H, s), 2.35 (1H, t), 2.60-2.80 (3H, m), 2.85-3.00 (2H, m), 3.40-3.60 (4H, m), 3.66 (1H, dd), 3.81 (1H, dd), 4.80 (1H, d), 4.94 (1H, d), 5.00 (2H, s), 5.47 (1H, d), 6.85 (3H, m), 7.06 (2H, d), 7.18 (1H, d), 7.30-7.50 (6H, m), 10.3 (1H, s). MS: 669 (M+1)⁺.

Example 128

4-{[[(2R,3S)-3-({[(3R,3aS,6aR)-hexahydrofuro[2,3-b]furan-3-yloxy]carbonyl}amino)-2-hydroxy-4-(4-hydroyphenyl) butyl] (isobutyl)amino]sulfonyl}-2-methylphenyl acetate (345)

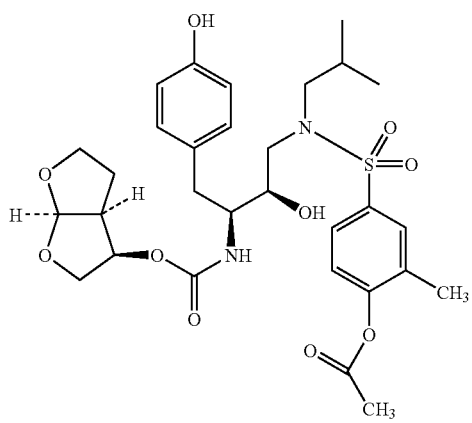 [SMILES: CC(=O)Oc1ccc(S(=O)(=O)N(CC(C)C)C[C@@H](O)[C@H](Cc2ccc(O)cc2)NC(=O)O[C@H]2CO[C@H]3OCC[C@H]32)cc1C]

The debenzylation was carried out as described for N-(3R, 3aS,6aR)-Hexahydrofuro[2,3-b]furan-3-yl-oxycarbonyl-, (4S,5R)-4-(4-hydroxybenzyl)-5-i-butyl-[(3,4-methylene-dioxyphenyl)sulfonyl]-aminomethyl-2,2-dimethyl-oxazolidine. (Y=quant.)

¹H-NMR (CDCl₃): δ 0.85 (3H, d), 0.88 (3H, d), 1.45 (1H, m), 1.62 (1H, m), 2.21 (3H, s), 2.32 (3H, s), 2.65 (1H, dd), 2.80-3.15 (6H, m), 3.60-3.70 (3H, m), 3.75-3.95 (3H, m), 5.00 (1H, m), 5.21 (1H, d), 5.60 (1H, d), 6.65 (2H, d), 6.90-7.00 (3H, m), 7.15 (1H, d), 7.56 (1H, d), 7.62 (1H, s).

Example 129

3R,3aS,6aR)-hexahydrofuro[2,3-b]furan-3-yl (1S,2R)-1-{4-[(3-cyanobenzyl)oxy]benzyl}-2-hydroxy-3-[[(4-hydroxy-3-methylphenyl)sulfonyl](isobutyl)amino]propylcarbamate (346)

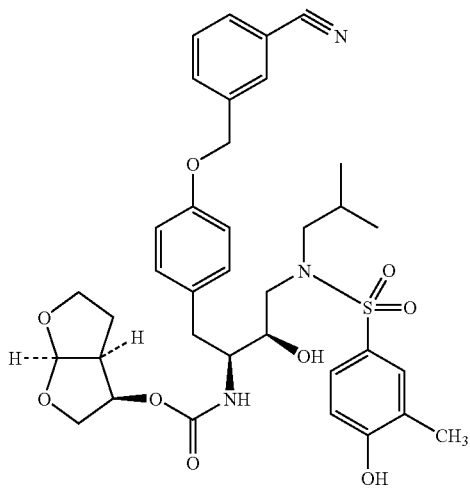 [SMILES: Cc1cc(S(=O)(=O)N(CC(C)C)C[C@@H](O)[C@H](Cc2ccc(OCc3cccc(C#N)c3)cc2)NC(=O)O[C@H]2CO[C@H]3OCC[C@H]32)ccc1O]

The alkylation step was carried out as described for N-(3R, 3aS,6aR)-Hexahydrofuro[2,3-b]furan-3-yl-oxycarbonyl-, (4S,5R)-4-[4-(3-cyanobenzyloxy)-benzyl]-5-i-butyl-[(3,4-methylenedioxyphenyl)sulfonyl]-aminomethyl-2,2-dimethyl-oxazolidine. The deacetylation step was carried out as described previously for (3R,3aS,6aR)-hexahydrofuro[2,3-b]furan-3-yl (1S,2R)-1-[4-(benzyloxy)benzyl]-2-hydroxy-3-[[(4-hydroxy-3-methylphenyl)sulfonyl](isobutyl)amino]propylcarbamate. The final product was isolated by preparative HPLC. (Column: Luna C18, Solvent: 75% to 100% MeOH/0.1% formic acid, $t_{ret}$: 4.08 min.) (Y=6%, 2 steps, overall.)

MS: 694 (M+1)

Example 130

Step 1 tert-butyl (1S)-2-{4-[(2-methyl-1,3-thiazol-4-yl)methoxy]phenyl}-1-[(2S)-oxiranyl]ethylcarbamate

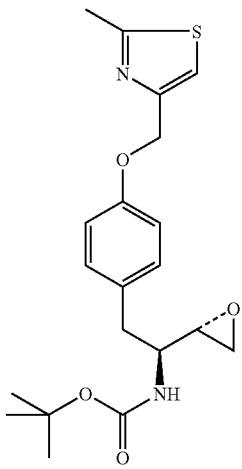

0.6 g (3.26 mmol) 4-Chloromethyl-2-methyl-thiazole hydrochloride was added to a stirred solution of 0.76 g (2.71 mmol) tert-butyl (1S)-2-(4-hydroxyphenyl)-1-[(2S)-oxiranyl]ethylcarbamate in 15 ml N,N-dimethylformamide. 3.25 g (10 mmol) cesium carbonate and 550 mg (3.66 mmol) sodium iodide was added, and the mixture was stirred at 20° C. for 24 hours. 200 ml ethyl acetate was added, and the mixture was filtered. The filtrate was extracted with water (5×50 ml), and the organic phase was dried with anhydrous magnesium sulfate, filtered and concentrated under reduced pressure. The residue was purified on silicagel column using hexane-ethyl acetate (1:1) as solvent to yield 820 mg (Y=78%) title compound.

¹H-NMR (CDCl₃): δ 1.36 (9H, s), 2.71 (3H, s), 2.75-2.95 (4H, m), 3.61 (1H, s(br)), 4.39 (1H, s(br)), 5.11 (2H, s), 6.91 (2H, d), 7.11 (2H, d), 7.12 (1H, s).

Step 2 tert-butyl (1S,2R)-2-hydroxy-3-(isobutylamino)-1-{4-[(2-methyl-1,3-thiazol-4-yl) methoxy]benzyl}propylcarbamate

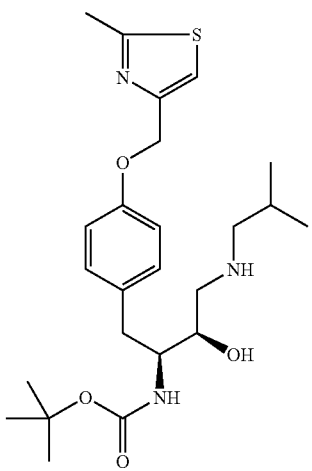 [SMILES: Cc1nc(COc2ccc(C[C@H](NC(=O)OC(C)(C)C)[C@H](O)CNCC(C)C)cc2)cs1]

The ring opening step was carried out as described previously for t-Butyl-(1S,2R)-1-(4-benzyloxy-benzyl)-3-1-butylamino-2-hydroxypropyl-carmamate. (Y=90%)

¹H NMR (CDCl₃): δ 0.94 (6H, d), 1.39 (9H, s), 1.74 (1H, m), 2.43 (2H, d), 2.70 (2H, m), 2.76 (3H, s), 2.80-3.00 (2H, m), 3.46 (1H, m), 3.79 (1H, m), 4.68 (1H, d), 5.16 (2H, s), 6.94 (2H, d), 7.17 (1H, s), 7.18 (2H, d).

Step 3

4-{[((2R,3S)-3-[(tert-butoxycarbonyl)amino]-2-hydroxy-4-{4-[(2-methyl-1,3-thiazol-4-yl)methoxy]phenyl}butyl)(isobutyl)amino]sulfonyl}-2-methylphenyl Acetate

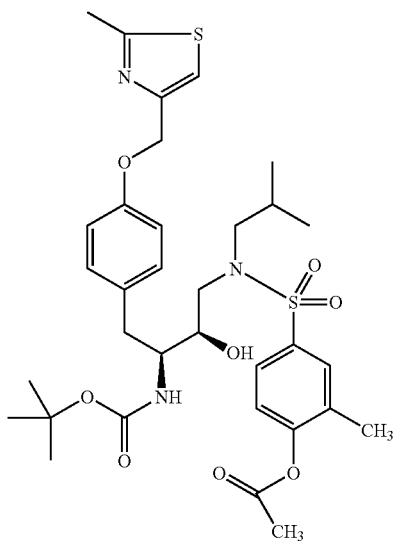 [SMILES: CC(=O)Oc1ccc(S(=O)(=O)N(CC(C)C)C[C@@H](O)[C@H](Cc2ccc(OCc3csc(C)n3)cc2)NC(=O)OC(C)(C)C)cc1C]

The sulfonamide formation was carried out as described for t-Butyl-N((1S,2R)-1-(4-benzyloxy-benzyl)-3-i-butyl-[(3,4-methylenedioxyphenyl)sulfonyl]-amino-2-hydroxypropyl-carmamate. (Y=65%)

¹H-NMR (CDCl₃): δ 0.85 (3H, d), 0.87 (3H, d), 1.33 (9H, s), 1.82 (1H, m), 2.23 (3H, s), 2.32 (3H, s), 2.71 (3H, s), 2.80-3.00 (4H, m), 3.10 (2H, m), 3.68 (1H, s(br)), 3.77 (1H, s(br)), 3.91 (1H, s), 4.57 (1H, d), 5.10 (2H, s), 6.90 (2H, d), 7.12 (1H, s), 7.13 (2H, d), 7.59 (1H, d), 7.64 (1H, s).

Step 4

4-{[((2R,3S)-3-({[(3R,3aS,6aR)-hexahydrofuro[2,3-b]furan-3-yloxy]carbonyl}amino)-2-hydroxy-4-{4-[(2-methyl-1,3-thiazol-4-yl)methoxy]phenyl}butyl)(isobutyl)amino]sulfonyl}-2-methylphenyl acetate (347)

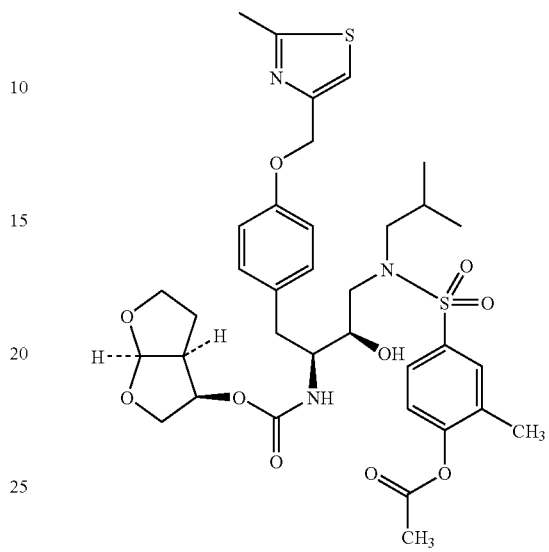

The carbamate formation was carried out as described for (3R,3aS,6aR)-Hexahydrofuro[2,3-b]furan-3-yl-N((1S,2R)-1-(4-benzyloxy-benzyl)-3-i-butyl-[(3,4 methylenedioxyphenyl)sulfonyl]-amino-2-hydroxypropyl-carmamate. (Y=44%)

¹H-NMR (DMSO-d₆): δ 0.76 (3H, d), 0.81 (3H, d), 1.34 (1H, m), 1.94 (1H, m), 2.16 (3H, s), 2.30 (3H, s), 2.36 (1H, t), 2.61 (3H, s), 2.70-3.10 (5H, m), 3.45-3.60 (3H, m), 3.68 (1H, t), 3.79 (1H, t), 4.81 (1H, m), 4.99 (3H, sm), 5.46 (1H, d), 6.84 (2H, d), 7.08 (2H, d), 7.20 (1H, d), 7.26 (1H, d), 7.48 (1H, d), 7.61 (1H, d), 7.70 (1H, s). MS: 732 (M+1)⁺.

Example 131

(3R,3aS,6aR)-hexahydrofuro[2,3-b]furan-3-yl (1S,2R)-2-hydroxy-3-[[(4-hydroxy-3-methylphenyl)sulfonyl](isobutyl) amino]-1-{4-[(2-methyl-1,3-thiazol-4-yl)methoxy]benzyl}propylcarbamate (348)

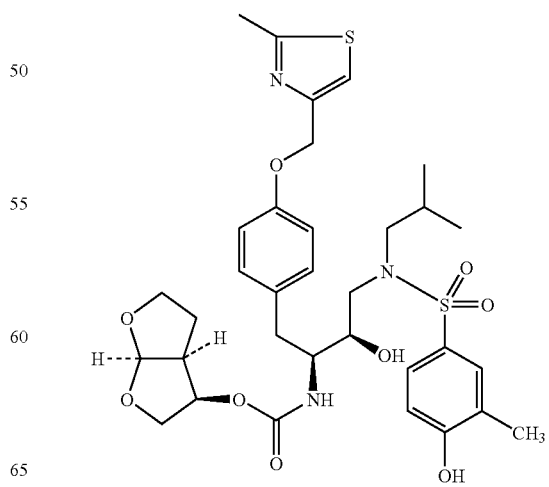

Procedure:

The deacetylation step was carried out as described previously for (3R,3aS,6aR)-hexahydrofuro[2,3-b]furan-3-yl (1S,2R)-1-[4-(benzyloxy)benzyl]-2-hydroxy-3-[[(4-hydroxy-3-methylphenyl)sulfonyl](isobutyl)amino]propylcarbamate. (Y=94%)

¹H-NMR (DMSO-d$_6$): δ 0.75 (3H, s(br)), 0.81 (3H, s(br)), 1.20 (1H, m), 1.32 (1H, m), 1.91 (1H, m), 2.12 (3H, s), 2.36 (1H, t), 2.61 (3H, s), 2.65-3.00 (5H, m), 3.40-3.60 (4H, m), 3.68 (1H, s(br)), 3.81 (1H, s(br)), 4.80 (1H, m), 4.99 (3H, s+m), 5.40 (1H, s(br)), 6.85 (4H, m), 7.07 (2H, m), 7.17 (1H, d), 7.35-7.50 (3H, m), 10.30 (1H, s). MS: 690 (M+1)⁺.

Example 132

Step 1

4-{(2S,3R)-4-[(1,3-benzodioxol-5-ylsulfonyl)(isobutyl) amino]-2-[(tert-butoxycarbonyl) amino]-3-hydroxybutyl}phenyl 1,3-benzodioxole-5-sulfonate

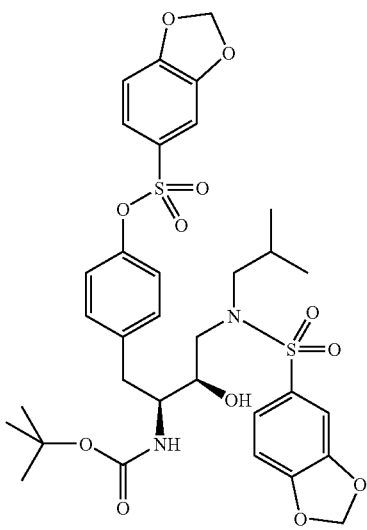 [SMILES: CC(C)CN(C[C@@H](O)[C@H](Cc1ccc(OS(=O)(=O)c2ccc3c(c2)OCO3)cc1)NC(=O)OC(C)(C)C)S(=O)(=O)c1ccc2c(c1)OCO2]

The reaction was carried as described for the synthesis of 4-((2S,3R)-2-[(tert-butoxycarbonyl)amino]-3-hydroxy-4-{isobutyl[(4-nitrophenyl)sulfonyl]amino}butyl)phenyl 4-nitrobenzenesulfonate.

¹H-NMR (CDCl$_3$): δ 0.86 (3H, d), 0.89 (3H, d), 1.33 (9H, s), 1.81 (1H, m), 2.75-3.10 (6H, m), 3.68 (1H, s(br)), 3.76 (1H, s(br)), 3.95 (1H, s), 4.60 (1H, d), 6.07 (2H, s), 6.09 (2H, s), 6.80-6.95 (4H, m), 7.10-7.35 (6H, m).

Step 2

4-{(2S,3R)-2-({[(3R,3aS,6aR)-hexahydrofuro[2,3-b]furan-3-yloxy]carbonyl}amino)-4-[(1,3-benzodioxol-5-ylsulfonyl)(isobutyl)amino]-3-hydroxybutyl}phenyl 1,3-benzodioxole-5-sulfonate (349)

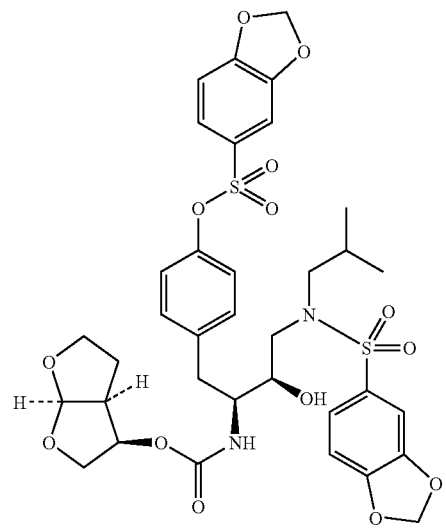 [SMILES: CC(C)CN(C[C@@H](O)[C@H](Cc1ccc(OS(=O)(=O)c2ccc3c(c2)OCO3)cc1)NC(=O)O[C@H]1CO[C@H]2OCC[C@H]21)S(=O)(=O)c1ccc2c(c1)OCO2]

The reaction was carried as described for the synthesis of 4-((2S,3R)-2-({[(3R,3aS,6aR)-hexahydrofuro[2,3-b]furan-3-yloxy]carbonyl}amino)-3-hydroxy-4 {isobutyl[(4-nitrophenyl)sulfonyl]amino}butyl)phenyl 4-nitrobenzenesulfonate.

¹H-NMR (DMSO-d$_6$): δ 0.75 (3H, d), 0.81 (3H, d), 1.20 (1H, m) 1.35 (1H, m), 1.91 (1H, m), 2.41 (1H, t), 2.60-2.80 (3H, m), 2.98 (2H, m), 3.20-3.40 (2H, m), 3.40-3.60 (4H, m), 3.66 (1H, t), 3.80 (1H, t), 4.80 (1H, dd), 5.04 (1H, s), 5.47 (1H, d), 6.13 (2H, s), 6.19 (2H, s), 6.90 (2H, d), 7.04 (2H, m), 7.10-7.40 (6H, m). MS: 777 (M+1)⁺.

Example 133

4-((2S,3R)-4-[(1,3-benzodioxol-5-ylsulfonyl)(isobutyl)amino]-2-{[(2,6-dimethylphenoxy)acetyl]amino}-3-hydroxybutyl)phenyl 1,3-benzdioxole-5-sulfonate (350)

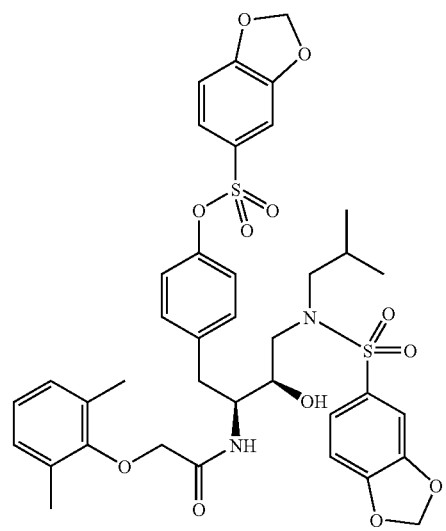 [SMILES: Cc1cccc(C)c1OCC(=O)N[C@@H](Cc1ccc(OS(=O)(=O)c2ccc3c(c2)OCO3)cc1)[C@H](O)CN(CC(C)C)S(=O)(=O)c1ccc2c(c1)OCO2]

The coupling reaction was carried as described for the synthesis of N-{(1S,2R)-3-[(1,3-benzodioxol-5-ylsulfonyl)(isobutyl)amino]-1-[4-(benzyloxy)benzyl]-2-hydroxypropyl}-2-(2,6-dimethylphenoxy)-acetamide.

¹H-NMR (DMSO-d₆): δ 0.77 (3H, d), 0.81 (3H, d), 1.94 (1H, m) 2.07 (6H, s), 2.60-2.90 (3H, m), 2.90-3.10 (2H, m), 3.68 (1H, m), 3.81 (1H, d), 3.96 (1H, m), 4.05 (1H, d), 5.10 (1H, d), 6.12 (4H, m), 6.85-7.05 (7H, m), 7.15-7.35 (6H, m), 7.93 (1H, d). MS: 783 (M+1)⁺

Example 134

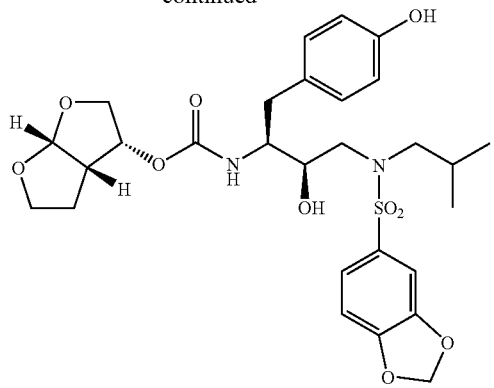

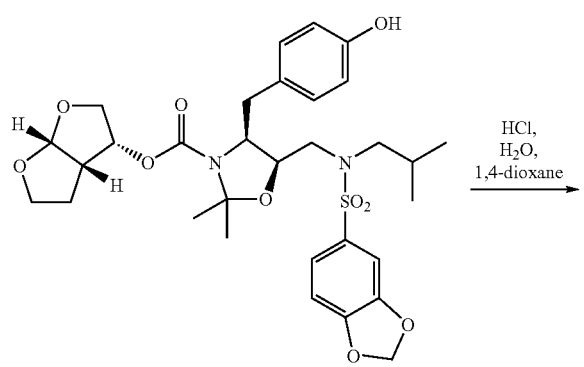

(3R,3aS,6aR)hexahydrofuro[2,3-b]furan-3-yl (1S,2R)-3-[(1,3-benzodioxol-5-ylsulfonyl)-(isobutyl)amino]-2-hydroxy-1-(4-hydroxybenzyl) propylcarbamate (351)

A solution of 0.60 g (0.95 mmol) of (3R,3aS,6aR)hexahydrofuro[2,3-b]furan-3-yl (4S,5R)-5-{[(1,3-benzodioxol-5-ylsulfonyl)(isobutyl)amino]methyl}-4-(4-hydroxybenzyl)-2,2-dimethyl-1,3-oxazolidine-3-carboxylate in 5 mL of 1,4-dioxane was treated with 0.25 mL of water followed by 5 mL of 4N HCl in 1,4-dioxane and the resulting solution was stirred at RT. After 1.5 hours the solution was diluted with 25 mL of CH₂Cl₂ and the pH adjusted to approximately 12 by addition of 1N aqueous NaOH. The mixture was diluted with water and extracted with CH₂Cl₂ (3×). The combined CH₂Cl₂ extracts were washed with aqueous brine (3×), dried over MgSO₄, and concentrated in vacuo. The residue was subjected to flash chromatography (SiO₂, 8:2 EtOAc/hexane) to afford the desired compound as a white solid in 81% yield. ¹H NMR (CDCl₃): 7.29 (dd, 1H), 7.13 (s, 1H), 7.01 (d, 2H), 6.85 (d, 2H), 6.70 (d, 2H), 6.05 (s, 2H), 5.61 (d, 1H), 5.01 (m, 2H), 3.92 (dd, 1H), 3.80 (m, 4H), 3.68 (m, 0.2H), 3.08 (dd, 1H), 2.91 (m, 5H), 2.81-2.62 (m, 2H), 1.80 (m, 1H), 1.64 (m, 1H), 1.47 (m, 1H), 0.90 (d, 3H), 0.82 (d, 3H) MS(ESI): 593(M+H).

Example 135

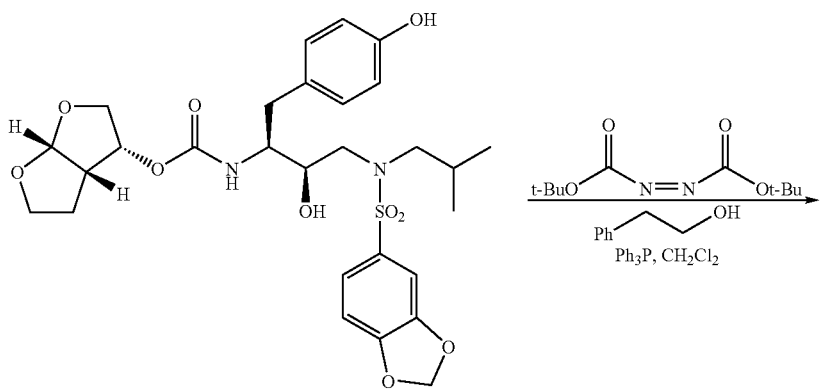

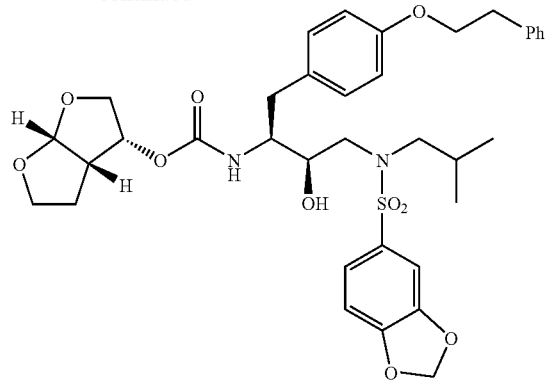

(3R,3aS,6aR)hexahydrofuro[2,3-b]furan-3-yl (1S, 2R)-3-[(1,3-benzodioxol-5-ylsulfonyl)(isobutyl) amino]-2-hydroxy-1-[4-(phenethyloxy)benzyl]propylcarbamate (352)

To a solution of 66 mg (0.25 mmol) of triphenylphosphine and 30 μL (0.25 mmol) of phenethyl alcohol in 3 mL of anhydrous CH$_2$Cl$_2$ was added 58 mg (0.25 mmol) of di-tert-butyl azodicarboxylate. The resulting solution was stirred at RT for 5 minutes and was then treated with a solution of 50 mg (0.084 mmol) of (3R,3aS,6aR)hexahydrofuro[2,3-b]furan-3-yl (1S,2R)-3-[(1,3-benzodioxol-5-ylsulfonyl)(isobutyl) amino]-2-hydroxy-1-(4-hydroxybenzyl)propylcarbamate in 2 mL of CH$_2$Cl$_2$. After stirring at RT for 1.5 hours the solution was concentrated to dryness and the residue purified by flash chromatography (SiO$_2$, 4:6 hexane/EtOAc) to give the desired product as a white foam in 72% yield. $^1$H NMR (CDCl$_3$): 7.34-7.17 (m, 6H), 7.15 (s, 1H), 7.07 (d, 2H), 6.86 (d, 1H), 6.78 (d, 2H), 6.03 (s, 2H), 5.61 (d, 1H), 4.98 (m, 1H), 4.86 (d, 1H), 4.09 (t, 2H), 3.92 (m, 1H), 3.84-3.56 (m, 6H), 3.17-3.01 (m, 3H), 3.00-2.81 (m, 4H) 2.80-2.64 (m, 2H), 1.78 (m, 1H), 1.56 (m, 1H), 1.47 (m, 1H), 0.91 (d, 3H), 0.85 (d, 3H). MS(ESI): 697(M+H).

Example 136

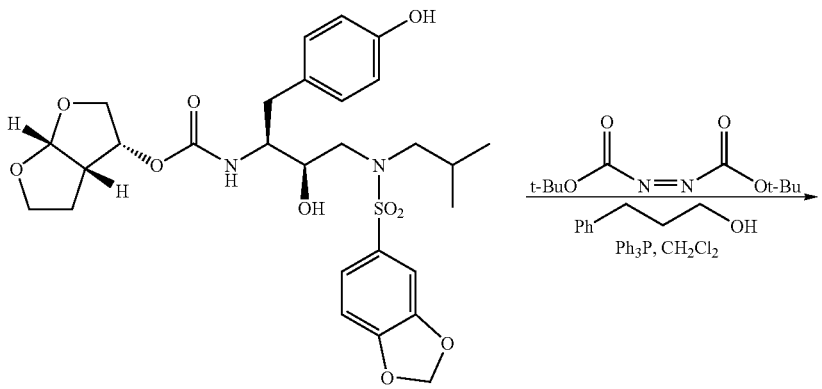

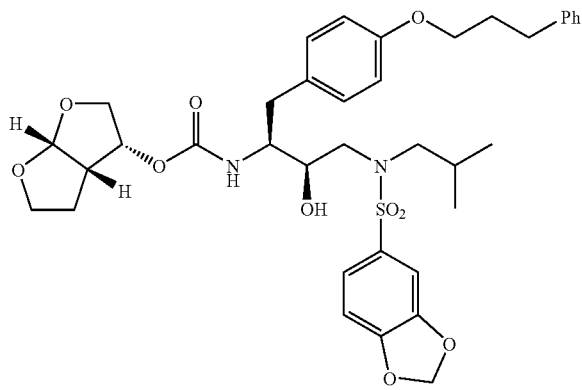

269

(3R,3aS,6aR)hexahydrofuro[2,3-b]furan-3-yl (1S, 2R)-3-[(1,3-benzodioxol-5-ylsulfonyl)(isobutyl) amino]-2-hydroxy-1-[4-([3-phenylpropyl]oxy)benzyl]propylcarbamate (353)

The title compound was prepared according to example 135 with the exception that 3-phenyl-1-propanol was used instead of phenethyl alcohol. $^1$H NMR (CDCl$_3$): 7.33-7.11 (m, 7H), 7.07 (d, 2H), 6.86 (d, 1H), 6.76 (d, 2H), 6.04 (S, 2H), 5.61 (d, 1H), 4.99 (q, 1H), 4.86 (d, 1H), 3.97-3.72 (m, 7H), 3.65 (m, 2H), 3.09 (dd, 1H), 3.01-2.81 (m, 4H), 2.80-2.64 (m, 4H), 2.06 (m, 2H), 1.85-1.40 (m, 3H), 0.91 (d, 3H), 0.84 (d, 3H). MS(ESI): 711(M+H).

Example 137

Step 1

270

(3R,3aS,6aR)hexahydrofuro[2,3-b]furan-3-yl (4S, 5R)-5-{[(1,3-benzodioxol-5-ylsulfonyl)(isobutyl)amino]methyl}-4-(4-[2-(tert-butoxycarbonylamino)ethoxy]benzyl)-2,2-dimethyl-1,3-oxazolidine-3-carboxylate

According to example 135 (with the exception that N-(tert-butoxycarbonyl)ethanolamine was used instead of phenethyl alcohol), (3R,3aS,6aR) hexahydrofuro[2,3-b]furan-3-yl (4S, 5R)-5-{[1,3-benzodioxol-5-ylsulfonyl)(isobutyl)amino]methyl}-4-(4-hydroxybenzyl)-2,2-dimethyl-1,3-oxazolidine-3-carboxylate was converted to the desired compound. MS(ESI): 798 (M+Na).

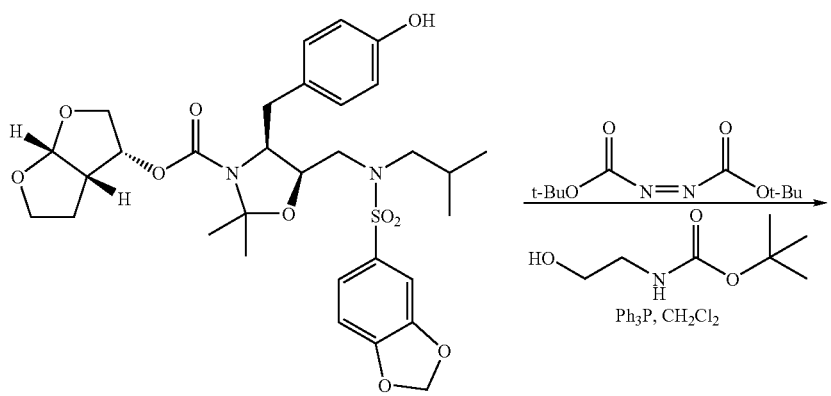

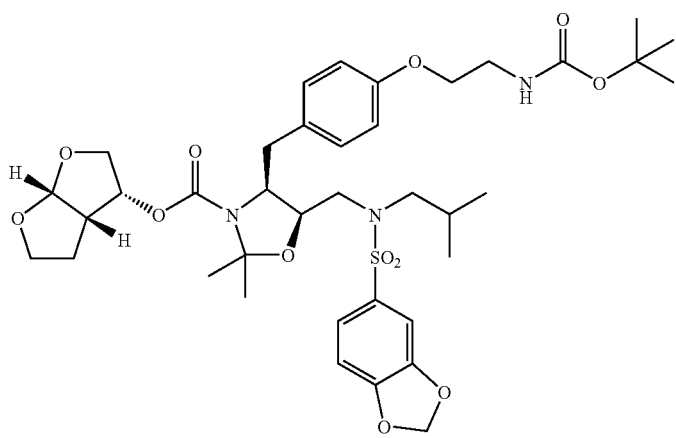

Step 2

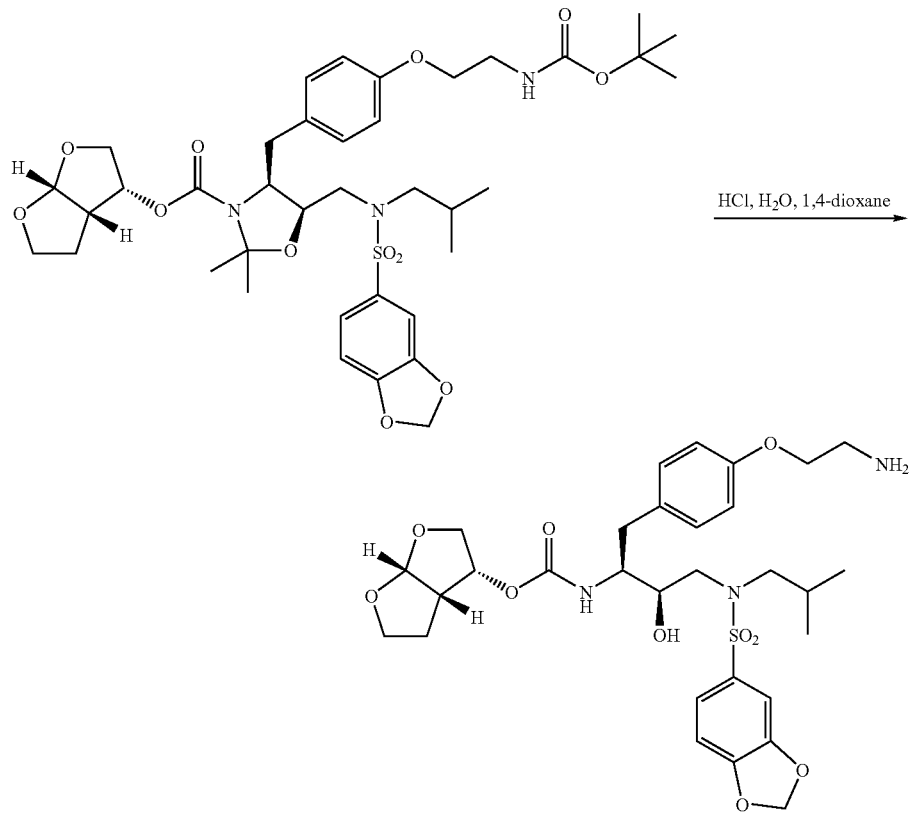

(3R,3aS,6aR)hexahydrofuro[2,3-b]furan-3-yl (1S,2R)-3-[(1,3-benzodioxol-5-ylsulfonyl)(isobutyl)amino]-2-hydroxy-1-[4-(2-aminoethoxy)benzyl]propylcarbamate (354)

The title compound was prepared according to example 134.

$^1$H NMR (CDCl$_3$): 7.39 (dd, 1H), 7.12 (s, 1H), 7.08 (d, 2H) 6.84 (d, 1H), 6.77 (d, 2H), 6.03 (s, 2H), 5.61 (d, 1H), 4.95 (m, 2H), 4.00-3.60 (m, 5H), 3.16-2.62 (m, 10H), 2.20-1.40 (m, 5H), 0.90 (d, 3H), 0.82 (d, 3H). MS(ESI): 636(M+H).

Example 138

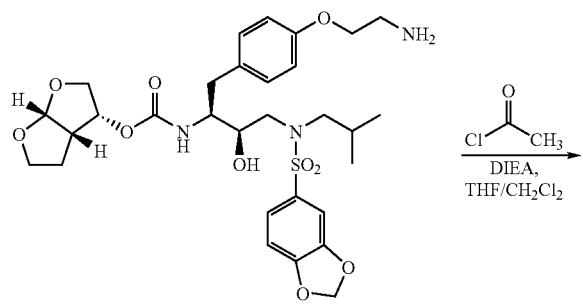

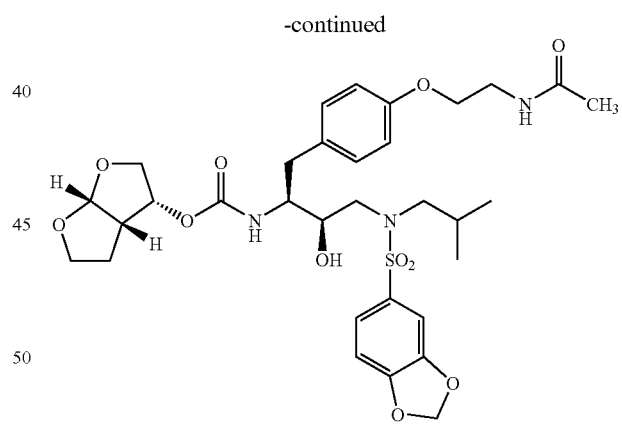

(3R,3aS,6aR)hexahydrofuro[2,3-b]furan-3-yl (1S,2R)-3-[(1,3-benzodioxol-5-ylsulfonyl)(isobutyl)amino]-2-hydroxy-1-[4-(2-[acetylamino]ethoxy)benzyl]propylcarbamate (355)

A solution of 21 mg (0.033 mmol) of (3R,3aS,6aR)hexahydrofuro[2,3-b]furan-3-yl (1S,2R)-3-[(1,3-benzodioxol-5-ylsulfonyl)(isobutyl)amino]-2-hydroxy-1-[4-(2-aminoethoxy)benzyl]propylcarbamate in 2 mL of 1:1 THF/CH$_2$Cl$_2$ was treated with 9 µL (0.050 mmol) of N,N-diisopropylethylamine followed by 2.6 µL (0.036 mmol) of acetyl chloride. The resulting solution was stirred at RT. After 1.5 hours the solution was concentrated in vacuo and the residue subjected to flash chromatography (SiO$_2$, 95:5 CH$_2$Cl$_2$/MeOH) to afford the desired compound in 86% yield as a white foam. $^1$H NMR (CDCl$_3$): 7.29 (dd, 1H), 7.16-7.04 (m, 3H), 7.05 (d, 1H), 6.76 (d, 2H), 6.05 (s, 2H), 5.91 (br s, 1H), 5.01 (d, 1H), 5.05-4.89 (m, 2H), 3.94 (m, 3H), 3.80 (m, 3H), 3.72-3.51 (m, 5H), 3.08 (dd, 1H), 3.01-2.83 (m, 44), 2.74 (m, 2H), 1.97 (s, 3H), 1.86-1.45 (m, 3H), 0.90 (d, 3H), 0.84 (d, 3H). MS(ESI): 678(M+H).

Example 139

Example 140

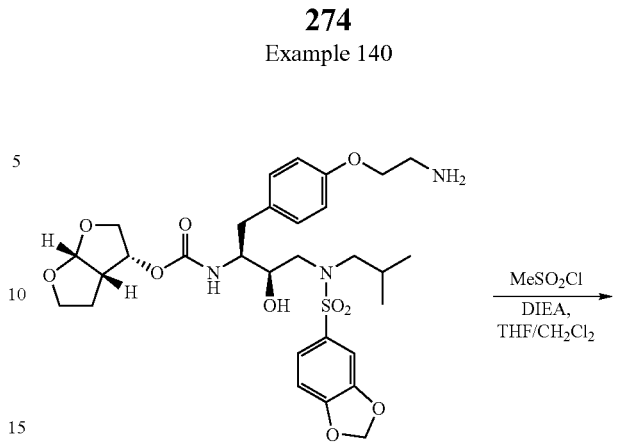

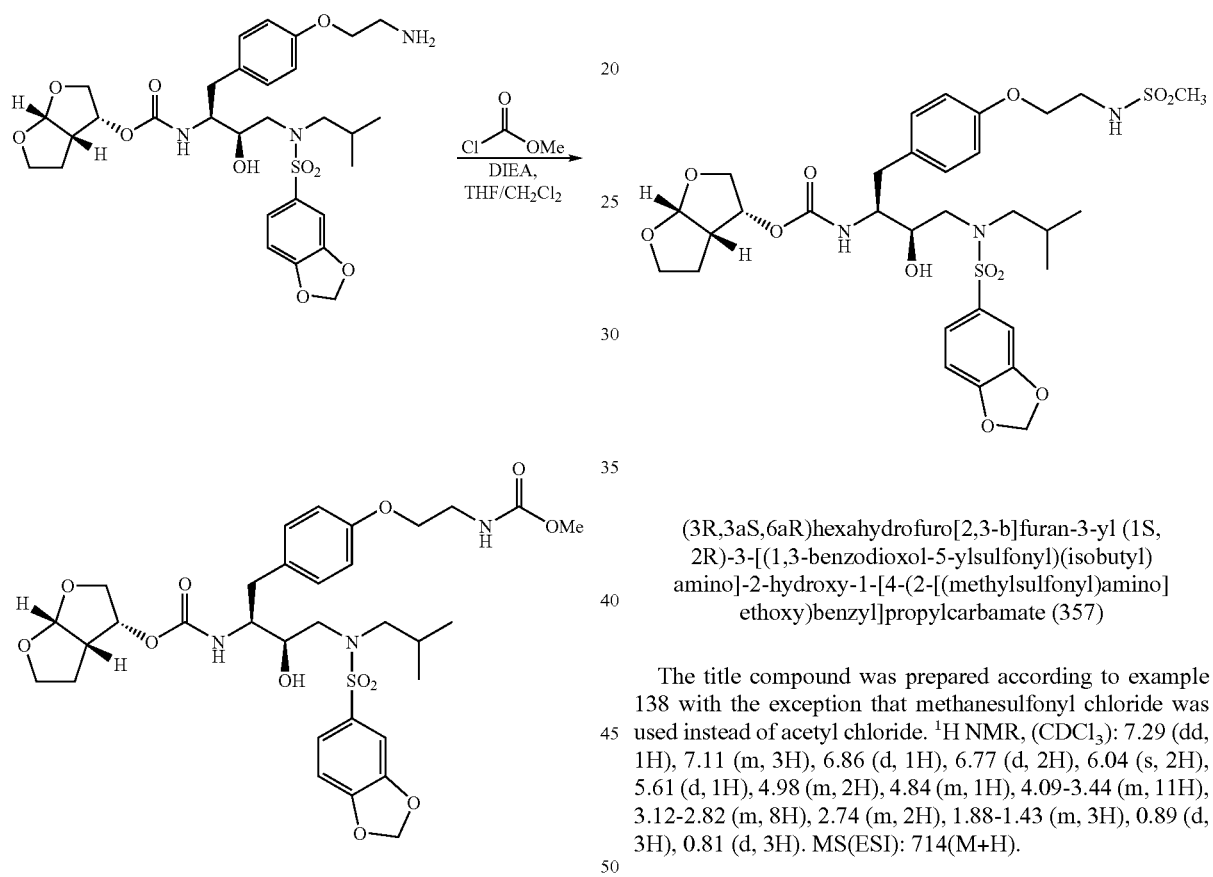

(3R,3aS,6aR)hexahydrofuro[2,3-b]furan-3-yl (1S, 2R)-3-[(1,3-benzodioxol-5-ylsulfonyl)(isobutyl)amino]-2-hydroxy-1-[4-(2-[(methylsulfonyl)amino]ethoxy)benzyl]propylcarbamate (357)

The title compound was prepared according to example 138 with the exception that methanesulfonyl chloride was used instead of acetyl chloride. $^1$H NMR, (CDCl$_3$): 7.29 (dd, 1H), 7.11 (m, 3H), 6.86 (d, 1H), 6.77 (d, 2H), 6.04 (s, 2H), 5.61 (d, 1H), 4.98 (m, 2H), 4.84 (m, 1H), 4.09-3.44 (m, 11H), 3.12-2.82 (m, 8H), 2.74 (m, 2H), 1.88-1.43 (m, 3H), 0.89 (d, 3H), 0.81 (d, 3H). MS(ESI): 714(M+H).

Example 141

(3R,3aS,6aR)hexahydrofuro[2,3-b]furan-3-yl (1S, 2R)-3-[(1,3-benzodioxol-5-ylsulfonyl)(isobutyl)amino]-2-hydroxy-1-[4-(2-[(methoxycarbonyl)amino]ethoxy)benzyl]propylcarbamate (356)

The title compound was prepared according to example 138, with the exception that methyl chloroformate was used instead of acetyl chloride. $^1$H NMR (CDCl$_3$): δ 7.29 (dd, 1H) 7.16-7.02 (m, 3H), 6.84 (d, 1H), 6.76 (d, 2H), 6.04 (s, 2H), 5.61 (d, 1H), 5.18-4.84 (m, 3H), 4.02-3.43 (m, 14H), 3.09 (m, 1H), 2.91 (m, 4H), 2.72 (m, 2H), 1.85-1.43 (m, 3H), 0.89 (d, 3H), 0.92 (d, 3H). MS(ESI): 694(M+H).

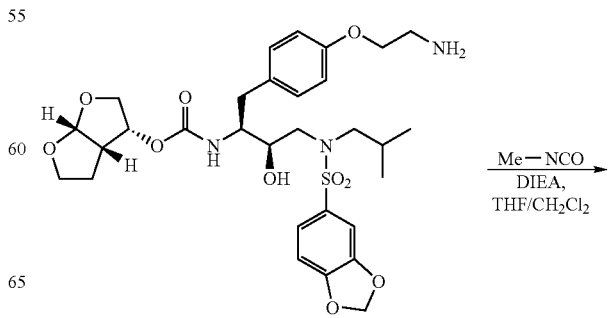

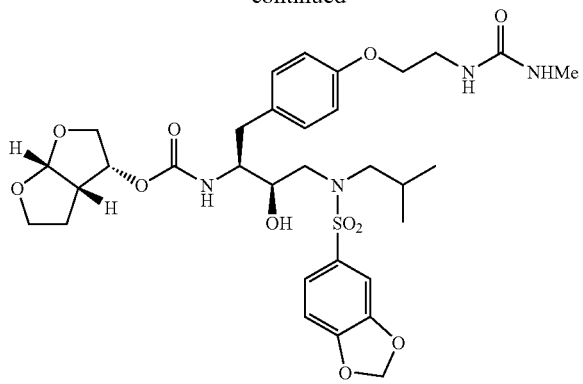

(3R,3aS,6aR)hexahydrofuro[2,3-b]furan-3-yl (1S,2R)-3-[(1,3-benzodioxol-5-ylsulfonyl)(isobutyl)amino]-2-hydroxy-1-[4-(2-[([methylamino]carbonyl) amino]ethoxy)benzyl]propylcarbamate (358)

The title compound was prepared according to example 138 with the exception that methyl isocyanate was used instead of acetyl chloride.

$^1$H NMR (CDCl$_3$): 7.29 (dd, 1H), 17.13 (s, 1H), 7.08 (d, 2H), 6.84 (d, 1H), 6.76 (d, 2H), 6.05 (s, 2H), 5.61 (d, 1H), 5.10-4.90 (m, 2H), 4.04-3.48 (m, 11H), 3.15-2.67 (m, 10H), 1.80 (m, 1H), 1.62 (m, 1H), 1.47 (m, 1H), 0.85 (m, 6H). MS(ESI): 693(M+H).

Example 142

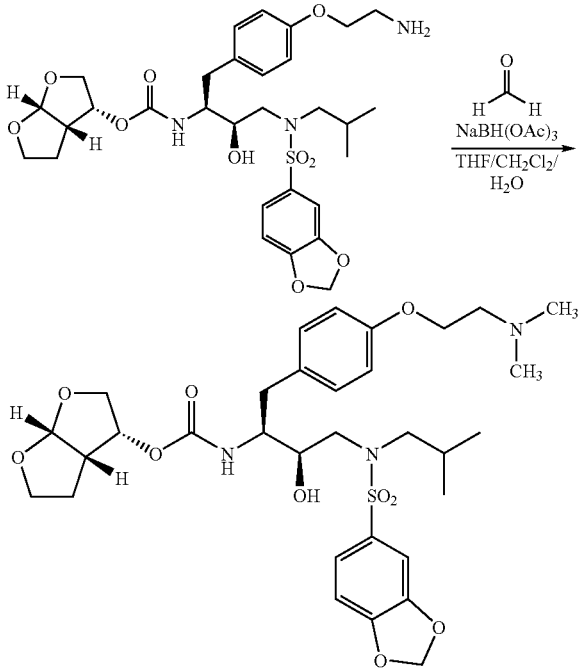

(3R,3aS,6aR)hexahydrofuro[2,3-b]furan-3-yl (1S,2R)-3-[(1,3-benzodioxol-5-ylsulfonyl)(isobutyl)amino]-2-hydroxy-1-[4-(2-[dimethylamino]ethoxy)benzyl]propylcarbamate (359)

A solution of 21 mg (0.033 mmol) of (3R,3aS,6aR)hexahydrofuro[2,3-b]furan-3-yl (1S,2R)-3-[(1,3-benzodioxol-5-yl-sulfonyl)(isobutyl)amino]-2-hydroxy-1-[4-(2-aminoethoxy)benzyl]propylcarbamate in 3 mL of 8:2 THF/CH$_2$Cl$_2$ was treated with 13 µL (0.17 mmol) of 37% aqueous formaldehyde followed by 35 mg (0.17 mmol) of NaBH(OAc)$_3$ and the resulting cloudy solution was stirred at RT. After 3 hours the solution was filtered to remove solids and the filtrate concentrated in vacuo. The residue was purified by flash chromatography (SiO$_2$, 95:5 CH$_2$Cl$_2$/2M NH$_3$ in MeOH) to give the desired compound as a white foam in 68% yield. $^1$H NMR (CDCl$_3$): 7.29 (dd, 1H), 7.13 (s, 1H), 7.07 (d, 2H), 6.85 (d, 1H), 6.80 (d, 2H), 6.03 (s, 2H), 5.61 (d, 1H), 4.98 (q, 1H), 4.89 (d, 1H), 4.01 (t, 2H), 3.92 (m, 1H), 3.80 (m, 3H), 3.66 (m, 2H), 3.09 (dd, 1H), 2.92 (m, 5H), 2.74 (m, 4H), 2.32 (s, 6H), 1.80 (m, 1H), 1.63 (m, 1H), 1.42 (m, 1H), 0.90 (d, 3H), 0.84 (d, 3H). MS(ESI): 664(M+H).

Example 143

(3R,3aS,6aR)-Hexahydro[2,3-b]furan-3-yl N-((1S, 2R)-1-benzyl-3-[6-(N'-carbonylimidazol-1-yl)amino-2,2-dimethylhexyl][(3,4-methylenedioxyphenyl) sulfonyl]amino-2-hydroxypropyl)carbamate (360)

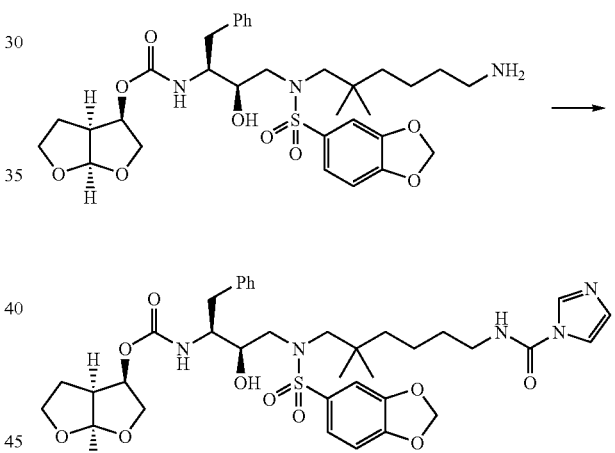

To a solution of (3R,3aS,6aR)-hexahydro[2,3-b]furan-3-yl N-((1S,2R)-1-benzyl-3-[6-amino-2,2-dimethylhexyl][(3,4-methylenedioxyphenyl)sulfonyl]amino-2-hydroxypropyl)carbamate (0.12 g, 0.19 mmol) in dichloromethane (1-5 mL) was added 1,1'-carbonyldiimidazole (0.06 g, 0.37 mmol) and the mixture was stirred for 30 min at ambient temperature. The mixture was diluted with dichloromethane and washed with 5% citric acid/water (2×), saturated sodium bicarbonate/water, dried (sodium sulfate), evaporated, and dried in vacuo to provide the title compound (0.14 g) as a solid foam; $^1$H NMR (DMSO-d$_6$): 0.90 (6H, s), 1.12 (1H, dd), 1.20-1.35 (4H, m), 1.5 (2H, br s), 2.4 (1H, t), 2.7-2.8 (2H, m), 2.9-3.0 (2H, m), 3.2 (2H, dd), 3.25-3.35 (3H, m), 3.4 (1H, quartet), 3.5-3.6 (2H, m), 3.65 (1H, t), 3.75 (1H, quartet), 3.8 (1H, dd), 4.8 (1H, quartet), 5.1 (1H, d), 5.5 (1H, d), 6.15 (2H, s), 6.98 (1H, s), 7.0 (1H, d), 7.10-7.25 (7H, m), 7.3 (1H, d), 7.6 (1H, s) 8.2 (1H, s), 8.4 (1H, t); MS: 742 (MH+); C$_{36}$H$_{47}$N$_5$O$_{10}$S.

Example 0.144

Step 1 tert-Butyl N-(1S,2R)-1-benzyl-3-amino-1-[(4-benzyloxy)benzyl]-2-hydroxypropylcarbamate

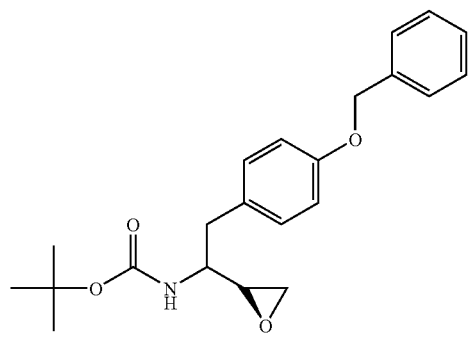

→

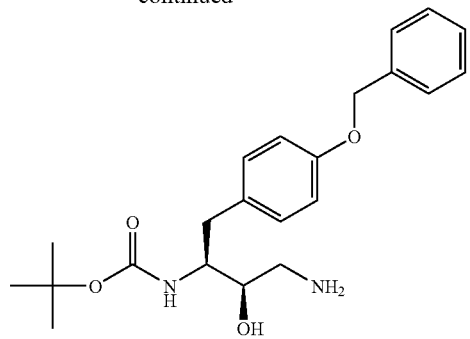

To a saturated solution of ammonia in methanol (100 mL) at 5° C. was added the epoxide (1.0 g, 2.8 mmol). Ammonia gas was continuously bubbled through the solution for an additional hour. The reaction was allowed to come to ambient temperature and stir for 48 hours. The methanol was removed in vacuo and the resulting solid was triturated with ether (50 mL), filtered and dried to afford the title compound (910 mg, 85%) as a white solid. 1H NMR (DMSO-$d_6$): 1.22 (9H, s), 1.58 (2H, br), 2.41-2.53 (3H, m), 2.89 (1H, dd), 3.15-3.19 (11H, m), 3.33-3.45 (1H, m), 4.70 (1H, br), 5.00 (2H, s), 6.58 (1H, d), 6.83 (2H, d), 7.04 (2H, d), 7.25-7.39 (5H, m)

Step 2 tert-Butyl N-(1S,2R) 1-[(4-benzyloxy)benzyl]-3-[(5-tert-butyldimethylsilyloxy-2,2-dimethyl)amino]-2-hydroxypropylcarbamate

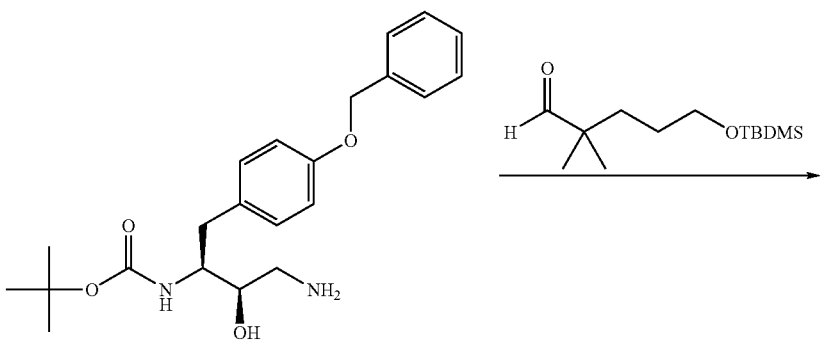

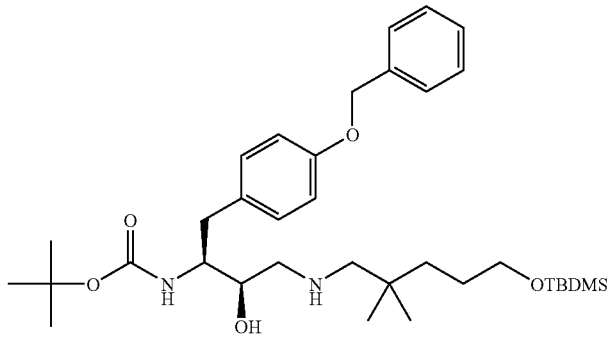

To a stirred suspension of the above amine) (5.04 g, 13.0 mmol) in N,N-dimethylformamide (35 mL), 1,2-dichloroethane (35 mL) and glacial acetic acid (0.5 mL) was added a solution of 5-tert-butyldimethylsilyloxy-2,2-dimethylpentanal (2.66 g, 10.9 mmol) in tetrahydrofuran (35 mL) over 15 minutes. Sodium triacetoxyborohydride (2.76 g, 13.0 mmol) was added and the mixture was stirred under nitrogen for 18 hours. The reaction was concentrated in vacuo to approximately ⅓ volume, added cold 2.5% sodium hydroxide (100 mL) and extracted with ethyl acetate (2×100 mL). The combined ethyl acetate was washed with water (2×50 mL), dried (magnesium sulfate) and concentrated. The residue was triturated with ether and the resulting solid (amine starting material) was filtered away. The filtrate was concentrated in vacuo to afford the desired crude product (6.80 g, 6.54 theory) as a thick paste. The material was used without further purification.

Step 3 tert-Butyl N-((1S,2R)-1-[(4-benzyloxy)benzyl]-3-(5-tert-butyldimethylsilyloxy-2,2-dimethylpentyl)[(3,4-methylenedioxyphenyl)sulfonyl]amino-2-hydroxypropyl)carbamate

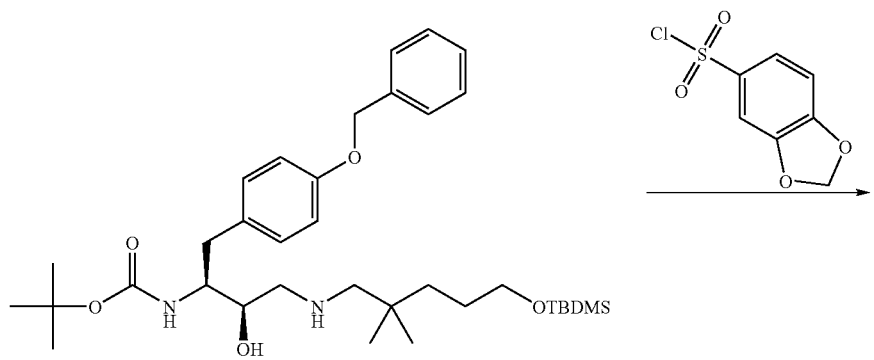

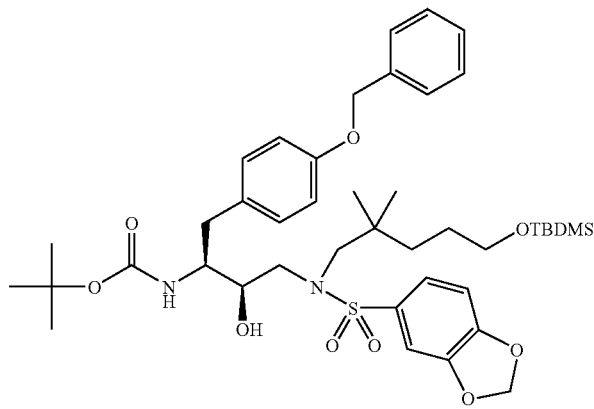

To a stirred solution of the crude amine from step 2, (6.10 g), and N,N-diisopropylethylamine (3.7 mL, 21.8 mmol) in anhydrous dichloromethane (70 mL) at 5° C. was added a solution of 3,4-methylenedioxyphenylsulfonyl chloride (2.88 g, 13.0 mmol) in dichloromethane (30 mL) over 15 minutes. The mixture was allowed to warm to ambient temperature and stir for 16 hours. The reaction was concentrated in vacuo, taken up in ethyl acetate (100 mL), washed with water (50 mL), 1N hydrochloric acid (2×50 mL), water (50 mL), saturated sodium bicarbonate (2×50 mL), dried (magnesium sulfate) and concentrated in vacuo to afford the desired crude product (8.55 g) as a white foam. The material was used without further purification.

Step 4 tert-Butyl N-((1S,2R)-1-[(4-benzyloxy)benzyl]-3-(2, 2-dimethyl-5-hydroxypentyl)[(3,4-methylenedioxyphenyl) sulfonyl]amino-2-hydroxypropyl)carbamate

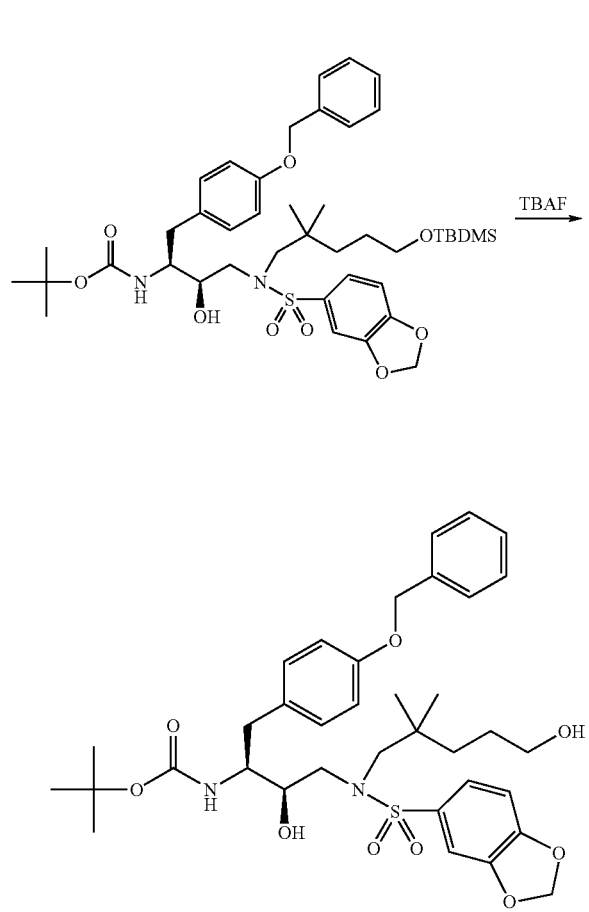

To a stirred solution of the crude product from step 3.) (8.5 g, 10.6 mmol) in tetrahydrofuran (85 mL) was added tetrabutylammonium fluoride (13.8 mL, 1M in tetrahydrofuran) over 15 minutes. After stirring for 18 hours, the reaction was concentrated in vacuo, added ether (100 mL) and washed with water (3×50 mL). The ether was dried (magnesium sulfate) and concentrated to a foam. Taken up in fresh ether (40 mL) and stirred at ambient temperature for 120 hours. The resulting precipitate was filtered, rinsed with ether/hexane (1:1, 25 mL) and dried to afford the title compound (3.2 g, 44%) as a white solid. The filtrate was concentrated to a foam (2.95 g). HPLC analysis showed approximately 65% product (not isolated) $^1$H NMR (DMSO-d$_6$): 0.86 (6H, s), 1.11-1.23 (2H, m), 1.19 (9H, s), 1.30-1.35 (2H, m), 2.37 (1H, dd), 2.77-2.82 (2H, m), 2.91-2.97 (1H, m) r 3.25-3.33 (5H, m), 3.61-3.67 (1H, m), 4.33 (1H, t), 4.89 (1H, d), 5.00 (2H, s), 6.11 (2H, s), 6.52 (1H, d), 6.82 (2H, d), 6.98-7.04 (3H, m), 7.22-7.38 (7H, m)

Step 5 tert-Butyl N-((1S,2R)-1-[(4-benzyloxy)benzyl]-3-(2, 2-dimethyl-5-N'-methylcarbamoyloxypentyl) [(3,4-methylenedioxyphenyl)sulfonyl]amino-2-hydroxypropyl) carbamate

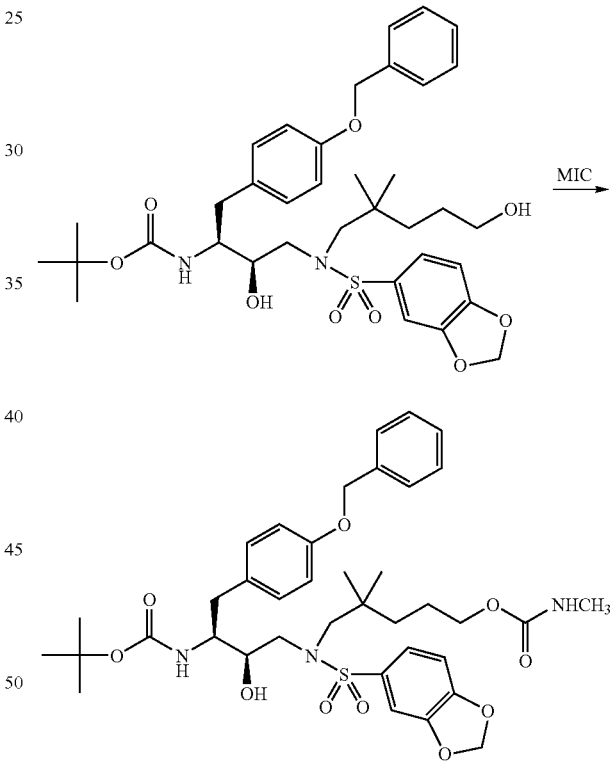

To a stirred solution of the alcohol from step 4.) (600 mg, 0.88 mmol) in dichloromethane (6 mL) was added methylisocyanate (1.0 mL, 17.50 mmol). After stirring at ambient temperature for 48 hours, the reaction was concentrated in vacuo and purified by silica gel:chromatography (1:1; ethyl acetate:hexane) to afford the title compound (870 mg, 88%) as a white foam. $^1$H NMR (DMSO-d$_6$): 0.86 (6H, d), 1.18-1.23 (2H, m), 1.19 (9H, s), 1.43-1.49 (2H, m), 2.37 (1H, dd), 2.50 (3H, d), 2.77-2.82 (2H, m), 2.90-2.96 (1H, m), 3.28-3.31 (3H, m), 3.61-3.67 (1H, m), 3.84 (2H, t), 4.91 (1H, d), 5.00 (2H, s), 6.11 (1H, d), 6.52 (1H, d), 6.81-6.86 (3H, m), 6.98-7.04 (3H, m), 7.23-7.38 (7H, m)

Step 6

N1-[(2R,3S)-3-amino-4-[(4-benzyloxy)phenyl]butyl]-N1-1-[2,2-dimethyl-5-(N2-methylcarbamoyloxy)pentyl]-3,4-methylenedioxy-1-benzenesulfonamide

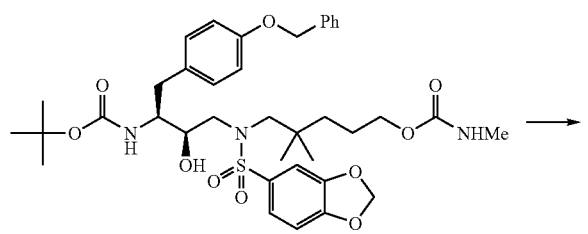

Treatment of the product from step 5 with trifluoroacetic acid/dichloromethane as previously described provided the title compound as a solid foam; $^1$H NMR (DMSO-$d_6$): 0.8 (6H, d), 1.2-1.3 (2H, m), 1.4-1.5 (2H, m), 2.2 (1H, dd), 2.55 (3H, d), 2.6-2.7 (2H, m), 2.9 (1H, d), 3.1 (1H, dd), 3.2-3.3 (3H, m), 3.5 (2H, br d), 3.85 (2H, t), 4.6 (1H, d), 5.05 (2H, s), 6.1 (2H, s), 6.9 (3H, br d), 7.0 (1H, d), 7.08 (2H, br d), 7.2-7.4 (7H, m); MS: 642 (MH+)

Step 7

(3R,3aS,6aR)-Hexahydrofuro[2,3-b]furan-3-yl N-((1S,2R)-1-[(4-benzyloxy)benzyl-3-[2,2-dimethyl-5-(N'-methylcarbamoyloxy)-pentyl][(3,4-methylenedioxyphenyl) sulfonyl]amino-2-hydroxypropyl)carbamate (361)

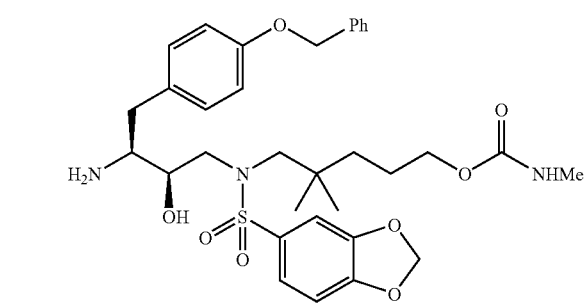

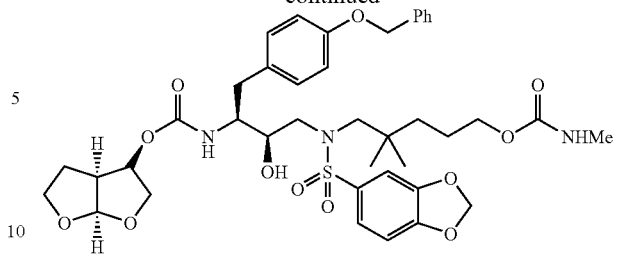

To a solution of the product from step 6 (0.11 g, 0.17 mmol) in acetonitrile (3 mL) was added diisopropylethylamine (0.076 mL, 0.057 g, 0.44 mmol) and [(3R,3aS,6aR)hexahydrofuro[2,3-b]furan-3-yl][4-nitrophenyl]carbonate (0.065 g, 0.22 mmol) and the fixture was stirred at ambient temperature for 24 h. Solvent was evaporated and the residue was dissolved in ethyl acetate, washed with saturated sodium bicarbonate/water (4×), dried (sodium sulfate) concentrated, and chromatographed (silica gel; hexanes/ethyl acetate) to provide the title compound as a solid foam; $^1$H NMR (DMSO-$d_6$): 0.9 (6H, d), 1.1-1.3 (4H, m), 1.5 (2H, br s), 2.3 (1H, dd), 2.55 (3H, d), 2.7-2.8 (2H, m), 2.85 (2H, dd), 3.2-3.4 (4H, m), 3.5-3.6 (2H, m), 3.6-3.8 (2H, m), 3.82-3.90 (3H, m), 4.8 (1H, quartet), 5.0 (2H, s), 5.05 (1H, hr d), 5.5 (1H, d), 6.1 (2H, s), 6.8-6.9 (3H, m), 7.0-7.1 (3H, m), 7.15-7.40 (7H, m); MS: 798 (MH+)

Example 145

(3S)-Tetrahydro-3-furanyl N-((1S,2R)-1-[(4-benzyloxy)benzyl-3-[2,2-dimethyl-5-(N'-methylcarbamoyloxy)-pentyl][(3,4-methylenedioxyphenyl)sulfonyl] amino-2-hydroxypropyl)carbamate (362)

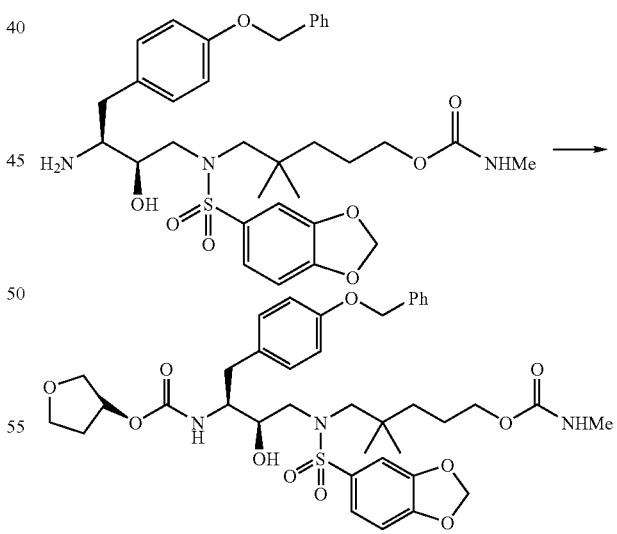

Treatment of the product from step 6 (Example 361) with (3S)-tetrahydro-3-furanyl N-succinimidyl carbonate as described in step g (example 801) provided the title compound as a solid foam; $^1$H NMR (DMSO-$d_6$): 0.8 (6H, d), 1.05-1.10 (2H, m), 1.4-1.5 (2H, m), 1.7 (1H, br s), 1.95-2.05 (1H, m), 2.4 (1H, t), 2.55 (3H, d), 2.8 (2H, t), 2.9 (1H, dd), 3.2-3.35 (3H, m), 3.5-3.5 (4H, m), 3.8 (2H, br s), 4.9-5.0 (4H, m), 5.7 (1H, s), 6.2 (2H, s), 6.8-6.9 (3H, m), 7.00-7.15 (4H, m), 7.2-7.4 (7H, m); MS: 756 (MH+)

Example 146

1,3-Dioxan-5-yl N-((1S,2R)-1-[(4-benzyloxy)benzyl-3-[2,2-dimethyl-5-(N'-methylcarbamoyloxy)-pentyl][(3,4-methylenedioxyphenyl)sulfonyl]amino-2-hydroxypropyl) carbamate (363)

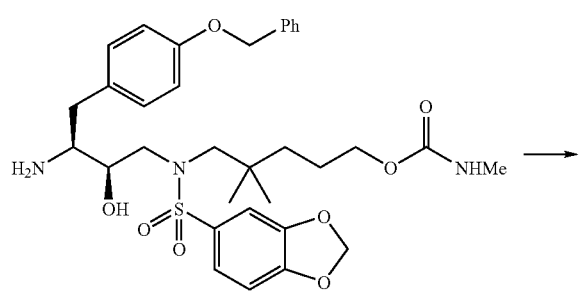

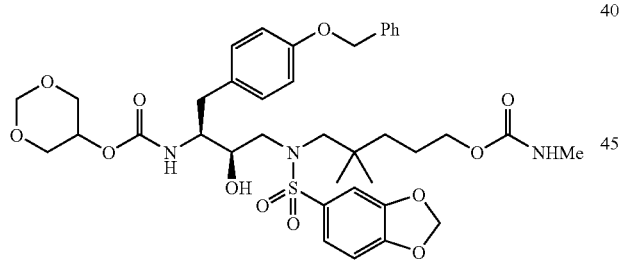

Treatment of the product from step 6 (example 361) with 1,3-dioxan-5-yl p-nitrophenyl carbonate as described in step 7 (example 627) provided the title compound as a solid foam; $^1$H NMR (DMSO-$d_6$): 0.8 (6H, s), 1.1-1.3 (2H, m), 1.4-1.5 (2H, m), 2.4 (1H, t), 2.55 (3H, d), 2.75-2.85 (2H, m), 2.9 (1H, dd), 3.20-3.35 (2H, m), 3.45 (1H, d), 3.6-3.9 (6H, m), 4.3 (1H, br s), 4.65 (1H, br d), 4.75 (1H, br d), 4.9-5.0 (3H, m), 5.7 (1H, s), 6.1 (2H, s), 6.75-6.85 (3H, m), 6.95-7.05 (3H, m), 7.2-7.4 (8H, m); MS: 772 (MH+);

Example 147

Step 1 t-Butyl-(1S,2R)-1-(4-benzyloxy-benzyl)-3-i-butylamino-2-hydroxypropyl-carbamate

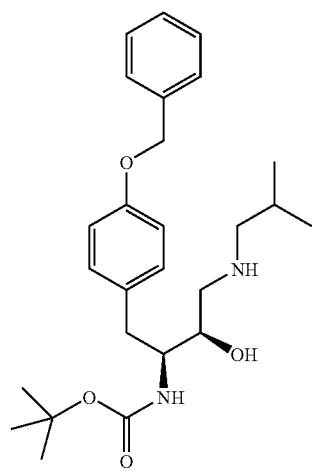 [SMILES: CC(C)CNC[C@@H](O)[C@H](Cc1ccc(OCc2ccccc2)cc1)NC(=O)OC(C)(C)C]

i-Butylamine (10.0 g, 137 mmol) was added to a solution of t-Butyl-(1S,2R)-1-(4-benzyloxy-benzyl)-2,3-epoxydo-propyl-carbamate (7.0 g, 18.9 mmol) (prepared according to the reference by Chen, P. at all., *Tetrahedron Letters*, Vol 38. p 3175-8, 1997), in 100 ml i-propanol. The mixture was stirred at 85° C. for 2 hours, then it was cooled to 5° C. and 500 ml water was added dropwise. The resulting suspension was stirred for 30 minutes at 5° C., then filtered. The solid was washed with water (3×100 ml) then dried under reduced pressure to obtain 8.3 g (99%) title compound. $^1$H-NMR: (CDCl$_3$): 0.88 (6H, d), 1.34 (9H, s), 1.68 (1H, m), 2.38 (2H, d), 2.64 (2H, d), 2.80 (1H, m), 2.86 (1H, dd), 3.40 (1H, m), 3.70 (2H, s(broad)), 4.63 (1H, d), 5.01 (2H, s), 6.88 (2H, d), 7.12 (2H, d), 7.40 (5H, m).

Step 2 t-Butyl-N((1S,2R)-1-(4-benzyloxy-benzyl)-3-i-butyl-[(3,4-methylenedioxyphenyl)sulfonyl]-amino-2-hydroxypropyl-carmamate

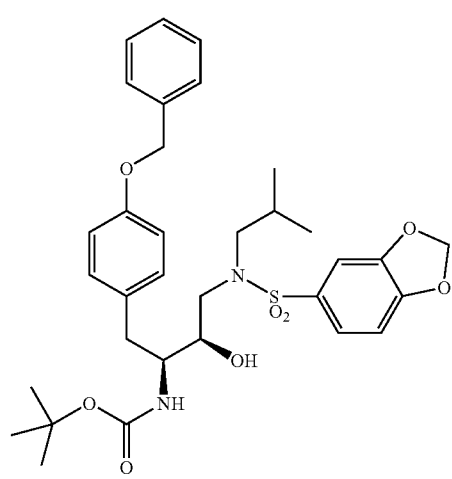 [SMILES: CC(C)CN(C[C@@H](O)[C@H](Cc1ccc(OCc2ccccc2)cc1)NC(=O)OC(C)(C)C)S(=O)(=O)c1ccc2c(c1)OCO2]

A solution of the product from Step 1 (8.3 g, 18.8 mmol), 3,4-methylenedioxysulfonylchloride (5.0 g, 22.7-mmol) and diisopropylethylamine (5.0 g, 38.7 mmol) stirred at 20° C. for 4 hours. 200 ml water was then added to the reaction mixture and the phases were separated. The aqueous phase was extracted with dichloromethane (3×100 ml), then the organic phases were combined, dried with magnesium sulfate, filtered and concentrated. The residue was dissolved in 300 ml ether, 50 g silicagel was added to the solution, then the mixture was filtered. The filtrate was concentrated under reduced pressure, and the residue was mixed with 300 ml hexane. The mix was stirred for three hours at 20° C., then the solid was filtered and dried to afford 10.9 g (93%) title compound. $^1$H NMR (CDCl$_3$): 0.85 (3H, d), 0.88 (3H, d), 1.34 (9H, s), 1.82 (1H, m), 3.04 (2H, m), 3.68 (1H, s(broad)), 3.75 (1H, s(broad)), 3.86 (1H, s), 4.60 (1H, d), 5.02 (2H, s), 6.04 (2H/s), 6.88 (3H, m), 7.15 (3H, m), 7.35 (6H, m).

residue was dissolved in 150 ml acetonitrile. Diisopropylethylamine (8.0 g, 62 mmol) and (3R,3aS,6aR)-Hexahydrofuro[2,3-b]furan-3-yl-4-nitrophenyl carbonate (8.0 g, 27.1 mmol) was added, and the solution was stirred for 12 hours at 20° C. 10 ml 25% aqueous ammonium hydroxide solution was added, then the mixture was stirred for an additional hour. The solvents were removed under reduced pressure, the residue dissolved in 500 ml ether, and the solution was extracted with 5% sodium carbonate solution (10×100 ml). The organic phase was dried with anhydrous sodium carbonate, filtered and concentrated under reduced pressure. 20 ml ether was added to the residue, then after a small amount of solid formation 200 ml hexane was added, and the mixture was stirred at 2.0° C. for 1 hour, then filtered and dried, to obtain 11.3 g (quant.) title compound. $^1$H NMR (DMSO-d$_6$): 0.76 (3H, d), 0.82 (3H, d), 1.2 (1H, m), 1.35 (1H, m), 1.92 (1H, m), 2.35 (1H, t), 2.70 (3H, m), 2.85-3.05 (2H, m), 3.45 (1H, m), 3.55 (3H, m), 3.66 (1H, t), 3.80 (1H, dd), 4.81 (1H, m), 5.00 (3H, s(broad)), 5.47 (1H, d), 6.13 (2H, s), 6.82 (2H, d), 7.06 (3H, m), 7.20-7.40 (7H, m); MS: 682 (M+).

Example 148

Step 1 t-Butyl-N((1S,2R)-1-(4-benzyloxy-benzyl)-3-i-butyl-[(3,4-ethylenedioxyphenyl)sulfonyl]-amino-2-hydroxypropyl-carmamate

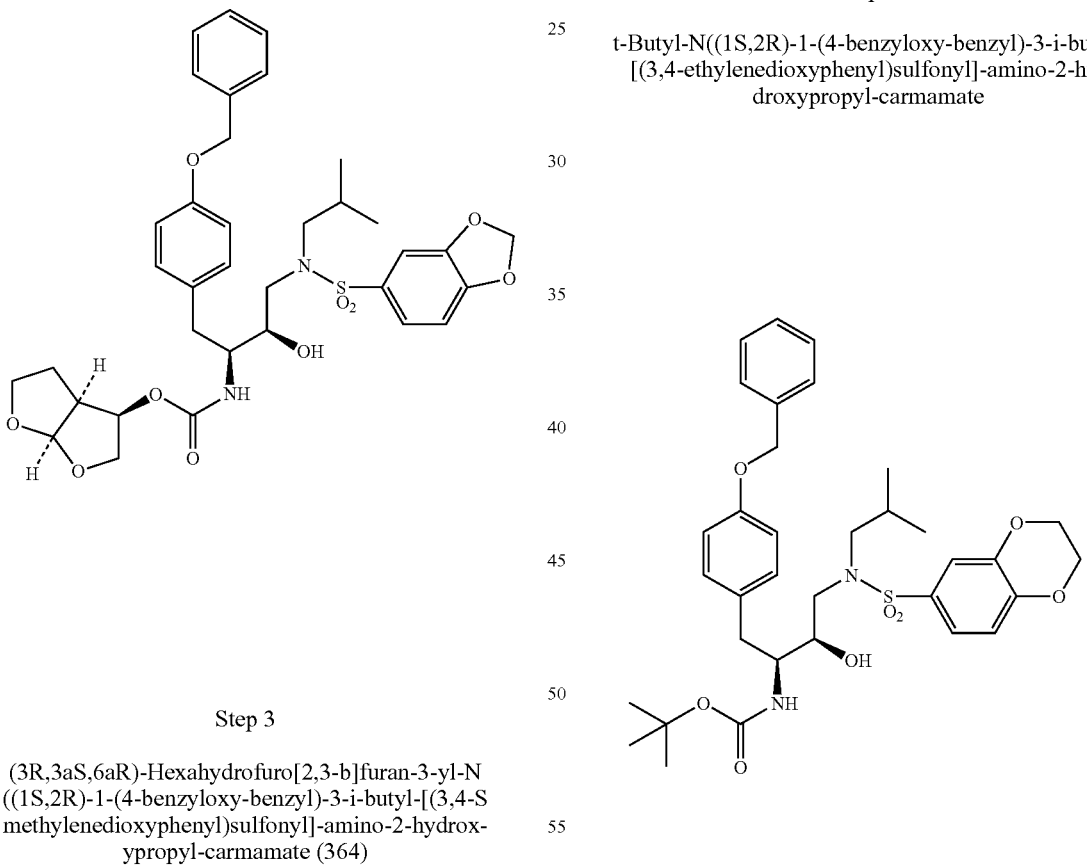

Step 3

(3R,3aS,6aR)-Hexahydrofuro[2,3-b]furan-3-yl-N((1S,2R)-1-(4-benzyloxy-benzyl)-3-i-butyl-[(3,4-S methylenedioxyphenyl)sulfonyl]-amino-2-hydroxypropyl-carmamate (364)

100 ml trifluoroacetic acid was added dropwise to a solution of the product from Step 2 (10.2 g, 16.3 mmol) in 200 ml dichloromethane. The mixture was stirred for 1 hour at 20° C., then the solvents were evaporated under reduced pressure. The residue was dissolved in 200 ml dichloromethane and 300 ml 5% aqueous sodium carbonate solution was added, then the mixture was stirred at 20° C. for 15 minutes. Phases were separated, then the aqueous phase was extracted with additional (2×100 ml) dichloromethane. Organic phases were combined then concentrated under reduced pressure. The The reaction was carried out as described in Step 2, Example 147, except 3,4-ethylenedioxyphenyl sulfonylchloride was used in the reaction (83%).

$^1$H NMR (CDCl$_3$): 0.86 (3H, d), 0.89 (3H, d), 1.34 (9H, s) 1.82 (1H, m), 2.85 (4H, m), 3.04 (2H, m), 3.69 (1H, s(broad)) 3.76 (1H, s(broad)), 3.91 (1H, s), 4.27 (4H, m), 4.61 (1H, d), 5.03 (2H, s), 6.89 (2H, d), 6.93 91H, d), 7.14 (2H, d), 7.20-7.45 (7H, m).

Step 2

(3R,3aS,6aR)-Hexahydrofuro[2,3-b]furan-3-yl-N((1S,2R)-1-(4-benzyloxy-benzyl)-3-i-butyl-[(3,4-ethylenedioxyphenyl)sulfonyl]-amino-2-hydroxypropyl-1-carmamate-(365)

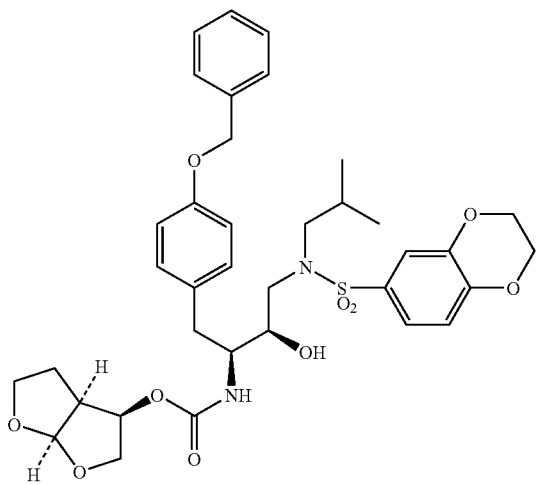 [SMILES: CC(C)CN(C[C@@H](O)[C@H](Cc1ccc(OCc2ccccc2)cc1)NC(=O)O[C@H]1CO[C@H]2OCC[C@H]21)S(=O)(=O)c1ccc2c(c1)OCCO2]

The reaction was carried out as described in Step 3, Example 147 except the product from Step 1, Example 144 was used in the reaction (43%). $^1$H NMR (DMSO-$d_6$): 0.78 (3H, d), 0.84 (3H, d), 1.20 (1H, m), 1.35 (1H, m), 1.95 (1H, m), 2.37 (1H, t), 2.70 (3H, m), 2.95 (2H, m), 3.45 (1H, m), 3.58 (3H, m), 3.68 (1H, t), 3.82 (1H, m), 4.28 (4H, d), 4.82 (1H, m), 5.01 (3H, s+m), 5.48 (1H, d), 6.84 (2H, d), 7.02 (1H, d), 7.08 (2H, d), 7.20-7.40 (7H, m); MS: 696 (M+).

Example 149

Step 1

N-(3R,3aS,6aR)-Hexahydrofuro[2,3-b]furan-3-yl-oxycarbonyl-, (4S,5R)-4-(4-benzyloxy-benzyl)-5-i-butyl-[(3,4-methylenedioxyphenyl)sulfonyl]-aminomethyl-2,2-dimethyl-oxazolidine

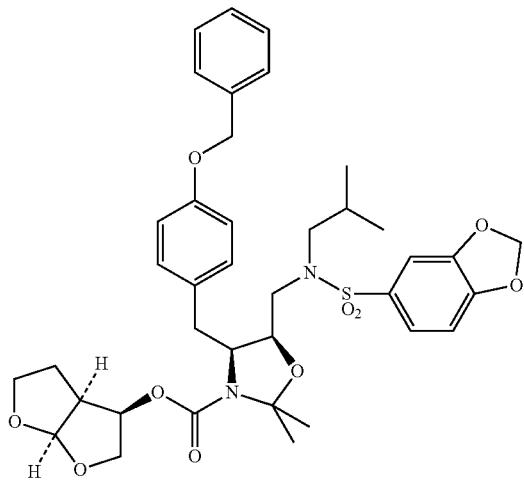 [SMILES: CC(C)CN(C[C@H]1OC(C)(C)N(C(=O)O[C@H]2CO[C@H]3OCC[C@H]32)[C@H]1Cc1ccc(OCc2ccccc2)cc1)S(=O)(=O)c1ccc2c(c1)OCO2]

2,2-dimethoxy-propane (20 g, 192 mmol) and p-toluenesulfonic acid (1.0 g, 5.8 mmol) was added to the solution of the product of Example 630 (11.3 g, 16.5 mmol) in 200 ml dichloromethane. The solution was refluxed for 4 hours, then cooled to 20° C. The mixture was extracted with 5% sodium carbonate solution, then the organic phase was dried with magnesium sulfate, filtered and concentrated under reduced pressure. The residue was purified on silicagel using hexane-ethyl acetate (1:1) as eluent, to provide 7.78 g (60%) title compound. $^1$H NMR (CDCl$_3$): 0.83 (3H, d), 0.91 (3H, d), 1.40, 1.48 (3H, s)*, 1.56, 1.64 (3H, s)*, 1.85 (2H, m), 2.0 (1H, m), 2.70 (3H, m), 2.80 (1H, m), 3.00 (3H, m), 3.40 (1H, m), 3.80 (2H, m), 3.95 (1H, t), 4.20 (1H, m), 4.30 (1H, m), 4.89 (1H, dd), 5.03 (2H, s), 5.65, 5.68 (1H, d)*, 6.00 (2H, s), 6.79 (1H, d), 6.89 (2H, d), 7.02 (2H, d), 7.10 (1H, m), 7.30-7.45 (6H, m).

*: possible indication for rotamers.

Step 2

N-(3R,3aS,6aR)-Hexahydrofuro[2,3-b]furan-3-yl-oxycarbonyl-(4S,5R)-4-(4-hydroxybenzyl)-5-i-butyl-[(3,4-methylenedioxyphenyl)sulfonyl]-aminomethyl-2,2-dimethyl-oxazolidine (366)

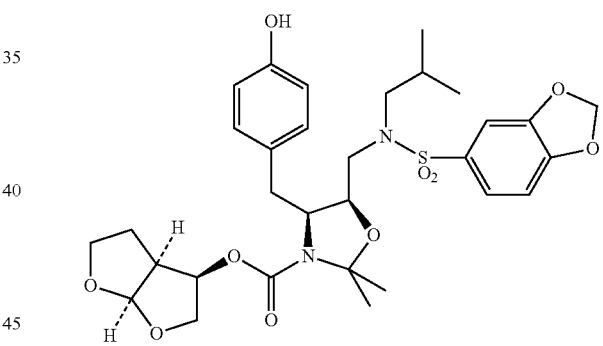

8 g palladium (on charcoal, 10% Pd, Degussa type) was added to a stirred solution of the product of Step 1 (7.7 g, 10.6 mmol) in 400 ml tetrahydrofuran. The mixture was stirred under atmospheric pressure of hydrogen for 12 hours. The catalyst was filtered, and the solvent was removed under reduced pressure.

The residue was stirred for 2 hours in 200 ml hexane, then the solid was filtered, washed with hexane (2×20 ml) to obtain 6.4 g (95%) title compound. $^1$H NMR (CDCl$_3$): 0.83 (3H, d), 0.91 (3H, d), 1.41, 1.48 (3H, s)*, 1.56, 1.65 (3H, s)*, 1.85 (2H, m), 2.00 (1H, m), 2.60-3.10 (6H, m), 3.40 (2H, m), 3.70-4.35 (6H, m), 4.90 (1H, dd), 5.05-5.30 (2H, m), 5.66, 5.69 (1H, d)*, 6.06 (2H, s), 6.75 (2H, d) 6.83 (1H, d), 6.97 92H, d), 7.00-7.15 (2H, m); MS: 632 (M+).

*: possible indication for rotamers.

Example 150

Step 1

General Procedure for the Aralkylation of N-(3R, 3aS,6aR)-Hexahydrofuro[2,3-b]furan-3-yl-oxycarbonyl-, (4S,5R)-4-(4-hydroxybenzyl)-5-i-butyl-[(3,4-methylenedioxyphenyl) sulfonyl]-aminomethyl-2,2-Dimethyl-oxazolidine 0.5 mmol aralkyl halide [1] was added to a stirred mixture of N-(3R,3aS,6aR)-Hexahydrofuro[2,3-b]furan-3-yl-oxycarbonyl-, (4S,5R)-4-(4-hydroxybenzyl)-5-i-butyl-[(3,4-methylenedioxyphenyl)sulfonyl]-aminomethyl-2,2-Dimethyl-oxazolidine (126 mg, 0.2 mmol) and cesium carbonate (250 mg, 0.76 mmol) in 2 ml N,N-dimethylformamide. The mixture was stirred at the indicated temperature [2] for indicated number of hours [3] then diluted with 100 ml ether at 20° C. The mixture was filtered, and the filtrate was extracted with water (10×20 ml). The organic phase was dried with magnesium sulfate, filtered and concentrated under reduced pressure to obtain the following compounds:

N-(3R,3aS,6aR)-Hexahydrofuro[2,3-b]furan-3-yl-oxycarbonyl-, (4S,5R)-4-{4-[3-(4-fluorophenyl)-1-propyloxy]-benzyl}-5-i-butyl-[(3,4-methylenedioxyphenyl) sulfonyl]-aminomethyl-2,2-dimethyl-oxazolidine

[1]: 1-chloro-3-(4-fluorophenyl)-propane; [2]: 60° C.; [3]: 6 hours; MS: 768 (M+).

Step 2

General Procedure for the Deprotection of N-(3R, 3aS,6aR)-Hexahydrofuro[2,3-b]furan-3-yl-oxycarbonyl-, (4S,5R)-4-(4-aralkyloxybenzyl)-5-i-butyl-[(3,4-methylenedioxyphenyl)sulfonyl]-aminomethyl-2,2-Dimethyl-oxazolidine (the Product of Step 1.)

4 M HCl in dioxane (7.5 ml) and water (0.2 g) was added to a stirred solution of the product of Step 1 in 15 ml dioxane. The solution was stirred for 5 hours, then the solvents were removed under reduced pressure. The residue was dissolved in 100 ml ethyl acetate, washed with 5% aqueous sodium biarbonate solution, then the organic phase dried with magnesium sulfate. The solvents were removed and the residue was purified either with filtration from silicagel slurry and crystallization (a) or silicagel chromatography (b), using the eluent(s) as indicated [1] to obtain the following compounds (yield: [2]):

(3R,3aS,6aR)-Hexahydrofuro[2,3-b]furan-3-yl-N ((1S,2R)-1-{4-[3-(4-fluorophenyl)-1-propyloxy]-benzyl}-3-i-butyl-[(3,4-methylenedioxyphenyl)sulfonyl]-amino-2-hydroxypropyl-carbamate (366)

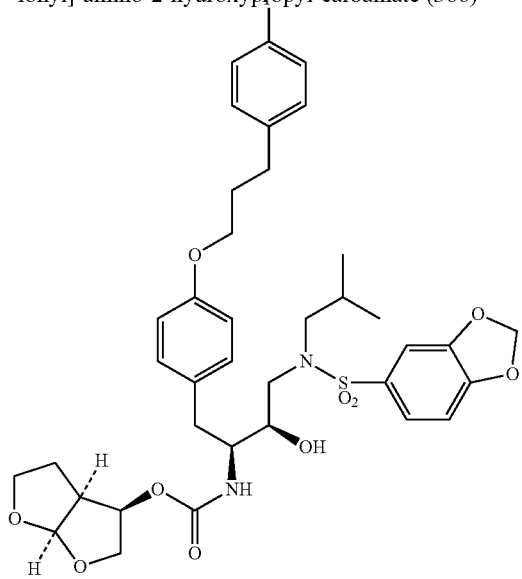

[1]: b, Hexane-EtOAc (1:1) then Hexane-EtOAc (1:2); [2]: 36%. $^1$H-NMR (DMSO-$d_6$): 0.76 (3H, d), 0.81 (3H, d), 1.15 (1H, m), 1.31 (1H, m), 1.93 (3H, m), 2.34 (1H, t), 2-0.68 (5H, m), 2.85-3.00 (3H, m), 3.40-3.90 (8H, m), 4.81 (1H, dd), 4.98 (1H, d), 5.47 (1H, d), 6.13 (2H, s), 6.74 (2H, d), 7.04 (4H, m), 7.20 (4H, m), 7.27 (1H, d); MS: 728 (M+).

Example 151

Step 1

N-(3R,3aS,6aR)-Hexahydrofuro[2,3-b]furan-3-yl-oxycarbonyl-, (4S,5R)-4-[4-(3-cyanobenzyloxy)-benzyl]-5-i-butyl-[(3,4-methylenedioxyphenyl)sulfonyl]-aminomethyl-2,2-dimethyl-oxazolidine

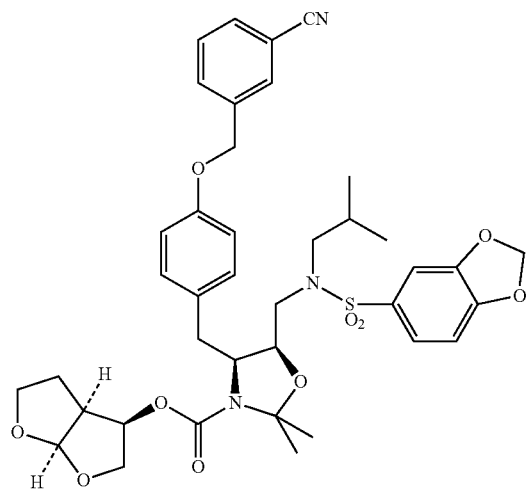 [SMILES: CC(C)CN(C[C@H]1OC(C)(C)N(C(=O)O[C@H]2CO[C@H]3OCC[C@H]32)[C@H]1Cc1ccc(OCc2cccc(C#N)c2)cc1)S(=O)(=O)c1ccc2c(c1)OCO2]

[1]: 3-cyanobenzyl bromide; (2): 20° C.; [3]: 1 hour; MS: 747 (M+).

Step 2

(3R,3aS,6aR)-Hexahydrofuro[2,3-b]furan-3-yl-N (1S,2R)-1-[4-(3-cyanobenzyloxy)-benzyl]-3-i-butyl-[(3,4-methylenedioxyphenyl)sulfonyl]-amino-2-hydroxypropyl-carbamate (367)

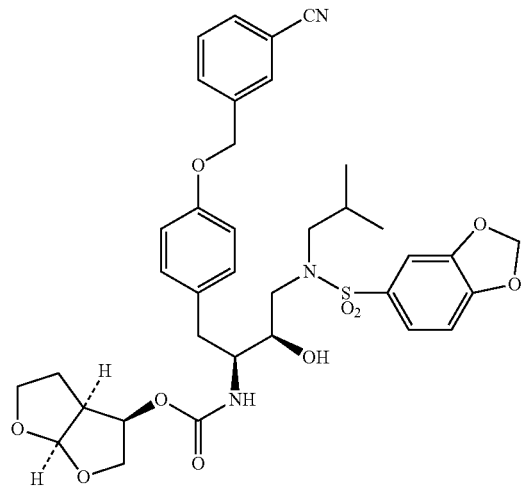

[1]: b, Hexane-EtOAc (1-1) then Hexane-EtOAc (1:2); [2]: 46% $^1$H NMR (DMSO-d$_6$): 0.75 (3H, d), 0.81 (3H, d), 1.19 (1H, m), 1.31 (1H, m), 1.92 (1H, m), 2.35 (1H, t), 2.41 (3H, m), 2.85-3.00 (3H, m), 3.40-3.60 (5H, m), 3.65 (1H, t); 3.80 (1H, dd), 4.81 (1H, dd), 4.99 (1H, d), 5.07 (2H, s), 5.47 (1H, d), 6.13 (2H, s), 6.83 (2H, d), 7.04 (3H, m), 7.20 (2H, m), 7.27 (1H, d), 7.56 (1H, t), 7.75 (2H, t), 7.85 (1H, s); MS: 707 (M$^+$).

Example 152

Step 1

N-(3R,3aS,6aR)-Hexahydrofuro[2,3-b]furan-3-yl-oxycarbonyl-, (4S,5R)-4-[4-(2-methylthiazolo-4-methyloxy)-benzyl]-5-i-butyl-[(3,4-methylenedioxyphenyl)sulfonyl]-aminomethyl-2,2-dimethyl-oxazolidine

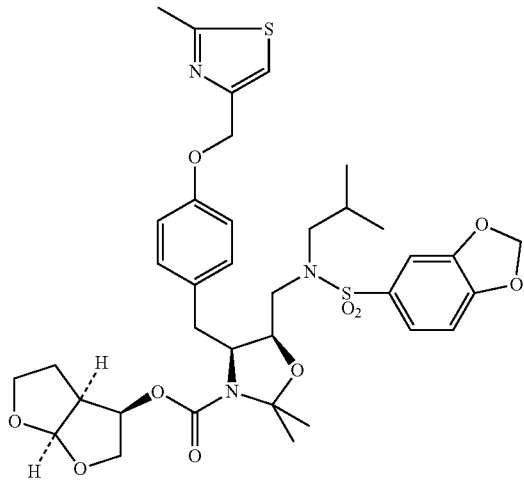 [SMILES: Cc1nc(COc2ccc(C[C@H]3[C@@H](CN(CC(C)C)S(=O)(=O)c4ccc5c(c4)OCO5)OC(C)(C)N3C(=O)O[C@H]3CO[C@H]4OCC[C@H]43)cc2)cs1]

[1]: 4-chloromethyl-2-methylthiazole hydrochloride; [2]: 70° C.; [3]: 5 hour; MS: 743 (M+).

Step 2

(3R,3aS,6aR)-Hexahydrofuro[2,3-b]furan-3-yl-N ((1S,2R)-1-[4-(2-methylthiazolo-4-methyloxy)-benzyl]-3-i-butyl-[(3,4-methylenedioxyphenyl)sulfonyl]-amino-2-hydroxypropyl-carmamate (368)

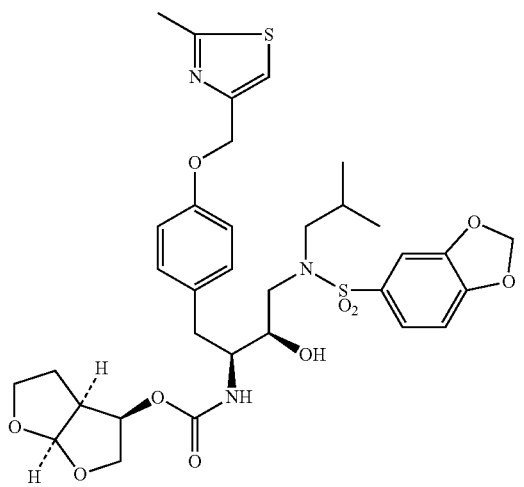

[1]: b, EtOAc (neat); [2]: 36%. $^1$H NMR (DMSO-d$_6$): 0.76 (3H, d), 0.82 (3H, d), 1.20 (1H, m), 1.33 (1H, nm), 1.92 (1H, m), 2.35 (1H, t), 2.61 (3H, s), 2.65 (1H, m), 2.85-3.00 (3H, m), 3.40-3.60 (5H, m), 3.68 (1H, t), 3.80 (1H, dd), 4.81 (1H, dd), 4.99 (3H, s(broad)), 5.47 (1H, d), 6.13 (2H, s), 6.83 (2H, d), 7.06 (3H, m), 7.20 (2H, m), 7.27 (1H, d), 7.47 (1H, s); MS: 703 (M+).

Example 153

Step 1

N-(3R,3aS,6aR)-Hexahydrofuro[2,3-b]furan-3-yl-oxycarbonyl-, (4S,5R)-4-[4-(4-methylthio-benzyloxy)-benzyl]-5-i-butyl-[(3,4-methylenedioxyphenyl)sulfonyl]-aminomethyl-2,2-dimethyl-oxazolidine

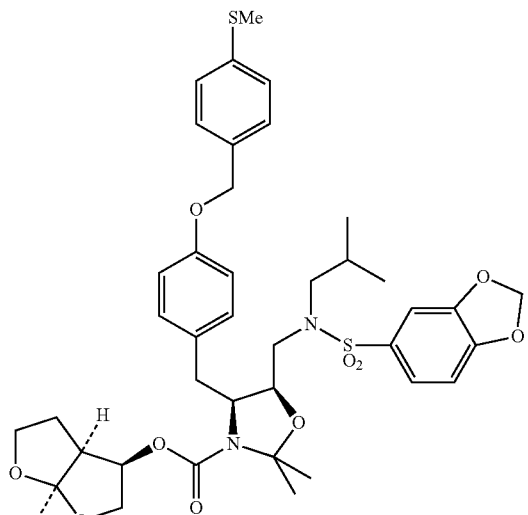

[1]-4-methylthiobenzylchloride; [2]: 40° C.; [3]: 4 hour; MS: 768 (M+).

Step 2

(3R,3aS,6aR)-Hexahydrofuro[2,3-b]furan-3-yl-N ((1S,2R)-1-[4-(4-methylthio-benzyloxy)-benzyl]-3-i-butyl-[(3,4-methylenedioxyphenyl)sulfonyl]-amino-2-hydroxypropyl-carmamate (369)

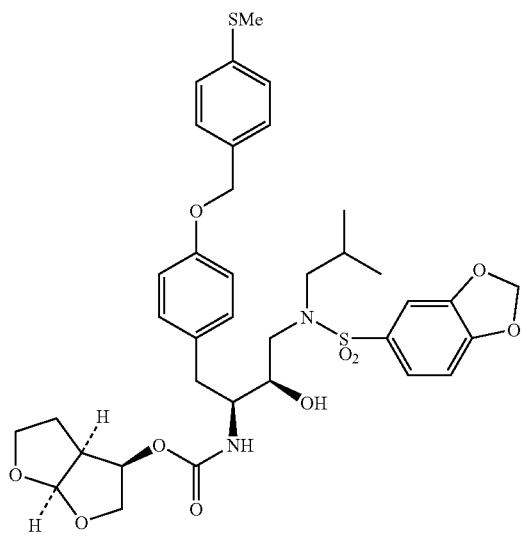 [SMILES: CSc1ccc(COc2ccc(C[C@H](NC(=O)O[C@H]3CO[C@H]4OCC[C@H]43)[C@H](O)CN(CC(C)C)S(=O)(=O)c3ccc4c(c3)OCO4)cc2)cc1]

[1]: b, Hexane-EtOAc (1:1) then Hexane-EtOAc (1:2); [2]: 17%. ¹H NMR (DMSO-d₆): 0.75 (3H, d), 0.81 (3H, d), 1.20 (1H, m), 1.30 (1H, m), 1.92 (1H, m), 2.35 (1H, m), 2.42 (3H, s), 2.70 (3H, m), 2.85-3.00 (3H, m), 3.45 (1H, m), 3.55 (3H, m), 3.66 (1H, t), 3.80 (1H, dd), 4.81 (1H, dd), 4.98 (3H, s+m), 5.47 (1H, d), 6.12 (2H, s), 6-80 (2H, d), 7.05 (3H, m), 7.15-7.35 (6H, m); MS: 728 (M+).

Example 154

Step 1

N-(3R,3aS,6aR)-Hexahydrofuro[2,3-b]furan-3-yl-oxycarbonyl-, (4S,5R)-4-[4-(5-t-butyl-1,2,4-oxadiazolo-3-methyloxy)-benzyl]-5-i-butyl-[(3,4-methylenedioxyphenyl)sulfonyl]-aminomethyl-2,2-dimethyl-oxazolidine

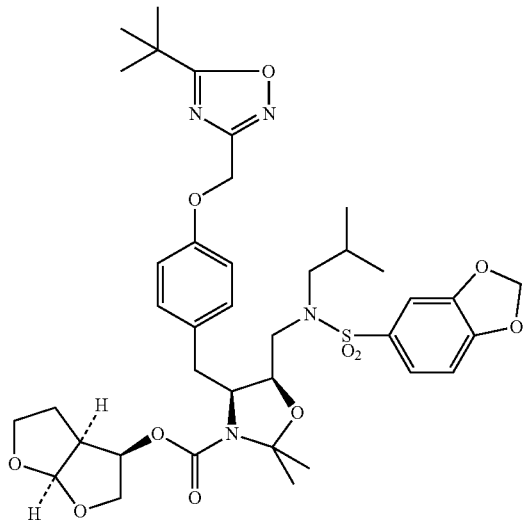 [SMILES: CC(C)CN(C[C@H]1OC(C)(C)N(C(=O)O[C@H]2CO[C@H]3OCC[C@H]32)[C@H]1Cc1ccc(OCc2noc(C(C)(C)C)n2)cc1)S(=O)(=O)c1ccc2c(c1)OCO2]

[1]: 5-t-butyl-3-chloromethyl-1,2,4-oxadiazole; [2]: 20° C.; [3]: 12 hour; MS: 770 (M+).

Step 2

(3R,3aS,6aR)-Hexahydrofuro[2,3-b]furan-3-yl-N ((1S,2R)-1-[4-(5-t-butyl-1,2,4-oxadiazolo-3-methyloxy)-benzyl]-3-i-butyl-[(3,4-methylenedioxyphenyl)sulfonyl]-amino-2-hydroxypropyl-carmamate (370)

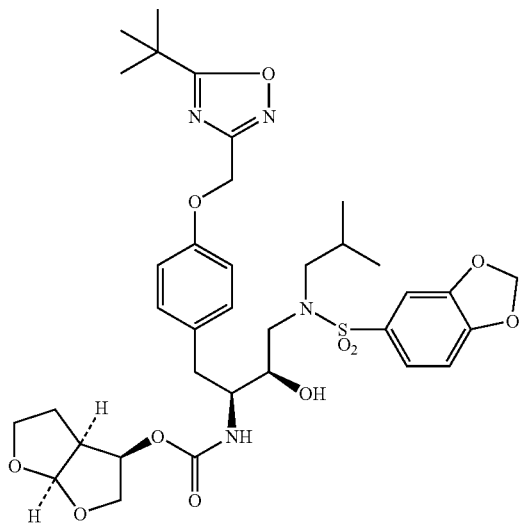 [SMILES: CC(C)CN(C[C@@H](O)[C@H](Cc1ccc(OCc2noc(C(C)(C)C)n2)cc1)NC(=O)O[C@H]1CO[C@H]2OCC[C@H]21)S(=O)(=O)c1ccc2c(c1)OCO2]

[1]: b, Hexane-EtOAc (1:1) then Hexane-EtOAc (1:2); [2]: 56%. ¹H NMR (DMSO-d₆): 0.76 (3H, d), 0.83 (3H, d), 1.19 (1H, m), 1.30 (1H, m), 1.36 (9H, s), 1.93 (1H, m), 2.37 (1H, t), 2.72 (3H, m), 2.90-3.02 (3H, m), 3.42-3.60 (4H, m), 3.68 (1H, t), 3.82 (1H, dd), 4.81 (1H, dd), 5.0 (1H, s(broad)), 5.12 (2H, s), 5.47 (1H, d), 6:13 (2H, s), 6.85 (2H, d), 7.03 (1H, d), 7.10 (2H, d), 7.20 (2H, d), 7.28 (1H, d); MS: 730 (M+).

Example 155

Step 1

N-(3R,3aS,6aR)-Hexahydrofuro[2,3-b]furan-3-yl-oxycarbonyl-, (4S,5R)-4-[4-(4-fluorobenzyloxy)-benzyl]-5-i-butyl-[(3,4-methylenedioxyphenyl)sulfonyl]-aminomethyl-2,2-dimethyl-oxazolidine (371)

[1]: 4-fluorobenzylbromide; [2]: 20° C.; [3]: 1 hour; MS: 741 (M+).

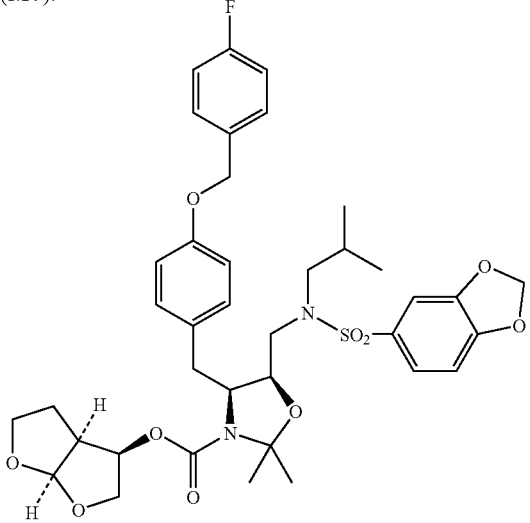

Step 2

(3R,3aS,6aR)-Hexahydrofuro[2,3-b]furan-3-yl-N ((1S,2R)-1-[4-(4-fluorobenzyloxy)-benzyl]-3-i-butyl-[(3,4-methylenedioxyphenyl)-sulfonyl]-amino-2-hydroxypropyl-carmamate (0.371)

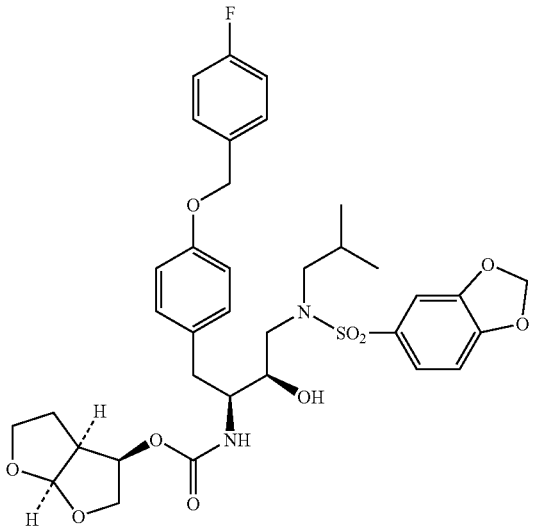

[1]: a, Hexane-EtOAc (1:1); [2]: 41%. 1H-NMR (DMSO-$d_6$): 0.75 (3H, d), 0.81 (3H, d), 1.18 (1H, m), 1.31 (1H, m), 1.90 (1H, m), 2.34 (1H, t), 2.62-2.74 (3H, m), 2.89-3.02 (2H, m), 3.40-3.49 (1H, m), 3.50-3.60 (3H, m), 3.65 (1H, m), 3.80 (1H, dd), 4.80 (1H, dd), 4.97 (2H, s(broad)), 4.99 (1H, d), 5.46 (1H, d), 6.12 (2H, s), 6.81 (2H, d), 7.02 (1H, d), 7.06 (2H, d), 7.15 (1H, d), 7.18-7.23 (3H, m), 7.27 (1H, dd), 7.43 (2H, dd). MS: 701 (M+).

Example 156

Step 1

N-(3R,3aS,6aR)-Hexahydrofuro[2,3-b]furan-3-yl-oxycarbonyl-, (4S,5R)-4-[4-(4-trifluoromethylbenzyloxy)-benzyl]-5-i-butyl-[(3,4-methylenedioxyphenyl)sulfonyl]-aminmethyl-2,2-dimethyl-oxazolidine

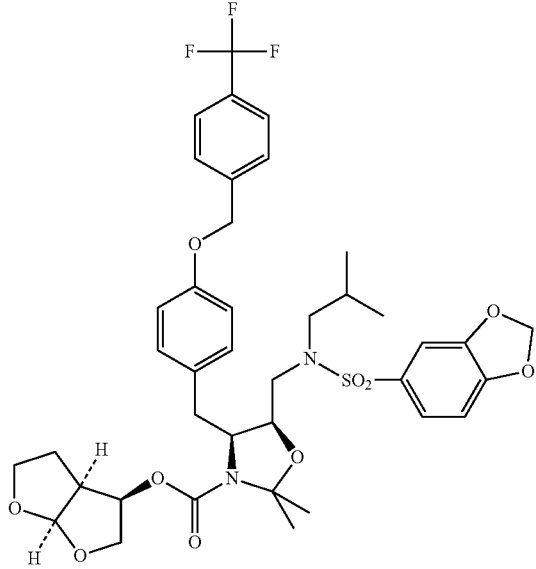

[1]: 4-trifluoromethylbenzylbromide; [2]: 20° C.; [3]: 1 hour; MS: 791 (M+).

Step 2

(3R,3aS,6aR)-Hexahydrofuro[2,3-b]furan-3-yl-N ((1S,2R)-1-[4-(4-trifluoromethylbenzyloxy)-benzyl]-3-i-butyl-[(3,4-methylenedioxyphenyl)sulfonyl]-amino-2-hydroxypropyl-carmamate (372)

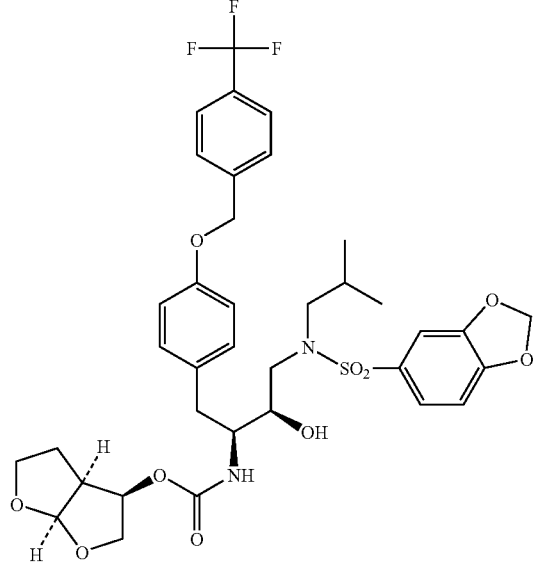

[1]: a, Hexane-EtOAc (1:1) [2]: 47%. $^1$H-NMR (DMSO-$d_6$) 0.75 (3H, d), 0.81 (3H, d), 1.16 (1H, m), 1.26 (1H, m), 1.91 (1H, m), 2.34 (1H, t), 2.65-2.76 (3H, m), 2.89-3.00 (2H, m), 3.45 (1H, m), 3.54 (3H, m), 3.63 (1H, m), 3.79 (1H, dd), 4.80 (1H, dd), 4.99 (1H, d), 5.12 (2H, s(broad)), 5.44 (1H, d), 6.12 (2H, s), 6.83 (2H, d), 7.02 (1H, d), 7.07 (2H, d), 7.21 (2H, d), 7.27 (1H, d), 7.60 (2H, d), 7.70 (2H, d); MS: 751 (M+).

Example 157

Step 1

N-(3R,3aS,6aR)-Hexahydrofuro[2,3-b]furan-3-yl-oxycarbonyl-, (4S,5R)-4-[4-(3-trifluoromethylbenzyloxy)-benzyl]-5-i-butyl-[(3,4-methylenedioxyphenyl)sulfonyl]-aminomethyl-2,2-dimethyl-oxazolidine

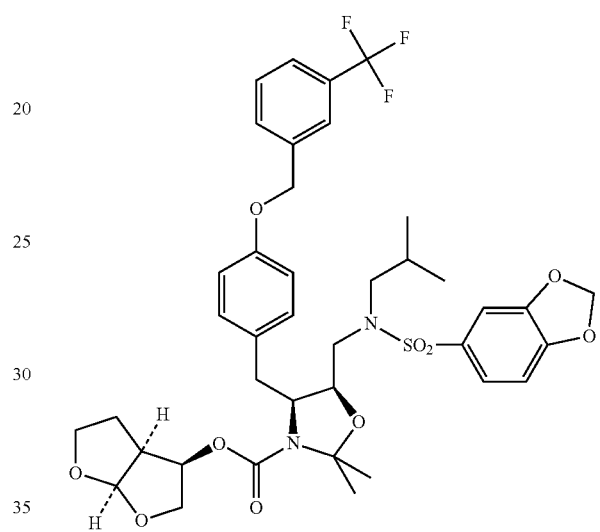

[1]: 3-trifluoromethylbenzylbromide; [2]: 20° C.; [3]: 1 hour; MS: 791 (M+).

Step 2

(3R,3aS,6aR)-Hexahydrofuro[2,3-b]furan-3-yl-N ((1S,2R)-1-[4-(3-trifluoromethylbenzyloxy)-benzyl]-3-i-butyl-[(3,4-methylenedioxyphenyl)sulfonyl]-amino-2-hydroxypropyl-carmamate (373)

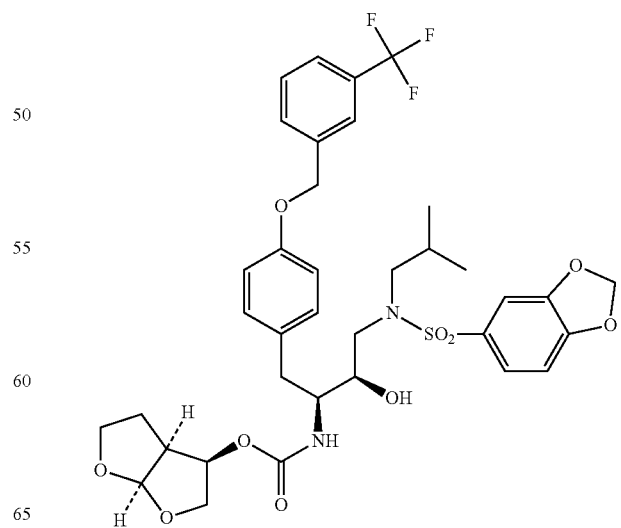

[1]: a, Hexane-EtOAc (1:1); [2]: 47%. ¹H-NMR (DMSO-d₆): 0.75 (3H, d), 0.81 (3H, d), 1.15-1.22 (1H, m), 1.30 (1H, m), 1.91 (1H, m), 2.34 (1H, t), 2.65-2.75 (3H, m), 2.89-3.01 (2H, m), 3.45 (1H, m), 3.52-3.59 (3H, m), 3.64 (1H, m), 3.80 (1H, dd), 4.80 (1H, dd), 4.99 (1H, d), 5.11 (2H, s(broad)), 5.45 (1H, d), 6.12 (2H, s), 6.84 (2H, d), 7.03 (1H, d), 7.07 (2H, d), 7.21 (2H, m), 7.2-7 (1H, dd), 7.58 (1H, t), 7.65 (1H, d), 7.70 (1H, d), 7.74 (1H, s); MS: 751 (M⁺).

Example 158

Step 1

N-(3R,3aS,6aR)-Hexahydrofuro[2,3-b]furan-3-yl-oxycarbonyl-, (4S,5R)-4-[4-(1,2,3-thiadiazole-4-benzyloxy)-benzyl]-5-i-butyl-[(3,4-methylenedioxyphenyl)sulfonyl]-aminomethyl-2,2-dimethyl-oxazolidine

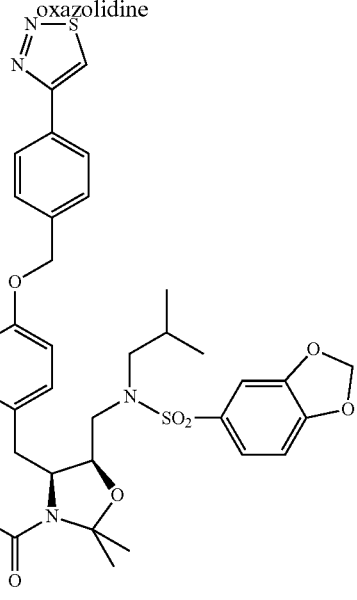

[1]: 4-[4-(bromomethyl)phenyl]-1,2,3-thiadiazole; [2]: 20° C.; [3]: 1 hour; MS: 807 (M+).

Step 2

(3R,3aS,6aR)-Hexahydrofuro[2,3-b]furan-3-yl-N((1S,2R)-1-[4-(1,2,3-thiadiazole-4-benzyloxy)-benzyl]-3-i-butyl-1-[(3,4-methylenedioxyphenyl)sulfonyl]-amino-2-hydroxypropyl-carmamate (374)

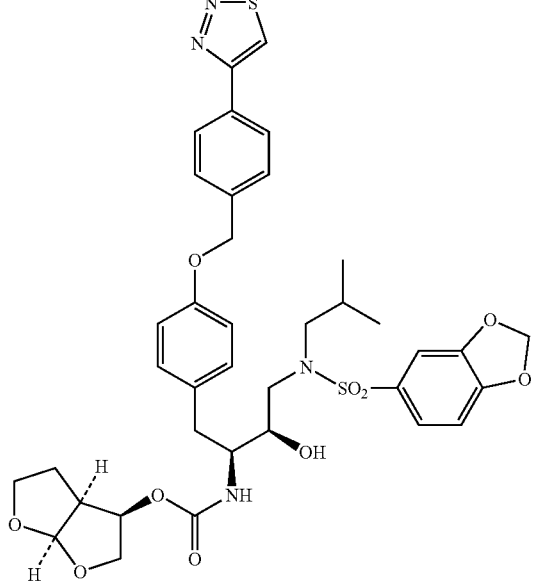

[1]: a, Hexane-EtOAc (1:3); [2]: 54%. 1 NMR (DMSO-d₆): 0.77 (3H, d), 0.83 (3H, d), 1.20 (1H, m), 1.31 (1H, m), 1.93 (1H, m), 2.37 (1H, t), 2.67-2.77 (3H, m), 2.91-3.03 (2H, m), 3.48 (1H, m), 3.53-3.61 (3H, m), 3.67 (1H, m), 3.81 (1H, dd), 4.82 (1H, dd), 5.00 (1H, m), 5.11 (2H, s(broad)), 5.43 (1H, d), 6.14 (2H, s), 6.87 (2H, d), 7.04 (1H, d), 7.10 (2H, d), 7.22 (2H, m), 7.29 (1H, d), 7.58 (2H, d), 8.13 (2H, d), 9.59 (1H, s); MS: 767 (M+).

Example 159

Step 1

N-(3R,3aS,6aR)-Hexahydrofuro[2,3-b]furan-3-yl-oxycarbonyl-, (4S,5R)-4-[4-(5-phenyl-1,2,4-oxadiazolo-3-methyloxy)-benzyl]-5-i-butyl-[(3,4-methylenedioxyphenyl)sulfonyl]-aminomethyl-2,2-dimethyl-oxazolidine

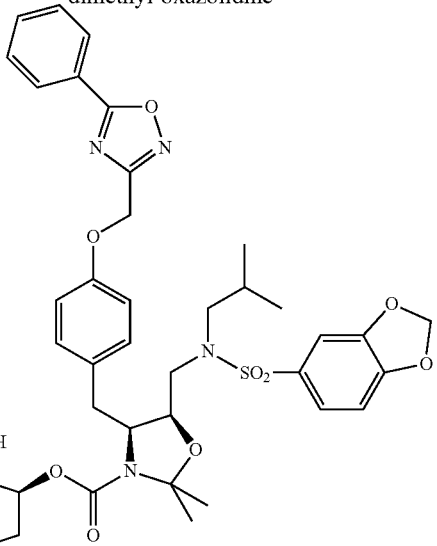

[1]: 3-chloromethyl-5-phenyl-1,2,4-oxadiazole; [2]: 20° C.; [3]: 24 hour; MS: 791 (M+).

Step 2

(3R,3aS,6aR)-Hexahydrofuro[2,3-b]furan-3-yl-N((1S,2R)-1-[4-(5-phenyl-1,2,4-oxadiazolo-3-methyloxy)-benzyl]-3-i-butyl-[(3,4-methylenedioxyphenyl)sulfonyl]-amino-2-hydroxypropyl-carmamate (375)

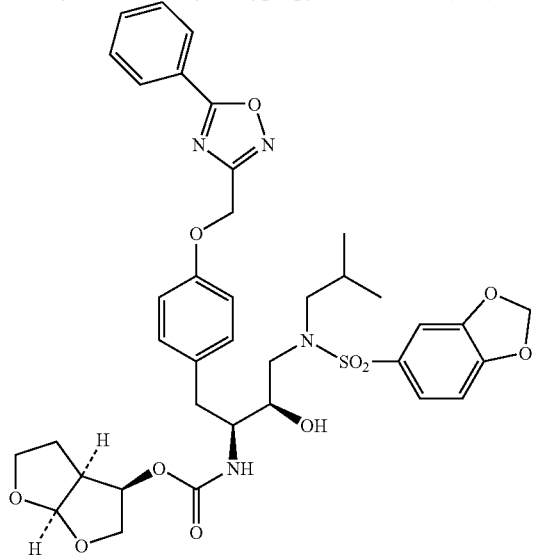

[1]: a, Hexane-EtOAc (1:3); [2]: 53%. ¹H NMR (DMSO-$d_6$): 0.77 (3H, d), 0.84 (3H, d), 1.18 (1H, m), 1.32 (1H, m), 1.94 (1H, m), 2.38 (1H, t), 2.68-2.78 (3H, m), 2.93-3.04 (2H, m), 3.46-3.60 (4H, m), 3.69 (1H, m), 3.81 (1H, dd), 4.82 (1H, dd), 5.01 (1H, m), 5.27 (2H, s(broad)), 5.42 (1H, d), 6.14 (2H, s), 6.91 (2H, d), 7.05 (1H, d), 7.12 (2H, d), 7.23 (2H, d), 7.29 (1H, d), 7.62 (2H, m), 7.71 (1H, m), 8.10 (2H, d); MS: 751 (M+).

[1]: c, Et$_2$O; [2] (Calc. from the product of Procedure 7): 92%.

¹H NMR (DMSO-$d_6$): δ 0.74 (3H, d), 0.80 (3H, d), 1.16 (1H, m), 1.25 (1H, m), 1.91 (1H, m), 2.33 (1H, t), 2.64-2.73 (3H, m), 2.88-2.99 (2H, m), 3.44 (1H, m), 3.50-3.56 (3H, m), 3.62 (1H, m), 3.77 (1H, dd), 4.78 (1H, dd), 4.97 (1H, s(broad)) 5.16 (2H, s), 5.40 (1H, d), 6.11 (2H, s), 6.86 (2H, d), 7.01 (1H, d), 7.06 (2H, d), 7.19 (2H, d), 7.26 (1H, d), 7.46 (2H, m), 7.50 (1H, d), 7.88 (3H, m); MS: 733 (M+).

Example 160

Step 1

(3R,3aS,6aR)-hexahydrofuro[2,3-b]furan-3-yl (4S,5R)-5-{[(1,3-benzodioxol-5-ylsulfonyl)(isobutyl)amino]methyl}-2,2-dimethyl-4-[4-(2-naphthylmethoxy)benzyl]-1,3-oxazolidine-3-carboxylate

Step 1

(3R,3aS,6aR)-hexahydrofuro[2,3-b]furan-3-yl (4S,5R)-5-{[(1,3-benzodioxol-5-ylsulfonyl)(isobutyl)amino]methyl}-2,2-dimethyl-4-{4-[(3-methylbenzyl)oxy]benzyl}-1,3-oxazolidine-3-carboxylate

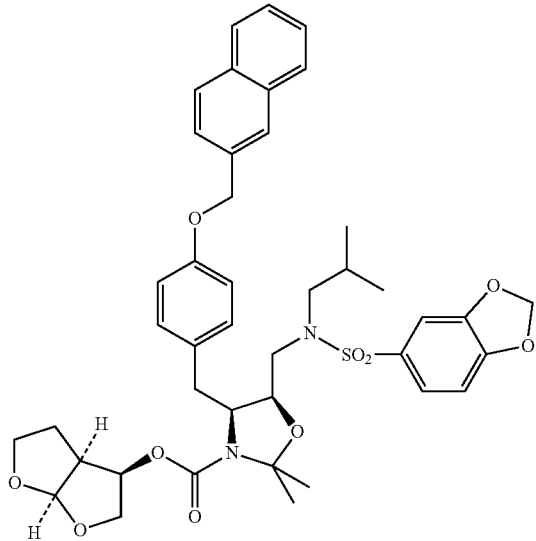

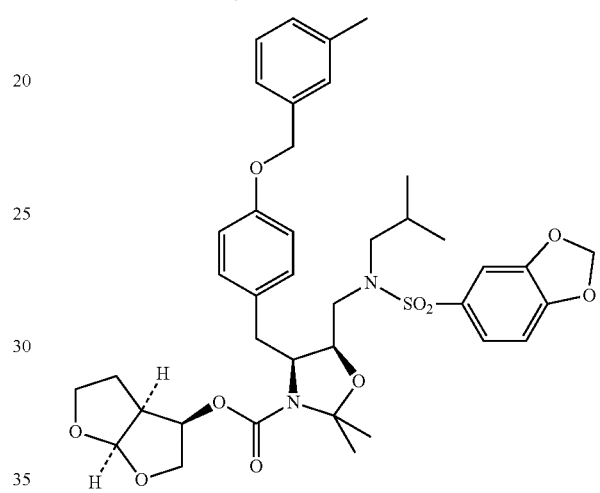

[1]: 2-(bromomethyl)napthalene; [2]: 20° C.; [3]: 12 hour; MS: 773 (M+).

[1]: 3-bromomethyltoluene; [2]: 20° C.; [3]: 12 hour; MS: 737 (M+).

Step 2

(3R,3aS,6aR)-hexahydrofuro[2,3-b]furan-3-yl (1S,2R)-3-[(1,3-benzodioxol-5-ylsulfonyl)(isobutyl)amino]-2-hydroxy-1-[4-(2-naphthylmethoxy)benzyl]propylcarbamate (376)

Step 2

(3R,3aS,6aR)-hexahydrofuro[2,3-b]furan-3-yl (1S,2R)-3-[(1,3-benzodioxol-5-ylsulfonyl)(isobutyl)amino]-2-hydroxy-1-{4-[(3-methylbenzyl) oxy]benzyl}propylcarbamate (377)

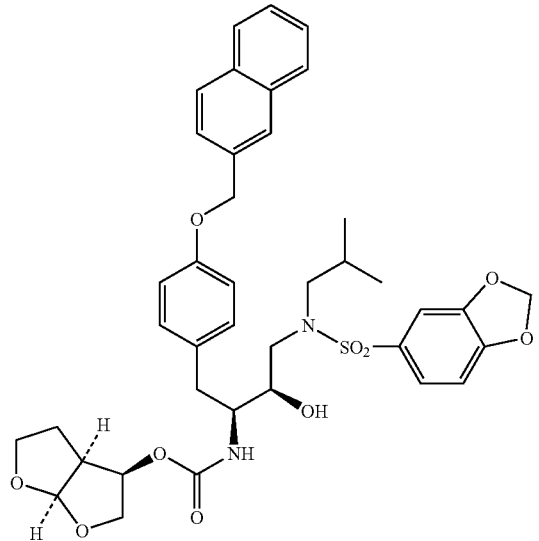

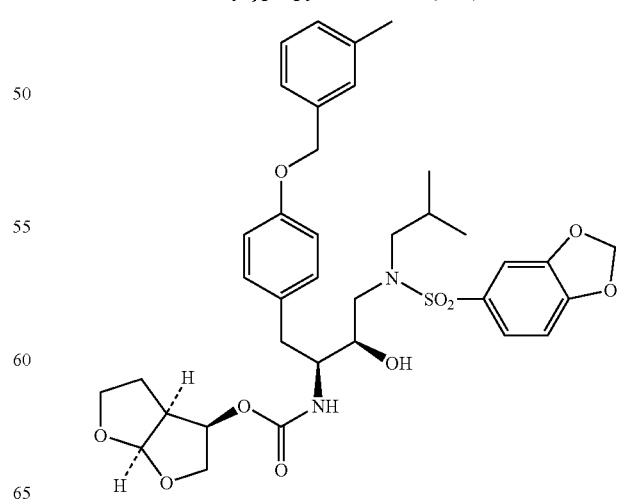

[1]: c, Et$_2$O; [2]: 72%.

$^1$H NMR (DMSO-d$_6$): δ 0.74 (3H, d), 0.80 (3H, d), 1.16 (1H, m) 1.28 (1H, m), 1.90 (1H, m), 2.25 (3H, s), 2.33 (1H, t), 2.64-2.73 (3H, m), 2.88-2.99 (2H, m), 3.44 (1H, m), 3.51-3.57 (3H, m), 3.64 (1H, m), 3.79 (1H, dd), 4.80 (1H, dd), 4.93 (2H, s), 4.97 (1H, s(broad)), 5.45 (1H, d), 6.11 (2H, s), 6.79 (2H, d), 7.00-7.08 (4H, m), 7.14-7.22 (4H, m), 7.25-7.27 (1H, m); MS: 697 (M+).

Example 162

Step 1

(3R,3aS,6aR)-hexahydrofuro[2,3-b]furan-3-yl (4S, 5R)-5-{[(1,3-benzodioxol-5-ylsulfonyl)(isobutyl)amino]methyl}-4-{4-[(3-fluorobenzyl)oxy]benzyl}-2,2-dimethyl-1,3-oxazolidine-3-carboxylate

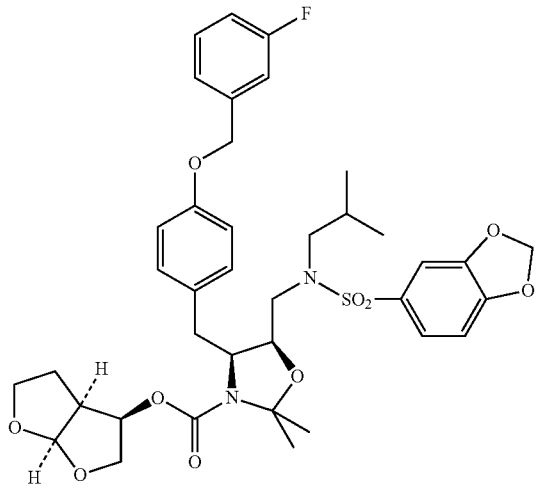

[1]: 3-fluorobenzylbromide; [2]: 20° C.; [3]: 12 hour; MS: 741 (M+).

Step 2

(3R,3aS,6aR)-hexahydrofuro[2,3-b]furan-3-yl (1S, 2R)-3-[(1,3-benzodioxol-5-ylsulfonyl)(isobutyl)amino]-1-{4-[(3-fluorobenzyl)oxy]benzyl}-2-hydroxypropylcarbamate (378)

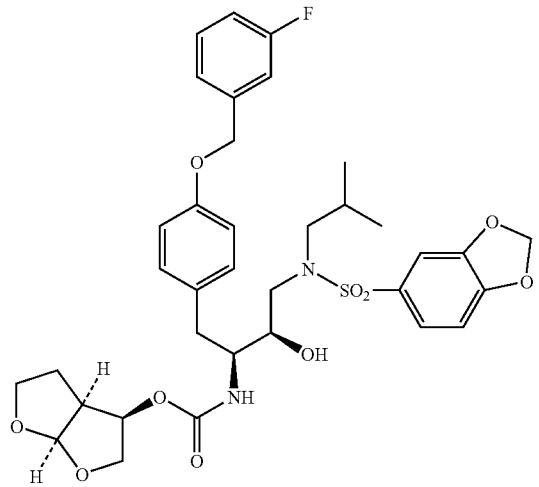

[1]: c, Et$_2$O; [2]: 67%.

$^1$H NMR (DMSO-d$_6$): δ 0.74 (3H, d), 0.80 (3H, d), 1.19 (1H, m) 1.25-1.33 (1H, m), 1.81-1.92 (1H, m), 2.33 (1H, t), 2.64-2.73 (3H, m), 2.88-3.00 (2H, m), 3.44 (1H, m), 3.51-3.58 (3H, m), 3.64 (1H, m), 3.79 (1H, dd), 4.80 (1H, dd), 4.98 (1H, d), 5.01 (2H, s), 5.45 (1H, d), 6.11 (2H, s), 6.81 (2H, d), 7.01-7.11 (4H, m), 7.19-7.27 (4H, m), 7.34-7.40 (1H, m); MS: 0.701 (M+).

Example 163

Step 1

(3R,3aS,6aR)-hexahydrofuro[2,3-b]furan-3-yl (4S, 5R)-5-{[(1,3-benzodioxol-5-ylsulfonyl)(isobutyl)amino]methyl}-4-{4-[(3,4-difluorobenzyl)oxy]benzyl}-2,2-dimethyl-1,3-oxazolidine-3-carboxylate

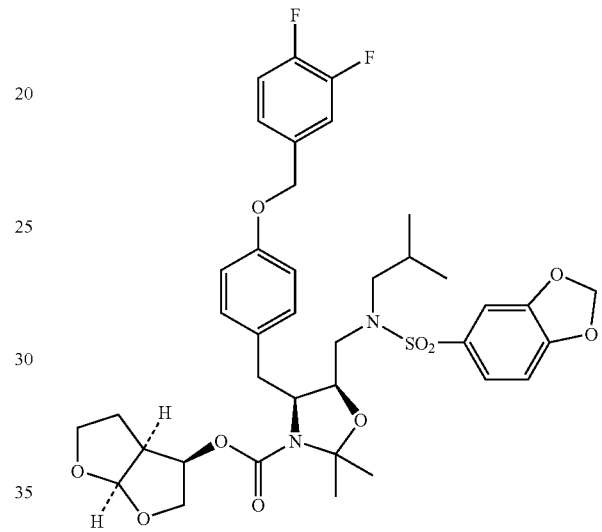

[1]: α-bromo-3,4-difluorotoluene; [2]: 20° C.; [3]: 12 hour; MS: 759 (M+).

Step 2

(3R,3aS,6aR)-hexahydrofuro[2,3-b]furan-3-yl (1S, 2R)-3[(1,3-benzodioxol-5-ylsulfonyl)(isobutyl)amino]-1-{4-[(3,4-difluorobenzyl) oxy]benzyl}-2-hydroxypropylcarbamate (379)

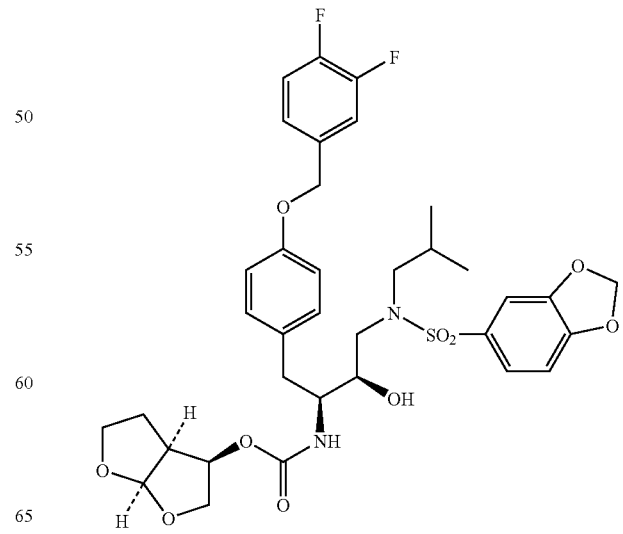

[1]: c, Et₂O; [2: 65%.
¹H NMR (DMSO-d₆): δ 0.74 (3H, d), 0.80 (3H, d), 1.17 (1H, m), 1.27-1.32 (1H, m), 1.88-1.92 (1H, m), 2.33 (1H, t), 2.64-2.73 (3H, m), 2.88-2.99 (2H, m), 3.42-3.46-1H, m), 3.53 (3H, m), 3.63 (1H, m), 3.78 (1H, dd), 4.80 (1H, dd), 4.97 (3H, s(broad)), 5.45 (1H, d), 6.11 (2H, s), 6.80 (2H, d), 7.00-7.07 (3H, m), 7.19-7.27 (3H, m), 7.35-7.46 (2H, m); MS: 719 (M+).

Example 164

Step 1

(3R,3aS,6aR)-hexahydrofuro[2,3-b]furan-3-yl (4S, 5R)-5-{[(1,3-benzodioxol-5-ylsulfonyl)(isobutyl)amino]methyl}-4-{4-[(3,5-difluorobenzyl)oxy]benzyl}-2,2-dimethyl-1,3-oxazolidine-3-carboxylate

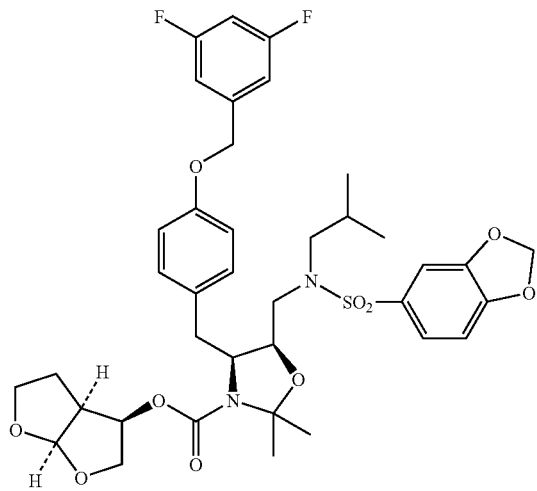

[1]: 3,5-difluorobenzylbromide; [2]: 20° C.; [3]: 12 hour; MS: 759 (M+).

Step 2

(3R,3aS,6aR)-hexahydrofuro[2,3-b]furan-3-yl (1S, 2R)-3-[(1,3-benzodioxol-5-ylsulfonyl)(isobutyl)amino]-1-{4-[(3,5-difluorobenzyl)oxy]benzyl}-2-hydroxypropylcarbamate (380)

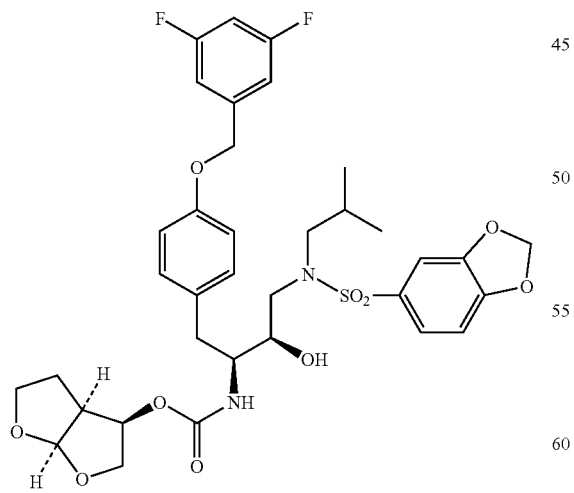

[1]: c, Et₂O; [2]:40 9.
¹H NMR (DMSO-d₆): δ 0.74 (3H, d), 0.80 (3H, d), 1.16-1.19 (1H, m), 1.30 (1H, m), 1.89-1.92 (1H, m), 2.34 (1H, t), 2.64-2.73 (3H, m), 2.88-2.99 (2H, m), 3.42-3.46 (1H, m), 3.51-3.58 (3H, m), 3.64 (1H, m), 3.79 (1H, dd), 4.80 (1H, dd), 4.98 (1H, d), 5.03 (2H, s), 5.45 (1H, d), 6.11 (2H, s), 6.81 (2H, d), 7.01-7.15 (6H, m)) 7.19-7.27 (2H, m); MS: 719 (M+).

Example 165

Step 1

(3R,3aS,6aR)-hexahydrofuro[2,3-b]furan-3-yl (4S, 5R)-5-{[(1,3-benzodioxol-5-ylsulfonyl)(isobutyl)amino]methyl}-4-{4-[(4-cyanobenzyl)oxy]benzyl}-2,2-dimethyl-1,3-oxazolidine-3-carboxylate

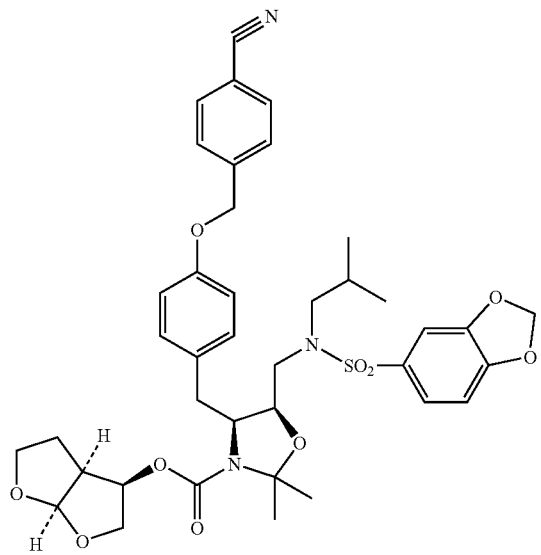

[1]: p-cyanobenzylbromide; [2]: 20° C.; [3]: 12 hour; MS: 748 (M+).

Step 2

(3R,3aS,6aR)-hexahydrofuro[2,3-b]furan-3-yl (1S, 2R)-3-[(1,3-benzodioxol-5-ylsulfonyl)(isobutyl)amino]-1-{4-[(4-cyanobenzyl) oxy]benzyl}-2-hydroxypropylcarbamate (381)

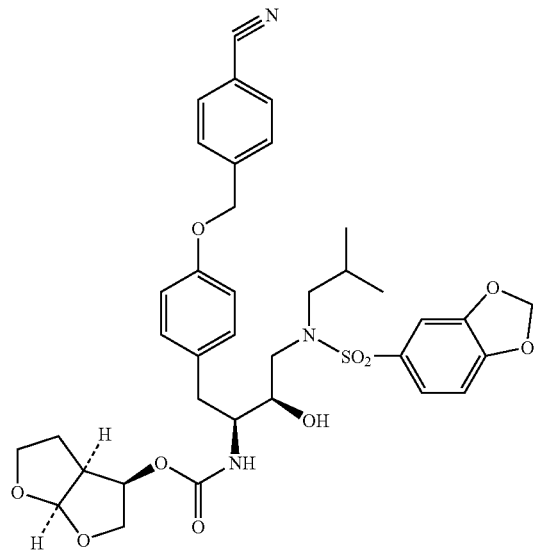

[1]: b, Hexane-EtOAc (1:3); [2]: 47%.
$^1$H NMR (DMSO-d$_6$): δ 0.75 (3H, d), 0.81 (3H, d), 1.13-1.30 (2H, m), 1.87-1.94 (1H, u), 2.34 (1H, m), 2.62-2.73 (3H, m), 2.89-3.00 (2H, m), 3.43-3.48 (1H, m), 3.51-3.57 (3H, m), 3.61-3.64 (1H, m), 3.79 (1H, dd), 4.80 (1H, dd), 4.99 (1H, d) 5.11 (2H, s), 5.45 (1H, d), 6.12 (2H, s), 6.82 (2H, d), 7.01-7.08 (3H, m), 7.19-7.28 (2H, m), 7.52 (2H, d), 7.81 (2H, d); MS: 708 (M+).

[1]: b, Hexane-EtOAc (1:3); [2]:47%.
$^1$H-NMR (DMSO-d$_6$): δ 0.75 (3H, d), 0.81 (3H, d), 1.19 (1H, m), 1.31-1.37 (1H, m), 1.91 (1H, m), 2.35 (1H, t), 2.65-2.74 (3H, m), 2.90-3.00 (2H, m), 3.44-3.49 (1H, m), 3.54 (3H, m), 3.66-3.70 (1H, m), 3.79 (1H, dd), 4.81 (1H, dd), 5.00 (1H, d), 5.12 (2H, s), 5.45 (1H, d), 6.12 (2H, s), 6.85 (2H, d), 7.01-7.28 (5H, m), 7.51 (1H, m), 7.62-7.71 (2H, m), 7.85 (1H, d); MS: 708 (M+).

Example 166

Step 1

(3R,3aS,6aR)-hexahydrofuro[2,3-b]furan-3-yl (4S,5R)-5-{[(1,3-benzodioxol-5-ylsulfonyl)(isobutyl)amino]methyl}-4-{4-[(2-cyanobenzyl)oxy]benzyl}-2,2-dimethyl-1,3-oxazolidine-3-carboxylate

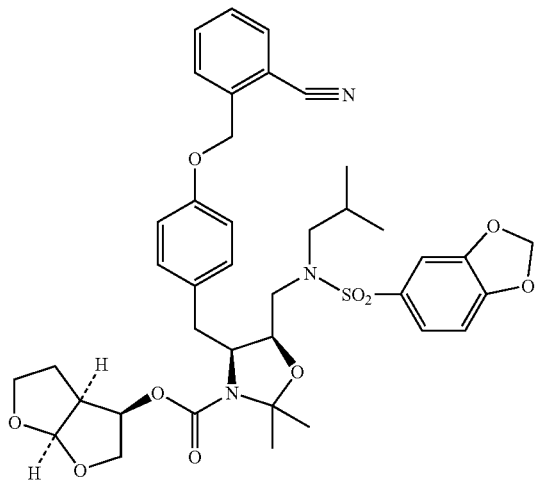

[1]: o-cyanobenzylbromide; [2]: 20° C.; [3]: 12 hour; MS: 748 (M+).

Step 2

(3R,3aS,6aR)-hexahydrofuro[2,3-b]furan-3-yl (1S,2R)-3-[(1,3-benzodioxol-5-ylsulfonyl)(isobutyl)amino]-1-{4-[(2-cyanobenzyl)oxy]benzyl}-2-hydroxypropylcarbamate (382)

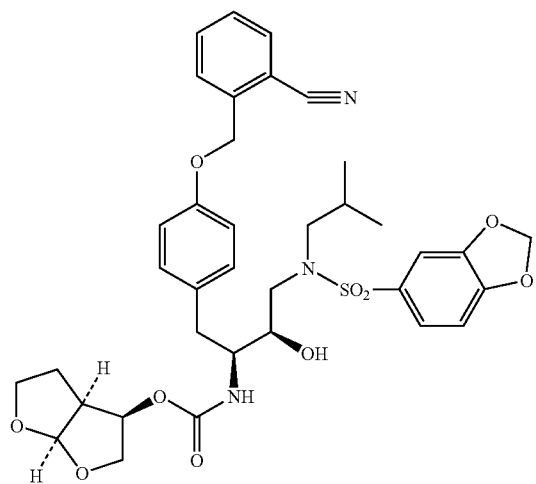

Example 167

Step 1

(3R,3aS,6aR)-hexahydrofuro[2,3-b]furan-3-yl (4S,5R)-5-{[(1,3-benzodioxol-5-ylsulfonyl)(isobutyl)amino]methyl}-2,2-dimethyl-4-{4-[(4-nitrobenzyl)oxy]benzyl}-1,3-oxazolidine-3-carboxylate

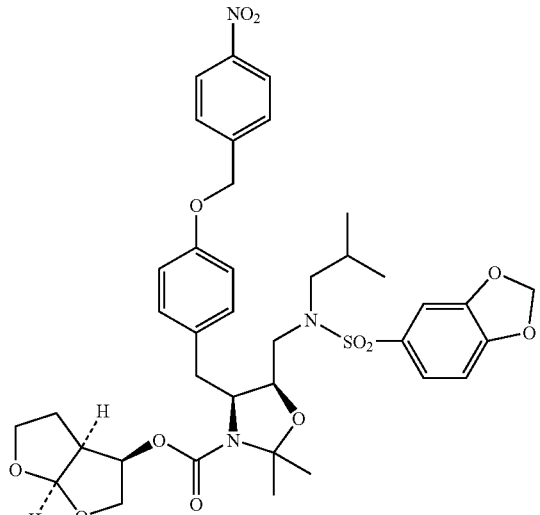

[1]: 4-nitrobenzylbromide; [2]: 20° C.; [3]: 3 hour; MS: 768 (M+).

Step 2

(3R,3aS,6aR)-hexahydrofuro[2,3-b]furan-3-yl (1S,2R)-3-[(1,3-benzodioxol-5-ylsulfonyl)(isobutyl)amino]-2-hydroxy 1-{4-[(4-nitrobenzyl)oxy]benzyl}propylcarbamate (383)

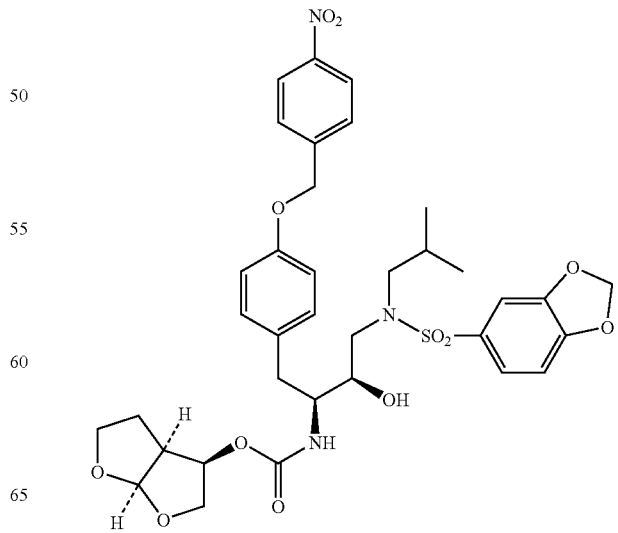

[1]: b, Hexane-EtOAc (1:2); [2]: 50%.
$^1$H NMR (DMSO-$d_6$): δ 0.79 (3H, d), 0.85 (3H, d), 1.24-1.34 (1H, m), 1.95 (1H, m), 2.39 (1H, t), 2.75 (3H, m), 2.93-3.05 (2H, m), 3.34 (1H, m), 3.50-3.68 (5H, m), 3.83 (1H, dd), 4.83 (1H, dd), 5.02 (1H, d), 5.22 (2H, s), 5.48 (1H, d), 6.16 (2H, s), 6.88 (2H, d), 7.05-7.13 (3H, m), 7.24 (2H, m), 7.31 (1H, d), 7.70 (2H, d), 8.24 (2H, d); MS: 728 (M+).

[1]: b, Hexane-EtOAc (1:2); [2]: 44%.
$^1$H-NMR (DMSO-$d_6$): 0.75 (3H, d), 0.81 (3H, d), 1.12-1.17 (11H, m), 1.24-1.30 (1H, m), 1.80-1.94 (1H, m), 2.34 (1H, t), 2.65-2.74 (3H, m), 2.89-3.00 (2H, m), 3.26 (1H, m), 3.43-3.48 (1H, m), 3.51-3.57 (3H, m), 3.61-3.64 (1H, m), 3.79 (1H, dd), 4.80 (1H, dd), 4.99 (1H, d), 5.17 (2H, s), 5.44 (1H, d), 6.12 (2H, s), 6.85 (2H, d), 7.02 (1H, d), 7.08 (2H, d), 7.20-7.22 (2H, m), 7.26 (1H, dd), 7.64 (1H, t), 7.85 (1H, d), 8.14 (1H, dd), 8.25 (1H, s); MS: 728 (M+).

Example 168

Step 1

(3R,3aS,6aR)-hexahydrofuro[2,3-b]furan-3-yl (4S,5R)-5-{[(1,3-benzodioxol-5-ylsulfonyl)(isobutyl)amino]methyl}-2,2-dimethyl-4-{4-[(3-nitrobenzyl)oxy]-benzyl}-1,3-oxazolidine-3-carboxylate

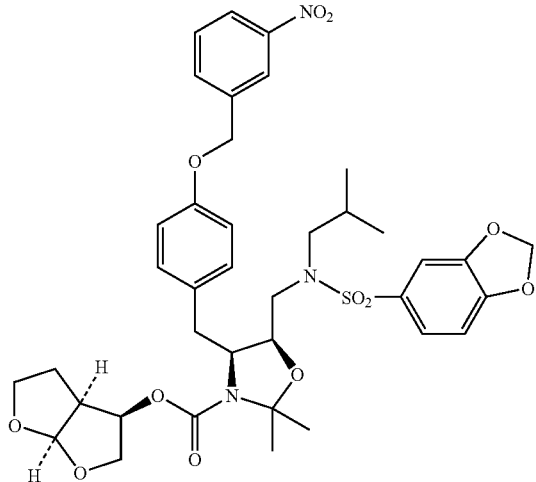

[1]: 3-nitrobenzylbromide; [2]: 20° C.; [3]: 3 hour; MS: 768 (M+).

Step 2

(3R,3aS,6aR)-hexahydrofuro[2,3-b]furan-3-yl (1S,2R)-3-[(1,3-benzodioxol-5-ylsulfonyl)(isobutyl)amino]-2-hydroxy-1-{4-[(3-nitrobenzyl)oxy]benzyl}propylcarbamate (384)

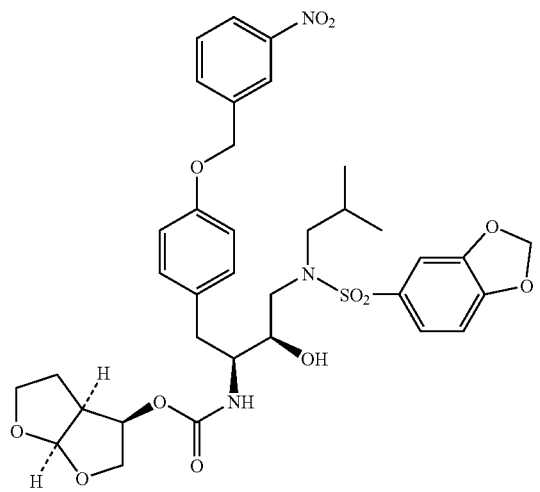

Example 169

Step 1

(3R,3aS,6aR)-hexahydrofuro[2,3-b]furan-3-yl (4S,5R)-5-{[(1,3-benzodioxol-5-ylsulfonyl)(isobutyl)amino]methyl}-4-{4-[(3,5-dimethyl-4-isoxazolyl)methoxy]benzyl}-2,2-dimethyl-1,3-oxazolidine-3-carboxylate

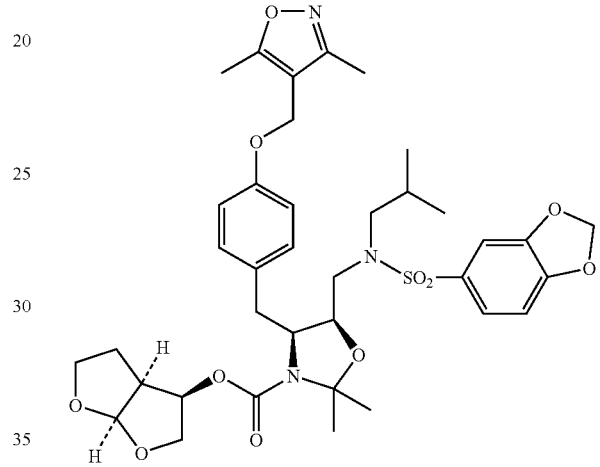

[1]: 4-(chloromethyl)-3,5-dimethylisoxazole; [2]: 20° C.; [3]: 12 hour; MS: 742 (M+).

Step 2

(3R,3aS,6aR)-hexahydrofuro[2,3-b]furan-3-yl (1S,2R)-3-[(1,3-benzodioxol-5-ylsulfonyl)(isobutyl)amino]-1-{4-[(3,5-dimethyl-4-isoxazolyl)methoxy]benzyl}-2-hydroxypropylcarbamate (385)

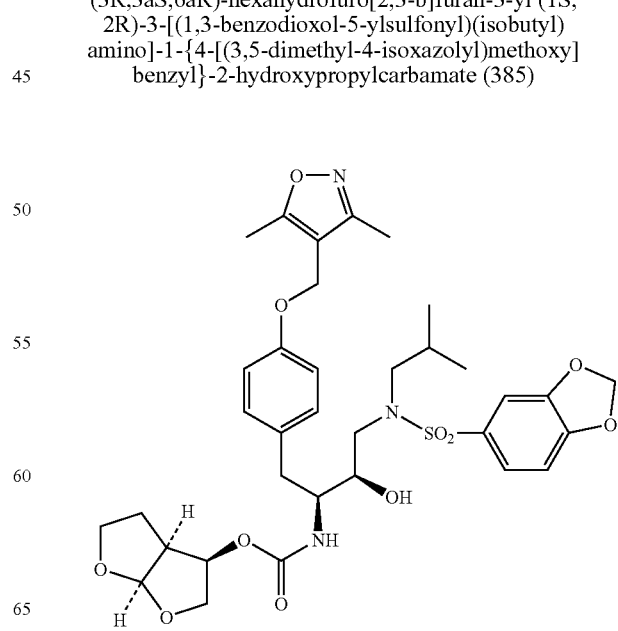

[1]: b, Hexane-EtOAc (1:3); [2]: 49%.
1H-NMR (DMSO-$d_6$): δ 0.75 (3H, d), 0.81 (3H, d), 1.19 (1H, m), 1.34 (1H, m), 1.94 (1H, m), 2.14 (3H, s), 2.32 (3H, s), 2.65-2.74 (3H, m), 2.93 (2H, m), 3.44 (1H, m), 3.52-3.57 (3H, m), 3.69 (1H, m), 3.78-3.82 (1H, m), 4.78-4.83 (3H, m), 4.99-5.00 (1H, m), 5.48 (1H, m), 6.12 (2H, s), 6.81 (2H, d), 7.03 (1H, d), 7.07 (2H, d), 7.20-7.28 (3H, m); MS: 702 (M+).

Example 170

Step 1

(3R,3aS,6aR)-hexahydrofuro[2,3-b]furan-3-yl (4S, 5R)-5-{[(1,3-benzodioxol-5-ylsulfonyl)(isobutyl) amino]methyl}-4-{4-[(5-chloro-1,2,3-thiadiazol-4-yl)methoxy]benzyl}-2,2-dimethyl-1,3-oxazolidine-3-carboxylate

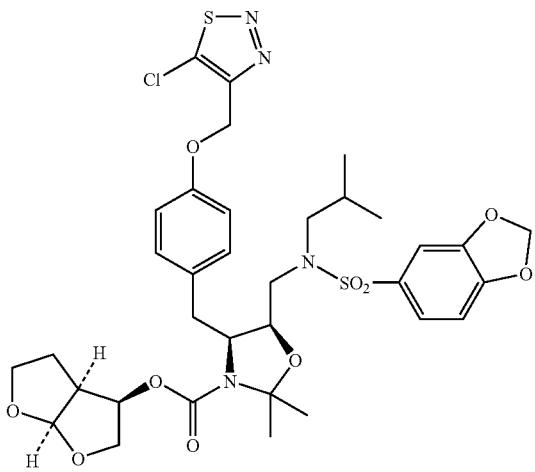

[1]: 5-chloro-4-(chloromethyl)1,2,3-thiadiazole; [2]: 20° C.; [3]: 12 hour; MS: 765 (M+).

Step 2

(3R,3aS,6aR)-hexahydrofuro[2,3-b]furan-3-yl (1S, 2R)-3-[(1,3-benzodioxol-5-ylsulfonyl)(isobutyl) amino]-1-{4-[(5-chloro-1,2,3-thiadiazol-4-yl)methoxy]benzyl}-2-hydroxypropylcarbamate (386)

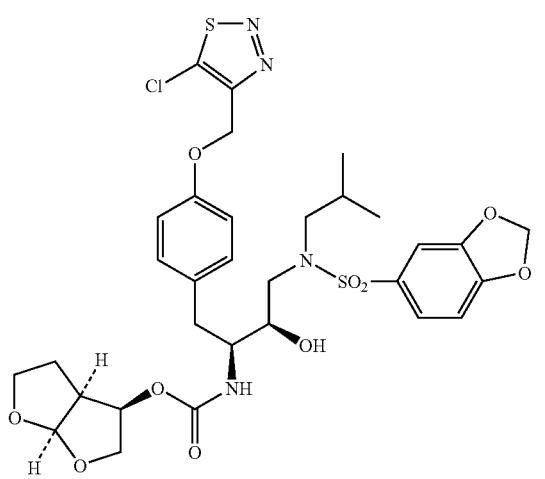

[1]: b, Hexane-EtOAc (1:3); [2]: 38%.
1H NMR (DMSO-$d_6$): δ 0.75 (3H, d), 0.81 (3H, d), 1.19 (1H, m), 1.32 (1H, m), 1.94 (1H, m), 2.25 (1H, m), 2.67-2.74 (3H, m), 2.91-3.01 (2H, m), 3.46 (1H, m), 3.52-3.56 (3H, m), 3.66-3.70 (1H, m), 3.80 (1H, dd), 4.81 (1H, dd), 5.00 (1H, d), 5.35 (2H, s), 5.46 (1H, d), 6.12 (2H, s), 6.90 (2H, d), 7.03 (1H, d), 7.10 (2H, d), 7.20-7.22 (2H, m), 7.26-7.31 (1H, m); MS: 725 (M+).

Example 171

Step 1

(3R,3aS,6aR)-hexahydrofuro[2,3-b]furan-3-yl (4S, 5R)-5-{[(1,3-benzodioxol-5-ylsulfonyl)(isobutyl) amino]methyl}-4-[4-(1-benzothien-3-ylmethoxy) benzyl]-2,2-dimethyl-1,3-oxazolidine-3-carboxylate

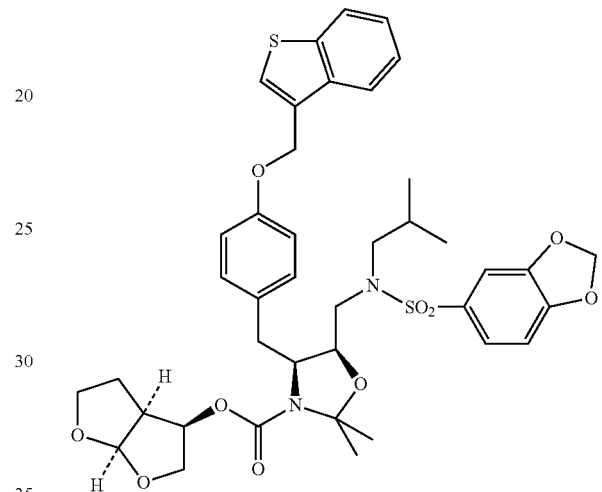

[1]: 3-(chloromethyl)-1-benzothiophene; [2]: 20° C.; [3]: 12 hour.

Step 2

(3R,3aS,6aR)-hexahydrofuro[2,3-b]furan-3-yl (1S, 2R)-3-[(1,3-benzodioxol-5-ylsulfonyl)(isobutyl) amino]-1-[4-(1-benzothien-3-ylmethoxy)benzyl]-2-hydroxypropylcarbamate (387)

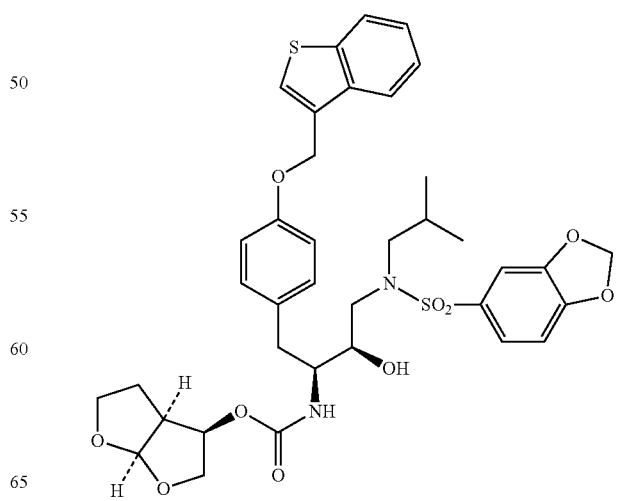

[1]: b, Hexane-EtOAc (1:3); [2]): 8.9%.
¹H NMR (DMSO-d₆): δ 0.75 (3H, d), 0.81 (3H, d), 1.15-1.19 (1H, m), 1.30 (1H, m), 1.90-1.93 (1H, m), 2.35 (1H, t), 2.65-2.74 (3H, m), 2.90-3.00 (2H, m), 3.27 (1H, m), 3.44-3.49 (1H, m), 3.52-3.58 (3H, m), 3.63-3.67 (1H, m), 3.80 (1H, dd), 4.81 (1H, dd), 5.00 (1H, d), 5.24 (2H, s), 5.45 (1H, d), 6.12 (2H, s), 6.89 (2H, d), 7.02 (1H, d), 7.08 (2H, d), 7.20-7.22 (2H, m), 7.26-7.28 (1H, m), 7.33-7.39 (2H, m), 7.80-7.83 (2H, m), 7.95-7.97 (1H, m); MS: 739 (M+).

Example 172

Step 1

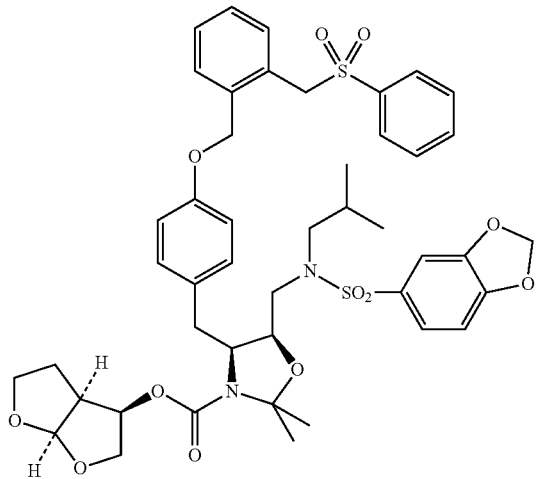

(3R,3aS,6aR)-hexahydrofuro[2,3-b]furan-3-yl (4S,5R)-5-{[(1,3-benzodioxol-5-ylsulfonyl)(isobutyl)amino]methyl}-2,2-dimethyl-4-[4-({2-[(phenylsulfonyl)methyl]benzyl}oxy)benzyl]-1,3-oxazolidine-3-carboxylate

[1]: 1-(bromomethyl)-2-[(phenylsulfonyl)methyl]benzene; [2]: 20° C.; [3]: 12 hour.

Step 2

(3R,3aS,6aR)-hexahydrofuro[2,3-b]furan-3-yl (1S,2R)-3-[(1,3-benzodioxol-5-ylsulfonyl)(isobutyl)amino]-2-hydroxy-1-[4-{(2-[(phenylsulfonyl)methyl]benzyl}oxy)benzyl]propylcarbamate (388)

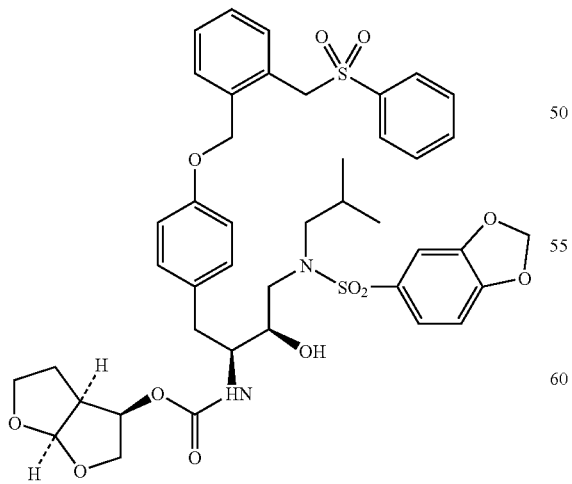

[1]: b, Hexane-EtOAc (1:1); [2]:16%.
¹H NMR (DMSO-d₆): δ 0.75 (3H, d), 0.81 (3H, d), 1.19 (1H, m), 1.31 (1H, m), 1.90-1.94 (1H, m), 2.35 (1H, t), 2.61-2.74 (3H, m), 2.90-3.01 (2H, m), 3.46 (1H, m), 3.52-3.56 (3H, m), 3.66 (1H, m), 3.79 (1H, dd), 4.75 (2H, s), 4.79-4.84 (1H, m), 4.99-5.02 (3H, m), 5.45 (1H, d), 6.12 (2H, s), 6.79 (2H, d), 7.01-7.08 (4H, m), 7.02 (2H, d), 7.23-7.32 (3H, m), 7.40 (1H, d), 7.54-7.61 (2H, m), 7.68-7.76 (3H, m); MS: 837 (M+).

Example 173

Step 1

(3R,3aS,6aR)-hexahydrofuro[2,3-b]furan-3-yl (4S,5R)-5-{[(1,3-benzodioxol-5-ylsulfonyl)(isobutyl)amino]methyl}-4-(4-{[5-(3,5-dimethyl-4-isoxazolyl)-1,2,4-oxadiazol-3-yl]methoxy}benzyl)-2,2-dimethyl-1,3-oxazolidine-3-carboxylate

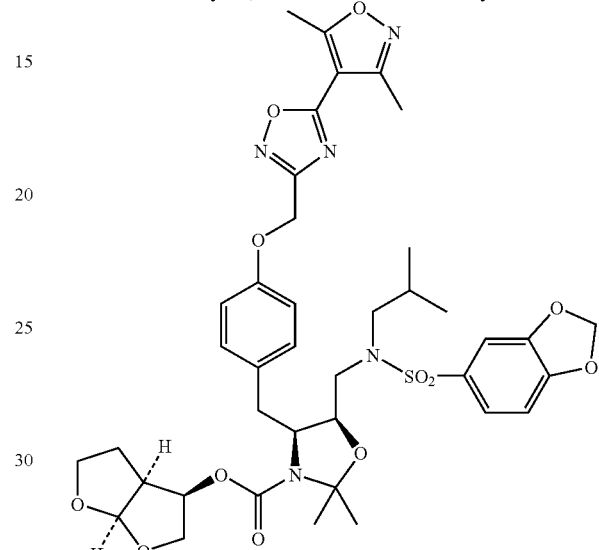

[1]: 3-(chloromethyl)-5-(3,5-dimethyl-4-isoxazolyl)-1,2,4-oxadiazole; [2]: 20° C.; [3]: 1 hour.

Step 2

(3R,3aS,6aR)-hexahydrofuro[2,3-b]furan-3-yl (1S,2R)-3-[(1,3-benzodioxol-5-ylsulfonyl)(isobutyl)amino]-1-(4-{[5-(3,5-dimethyl-4-isoxazolyl)-1,2,4-oxadiazol-3-yl]methoxy}benzyl)-2-hydroxypropylcarbamate (389)

[1]: b, Hexane-EtOAc (1:3); [2]:4%

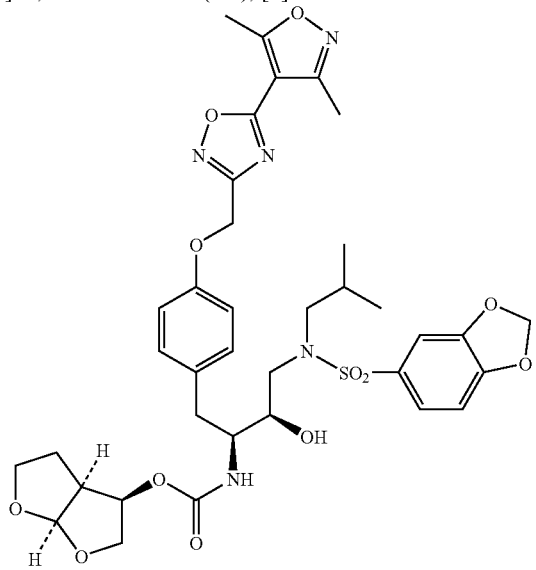

¹H NMR (DMSO-d₆); δ 0.74 (3H, d), 0.81 (3H, d), 1.13-1.28 (2H, m), 1.90 (1H, m), 2.31-2.37 (2H, m), 2.71 (6H, m), 2.90-3.00 (2H, m), 3.46-3.53 (4H, m), 3.64 (1H, m), 3.78 (1H, m), 4.80 (1H, m), 5.01 (1H, m), 5.23 (2H, m), 6.11 (2H, s), 6.88 (2H, d), 7.02 (1H, dd), 7.09 (1H, d), 7.19-7.22 (2H, m), 7.26 (1H, d); MS: 770 (M+).

Example 174

Step 1

(3R,3aS,6aR)-hexahydrofuro[2,3-b]furan-3-yl (4S,5R)—S-{[(1,3-benzodioxol-5-ylsulfonyl)(isobutyl)amino]methyl}-4-(4-{[5-(2-methoxyphenyl)-1,2,4-oxadiazol-3-yl]methoxy}benzyl)-2,2-dimethyl-1,3-oxazolidine-3-carboxylate

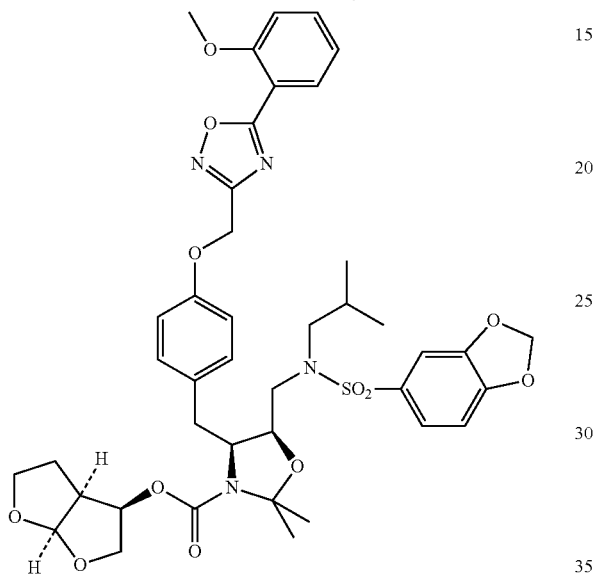

[1]: 3-(chloromethyl)-5-(2-methoxyphenyl)-1,2,4-oxadiazole; [2]: 20° C.; [3]: 1 hour.

Step 2

(3R,3aS,6aR)-hexahydrofuro[2,3-b]furan-3-yl (1S,2R)-3-[(1,3-benzodioxol-5-ylsulfonyl)(isobutyl)amino]-2-hydroxy-1-(4-{[5-(2-methoxyphenyl)-1,2,4-oxadiazol-3-yl]methoxy}benzyl) propylcarbamate (390)

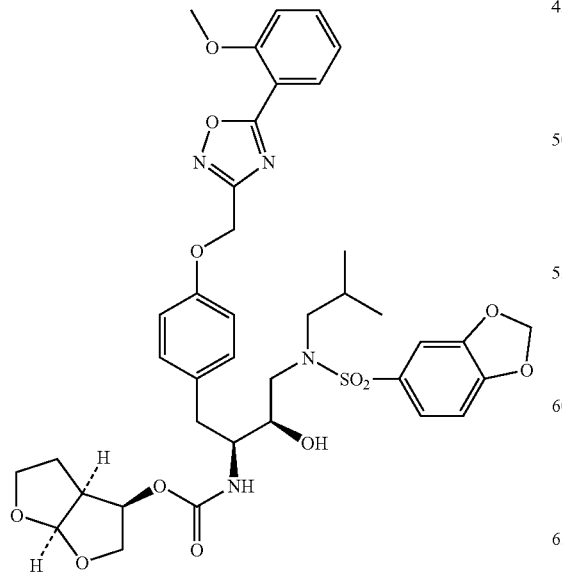

[1]: b, Hexane-EtOAc (1:2); [2]:24%.

¹H NMR (DMSO-d₆): δ 0.75 (3H, d), 0.81 (3H, d), 1.12-1.19 (1H, m), 1.26-1.37 (1H, m), 1.90-1.93 (1H, m), 2.28-2.38 (1H, m), 2.62-2.74 (3H, m), 2.90-3.00 (2H, m), 3.45 (1H, m), 3.51-3.55 (3H, m), 3.64-3.69 (1H, m), 3.78 (1H, dd), 3.88 (3H, s), 4.79 (1H, dd), 5.00 (1H, d), 5.22 (2H, s), 5.40 (1H, d), 6.12 (2H, s), 6.88 (2H, d), 7.02 (1H, d), 7.08-7.12 (3H, m), 7.20-7.23 (2H, m), 7.26 (2H, d), 7.63 (1H, t), 7.94 (1H, d); MS: 781 (M+).

Example 175

Step 1

(3R,3aS,6aR)-hexahydrofuro[2,3-b]furan-3-yl (4S,5R)-5-{[(1,3-benzodioxol-5-ylsulfonyl)(isobutyl)amino]methyl}-4-(4-{[5-(4-methoxyphenyl)-1,2,4-oxadiazol-3-yl]methoxy}benzyl)-2,2-dimethyl-1,3-oxazolidine-3-carboxylate

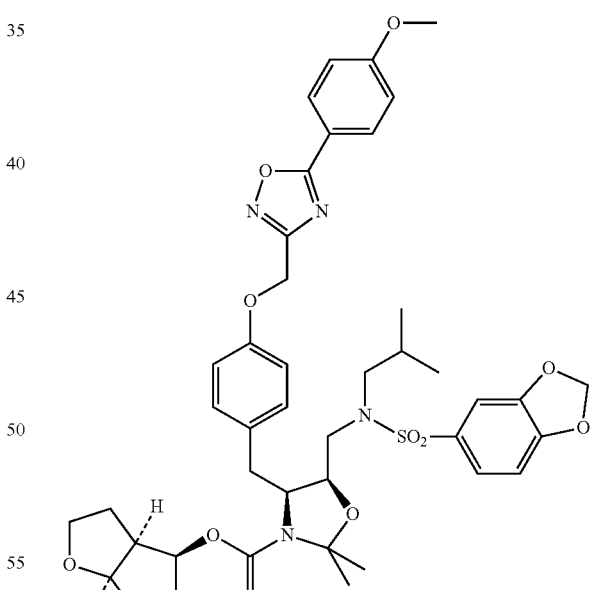

[1]: 3-(chloromethyl)-5-(4-methoxyphenyl)-1,2,4-oxadiazole; [2]: 20° C.; [3]: 1 hour.

Step 2

(3R,3aS,6aR)-hexahydrofuro[2,3-b]furan-3-yl (1S, 2R)-3-[(1,3-benzodioxol-5-ylsulfonyl)(isobutyl)amino]-2-hydroxy-1-(4-{[5-(4-methoxyphenyl)-1,2,4-oxadiazol-3-yl]methoxy}benzyl)propylcarbamate (391)

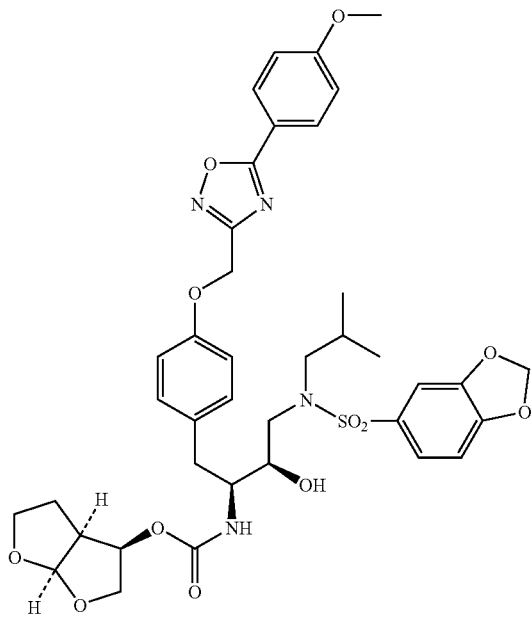

[1]: a, Hexane-EtOAc (1:5); [2]: 44%.
¹H NMR (DMSO-d₆): δ 0.75 (3H, d), 0.81 (3H, d), 1.12-1.19 (1H, m), 1.24-1.36 (1H, m), 1.91 (1H, m), 2.32-2.38 (1H, m), 2.62-2.74 (3H, m), 2.9-3.00 (2H, m), 3.46 (1H, m), 3.51-3.55 (3H, m), 3.66 (1H, m), 3.76-3.79 (1H, m), 3.82 (3H, m), 4.79 (1H, dd), 5.00 (1H, d), 5.20 (1H, s), 5.40 (1H, d), 6.12 (2H, s), 6.88 (2H, d), 7.02 (1H, d), 7.08-7.13 (3H, m), 7.20-7.23 (2H, m), 7.26 (1H, d), 8.02 (2H, d); MS: 781 (M+).

Example 176

Step 1

(3R,3aS,6aR)-hexahydrofuro[2,3-b]furan-3-yl (4S, 5R)-5-{[(1,3-benzodioxol-5-ylsulfonyl)(isobutyl)amino]methyl}-4-{4-[(2'-cyano[1,1-biphenyl]-4-yl)methoxy]benzyl}-2,2-dimethyl-1,3-oxazolidine-3-carboxylate

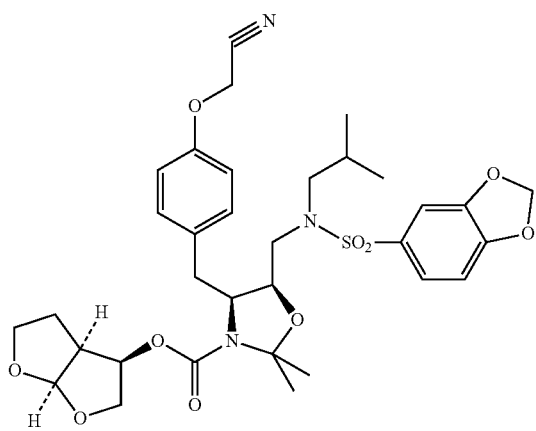

[1]: 4'-(bromomethyl) [1,1'-biphenyl]-2-carbonitrile; [2]: 20° C.; [3]: 3 hour; MS: 824 (M+).

Step 2

(3R,3aS,6aR)-hexahydrofuro[2,3-b]furan-3-yl (1S, 2R)-3-[(1,3-benzodioxol-5-ylsulfonyl)(isobutyl)amino]-1-{4-[(2'-cyano[1,1-biphenyl]-4-yl)methoxy]benzyl}-2-hydroxypropylcarbamate (392)

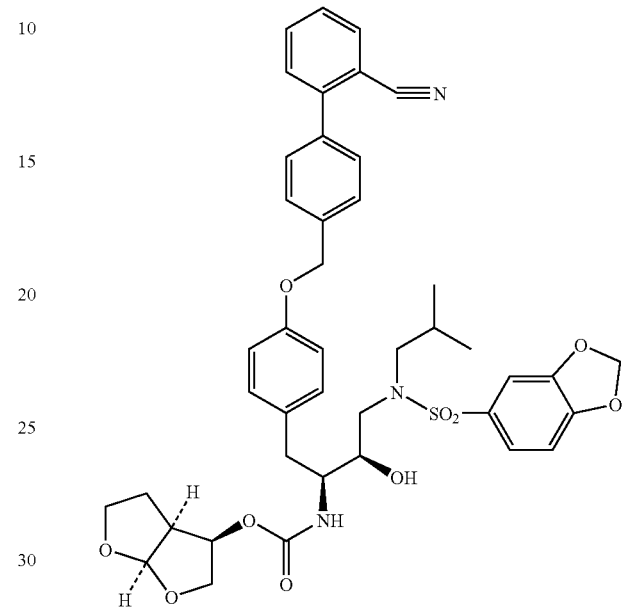

[1]: b, Hexane-EtOAc (1:2); [2]:54%.
¹H NMR (DMSO-d₆): δ 0.75 (3H, d), 0.81 (3H, d), 1.11 (1H, m), 1.26-1.38 (1H, m), 1.92 (1H, m), 2.32-2.38 (1H, m), 2.65-2.75 (3H, m), 2.90-3.01 (2H, m), 3.30 (1H, m), 3.46 (1H, m), 3.52-3.56 (3H, m), 3.66 (1H, m), 3.79 (H, dd), 4.81 (1H, dd), 4.99 (1H, d), 5.08 (2H, s), 5.44 (1H, d), 6.12 (2H, s); 6.86 (2H, d), 7.02 (1H, d), 7.08 (2H, d), 7.20-7.22 (2H, m), 7.27 (1H, dd), 7.52-7.60 (6H, m), 7.75 (1H, t), 7.91 (1H, d); MS: 784 (M⁺).

Example 177

Step 1

(3R,3aS,6aR)-hexahydrofuro[2,3-b]furan-3-yl (4S, 5R)-5-{[(1,3-benzodioxol-5-ylsulfonyl)(isobutyl)amino]methyl}-4-[4-(cyanomethoxy)benzyl]-2,2-dimethyl-1,3-oxazolidine-3-carboxylate

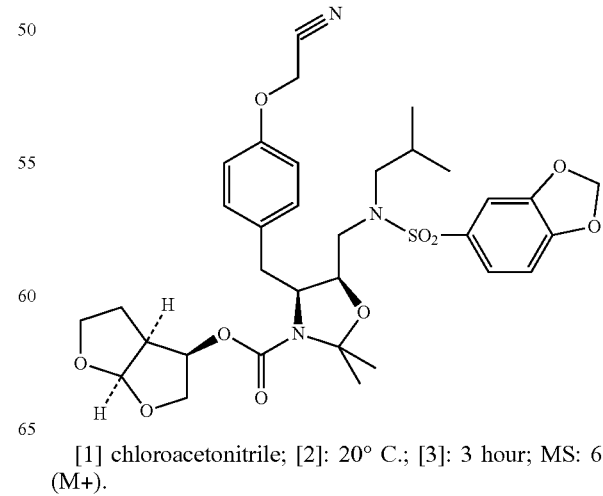

[1] chloroacetonitrile; [2]: 20° C.; [3]: 3 hour; MS: 672 (M+).

319

Step 2

(3R,3aS,6aR)-hexahydrofuro[2,3-b]furan-3-yl (1S, 2R)-3-[(1,3-benzodioxol-5-ylsulfonyl)(isobutyl) amino]-1-[4-(cyanomethoxy)benzyl]-2-hydroxypropylcarbamate (393)

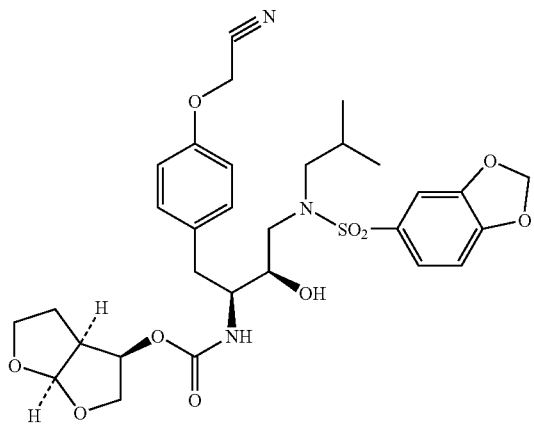

[1]: c, Hexane-EtOAc (50:1); [2]; 48%.
$^1$H NMR (DMSO-d$_6$): δ 0.75 (3H, d), 0.81 (3H, d), 1.20 (1H, m), 1.36-1.41 (1H, m), 1.91 (1H, m), 2.31-2.37 (1H, m), 2.65-2.74 (3H, m), 2.89-3.00 (2H, m), 3.43 (1H, m), 3.52-3.60 (2H, m), 3.71 (1H, m), 3.78-3.82 (1H, m), 4.29-4.34 (2H, m), 4.79-4.84 (1H, m), 5.00 (1H, d), 5.46 (11H, d), 6.12 (2H, s), 6.76 (2H, d), 7.01-7.07 (3H, m), 7.20-7.28 (1H, m), 7.26 (1H, m), 7.33 (1H, m), 7.45 (1H, m); MS: 632 (M+).

Example 178

Step 1

(3R,3aS,6aR)-hexahydrofuro[2,3-b]furan-3-yl (4S, 5R)-5-{[(1,3-benzodioxol-5-ylsulfonyl)(isobutyl) amino]methyl}-4-{4-[(1-benzyl-1H-imidazol-2-yl) methoxy]benzyl}-2,2-dimethyl-1,3-oxazolidine-3-carboxylate

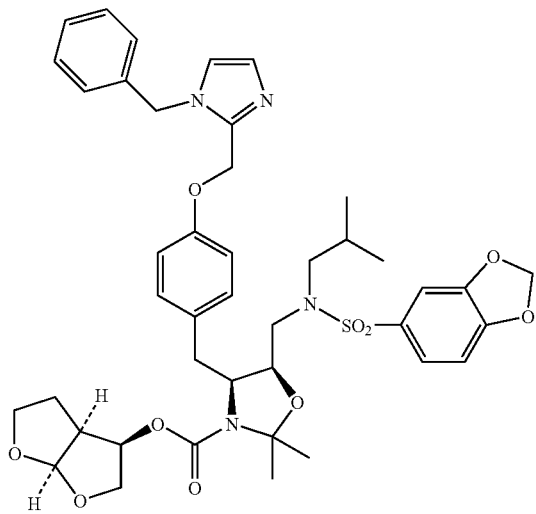

320

[1]: 1-benzyl-2-(chloromethyl)-1H-imidazole hydrochloride; [2]: 20° C.; [3]: 3 hour; MS: 803 (M+).

Step 2

(3R,3aS,6aR)-hexahydrofuro[2,3-b]furan-3-yl (1S, 2R)-3-[(1,3-benzodioxol-5-ylsulfonyl)(isobutyl) amino]-1-{4-[(1-benzyl-1H-imidazol-2-ylmethoxy] benzyl}-2-hydroxypropylcarbamate (394)

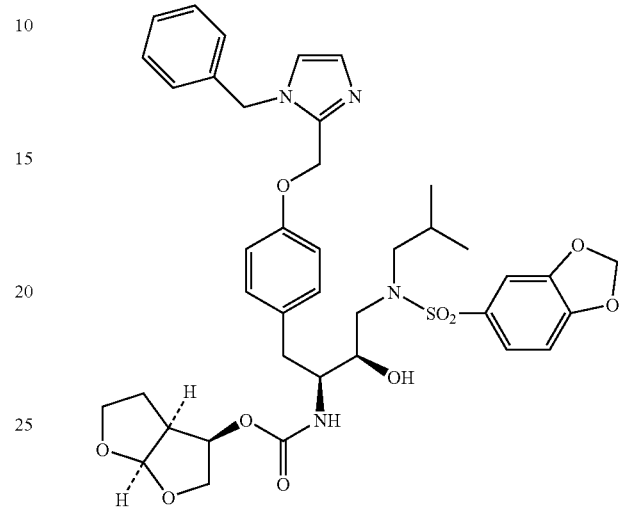

[1]: b, EtOAc-EtOH (1:1); [2]: 29%.
$^1$H-NMR (DMSO-d$_6$): δ 0.75 (3H, d), 0.81 (3H, d), 1.11-1.32 (2H, m), 1.88-1.94 (1H, m), 2.28-2.40 (1H, m), 2.65-2.74 (3H, m), 2.86-3.01 (2H, m), 3.26 (1H, m), 3.43-3.48 (1H, m), 3.52-3.57 (2H, m), 3.62-3.66 (1H, m), 3.79 (1H, dd), 4.81 (1H, dd), 4.95-5.05 (3H, m), 5.19 (2H, s), 5.45 (1H, d), 6.12 (2H, s), 6.80 (2H, d), 6.88 (1H, m), 7.02-7.06 (3H, m), 7.11-7.15 (2H, m), 7.20-7.30 (6H, m); MS: 763 (M+).

Example 179

Step 1

(3R,3aS,6aR)-hexahydrofuro[2,3-b]furan-3-yl (4S, 5R)-5-{[(1,3-benzodioxol-5-ylsulfonyl)(cyclopentylmethyl)amino]methyl}-4-[4-(benzyloxy)benzyl]-2,2-dimethyl-1,3-oxazolidine-3-carboxylate

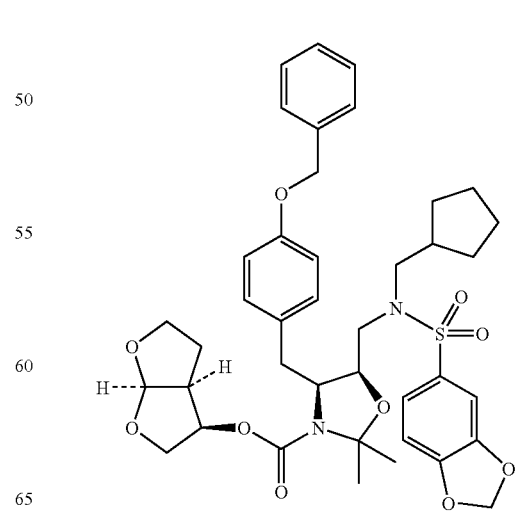

The reaction was carried out as described for N-(3R,3aS, 6aR)-Hexahydrofuro[2,3-b]furan-3-yl-oxycarbonyl-, (4S, 5R)-4-(4-benzyloxy-benzyl)-5-i-butyl-[(3,4-methylenedioxyphenyl)sulfonyl]-aminomethyl-2,2-dimethyl-oxazolidine. (Y=67%)

$^1$H NMR (CDCl$_3$): δ 1.08 (1H, m), 1.25 (2H, m), 1.45-1.80 (5H, m), 1.48 (3H, s), 1.64 (3H, s), 1.85 (2H, m), 2.25 (1H, m), 2.65-3.45 (7H, m), 3.80 (3H, m), 3.95 (1H, m), 4.21 (1H, m), 4.28 (1H, m), 4.88 (1H, dd), 5.03 (2H, s), 5.65 (1H, d), 6.01 (2H, s), 6.80-7.50 (12H, m).

Step 2

(3R,3aS,6aR)-hexahydrofuro[2,3-b]furan-3-yl (1S, 2R)-3-[(1,3-benzodioxol-5-ylsulfonyl) (cyclopentylmethyl)amino]-1-[4-(benzyloxy)benzyl]-2-hydroxypropylcarbamate (395)

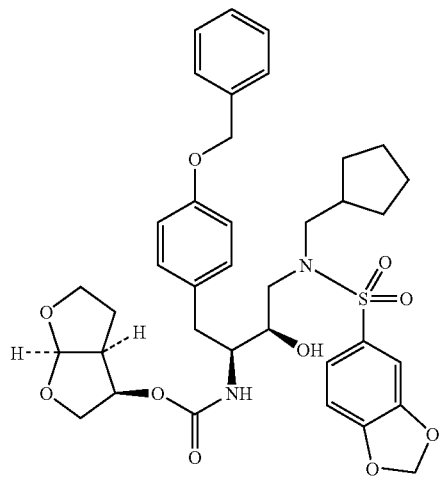 [SMILES: O=C(N[C@@H](Cc1ccc(OCc2ccccc2)cc1)[C@H](O)CN(CC1CCCC1)S(=O)(=O)c1ccc2c(c1)OCO2)O[C@H]1CO[C@H]2OCC[C@H]21]

The carbamate formation was carried out as described for (3R,3aS,6aR)-Hexahydrofuro[2,3-b]furan-3-yl-N((1S,2R)-1-(4-benzyloxy-benzyl)-3-i-butyl-[(3,4-methylenedioxyphenyl)sulfonyl]-amino-2-hydroxypropyl-carmamate. (Y=79%)

$^1$H NMR (DMSO-d$_6$): δ 1.05 (1H, m), 1.20 (1H, m), 1.30-1.70 (8H, m), 2.19 (1H, m), 2.36 (1H, t), 2.70-2.95 (4H, m), 3.10 (1H, dd), 3.40-3.60 (4H, m), 3.65 (1H, dd), 3.80 (1H, dd), 4.81 (1H, dd), 5.00 (3H, s+d), 5.46 (1H, m), 6.13 (2H, s), 6.83 (2H, d), 7.00-7.41 (1H, m). MS: 708 (M)+.

Example 180

Step 1 tert-butyl (1S,2R)-1-[4-(benzyloxy)benzyl]-3-[(cyclopentylmethyl)amino]-2-hydroxypropylcarbamate

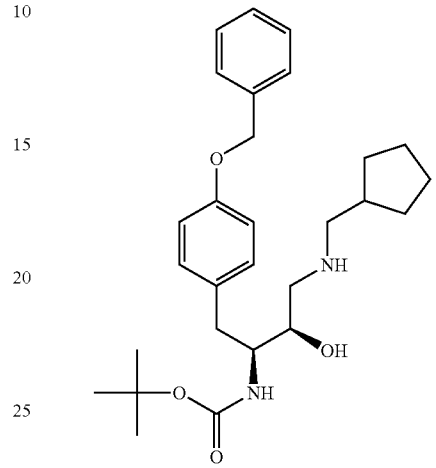

The reaction was carried out as described above except cyclopentylmethylamine was used in the reaction. (Y: 91%)

$^1$H NMR: (CDCl$_3$): δ 1.08-1.23 (2H, m), 1.34 (9H, s), 1.48-1.59 (4H, m), 1.72-1.77 (2H, m), 1.91-2.02 (1H, m), 2.45-2.54 (2H, m), 2.67 (2H, m), 2.77-2.82 (1H, m), 2.88 (1H, dd), 3.41 (1H, m), 3.73 (1H, m), 4.64 (1H, d), 5.01 (2H, s), 6.88 (2H, d), 7.12 (2H, d), 7.28-7.41 (4H, m).

Step 2 tert-butyl (1S,2R)-3-[(1,3-benzodioxol-5-ylsulfonyl) (cyclopentylmethyl)amino]-1-[4-(benzyloxy)benzyl]-2-hydroxypropylcarbamate

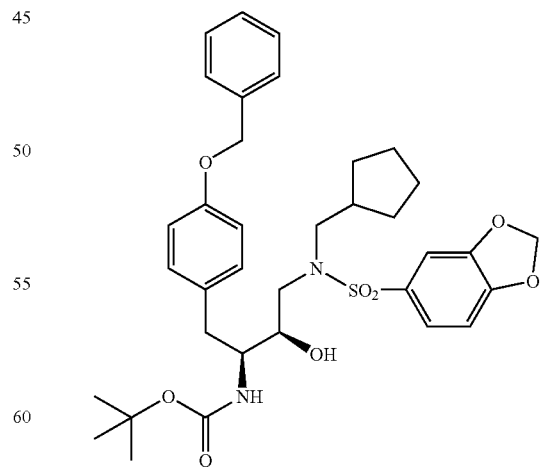

The reaction was carried out as described above except tert-butyl (1S,2R)-1-[4-(benzyloxy)benzyl]-3-[(cyclopentylmethyl)amino]-2-hydroxypropylcarbamate was used in the reaction. (Y: 88%)

323

This compound was used as is in the next step without additional purification.

Step 3

(3R,3aS,6aR)-hexahydrofuro[2,3-b]furan-3-yl (4S,5R)-5-{[(1,3-benzodioxol-5-ylsulfonyl)(cyclopentylmethyl)amino]methyl}-4-(4-hydroxybenzyl)-2,2-dimethyl-1,3-oxazolidine-3-carboxylate

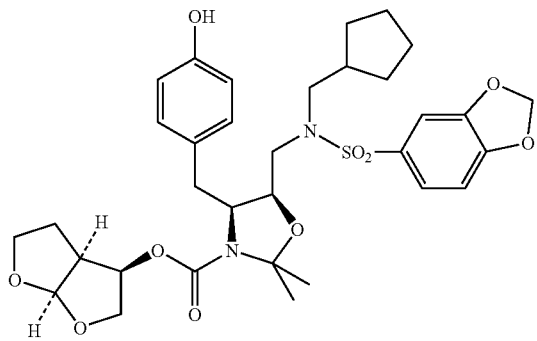

This reaction was carried out as described above except tert-butyl (1S,2R)-3-[(1,3-benzodioxol-5-ylsulfonyl)(cyclopentylmethyl)amino]-1-[4-(benzyloxy)benzyl]-2-hydroxypropylcarbamate was used in the reaction. (Y: 59%)
¹H NMR: (CDCl₃): δ 1.02-1.12 (1H, m), 1.20-1.33 (1H, m) 1.45-1.76 (5H, m), 1.47 (3H, s), 1.65 (3H, s), 1.87 (2H, m), 2.16-2.30 (1H, m), 2.66-2.70 (2H, m), 2.78-2.88 (2H, m) 2.98-3.04 (1H, m), 3.11-3.20 (1H, m), 3.37-3.41 (2H, m), 3.75-3.85 (2H, m), 3.91-3.96 (1H, m), 4.17-4.21 (1H, m), 4.26-4.28 (1H, m), 4.87 (1H, dd), 5.66 (1H, dd), 6.04 (2H, s), 6.74 (2H, d), 6.82 (1H, d), 6.96 (2H, d), 7.02 (1H, d), 7.04-7.07 (1H, m), 7.11 (1H, dd)

Step 4

General Procedure for the Aralkylation of (3R,3aS,6aR)-hexahydrofuro[2,3-b]furan-3-yl (4S,5R)-5-{[(1,3-benzodioxol-5-ylsulfonyl) (cyclopentylmethyl)amino]methyl}-4-(4-hydroxybenzyl)-2,2-dimethyl-1,3-oxazolidine-3-carboxylate This procedure was carried out as described before using aralkyl halide [1], stirring at the indicated temperature [2] for the indicated number of hours [3].

(3R,3aS,6aR)-hexahydrofuro[2,3-b]furan-3-yl (4S,5R)-5-{[(1,3-benzodioxol-5-ylsulfonyl)(cyclopentylmethyl) amino]methyl}-4-{4-[(3-cyanobenzyl)oxy]benzyl}-2,2-dimethyl-1,3-oxazolidine-3-carboxylate

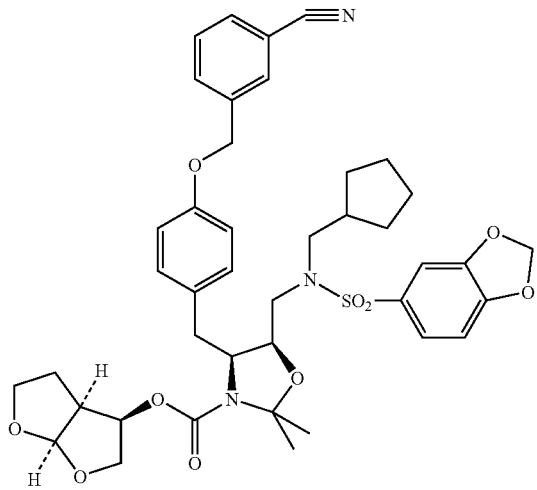

324

[1]: 3-cyanobenzyl bromide; [2]: 20° C.; [3]: 12 hour; MS: 774 (M+).

Step 5

General Procedure for the Deprotection

This reaction was carried out as before using HCl/dioxane (3R,3aS,6aR)-hexahydrofuro[2,3-b]furan-3-yl (1S,2R)-3-[(1,3-benzodioxol-5-ylsulfonyl)(cyclopentylmethyl)amino-]-1-{4-[(3-cyanobenzyl)oxy]benzyl}-2-hydroxypropylcarbamate (396)

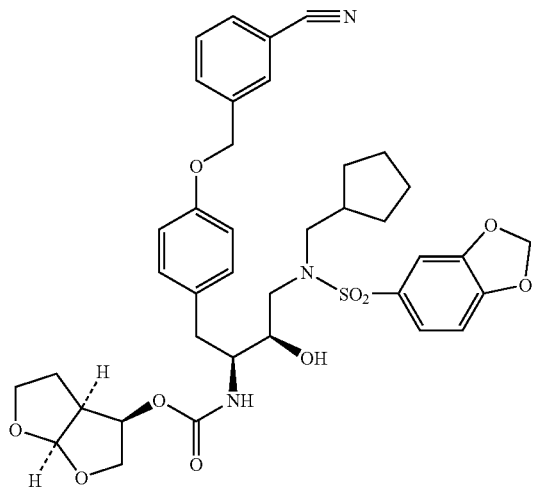

[1]: c, EtOAc-Hexane; [2]:60%.
¹H-NMR: (DMSO): δ 1.10 (1H, m), 1.17-1.32 (2H, m), 1.35-1.72 (5H, m), 2.21 (1H, m), 2.39 (1H, m), 2.74-3.00 (4H, m), 3.11-3.18 (1H, m), 3.46-3.62 (4H, m), 3.64-3.70 (1H, m), 3.84 (1H, dd), 4.85 (1H, dd), 5.03 (1H, m), 5.11 (2H, s), 5.50 (1H, d), 6.16 (2H, s), 6.87 (2H, d), 7.05-7.13 (3H, m), 7.25 (2H, d), 7.31 (1H, d), 7.60 (1H, t), 7.76-7.80 (2H, m), 7.88 (1H, s); MS: 734 (M+).

Example 181

Step 1

(3R,3aS,6aR)-hexahydrofuro[2,3-b]furan-3-yl (4S,5R)-5-{[(1,3-benzodioxol-5-ylsulfonyl) (cyclopentylmethyl) amino]methyl}-4-[4-(cyanomethoxy)benzyl]-2,2-dimethyl-1,3-oxazolidine-3-carboxylate

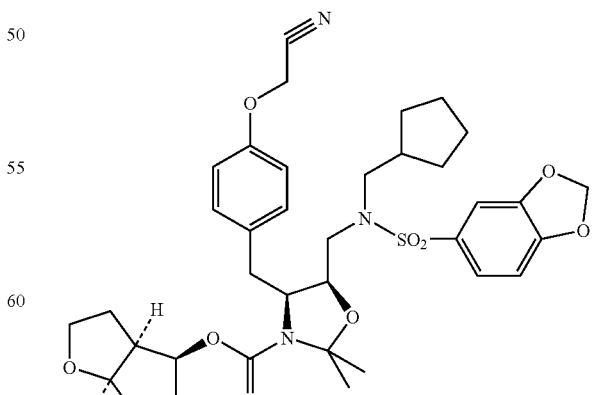

[1]: chloroacetonitrile; [2]: 20° C.; [3]: 12 hour; MS: 698 (M+).

Step 2

(3R,3aS,6aR)-hexahydrofuro[2,3-b]furan-3-yl (1S,2R)-3-[(1,3-benzodioxol-5-ylsulfonyl)(cyclopentyl-methyl)amino]-1-[4-(cyanomethoxy)benzyl]-2-hydroxypropylcarbamate (397)

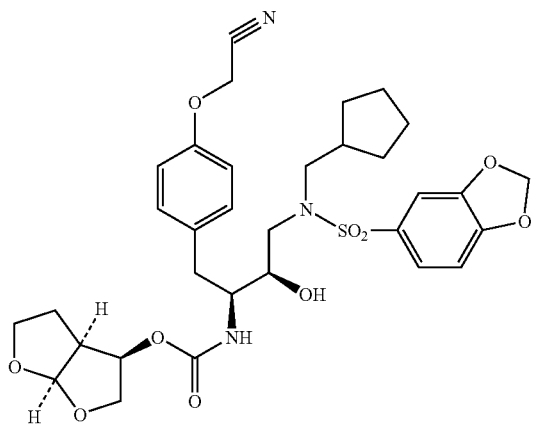

[1]: b, EtOAc-Hexane (2:1); [2]: 77%.
$^1$H NMR: (DMSO): δ 1.10 (1H, m), 1.24 (2H, m), 1.40-1.70 (7H, m), 2.20-2.26 (1H, m), 2.35-2.43 (1H, m), 2.78-2.98 (4H, m), 3.11-3.19 (1H, m), 3.48-3.51 (1H, m), 3.55-3.65 (3H, m), 3.73-3.78 (1H, m), 3.84 (1H, dd), 4.33 (2H, s), 4.85 (1H, dd), 5.02 (1H, d), 5.51 (1H, d), 6.16 (2H, s), 6.80 (2H, d), 7.05-7.12 (3H, m), 7.22-7.25 (1H, m), 7.31 (1H, dd), 7.36 (1H, m), 7.46 (1H, M); MS: 658 (M+).

Example 182

Step 1

(3R,3aS,6aR)-hexahydrofuro[2,3-b]furan-3-yl (4S,5R)-5-{[(1,3-benzodioxol-5-ylsulfonyl)(cyclopentyl-methyl) amino]methyl}-2,2-dimethyl-4-[4-(2-pyridinylmethoxy)benzyl]-1,3-oxazolidine-3-carboxylate

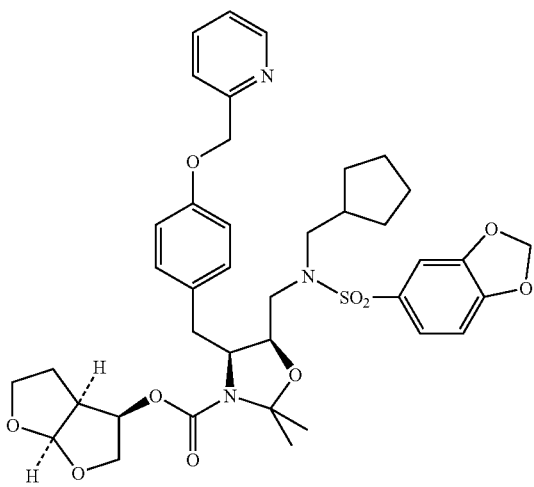

[1]: 2-picolylchloride HCl; [2]: 20° C.; [3]: 12 hour; MS: 750 (M+).

Step 2

(3R,3aS,6aR)-hexahydrofuro[2,3-b]furan-3-yl (1S,2R)-3-[(1,3-benzodioxol-5-ylsulfonyl) (cyclopentyl-methyl)amino]-2-hydroxy-1-[4-(2-pyridinyl-methoxy)benzyl]propylcarbamate (398)

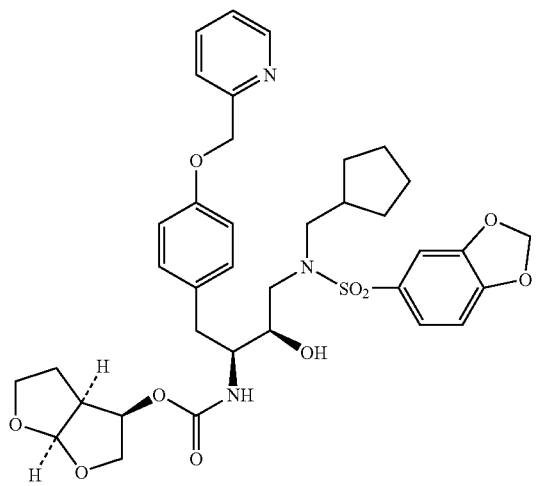

[1]: b, EtOAc; [2]: 47%.
$^1$H NMR: (DMSO): δ 1.14 (1H, m), 1.24 (2H, m), 1.40-1.70 (7H, m), 2.22 (1H, m), 2.39 (1H, m), 2.74-2.96 (4H, m), 3.10-3.15 (1H, m), 3.51-3.59 (4H, m), 3.63-3.70 (1H, m), 3.83 (1H, dd), 4.84 (1H, dd), 5.01 (1H, m), 5.10 (2H, s), 5.27 (1H, d), 6.15 (2H, s), 6.87 (2H, d), 7.04-7.12 (3H, m), 7.21-7.25 (2H, m), 7.30-7.34 (2H, m), 7.48 (1H, d), 7.81 (1H, t), 8.55 (1H, d); MS: 710 (M+).

Example 183

Anti-Viral Activity

We measured the enzyme inhibition constants of the compounds listed in Table I against HIV-1 protease using the methods of: B. Maschera et al., "Human Immunodeficiency Virus: Mutations in the Viral Protease that Confer Resistance to Saquinavir Increase the Dissociation Rate Constant for the Protease Saquinavir Complex,", J. Biol. Chem., 271, pp. 33231-35 (1996); and M. V. Toth et al., Int. J. Peptide Protein Res. 36, pp. 544-50 (1990)

Antiviral Activity Assay in MT4 Cells

Antiviral HIV activity and compound induced cytotoxicity were measured in parallel by means of a propidium iodide based procedure in the human T-cell lymphotropic virus transformed cell line MT4. Aliquots of the test compounds were serially diluted in medium (RPMI 1640, 10% fetal calf serum (FCS), and gentamycin) in 96-well plates (Costar 3598) using a Cetus Pro/Pette. Exponentially growing MT4 cells were harvested and centrifuged at 1000 rpm for 10 min in a Jouan centrifuge (model CR 4 12). Cell pellets were resuspended in fresh medium (RPMI 1640, 20% FCS, 20% IL-2, and gentamycin) to a density of $5×10^5$ cells/ml. Cell aliquots were infected by the addition of HIV-1 (strain IIIB) diluted to give a viral multiplicity of infection of 100×

TCID$_{50}$. A similar cell aliquot was diluted with medium to provide a mock-infected control. Cell infection was allowed to proceed for 1 hr at 37° in a tissue culture incubator with humidified 5% CO$_2$ atmosphere. After the 1 hr incubation the virus/cell suspensions were diluted 6-fold with fresh medium, and 125 µl of the cell suspension was added to each well of the plate containing pre-diluted compound. Plates were then placed in a tissue culture incubator with humidified 5% CO$_2$ for 5 days. At the end of the incubation period, 27 µl of 5% Nonidet-40 was added to each well of the incubation plate. After thorough mixing with a Costar multitip pipetter, 60 µl of the mixture was transferred to filter-bottomed 96-well plates. The plates were analyzed in an automated assay instrument (Screen Machine, Idexx Laboratories). The assay makes use of a propidium iodide dye to estimate the DNA content of each well.

REFERENCES

1. Averett, D. R. 1989. Anti-HIV compound assessment by two novel high capacity assays. *J. Viral. Methods* 23: 263-276.
2. Schwartz, O., et al. 1988. A rapid and simple calorimetric test for the study of anti-HIV agents. *AIDS Res. and Human Retroviruses,* 4(6):441-447.
3. Daluge, S. M., et al. 1994. 5-chloro-2'3'-deoxy-3' fluorouridine (935U83), a selective anti-human immuno-deficiency virus agent with an improved metabolic and toxicological profile. *Antimicro. Agents and Chemother.,* 38 (7):1590-1603.

The anti-viral potency in MT-4 cells of the compounds set forth in Tables 1 and 2 was determined using the above technique. The results are shown in Table A.

TABLE A

Antiviral Activity of Compounds of the Invention.

| Cmpd # | IC$_{50}$ |
|---|---|
| 5a | NA |
| 5b | NA |
| 5c | NA |
| 5d | NA |
| 5e | NA |
| 5f | NA |
| 5g | NA |
| 6e | NA |
| 10 | D |
| 11 | D |
| 12 | E |
| 13 | D |
| 14 | NA |
| 15 | D |
| 16 | D |
| 17 | D |
| 18 | C |
| 19 | E |
| 20 | C |
| 21 | C |
| 22 | C |
| 23 | C |
| 24 | C |
| 25 | C |
| 26 | A |
| 27 | D |
| 28 | E |
| 29 | C |
| 30 | C |
| 31 | B |
| 32 | C |
| 33 | C |
| 34 | D |
| 35 | C |
| 36 | C |
| 37 | C |
| 38 | A |
| 39 | NA |
| 40 | NA |
| 41 | NA |
| 42 | D |
| 43 | C |
| 44 | A |
| 46 | A |
| 47 | NA |
| 48 | B |
| 49 | B |
| 50 | C |
| 51 | B |
| 52 | B |
| 53 | B |
| 54 | B |
| 55 | A |
| 56 | C |
| 57 | B |
| 58 | E |
| 59 | NA |
| 60 | NA |
| 61 | NA |
| 67 | D |
| 68 | D |
| 69 | D |
| 70 | D |
| 71 | B |
| 72 | B |
| 73 | C |
| 74 | D |

In Table A, the following classifications have been employed:

A<0.001 µM 0.010>B>0.001 µM 0.100>C>0.010 µM

D>0.1 µM

"NA"=compound was not tested.

Anti-Viral Activity Against Resistant Viruses

EP13 and DS45701, two multi protease inhibitor resistant viruses were used to assess potency against mutant viruses. These viruses contain the following mutations relative to the consensus sequence of wild type virus:

D545701-14: Protease amino acid sequence: L10I, L19Q, K20R, E35D, M36I, S37N, M46I, I50V, I54V, I62V, L63P, A71V, V82A, L90M; reverse transcriptase amino acid sequence: E28K, K32E, V35I, T39S/T, E40D/V/Y/F, M41M/L, K43E, Y181Y/C EP13: Protease amino acid sequence: M46I, L63P, A71V, V82F/L, I84V; No reverse transcriptase mutations.

Reference data for the following protease inhibitors are (D545701-14; EP13):

Amprenavir™: >1000 nM; 600 nM

Indinavir™: 700M; 560 nM

Nelfinavir™: 690 nM; N/A

Ritonavir™: >10000 nM; >600 nM

Saguinavir™: 900 nM; N/A

Assays of the above mutant viruses were carried out as described above for the wild type virus and the results are shown below in Table B.

TABLE B

| Compound No. | Wildtype virus - $IC_{50}$ | EP13 mutant $IC_{50}$ | D545701-14 mutant - $IC_{50}$ |
|---|---|---|---|
| 52 | C | B | B |
| 53 | B | B | B |
| 54 | C | B | B |
| 55 | NA | B | B |
| 201 | NA | NA | NA |
| 202 | A | A | B |
| 203 | A | B | C |
| 204 | B | B | B |
| 205 | B | C | C |
| 206 | B | C | C |
| 207 | B | B | B |
| 208 | C | NA | NA |
| 209 | B | B | B |
| 210 | B | B | C |
| 211 | B | B | B |
| 212 | B | B | C |
| 213 | B | B | B |
| 214 | B | B | B |
| 215 | B | B | B |
| 216 | B | B | B |
| 217 | B | B | B |
| 218 | NA | NA | NA |
| 219 | B | B | B |
| 220 | NA | NA | NA |
| 221 | B | B | B |
| 222 | C | NA | NA |
| 223 | B | B | B |
| 224 | C | NA | NA |
| 225 | C | C | C |
| 226 | A | A | B |
| 227 | NA | NA | NA |
| 228 | C | NA | NA |
| 229 | C | B | B |
| 230 | C | B | B |
| 231 | B | B | B |
| 232 | B | B | NA |
| 233 | B | B | C |
| 234 | B | B | B |
| 235 | B | B | B |
| 236 | B | B | B |
| 237 | B | A | B |
| 238 | B | B | B |
| 239 | C | B | B |
| 240 | C | B | B |
| 241 | B | B | B |
| 242 | B | B | B |
| 243 | B | B | B |
| 244 | B | B | A |
| 245 | B | B | B |
| 246 | B | B | B |
| 247 | B | B | B |
| 248 | B | B | B |
| 249 | B | B | B |
| 250 | B | B | B |
| 251 | C | B | B |
| 252 | B | B | B |
| 253 | C | B | B |
| 254 | B | B | B |
| 255 | C | NA | NA |
| 256 | C | NA | NA |
| 257 | NA | NA | NA |
| 258 | C | NA | NA |
| 259 | C | B | B |
| 260 | B | B | B |
| 261 | B | B | B |
| 262 | B | B | B |
| 263 | B | B | B |
| 264 | C | C | NA |
| 265 | C | C | C |
| 266 | C | NA | NA |
| 267 | C | NA | NA |
| 268 | C | B | C |
| 269 | C | B | C |
| 270 | B | B | B |
| 271 | B | B | B |
| 272 | B | B | B |
| 273 | NA | NA | NA |
| 274 | C | B | C |
| 275 | C | B | C |
| 276 | NA | NA | NA |
| 277 | B | B | B |
| 278 | C | B | B |
| 279 | B | B | B |
| 280 | C | B | B |
| 281 | B | B | B |
| 282 | C | B | C |
| 283 | C | B | C |
| 284 | B | B | B |
| 285 | C | NA | NA |
| 286 | C | B | B |
| 287 | B | B | B |
| 288 | B | B | B |
| 289 | B | B | B |
| 290 | NA | NA | NA |
| 291 | NA | NA | NA |
| 292 | C | C | C |
| 293 | B | B | B |
| 294 | B | B | B |
| 295 | B | B | B |
| 296 | NA | NA | NA |
| 297 | C | C | NA |
| 298 | C | B | B |
| 299 | B | B | B |
| 300 | B | B | B |
| 301 | B | B | B |
| 302 | B | B | C |
| 303 | C | C | C |
| 304 | B | B | B |
| 305 | B | B | B |
| 306 | C | NA | NA |
| 307 | C | NA | NA |
| 308 | C | B | B |
| 309 | B | B | B |
| 310 | B | B | C |
| 311 | B | B | C |
| 312 | C | B | C |
| 313 | C | B | B |
| 314 | C | C | C |
| 315 | C | B | B |
| 316 | NA | NA | NA |
| 317 | B | B | B |
| 318 | B | B | B |
| 319 | B | B | B |
| 320 | B | B | B |
| 321 | B | B | B |
| 322 | B | B | B |
| 323 | B | B | B |
| 324 | B | B | B |
| 325 | C | NA | NA |
| 326 | B | C | C |
| 327 | NA | NA | NA |
| 328 | C | NA | NA |
| 329 | B | C | C |
| 330 | C | NA | NA |
| 331 | C | C | C |
| 332 | B | B | C |
| 333 | B | B | B |
| 334 | B | B | B |
| 335 | B | B | B |
| 336 | B | B | B |
| 337 | B | B | B |
| 338 | B | B | B |
| 339 | C | NA | NA |
| 340 | C | NA | NA |
| 341 | NA | NA | NA |
| 342 | C | C | C |
| 343 | NA | NA | NA |
| 344 | NA | NA | NA |
| 345 | NA | NA | NA |
| 346 | C | NA | NA |
| 347 | B | B | B |
| 348 | B | B | B |
| 349 | B | B | B |
| 350 | C | NA | NA |

TABLE B-continued

| Compound No. | Wildtype virus - $IC_{50}$ | EP13 mutant $IC_{50}$ | D545701-14 mutant - $IC_{50}$ |
|---|---|---|---|
| 351 | NA | NA | NA |
| 352 | A | A | B |
| 353 | A | A | B |
| 354 | C | NA | NA |
| 355 | C | C | C |
| 356 | B | B | A |
| 357 | C | B | C |
| 358 | C | C | C |
| 359 | C | C | C |
| 360 | NA | NA | NA |
| 361 | B | C | C |
| 362 | C | NA | NA |
| 363 | C | NA | NA |
| 364 | NA | NA | NA |
| 365 | B | B | B |
| 366 | B | B | B |
| 367 | A | A | B |
| 368 | A | A | B |
| 369 | B | NA | NA |
| 370 | A | B | B |
| 371 | C | B | C |
| 372 | B | B | C |
| 373 | B | B | C |
| 374 | B | B | B |
| 375 | B | B | C |
| 376 | B | C | C |
| 377 | B | B | C |
| 378 | B | B | C |
| 379 | B | B | B |
| 380 | B | B | C |
| 381 | B | B | B |
| 382 | B | B | B |
| 383 | B | B | B |
| 384 | B | B | B |
| 385 | B | B | C |
| 386 | B | B | C |
| 387 | B | B | B |
| 388 | B | B | B |
| 389 | B | B | B |
| 390 | B | B | C |
| 391 | B | B | B |
| 392 | B | B | B |
| 393 | C | C | C |
| 394 | B | B | B |
| 395 | B | B | B |
| 396 | B | B | B |
| 397 | C | B | B |
| 398 | NA | NA | NA |
| 399 | NA | NA | NA |
| 400 | NA | NA | NA |

In Table B, the following classifications have been employed:

A<0.001 µM 0.010>B>0.001 µM 0.100>C>0.010 µM

D>0.1 µM

"NA"=compound was not tested.

While we have hereinbefore presented a number of embodiments of this invention, it is apparent that our basic construction can be altered to provide other embodiments which utilize the methods of this invention. Therefore, it will be appreciated that the scope of this invention is to be defined by the claims appended hereto rather than the specific embodiments which have been presented hereinbefore by way of example.

The invention claimed is:

1. A compound of the formula (I):

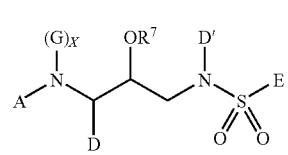

(I)

and pharmaceutically acceptable salts thereof; wherein:
A is selected from

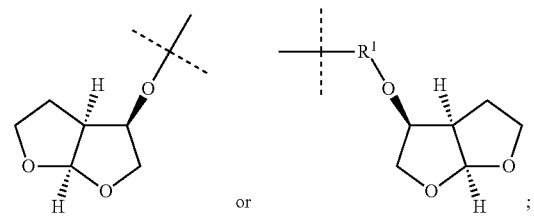

each $R^1$ is independently selected from —C(O)—, —S(O)$_2$—, —C(O)—C(O)—, —O—C(O)—, —O—S(O)$_2$, —NR$^2$—, —NR$^2$—S(O)$_2$—, —NR$^2$—C(O)— or —NR$^2$—C(O)—C(O)—;

each Ht is independently selected from $C_3$-$C_7$ cycloalkyl; $C_5$-$C_7$ cycloalkenyl; $C_6$-$C_{14}$ aryl; or a 5-7 membered saturated or unsaturated heterocycle, containing one or more heteroatoms selected from N, N(R$^2$), O, S and S(O)$_n$; wherein said aryl or said heterocycle is optionally fused to Q; and wherein any member of said Ht is optionally substituted with one or more substituents independently selected from oxo, —OR$^2$, SR$^2$, —R$^2$, —N(R$^2$)(R$^2$), —R$^2$—OH, —CN, —CO$_2$R$^2$, —C(O)—N(R$^2$)$_2$, —S(O)$_2$—N(R$^2$)$_2$, N(R$^2$)—C(O)R$^2$, —N(R$^2$)—C(O)O—R$^2$, —C(O)—R$^2$, —S(O)$_n$—R$^2$, —OCF$_3$, —S(O)$_n$-Q, methylenedioxy, —N(R$^2$)—S(O)$_2$(R$^2$), halo, —CF$_3$, —NO$_2$, Q, —OQ, —OR$^7$, —SR$^7$, —N(R$^2$)(R$^7$) or —N(R$^7$)$_2$;

each $R^2$ is independently selected from H, or $C_1$-$C_4$ alkyl optionally substituted with a 3-7 membered saturated, partially saturated or unsaturated carbocyclic ring system; or a 5-7 membered saturated, partially saturated or unsaturated heterocyclic ring containing one or more heteroatoms selected from 0, N, S, S(O)$_n$ or N(R$^{33}$); wherein any of said ring systems or N(R$^{33}$) is optionally substituted with 1 to 4 substituents independently selected from —X'—Y', —O-arylalkyl, —S-arylalkyl, —N(Y')$_2$, —N(H)-arylalkyl, —N(C$_1$-C$_4$ alkyl)-arylalkyl, oxo, —O—(C$_1$-C$_4$ alkyl), OH, C$_1$-C$_4$ alkyl, —SO$_2$H, —SO$_2$—(C$_1$-C$_4$ alkyl), —SO$_2$—NH$_2$, —SO$_2$—NH(C$_1$-C$_4$ alkyl), —SO$_2$—N(C$_1$-C$_4$ alkyl)$_2$, —NH$_2$, —NH(C$_1$-C$_4$ alkyl), —N(C$_1$-C$_4$ alkyl)$_2$, —NH—C(O)H, —N(C$_1$-C$_4$ alkyl)-C(O)H, —NH—C(O)—C$_1$-C$_4$ alkyl, —C$_1$-C$_4$ alkyl-OH, —OH, —CN, —C(O)OH, —C(O)O—C$_1$-C$_4$ alkyl, —C(O)—NH$_2$, —C(O)—NH(C$_1$-C$_4$ alkyl), —C(O)—N(C$_1$-C$_4$ alkyl)$_2$, halo or —CF$_3$;

X' is —O—, —S—, —NH—, —NHC(O)—, —NHC(O)O—, —NHSO$_2$—, or —N(C$_1$-C$_4$)alkyl-;

Y' is $C_1$-$C_{15}$ alkyl, $C_2$-$C_{15}$ alkenyl or alkynyl, wherein one to five carbon atoms in Y' are optionally substituted with $C_3$-$C_7$ cycloalkyl or $C_5$-$C_6$ cycloalkenyl, $C_6$-$C_{14}$ aryl or a 5-7 membered saturated or unsaturated heterocycle, containing one or more heteroatoms selected from N, NH, O, S and $S(O)_n$;

each $R^3$ is independently selected from H, Ht, $C_1$-$C_6$ alkyl, $C_2$-$C_6$ alkenyl, $C_2$-$C_6$ alkynyl, $C_3$-$C_6$ cycloalkyl or $C_5$-$C_6$ cycloalkenyl; wherein any member of said $R^3$, except H, is optionally substituted with one or more substituents selected from —$OR^2$, —C(O)—$N(R^2)_2$, —$S(O)_n$—$N(R^2)_2$, —$N(R^2)_2$, —$N(R^2)$—C(O)O($R^2$), —$N(R^2)$—C(O)N($R^2$)$_2$, Ht, —CN, —$SR^2$, —C(O)$OR^2$, or —$N(R^2)$—C(O)—$R^2$;

each $R^{33}$ is selected from H, $C_1$-$C_6$ alkyl, $C_2$-$C_6$ alkenyl, $C_2$-$C_6$ alkynyl, $C_3$-$C_6$ cycloalkyl or $C_5$-$C_6$ cycloalkenyl, $C_6$-$C_{14}$ aryl or a 5-7 membered saturated or unsaturated heterocycle, containing one or more heteroatoms selected from N, NH, O, S and $S(O)_n$;

each n is independently 1 or 2;

G is selected from H, $R^7$ or $C_1$-$C_4$ alkyl

D is selected from $C_1$-$C_6$ alkyl which is substituted with Q, wherein said $C_1$-$C_6$ alkyl is optionally substituted with one or more groups selected from $C_3$-$C_6$ cycloalkyl, —$R^3$, —O-Q or Q; $C_2$-$C_4$ alkenyl which is substituted with Q, wherein said $C_2$-$C_4$ alkenyl is optionally substituted with one or more groups selected from —$OR^2$, —S-Ht, —$R^3$, —O-Q or Q; $C_3$-$C_6$ cycloalkyl, which is substituted with or fused to Q; or $C_5$-$C_6$ cycloalkenyl, which is substituted with or fused to Q;

each Q is independently selected from a 3-7 membered saturated, partially saturated or unsaturated carbocyclic ring system; or a 5-7 membered saturated, partially saturated or unsaturated heterocyclic ring containing one or more heteroatoms selected from O, N, S, $S(O)_n$ or $N(R^2)$; wherein Q contains one substituent selected from —$OR^8$, —$SR^8$, —S-arylalkyl, or —$N(R^2)R^8$, and may be optionally substituted with one or more additional substituents independently selected from oxo, —$OR^8$, —O-arylalkyl —$SR^8$, —S-arylalkyl, —$N(R^2)R^8$, —$N(R^2)$-arylalkyl, —$OR^2$, —$R^2$, —$SO_2R^2$, —$SO_2$—N$(R^2)_2$, —$N(R^2)_2$, —$N(R^2)$—C(O)—$R^2$, —OH, —CN, —$CO_2R^2$—C(O)—$N(R^2)_2$, halo or —$CF_3$;

each $R^8$ is independently selected from Ht, $C_1$-$C_{15}$ branched or straight chain alkyl, $C_2$-$C_{15}$ branched or straight chain alkenyl or $C_2$-$C_{15}$ branched or straight chain alkynyl wherein one to five carbon atoms in said alkyl, alkenyl or alkynyl are independently replaced by W, or wherein one to five carbon atoms in said alkyl, alkenyl or alkynyl are substituted with Ht; and wherein $R^8$ is additionally and optionally substituted with one or more groups independently selected from —OH, —S($C_1$-$C_6$ alkyl), —CN, —$CF_3$, —$N(R^2)_2$, halo, —$C_1$-$C_4$-alkyl, —$C_1$-$C_4$-alkoxy; -Ht; —O-Ht; —$NR^2$—CO—$N(R^2)_2$; —CO—$N(R^2)_2$; —$R^1$—$C_2$-$C_6$ alkenyl, which is optionally substituted with one or more groups independently selected from hydroxy, $C_1$-$C_4$ alkoxy, Ht, —O-Ht, —$NR^2$—CO—$N(R^2)_2$ or —CO—$N(R^2)_2$; or $R^7$;

wherein W is —O—, —$NR^2$—, —S—, —C(O)—, —C(S)—, —C(=$NR^2$)—, —$S(O)_2$—, —$NR^2$—S$(O)_2$—, —$S(O)_2$—$NR^2$—, —$NR^2$—C(O)O—, —O—C(O)$NR^2$—, —$NR^2$—C(O)$NR^2$—, —$NR^2$—C(S)$NR^2$—, —$CONR^2$—, —$NR^2$C(O)—, —C(S)$NR^2$—, —$NR^2$C(S)—, —$NR^2$—C(=N—CN)—$NR^2$—, —$NR^2$C(=N—CN)O— or —C(O)O—;

D' is selected from $C_1$-$C_{15}$ alkyl, $C_2$-$C_{15}$ alkenyl, or $C_2$-$C_{15}$ alkynyl, wherein D' is optionally substituted with one or more substituents independently selected from Ht, oxo, halo, —$CF_3$, —$OCF_3$, —$NO_2$, azido, —SH, —$SR^3$, —$N(R^3)$—$N(R^3)_2$, —O—$N(R^3)_2$, —($R^3$)N—O—($R^3$), —$N(R^3)_2$, —CN, —$CO_2R^3$, —C(O)—$N(R^3)_2$, —S$(O)_n$—$N(R^3)_2$, —$N(R^3)$—C(O)—$R^3$, —$N(R^3)$—C(O)—$N(R^3)_2$, —C(O)—$R^3$, —$S(O)_n$—$R^3$, —$N(R^3)$—S$(O)_n(R^3)$, —$N(R^3)$—S$(O)_n$—$N(R^3)_2$, —S—$NR^3$—C(O)$R^3$, —C(S)N($R^3$)$_2$, —C(S)$R^3$, —$NR^3$—C(O)$OR^3$, —O—C(O)$OR^3$, —O—C(O)N($R^3$)$_2$, —$NR^3$—C(S)$R^3$, =N—OH, =N—$OR^3$, =N—$N(R^3)_2$, =$NR^3$, =$NNR^3$C(O)N($R^3$)$_2$, =$NNR^3$C(O)$OR^3$, =$NNR^3$S$(O)_n$—$N(R^3)_2$, —$NR^3$—C(S)$OR^3$, —$NR^3$—C(S)N($R^3$)$_2$, —$NR^3$—C[=N($R^3$)]—$N(R^3)_2$, —$NR^3$—C[=N—$NO_2$]—$N(R^3)_2$, —$NR^3$—C[=N—$NO_2$]—$OR^3$, —$OC(O)R^3$, —$OC(S)R^3$, —$OC(O)N(R^3)_2$, —C(O)N($R^3$)—$N(R^3)_2$, —$N(R^3)$—$N(R^3)C(O)R^3$, —$N(R^3)$—$OC(O)R^3$, —$OC(S)N(R^3)_2$, or —$PO_3$—$R^3$;

E is selected from

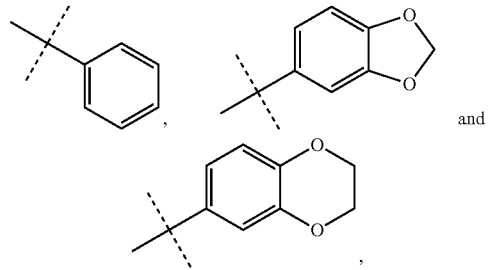

each of which is optionally substituted with oxo, —$OR^2$, $SR^2$, —$R^2$, —$N(R^2)(R^2)$, —$R^2$—OH, —CN, —$CO_2R^2$—C(O)—$N(R^2)_2$, —$S(O)_2$—$N(R^2)_2$, —$N(R^2)$—C(O)—$R^2$, —$N(R^2)$—C(O)O—$R^2$, —C(O)—$R^2$, —$S(O)_n$—$R^2$, —$OCF_3$, —$S(O)_n$-Q, methylenedioxy, —$N(R^2)$—S$(O)_2$($R^2$), halo, —$CF_3$—$NO_2$, Q, —OQ, —$OR^7$, —$SR^7$, —$R^7$, —$N(R^2)(R^7)$ or —$N(R^7)_2$;

each $R^7$ is hydrogen; and x is 0 or 1.

2. The compound according to claim 1, wherein $R^8$ is —$C_1$-$C_4$-branched or straight chain alkyl, wherein one to two carbon atoms in said alkyl are independently replaced by W, wherein $R^8$ is additionally and optionally substituted with one or more groups independently selected from —OH; —$C_1$-$C_4$-alkoxy; -Ht; —O-Ht; —$NR^2$—CO—$N(R^2)_2$; —CO—N$(R^2)_2$; —$R^1$—$C_2$-$C_6$ alkenyl, which is optionally substituted with one or more groups independently selected from hydroxy, $C_1$-$C_4$ alkoxy, Ht, —O-Ht, —$NR^2$—CO—$N(R^2)_2$ or —CO—$N(R^2)_2$; or $R^7$;

wherein W is —O—, —$NR^2$—, —$NR^2$—$S(O)_2$—, —$NR^2$—C(O)O—, —O—C(O)$NR^2$—, —$NR^2$—C(O)$NR^2$—, —$NR^2$—C(S)$NR^2$—, —$NR^2$C(O)—, —C(=$NR^2$)—, —C(O)$NR^2$—, —$NR^2$—C(=N—CN)—$NR^2$—, —$NR^2$C(=N—CN)O— or —C(O)O—; and wherein Ht, $R^1$, $R^2$ and $R^7$ are as defined in claim 1.

3. The compound according to claim 1, wherein $R^8$ is a —$C_1$-$C_4$-branched or straight alkyl chain, wherein one to two carbon atoms are substituted with Ht;

wherein Ht is $C_{6-14}$ aryl or a 5-7 membered saturated or unsaturated heterocycle, containing one or more heteroatoms selected from N,N($R^2$), O, S and $S(O)_n$, wherein any member of Ht is optionally substituted with one or more substituents independently selected from oxo, —$OR^2$, $SR^2$, —$R^2$, —$N(R^2)(R^2)$, —$R^2$—OH, —CN, —$CO_2R^2$, —C(O)—$N(R^2)_2$, —$S(O)_2$—$N(R^2)_2$, —$N(R^2)$—C(O)—$R^2$, —$N(R^2)$—C(O)O—$R^2$, —C(O)—R², —S(O)ₙ—R², —OCF₃, —S(O)ₙ-Q, methylenedioxy, —N(R²)—S(O)₂(R²), halo, —CF₃, —NO₂, Q, —OQ, —OR⁷, —SR⁷, —R⁷, —N(R²)(R⁷) or —N(R⁷)₂.
4. The compound according to claim 1, wherein $R^8$ is selected from:
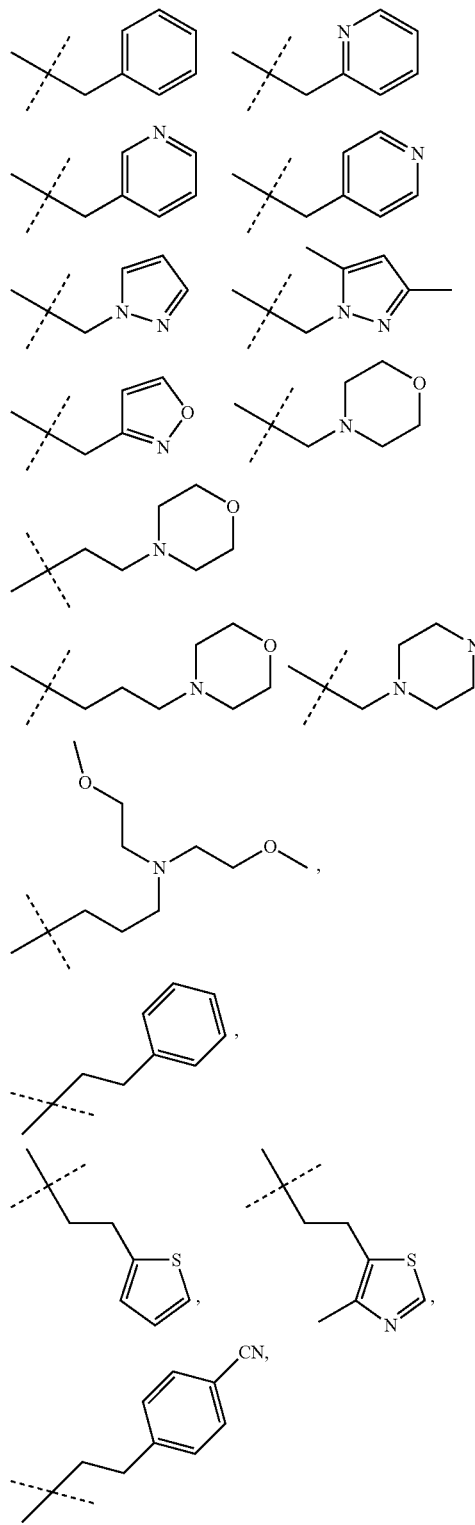
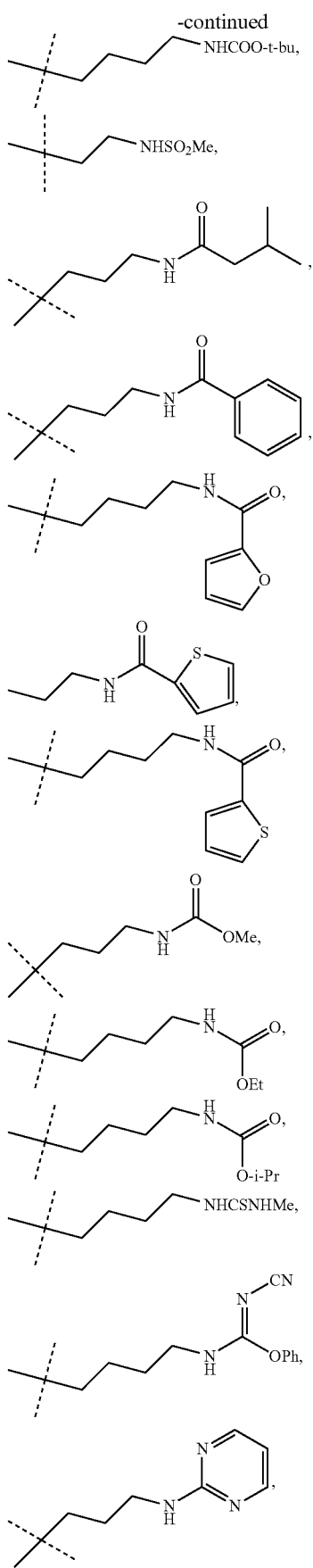

-continued
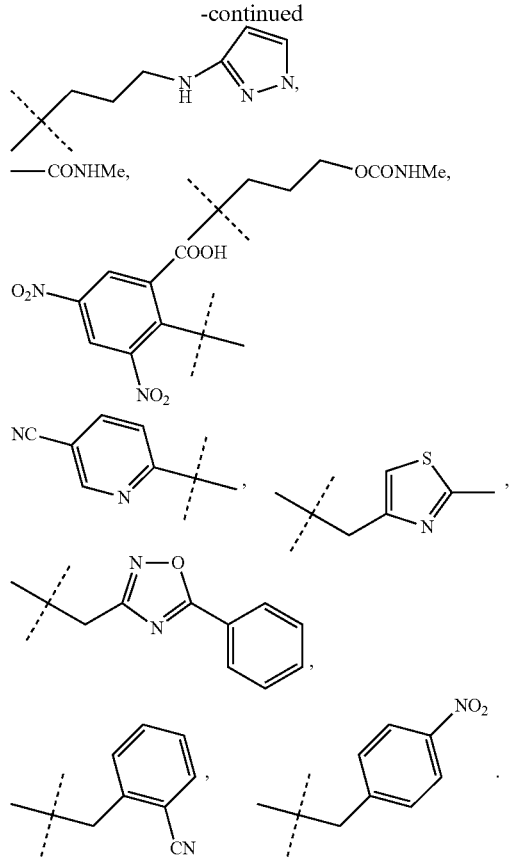
5. The compound according to claim 1, wherein:
D' is —CH$_2$—R'', wherein R'' is selected from:
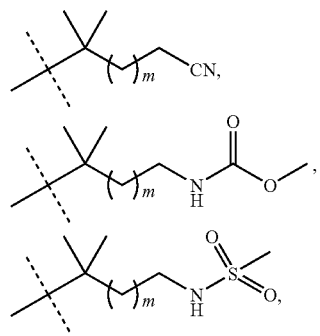
isobutyl,
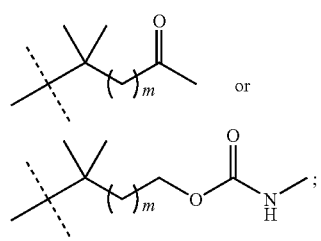
wherein m is 0 to 3.
6. The compound according to claim 1, wherein:
E is selected from:
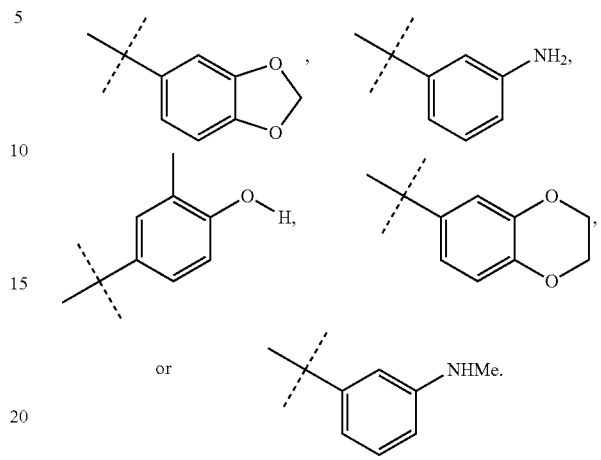
or
7. The compound according to claim 1, of the formula (II):
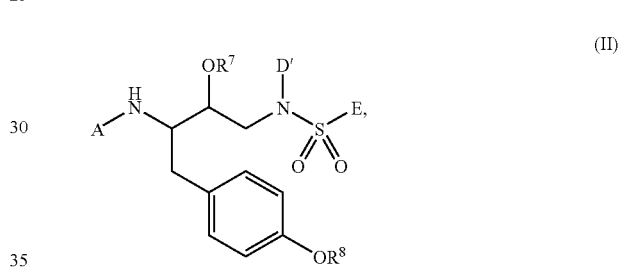
(II)
wherein A, R$^7$, D', R$^8$ and E are as defined in claim 1.
8. The compound according to claim 7, wherein R$^8$ is selected from:
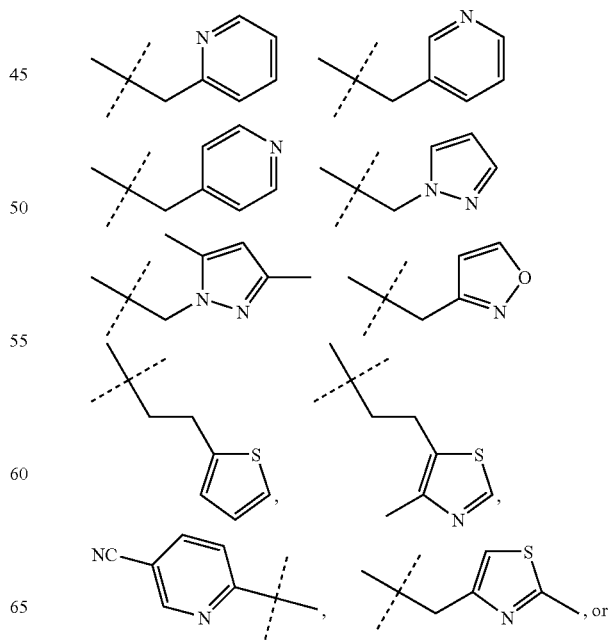

-continued
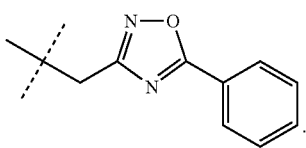
9. The compound according to claim 7, wherein R[8] is selected from:
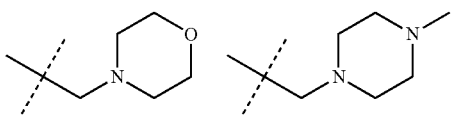
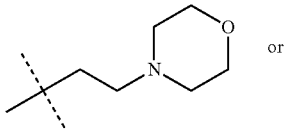 or
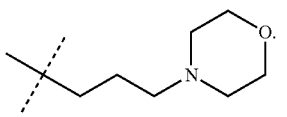
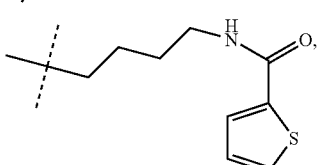
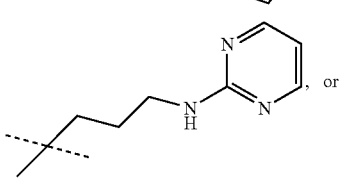, or
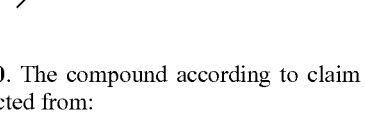
10. The compound according to claim 7, wherein R[8] is selected from:
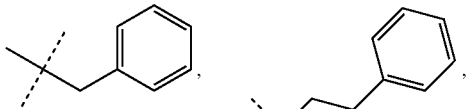
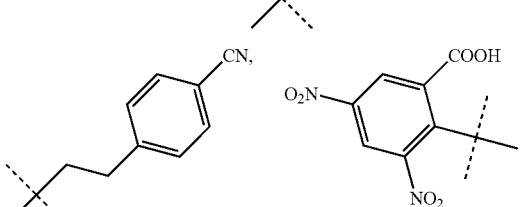
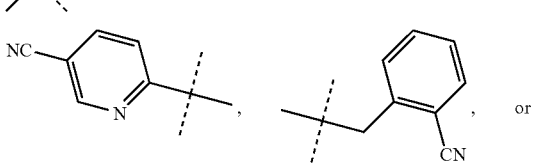, or
-continued
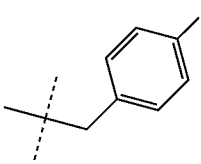
11. The compound according to claim 7, wherein R[8] is selected from:
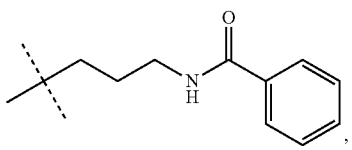
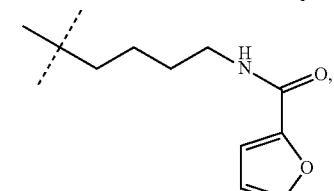
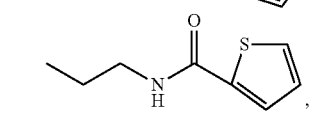
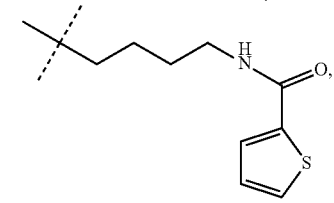
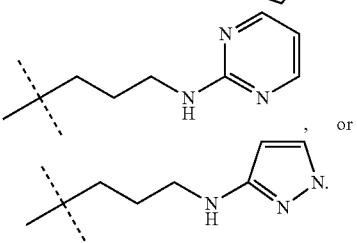, or
12. The compound according to claim 7, wherein R[8] is selected from:
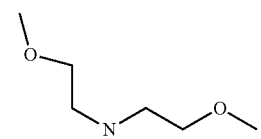
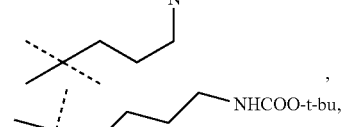
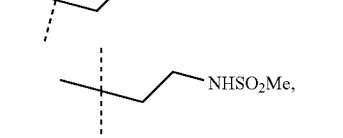

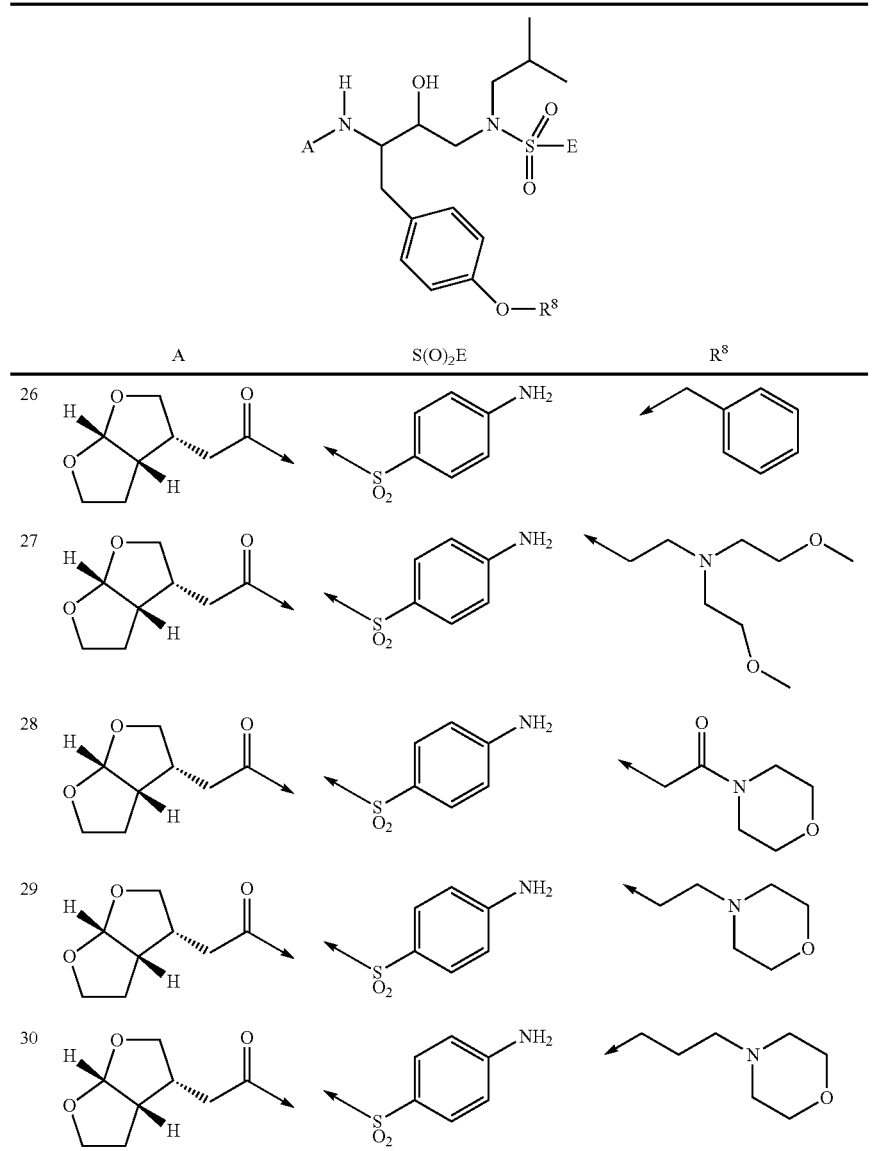
13. A compound selected from a compound of the structure

-continued
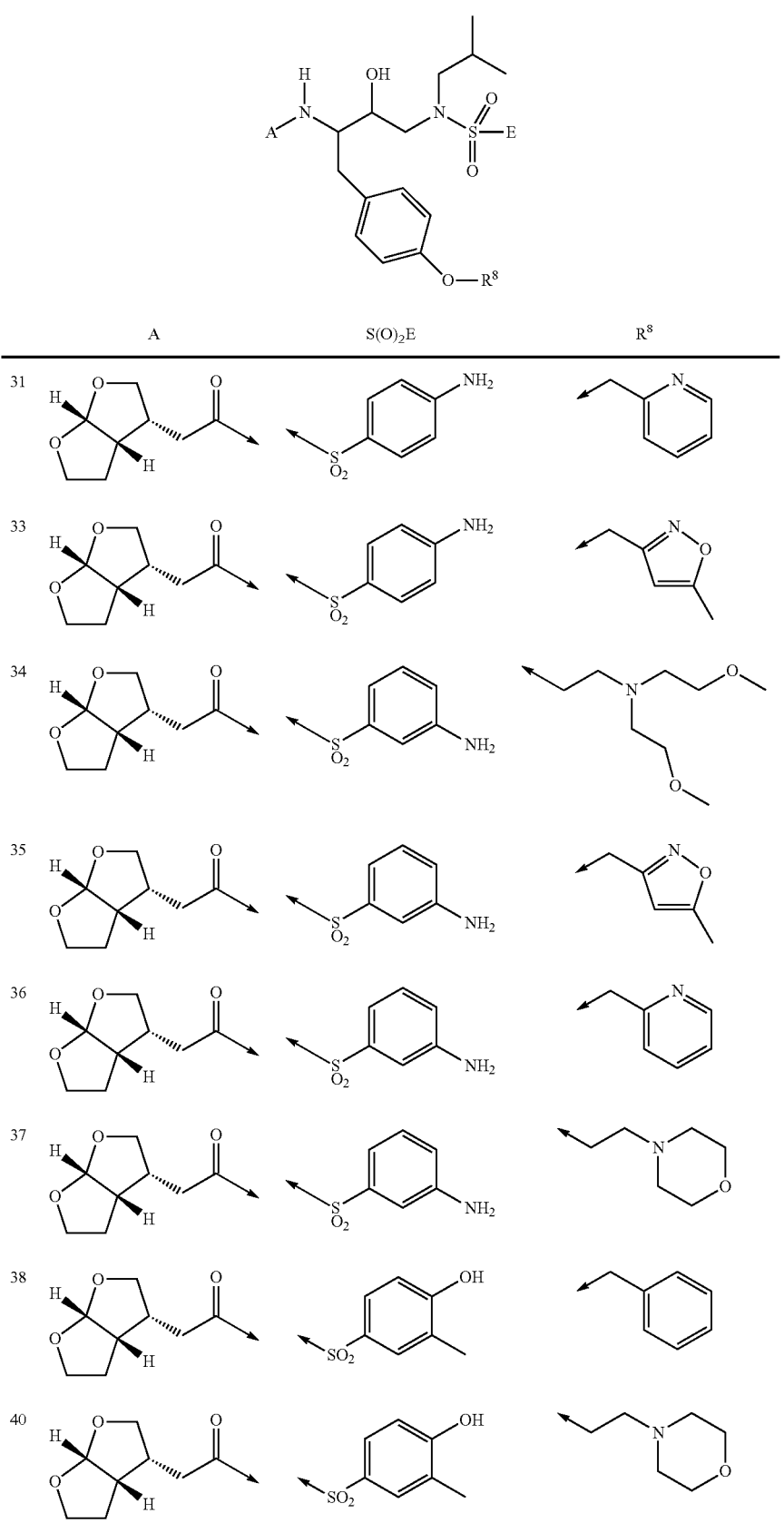

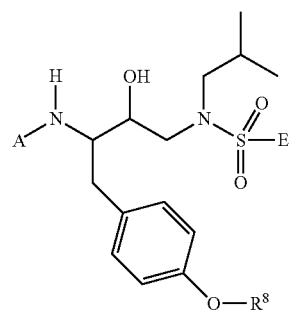

-continued

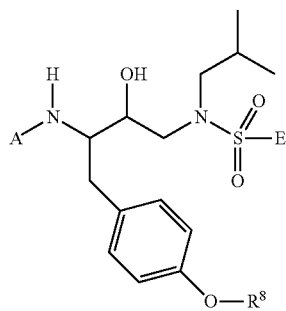

| | A | S(O)₂E | R⁸ |
|---|---|---|---|
| 52 | hexahydrofuro[3,2-b]furan-CH₂C(O)- | benzo[1,3]dioxol-5-ylsulfonyl | CH₂-(pyridin-3-yl) |
| 53 | hexahydrofuro[3,2-b]furan-CH₂C(O)- | benzo[1,3]dioxol-5-ylsulfonyl | CH₂-(pyridin-2-yl) |
| 54 | hexahydrofuro[3,2-b]furan-CH₂C(O)- | benzo[1,3]dioxol-5-ylsulfonyl | CH₂-(pyridin-4-yl) |
| 55 | hexahydrofuro[3,2-b]furan-CH₂C(O)- | benzo[1,3]dioxol-5-ylsulfonyl | CH₂-(5-methylisoxazol-3-yl) |
| 56 | hexahydrofuro[3,2-b]furan-CH₂C(O)- | benzo[1,3]dioxol-5-ylsulfonyl | CH₂CH₂-(3,5-dimethylpyrazol-1-yl) |
| 57 | hexahydrofuro[3,2-b]furan-CH₂C(O)- | benzo[1,3]dioxol-5-ylsulfonyl | CH₂CH₂-(pyrazol-1-yl) |
| 62 | hexahydrofuro[3,2-b]furan-CH₂C(O)- | 3-aminophenylsulfonyl | CH₂-phenyl |
| 63 | hexahydrofuro[3,2-b]furan-CH₂C(O)- | 3-aminophenylsulfonyl | CH₂C(O)-morpholin-4-yl |

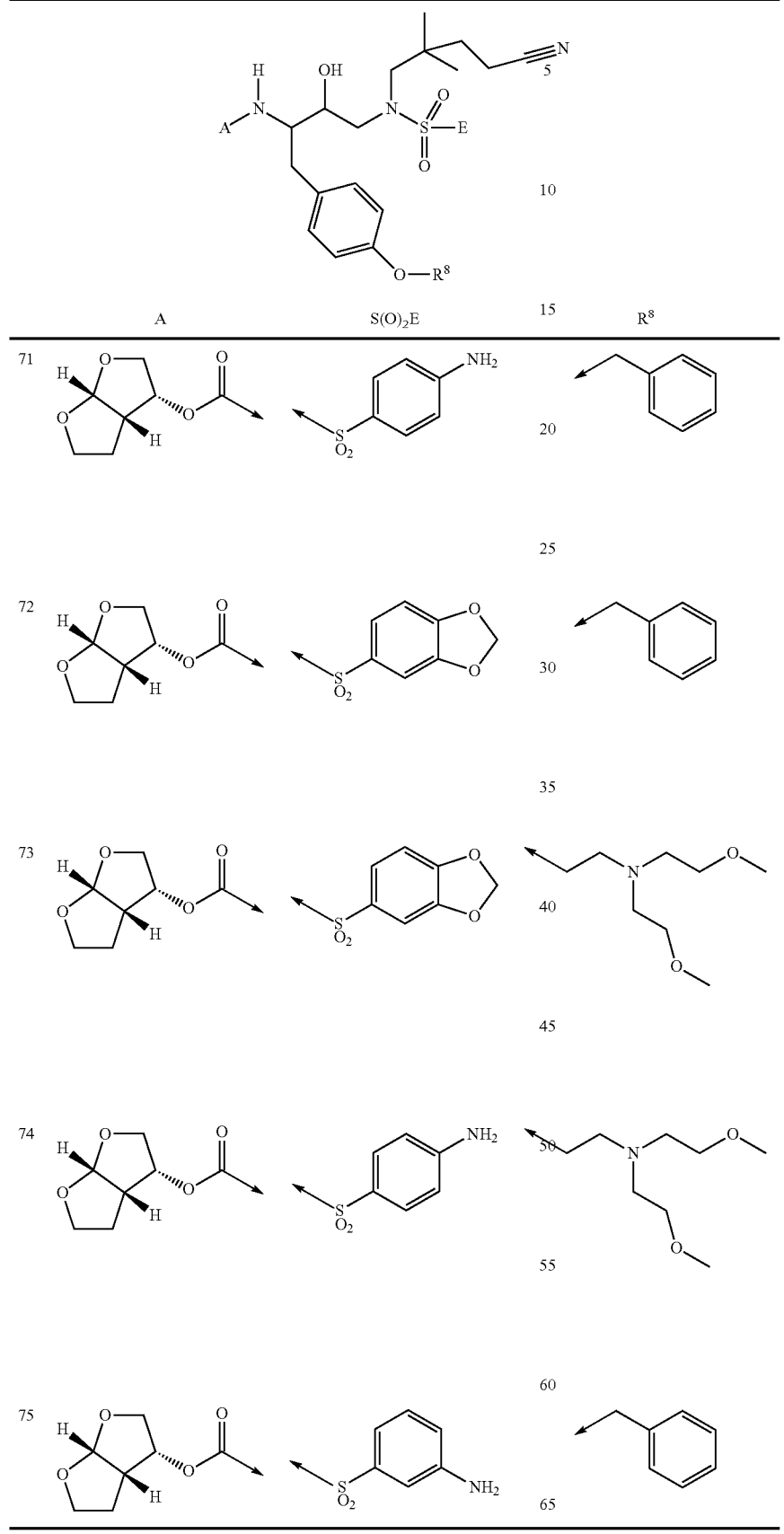

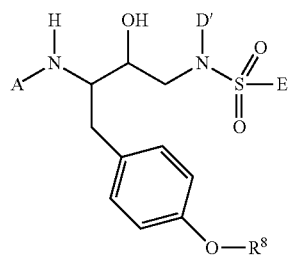

-continued
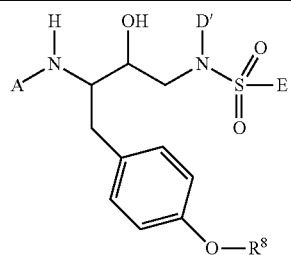
| | A | R⁸ | D' | E |
|---|---|---|---|---|
| 210 | | | | |
| 211 | | | | |
| 212 | | | | |
| 213 | | | | |
| 214 | | | | |
| 215 | | | | |
| 218 | | | | |

-continued

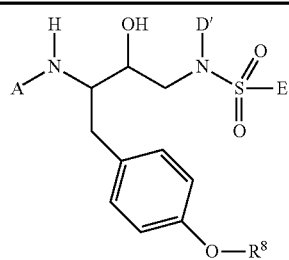

| | A | R⁸ | D' | E |
|---|---|---|---|---|
| 219 | hexahydrofuro[3,2-b]furan-3-yl 2-methylpropanoate | —C(CH₃)₂CH₂—NHCOOt-bu | isobutyl | benzo[1,3]dioxol-5-yl |
| 220 | hexahydrofuro[3,2-b]furan-3-yl 2-methylpropanoate | —C(CH₃)₂CH₂—NH₂ | isobutyl | benzo[1,3]dioxol-5-yl |
| 221 | hexahydrofuro[3,2-b]furan-3-yl 2-methylpropanoate | —C(CH₃)₂CH₂CH₂—NHCOOt-bu | isobutyl | benzo[1,3]dioxol-5-yl |
| 222 | hexahydrofuro[3,2-b]furan-3-yl 2-methylpropanoate | —C(CH₃)₂CH₂CH₂—NH₂ | isobutyl | benzo[1,3]dioxol-5-yl |
| 223 | hexahydrofuro[3,2-b]furan-3-yl 2-methylpropanoate | —C(CH₃)₂CH₂CH₂CH₂—NHCOO-t-bu | isobutyl | benzo[1,3]dioxol-5-yl |
| 224 | hexahydrofuro[3,2-b]furan-3-yl 2-methylpropanoate | —C(CH₃)₂CH₂CH₂CH₂—NH₂ | isobutyl | benzo[1,3]dioxol-5-yl |
| 225 | hexahydrofuro[3,2-b]furan-3-yl 2-methylpropanoate | —C(CH₃)₂CH₂—NHAc | isobutyl | benzo[1,3]dioxol-5-yl |
| 226 | hexahydrofuro[3,2-b]furan-3-yl 2-methylpropanoate | —C(CH₃)₂CH₂—NHCOOMe | isobutyl | benzo[1,3]dioxol-5-yl |
| 227 | hexahydrofuro[3,2-b]furan-3-yl 2-methylpropanoate | —C(CH₃)₂CH₂—NHSO₂Me | isobutyl | benzo[1,3]dioxol-5-yl |

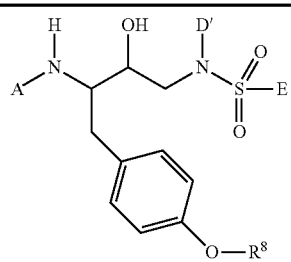

-continued
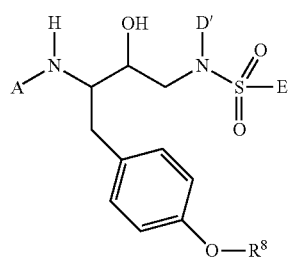
| | A | R⁸ | D' | E |
|---|---|---|---|---|
| 237 | | | | |
| 238 | | | | |
| 239 | | | | |
| 240 | | | | |
| 241 | | | | |
| 242 | | | | |
| 243 | | | | |
| 244 | | | | |

-continued
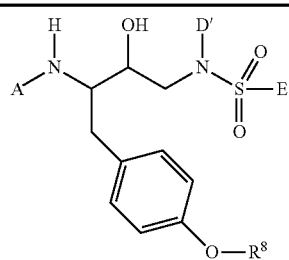

-continued

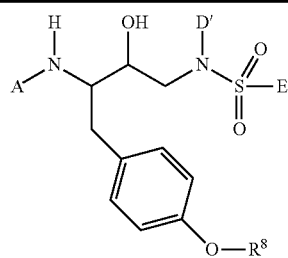

| | A | R8 | D' | E |
|---|---|---|---|---|
| 254 | hexahydrofuro[3,2-b]furan-3-yl isobutyrate | NHCONME2 (butyl) | isobutyl | benzo[1,3]dioxole |
| 255 | hexahydrofuro[3,2-b]furan-3-yl isobutyrate | NHCONMe2 (pentyl) | isobutyl | benzo[1,3]dioxole |
| 256 | hexahydrofuro[3,2-b]furan-3-yl isobutyrate | NHCONMe (butyl) | isobutyl | benzo[1,3]dioxole |
| 257 | hexahydrofuro[3,2-b]furan-3-yl isobutyrate | NHCONHMe (pentyl) | isobutyl | benzo[1,3]dioxole |
| 258 | hexahydrofuro[3,2-b]furan-3-yl isobutyrate | NHCSNHMe (propyl) | isobutyl | benzo[1,3]dioxole |
| 259 | hexahydrofuro[3,2-b]furan-3-yl isobutyrate | NHCSNHMe (butyl) | isobutyl | benzo[1,3]dioxole |
| 260 | hexahydrofuro[3,2-b]furan-3-yl isobutyrate | NHCSNHMe (pentyl) | isobutyl | benzo[1,3]dioxole |
| 261 | hexahydrofuro[3,2-b]furan-3-yl isobutyrate | furan-3-carboxamide propyl | isobutyl | benzo[1,3]dioxole |
| 262 | hexahydrofuro[3,2-b]furan-3-yl isobutyrate | N-cyano-O-phenyl isourea propyl | isobutyl | benzo[1,3]dioxole |

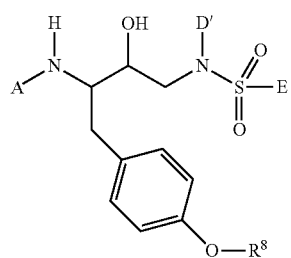

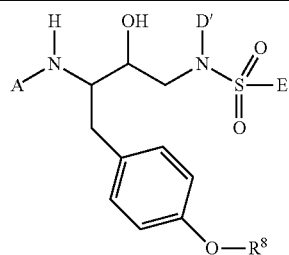

-continued

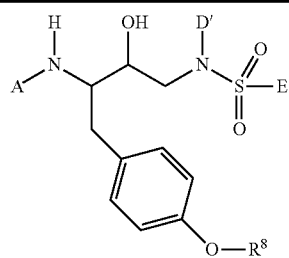

| | A | R⁸ | D' | E |
|---|---|---|---|---|
| 280 | 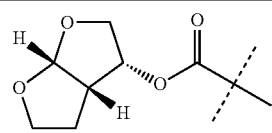 | pyrrolidine-butyl | isobutyl | benzodioxole |
| 281 | 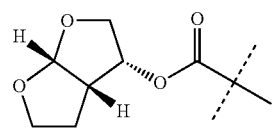 | pyrazol-3-ylamino-butyl | isobutyl | benzodioxole |
| 282 | 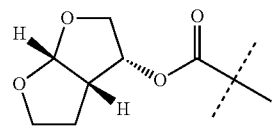 | 4-methylpiperazin-1-yl-butyl | isobutyl | benzodioxole |
| 283 | 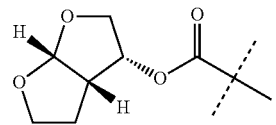 | (2-methoxyethylamino)butyl | isobutyl | benzodioxole |
| 284 | 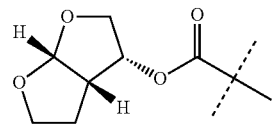 | pyrazol-1-yl-butyl | isobutyl | benzodioxole |
| 285 | 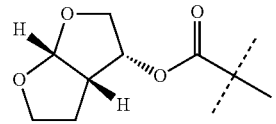 | -(CH₂)₅-CONH₂ | isobutyl | benzodioxole |
| 286 | 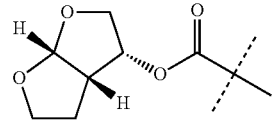 | -(CH₂)₅-CONHMe | isobutyl | benzodioxole |
| 287 | 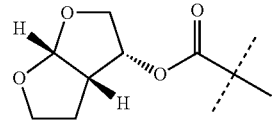 | -(CH₂)₅-CONMe₂ | isobutyl | benzodioxole |
| 288 | 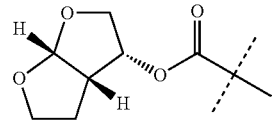 | -(CH₂)₅-CONHBu | isobutyl | benzodioxole |

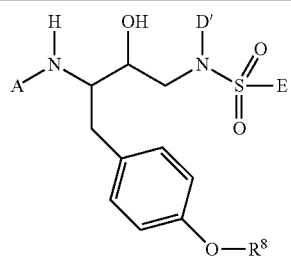

-continued
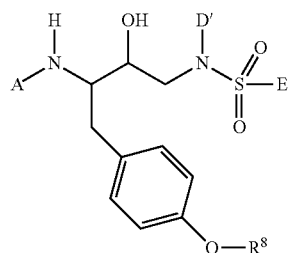
| | A | R⁸ | D' | E |
|---|---|---|---|---|
| 298 | | | | |
| 299 | | | | |
| 300 | | | | |
| 301 | | | | |
| 303 | | | | |
| 305 | | | | |
| 309 | | —CONHMe | | |
| 310 | | —CONH-i-Pr | | |

-continued
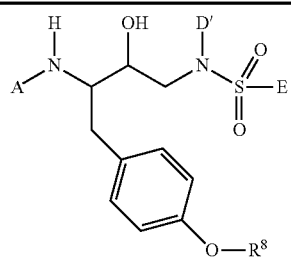
| | A | R⁸ | D' | E |
|---|---|---|---|---|
| 311 | | —CONMe₂ | | |
| 312 | | —CONH₂ | | |
| 313 | | | | |
| 314 | | | | |
| 315 | | | | |
| 316 | | | | |
| 317 | | | | |
| 318 | | | | |
| 319 | | | | |

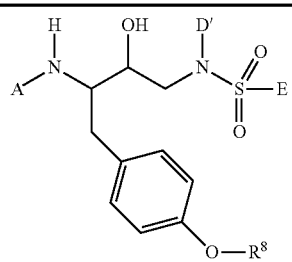

-continued

| | A | R⁸ | D' | E |
|---|---|---|---|---|
| 332 | hexahydrofuro[2,3-b]furan-3-yl pivalate ester | 2,3,4,5-tetrafluoropyridin-6-yl | isobutyl | benzo[d][1,3]dioxol-5-yl |
| 333 | hexahydrofuro[2,3-b]furan-3-yl pivalate ester | 5-nitropyridin-2-yl | isobutyl | benzo[d][1,3]dioxol-5-yl |
| 334 | hexahydrofuro[2,3-b]furan-3-yl pivalate ester | 2-carboxy-4,6-dinitrophenyl | isobutyl | benzo[d][1,3]dioxol-5-yl |
| 335 | hexahydrofuro[2,3-b]furan-3-yl pivalate ester | 5-cyanopyridin-2-yl | isobutyl | benzo[d][1,3]dioxol-5-yl |
| 336 | hexahydrofuro[2,3-b]furan-3-yl pivalate ester | 2,4-dinitrophenyl | isobutyl | benzo[d][1,3]dioxol-5-yl |
| 337 | hexahydrofuro[2,3-b]furan-3-yl pivalate ester | pyridin-2-ylmethyl | isobutyl | 2,3-dihydrobenzo[b][1,4]dioxin-6-yl |
| 338 | hexahydrofuro[2,3-b]furan-3-yl pivalate ester | 3-cyanobenzyl | isobutyl | 2,3-dihydrobenzo[b][1,4]dioxin-6-yl |
| 339 | hexahydrofuro[2,3-b]furan-3-yl pivalate ester | 4-carboxybutyl | isobutyl | benzo[d][1,3]dioxol-5-yl |

-continued
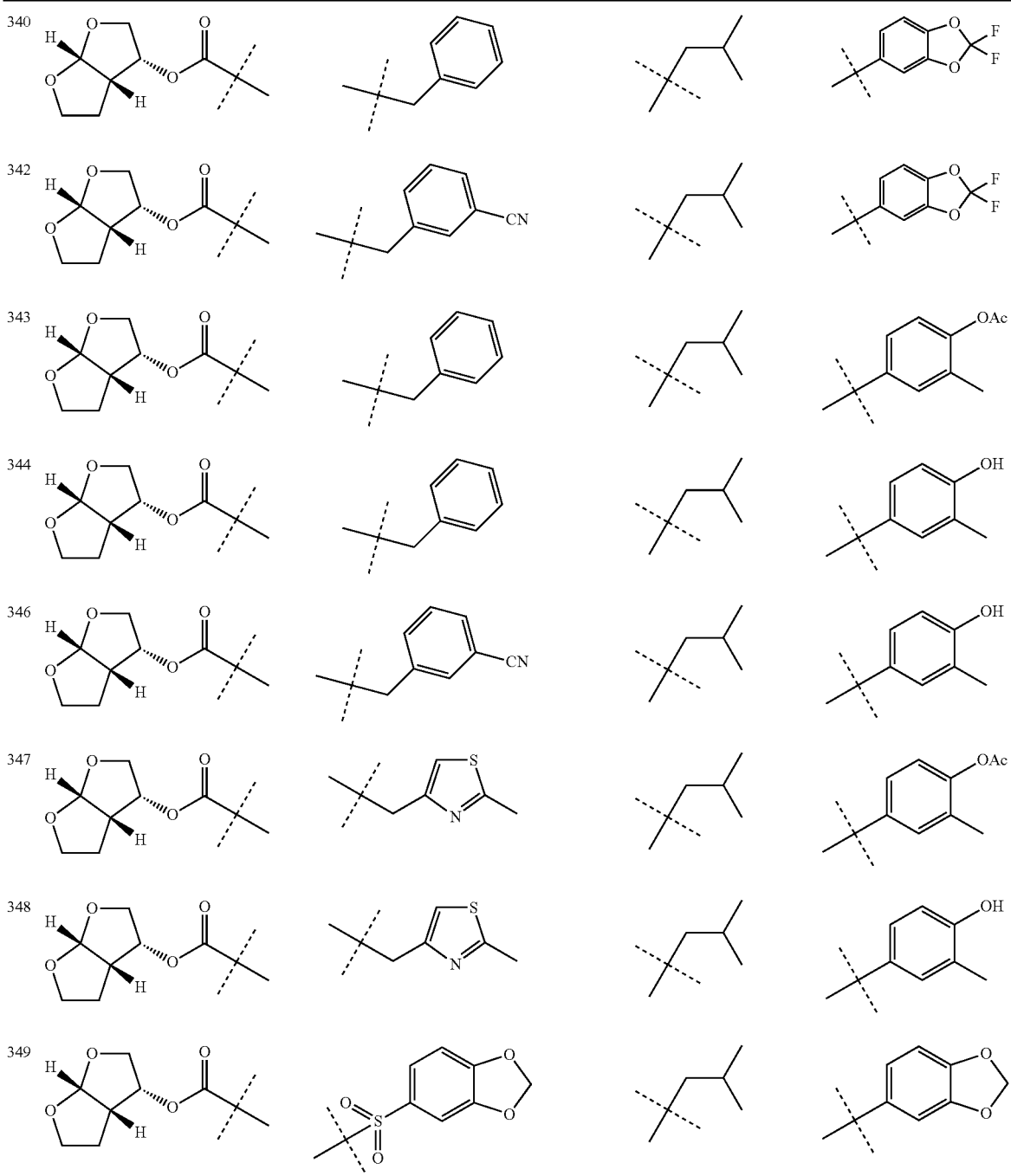

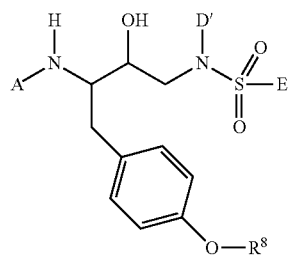

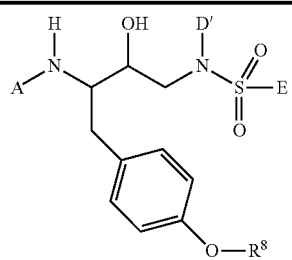

-continued
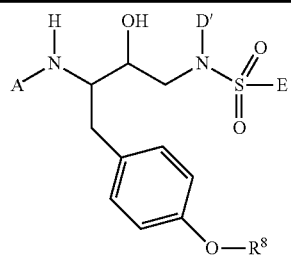

-continued
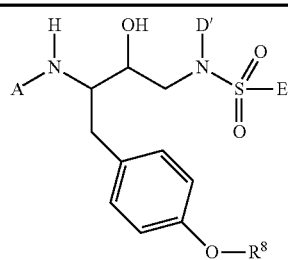
| | A | R⁸ | D' | E |
|---|---|---|---|---|
| 379 | 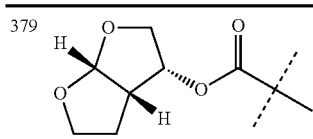 | 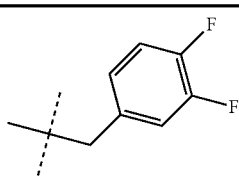 | 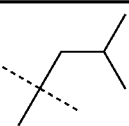 | 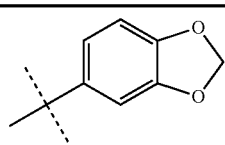 |
| 380 | 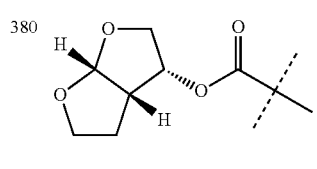 | 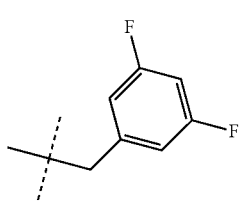 | 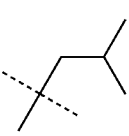 | 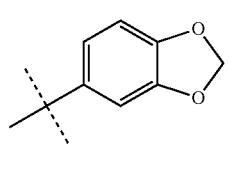 |
| 381 | 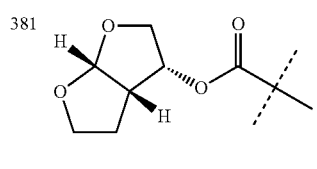 | 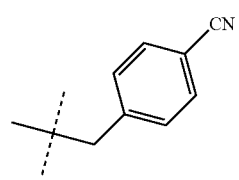 | 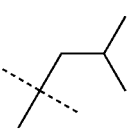 | 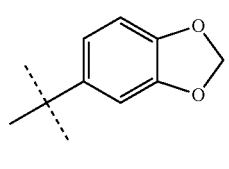 |
| 382 | 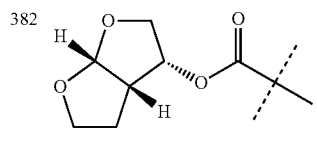 | 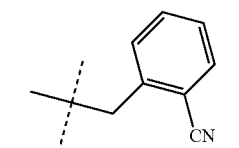 | 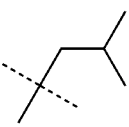 | 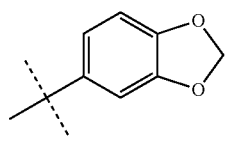 |
| 383 | 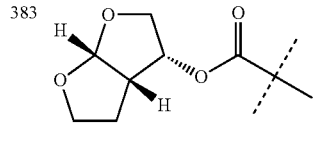 | 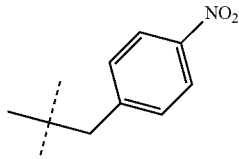 | 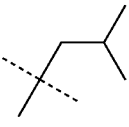 | 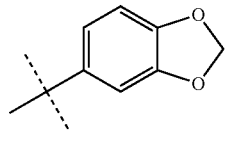 |
| 384 | 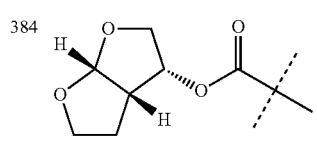 | 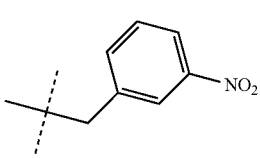 | 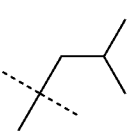 | 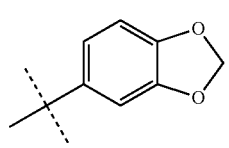 |
| 385 | 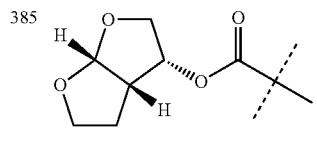 | 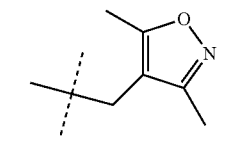 | 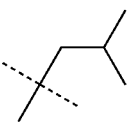 | 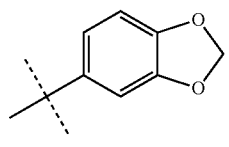 |
| 386 | 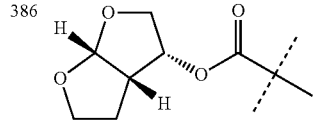 | 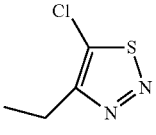 | 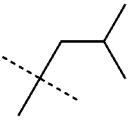 | 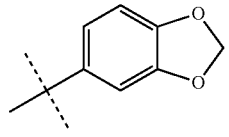 |

-continued
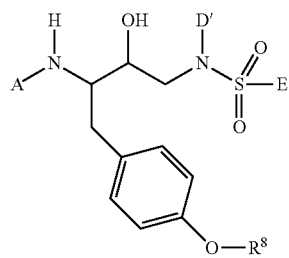
| | A | R⁸ | D' | E |
|---|---|---|---|---|
| 387 | 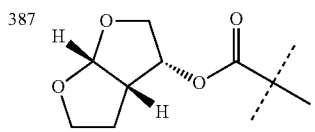 | 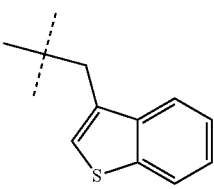 | 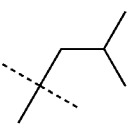 | 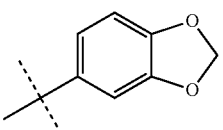 |
| 388 | 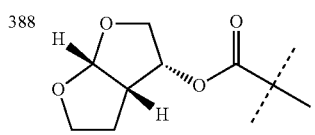 | 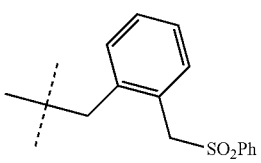 | 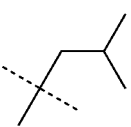 | 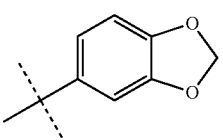 |
| 389 | 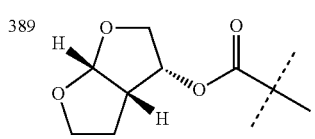 | 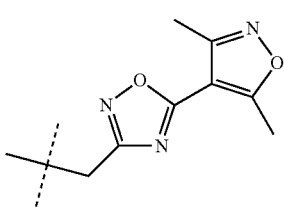 | 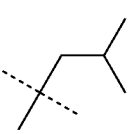 | 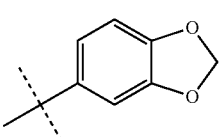 |
| 390 | 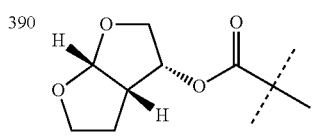 | 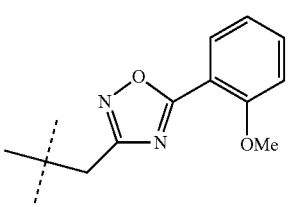 | 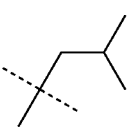 | 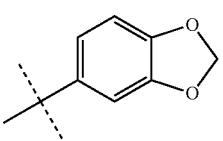 |
| 391 | 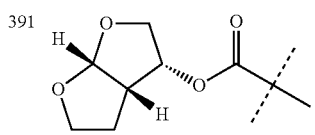 | 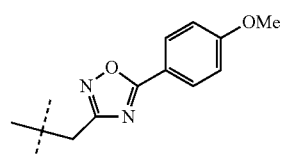 | 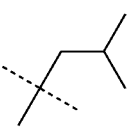 | 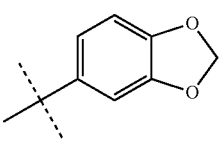 |
| 392 | 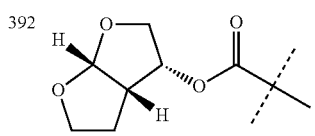 | 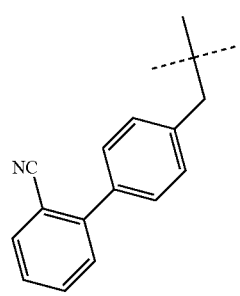 | 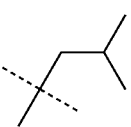 | 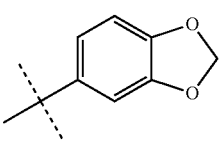 |

-continued
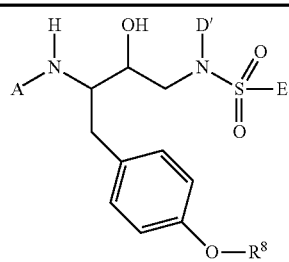
| | A | R⁸ | D' | E |
|---|---|---|---|---|
| 394 | | | | |
| 395 | | | | |
| 396 | | | | |
| 398 | | | | |
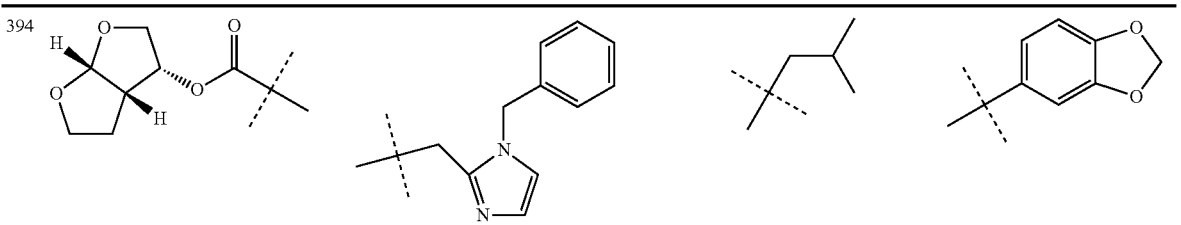
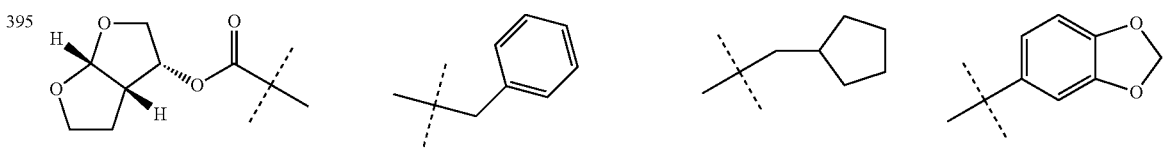
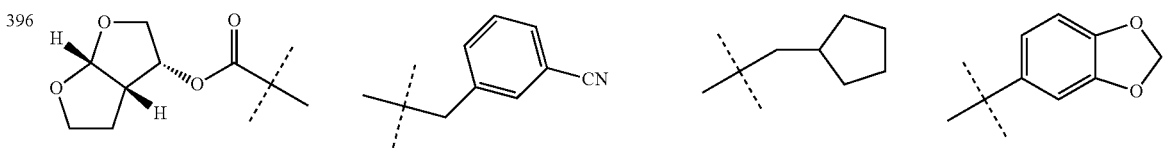
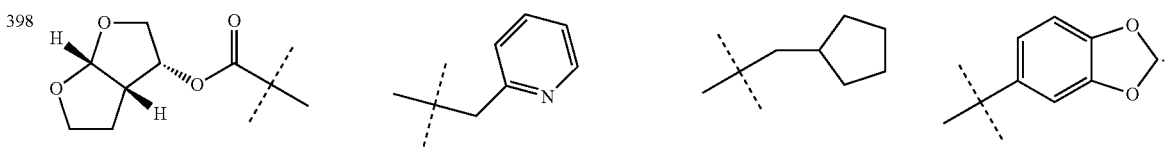
14. The compound according to claim 13, wherein said compound is selected from a compound of the structure
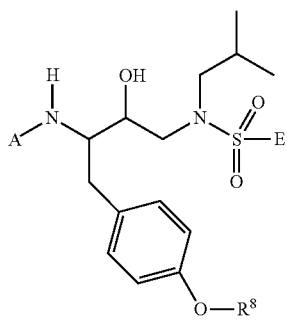
| | A | S(O)₂E | R⁸ |
|---|---|---|---|
| 26 | | | |
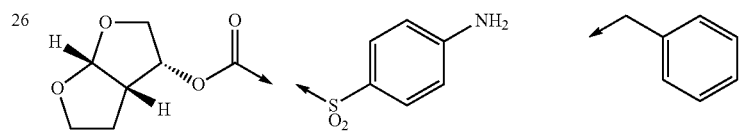

-continued
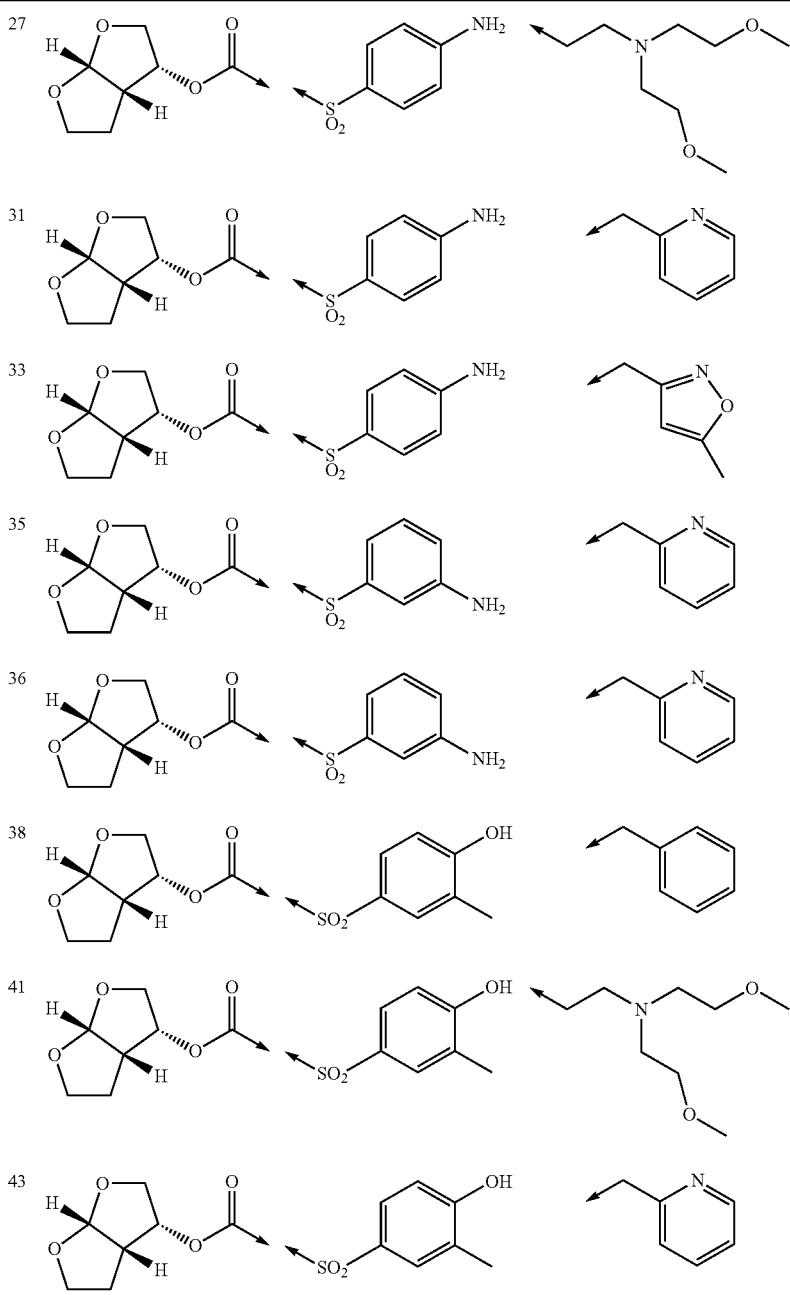

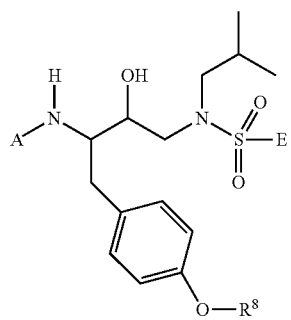

-continued
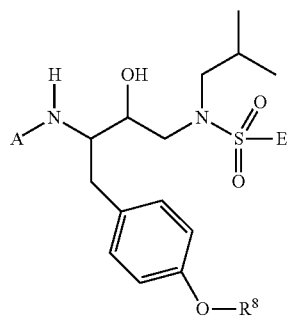
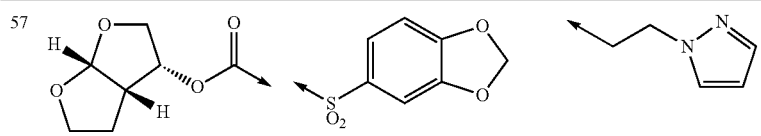
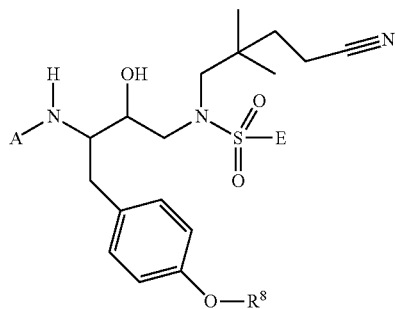
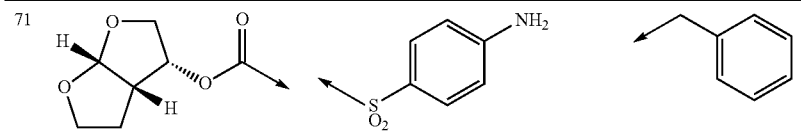
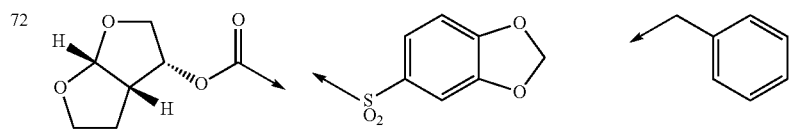
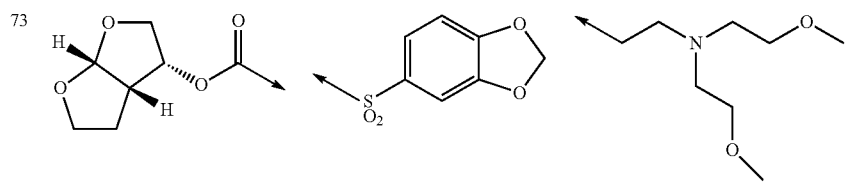
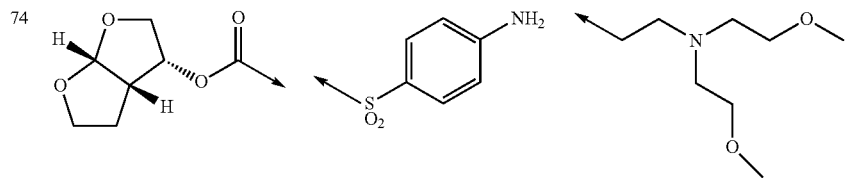

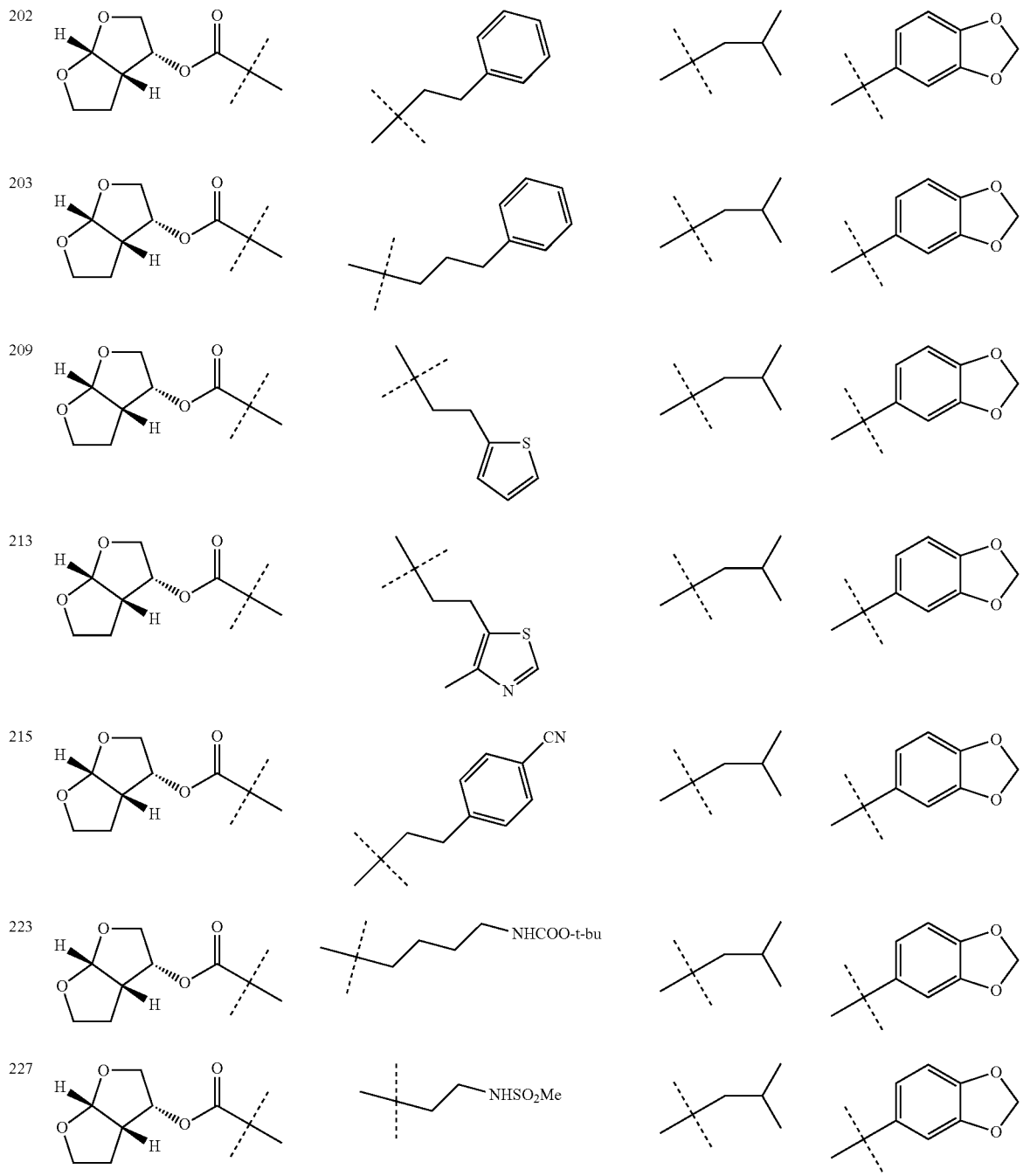

-continued
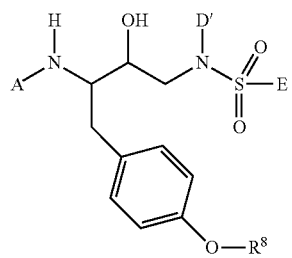

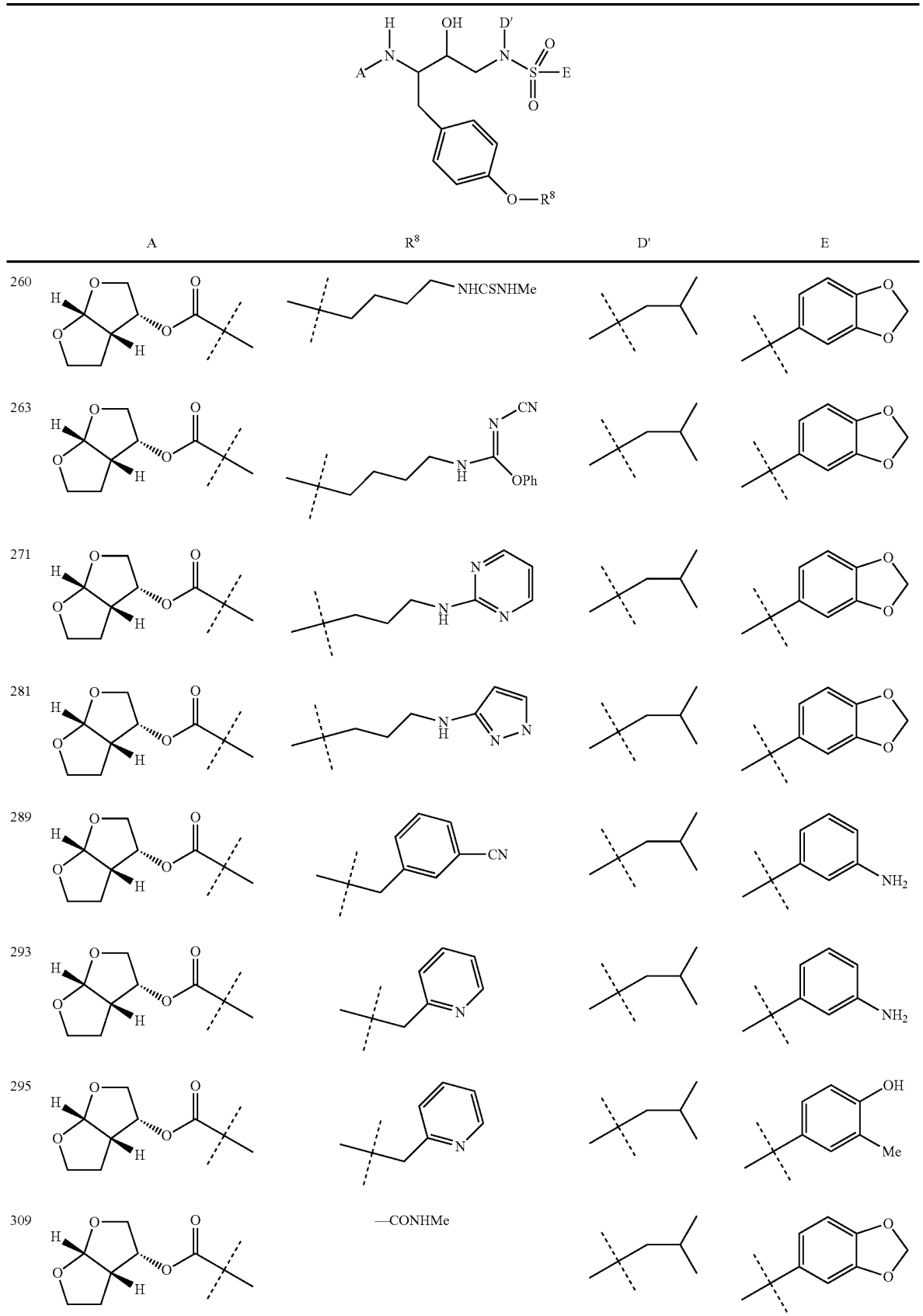

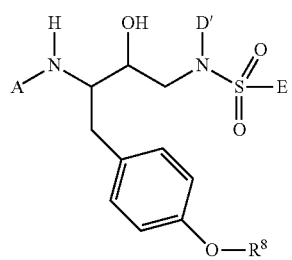

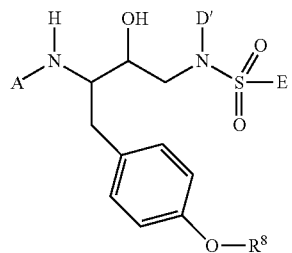

15. The compound according to claim 14, wherein said compound is selected from a compound of the structure
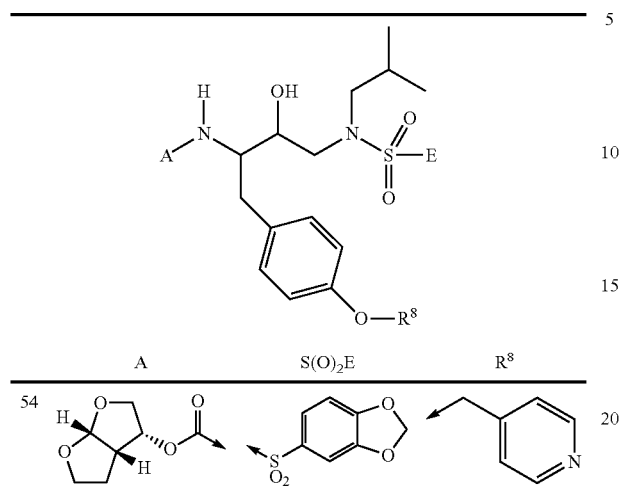
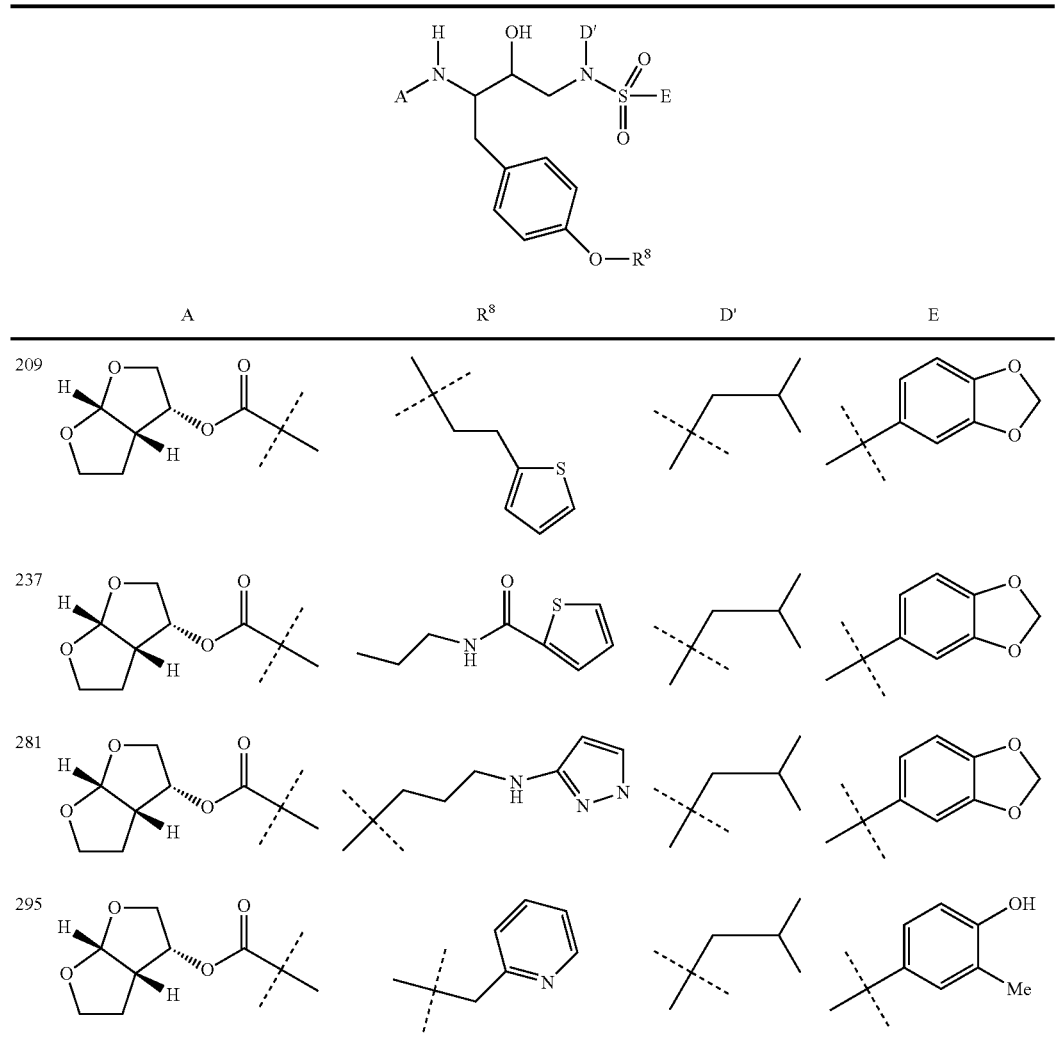

-continued

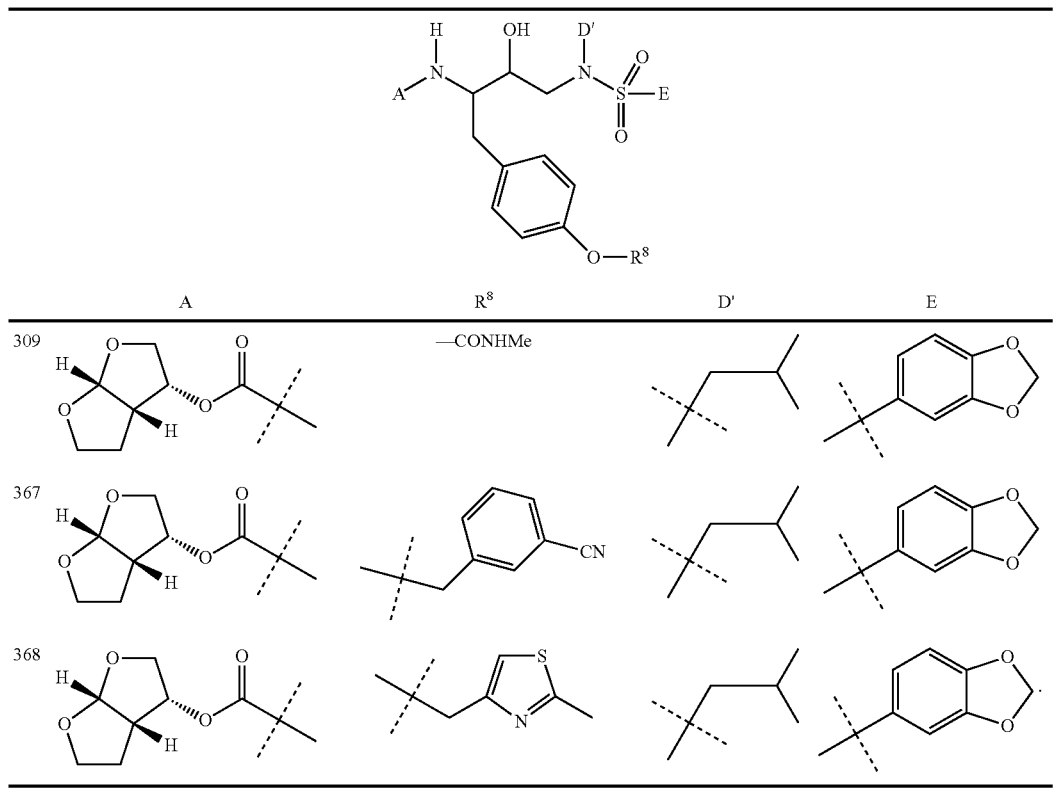

16. A composition comprising a compound according to claim 1, in an amount sufficient to inhibit an aspartyl protease; and a pharmaceutically acceptable carrier.

17. The composition according to claim 16, wherein said composition is in a pharmaceutically acceptable form for administration to a human being.

18. The composition according to claim 16, wherein said composition additionally comprises an anti-viral agent.

19. The composition according to claim 16, wherein said composition comprises at least one additional therapeutic agent selected from (1 alpha, 2 beta, 3 alpha)-9-[2,3-bis(hydroxymethyl)cyclobutyl]-guanine [(−)BHCG, S Q-34514]; oxetanocin-G (3,4-bis-(hydroxymethyl)-2-oxetanosyl]guanine); acyclic nucleosides; acyclic nucleoside phosphonates; ribonucleotide reductase inhibitors; 2',3'-dideoxynucleosides; aspartyl protease inhibitors; oxathiolane nucleoside analogues; 3'-deoxy-3'-fluorothymidine; 5-chloro-2',3'-dideoxy-3'-fluorouridine; (−)-cis-4-[2-amino-6-(cyclopropylamino)-9H-purin-9-yl]-2-cyclopentene-1-methanol; ribavirin; 9-[4-hydroxy-2-(hydroxymethyl)but-1-yl]-guanine (H2G); tat inhibitors; interferons; renal excretion inhibitors; nucleoside transport inhibitors; pentoxifylline; N-acetylcysteine (NAC); Procysteine; α-trichosanthin; phosphonoformic acid; immunomodulators; granulocyte macrophage colony stimulating factors; erythropoetin; soluble $CD_4$; non-nucleoside reverse transcriptase inhibitors (NNRTIs); phosphonoformic acid; 1,4-dihydro-2H-3,1-benzoxazin-2-ones NNRTIs; or quinoxaline NNRTIs.

20. The composition according to any one of claims 16-19, wherein said composition is in an orally available dosage form.

21. A method of treating a patient infected with a virus that depends upon an aspartyl protease for an obligatory event in its life cycle comprising the step of administering to said patient a composition according to claim 16.

22. A method of treating a patient infected with HIV-I or HIV-II comprising the step of administering to said patient a composition according to claim 16.

23. The method according to claim 21 or 22, comprising the additional step of administering to said patient an additional therapeutic agent selected from (1 alpha, 2 beta, 3 alpha)-9-[2,3-bis(hydroxymethyl)cyclobutyl] guanine [(−)BHCG, SQ-34514]; oxetanocin-G (3,4-bis-(hydroxymethyl)-2-oxetanosyl]guanine); acyclic nucleosides; acyclic nucleoside phosphonates; ribonucleotide reductase inhibitors; 2',3'-dideoxynucleosides; aspartyl protease inhibitors; oxathiolane nucleoside analogues; 3'-deoxy-3'-fluorothymidine; 5-chloro-2',3'-dideoxy-3'-fluorouridine; (−)-cis-4-[2-amino-6-(cyclopropylamino)-9H-purin-9-yl]-2-cyclopentene-1-methanol; ribavirin; 9-[4-hydroxy-2-(hydroxymethyl)but-1-yl]-guanine (H2G); tat inhibitors; interferons; renal excretion inhibitors; nucleoside transport inhibitors; pentoxifylline; N-acetylcysteine (NAC); Procysteine; α-trichosanthin; phosphonoformic acid; immunomodulators; granulocyte macrophage colony stimulating factors; erythropoetin; soluble $CD_4$; non-nucleoside reverse transcriptase inhibitors (NNRTIs); phosphonoformic acid; 1,4-dihydro-2H-3,1-benzoxazin-2-ones NNRTIs; or quinoxaline NNRTIs, wherein said additional agent is administered to said patient as either a separate dosage form or as a single dosage form together with said compound.

24. A method of treating a patient diagnosed with AIDS; AIDS related complex (ARC); progressive generalized lymphadenopathy (PGL); Kaposi's sarcoma, thrombocytopenic purpura; AIDS-related neurological conditions such as AIDS dementia complex, multiple sclerosis or tropical paraperesis; anti-HIV antibody-positive conditions; or HIV-positive conditions, comprising the step of administering to said patient a composition according to claim 16.

25. The method according to claim 24, comprising the additional step of administering to said patient an additional therapeutic agent selected from (1 alpha, 2 beta, 3 alpha)-9-[2,3-bis(hydroxymethyl)cyclobutyl]guanine [(−)BHCG, SQ-34514]; oxetanocin-G (3,4-bis-(hydroxymethyl)-2-oxetanosyl]guanine); acyclic nucleosides; acyclic nucleoside phosphonates; ribonucleotide reductase inhibitors; 2',3'-dideoxynucleosides; aspartyl protease inhibitors; oxathiolane nucleoside analogues; 3'-deoxy-3'-fluorothymidine; 5-chloro-2',3'-dideoxy-3'-fluorouridine; (−)-cis-4-[2-amino-6-(cyclopropylamino)-9H-purin-9-yl]-2-cyclopentene-1-methanol; ribavirin; 9-[4-hydroxy-2-(hydroxymethyl)but-1-yl]-guanine (H2G); tat inhibitors; interferons; renal excretion inhibitors; nucleoside transport inhibitors; pentoxifylline; N-acetylcysteine (NAC); Procysteine; c'-trichosanthin; phosphonoformic acid; immunomodulators; granulocyte macrophage colony stimulating factors; erythropoetin; soluble $CD_4$; non-nucleoside reverse transcriptase inhibitors (NNRTIs); phosphonoformic acid; 1,4-dihydro-2H-3,1-benzoxazin-2-ones NNRTIs; or quinoxaline NNRTIs, wherein said additional agent is administered to said patient as either a separate dosage form or as a single dosage form together with said compound.

26. The compound according to claim 15, wherein said compound is of the structure

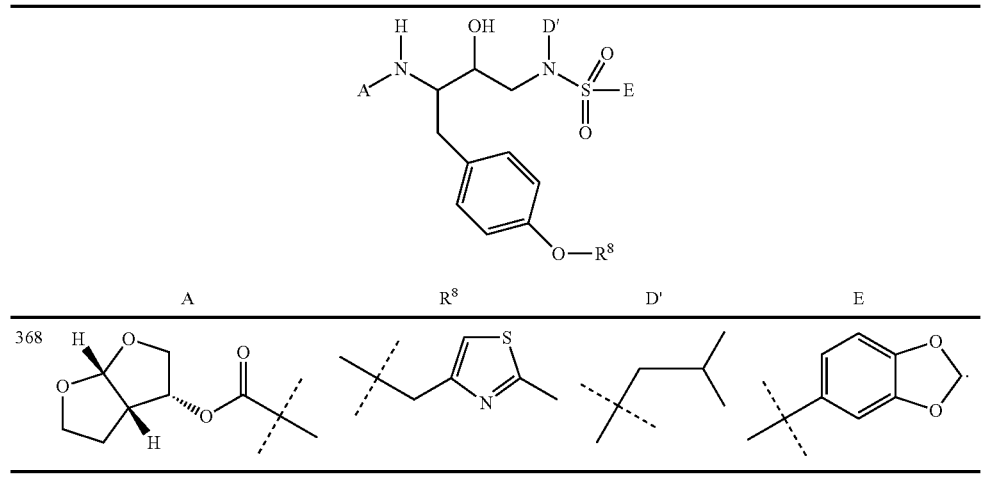

27. The composition according to claim 19, wherein said at least one additional therapeutic agent is selected from (1 alpha, 2 beta, 3 alpha)-9-[2,3-bis(hydroxymethyl)cyclobutyl]-guanine [(−)BHCG, SQ-34514]; oxetanocin-G (3,4-bis-(hydroxymethyl)-2-oxetanosyl]guanine); acyclovir; valaciclovir; famciclovir; ganciclovir; penciclovir; (S)-1-(3-hydroxy-2-phosphonyl-methoxypropyl)cytosine (HPMPC); 2-acetylpyridine 5-[(2-chloroanilino)thiocarbonyl) thiocarbonohydrazone; 3' azido-3'-deoxythymidine; 2',3'-dideoxycytidine; 2',3'-dideoxyadenosine; 2',3'-dideoxyinosine; 2',3'-didehydrothymidine; indinavir; ritonavir; nelfinavir; [3S-[3R*(1R*,2S*)]]-[3-[[(4-aminophenyl)sulfonyl](2-methylpropyl)amino]-2-hydroxy-1-(phenylmethyl)propyl]-tetrahydro-3-furanyl ester (amprenavir); (−)-cis-1-(2-hydroxymethyl)-1,3-oxathiolane 5-yl)-cytosine (lamivudine); cis-1-(2-(hydroxymethyl)-1,3-oxathiolan-5-yl)-5-fluorocytosine (FTC); 3'-deoxy-3'-fluorothymidine; 5-chloro-2',3'-dideoxy-3'-fluorouridine; (−)-cis-4-[2-amino-6-(cyclopropylamino)-9H-purin-9-yl]-2-cyclopentene-1-methanol; ribavirin; 9-[4-hydroxy-2-(hydroxymethyl)but-1-yl]-guanine (H2G); 7-chloro-5-(2-pyrryl)-3H-1,4-benzodiazepin-2-(H)one (Ro5-3335); 7-chloro-1,3-dihydro-5-(1H-pyrrol-2-yl)-3H-1,4-benzodiazepin-2-amine ($R^{o24}$-7429); α-interferon; probenecid; dipyridamole; pentoxifylline; N-acetylcysteine (NAC); Procysteine; c'-trichosanthin; phosphonoformic acid; interleukin II; thymosin; granulocyte macrophage colony stimulating factors; erythropoetin; soluble $CD_4$; nevirapine (BI-RG-587); loviride (α-APA); delavuridine (BHAP); phosphonoformic acid; (−)-6-chloro-4-cyclopropylethynyl-4-trifluoromethyl-1,4-dihydro-2H-3,1-benzoxazin-2-one (L-743,726 or DMP-266); or isopropyl (2S)-7-fluoro-3,4-dihydro-2-ethyl-3-oxo-1(2H)-quinoxalinecarboxylate (HBY1293).

28. The method according to claim 21 or 22, comprising the additional step of administering to said patient an additional therapeutic agent selected from (1 alpha, 2 beta, 3 alpha)-9[2,3-bis(hydroxymethyl)cyclobutyl]guanine [(−)BHCG, SQ-34514]; oxetanocin-G (3,4-bis-(hydroxymethyl)-2-oxetanosyl]guanine); acyclovir; valaciclovir; famciclovir; ganciclovir; penciclovir; (S)-1-(3-hydroxy-2-phosphonyl-methoxypropyl)cytosine (HPMPC); 2-acetylpyridine 5-[(2-chloroanilino)thiocarbonyl) thiocarbonohydrazone; 3' azido-3'-deoxythymidine; 2',3'-dideoxycytidine; 2',3'-dideoxyadenosine; 2',3'-dideoxyinosine; 2',3'-didehydrothymidine; indinavir; ritonavir; nelfinavir; [3S-

6-chloro-4-cyclopropylethynyl-4-trifluoromethyl-1,4-dihydro-2H-3,1-benzoxazin-2-one (L-743,726 or DMP-266); or isopropyl (2S)-7-fluoro-3,4-dihydro-2-ethyl-3-oxo-1(2H)-quinoxalinecarboxylate (HBY1293).

29. The method according to claim 24, comprising the additional step of administering to said patient an additional therapeutic agent selected from (1 alpha, 2 beta, 3 alpha)-9-[2,3-bis(hydroxymethyl)cyclobutyl]guanine [(−)BHCG, SQ-34514]; oxetanocin-G (3,4-bis-(hydroxymethyl)-2-oxetanosyl]guanine); acyclovir; valaciclovir; famciclovir; ganciclovir; penciclovir; (S)-1-(3-hydroxy-2-phosphonyl-methoxypropyl)cytosine (HPMPC); 2-acetylpyridine 5-[(2-chloroanilino)thiocarbonyl) thiocarbonohydrazone; 3' azido-3'-deoxythymidine; 2',3'-dideoxycytidine, 2',3'-dideoxyadenosine; 2',3'-dideoxyinosine; 2',3'-didehydrothymidine; indinavir; ritonavir; nelfinavir; [3S-[3R*(1R*,2S*)]]-[3-[[(4-aminophenyl)sulfonyl](2-methylpropyl)amino]-2-hydroxy-1-(phenylmethyl)propyl]-tetrahydro-3-furanyl ester (amprenavir); (−)-cis-1-(2-hydroxymethyl)-1,3-oxathiolane 5-yl)-cytosine (lamivudine); cis-1-(2-(hydroxymethyl)-1,3-oxathiolan-5-yl)-5-fluorocytosine (FTC); 3'-deoxy-3'-fluorothymidine; 5-chloro-2',3'-dideoxy-3'-fluorouridine; (−)-cis-4-[2-amino-6-(cyclopropylamino)-9H-purin-9-yl]-2-cyclopentene-1-methanol; ribavirin; 9-[4-hydroxy-2-(hydroxymethyl)but-1-yl]-guanine (H2G); 7-chloro-5-(2-pyrryl)-3H-1,4-benzodiazepin-2-(H)one (Ro5-3335); 7-chloro-1,3-dihydro-5-(1H-pyrrol-2-yl)-3H-1,4-benzodiazepin-2-amine (Ro24-7429); α-interferon; probenecid; dipyridamole; pentoxifylline; N-acetylcysteine (NAC); Procysteine; α-trichosanthin; phosphonoformic acid; interleukin II; thymosin; granulocyte macrophage colony stimulating factors; erythropoetin; soluble $CD_4$; nevirapine (BI-RG-587); loviride (α-APA); delavuridine (BHAP); phosphonoformic acid; (−)-6-chloro-4-cyclopropylethynyl-4-trifluoromethyl-1,4-dihydro-2H-3,1-benzoxazin-2-one (L-743,726 or DMP-266); or isopropyl (2S)-7-fluoro-3,4-dihydro-2-ethyl-3-oxo-1(2H)-quinoxalinecarboxylate (HBY1293).

30. A composition comprising a compound according to claim 26, in an amount sufficient to inhibit an aspartyl protease; and a pharmaceutically acceptable carrier.

31. The composition according to claim 30, wherein said composition is in a pharmaceutically acceptable form for administration to a human being.

32. The composition according to claim 30, wherein said composition additionally comprises an anti-viral agent.

33. The composition according to claim 30, wherein said composition comprises at least one additional therapeutic agent selected from (1 alpha, 2 beta, 3 alpha)-9-[2,3-bis(hydroxymethyl)cyclobutyl]-guanine [(−)BHCG, SQ-34514]; oxetanocin-G (3,4-bis-(hydroxymethyl)-2-oxetanosyl]guanine); acyclic nucleosides; acyclic nucleoside phosphonates; ribonucleotide reductase inhibitors; 2',3'-dideoxynucleosides; aspartyl protease inhibitors; oxathiolane nucleoside analogues; 3'-deoxy-3'-fluorothymidine; 5-chloro-2',3'-dideoxy-3'-fluorouridine; (−)-cis-4-[2-amino-6-(cyclopropylamino)-9H-purin-9-yl]-2-cyclopentene-1-methanol; ribavirin; 9-[4-hydroxy-2-(hydroxymethyl)but-1-yl]-guanine (H2G); tat inhibitors; interferons; renal excretion inhibitors; nucleoside transport inhibitors; pentoxifylline; N-acetylcysteine (NAC); Procysteine; α-trichosanthin; phosphonoformic acid; immunomodulators; granulocyte macrophage colony stimulating factors; erythropoetin; soluble $CD_4$; non-nucleoside reverse transcriptase inhibitors (NNRTIs); phosphonoformic acid; 1,4dihydro-2H-3,1-benzoxazin-2-ones NNRTIs; or quinoxaline NNRTIs.

34. The composition according to claim 33, wherein said at least one additional therapeutic agent is selected from (1 alpha, 2 beta, 3 alpha)-9-[2,3-bis(hydroxymethyl)cyclobutyl]-guanine [(−)BHCG, SQ-34514]; oxetanocin-G (3,4-bis-(hydroxymethyl)-2-oxetanosyl]guanine); acyclovir; valaciclovir; famciclovir; ganciclovir; penciclovir; (S)-1-(3-hydroxy-2-phosphonyl-methoxypropyl)cytosine (HPMPC); 2-acetylpyridine 5-[(2-chloroanilino)thiocarbonyl)thiocarbonohydrazone; 3' azido-3'-deoxythymidine; 2',3'-dideoxycytidine; 2',3'-dideoxyadenosine; 2',3'-dideoxyinosine; 2',3'-didehydrothymidine; indinavir; ritonavir; nelfinavir; [3S-[3R*(1R*,2S*)]]-[3-[[(4-aminophenyl)sulfonyl](2-methylpropyl)amino]-2-hydroxy-1-(phenylmethyl)propyl]-tetrahydro-3-furanyl ester (amprenavir); (−)-cis-1-(2-hydroxymethyl)-1,3-oxathiolane 5-yl)-cytosine (lamivudine); cis-1-(2-(hydroxymethyl)-1,3-oxathiolan-5-yl)-5-fluorocytosine (FTC); 3'-deoxy-3'-fluorothymidine; 5-chloro-2',3'-dideoxy-3'-fluorouridine; (−)-cis-4-[2-amino-6-(cyclopropylamino)-9H-purin-9-yl]-2-cyclopentene-1-methanol; ribavirin; 9-[4-hydroxy-2-(hydroxymethyl)but-1-yl]-guanine (H2G); 7-chloro-5-(2-pyrryl)-3H-1,4-benzodiazepin-2-(H)one (Ro5-3335); 7-chloro-1,3-dihydro-5-(1H-pyrrol-2-yl)-3H-1,4-benzodiazepin-2-amine (Ro24-7429); α-interferon; probenecid; dipyridamole; pentoxifylline; N-acetylcysteine (NAC); Procysteine; α-trichosanthin; phosphonoformic acid; interleukin II; thymosin; granulocyte macrophage colony stimulating factors; erythropoetin; soluble $CD_4$; nevirapine (BI-RG-587); loviride (α-APA); delavuridine (BHAP); phosphonoformic acid; (−)-6-chloro-4-cyclopropylethynyl-4-trifluoromethyl-1,4-dihydro-2H-3,1-benzoxazin-2-one (L-743,726 or DMP-266); or isopropyl (2S)-7-fluoro-3,4-dihydro-2-ethyl-3-oxo-1(2H)-quinoxalinecarboxylate (HBY1293).

35. The composition according to any one of claims 30 to 34, wherein said composition is in an orally available dosage form.

36. A method of treating a patient infected with a virus that depends upon an aspartyl protease for an obligatory event in its life cycle comprising the step of administering to said patient a composition according to claim 30.

37. A method of treating a patient infected with HIV-I or HIV-II comprising the step of administering to said patient a composition according to claim 30.

38. A method of treating a patient diagnosed with AIDS; AIDS related complex (ARC); progressive generalized lymphadenopathy (PGL); Kaposi's sarcoma, thrombocytopenic purpura; AIDS-related neurological conditions such as AIDS dementia complex, multiple sclerosis or tropical paraperesis; anti-HIV antibody-positive conditions; or HIV-positive conditions, comprising the step of administering to said patient a composition according to claim 30.

39. The method according to any one of claims 36-38, comprising the additional step of administering to said patient an additional therapeutic agent selected from (1 alpha, 2 beta, 3 alpha)-9-[2,3-bis(hydroxymethyl)cyclobutyl]-guanine [(−) BHCG, SQ-34514]; oxetanocin-G (3,4-bis-(hydroxymethyl)-2-oxetanosyl]guanine); acyclic nucleosides; acyclic nucleoside phosphonates; ribonucleotide reductase inhibitors; 2',3'-dideoxynucleosides; aspartyl protease inhibitors; oxathiolane nucleoside analogues; 3'-deoxy-3'-fluorothymidine; 5-chloro-2',3'-dideoxy-3'-fluorouridine; (−)-cis-4-[2-amino-6-(cyclopropylamino)-9H-purin-9-yl]-2-cyclopentene-1-methanol; ribavirin; 9-[4-hydroxy-2-(hydroxymethyl)but-1-yl]-guanine (H2G); tat inhibitors; interferons; renal excretion inhibitors; nucleoside transport inhibitors; pentoxifylline; N-acetylcysteine (NAC); Procysteine; α-trichosanthin; phosphonoformic acid; immunomodulators; granulocyte macrophage colony stimulating factors; erythropoetin; soluble $CD_4$; non-nucleoside reverse transcriptase inhibitors (NNRTIs); phosphonoformic acid; 1,4-dihydro-2H-3,1-benzoxazin-2-ones NNRTIs; or quinoxaline NNRTIs.

40. The method according to any one of claim 36-38, comprising the additional step of administering to said patient an additional therapeutic agent selected from (1 alpha, 2 beta, 3 alpha)-9-[2,3-bis(hydroxymethyl)cyclobutyl]-guanine [(−) BHCG, SQ-34514]; oxetanocin-G (3,4-bis-(hydroxymethyl)-2-oxetanosyl]guanine); acyclovir; valaciclovir; famciclovir; ganciclovir; penciclovir; (S)-1-(3-hydroxy-2-phosphonyl-methoxypropyl)cytosine (HPMPC); 2-acetylpyridine 5-[(2-chloroanilino)thiocarbonyl] thiocarbonohydrazone; 3' azido-3'-deoxythymidine; 2',3'-dideoxycytidine; 2',3'-dideoxyadenosine; 2',3'-dideoxyinosine; 2',3'-didehydrothymidine; indinavir; ritonavir; nelfinavir; [3S-[3R*(1R*,2S*)]]-[3-[[(4-aminophenyl)sulfonyl](2-methylpropyl)amino]-2-hydroxy-1-(phenylmethyl)propyl]-tetrahydro-3-furanyl ester (amprenavir); (−)-cis-1-(2-hydroxymethyl)-1,3-oxathiolane 5-yl)-cytosine (lamivudine); cis-1-(2-(hydroxymethyl)-1,3-oxathiolan-5-yl)-5-fluorocytosine (FTC); 3'-deoxy-3'-fluorothymidine; 5-chloro-2',3'-dideoxy-3'-fluorouridine; (−)-cis-4-[2-amino-6-(cyclopropylamino)-9H-purin-9-yl]-2-cyclopentene-1-methanol; ribavirin; 9-[4-hydroxy-2(hydroxymethyl)but-1-yl]-guanine (H2G); 7-chloro-5-(2-pyrryl)-3H-1,4-benzodiazepin-2-(H)one (Ro5-3335); 7-chloro-1,3-dihydro-5-(1H-pyrrol-2-yl)-3H-1,4-benzodiazepin-2-amine (Ro24-7429); α-interferon; probenecid; dipyridamole; pentoxifylline; N-acetylcysteine (NAC); Procysteine; α-trichosanthin; phosphonoformic acid; interleukin II; thymosin; granulocyte macrophage colony stimulating factors; erythropoetin; soluble $CD_4$; nevirapine (BI-RG-587); loviride (α-APA); delavuridine (BHAP); phosphonoformic acid; (−)-6-chloro-4-cyclopropylethynyl-4-trifluoromethyl-1,4-dihydro-2H-3,1-benzoxazin-2-one (L-743,726 or DMP-266); or isopropyl (2S)-7-fluoro-3,4-dihydro-2-ethyl-3-oxo-1(2H)-quinoxalinecarboxylate (HBY1293).

\* \* \* \* \*